United States Patent
Bearss et al.

(10) Patent No.: US 12,428,404 B2
(45) Date of Patent: *Sep. 30, 2025

(54) INHIBITORS OF LRRK2 KINASE

(71) Applicant: Halia Therapeutics, Inc., Lehi, UT (US)

(72) Inventors: David James Bearss, Lehi, UT (US); John Sai Keong Kauwe, III, Lehi, UT (US); Alexis Henri Abel Mollard, Lehi, UT (US)

(73) Assignee: Halia Therapeutics, Inc., Lehi, UT (US)

( * ) Notice: Subject to any disclaimer, the term of this patent is extended or adjusted under 35 U.S.C. 154(b) by 11 days.

This patent is subject to a terminal disclaimer.

(21) Appl. No.: 18/514,959

(22) Filed: Nov. 20, 2023

(65) Prior Publication Data

US 2024/0190848 A1 Jun. 13, 2024

Related U.S. Application Data

(60) Continuation of application No. 18/065,259, filed on Dec. 13, 2022, now Pat. No. 11,866,423, which is a division of application No. 17/702,600, filed on Mar. 23, 2022, now Pat. No. 11,578,061.

(60) Provisional application No. 63/164,804, filed on Mar. 23, 2021.

(51) Int. Cl.
| | |
|---|---|
| C07D 239/47 | (2006.01) |
| A61K 31/505 | (2006.01) |
| A61K 31/506 | (2006.01) |
| C07D 401/14 | (2006.01) |
| C07D 403/12 | (2006.01) |
| C07D 403/14 | (2006.01) |
| C07D 405/14 | (2006.01) |
| C07D 413/12 | (2006.01) |
| C07D 413/14 | (2006.01) |
| C07D 491/107 | (2006.01) |
| C07D 498/08 | (2006.01) |

(52) U.S. Cl.
CPC ......... *C07D 403/14* (2013.01); *C07D 239/47* (2013.01); *C07D 401/14* (2013.01); *C07D 403/12* (2013.01); *C07D 405/14* (2013.01); *C07D 413/12* (2013.01); *C07D 413/14* (2013.01); *C07D 491/107* (2013.01); *C07D 498/08* (2013.01)

(58) Field of Classification Search
CPC .. C07D 239/47; C07D 401/14; C07D 403/12; C07D 403/14; C07D 405/14; C07D 413/12; C07D 413/14; A61K 31/505; A61K 31/506

See application file for complete search history.

(56) References Cited

U.S. PATENT DOCUMENTS

| | | |
|---|---|---|
| 11,578,061 B2 | 2/2023 | Bearss et al. |
| 11,866,423 B2 * | 1/2024 | Bearss ............... C07D 403/14 |
| 2011/0288109 A1 | 11/2011 | Stadtmueller et al. |
| 2012/0309735 A1 | 12/2012 | Altman et al. |
| 2014/0243290 A1 | 8/2014 | Altman et al. |
| 2016/0129002 A1 | 5/2016 | Besidski et al. |
| 2017/0057957 A1 | 3/2017 | Lan et al. |
| 2021/0230143 A1 | 7/2021 | Shi et al. |

FOREIGN PATENT DOCUMENTS

| | | |
|---|---|---|
| CN | 110872277 A | 3/2020 |
| WO | WO 2008038011 A1 | 4/2008 |
| WO | WO 2011151360 A1 | 12/2011 |
| WO | WO 2015113451 A1 | 8/2015 |
| WO | WO 2017087905 A1 | 5/2017 |
| WO | WO 2017156493 A1 | 9/2017 |
| WO | WO 2019074810 A1 | 4/2019 |

OTHER PUBLICATIONS

Aasly, "Inflammatory Diseases Among Norwegian LRRK2 Mutation Carriers. A 15-Years Follow-Up of a Cohort," *Frontiers in Neuroscience* 15(634666):1-11, Jan. 28, 2021.
Acute Leukemia, Merck Manual (Online Edition), last full review/revision Jul. 2012 by Michael E. Rytting, accessed: 2013. (6 pages).
Agalliu et al., "Higher frequency of certain cancers in LRRK2 G2019S mutation carriers with Parkinson's disease: A pooled analysis," *JAMA Neurol.* 72(1):58-65, Jan. 2015. (19 pages).
Banker et al., "Prodrugs," *Modern Pharmaceutics*, Third Edition, Revised and Expanded, pp. 451 and 596, 1996. (3 pages).
Bundgaard, "Design of prodrugs: Bioreversible derivatives for various functional groups and chemical entities: Introduction," Design of Prodrugs, 1985. (3 pages).

(Continued)

*Primary Examiner* — Brenda L Coleman
(74) *Attorney, Agent, or Firm* — Seed IP Law Group LLP

(57) ABSTRACT

Compounds having activity as inhibitors of LRRK2 kinase are provided. The compounds have Structure (I):

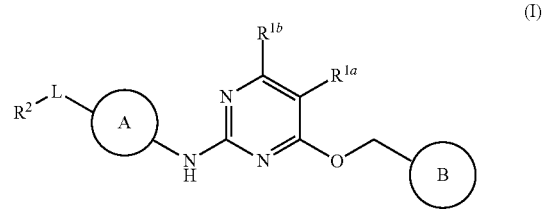

or a pharmaceutically acceptable salt, stereoisomer or prodrug thereof, wherein A, B, $R^{1a}$, $R^{1b}$, $R^2$, and L are as defined herein. Methods associated with preparation and use of such compounds, pharmaceutical compositions comprising such compounds and methods to modulate the activity of LRRK2 kinase are also provided.

22 Claims, No Drawings

Specification includes a Sequence Listing.

(56) References Cited

OTHER PUBLICATIONS

Chan et al., "Discovery of a Highly Selective, Brain-Penetrant Aminopyrazole LRRK2 Inhibitor," *ACS Med. Chem. Lett.* 4:85-90, 2013.
Chen et al., "Discovery of Selective LRRK2 Inhibitors Guided by Computational Analysis and Molecular Modeling," *J. Med. Chem.*, p. A-J, Received: Mar. 31, 2012. (10 pages).
Damasio, "Part XXIV Neurology: Alzheimer's Disease and Related Dementias," in Bennett et al. (eds.), *Cecil Textbook of Medicine, 20th edition*, vol. 2, p. 1992-1996, 1996. (6 pages).
Deng et al., "Characterization of a selective inhibitor of the Parkinson's disease kinase LRRK2," *Nat. Chem. Biol.* 7(4):203-205, Apr. 2011. (10 pages).
Estrada et al., "Discovery of Highly Potent, Selective, and Brain-Penetrable Leucine-Rich Repeat Kinase 2 (LRRK2) Small Molecule Inhibitors," *J. Med. Chem.* 55:9416-9433, 2012.
Estrada et al., "Discovery of Highly Potent, Selective, and Brain-Penetrant Aminopyrazole Leucine-Rich Repeat Kinase 2 (LRRK2) Small Molecule Inhibitors," *J. Med. Chem.*, p. A-P, Received: Oct. 25, 2013. (16 pages).
Gura, "Cancer Models: Systems for Identifying New Drugs Are Often Faulty," *Science* 278(5340):1041-1042, Nov. 7, 1997. (5 pages).
Hui et al., "Functional Variants in LRRK2 Confer Pleiotropic Effects on Risk for Crohn's Disease and Parkinson's Disease," *Sci. Transl. Med.* 10(423):1-31, Jan. 10, 2018.
Jennings et al., "LRRK2 Inhibition by BIIB122 in Healthy Participants and Patients with Parkinson's Disease," *Movement Disorders* 38(3):386-398, Feb. 18, 2023. (13 pages).
Johnson et al., "Relationships between drug activity in NCI preclinical in vitro and in vivo models and early clinical trials," *British Journal of Cancer* 84(10):1424-1431, 2001.
Layzer, "Section Five—Degenerative Diseases of the Nervous System," in Bennett et al. (eds.), *Cecil Textbook of Medicine, 20th edition*, vol. 2, p. 2050-2057, 1996. (9 pages).
Looyenga et al., "Chromosomal amplification of leucine-rich repeat kinase-2 (LRRK2) is required for oncogenic MET signaling in papillary renal and thyroid carcinomas," *PNAS* 108(4):1439-1444, Jan. 25, 2011.
Mutti et al., "LRRK2 Kinase Inhibition Attenuates Neuroinflammation and Cytotoxicity in Animal Models of Alzheimer's and Parkinson's Disease-Related Neuroinflammation," *Cells* 12(1799):1-16, Jul. 6, 2023.
Pearce et al., "Chapter 18: Failure modes in anticancer drug discovery and development," in Neidle (ed.), *Cancer Drug Design and Discovery*, p. 424-435, 2008. (12 pages).
Ramsden et al., "Chemoproteomics-based design of potent LRRK2-selective lead compounds that attenuate Parkinson's disease-related toxicity in human neurons," *ACS Chem. Biol.* 6(10):1021-1028, Oct. 21, 2011. (13 pages).
Saunders-Pullman et al., "LRRK2 G2019S Mutations are associated with an increased cancer risk in Parkinson Disease," *Mov. Disord.* 25(15):2536-2541, Nov. 15, 2010. (11 pages).
Shtilbans et al., "Differential gene expression in patients with amyotrophic lateral sclerosis," *Amyotrophic Lateral Sclerosis* 12:250-256, 2011.
Silverman, "Chapter 8: Prodrugs and Drug Delivery Systems," *The Organic Chemistry of Drug Design and Drug Action*, p. 352-400, 1992. (51 pages).
Simone, "Part XIV Oncology: Introduction," in Bennett et al. (eds.), *Cecil Textbook of Medicine, 20th edition*, vol. 1, p. 1004-1010, 1996. (8 pages).
Stanic et al., "LRRK2 phosphorylation level correlates with abnormal motor behaviour in an experimental model of levodopa-induced dyskinesias," *Molecular Brain* 9(53):1-6, 2016.
Wojewska et al., "LRRK2 Targeting Strategies as Potential Treatment of Parkinson's Disease," *Biomolecules* 11(1101):1-18, Jul. 26, 2021.
Wolff, "9. Some Consideration for Prodrug Design," *Burger's Medicinal Chemistry and Drug Discovery*, 5th Edition, vol. 1: Principles and Practice, p. 975-977, 1995. (3 pages).
Yang et al., "LRRK2 is a candidate prognostic biomarker for clear cell renal cell carcinoma," *Cancer Cell Int.* 21(343):1-20, Jul. 3, 2021.
Zhang et al., "Characterization of TAE684 as a potent LRRK2 kinase inhibitor," *Bioorg. Med. Chem. Lett.* 22(5):1864-1869, Mar. 1, 2012.
Zhang et al., "Genomewide Association Study of Leprosy," *N. Engl. J. Med.* 361(27):2609-2618, Dec. 31, 2009.
Zhao et al., "LRRK2 variant associated with Alzheimer's disease," *Neurobiology of Aging* 32(2011):1990-1993, Dec. 16, 2009.
Zhu et al., "LRRK2 in Parkinson's disease and dementia with Lewy bodies," *Molecular Neurodegeneration* 1(17):1-9, Nov. 30, 2006.

\* cited by examiner

SEQUENCE LISTING

```
Sequence total quantity: 1
SEQ ID NO: 1            moltype = AA  length = 15
FEATURE                 Location/Qualifiers
source                  1..15
                        mol_type = protein
                        organism = synthetic construct
SEQUENCE: 1
RLGRDKYKTL RQIRQ                                                      15
```

INHIBITORS OF LRRK2 KINASE

REFERENCE TO AN ELECTRONIC SEQUENCE LISTING

The contents of the electronic sequence listing (405C1_SeqListing.xml; Size: 1,922 bytes; and Date of Creation: Oct. 24, 2023) is herein incorporated by reference in its entirety.

BACKGROUND

Technical Field

Embodiments of the present disclosure are generally directed to compounds and methods for their preparation and use as therapeutic or prophylactic agents, for example for treatment of neurodegenerative diseases, central nervous system (CNS) disorders, cancers, and inflammatory diseases.

Description of the Related Art

Neurodegenerative diseases such as Parkinson's disease, Lewy body dementia, and Huntington's disease affect millions of individuals. Parkinson's disease is a chronic, progressive motor system disorder that afflicts approximately one out of every 1000 people, with hereditary Parkinson's disease accounting for 5-10% of all of patients. Parkinson's disease is caused by progressive loss of mid-brain dopamine neurons, leaving patients with impaired ability to direct and control their movements. The primary Parkinson's disease symptoms are trembling, rigidity, slowness of movement, and impaired balance.

The gene encoding the leucine-rich repeat kinase 2 protein (LRRK2) has been identified in association with hereditary Parkinson's disease (see, e.g., Paisan-Ruiz et al., Neuron, Vol. 44(4), 2004, pp 595-600; Zimprich et al., Neuron, Vol. 44(4), 2004, 601-607). In-vitro studies show that Parkinson's disease-associated mutation leads to increased LRRK2 kinase activity and decreased rate of GTP hydrolysis compared to wild-type (Guo et al., Experimental Cell Research, Vol. 313(16), 2007, pp. 3658-3670). Anti-LRRK2 antibodies have been used to label brainstem Lewy bodies associated with Parkinson's disease and cortical antibodies associated with Lewis body dementia suggesting that LRRK2 may play an important role in Lewy body formation and pathogenesis associated with these diseases (Zhou et al., Molecular Degeneration, 2006, 1:17 doi: 10.1186/1750-1326-1-17). LRRK2 has also been identified as a gene potentially associated with increased susceptibility to Crohn's disease and susceptibility to leprosy (Zhang et al., New England J. Med. Vol. 361 (2009) pp. 2609-2618.

LRRK2 has also been associated with L-DOPA induced dyskinesia (Hurley et al., Eur. J. Neurosci., Vol. 26, 2007, pp. 171-177); CNS disorders associated with neuronal progenitor differentiation (Milosevic et al., Neurodegen., Vol. 4, 2009, p. 25); cancers such as kidney, breast, prostate, blood and lung cancers and acute myelogenous leukemia (see, e.g., PCT Publication No. WO 2011/038572); papillary renal and thyroid carcinomas (Looyenga et al., www.pnas.org/cgi/doi/10.1073/pnas. 1012500108); multiple myeloma (Chapman et al., Nature Vol. 471, 2011, pp. 467-472); amyotrophic lateral sclerosis (Shtilbans et al., Amyotrophic Lateral Sclerosis "Early Online 2011, pp. 1-7); rheumatoid arthritis (Nakamura et al., DNA Res. Vol. 13(4), 2006, pp. 169-183); and ankylosing spondylitis (Danoy et al., PLOS Genetics, Vol. 6(12), 2010, e1001195, pp. 1-5).

Accordingly, compounds and compositions effective at modulating LRRK2 kinase activity may provide a treatment for neurodegenerative diseases such as Parkinson's disease and Lewy body dementia, for CNS disorders such as Alzheimer's disease and L-DOPA induced dyskinesia, for cancers such as kidney, breast, prostate, blood, papillary, and lung cancers, acute myelogenous leukemia, and multiple myeloma, and for inflammatory diseases such as leprosy, Crohn's disease, amyotrophic lateral sclerosis, rheumatoid arthritis, and ankylosing spondylitis. Embodiments of the present disclosure fulfill this need and provide further related advantages.

BRIEF SUMMARY

In brief, embodiments of the present disclosure provide compounds, including pharmaceutically acceptable salts, stereoisomers, and prodrugs thereof, which are capable of modulating the kinase activity of LRRK2.

In one aspect, the disclosure provides compounds of Structure (I):

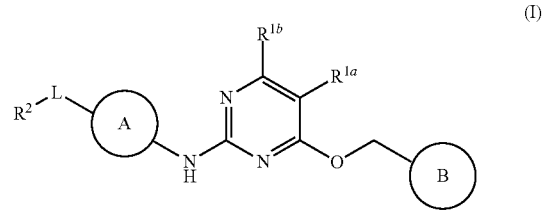

pharmaceutically acceptable salts, stereoisomers, or prodrug thereof, wherein each of A, B, $R^{1a}$, $R^{1b}$, $R^2$, and L are as defined below.

In another aspect, pharmaceutical compositions comprising the disclosed compounds, and methods of use of the same for treatment of neurodegenerative diseases, central nervous system (CNS) disorders, cancer, inflammatory diseases, and combinations thereof are also provided.

DETAILED DESCRIPTION

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, the terms "about" and "approximately" mean ±20%, ±10%, ±5% or ±1% of the indicated range, value, or structure, unless otherwise indicated. It should be understood that the terms "a" and "an" as used herein refer to "one or more" of the enumerated components.

The use of the alternative (e.g., "or") should be understood to mean either one, both, or any combination thereof of the alternatives.

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this disclosure belongs. As used in the specification and claims, the singular form "a", "an" and "the" include plural references unless the context clearly dictates otherwise.

"Amino" refers to the —$NH_2$ radical.

"Carboxy" or "carboxyl" refers to the —$CO_2H$ radical, which may also exist as a —$CO_2$ radical depending on the conditions (e.g., pH, counter ion, etc.).

"Cyano" refers to the —CN radical.

"Hydroxy" or "hydroxyl" refers to the —OH radical.

"Alkyl" refers to a saturated, straight or branched hydrocarbon chain radical consisting solely of carbon and hydrogen atoms, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), or any value within these ranges, such as $C_4$-$C_6$ alkyl and the like, and which is attached to the rest of the molecule by a single bond, e.g., methyl, ethyl, n-propyl, 1-methylethyl (iso-propyl), n-butyl, n-pentyl, 1,1-dimethylethyl (1-butyl), 3-methylhexyl, 2-methylhexyl and the like. The number of carbons referred to relates to the carbon backbone and carbon branching, but does not include carbon atoms belonging to any substituents. Unless stated otherwise specifically in the specification, an alkyl group is optionally substituted.

"Alkoxy" refers to a radical of the formula —$OR_a$ where $R_a$ is an alkyl radical as defined above containing one to twelve carbon atoms ($C_1$-$C_{12}$ alkoxy), one to eight carbon atoms ($C_1$-$C_8$ alkoxy) or one to six carbon atoms ($C_1$-$C_6$ alkoxy), or any value within these ranges. Unless stated otherwise specifically in the specification, an alkoxy group is optionally substituted.

"Aminyl" refers to a radical of the formula —$NR_aR_b$, where $R_a$ and $R_b$ are each independently H or $C_1$-$C_6$ alkyl as defined above. When both of $R_a$ and $R_b$ are H, an "aminyl" group is the same as an "amino" group as defined above. The $C_1$-$C_6$ alkyl portion of an aminyl group is optionally substituted unless stated otherwise.

"Aromatic ring" refers to a cyclic planar molecule or portion of a molecule (i.e., a radical) with a ring of resonance bonds that exhibits increased stability relative to other connective arrangements with the same sets of atoms. Generally, aromatic rings contain a set of covalently bound co-planar atoms and comprises a number of π-electrons (for example, alternating double and single bonds) that is even but not a multiple of 4 (i.e., 4n+2 π-electrons, where n=0, 1, 2, 3, etc.). Aromatic rings include, but are not limited to, phenyl, naphthenyl, imidazolyl, pyrrolyl, pyridinyl, pyrimidinyl, pyrazinyl, pyridonyl, pyridazinyl, pyrimidonyl. Unless stated otherwise specifically in the specification, an "aromatic ring" includes all radicals that are optionally substituted.

"Aryl" refers to a carbocyclic ring system radical comprising 6 to 18 carbon atoms, for example 6 to 10 carbon atoms ($C_6$-$C_{10}$ aryl) and at least one carbocyclic aromatic ring. For purposes of embodiments of this disclosure, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

As used herein, "arylene" refers to a divalent or multivalent aryl group (i.e., as defined above) which links a portion of a molecule to a radical group, two or more radical groups, or a portion of a first molecule to a portion of a second molecule. Arylene groups include, but are not limited to phenylene. Unless stated specifically otherwise, an arylene is optionally substituted.

"Carbocyclic" or "carbocycle" refers to a ring system, wherein each of the ring atoms are carbon.

"Cycloalkyl" refers to a non-aromatic monocyclic or polycyclic carbocyclic radical consisting solely of carbon and hydrogen atoms, which may include fused or bridged ring systems, having from three to fifteen ring carbon atoms ($C_3$-$C_{15}$ cycloalkyl), from three to ten ring carbon atoms ($C_3$-$C_{10}$ cycloalkyl), or from three to eight ring carbon atoms ($C_3$-$C_8$ cycloalkyl), or any value within these ranges such as three to four carbon atoms ($C_3$-$C_4$ cycloalkyl), and which is saturated or partially unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, (1S, 2S, 3S, 4S, 6S, 7S')-cubanyl, and the like. Unless otherwise stated specifically in the specification, a cycloalkyl group is optionally substituted.

"Fused" refers to any ring structure with two or more rings and at least two rings share two adjacent atoms. For example, in some embodiments, a fused ring group has one of the following structures:

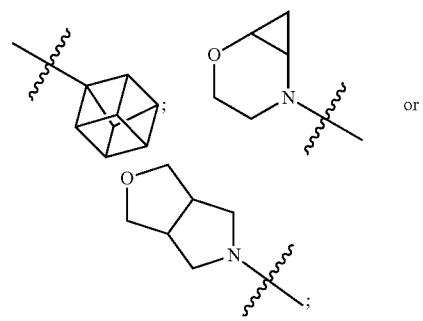

Unless otherwise stated specifically in the specification, a fused ring group is optionally substituted.

"Bridged" or refers to any ring structure described herein having two or more joined rings that share three or more atoms and can be carbocyclic (i.e., all ring atoms are carbons) or heterocyclic (i.e. the rings comprise carbon and one or more heteroatoms). For example, in some embodiments, a bridged ring group has one of the following structures:

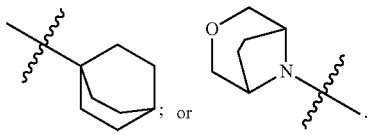

Unless otherwise stated specifically in the specification, a fused ring group is optionally substituted.

"Spiro" refers to any ring structure described herein having at least 2 molecular rings with only one common atom. In some embodiments, a spiro ring group has one of the following structures:

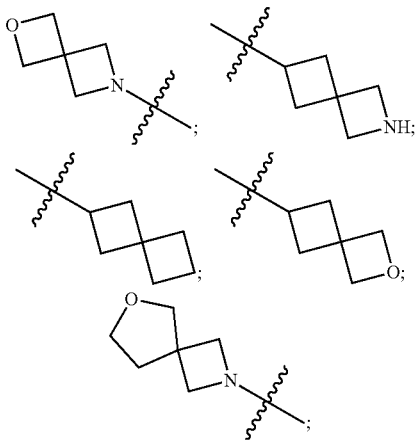

Unless otherwise stated specifically in the specification, a spiro ring group is optionally substituted.

"Halo" refers to bromo, chloro, fluoro, or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Halocycloalkyl" refers to a cycloalkyl radical, as defined above, that is substituted by one or more halo radicals, as defined above, e.g., trifluorocyclopropyl, difluorocyclobutyl, trichlorocyclopentyl, 2,2,2-trifluorocyclohexyl, 1,2-difluorocyclopropyl, 3-bromo-2-fluorocyclopropyl, 1,2-dibromocyclopentyl, and the like. Unless stated otherwise specifically in the specification, a halocycloalkyl group is optionally substituted.

"Hydroxylalkyl" refers to an alkyl radical, as defined above that is substituted by one or more hydroxyl radical. The hydroxyalkyl radical is joined at the main chain through the alkyl carbon atom. Unless stated otherwise specifically in the specification, a hydroxylalkyl group is optionally substituted.

"Alkylaminyl" refers to a radical of the formula —NHR$_a$ or —NR$_a$R$_a$ where each R$_a$ is, independently, an alkyl radical as defined above containing one to twelve carbon atoms. A "haloalkylaminyl" group is an alkylaminyl group comprising at least one halo substituent on the alkyl group.

A "hydroxylalkylaminyl" group is an alkylaminyl group comprising at least one hydroxyl substituent on the alkyl group. An "amidinylalkylaminyl" group is an alkylaminyl group comprising at least one amidinyl substituent on the alkyl group. Unless stated otherwise specifically in the specification, an alkylaminyl, haloalkylaminyl, hydroxylalkylaminyl, and/or amidinylalkylaminyl group is optionally substituted.

"Alkylaminylalkyl" refers to an alkyl group comprising at least one alkylaminyl substituent. The alkylaminyl substituent can be on a tertiary, secondary, or primary carbon. Unless stated otherwise specifically in the specification, an alkylaminylalkyl group is optionally substituted.

"Alkylcarbonyl" refers to a radical of the formula —C(=O)R$_a$ where R$_a$ is an alkyl radical as defined above containing one to twelve carbon atoms. Unless stated otherwise specifically in the specification, an alkylcarbonyl group is optionally substituted.

"Haloalkylcarbonyl" refers to a radical of the formula —C(=O)R$_a$ where R$_a$ is an haloalkyl radical as defined above containing one to twelve carbon atoms. Unless stated otherwise specifically in the specification, a haloalkylcarbonyl group is optionally substituted.

"Cycloalkylcarbonyl" refers to a radical of the formula —C(=O)R$_a$ where R$_a$ is cycloalkyl as defined above. Unless stated otherwise specifically in the specification, a cycloalkylcarbonyl group is optionally substituted.

"Halocycloalkylaminyl" refers to a radical of the formula —NR$_a$R$_b$, where R$_a$ and R$_b$ are each independently H or $C_1$-$C_6$ alkyl and the other comprises a halocycloalkyl radical as defined above. The $C_1$-$C_6$ alkyl and/or halocycloalkyl portion of a halocycloalkylaminyl group is optionally substituted unless stated otherwise.

"Alkylcarbonylaminyl" refers to a radical of the formula —NR$_a$R$_b$ where R$_a$ is H or $C_1$-$C_6$ alkyl and R$_b$ is an alkylcarbonyl radical as defined above. The $C_1$-$C_6$ alkyl and/or alkylcarbonyl portion of an alkylcarbonylaminyl group is optionally substituted unless stated otherwise. In some embodiments, an alkylcarbonylaminyl has one of the following structures:

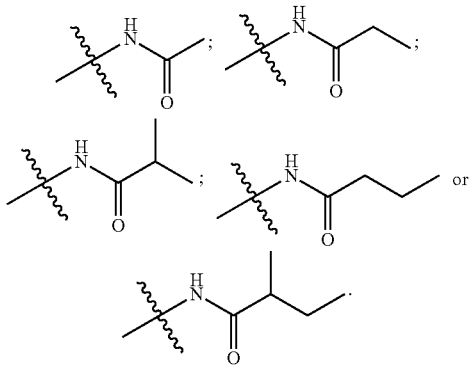

"Haloalkylcarbonylaminyl" refers to a radical of the formula —NR$_a$R$_b$ where R$_a$ is H or $C_1$-$C_6$ alkyl and R$_b$ is a haloalkylcarbonyl radical as defined above. The $C_1$-$C_6$ alkyl and/or haloalkylcarbonyl portion of a haloalkylcarbonylaminyl group is optionally substituted unless stated otherwise.

"Cycloalkylcarbonylaminyl" refers to a radical of the formula —NR$_a$R$_b$ where R$_a$ is H or $C_1$-$C_6$ alkyl and R$_b$ is cycloalkylcarbonyl radical as defined above. The $C_1$-$C_6$ alkyl and/or cycloalkylcarbonyl portion of a cycloalkylcarbonylaminyl group is optionally substituted unless stated otherwise.

"Heterocyclyl" refers to a 3- to 18-membered, for example 3- to 10-membered or 3- to 8-membered, non-aromatic ring radical having one to ten ring carbon atoms (e.g., two to ten) and from one to six ring heteroatoms selected from the group consisting of nitrogen, oxygen and sulfur. Unless stated otherwise specifically in the specification, the heterocyclyl radical is partially or fully saturated and is a monocyclic, bicyclic, tricyclic or tetracyclic ring system, which may include fused, spirocyclic and/or bridged ring systems. Nitrogen and sulfur atoms in a heterocyclyl radical are optionally oxidized, and nitrogen atoms may be optionally quaternized. Examples of such heterocyclyl radicals include, but are not limited to, dioxolanyl, thienyl[1,3]dithianyl, decahydroisoquinolyl, furanonyl, imidazolinyl, imidazolidinyl, isothiazolidinyl, isoxazolidinyl, morpholinyl, octahydroindolyl, octahydroisoindolyl, hexahydro-1H-pyrrolizine, 2-oxopiperazinyl, 2-oxopiperidinyl, 2-oxopyrrolidinyl, oxazolidinyl, oxiranyl, piperidinyl, piperazinyl, 4-piperidonyl, azetidinyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 2-oxaspiro[3.3]heptanyl, and 1,1-dioxo-thiomorpholinyl. Unless stated otherwise specifically in the specification, a heterocyclyl group is optionally substituted.

"Heterocyclylalkyl" refers to an alkyl group comprising at least one heterocyclyl substituent. Unless stated otherwise specifically in the specification, a heterocyclylalkyl group is optionally substituted.

"Heteroaryl" refers to a 5- to 18-membered, for example 5- to 6-membered, ring system radical comprising one to thirteen ring carbon atoms, one to six ring heteroatoms selected from the group consisting of nitrogen, oxygen and sulfur, and at least one aromatic ring. Heteroaryl radicals may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e., thienyl). "Heteroarylene" is a divalent or multivalent heteroaryl radical. Unless stated otherwise specifically in the specification, heteroaryl and heteroarylene groups are optionally substituted.

The term "substituted" as used herein means any of the above groups (e.g., alkyl, alkenyl, alkylene, alkylcarbonyl, alkoxy, alkoxyalkyl, aminylalkyl, aryl, cyanoalkyl, cycloalkyl, haloalkyl, heterocyclyl, heterocyclene, heterocyclylalkyl, heteroaryl, heteroarylalkyl and/or hydroxylalkyl) wherein at least one hydrogen atom (e.g., 1, 2, 3 or all hydrogen atoms) is replaced by a bond to a non-hydrogen substituent. Examples of non-hydrogen substituents include, but are not limited to: amino, carboxyl, cyano, hydroxyl, halo, nitro, oxo, thiol, thioxo, alkyl, alkenyl, alkylcarbonyl, alkoxy, aryl, cyanoalkyl, cycloalkyl, haloalkyl, heterocyclyl, heterocyclylalkyl, heteroaryl, heteroarylalkyl and/or hydroxylalkyl substituents, each of which may also be optionally substituted with one or more of the above substituents.

In some specific embodiments, the optional substitutions are independently selected from the group consisting of halo, $C_1$-$C_6$ alkyl and $C_1$-$C_6$ alkoxy. In other embodiments, the optional substituents are independently selected from the group consisting of amino, halo, hydroxyl, oxo, cyano, $C_1$-$C_6$ alkyl, $C_1$-$C_6$ haloalkyl, $C_1$-$C_6$ hydroxylalkyl, $C_1$-$C_6$ aminoalkyl, $C_1$-$C_6$ alkylaminylalkyl, $C_1$-$C_6$ alkoxy; $C_1$-$C_6$ haloalkoxy $C_1$-$C_6$ alkylcarbonyl, $C_1$-$C_6$ haloalkylcarbonyl, $C_1$-$C_6$ alkylaminyl, $C_1$-$C_6$ haloalkylaminyl, $C_1$-$C_6$ alkylcarbonylaminyl, $C_1$-$C_6$ haloalkylcarbonylaminyl, $C_3$-$C_8$ cycloalkyl, $C_3$-$C_8$ cycloalkylcarbonyl, $C_3$-$C_8$ halocycloalkylaminyl, and $C_3$-$C_8$ cycloalkylcarbonylaminyl. In some more specific embodiments, the optional substituents are independently selected from the group consisting of halo, cyano, $C_1$-$C_6$ alkyl, and $C_1$-$C_6$ haloalkyl.

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to a disease, disorder or medical condition including but not limited to a therapeutic effect and/or a prophylactic effect. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. A prophylactic effect includes delaying or eliminating the appearance of a disease or condition, delaying or eliminating the onset of symptoms of a disease or condition, slowing, halting, or reversing the progression of a disease or condition, or any combination thereof. In certain embodiments, for prophylactic benefit, the compositions are administered to a subject at risk of developing a particular disease, or to a subject reporting one or more of the physiological symptoms of a disease, even though a diagnosis of this disease may not have been made.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness of the free bases, which are biologically tolerable, or otherwise biologically suitable for administration to the subject. See, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002. Preferred pharmaceutically acceptable acid addition salts are those that are pharmacologically effective and suitable for contact with the tissues of patients without undue toxicity, irritation, or allergic response. Pharmaceutically acceptable acid addition salts which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness of the free acids, which are biologically tolerable, or otherwise biologically suitable for administration to the subject. See, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002. Preferred pharmaceutically acceptable base addition salts are those that are pharmacologically effective and suitable for contact with the tissues of patients without undue toxicity, irritation, or allergic response. Pharmaceutically acceptable base addition salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

In some embodiments, pharmaceutically acceptable salts include quaternary ammonium salts such as quaternary amine alkyl halide salts (e.g., methyl bromide).

The terms "antagonist" and "inhibitor" are used interchangeably, and they refer to a compound having the ability to inhibit a biological function of a target protein, whether by inhibiting the activity or expression of the protein, such as LRRK2. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Prodrug" is meant to indicate a compound that may be converted under physiological conditions or by solvolysis to a biologically active compound described herein (e.g., compounds of Structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or thiol group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

Embodiments disclosed herein are also meant to encompass all pharmaceutically acceptable compounds of Structure (I).

Certain embodiments are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments include compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compounds disclosed herein. As used herein, the term "solvate" refers to an aggregate that comprises one or more compounds of the disclosure with one or more molecules of solvent. In some embodiments, the solvent is water, in which case the solvate is a hydrate. Alternatively, in other embodiments, the solvent is an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. In some aspects, the compounds of the disclosure are a true solvate, while in other cases, the compounds of the disclosure merely retain adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to formulations of compounds of the disclosure and a medium generally accepted in the art for the delivery of compounds of the disclosure to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

The compounds of the disclosure (i.e., compounds of Structure (I)) or their pharmaceutically acceptable salts may contain one or more centers of geometric asymmetry and may thus give rise to stereoisomers such as enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

Embodiments of the present disclosure include all manner of rotamers and conformationally restricted states of a compound of the disclosure. Atropisomers, which are stereoisomers arising because of hindered rotation about a single bond, where energy differences due to steric strain or other contributors create a barrier to rotation that is high enough to allow for isolation of individual conformers, are also included. As an example, certain compounds of the disclosure may exist as mixtures of atropisomers or purified or enriched for the presence of one atropisomer.

In some embodiments, the compounds of Structure (I) are a mixture of enantiomers or diastereomers. In other embodiments, the compounds of Structure (I) are substantially one enantiomer or diastereomer.

A "tautomer" refers to a proton shift from one atom of a molecule to another atom of the same molecule. Embodiments thus include tautomers of the disclosed compounds.

The chemical naming protocol and structure diagrams used herein are a modified form of the I.U.P.A.C. nomenclature system, using the ACD/Name Version 9.07 software program and/or ChemDraw Professional Version 17.0.0.206 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Compounds

The disclosure provides compounds including pharmaceutically acceptable salts, stereoisomers and prodrugs thereof, which are capable of inhibiting LRRK2 kinase.

Accordingly, one embodiment provides a compound having the following Structure (I):

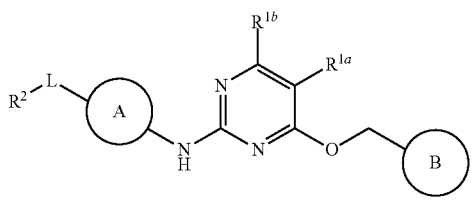

(I)

or a pharmaceutically acceptable salt, stereoisomer or prodrug thereof, wherein:

A is phenylene or 5 or 6-membered heteroarylene, each of which is optionally substituted with one or more substituents selected from halo, $C_1$-$C_6$ alkyl and $C_1$-$C_6$ alkoxy;

B is $C_3$-$C_8$ monocyclic cycloalkyl, $C_6$-$C_{10}$ spirocyclic cyclocalkyl, $C_6$-$C_{10}$ fused-multicyclic cycloalkyl, $C_6$-$C_{10}$ bridged-multicyclic cycloalkyl, 3-8-membered monocyclic heterocyclyl, 3-8-membered monocyclic heterocyclylalkyl, 6-10-membered spirocyclic heterocyclyl, 6-10-membered fused-multicyclic heterocyclyl or 6-10-membered bridged-multicyclic heterocyclyl, each of which is optionally substituted with one or more substituents selected from amino, halo, hydroxyl, oxo, cyano, $C_1$-$C_6$ alkyl, $C_1$-$C_6$ haloalkyl, $C_1$-$C_6$ hydroxylalkyl, $C_1$-$C_6$ aminoalkyl, $C_1$-$C_6$ alkylaminylalkyl, $C_1$-$C_6$ alkoxy; $C_1$-$C_6$ haloalkoxy $C_1$-$C_6$ alkylcarbonyl, $C_1$-$C_6$ haloalkylcarbonyl, $C_1$-$C_6$ alkylaminyl, $C_1$-$C_6$ haloalkylaminyl, $C_1$-$C_6$ alkylcarbonylaminyl, $C_1$-$C_6$ haloalkylcarbonylaminyl, $C_3$-$C_8$ cycloalkyl, $C_3$-$C_8$ cycloalkylcarbonyl, $C_3$-$C_8$ halocycloalkylaminyl, and $C_3$-$C_8$ cycloalkylcarbonylaminyl;

L is a direct bond, $CH_2$ or C=O;

$R^{1a}$ and $R^{1b}$ are each independently H, halo, cyano, $C_1$-$C_6$ alkyl, $C_1$-$C_6$ haloalkyl, $C_1$-$C_6$ alkoxy or $C_3$-$C_8$ cycloalkyl; and $R^2$ is $C_1$-$C_6$ alkyl, $C_3$-$C_8$ cycloalkyl, 3-8-membered heterocyclyl, 6-10-membered spirocyclic heterocyclyl, 6-10-membered fused-multicyclic heterocyclyl or 6-10-membered bridged-multicyclic heterocyclyl, each of which is optionally substituted with one or more substituents selected from halo, cyano, $C_1$-$C_6$ alkyl, and $C_1$-$C_6$ haloalkyl.

One embodiment provides a compound having the following Structure (I):

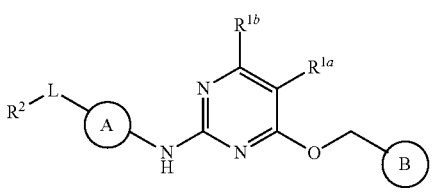

(I)

or a pharmaceutically acceptable salt, stereoisomer or prodrug thereof, wherein:

A is phenylene or 5 or 6-membered heteroarylene, each of which is optionally substituted with one or more substituents selected from halo, $C_1$-$C_6$ alkyl, $C_1$-$C_6$ cycloalkyl (e.g., cyclopropyl, cyclobutyl), and $C_1$-$C_6$ alkoxy;

B is $C_3$-$C_8$ monocyclic cycloalkyl, $C_6$-$C_{10}$ spirocyclic cyclocalkyl, $C_6$-$C_{10}$ fused-multicyclic cycloalkyl, $C_6$-$C_{10}$ bridged-multicyclic cycloalkyl, 3-8-membered monocyclic heterocyclyl, 3-8-membered monocyclic heterocyclylalkyl, 6-10-membered spirocyclic heterocyclyl, 6-10-membered fused-multicyclic heterocyclyl or 6-10-membered bridged-multicyclic heterocyclyl, each of which is optionally substituted with one or more substituents selected from amino, halo, hydroxyl, oxo, cyano, $C_1$-$C_6$ alkyl, $C_1$-$C_6$ haloalkyl, $C_1$-$C_6$ hydroxylalkyl, $C_1$-$C_6$ aminoalkyl, $C_1$-$C_6$ alkylaminylalkyl, $C_1$-$C_6$ alkoxy; $C_1$-$C_6$ haloalkoxy $C_1$-$C_6$ alkylcarbonyl, $C_1$-$C_6$ haloalkylcarbonyl, $C_1$-$C_6$ alkylaminyl, $C_1$-$C_6$ haloalkylaminyl, $C_1$-$C_6$ alkylcarbonylaminyl, $C_1$-$C_6$ haloalkylcarbonylaminyl, $C_3$-$C_8$ cycloalkyl, $C_3$-$C_8$ cycloalkylcarbonyl, $C_3$-$C_8$ halocycloalkylaminyl, and $C_3$-$C_8$ cycloalkylcarbonylaminyl;

L is a direct bond or $C(R^aR^b)$, wherein $R^a$ and $R^b$ are each independently hydrogen, $C_1$-$C_6$ alkyl (e.g., methyl), or $R_a$ and $R_b$, together with the carbon to which they are attached can join to form a $C_1$-$C_6$ cycloalkyl (e.g., cyclopropyl, or cyclobutyl);

$R^{1a}$ and $R^{1b}$ are each independently H, halo, cyano, $C_1$-$C_6$ alkyl, $C_1$-$C_6$ haloalkyl, $C_1$-$C_6$ alkoxy or $C_3$-$C_8$ cycloalkyl; and $R^2$ is $C_1$-$C_6$ alkyl, $C_3$-$C_8$ cycloalkyl, 3-8-membered heterocyclyl, 6-10-membered spirocyclic heterocyclyl, 6-10-membered fused-multicyclic heterocyclyl or 6-10-membered bridged-multicyclic heterocyclyl, each of which is optionally substituted with one or more substituents selected from halo, cyano, $C_1$-$C_6$ alkyl, and $C_1$-$C_6$ haloalkyl.

One embodiment provides a compound having the following Structure (I):

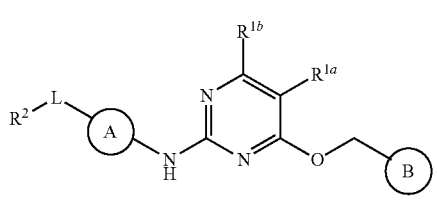

(I)

L is a direct bond or C($R^a R^b$), wherein $R^a$ and $R^b$ are each independently hydrogen, $C_1$-$C_6$ alkyl (e.g., methyl), or $R_a$ and $R_b$, together with the carbon to which they are attached can join to form a $C_3$-$C_8$ cycloalkyl (e.g., cyclopropyl, or cyclobutyl);

$R^{1a}$ and $R^{1b}$ are each independently H, halo, cyano, $C_1$-$C_6$ alkyl, $C_1$-$C_6$ haloalkyl, $C_1$-$C_6$ alkoxy or $C_3$-$C_8$ cycloalkyl; and $R^2$ is $C_1$-$C_6$ alkyl, $C_3$-$C_8$ cycloalkyl, 3-8-membered heterocyclyl, 6-10-membered spirocyclic heterocyclyl, 6-10-membered fused-multicyclic heterocyclyl or 6-10-membered bridged-multicyclic heterocyclyl, each of which is optionally substituted with one or more substituents selected from halo, cyano, $C_1$-$C_6$ alkyl, hydroxyl, alkoxy, and $C_1$-$C_6$ haloalkyl.

In certain embodiments, A is phenylene. In some more specific embodiments, A is substituted phenylene. In certain more specific embodiments, A is phenylene substituted with one or more substituents selected from the group consisting of halo, $C_1$-$C_6$ alkoxy, and combinations thereof. In some embodiments, A is phenylene substituted with one or more substituents selected from the group consisting of halo and $C_1$-$C_6$ alkoxy. In some embodiments, A is unsubstituted phenylene.

In other embodiments, A is a 5 or 6-membered heteroarylene. In more specific embodiments, A is a pyridinylene or pyrazolylene. In certain embodiments, A is substituted with one or more substituents selected from halo, $C_1$-$C_6$ alkyl, and $C_1$-$C_6$ alkoxy. In some embodiments, A is monocyclic. In some embodiments, A is substituted with one or more substituents selected from halo, $C_1$-$C_6$ alkyl, $C_3$-$C_8$ cycloalkyl, and $C_1$-$C_6$ alkoxy.

In some embodiments, B is a $C_3$-$C_8$ monocyclic cycloalkyl. In some embodiments, B is 3-8-membered monocyclic heterocyclyl. In some embodiments, B is 3-8-membered spirocyclic heterocyclyl. In some embodiments, B is a $C_3$-$C_8$ fused-multicyclic cycloalkyl. In certain specific embodiments, B is 3-8-membered monocyclic heterocyclylalkyl. In some embodiments, B is $C_6$-$C_{10}$ spirocyclic cyclocalkyl.

In more embodiments, B is substituted. In more specific embodiments, B is substituted with one or more substituents selected from the group consisting of amino, halo, hydroxyl, oxo, cyano, $C_1$-$C_6$ alkyl, $C_1$-$C_6$ haloalkyl, $C_1$-$C_6$ hydroxylalkyl, $C_1$-$C_6$ aminoalkyl, $C_1$-$C_6$ alkylaminylalkyl, $C_1$-$C_6$ alkoxy, $C_1$-$C_6$ haloalkylcarbonyl, $C_1$-$C_6$ alkylaminyl, $C_1$-$C_6$ haloalkylaminyl, $C_1$-$C_6$ alkylcarbonylaminyl, $C_1$-$C_6$ haloalkylcarbonylaminyl, $C_3$-$C_8$ cycloalkylcarbonylaminyl, $C_3$-$C_8$ halocycloalkylaminyl, and combinations thereof. In some specific embodiments, B is unsubstituted.

In more embodiments, B is substituted. In more specific embodiments, B is substituted with one or more substituents selected from the group consisting of amino, halo, hydroxyl, oxo, cyano, $C_1$-$C_6$ alkyl, $C_1$-$C_6$ haloalkyl, $C_1$-$C_6$ hydroxylalkyl, $C_1$-$C_6$ aminoalkyl, $C_1$-$C_6$ alkylaminylalkyl, $C_1$-$C_6$ alkoxy, $C_1$-$C_6$ haloalkylcarbonyl, $C_1$-$C_6$ alkylaminyl, $C_1$-$C_6$ haloalkylaminyl, $C_1$-$C_6$ alkylcarbonylaminyl, $C_1$-$C_6$ haloalkylcarbonylaminyl, $C_3$-$C_8$ cycloalkylcarbonylaminyl, and $C_3$-$C_8$ halocycloalkylaminyl.

In some more specific embodiments, B has one of the following structures:

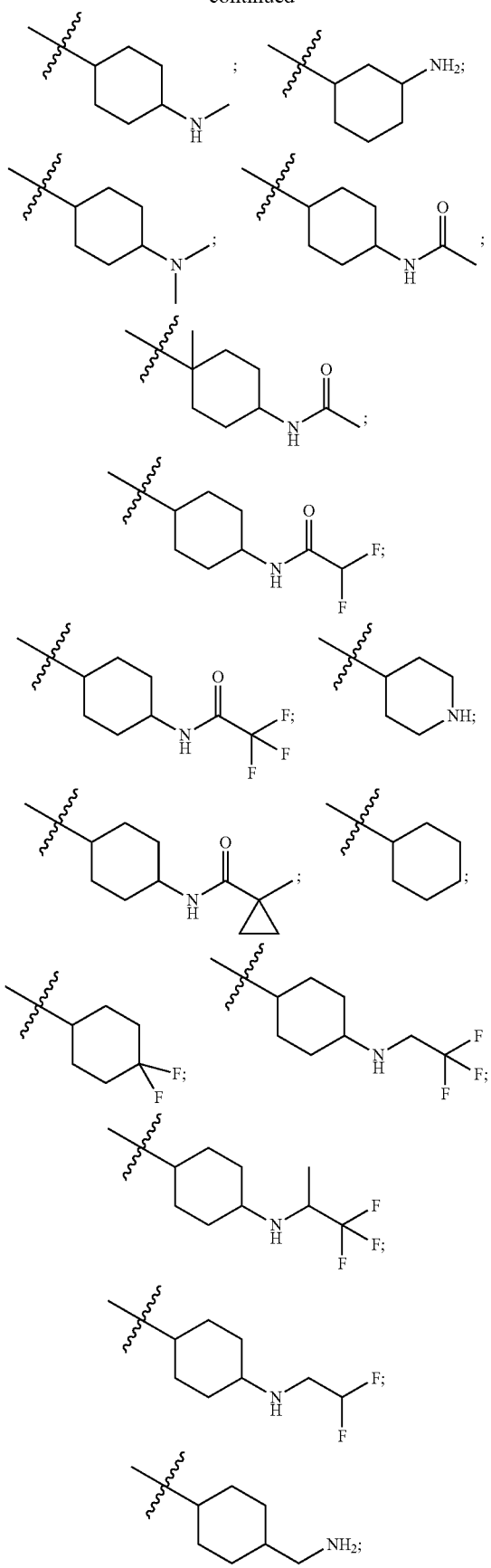

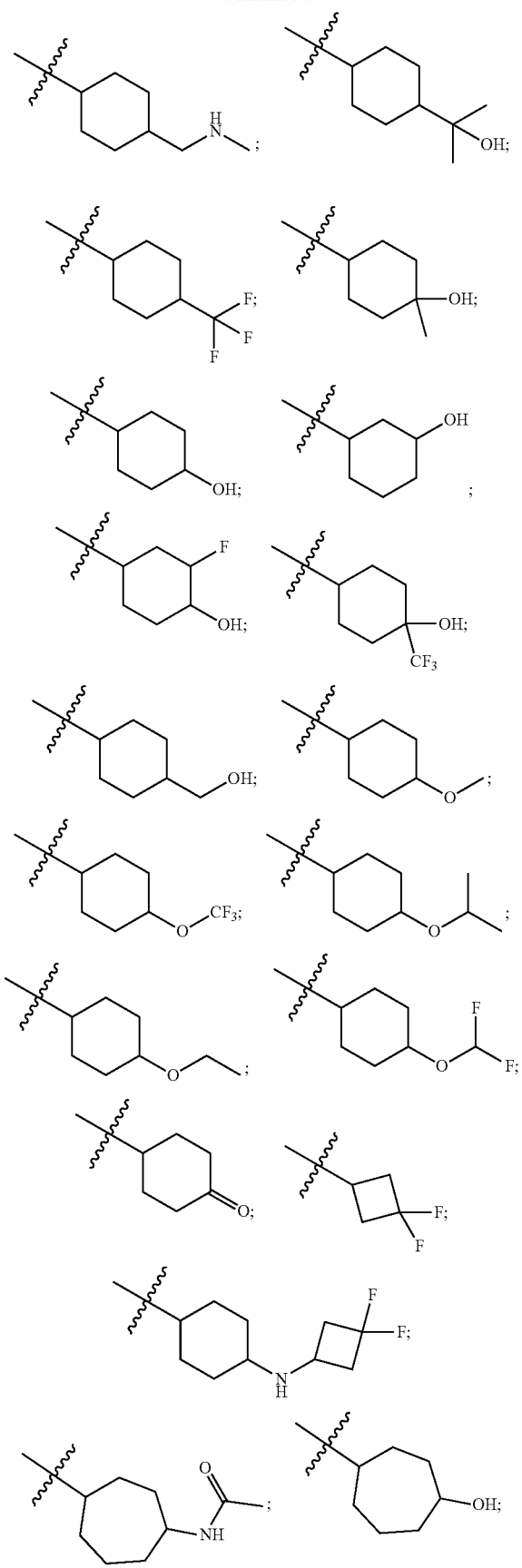
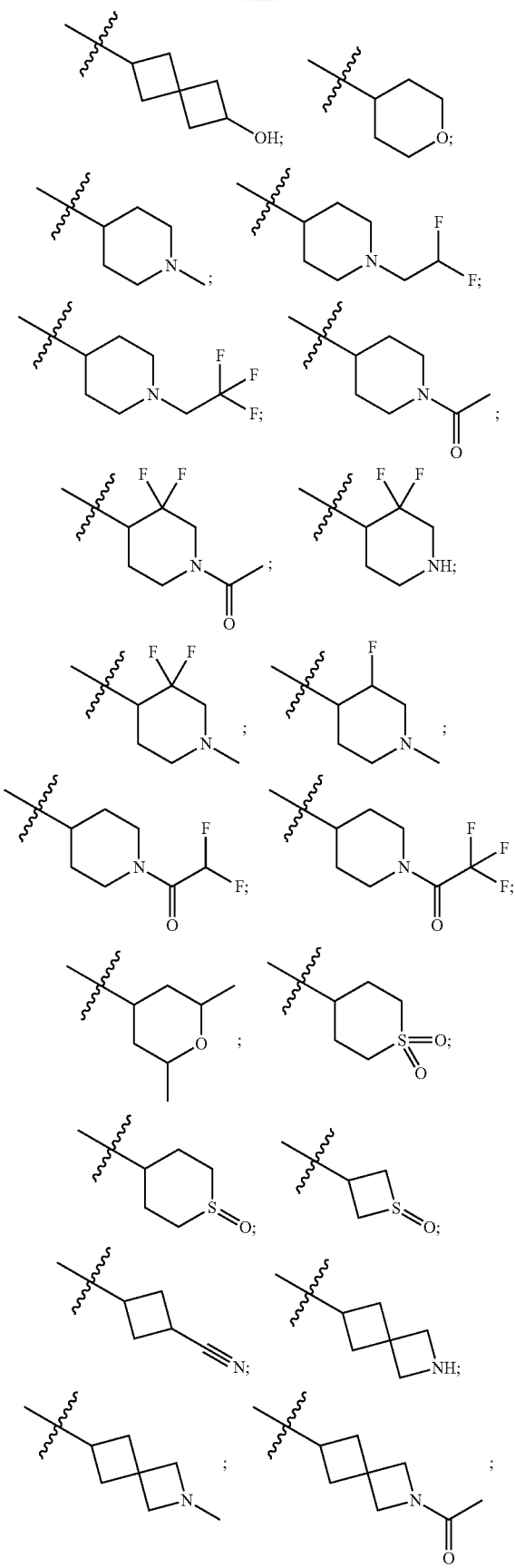

-continued
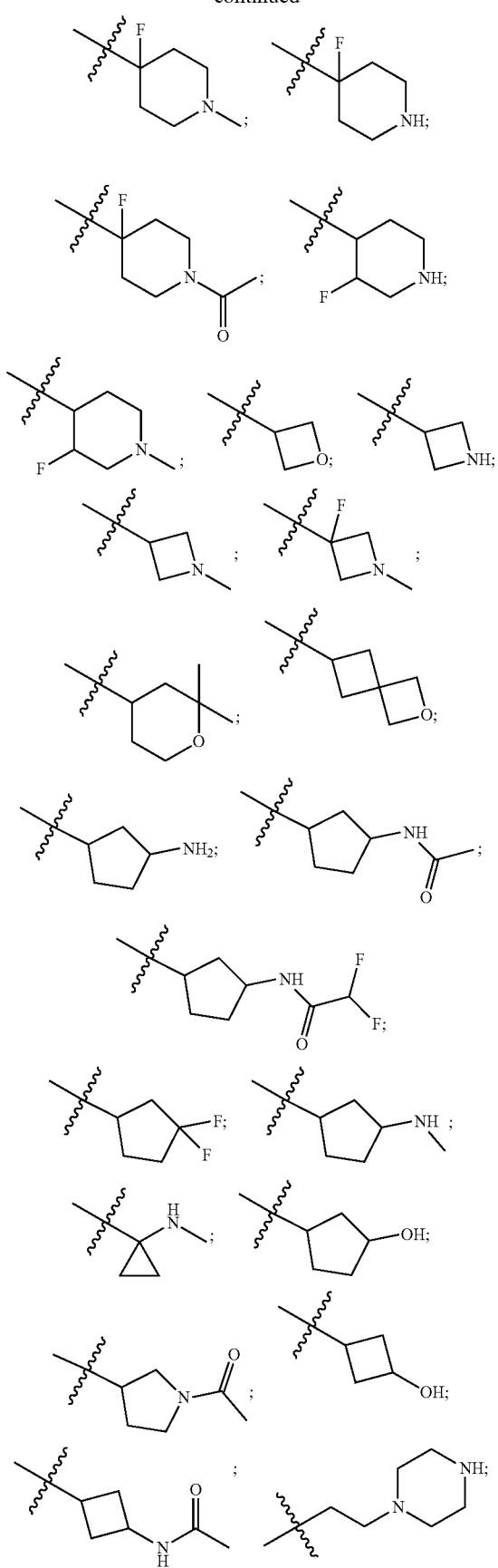
-continued
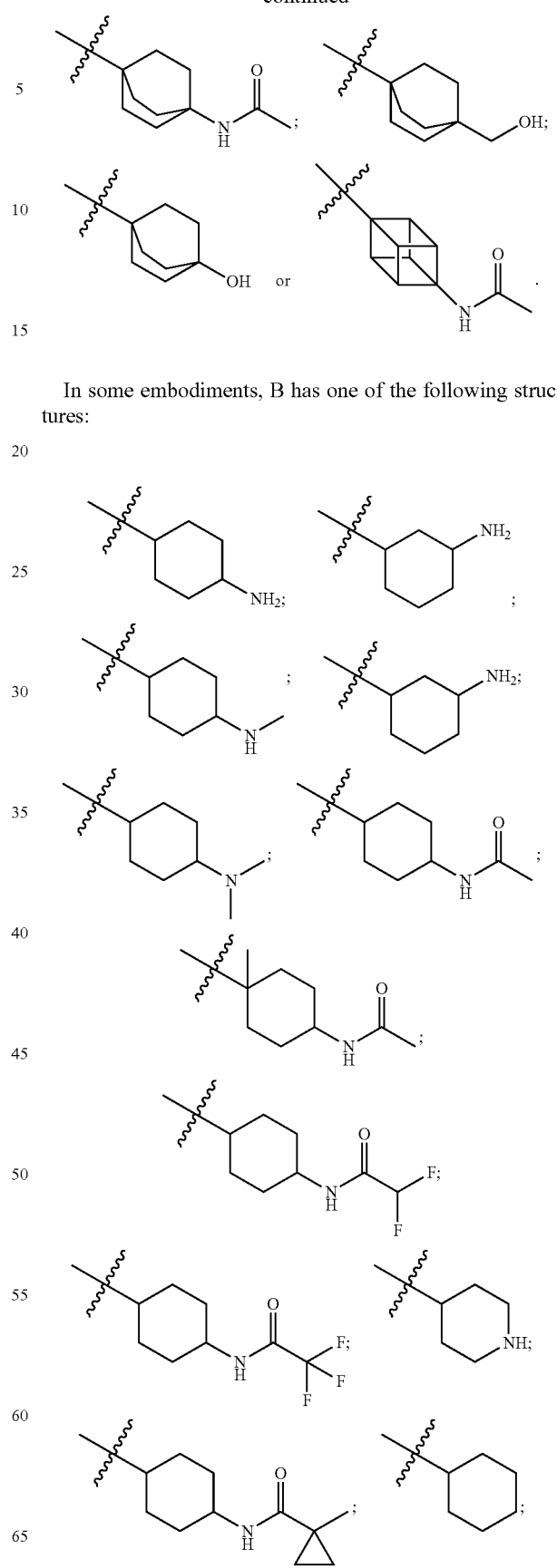
In some embodiments, B has one of the following structures:

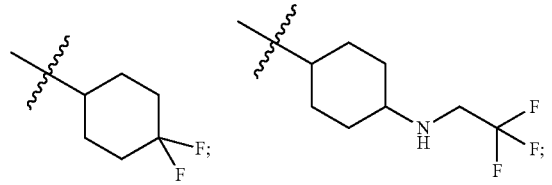
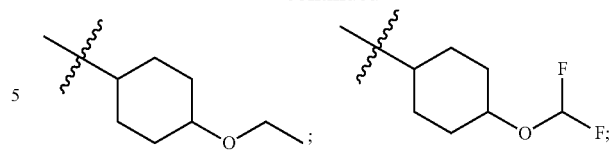

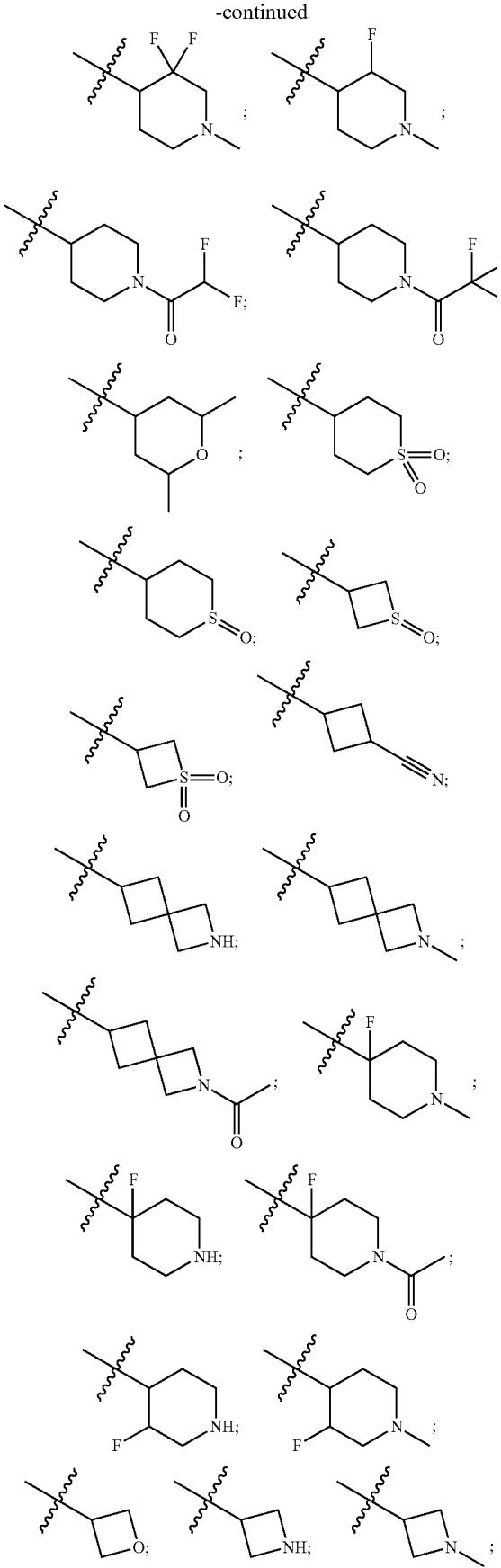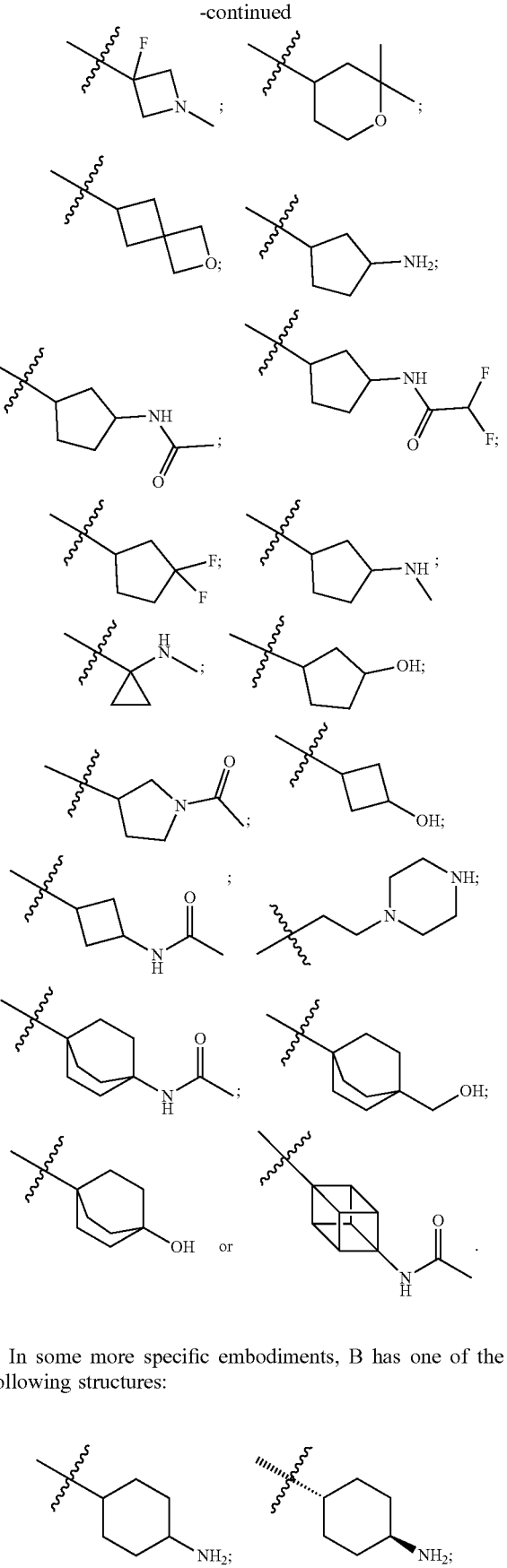
In some more specific embodiments, B has one of the following structures:
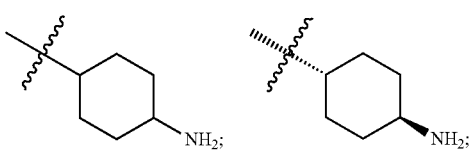

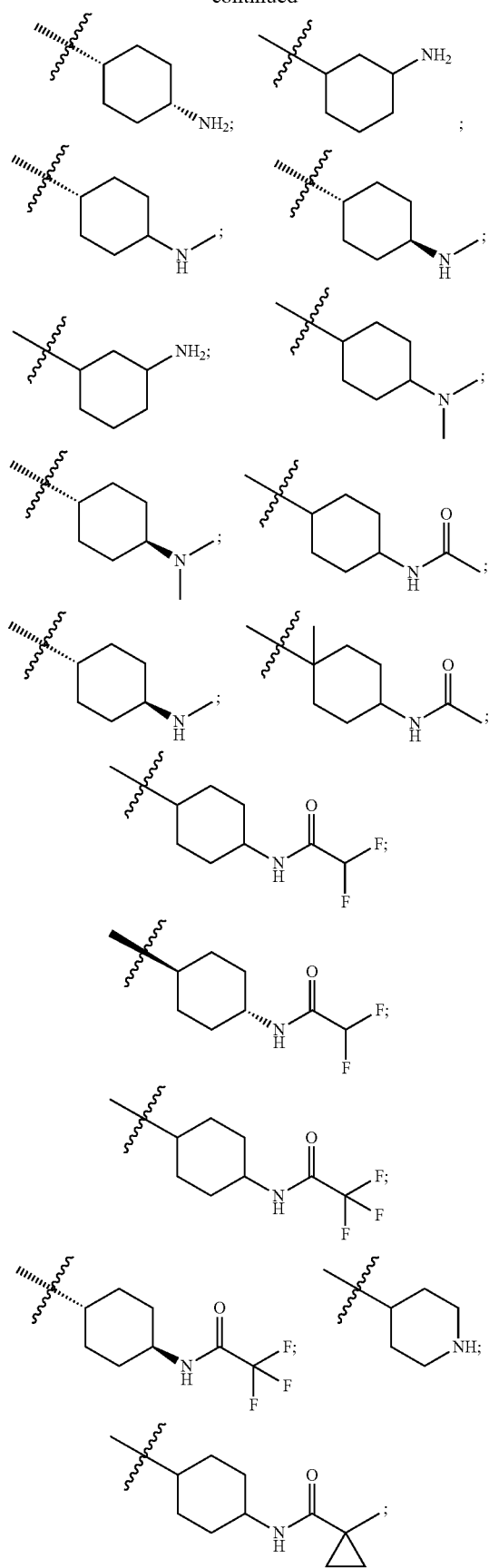
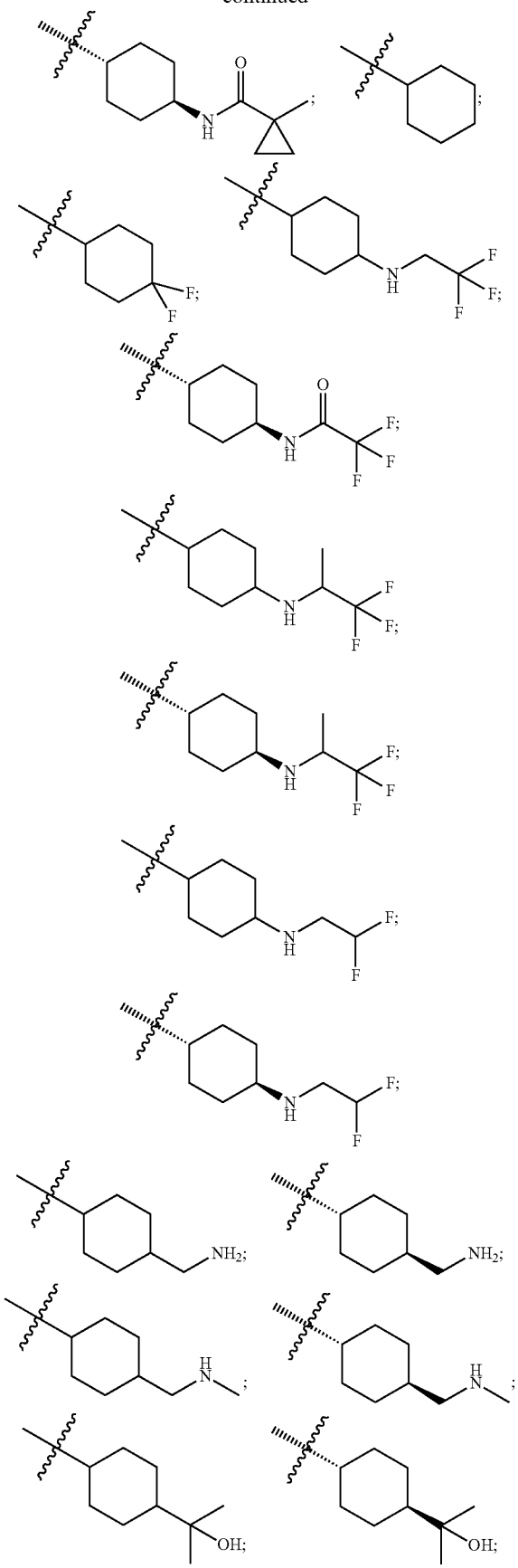

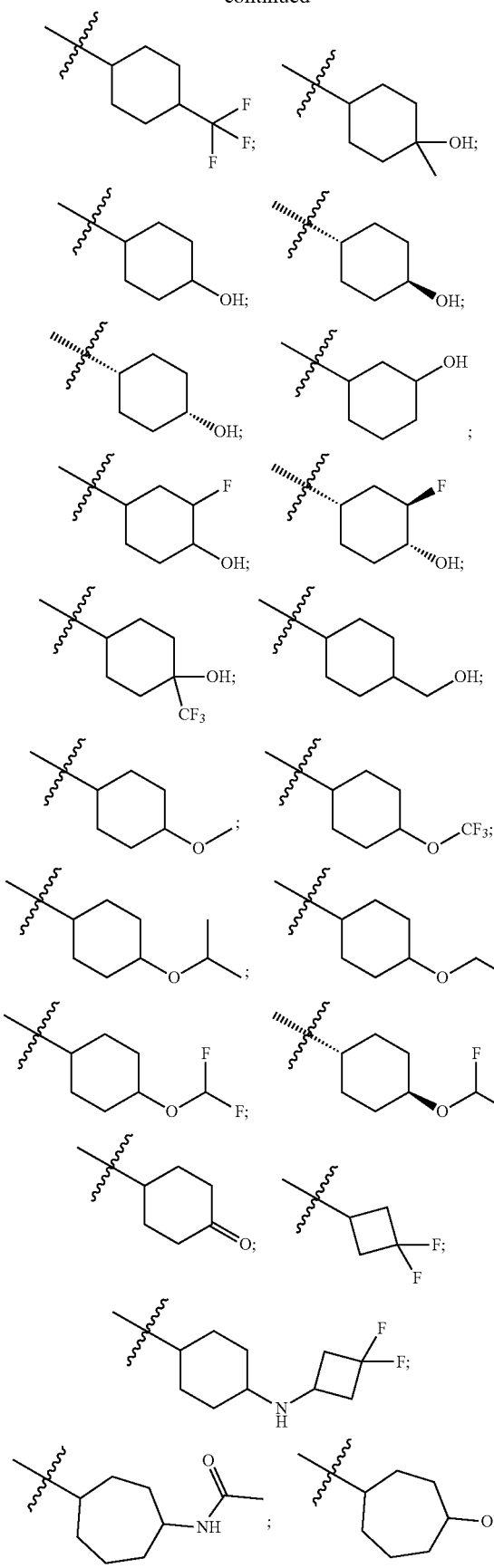
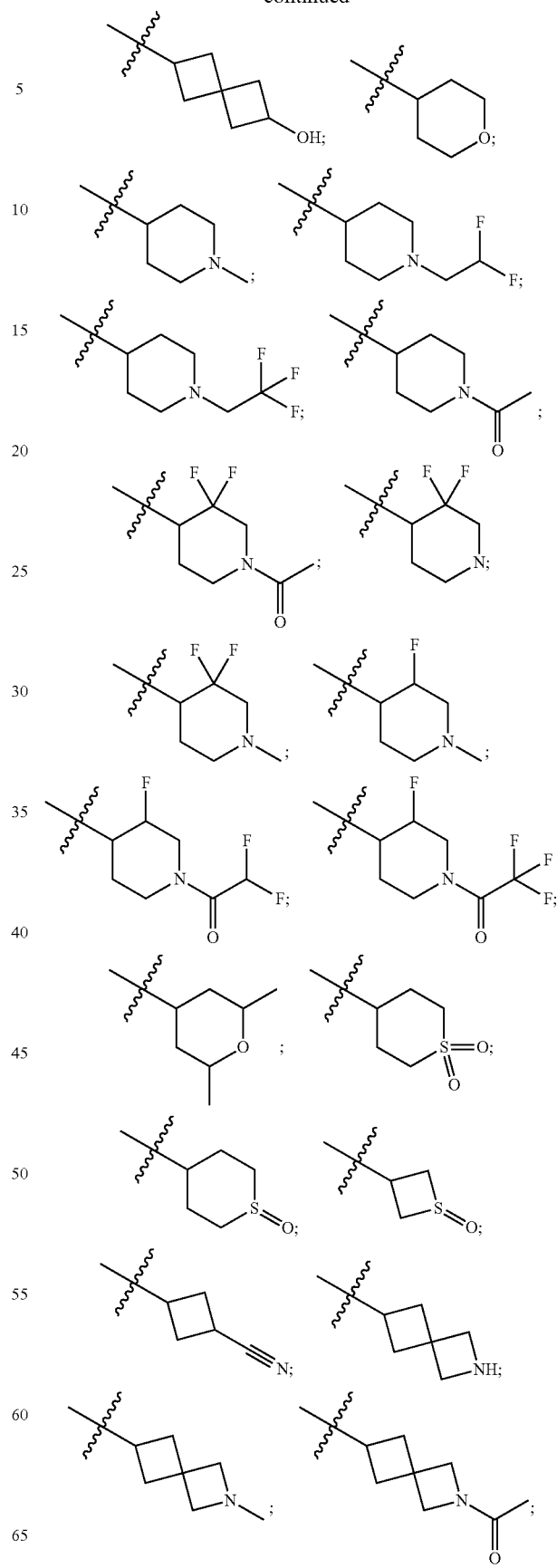

-continued
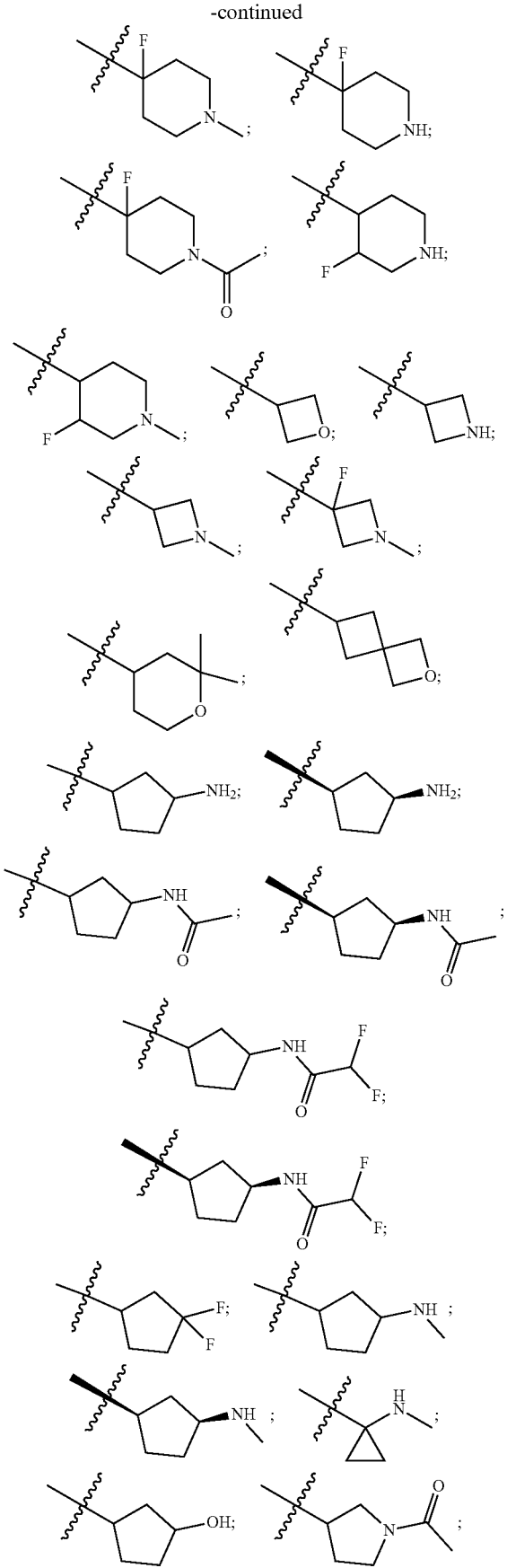
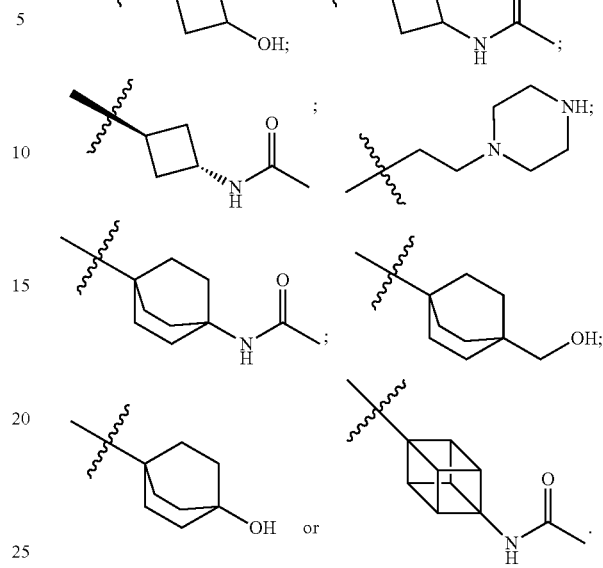
In some embodiments, B has one of the following structures:
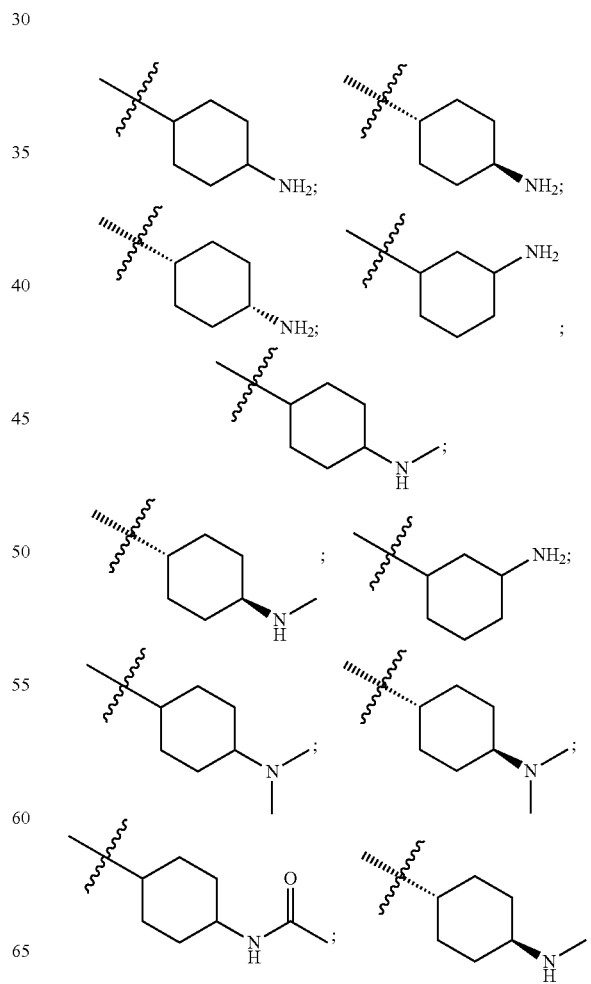

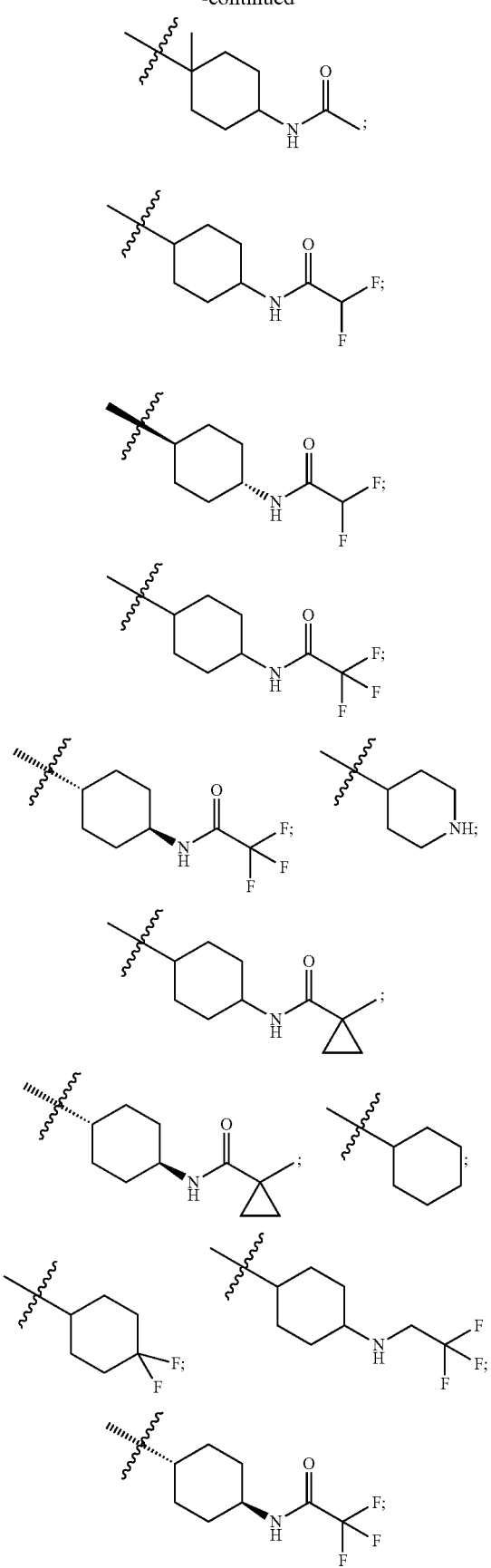
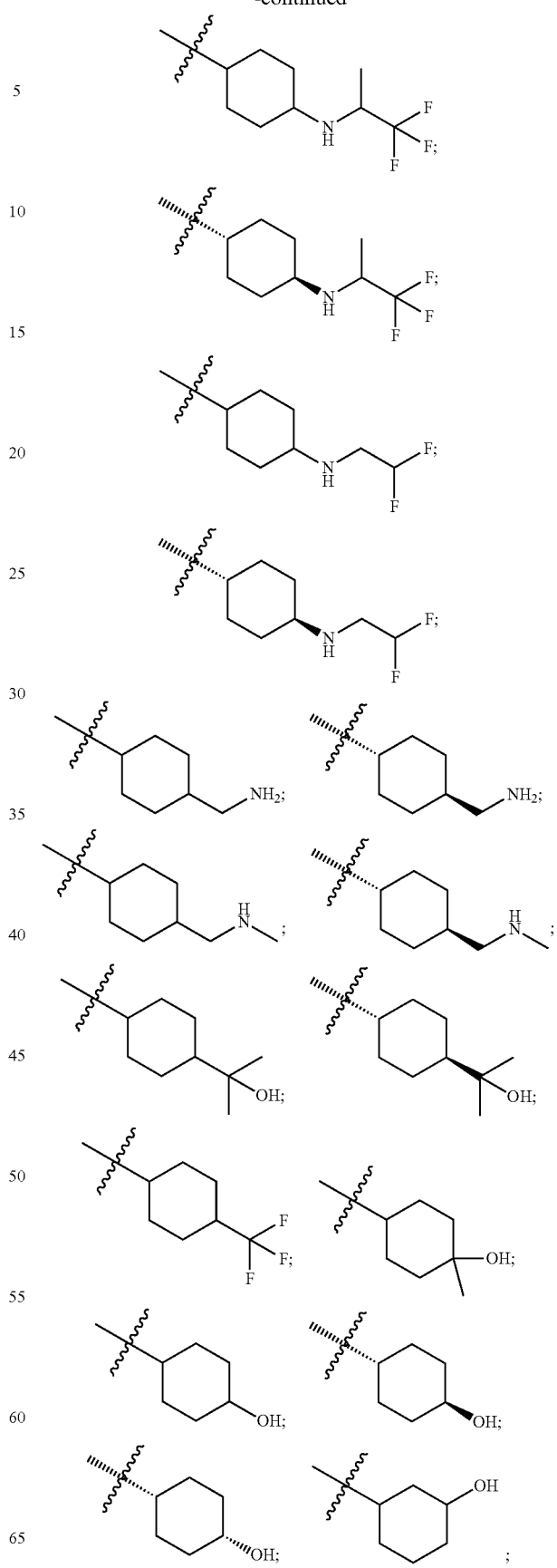

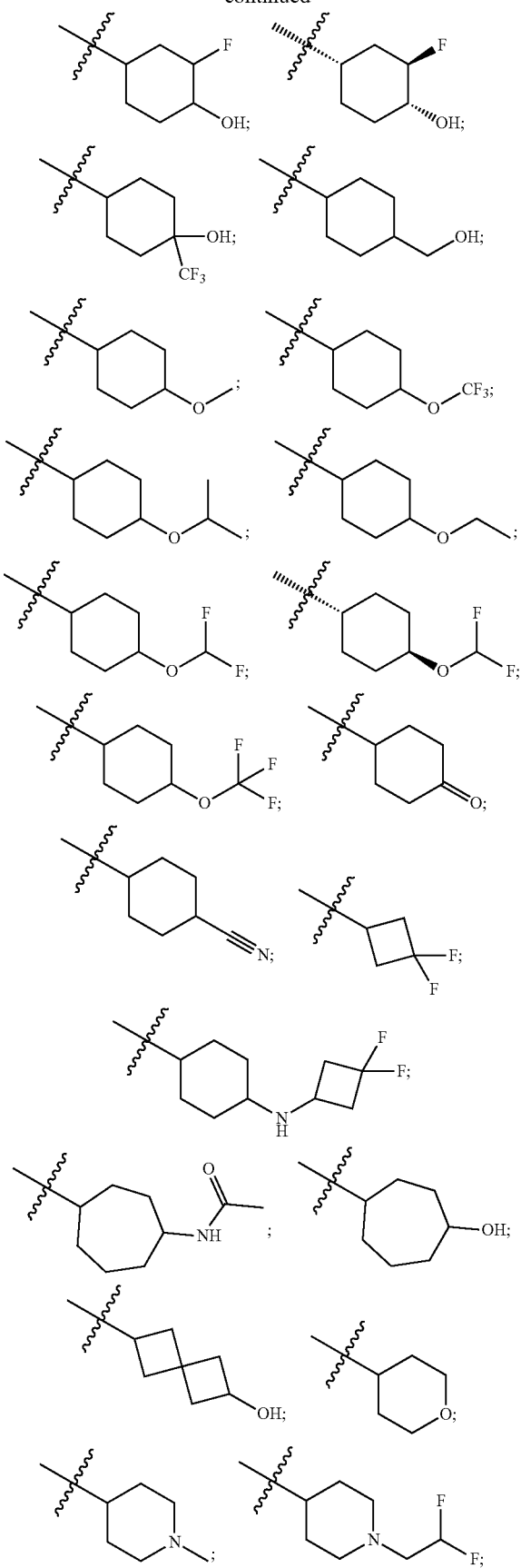
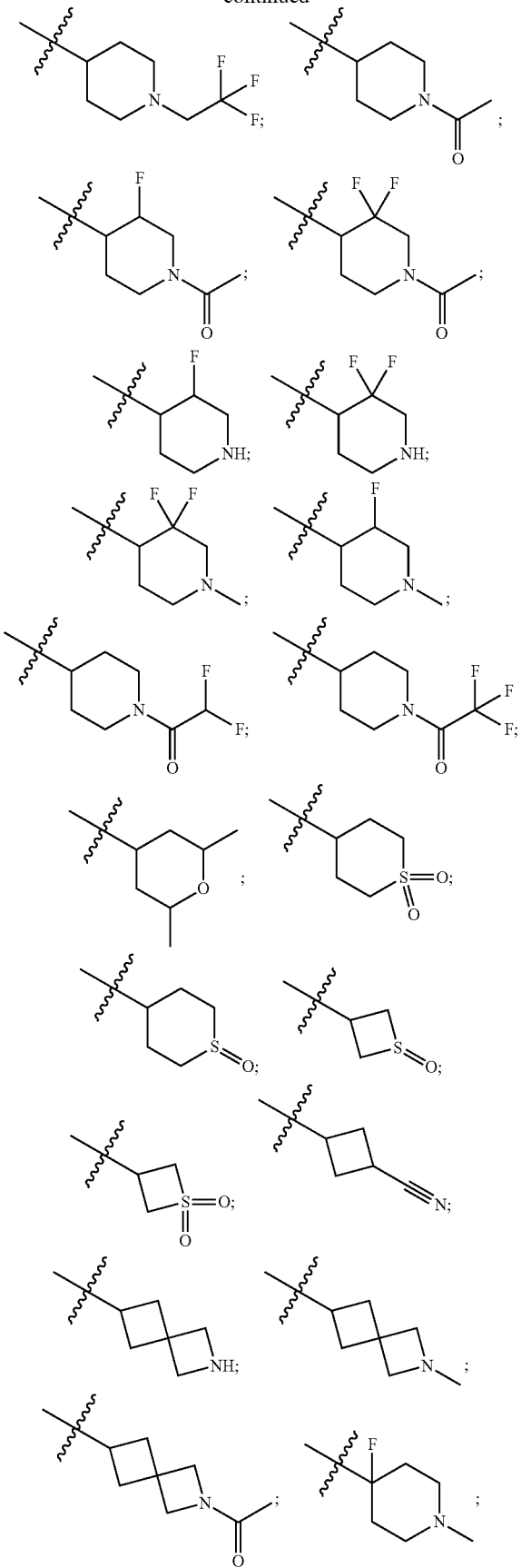

-continued

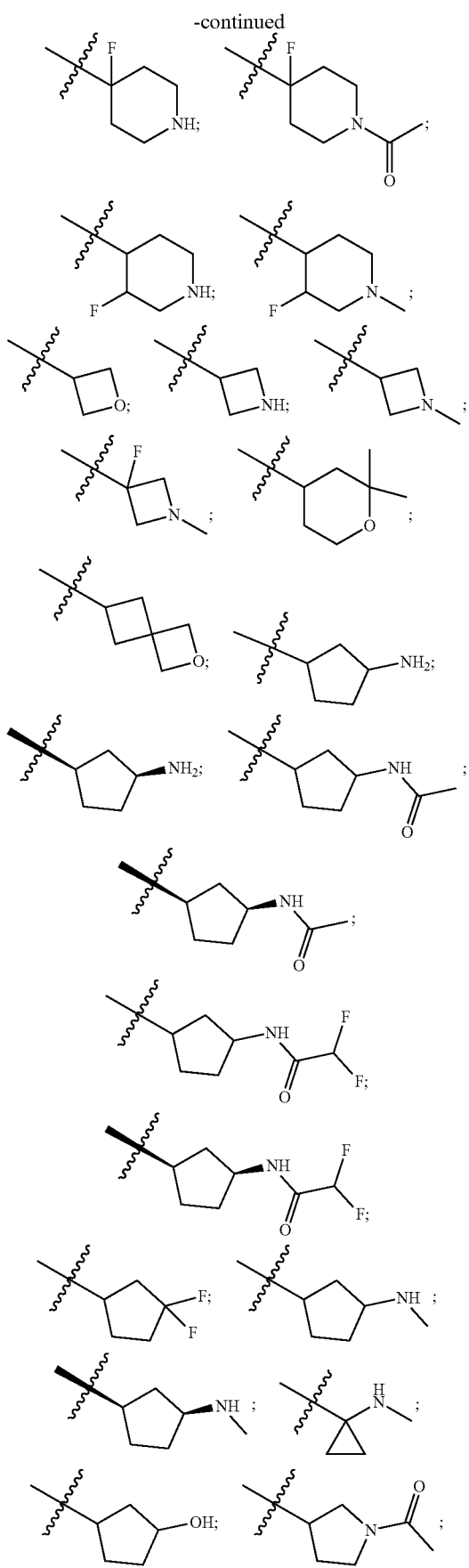

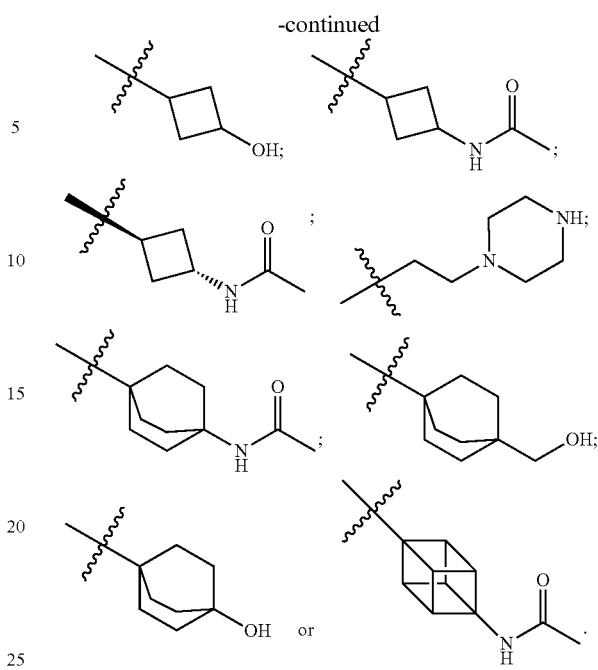

In some embodiments, L is a direct bond. In certain other embodiments, L is $CH_2$. In some other embodiments, L is C=O.

In some embodiments, $R^{1a}$ or $R^{1b}$, or both, are selected from the group consisting of H, methyl, fluoro, chloro, cyano, methoxy, trifluoromethyl, and cyclopropyl. In certain embodiments, $R^{1b}$ is H and $R_a$ is fluoro or chloro. In some specific embodiments, $R^{1b}$ is H and $R^{1a}$ is cyclopropyl. In certain specific embodiments, $R^{1b}$ is H and $R^{1a}$ is methyl. In some more specific embodiments, $R^{1b}$ is H and $R^{1a}$ is cyano. In certain more specific embodiments, $R^{1b}$ is H and $R^{1a}$ is H. In some specific embodiments, $R^{1b}$ is H and $R^{1a}$ is methoxy. In certain embodiments, $R^{1b}$ is H and $R^{1a}$ is trifluoromethyl. In some embodiments, $R^{1b}$ is methyl and $R^{1a}$ is fluoro or chloro. In certain embodiments, $R^{1b}$ is chloro or fluoro and $R^{1a}$ is fluoro or chloro.

In some embodiments, $R^2$ is $C_1$-$C_6$ alkyl. In certain embodiments, $R^2$ is $C_3$-$C_8$ cycloalkyl. In some specific embodiments, $R^2$ is a 3-8-membered heterocyclyl. In some embodiments, $R^2$ is a 6-10-membered spirocyclic heterocyclyl. In certain more specific embodiments, $R^2$ is a 6-10-membered fused-multicyclic heterocyclyl. In some specific embodiments, $R^2$ is a 6-10-membered bridged-multicyclic heterocyclyl.

In certain specific embodiments, $R^2$ is substituted. In some more specific embodiments, $R^2$ is substituted with one or more substituents selected from the group consisting of methyl, ethyl, iso-propyl, fluoro, trifluoromethyl, and cyano. In certain more specific embodiments, $R^2$ is unsubstituted.

In some embodiments,

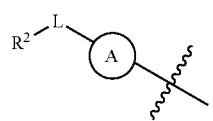

has one of the following structures:
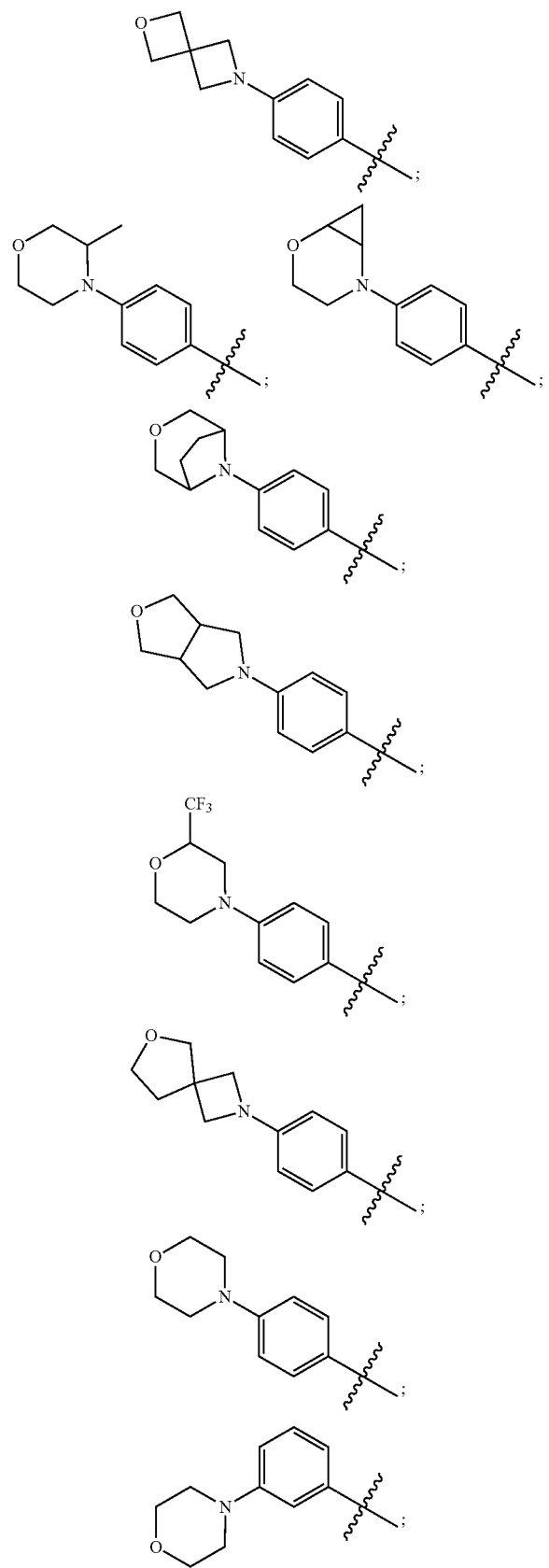
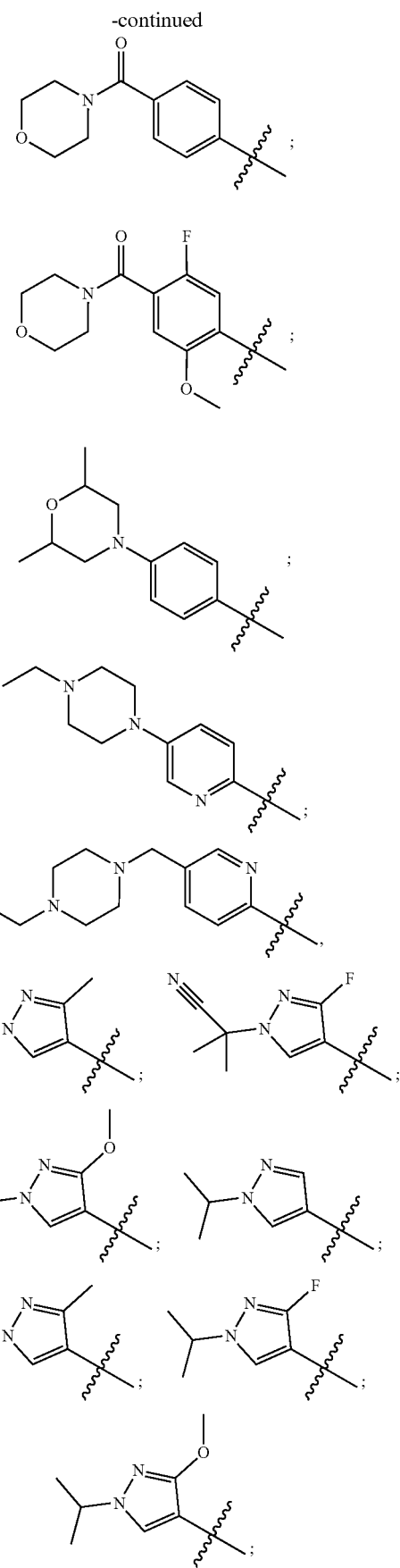

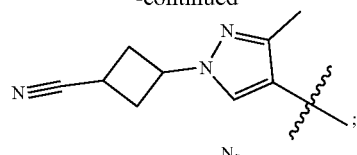;
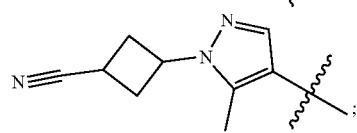;
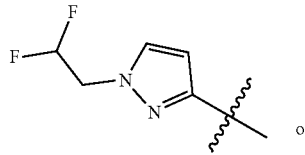 or
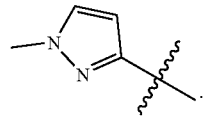.
In some embodiments,
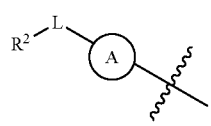
has one of the following structures:
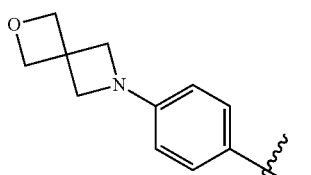;
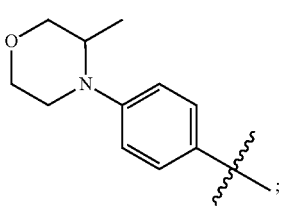; 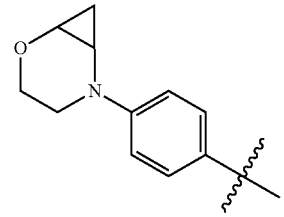;
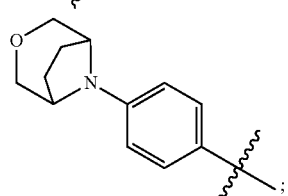;
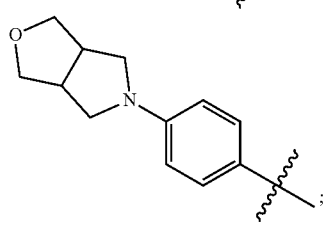;
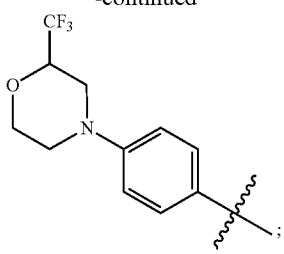;
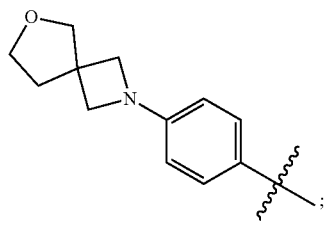;
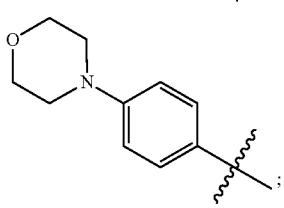;
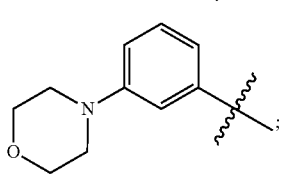;
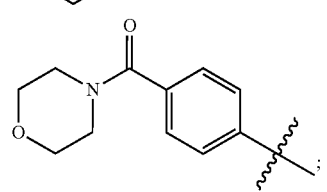;
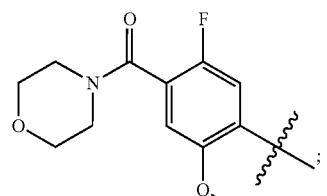;
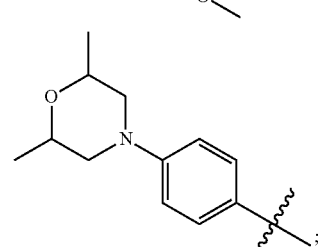;
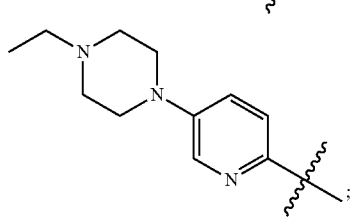;

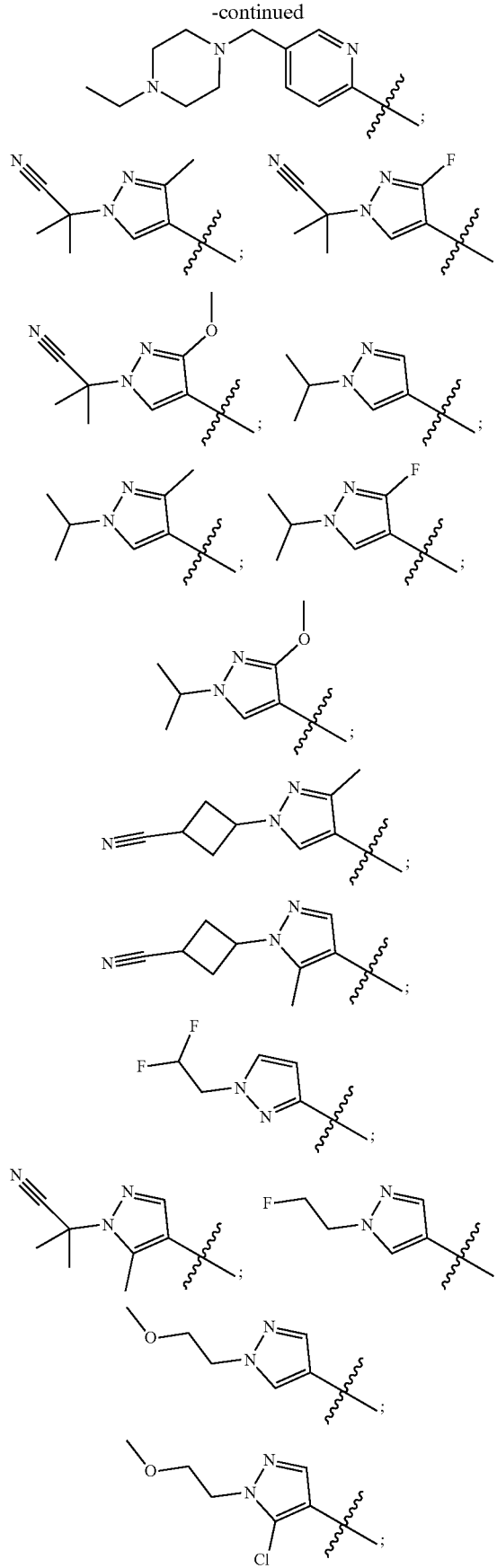
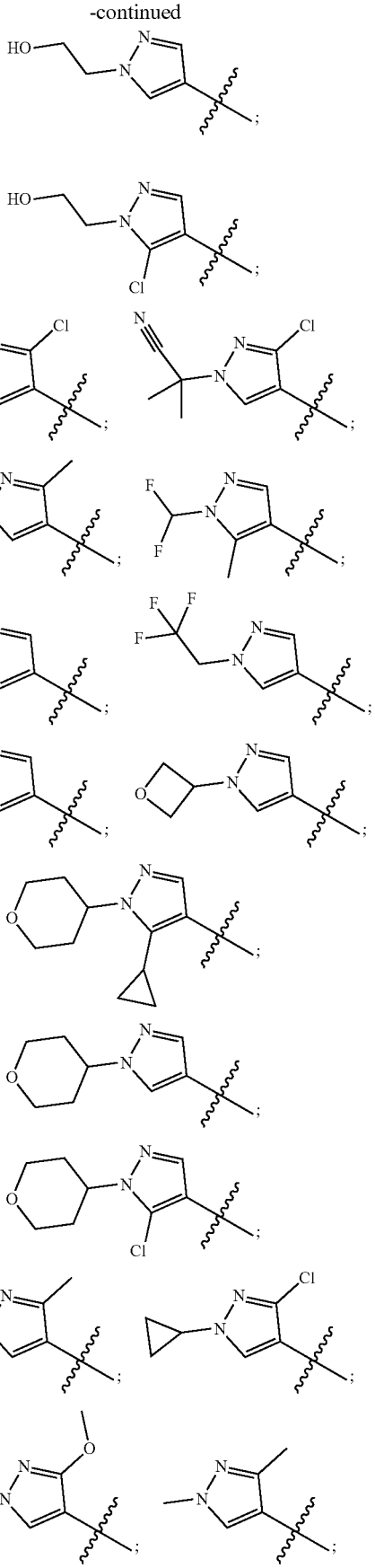

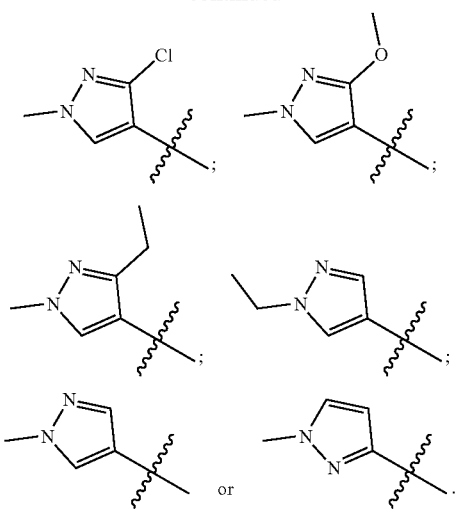
In certain embodiments,
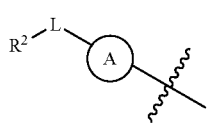
has one of the following structures:
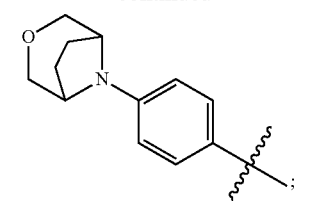
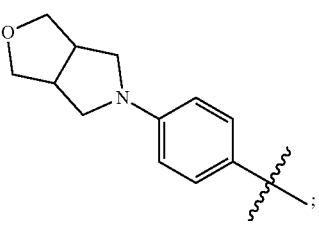
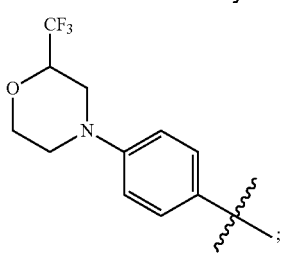
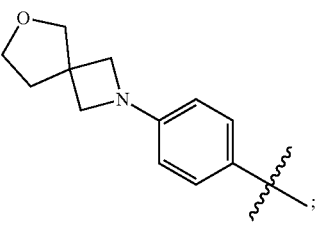
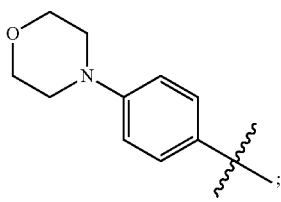
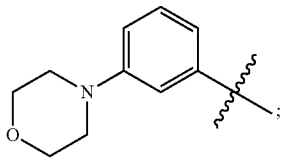
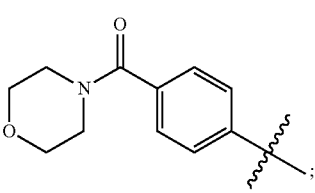
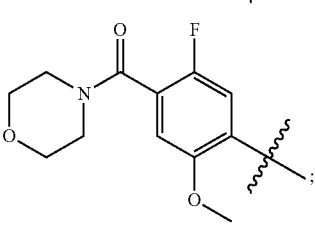

-continued
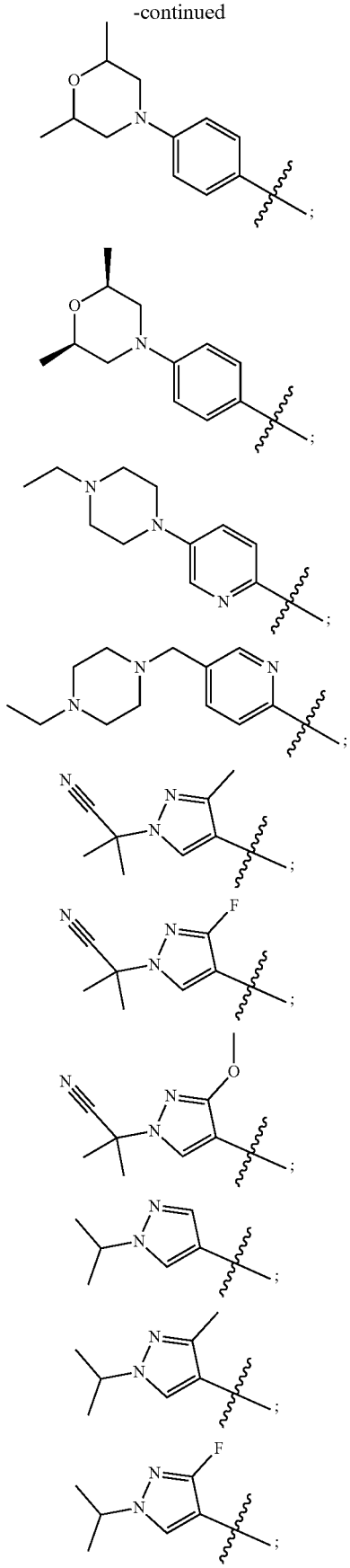
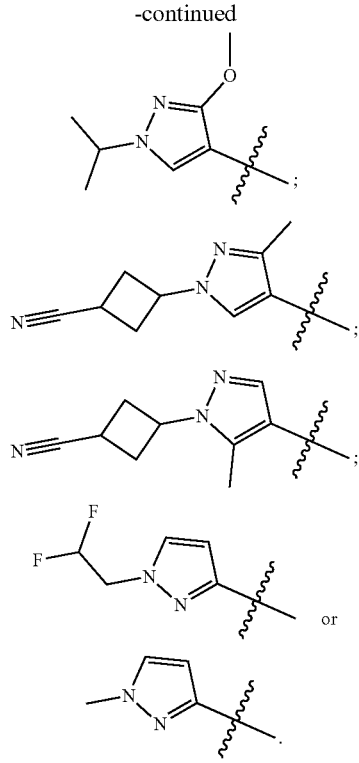
In certain embodiments
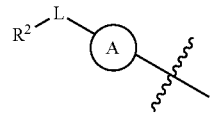
has one of the following structures:
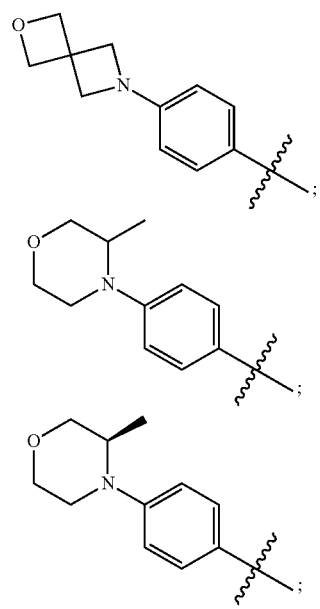

-continued
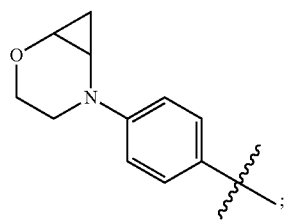
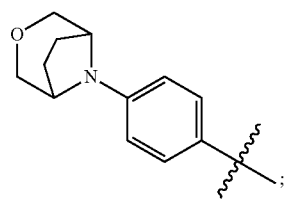
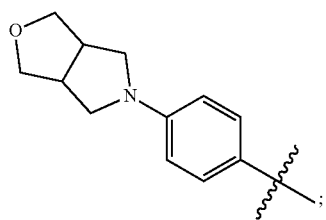
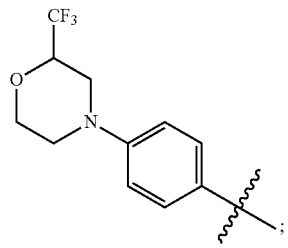
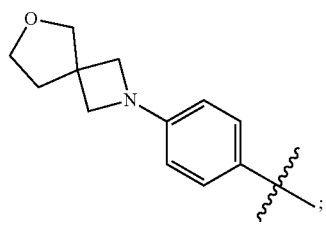
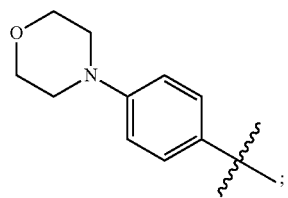
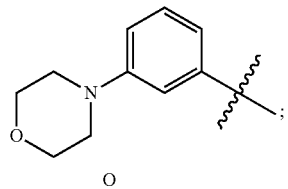
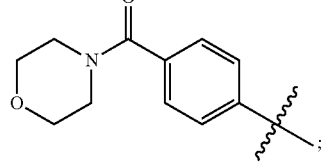
-continued
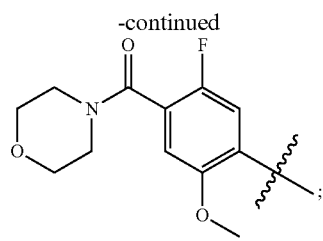
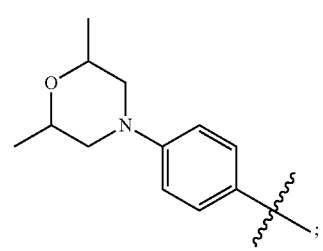
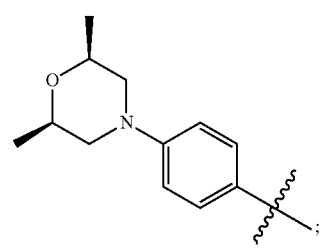
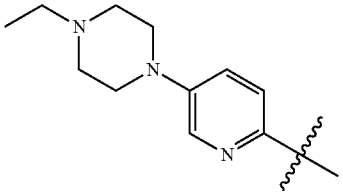
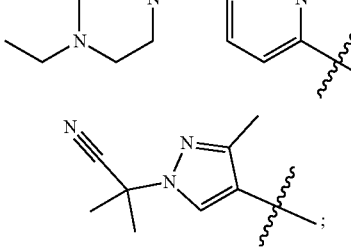
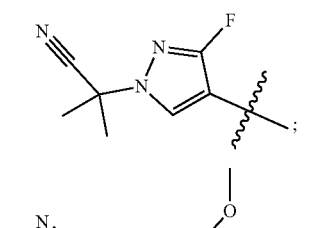
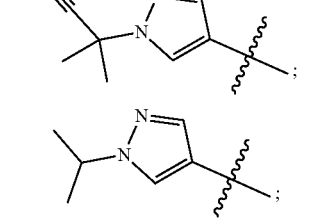

-continued
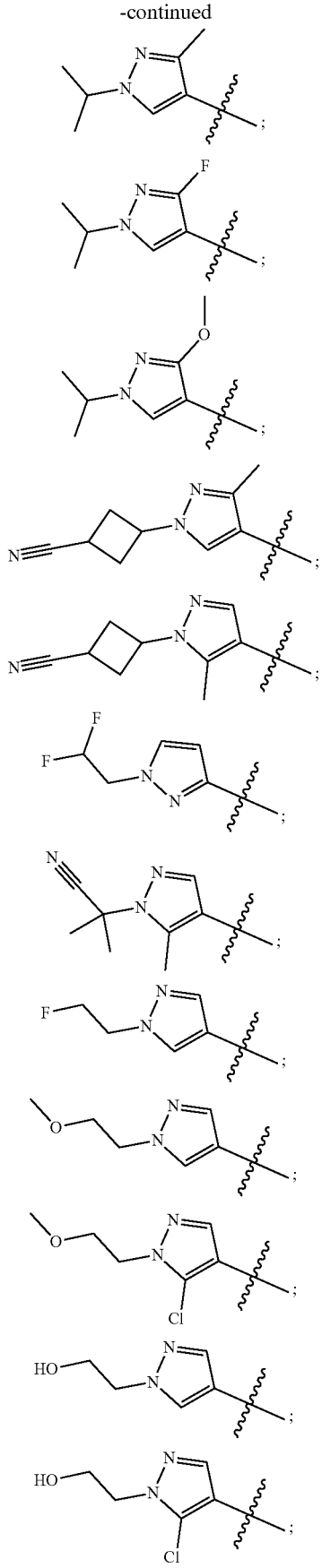
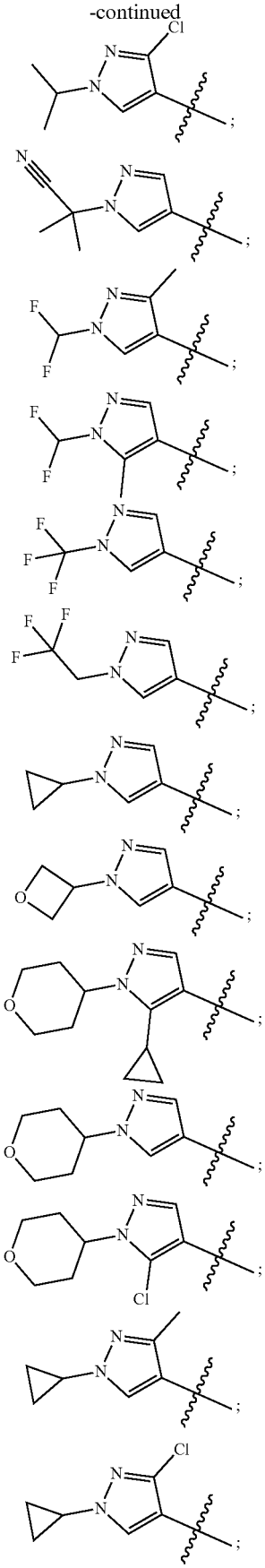

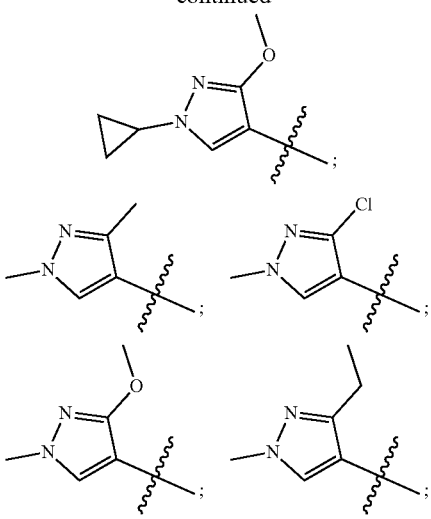

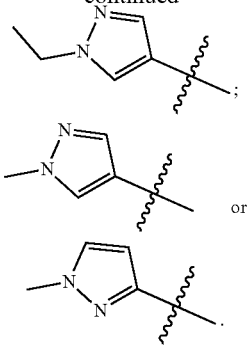

In various different embodiments, the compound has one of the structures set forth in Table 1 below, or a pharmaceutically acceptable salt, stereoisomer, or prodrug thereof. Compounds in Table 1 were prepared as described in the Examples or methods known in the art and analyzed by mass spectrometry and/or 1H NMR spectroscopy.

TABLE 1

Representative Compounds of Structure (I)

| Example | Structure | Name |
|---|---|---|
| 1 | 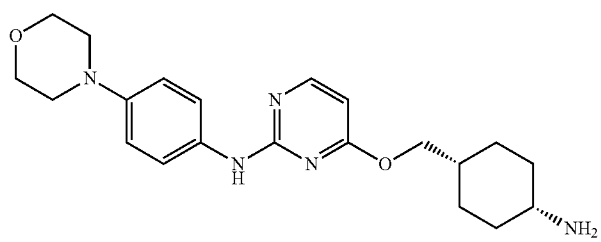 | 4-(((1S,4S)-4-aminocyclohexyl)methoxy)-N-(4-morpholinophenyl)pyrimidin-2-amine |
| 2 | 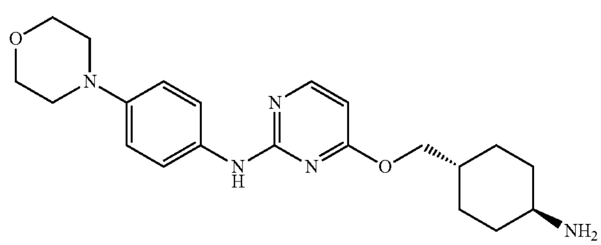 [SMILES: N[C@H]1CC[C@H](COc2ccnc(Nc3ccc(N4CCOCC4)cc3)n2)CC1] | 4-(((1R,4R)-4-aminocyclohexyl)methoxy)-N-(4-morpholinophenyl)pyrimidin-2-amine |
| 3 | 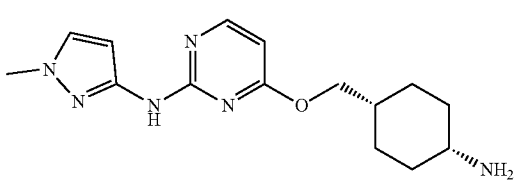 [SMILES: Cn1ccc(Nc2nccc(OC[C@H]3CC[C@@H](N)CC3)n2)n1] | 4-(((1S,4S)-4-aminocyclohexyl)methoxy)-N-(1-methyl-1H-pyrazol-3-yl)pyrimidin-2-amine |
| 4 | 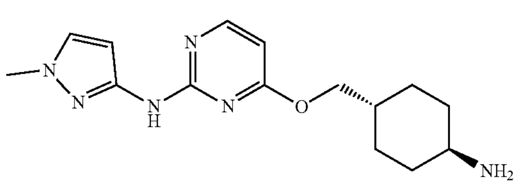 [SMILES: Cn1ccc(Nc2nccc(OC[C@H]3CC[C@H](N)CC3)n2)n1] | 4-(((1R,4R)-4-aminocyclohexyl)methoxy)-N-(1-methyl-1H-pyrazol-3-yl)pyrimidin-2-amine |

TABLE 1-continued

Representative Compounds of Structure (I)

| Example | Structure | Name |
|---|---|---|
| 5 | 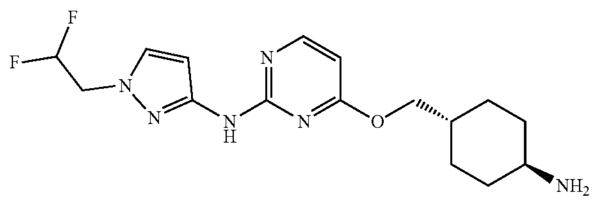 [SMILES: N[C@H]1CC[C@H](COc2ccnc(Nc3ccn(CC(F)F)n3)n2)CC1] | 4-(((1R,4R)-4-aminocyclohexyl)methoxy)-N-(1-(2,2-difluoroethyl)-1H-pyrazol-3-yl)pyrimidin-2-amine |
| 6 | 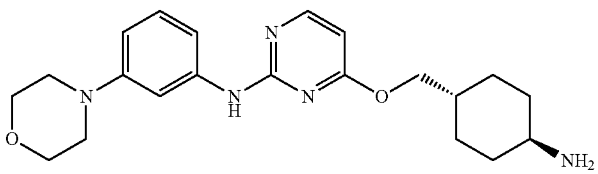 [SMILES: N[C@H]1CC[C@H](COc2ccnc(Nc3cccc(N4CCOCC4)c3)n2)CC1] | 4-(((1R,4R)-4-aminocyclohexyl)methoxy)-N-(3-morpholinophenyl)pyrimidin-2-amine |
| 7 | 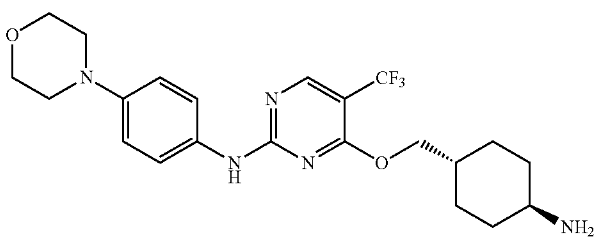 | 4-(((1R,4R)-4-aminocyclohexyl)methoxy)-N-(4-morpholinophenyl)-5-(trifluoromethyl)pyrimidin-2-amine |
| 8 | 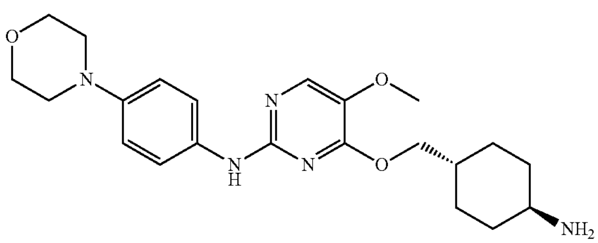 [SMILES: COc1cnc(Nc2ccc(N3CCOCC3)cc2)nc1OC[C@H]1CC[C@H](N)CC1] | 4-(((1R,4R)-4-aminocyclohexyl)methoxy)-5-methoxy-N-(4-morpholinophenyl)pyrimidin-2-amine |
| 9 | 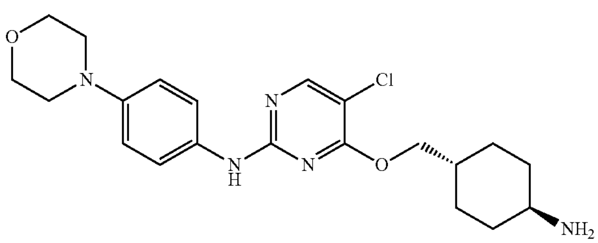 | 4-(((1R,4R)-4-aminocyclohexyl)methoxy)-5-chloro-N-(4-morpholinophenyl)pyrimidin-2-amine |
| 10 | 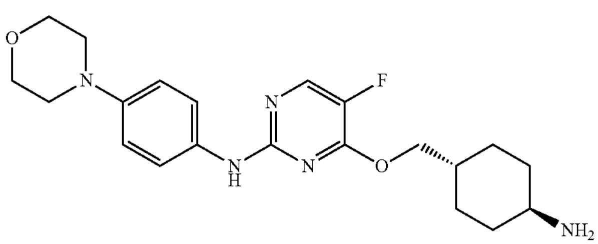 [SMILES: N[C@H]1CC[C@H](COc2nc(Nc3ccc(N4CCOCC4)cc3)ncc2F)CC1] | 4-(((1R,4R)-4-aminocyclohexyl)methoxy)-5-fluoro-N-(4-morpholinophenyl)pyrimidin-2-amine |

TABLE 1-continued

Representative Compounds of Structure (I)

| Example | Structure | Name |
|---|---|---|
| 11 | 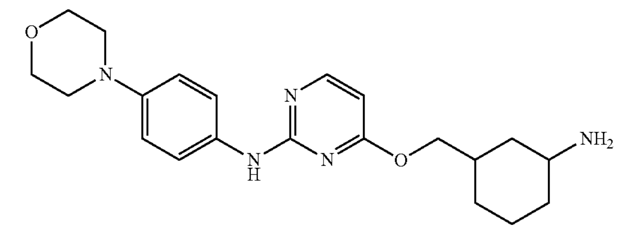 [SMILES: NC1CCCC(COc2ccnc(Nc3ccc(N4CCOCC4)cc3)n2)C1] | 4-((3-aminocyclohexyl)methoxy)-N-(4-morpholinophenyl)pyrimidin-2-amine |
| 12 | 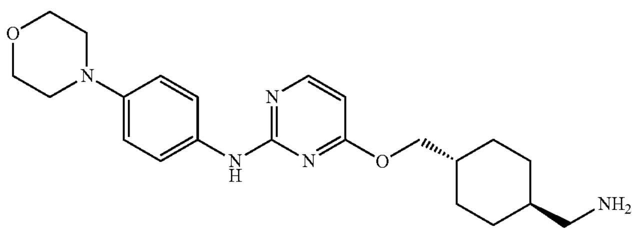 [SMILES: NC[C@H]1CC[C@H](COc2ccnc(Nc3ccc(N4CCOCC4)cc3)n2)CC1] | 4-(((1R,4R)-4-(aminomethyl)cyclohexyl)methoxy)-N-(4-morpholinophenyl)pyrimidin-2-amine |
| 13 | 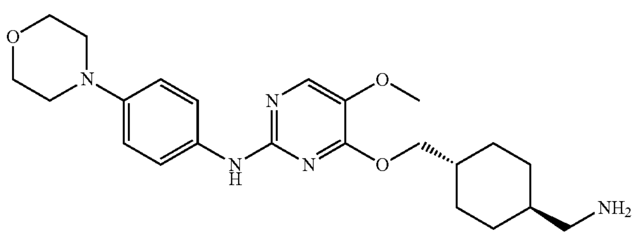 [SMILES: COc1cnc(Nc2ccc(N3CCOCC3)cc2)nc1OC[C@H]1CC[C@H](CN)CC1] | 4-(((1R,4R)-4-(aminomethyl)cyclohexyl)methoxy)-5-methoxy-N-(4-morpholinophenyl)pyrimidin-2-amine |
| 14 | 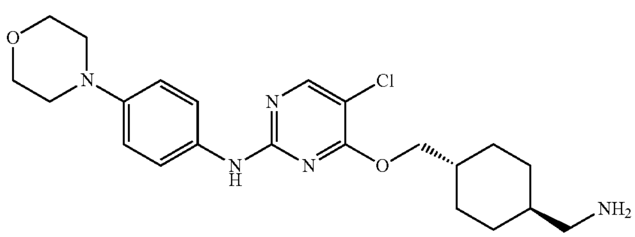 [SMILES: NC[C@H]1CC[C@H](COc2nc(Nc3ccc(N4CCOCC4)cc3)ncc2Cl)CC1] | 4-(((1R,4R)-4-(aminomethyl)cyclohexyl)methoxy)-5-chloro-N-(4-morpholinophenyl)pyrimidin-2-amine |
| 15 | 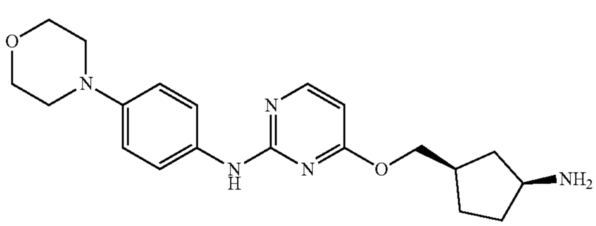 [SMILES: N[C@H]1CC[C@@H](COc2ccnc(Nc3ccc(N4CCOCC4)cc3)n2)C1] | 4-(((1R,3S)-3-aminocyclopentyl)methoxy)-N-(4-morpholinophenyl)pyrimidin-2-amine |
| 16 | 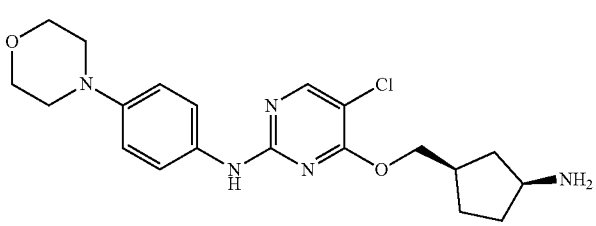 [SMILES: N[C@H]1CC[C@@H](COc2nc(Nc3ccc(N4CCOCC4)cc3)ncc2Cl)C1] | 4-(((1R,3S)-3-aminocyclopentyl)methoxy)-5-chloro-N-(4-morpholinophenyl)pyrimidin-2-amine |

TABLE 1-continued

Representative Compounds of Structure (I)

| Example | Structure | Name |
|---|---|---|
| 17 | 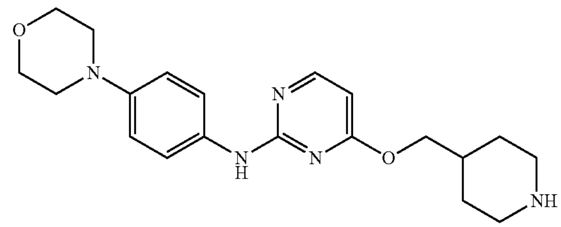 [SMILES: c1cc(OCC2CCNCC2)nc(Nc2ccc(N3CCOCC3)cc2)n1] | N-(4-morpholinophenyl)-4-(piperidin-4-ylmethoxy)pyrimidin-2-amine |
| 18 | 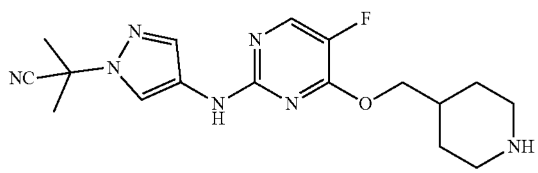 [SMILES: CC(C)(C#N)n1cc(Nc2ncc(F)c(OCC3CCNCC3)n2)cn1] | 2-(4-((5-fluoro-4-(piperidin-4-ylmethoxy)pyrimidin-2-yl)amino)-3-methyl-1H-pyrazol-1-yl)-2-methylpropanenitrile |
| 19 | 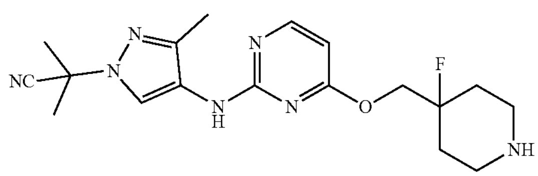 [SMILES: Cc1nn(C(C)(C)C#N)cc1Nc1nccc(OCC2(F)CCNCC2)n1] | 2-(4-((4-((4-fluoropiperidin-4-yl)methoxy)pyrimidin-2-yl)amino)-3-methyl-1H-pyrazol-1-yl)-2-methylpropanenitrile |
| 20 | 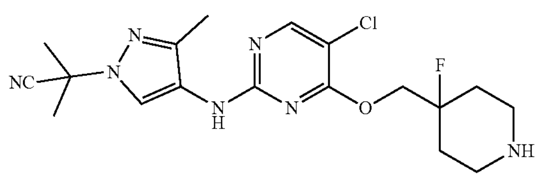 [SMILES: Cc1nn(C(C)(C)C#N)cc1Nc1ncc(Cl)c(OCC2(F)CCNCC2)n1] | 2-(4-((5-chloro-4-((4-fluoropiperidin-4-yl)methoxy)pyrimidin-2-yl)amino)-3-methyl-1H-pyrazol-1-yl)-2-methylpropanenitrile |
| 21 | 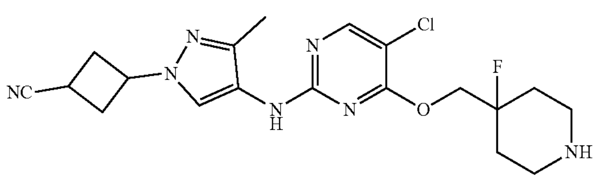 [SMILES: Cc1nn(C2CC(C#N)C2)cc1Nc1ncc(Cl)c(OCC2(F)CCNCC2)n1] | 3-(4-((5-chloro-4-((4-fluoropiperidin-4-yl)methoxy)pyrimidin-2-yl)amino)-3-methyl-1H-pyrazol-1-yl)cyclobutane-1-carbonitrile |
| 22 | 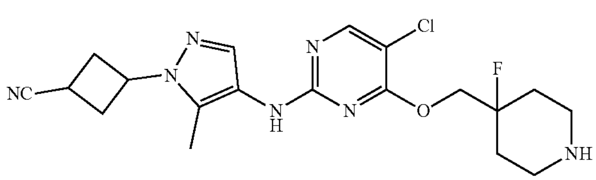 [SMILES: Cc1c(Nc2ncc(Cl)c(OCC3(F)CCNCC3)n2)cnn1C1CC(C#N)C1] | 3-(4-((5-chloro-4-((4-fluoropiperidin-4-yl)methoxy)pyrimidin-2-yl)amino)-5-methyl-1H-pyrazol-1-yl)cyclobutane-1-carbonitrile |
| 23 | 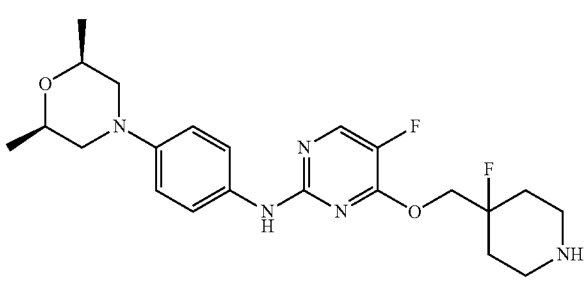 [SMILES: C[C@@H]1CN(c2ccc(Nc3ncc(F)c(OCC4(F)CCNCC4)n3)cc2)C[C@H](C)O1] | N-(4-((2R,6S)-2,6-dimethylmorpholino)phenyl)-5-fluoro-4-((4-fluoropiperidin-4-yl)methoxy)pyrimidin-2-amine |

TABLE 1-continued

Representative Compounds of Structure (I)

| Example | Structure | Name |
|---|---|---|
| 24 | 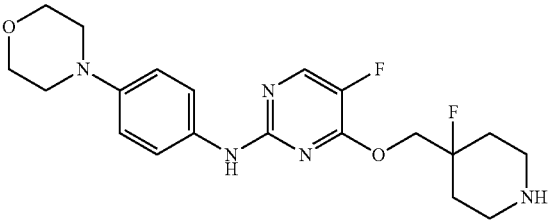 [SMILES: Fc1cnc(Nc2ccc(N3CCOCC3)cc2)nc1OCC1(F)CCNCC1] | 5-fluoro-4-((4-fluoropiperidin-4-yl)methoxy)-N-(4-morpholinophenyl)pyrimidin-2-amine |
| 25 | 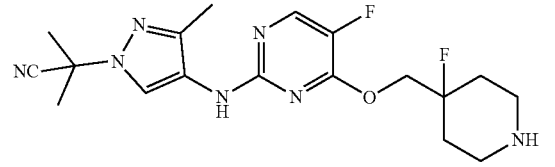 [SMILES: Cc1nn(C(C)(C)C#N)cc1Nc1ncc(F)c(OCC2(F)CCNCC2)n1] | 2-(4-((5-fluoro-4-((4-fluoropiperidin-4-yl)methoxy)pyrimidin-2-yl)amino)-3-methyl-1H-pyrazol-1-yl)-2-methylpropanenitrile |
| 26 | 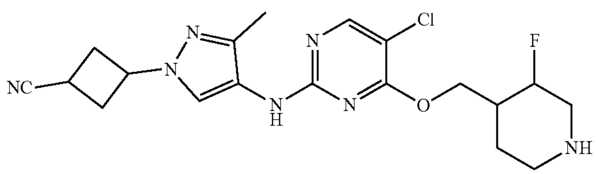 [SMILES: Cc1nn(C2CC(C#N)C2)cc1Nc1ncc(Cl)c(OCC2CCNCC2F)n1] | 3-(4-((5-chloro-4-((3-fluoropiperidin-4-yl)methoxy)pyrimidin-2-yl)amino)-3-methyl-1H-pyrazol-1-yl)cyclobutane-1-carbonitrile |
| 27 | 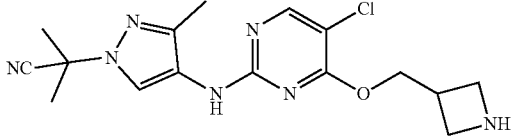 [SMILES: Cc1nn(C(C)(C)C#N)cc1Nc1ncc(Cl)c(OCC2CNC2)n1] | 2-(4-((4-(azetidin-3-ylmethoxy)-5-chloropyrimidin-2-yl)amino)-3-methyl-1H-pyrazol-1-yl)-2-methylpropanenitrile |
| 28 | 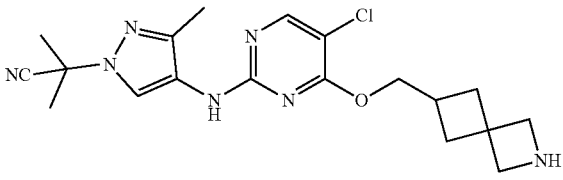 [SMILES: Cc1nn(C(C)(C)C#N)cc1Nc1ncc(Cl)c(OCC2CC3(CNC3)C2)n1] | 2-(4-((4-((2-azaspiro[3.3]heptan-6-yl)methoxy)-5-chloropyrimidin-2-yl)amino)-3-methyl-1H-pyrazol-1-yl)-2-methylpropanenitrile |
| 29 | 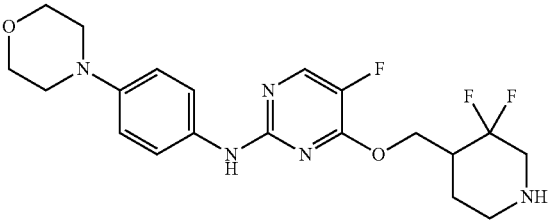 [SMILES: Fc1cnc(Nc2ccc(N3CCOCC3)cc2)nc1OCC1CCNCC1(F)F] | 4-((3,3-difluoropiperidin-4-yl)methoxy)-5-fluoro-N-(4-morpholinophenyl)pyrimidin-2-amine |
| 30 | 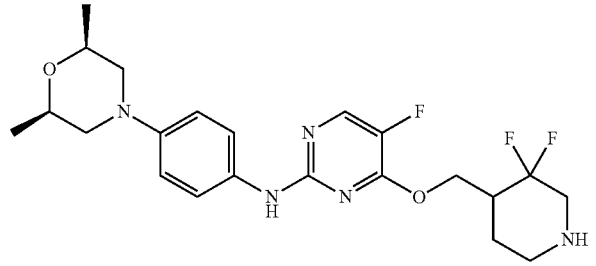 [SMILES: C[C@@H]1CN(c2ccc(Nc3ncc(F)c(OCC4CCNCC4(F)F)n3)cc2)C[C@H](C)O1] | 4-((3,3-difluoropiperidin-4-yl)methoxy)-N-(4-((2S,6R)-2,6-dimethylmorpholino)phenyl)-5-fluoropyrimidin-2-amine |

TABLE 1-continued

Representative Compounds of Structure (I)

| Example | Structure | Name |
|---------|-----------|------|
| 31 | 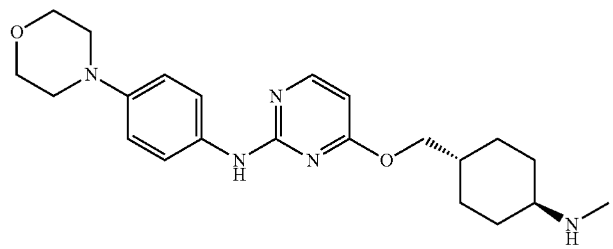 [SMILES: CN[C@H]1CC[C@H](COc2ccnc(Nc3ccc(N4CCOCC4)cc3)n2)CC1] | 4-(((1R,4R)-4-(methylamino)cyclohexyl)methoxy)-N-(4-morpholinophenyl)pyrimidin-2-amine |
| 32 | 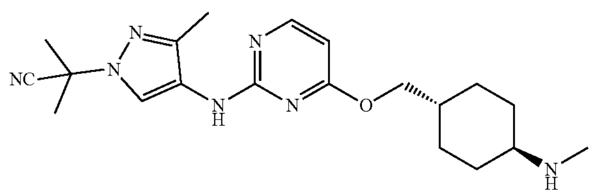 [SMILES: CN[C@H]1CC[C@H](COc2ccnc(Nc3cn(C(C)(C)C#N)nc3C)n2)CC1] | 2-methyl-2-(3-methyl-4-((4-(((1R,4R)-4-(methylamino)cyclohexyl)methoxy)pyrimidin-2-yl)amino)-1H-pyrazol-1-yl)propanenitrile |
| 33 | 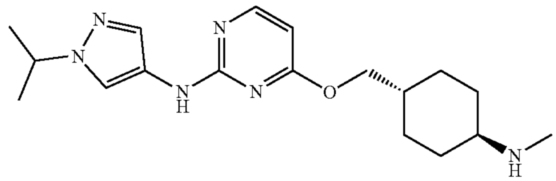 [SMILES: CN[C@H]1CC[C@H](COc2ccnc(Nc3cnn(C(C)C)c3)n2)CC1] | N-(1-isopropyl-1H-pyrazol-4-yl)-4-(((1R,4R)-4-(methylamino)cyclohexyl)methoxy)pyrimidin-2-amine |
| 34 | 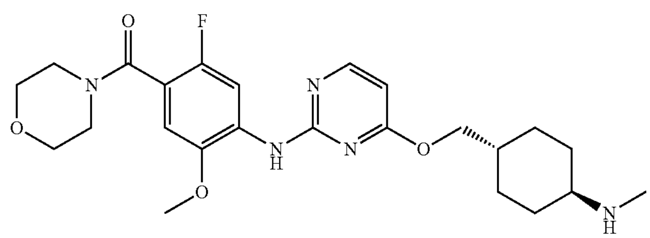 [SMILES: CN[C@H]1CC[C@H](COc2ccnc(Nc3cc(F)c(C(=O)N4CCOCC4)cc3OC)n2)CC1] | (2-fluoro-5-methoxy-4-((4-(((1R,4R)-4-(methylamino)cyclohexyl)methoxy)pyrimidin-2-yl)amino)phenyl)(morpholino)methanone |
| 35 | 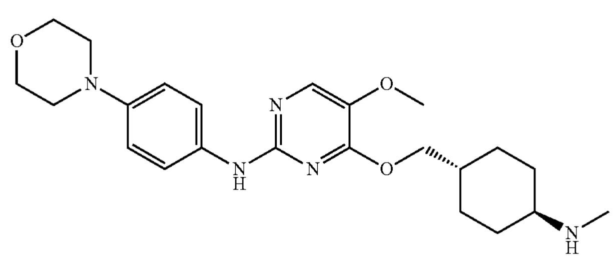 [SMILES: CN[C@H]1CC[C@H](COc2nc(Nc3ccc(N4CCOCC4)cc3)ncc2OC)CC1] | 5-methoxy-4-(((1R,4R)-4-(methylamino)cyclohexyl)methoxy)-N-(4-morpholinophenyl)pyrimidin-2-amine |
| 36 | 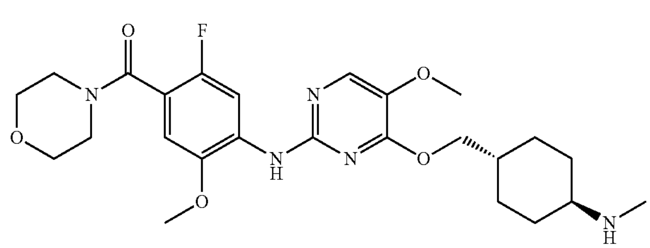 [SMILES: CN[C@H]1CC[C@H](COc2nc(Nc3cc(F)c(C(=O)N4CCOCC4)cc3OC)ncc2OC)CC1] | (2-fluoro-5-methoxy-4-((5-methoxy-4-(((1R,4R)-4-(methylamino)cyclohexyl)methoxy)pyrimidin-2-yl)amino)phenyl)(morpholino)methanone |

TABLE 1-continued

Representative Compounds of Structure (I)

| Example | Structure | Name |
|---|---|---|
| 37 | 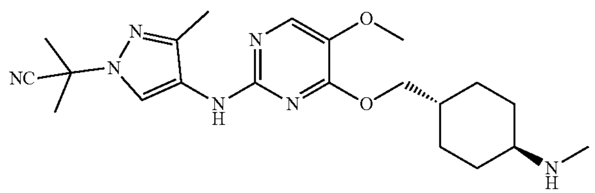 [SMILES: CN[C@H]1CC[C@H](COc2nc(Nc3cn(C(C)(C)C#N)nc3C)ncc2OC)CC1] | 2-(4-((5-methoxy-4-(((1R,4R)-4-(methylamino)cyclohexyl)methoxy)pyrimidin-2-yl)amino)-3-methyl-1H-pyrazol-1-yl)-2-methylpropanenitrile |
| 38 | 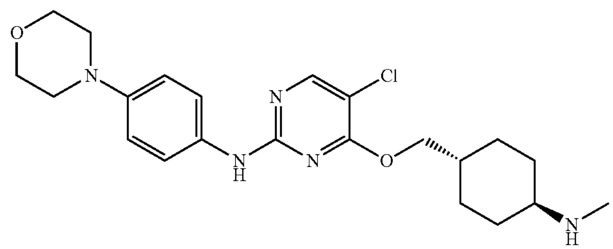 | 5-chloro-4-(((1R,4R)-4-(methylamino)cyclohexyl)methoxy)-N-(4-morpholinophenyl)pyrimidin-2-amine |
| 39 | 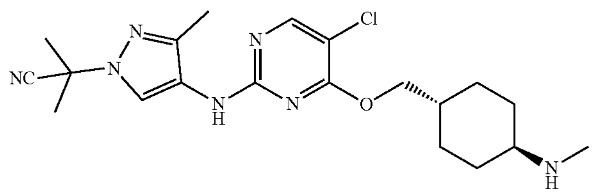 | 2-(4-((5-chloro-4-(((1R,4R)-4-(methylamino)cyclohexyl)methoxy)pyrimidin-2-yl)amino)-3-methyl-1H-pyrazol-1-yl)-2-methylpropanenitrile |
| 40 | 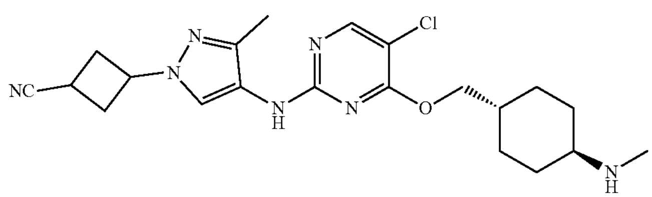 [SMILES: CN[C@H]1CC[C@H](COc2nc(Nc3cn(C4CC(C#N)C4)nc3C)ncc2Cl)CC1] | 3-(4-((5-chloro-4-(((1R,4R)-4-(methylamino)cyclohexyl)methoxy)pyrimidin-2-yl)amino)-3-methyl-1H-pyrazol-1-yl)cyclobutane-1-carbonitrile |
| 41 | 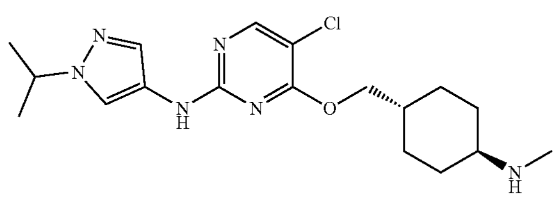 [SMILES: CN[C@H]1CC[C@H](COc2nc(Nc3cnn(C(C)C)c3)ncc2Cl)CC1] | 5-chloro-N-(1-isopropyl-1H-pyrazol-4-yl)-4-(((1R,4R)-4-(methylamino)cyclohexyl)methoxy)pyrimidin-2-amine |
| 42 | 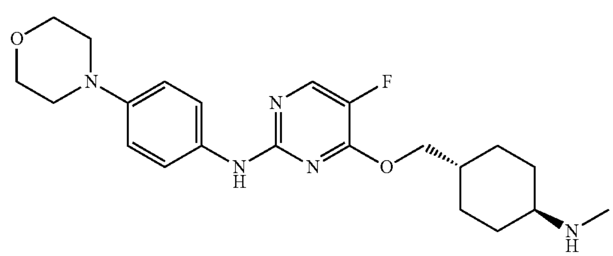 [SMILES: CN[C@H]1CC[C@H](COc2nc(Nc3ccc(N4CCOCC4)cc3)ncc2F)CC1] | 5-fluoro-4-(((1R,4R)-4-(methylamino)cyclohexyl)methoxy)-N-(4-morpholinophenyl)pyrimidin-2-amine |
| 43 | 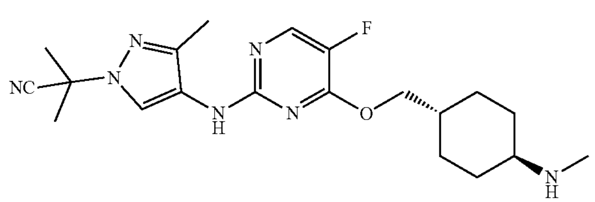 [SMILES: CN[C@H]1CC[C@H](COc2nc(Nc3cn(C(C)(C)C#N)nc3C)ncc2F)CC1] | 2-(4-((5-fluoro-4-(((1R,4R)-4-(methylamino)cyclohexyl)methoxy)pyrimidin-2-yl)amino)-3-methyl-1H-pyrazol-1-yl)-2-methylpropanenitrile |

TABLE 1-continued

Representative Compounds of Structure (I)

| Example | Structure | Name |
|---|---|---|
| 44 | 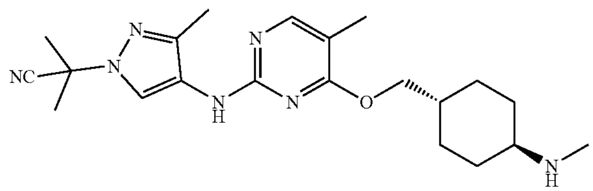 [SMILES: CN[C@H]1CC[C@H](COc2nc(Nc3cn(C(C)(C)C#N)nc3C)ncc2C)CC1] | 2-methyl-2-(3-methyl-4-((5-methyl-4-(((1R,4R)-4-(methylamino)cyclohexyl)methoxy)pyrimidin-2-yl)amino)-1H-pyrazol-1-yl)propanenitrile |
| 45 | 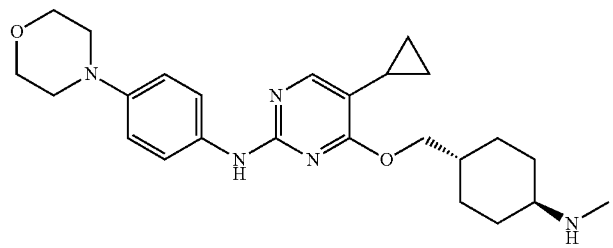 [SMILES: CN[C@H]1CC[C@H](COc2nc(Nc3ccc(N4CCOCC4)cc3)ncc2C2CC2)CC1] | 5-cyclopropyl-4-(((1R,4R)-4-(methylamino)cyclohexyl)methoxy)-N-(4-morpholinophenyl)pyrimidin-2-amine |
| 46 | 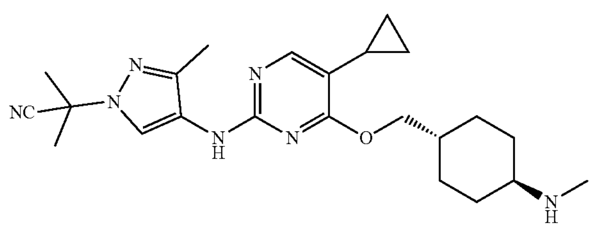 [SMILES: CN[C@H]1CC[C@H](COc2nc(Nc3cn(C(C)(C)C#N)nc3C)ncc2C2CC2)CC1] | 2-(4-((5-cyclopropyl-4-(((1R,4R)-4-(methylamino)cyclohexyl)methoxy)pyrimidin-2-yl)amino)-3-methyl-1H-pyrazol-1-yl)-2-methylpropanenitrile |
| 47 | 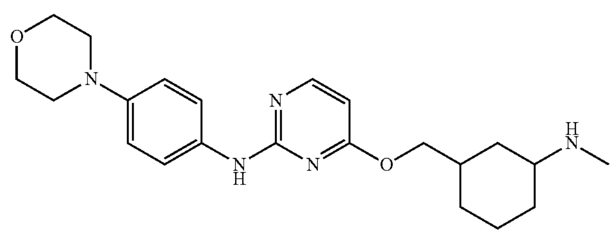 [SMILES: CNC1CCCC(COc2ccnc(Nc3ccc(N4CCOCC4)cc3)n2)C1] | 4-((3-(methylamino)cyclohexyl)methoxy)-N-(4-morpholinophenyl)pyrimidin-2-amine |
| 48 | 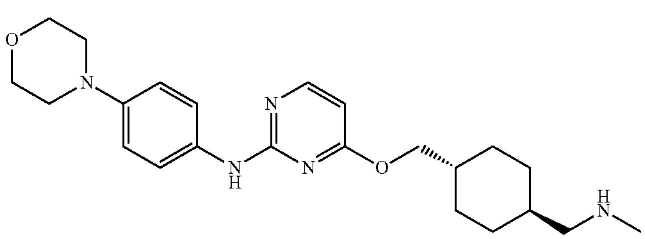 [SMILES: CNC[C@H]1CC[C@H](COc2ccnc(Nc3ccc(N4CCOCC4)cc3)n2)CC1] | 4-(((1R,4R)-4-((methylamino)methyl)cyclohexyl)methoxy)-N-(4-morpholinophenyl)pyrimidin-2-amine |
| 49 | 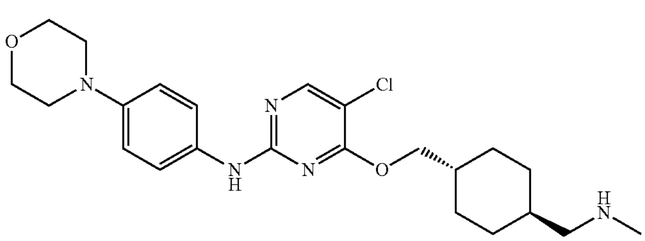 [SMILES: CNC[C@H]1CC[C@H](COc2nc(Nc3ccc(N4CCOCC4)cc3)ncc2Cl)CC1] | 5-chloro-4-(((1R,4R)-4-((methylamino)methyl)cyclohexyl)methoxy)-N-(4-morpholinophenyl)pyrimidin-2-amine |

TABLE 1-continued

Representative Compounds of Structure (I)

| Example | Structure | Name |
|---|---|---|
| 50 | 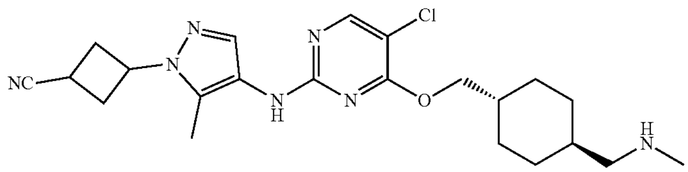 [SMILES: CNC[C@H]1CC[C@H](COc2nc(Nc3cnn(C4CC(C#N)C4)c3C)ncc2Cl)CC1] | 3-(4-((5-chloro-4-(((1R,4R)-4-((methylamino)methyl)cyclohexyl)methoxy)pyrimidin-2-yl)amino)-5-methyl-1H-pyrazol-1-yl)cyclobutane-1-carbonitrile |
| 51 | 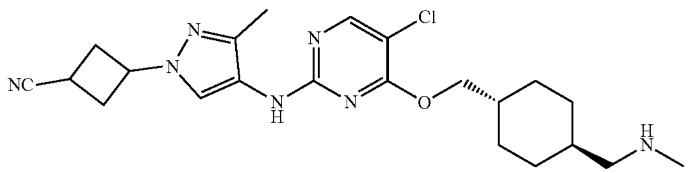 [SMILES: CNC[C@H]1CC[C@H](COc2nc(Nc3cn(C4CC(C#N)C4)nc3C)ncc2Cl)CC1] | 3-(4-((5-chloro-4-(((1R,4R)-4-((methylamino)methyl)cyclohexyl)methoxy)pyrimidin-2-yl)amino)-3-methyl-1H-pyrazol-1-yl)cyclobutane-1-carbonitrile |
| 52 | 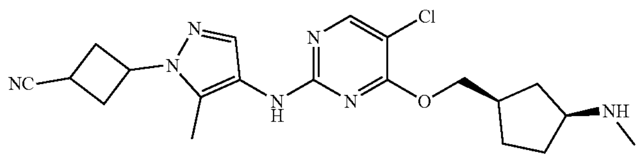 | 3-(4-((5-chloro-4-(((1R,3S)-3-(methylamino)cyclopentyl)methoxy)pyrimidin-2-yl)amino)-5-methyl-1H-pyrazol-1-yl)cyclobutane-1-carbonitrile |
| 53 | 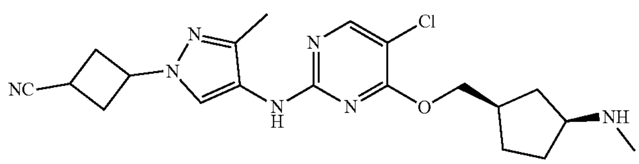 [SMILES: CN[C@H]1CC[C@@H](COc2nc(Nc3cn(C4CC(C#N)C4)nc3C)ncc2Cl)C1] | 3-(4-((5-chloro-4-(((1R,3S)-3-(methylamino)cyclopentyl)methoxy)pyrimidin-2-yl)amino)-3-methyl-1H-pyrazol-1-yl)cyclobutane-1-carbonitrile |
| 54 | 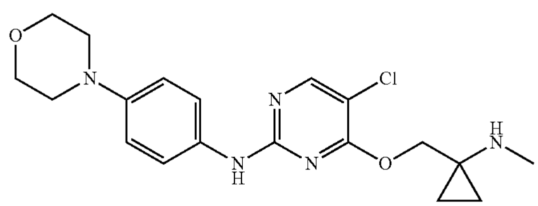 [SMILES: CNC1(COc2nc(Nc3ccc(N4CCOCC4)cc3)ncc2Cl)CC1] | 5-chloro-4-((1-(methylamino)cyclopropyl)methoxy)-N-(4-morpholinophenyl)pyrimidin-2-amine |
| 55 | 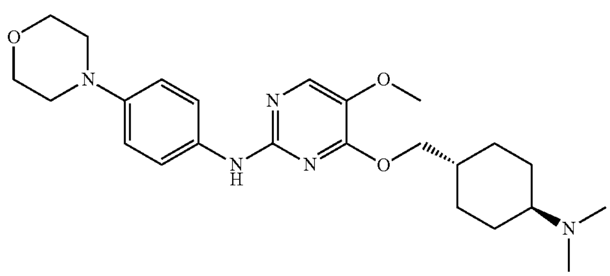 [SMILES: COc1cnc(Nc2ccc(N3CCOCC3)cc2)nc1OC[C@H]1CC[C@H](N(C)C)CC1] | 4-(((1R,4R)-4-(dimethylamino)cyclohexyl)methoxy)-5-methoxy-N-(4-morpholinophenyl)pyrimidin-2-amine |
| 56 | 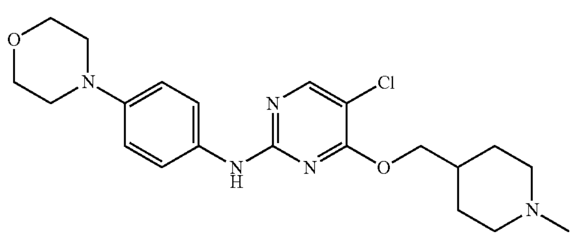 [SMILES: CN1CCC(COc2nc(Nc3ccc(N4CCOCC4)cc3)ncc2Cl)CC1] | 5-chloro-4-((1-methylpiperidin-4-yl)methoxy)-N-(4-morpholinophenyl)pyrimidin-2-amine |

TABLE 1-continued

Representative Compounds of Structure (I)

| Example | Structure | Name |
|---|---|---|
| 57 | 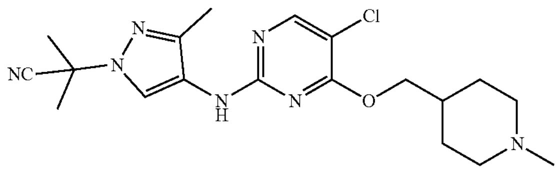 [SMILES: Cc1nn(C(C)(C)C#N)cc1Nc1ncc(Cl)c(OCC2CCN(C)CC2)n1] | 2-(4-((5-chloro-4-((1-methylpiperidin-4-yl)methoxy)pyrimidin-2-yl)amino)-3-methyl-1H-pyrazol-1-yl)-2-methylpropanenitrile |
| 58 | 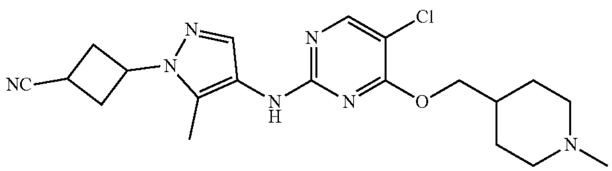 [SMILES: Cc1c(Nc2ncc(Cl)c(OCC3CCN(C)CC3)n2)cnn1C1CC(C#N)C1] | 3-(4-((5-chloro-4-((1-methylpiperidin-4-yl)methoxy)pyrimidin-2-yl)amino)-5-methyl-1H-pyrazol-1-yl)cyclobutane-1-carbonitrile |
| 59 | 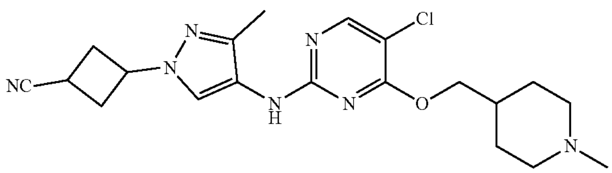 [SMILES: Cc1nn(C2CC(C#N)C2)cc1Nc1ncc(Cl)c(OCC2CCN(C)CC2)n1] | 3-(4-((5-chloro-4-((1-methylpiperidin-4-yl)methoxy)pyrimidin-2-yl)amino)-3-methyl-1H-pyrazol-1-yl)cyclobutane-1-carbonitrile |
| 60 | 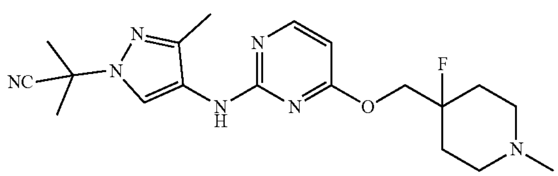 [SMILES: Cc1nn(C(C)(C)C#N)cc1Nc1nccc(OCC2(F)CCN(C)CC2)n1] | 2-(4-((4-((4-fluoro-1-methylpiperidin-4-yl)methoxy)pyrimidin-2-yl)amino)-3-methyl-1H-pyrazol-1-yl)-2-methylpropanenitrile |
| 61 | 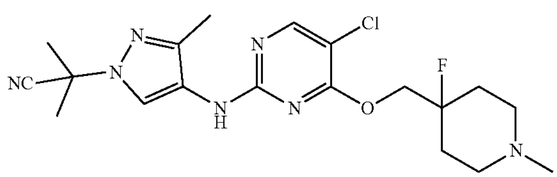 [SMILES: Cc1nn(C(C)(C)C#N)cc1Nc1ncc(Cl)c(OCC2(F)CCN(C)CC2)n1] | 2-(4-((5-chloro-4-((4-fluoro-1-methylpiperidin-4-yl)methoxy)pyrimidin-2-yl)amino)-3-methyl-1H-pyrazol-1-yl)-2-methylpropanenitrile |
| 62 | 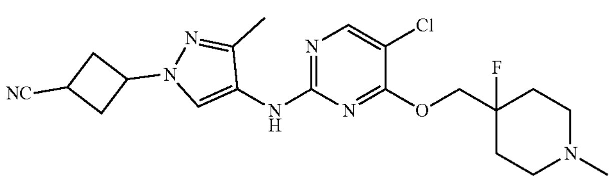 [SMILES: Cc1nn(C2CC(C#N)C2)cc1Nc1ncc(Cl)c(OCC2(F)CCN(C)CC2)n1] | 3-(4-((5-chloro-4-((4-fluoro-1-methylpiperidin-4-yl)methoxy)pyrimidin-2-yl)amino)-3-methyl-1H-pyrazol-1-yl)cyclobutane-1-carbonitrile |
| 63 | 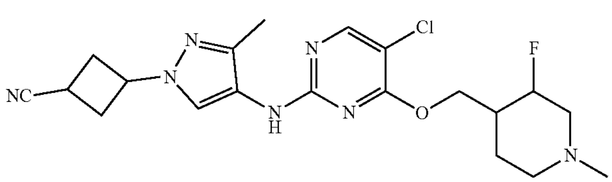 [SMILES: Cc1nn(C2CC(C#N)C2)cc1Nc1ncc(Cl)c(OCC2CCN(C)CC2F)n1] | 3-(4-((5-chloro-4-((3-fluoro-1-methylpiperidin-4-yl)methoxy)pyrimidin-2-yl)amino)-3-methyl-1H-pyrazol-1-yl)cyclobutane-1-carbonitrile |
| 64 | 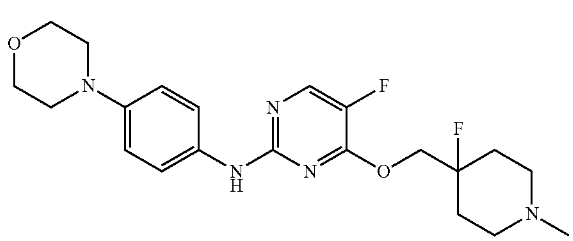 [SMILES: CN1CCC(F)(COc2nc(Nc3ccc(N4CCOCC4)cc3)ncc2F)CC1] | 5-fluoro-4-((4-fluoro-1-methylpiperidin-4-yl)methoxy)-N-(4-morpholinophenyl)pyrimidin-2-amine |

TABLE 1-continued

Representative Compounds of Structure (I)

| Example | Structure | Name |
|---|---|---|
| 65 | 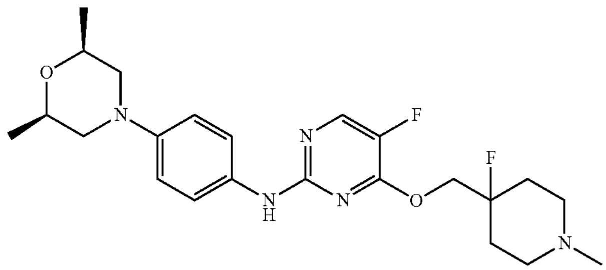 | N-(4-((2R,6S)-2,6-dimethylmorpholino)phenyl)-5-fluoro-4-((4-fluoro-1-methylpiperidin-4-yl)methoxy)pyrimidin-2-amine |
| 66 | 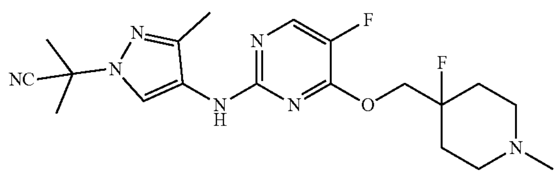 [SMILES: Cc1nn(C(C)(C)C#N)cc1Nc1ncc(F)c(OCC2(F)CCN(C)CC2)n1] | 2-(4-((5-fluoro-4-((4-fluoro-1-methylpiperidin-4-yl)methoxy)pyrimidin-2-yl)amino)-3-methyl-1H-pyrazol-1-yl)-2-methylpropanenitrile |
| 67 | 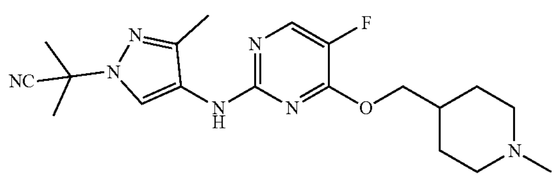 [SMILES: Cc1nn(C(C)(C)C#N)cc1Nc1ncc(F)c(OCC2CCN(C)CC2)n1] | 2-(4-((5-fluoro-4-((1-methylpiperidin-4-yl)methoxy)pyrimidin-2-yl)amino)-3-methyl-1H-pyrazol-1-yl)-2-methylpropanenitrile |
| 68 | 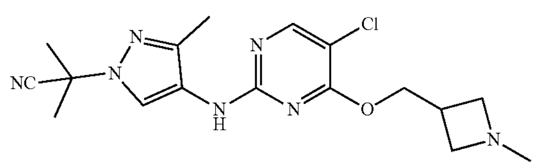 [SMILES: Cc1nn(C(C)(C)C#N)cc1Nc1ncc(Cl)c(OCC2CN(C)C2)n1] | 2-(4-((5-chloro-4-((1-methylazetidin-3-yl)methoxy)pyrimidin-2-yl)amino)-3-methyl-1H-pyrazol-1-yl)-2-methylpropanenitrile |
| 69 | 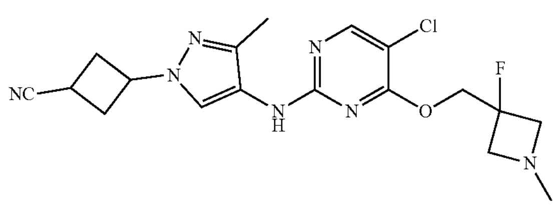 [SMILES: Cc1nn(C2CC(C#N)C2)cc1Nc1ncc(Cl)c(OCC2(F)CN(C)C2)n1] | 3-(4-((5-chloro-4-((3-fluoro-1-methylazetidin-3-yl)methoxy)pyrimidin-2-yl)amino)-3-methyl-1H-pyrazol-1-yl)cyclobutane-1-carbonitrile |
| 70 | 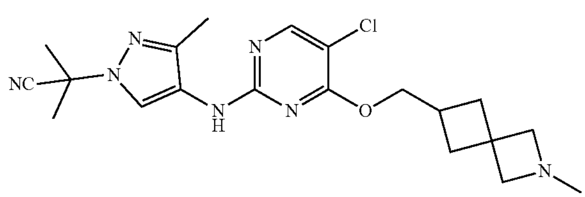 [SMILES: Cc1nn(C(C)(C)C#N)cc1Nc1ncc(Cl)c(OCC2CC3(C2)CN(C)C3)n1] | 2-(4-((5-chloro-4-((2-methyl-2-azaspiro[3.3]heptan-6-yl)methoxy)pyrimidin-2-yl)amino)-3-methyl-1H-pyrazol-1-yl)-2-methylpropanenitrile |
| 71 | 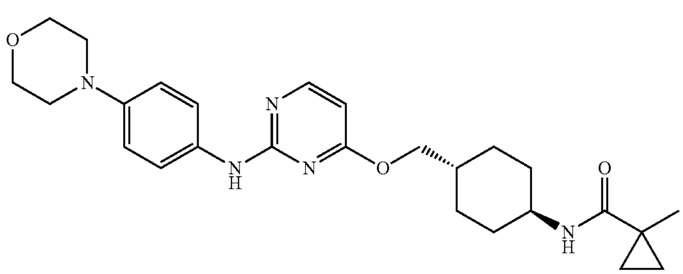 [SMILES: CC1(C(=O)N[C@H]2CC[C@H](COc3ccnc(Nc4ccc(N5CCOCC5)cc4)n3)CC2)CC1] | 1-methyl-N-((1R,4R)-4-(((2-((4-morpholinophenyl)amino)pyrimidin-4-yl)oxy)methyl)cyclohexyl)cyclopropane-1-carboxamide |

TABLE 1-continued

Representative Compounds of Structure (I)

| Example | Structure | Name |
|---|---|---|
| 72 | 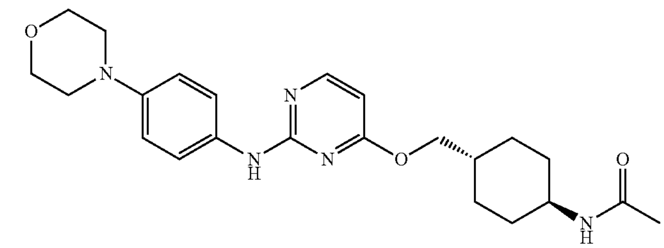 [SMILES: CC(=O)N[C@H]1CC[C@H](COc2ccnc(Nc3ccc(N4CCOCC4)cc3)n2)CC1] | N-((1R,4R)-4-(((2-((4-morpholinophenyl)amino)pyrimidin-4-yl)oxy)methyl)cyclohexyl)acetamide |
| 73 | 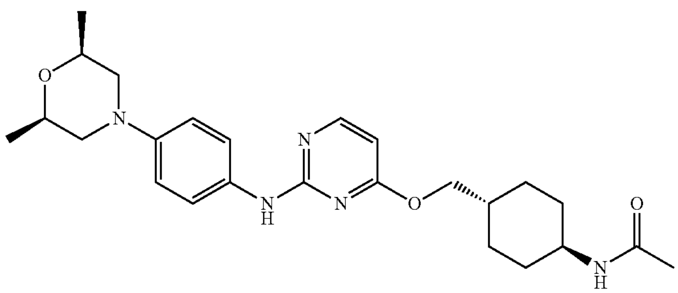 [SMILES: CC(=O)N[C@H]1CC[C@H](COc2ccnc(Nc3ccc(N4C[C@@H](C)O[C@@H](C)C4)cc3)n2)CC1] | N-((1R,4R)-4-(((2-((4-((2R,6S)-2,6-dimethylmorpholino)phenyl)amino)pyrimidin-4-yl)oxy)methyl)cyclohexyl)acetamide |
| 74 | 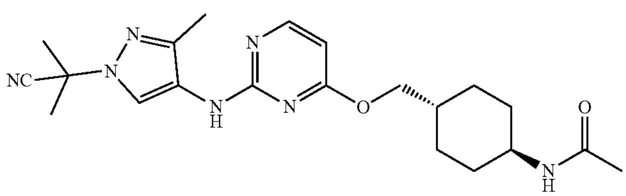 [SMILES: CC(=O)N[C@H]1CC[C@H](COc2ccnc(Nc3cn(C(C)(C)C#N)nc3C)n2)CC1] | N-((1R,4R)-4-(((2-((1-(2-cyanopropan-2-yl)-3-methyl-1H-pyrazol-4-yl)amino)pyrimidin-4-yl)oxy)methyl)cyclohexyl)acetamide |
| 75 | 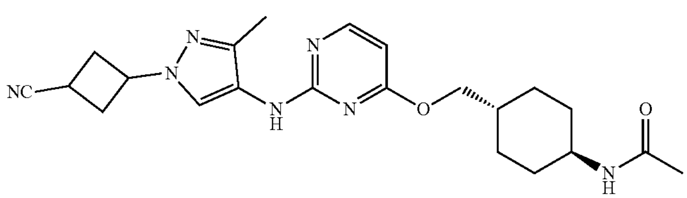 [SMILES: CC(=O)N[C@H]1CC[C@H](COc2ccnc(Nc3cn(C4CC(C#N)C4)nc3C)n2)CC1] | N-((1R,4R)-4-(((2-((1-(3-cyanocyclobutyl)-3-methyl-1H-pyrazol-4-yl)amino)pyrimidin-4-yl)oxy)methyl)cyclohexyl)acetamide |
| 76 | 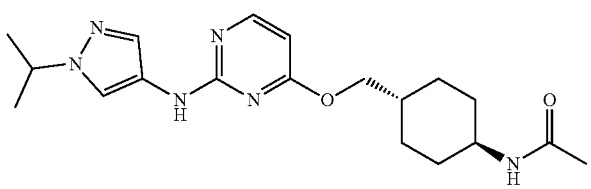 [SMILES: CC(=O)N[C@H]1CC[C@H](COc2ccnc(Nc3cnn(C(C)C)c3)n2)CC1] | N-((1R,4R)-4-((2-((1-isopropyl-1H-pyrazol-4-yl)amino)pyrimidin-4-yl)oxy)methyl)cyclohexyl)acetamide |
| 77 | 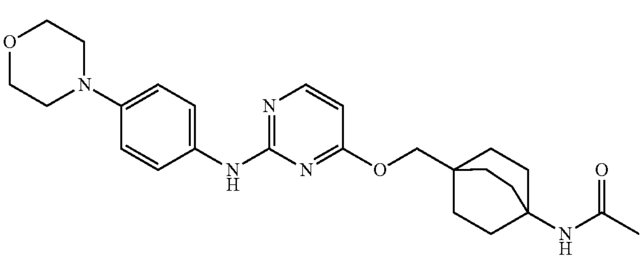 [SMILES: CC(=O)NC12CCC(COc3ccnc(Nc4ccc(N5CCOCC5)cc4)n3)(CC1)CC2] | N-(4-(((2-((4-morpholinophenyl)amino)pyrimidin-4-yl)oxy)methyl)bicyclo[2.2.2]octan-1-yl)acetamide |

TABLE 1-continued

Representative Compounds of Structure (I)

| Example | Structure | Name |
|---|---|---|
| 78 | 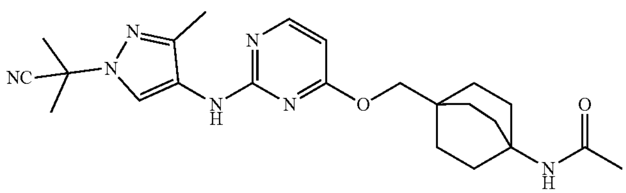 [SMILES: CC(=O)NC12CCC(COc3ccnc(Nc4cn(C(C)(C)C#N)nc4C)n3)(CC1)CC2] | N-(4-(((2-((1-(2-cyanopropan-2-yl)-3-methyl-1H-pyrazol-4-yl)amino)pyrimidin-4-yl)oxy)methyl)bicyclo[2.2.2]octan-1-yl)acetamide |
| 79 | 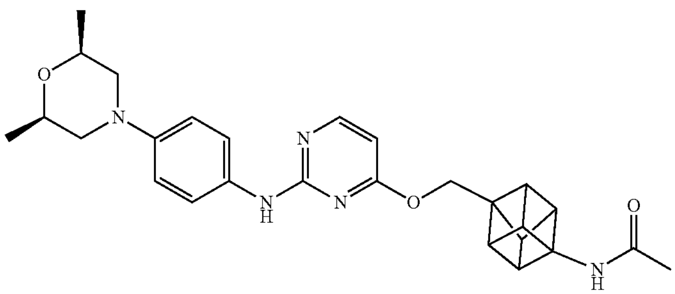 [SMILES: CC(=O)NC12C3C4C1C1C2C3C41COc1ccnc(Nc2ccc(N3C[C@@H](C)O[C@@H](C)C3)cc2)n1] | N-(4-(((2-((4-((2S,6R)-2,6-dimethylmorpholino)phenyl)amino)pyrimidin-4-yl)oxy)methyl)cuban-1-yl)acetamide |
| 80 | 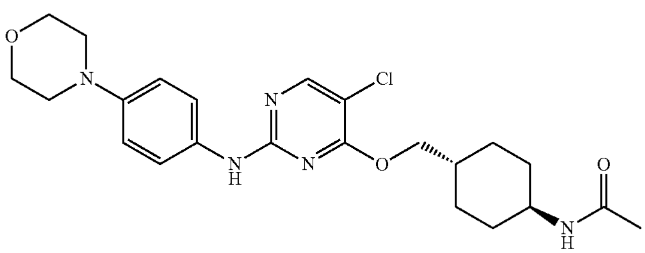 [SMILES: CC(=O)N[C@H]1CC[C@H](COc2nc(Nc3ccc(N4CCOCC4)cc3)ncc2Cl)CC1] | N-((1R,4R)-4-(((5-chloro-2-((4-morpholinophenyl)amino)pyrimidin-4-yl)oxy)methyl)cyclohexyl)acetamide |
| 81 | 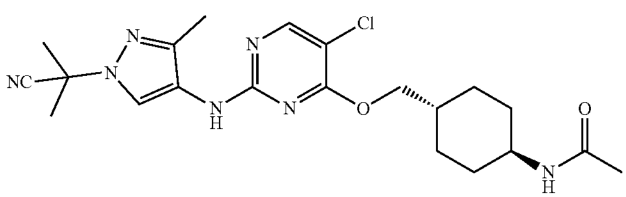 [SMILES: CC(=O)N[C@H]1CC[C@H](COc2nc(Nc3cn(C(C)(C)C#N)nc3C)ncc2Cl)CC1] | N-((1R,4R)-4-(((5-chloro-2-((1-(2-cyanopropan-2-yl)-3-methyl-1H-pyrazol-4-yl)amino)pyrimidin-4-yl)oxy)methyl)cyclohexyl)acetamide |
| 82 | 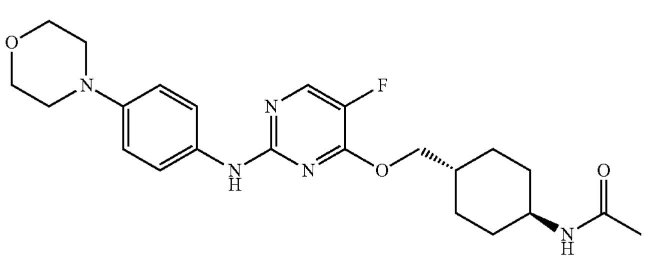 [SMILES: CC(=O)N[C@H]1CC[C@H](COc2nc(Nc3ccc(N4CCOCC4)cc3)ncc2F)CC1] | N-((1R,4R)-4-(((5-fluoro-2-((4-morpholinophenyl)amino)pyrimidin-4-yl)oxy)methyl)cyclohexyl)acetamide |
| 83 | 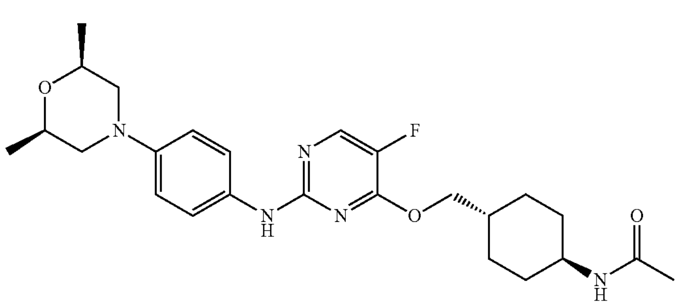 [SMILES: CC(=O)N[C@H]1CC[C@H](COc2nc(Nc3ccc(N4C[C@@H](C)O[C@@H](C)C4)cc3)ncc2F)CC1] | N-((1R,4R)-4-(((2-((4-((2R,6S)-2,6-dimethylmorpholino)phenyl)amino)-5-fluoropyrimidin-4-yl)oxy)methyl)cyclohexyl)acetamide |

TABLE 1-continued

Representative Compounds of Structure (I)

| Example | Structure | Name |
|---|---|---|
| 84 | 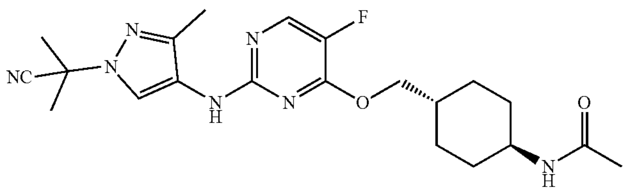 [SMILES: CC(=O)N[C@H]1CC[C@H](COc2nc(Nc3cn(C(C)(C)C#N)nc3C)ncc2F)CC1] | N-((1R,4R)-4-(((2-((1-(2-cyanopropan-2-yl)-3-methyl-1H-pyrazol-4-yl)amino)-5-fluoropyrimidin-4-yl)oxy)methyl)cyclohexyl)acetamide |
| 85 | 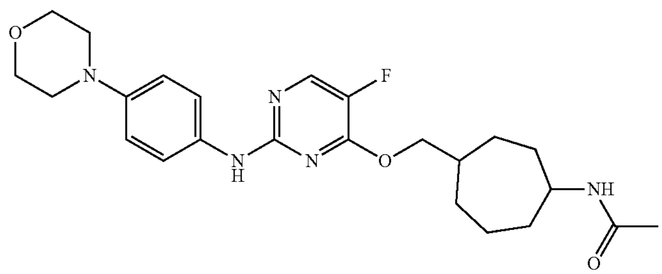 [SMILES: CC(=O)NC1CCCC(COc2nc(Nc3ccc(N4CCOCC4)cc3)ncc2F)CC1] | N-(4-(((5-fluoro-2-((4-morpholinophenyl)amino)pyrimidin-4-yl)oxy)methyl)cycloheptyl)acetamide |
| 86 | 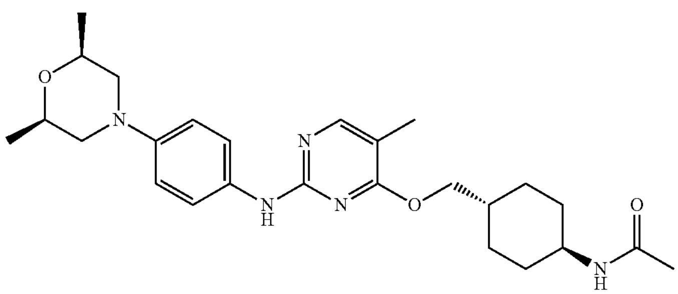 [SMILES: CC(=O)N[C@H]1CC[C@H](COc2nc(Nc3ccc(N4C[C@@H](C)O[C@@H](C)C4)cc3)ncc2C)CC1] | N-((1R,4R)-4-(((2-((4-((2S,6R)-2,6-dimethylmorpholino)phenyl)amino)-5-methylpyrimidin-4-yl)oxy)methyl)cyclohexyl)acetamide |
| 87 | 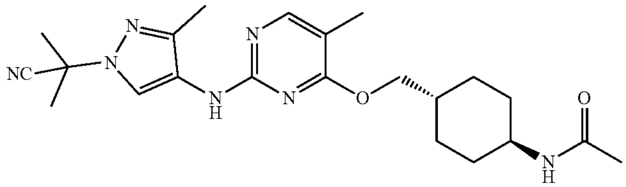 [SMILES: CC(=O)N[C@H]1CC[C@H](COc2nc(Nc3cn(C(C)(C)C#N)nc3C)ncc2C)CC1] | N-((1R,4R)-4-(((2-((1-(2-cyanopropan-2-yl)-3-methyl-1H-pyrazol-4-yl)amino)-5-methylpyrimidin-4-yl)oxy)methyl)cyclohexyl)acetamide |
| 88 | 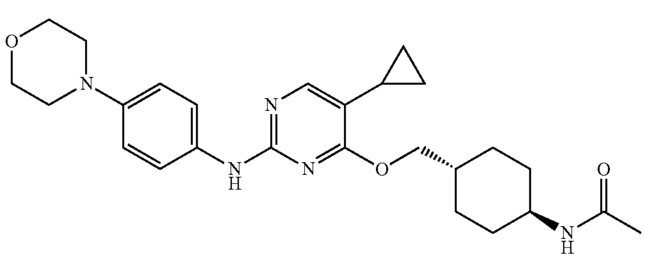 [SMILES: CC(=O)N[C@H]1CC[C@H](COc2nc(Nc3ccc(N4CCOCC4)cc3)ncc2C2CC2)CC1] | N-((1R,4R)-4-(((5-cyclopropyl-2-((4-morpholinophenyl)amino)pyrimidin-4-yl)oxy)methyl)cyclohexyl)acetamide |
| 89 | 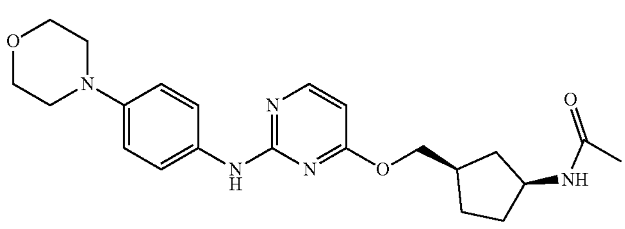 [SMILES: CC(=O)N[C@H]1CC[C@@H](COc2ccnc(Nc3ccc(N4CCOCC4)cc3)n2)C1] | N-((1S,3R)-3-(((2-((4-morpholinophenyl)amino)pyrimidin-4-yl)oxy)methyl)cyclopentyl)acetamide |

TABLE 1-continued

Representative Compounds of Structure (I)

| Example | Structure | Name |
|---|---|---|
| 90 | 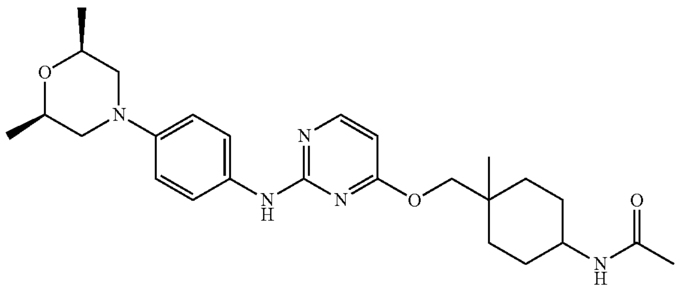 [SMILES: CC(=O)NC1CCC(C)(COc2ccnc(Nc3ccc(N4C[C@@H](C)O[C@@H](C)C4)cc3)n2)CC1] | N-(4-((2-((4-((2S,6R)-2,6-dimethylmorpholino)phenyl)amino)pyrimidin-4-yl)oxy)methyl)-4-methylcyclohexyl)acetamide |
| 91 | 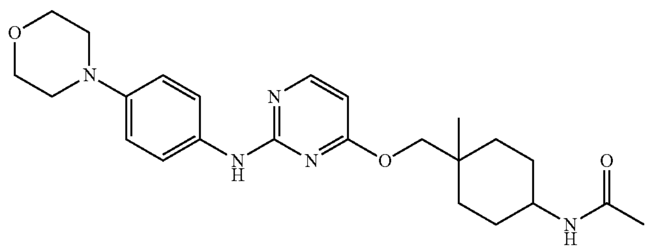 [SMILES: CC(=O)NC1CCC(C)(COc2ccnc(Nc3ccc(N4CCOCC4)cc3)n2)CC1] | N-(4-methyl-4-(((2-((4-morpholinophenyl)amino)pyrimidin-4-yl)oxy)methyl)cyclohexyl)acetamide |
| 92 | 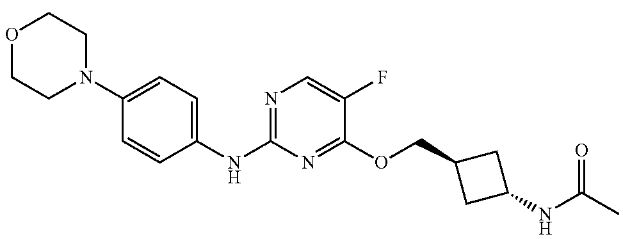 [SMILES: CC(=O)N[C@H]1C[C@H](COc2nc(Nc3ccc(N4CCOCC4)cc3)ncc2F)C1] | N-((1R,3R)-3-(((5-fluoro-2-((4-morpholinophenyl)amino)pyrimidin-4-yl)oxy)methyl)cyclobutyl)acetamide |
| 93 | 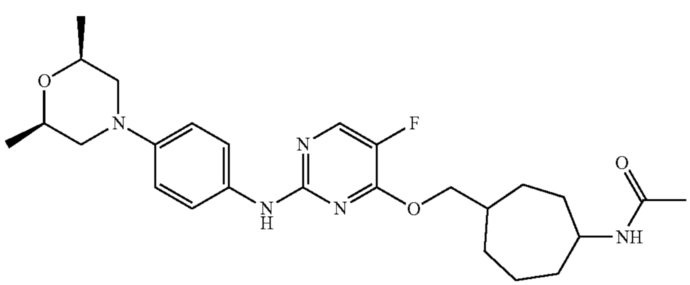 [SMILES: CC(=O)NC1CCCC(COc2nc(Nc3ccc(N4C[C@@H](C)O[C@@H](C)C4)cc3)ncc2F)CC1] | N-(4-((2-((4-((2S,6R)-2,6-dimethylmorpholino)phenyl)amino)-5-fluoropyrimidin-4-yl)oxy)methyl)cycloheptyl)acetamide |
| 94 | 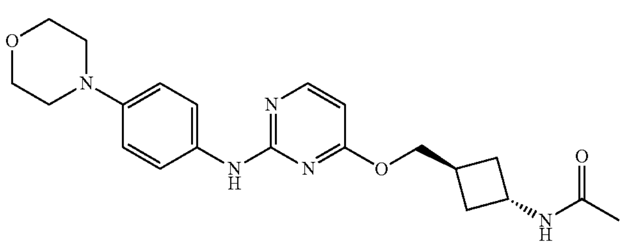 [SMILES: CC(=O)N[C@H]1C[C@H](COc2ccnc(Nc3ccc(N4CCOCC4)cc3)n2)C1] | N-((1R,3R)-3-(((2-((4-morpholinophenyl)amino)pyrimidin-4-yl)oxy)methyl)cyclobutyl)acetamide |

TABLE 1-continued

Representative Compounds of Structure (I)

| Example | Structure | Name |
|---|---|---|
| 95 | 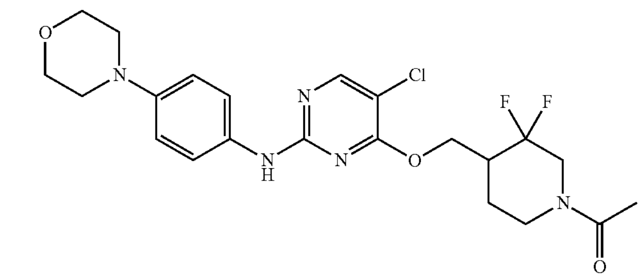 [SMILES: CC(=O)N1CCC(COc2nc(Nc3ccc(N4CCOCC4)cc3)ncc2Cl)C(F)(F)C1] | 1-(4-(((5-chloro-2-((4-morpholinophenyl)amino)pyrimidin-4-yl)oxy)methyl)-3,3-difluoropiperidin-1-yl)ethan-1-one |
| 96 | 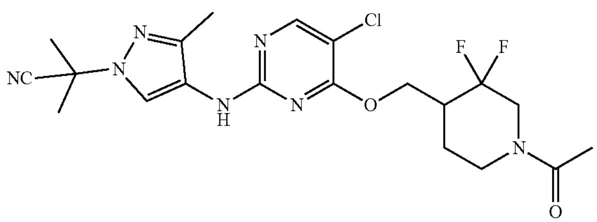 [SMILES: CC(=O)N1CCC(COc2nc(Nc3cn(C(C)(C)C#N)nc3C)ncc2Cl)C(F)(F)C1] | 2-(4-((4-(((1-acetyl-3,3-difluoropiperidin-4-yl)methoxy)-5-chloropyrimidin-2-yl)amino)-3-methyl-1H-pyrazol-1-yl)-2-methylpropanenitrile |
| 97 | 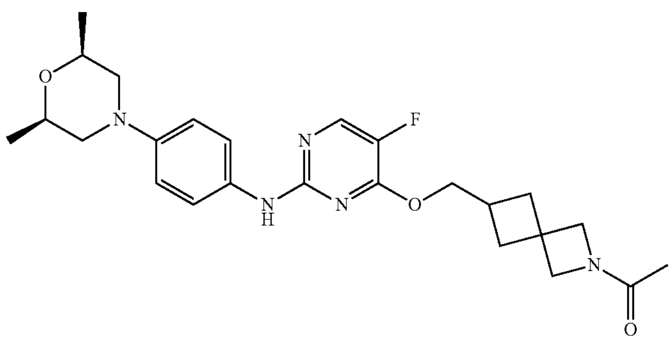 [SMILES: CC(=O)N1CC2(CC(COc3nc(Nc4ccc(N5C[C@@H](C)O[C@@H](C)C5)cc4)ncc3F)C2)C1] | 1-(6-(((2-((4-((2S,6R)-2,6-dimethylmorpholino)phenyl)amino)-5-fluoropyrimidin-4-yl)oxy)methyl)-2-azaspiro[3.3]heptan-2-yl)ethan-1-one |
| 98 | 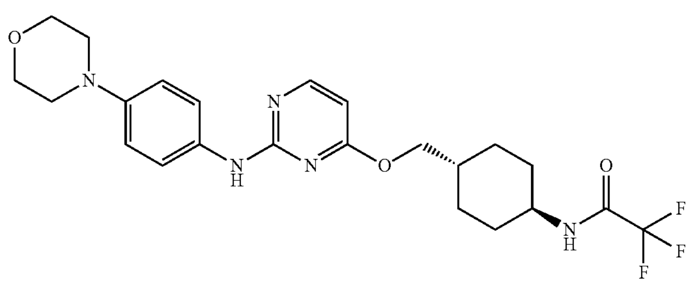 [SMILES: O=C(N[C@H]1CC[C@H](COc2ccnc(Nc3ccc(N4CCOCC4)cc3)n2)CC1)C(F)(F)F] | 2,2,2-trifluoro-N-((1R,4R)-4-(((2-((4-morpholinophenyl)amino)pyrimidin-4-yl)oxy)methyl)cyclohexyl)acetamide |
| 99 | 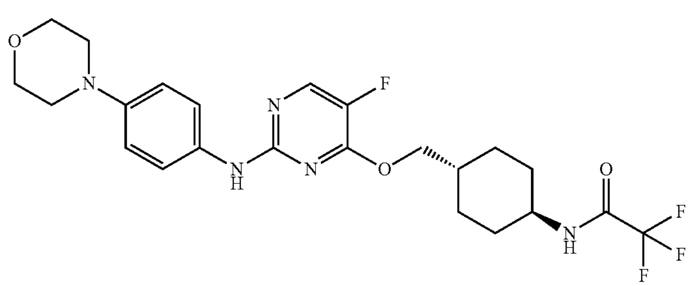 [SMILES: O=C(N[C@H]1CC[C@H](COc2nc(Nc3ccc(N4CCOCC4)cc3)ncc2F)CC1)C(F)(F)F] | 2,2,2-trifluoro-N-((1R,4R)-4-(((5-fluoro-2-((4-morpholinophenyl)amino)pyrimidin-4-yl)oxy)methyl)cyclohexyl)acetamide |

TABLE 1-continued

Representative Compounds of Structure (I)

| Example | Structure | Name |
|---|---|---|
| 100 | 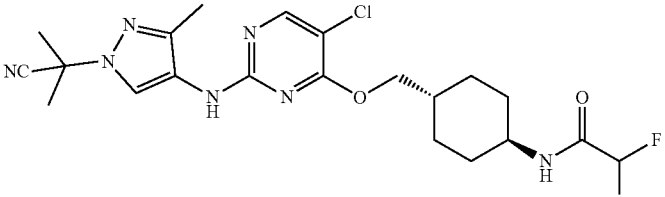 | N-((1R,4R)-4-(((5-chloro-2-((1-(2-cyanopropan-2-yl)-3-methyl-1H-pyrazol-4-yl)amino)pyrimidin-4-yl)oxy)methyl)cyclohexyl)-2,2-difluoroacetamide |
| 101 | 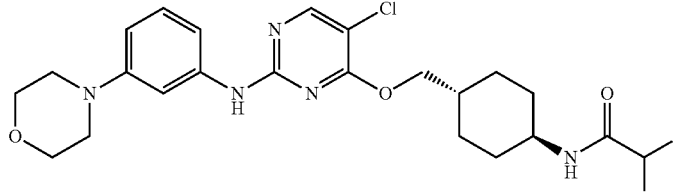 | N-((1R,4R)-4-((5-chloro-2-((3-morpholinophenyl)amino)pyrimidin-4-yl)oxy)methyl)cyclohexyl)-2,2-difluoroacetamide |
| 102 | 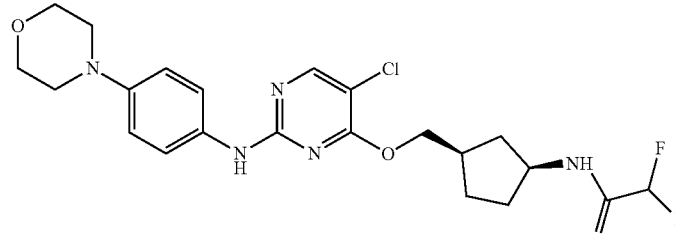 | N-((1S,3R)-3-(((5-chloro-2-((4-morpholinophenyl)amino)pyrimidin-4-yl)oxy)methyl)cyclopentyl)-2,2-difluoroacetamide |
| 103 | 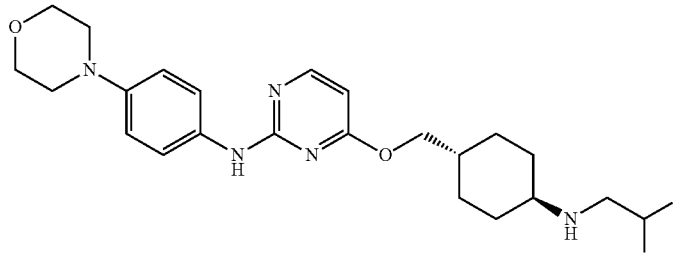 | 4-(((1R,4R)-4-((2,2-difluoroethyl)amino)cyclohexyl)methoxy)-N-(4-morpholinophenyl)pyrimidin-2-amine |
| 104 | 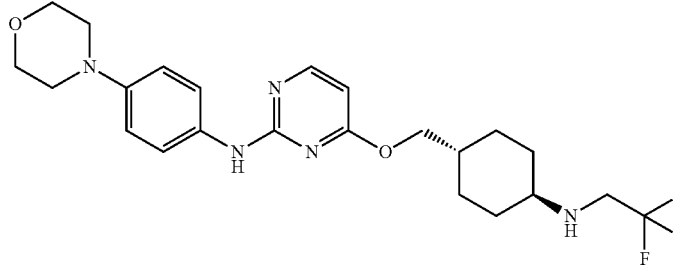 | N-(4-morpholinophenyl)-4-(((1R,4R)-4-((2,2,2-trifluoroethyl)amino)cyclohexyl)methoxy)pyrimidin-2-amine |
| 105 | 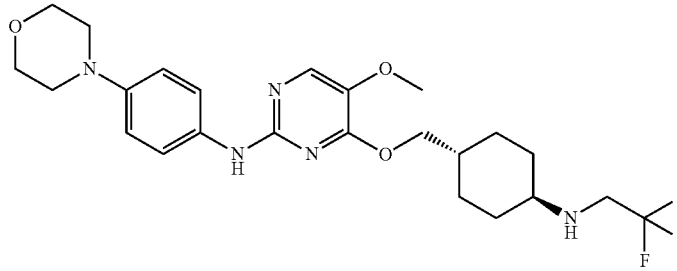 | 5-methoxy-N-(4-morpholinophenyl)-4-(((1R,4R)-4-((2,2,2-trifluoroethyl)amino)cyclohexyl)methoxy)pyrimidin-2-amine |

TABLE 1-continued

Representative Compounds of Structure (I)

| Example | Structure | Name |
|---|---|---|
| 106 | 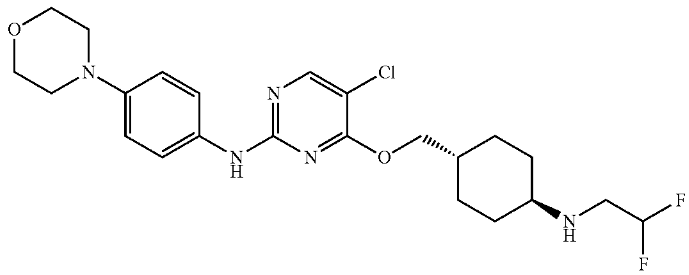 [SMILES: FC(F)CN[C@H]1CC[C@H](COc2nc(Nc3ccc(N4CCOCC4)cc3)ncc2Cl)CC1] | 5-chloro-4-(((1R,4R)-4-((2,2-difluoroethyl)amino)cyclohexyl)methoxy)-N-(4-morpholinophenyl)pyrimidin-2-amine |
| 107 | 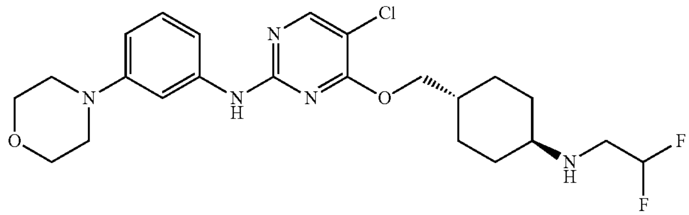 [SMILES: FC(F)CN[C@H]1CC[C@H](COc2nc(Nc3cccc(N4CCOCC4)c3)ncc2Cl)CC1] | 5-chloro-4-(((1R,4R)-4-((2,2-difluoroethyl)amino)cyclohexyl)methoxy)-N-(3-morpholinophenyl)pyrimidin-2-amine |
| 108 | 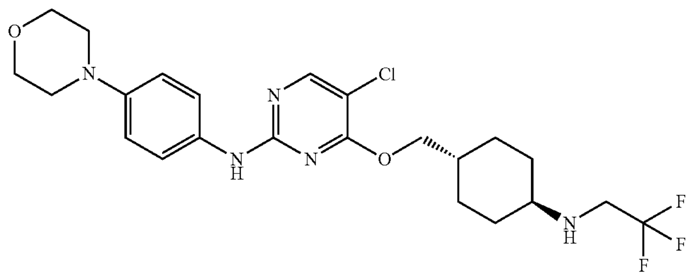 [SMILES: FC(F)(F)CN[C@H]1CC[C@H](COc2nc(Nc3ccc(N4CCOCC4)cc3)ncc2Cl)CC1] | 5-chloro-N-(4-morpholinophenyl)-4-(((1R,4R)-4-((2,2,2-trifluoroethyl)amino)cyclohexyl)methoxy)pyrimidin-2-amine |
| 109 | 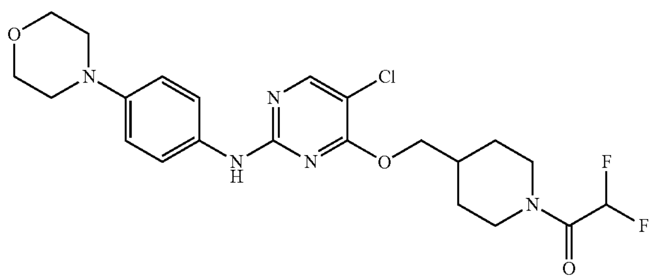 [SMILES: O=C(C(F)F)N1CCC(COc2nc(Nc3ccc(N4CCOCC4)cc3)ncc2Cl)CC1] | 1-(4-(((5-chloro-2-((4-morpholinophenyl)amino)pyrimidin-4-yl)oxy)methyl)piperidin-1-yl)-2,2-difluoroethan-1-one |
| 110 | 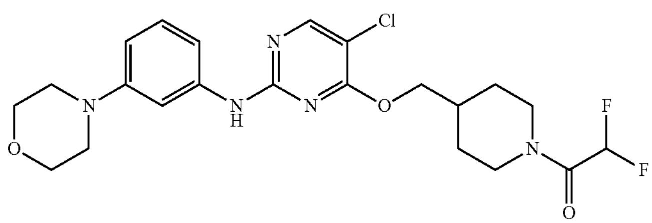 [SMILES: O=C(C(F)F)N1CCC(COc2nc(Nc3cccc(N4CCOCC4)c3)ncc2Cl)CC1] | 1-(4-(((5-chloro-2-((3-morpholinophenyl)amino)pyrimidin-4-yl)oxy)methyl)piperidin-1-yl)-2,2-difluoroethan-1-one |
| 111 | 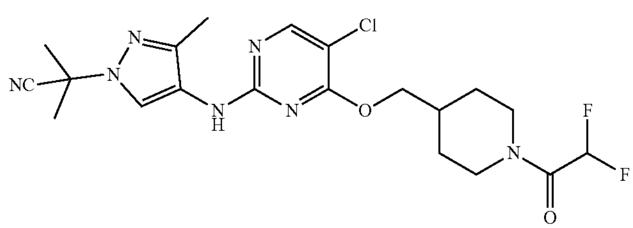 [SMILES: Cc1nn(C(C)(C)C#N)cc1Nc1ncc(Cl)c(OCC2CCN(C(=O)C(F)F)CC2)n1] | 2-(4-((5-chloro-4-((1-(2,2-difluoroacetyl)piperidin-4-yl)methoxy)pyrimidin-2-yl)amino)-3-methyl-1H-pyrazol-1-yl)-2-methylpropanenitrile |

TABLE 1-continued

Representative Compounds of Structure (I)

| Example | Structure | Name |
|---|---|---|
| 112 | 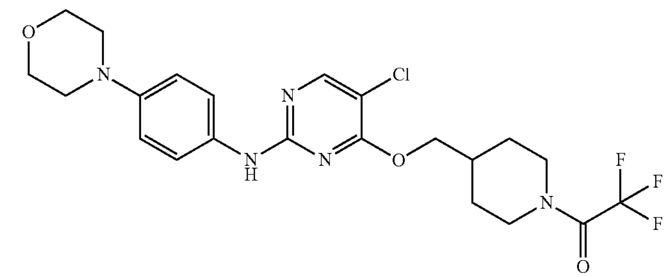 [SMILES: O=C(N1CCC(COc2nc(Nc3ccc(N4CCOCC4)cc3)ncc2Cl)CC1)C(F)(F)F] | 1-(4-(((5-chloro-2-((4-morpholinophenyl)amino)pyrimidin-4-yl)oxy)methyl)piperidin-1-yl)-2,2,2-trifluoroethan-1-one |
| 113 | 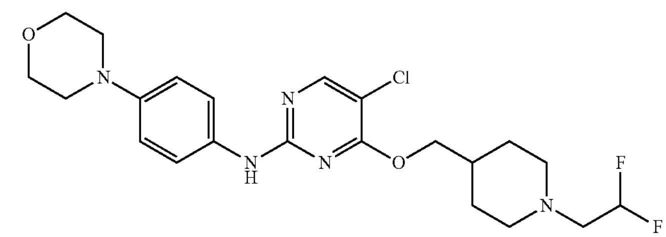 [SMILES: FC(F)CN1CCC(COc2nc(Nc3ccc(N4CCOCC4)cc3)ncc2Cl)CC1] | 5-chloro-4-((1-(2,2-difluoroethyl)piperidin-4-yl)methoxy)-N-(4-morpholinophenyl)pyrimidin-2-amine |
| 114 | 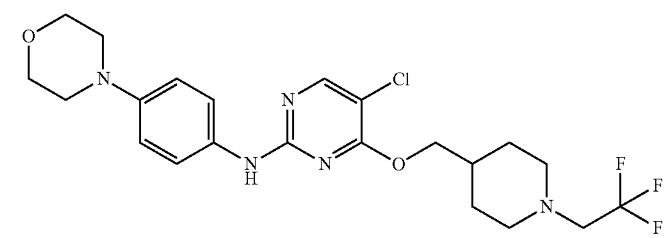 [SMILES: FC(F)(F)CN1CCC(COc2nc(Nc3ccc(N4CCOCC4)cc3)ncc2Cl)CC1] | 5-chloro-N-(4-morpholinophenyl)-4-((1-(2,2,2-trifluoroethyl)piperidin-4-yl)methoxy)pyrimidin-2-amine |
| 115 | 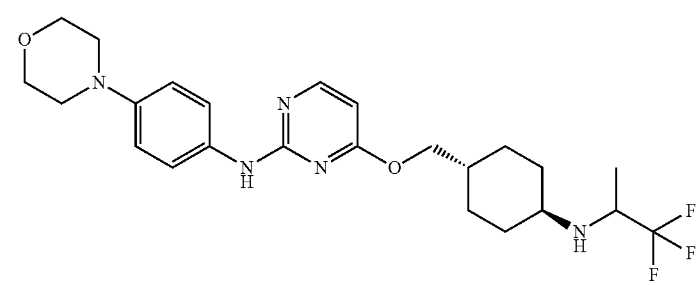 [SMILES: CC(N[C@H]1CC[C@H](COc2ccnc(Nc3ccc(N4CCOCC4)cc3)n2)CC1)C(F)(F)F] | N-(4-morpholinophenyl)-4-(((1R,4R)-4-((1,1,1-trifluoropropan-2-yl)amino)cyclohexyl)methoxy)pyrimidin-2-amine |
| 116 | 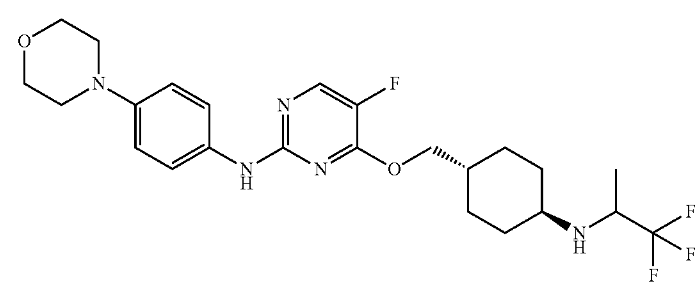 [SMILES: CC(N[C@H]1CC[C@H](COc2nc(Nc3ccc(N4CCOCC4)cc3)ncc2F)CC1)C(F)(F)F] | 5-fluoro-N-(4-morpholinophenyl)-4-(((1R,4R)-4-((1,1,1-trifluoropropan-2-yl)amino)cyclohexyl)methoxy)pyrimidin-2-amine |

TABLE 1-continued

Representative Compounds of Structure (I)

| Example | Structure | Name |
|---|---|---|
| 117 | 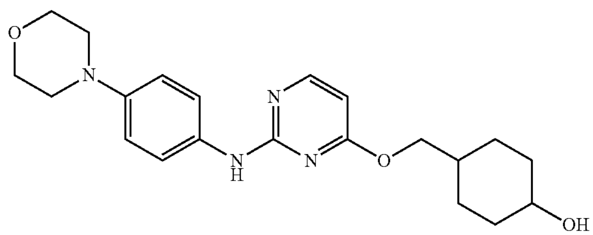 [SMILES: OC1CCC(COc2ccnc(Nc3ccc(N4CCOCC4)cc3)n2)CC1] | 4-(((2-((4-morpholinophenyl)amino)pyrimidin-4-yl)oxy)methyl)cyclohexanol |
| 118 | 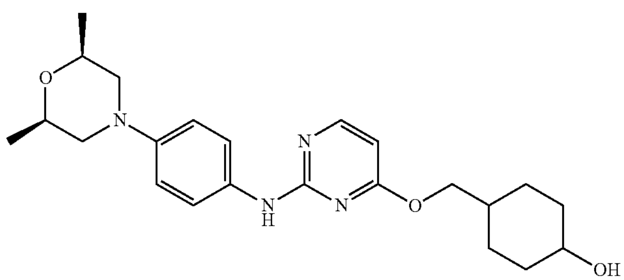 [SMILES: C[C@@H]1CN(c2ccc(Nc3nccc(OCC4CCC(O)CC4)n3)cc2)C[C@H](C)O1] | 4-(((2-((4-((2S,6R)-2,6-dimethylmorpholino)phenyl)amino)pyrimidin-4-yl)oxy)methyl)cyclohexan-1-ol |
| 119 | 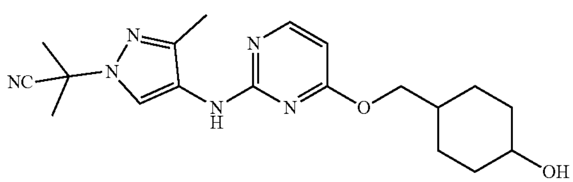 [SMILES: Cc1nn(C(C)(C)C#N)cc1Nc1nccc(OCC2CCC(O)CC2)n1] | 2-(4-((4-((4-hydroxycyclohexyl)methoxy)pyrimidin-2-yl)amino)-3-methyl-1H-pyrazol-1-yl)-2-methylpropanenitrile |
| 120 | 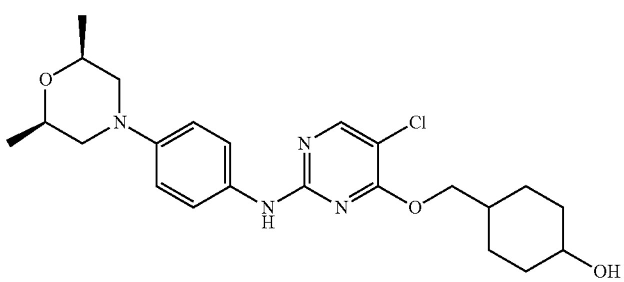 | 4-(((5-chloro-2-((4-((2S,6R)-2,6-dimethylmorpholino)phenyl)amino)pyrimidin-4-yl)oxy)methyl)cyclohexan-1-ol |
| 121 | 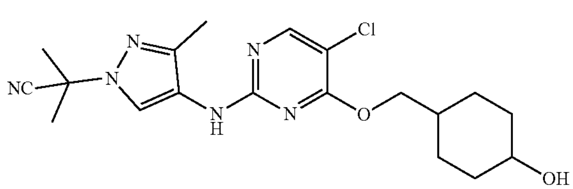 | 2-(4-((5-chloro-4-((4-hydroxycyclohexyl)methoxy)pyrimidin-2-yl)amino)-3-methyl-1H-pyrazol-1-yl)-2-methylpropanenitrile |
| 122 | 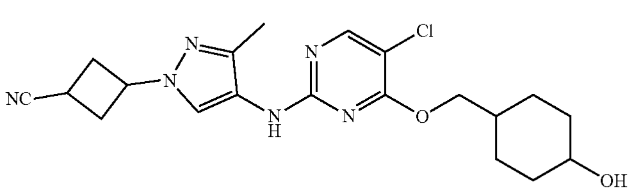 [SMILES: Cc1nn(C2CC(C#N)C2)cc1Nc1ncc(Cl)c(OCC2CCC(O)CC2)n1] | 3-(4-((5-chloro-4-((4-hydroxycyclohexyl)methoxy)pyrimidin-2-yl)amino)-3-methyl-1H-pyrazol-1-yl)cyclobutane-1-carbonitrile |

TABLE 1-continued

Representative Compounds of Structure (I)

| Example | Structure | Name |
|---|---|---|
| 123 | 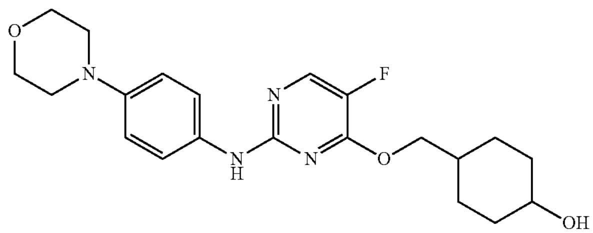 [SMILES: OC1CCC(COc2nc(Nc3ccc(N4CCOCC4)cc3)ncc2F)CC1] | 4-(((5-fluoro-2-((4-morpholinophenyl)amino)pyrimidin-4-yl)oxy)methyl)cyclohexan-1-ol |
| 124 | 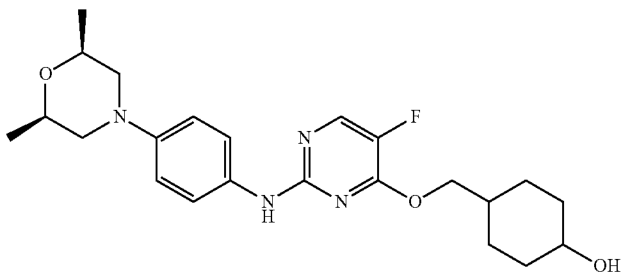 | 4-(((2-((4-((2S,6R)-2,6-dimethylmorpholino)phenyl)amino)-5-fluoropyrimidin-4-yl)oxy)methyl)cyclohexan-1-ol |
| 125 | 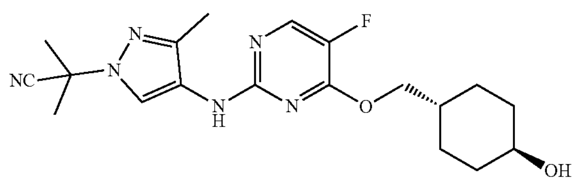 [SMILES: Cc1nn(C(C)(C)C#N)cc1Nc1ncc(F)c(OC[C@H]2CC[C@H](O)CC2)n1] | 2-(4-((5-fluoro-4-(((1R,4R)-4-hydroxycyclohexyl)methoxy)pyrimidin-2-yl)amino)-3-methyl-1H-pyrazol-1-yl)-2-methylpropanenitrile |
| 126 | 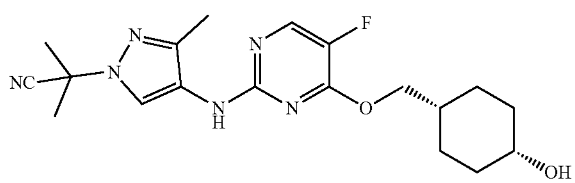 [SMILES: Cc1nn(C(C)(C)C#N)cc1Nc1ncc(F)c(OC[C@H]2CC[C@@H](O)CC2)n1] | 2-(4-((5-fluoro-4-(((1S,4S)-4-hydroxycyclohexyl)methoxy)pyrimidin-2-yl)amino)-3-methyl-1H-pyrazol-1-yl)-2-methylpropanenitrile |
| 127 | 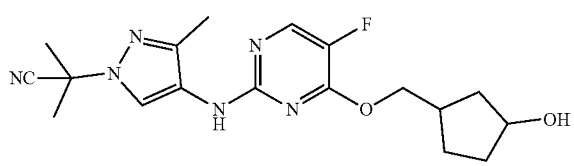 [SMILES: Cc1nn(C(C)(C)C#N)cc1Nc1ncc(F)c(OCC2CCC(O)C2)n1] | 2-(4-((5-fluoro-4-((3-hydroxycyclopentyl)methoxy)pyrimidin-2-yl)amino)-3-methyl-1H-pyrazol-1-yl)-2-methylpropanenitrile |
| 128 | 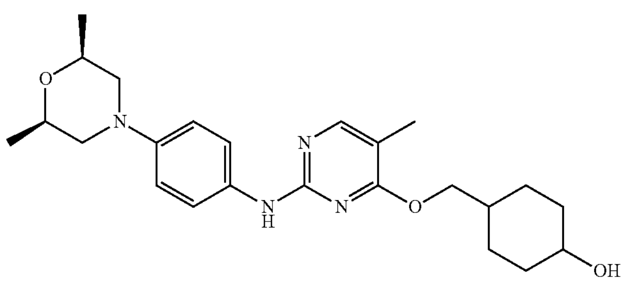 [SMILES: Cc1cnc(Nc2ccc(N3C[C@@H](C)O[C@@H](C)C3)cc2)nc1OCC1CCC(O)CC1] | 4-(((2-((4-((2S,6R)-2,6-dimethylmorpholino)phenyl)amino)-5-methylpyrimidin-4-yl)oxy)methyl)cyclohexan-1-ol |

TABLE 1-continued

Representative Compounds of Structure (I)

| Example | Structure | Name |
|---|---|---|
| 129 | 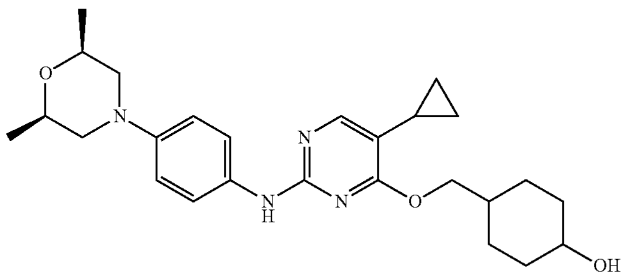 [SMILES: C[C@@H]1CN(c2ccc(Nc3ncc(C4CC4)c(OCC4CCC(O)CC4)n3)cc2)C[C@H](C)O1] | 4-(((5-cyclopropyl-2-((4-((2S,6R)-2,6-dimethylmorpholino)phenyl)amino)pyrimidin-4-yl)oxy)methyl)cyclohexan-1-ol |
| 130 | 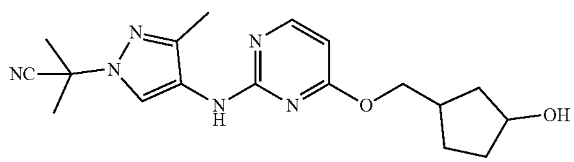 [SMILES: Cc1nn(C(C)(C)C#N)cc1Nc1nccc(OCC2CCC(O)C2)n1] | 2-(4-((4-((3-hydroxycyclopentyl)methoxy)pyrimidin-2-yl)amino)-3-methyl-1H-pyrazol-1-yl)-2-methylpropanenitrile |
| 131 | 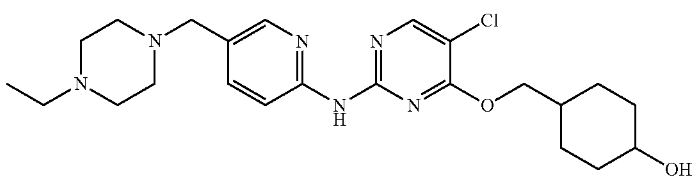 [SMILES: CCN1CCN(Cc2ccc(Nc3ncc(Cl)c(OCC4CCC(O)CC4)n3)nc2)CC1] | 4-(((5-chloro-2-((5-((4-ethylpiperazin-1-yl)methyl)pyridin-2-yl)amino)pyrimidin-4-yl)oxy)methyl)cyclohexan-1-ol |
| 132 | 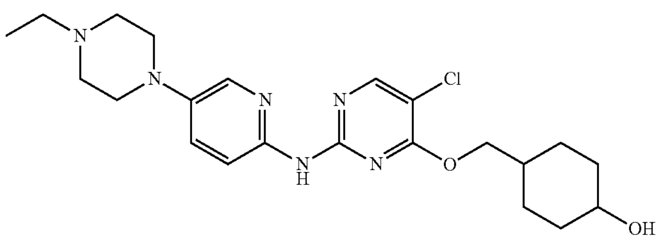 [SMILES: CCN1CCN(c2ccc(Nc3ncc(Cl)c(OCC4CCC(O)CC4)n3)nc2)CC1] | 4-(((5-chloro-2-((5-(4-ethylpiperazin-1-yl)pyridin-2-yl)amino)pyrimidin-4-yl)oxy)methyl)cyclohexan-1-ol |
| 133 | 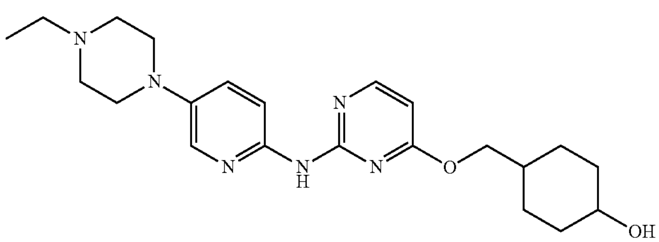 [SMILES: CCN1CCN(c2ccc(Nc3nccc(OCC4CCC(O)CC4)n3)nc2)CC1] | 4-(((2-((5-(4-ethylpiperazin-1-yl)pyridin-2-yl)amino)pyrimidin-4-yl)oxy)methyl)cyclohexan-1-ol |
| 134 | 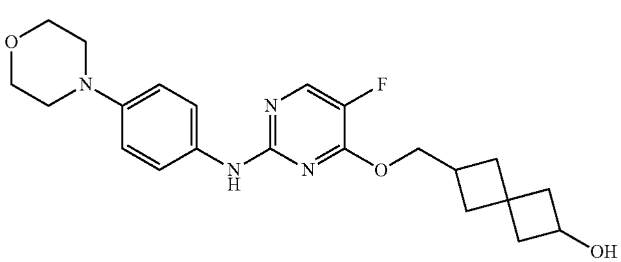 [SMILES: OC1CC2(C1)CC(COc1nc(Nc3ccc(N4CCOCC4)cc3)ncc1F)C2] | 6-(((5-fluoro-2-((4-morpholinophenyl)amino)pyrimidin-4-yl)oxy)methyl)spiro[3.3]heptan-2-ol |

TABLE 1-continued

Representative Compounds of Structure (I)

| Example | Structure | Name |
|---|---|---|
| 135 | 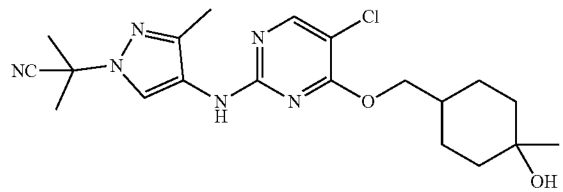 [SMILES: Cc1nn(C(C)(C)C#N)cc1Nc1ncc(Cl)c(OCC2CCC(C)(O)CC2)n1] | 2-(4-((5-chloro-4-((4-hydroxy-4-methylcyclohexyl)methoxy)pyrimidin-2-yl)amino)-3-methyl-1H-pyrazol-1-yl)-2-methylpropanenitrile |
| 136 | 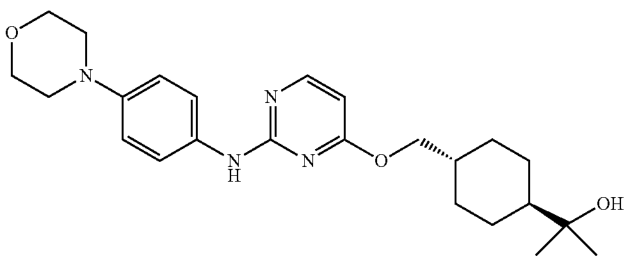 [SMILES: CC(C)(O)[C@H]1CC[C@H](COc2ccnc(Nc3ccc(N4CCOCC4)cc3)n2)CC1] | 2-((1R,4R)-4-(((2-((4-morpholinophenyl)amino)pyrimidin-4-yl)oxy)methyl)cyclohexyl)propan-2-ol |
| 137 | 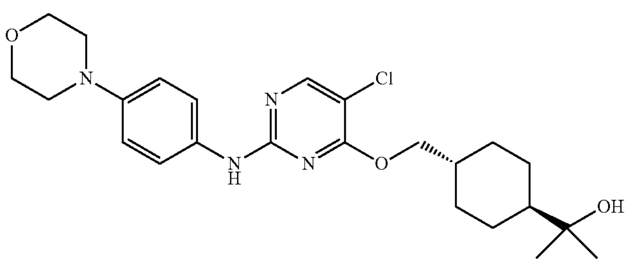 | 2-((1R,4R)-4-(((5-chloro-2-((4-morpholinophenyl)amino)pyrimidin-4-yl)oxy)methyl)cyclohexyl)propan-2-ol |
| 138 | 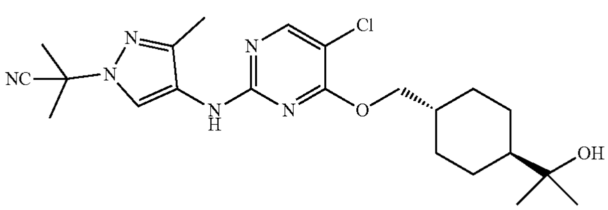 [SMILES: Cc1nn(C(C)(C)C#N)cc1Nc1ncc(Cl)c(OC[C@H]2CC[C@H](C(C)(C)O)CC2)n1] | 2-(4-((5-chloro-4-(((1R,4R)-4-(2-hydroxypropan-2-yl)cyclohexyl)methoxy)pyrimidin-2-yl)amino)-3-methyl-1H-pyrazol-1-yl)-2-methylpropanenitrile |
| 139 | 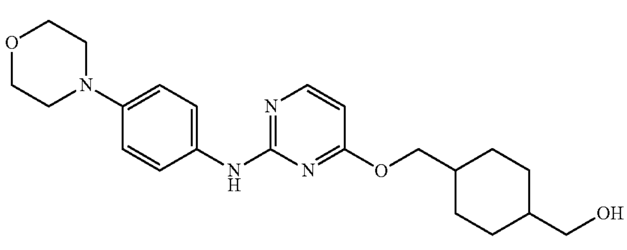 [SMILES: OCC1CCC(COc2ccnc(Nc3ccc(N4CCOCC4)cc3)n2)CC1] | (4-(((2-((4-morpholinophenyl)amino)pyrimidin-4-yl)oxy)methyl)cyclohexyl)methanol22 |
| 140 | 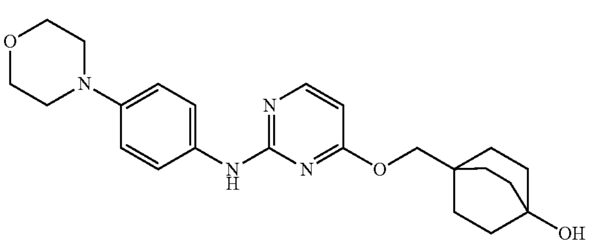 [SMILES: OC12CCC(COc3ccnc(Nc4ccc(N5CCOCC5)cc4)n3)(CC1)CC2] | 4-(((2-((4-morpholinophenyl)amino)pyrimidin-4-yl)oxy)methyl)bicyclo[2.2.2]octan-1-ol |

TABLE 1-continued

Representative Compounds of Structure (I)

| Example | Structure | Name |
|---|---|---|
| 141 | 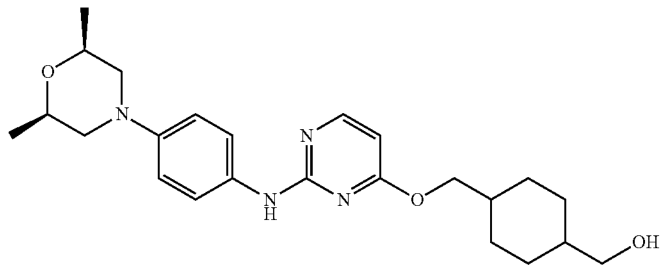 [SMILES: C[C@@H]1CN(c2ccc(Nc3nccc(OCC4CCC(CO)CC4)n3)cc2)C[C@H](C)O1] | (4-(((2-((4-((2R,6S)-2,6-dimethylmorpholino)phenyl)amino)pyrimidin-4-yl)oxy)methyl)cyclohexyl)methanol |
| 142 | 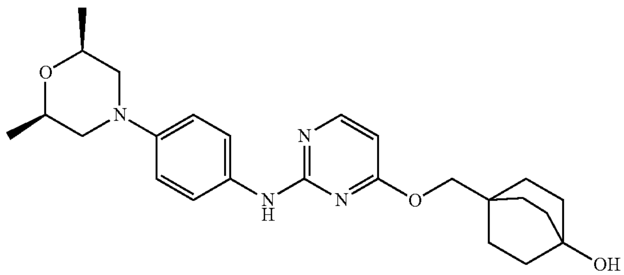 [SMILES: C[C@@H]1CN(c2ccc(Nc3nccc(OCC45CCC(O)(CC4)CC5)n3)cc2)C[C@H](C)O1] | 4-(((2-((4-((2S,6R)-2,6-dimethylmorpholino)phenyl)amino)pyrimidin-4-yl)oxy)methyl)bicyclo[2.2.2]octan-1-ol |
| 143 | 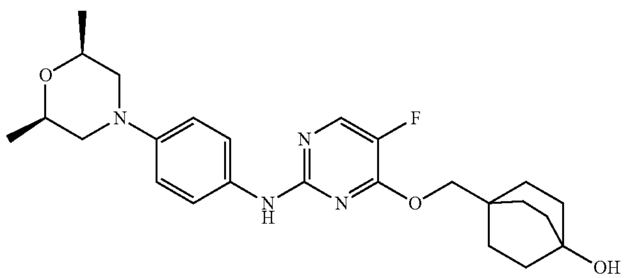 [SMILES: C[C@@H]1CN(c2ccc(Nc3ncc(F)c(OCC45CCC(O)(CC4)CC5)n3)cc2)C[C@H](C)O1] | 4-(((2-((4-((2S,6R)-2,6-dimethylmorpholino)phenyl)amino)-5-fluoropyrimidin-4-yl)oxy)methyl)bicyclo[2.2.2]octan-1-ol |
| 144 | 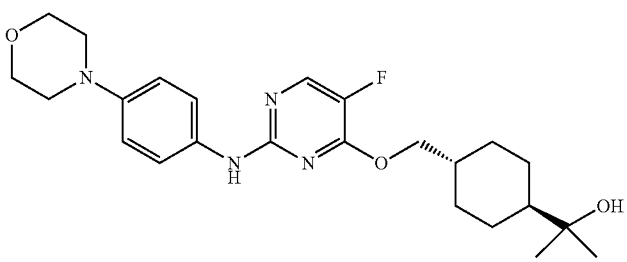 [SMILES: CC(C)(O)[C@H]1CC[C@H](COc2nc(Nc3ccc(N4CCOCC4)cc3)ncc2F)CC1] | 2-((1R,4R)-4-(((5-fluoro-2-((4-morpholinophenyl)amino)pyrimidin-4-yl)oxy)methyl)cyclohexyl)propan-2-ol |
| 145 | 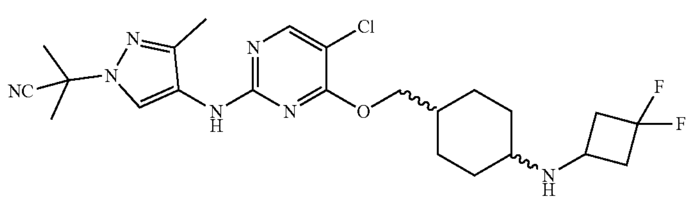 [SMILES: Cc1nn(C(C)(C)C#N)cc1Nc1ncc(Cl)c(OCC2CCC(NC3CC(F)(F)C3)CC2)n1] | 2-(4-((5-chloro-4-((4-((3,3-difluorocyclobutyl)amino)cyclohexyl)methoxy)pyrimidin-2-yl)amino)-3-methyl-1H-pyrazol-1-yl)-2-methylpropanenitrile (1$^{st}$ eluting peak) |
| 146 | 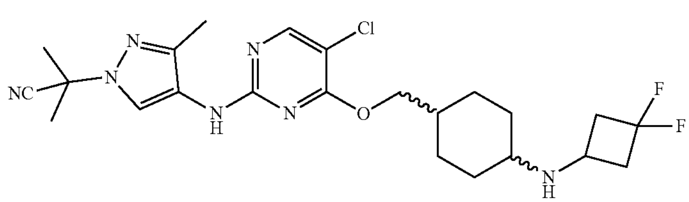 [SMILES: Cc1nn(C(C)(C)C#N)cc1Nc1ncc(Cl)c(OCC2CCC(NC3CC(F)(F)C3)CC2)n1] | 2-(4-((5-chloro-4-((4-((3,3-difluorocyclobutyl)amino)cyclohexyl)methoxy)pyrimidin-2-yl)amino)-3-methyl-1H-pyrazol-1-yl)-2-methylpropanenitrile (2$^{nd}$ eluting peak) |

TABLE 1-continued

Representative Compounds of Structure (I)

| Example | Structure | Name |
|---|---|---|
| 147 | 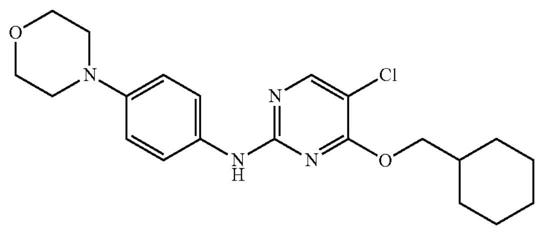 [SMILES: Clc1cnc(Nc2ccc(N3CCOCC3)cc2)nc1OCC1CCCCC1] | 5-chloro-4-(cyclohexylmethoxy)-N-(4-morpholinophenyl)pyrimidin-2-amine |
| 148 | 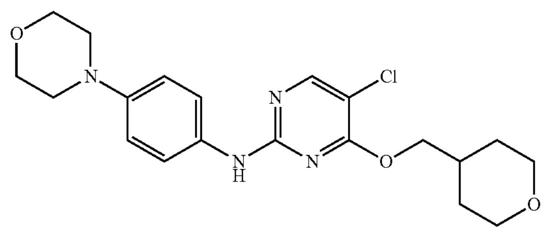 [SMILES: Clc1cnc(Nc2ccc(N3CCOCC3)cc2)nc1OCC1CCOCC1] | 5-chloro-N-(4-morpholinophenyl)-4-((tetrahydro-2H-pyran-4-yl)methoxy)pyrimidin-2-amine |
| 149 | 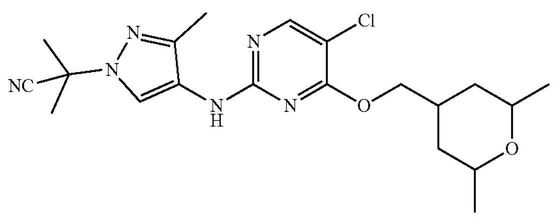 [SMILES: Cc1nn(C(C)(C)C#N)cc1Nc1ncc(Cl)c(OCC2CC(C)OC(C)C2)n1] | 2-(4-((5-chloro-4-((2,6-dimethyltetrahydro-2H-pyran-4-yl)methoxy)pyrimidin-2-yl)amino)-3-methyl-1H-pyrazol-1-yl)-2-methylpropanenitrile |
| 150 | 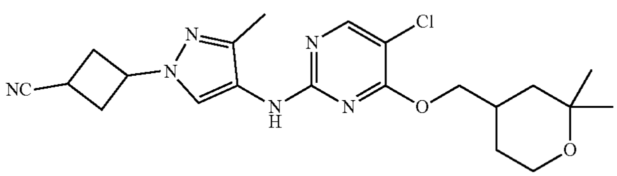 [SMILES: Cc1nn(C2CC(C#N)C2)cc1Nc1ncc(Cl)c(OCC2CCOC(C)(C)C2)n1] | 3-(4-((5-chloro-4-((2,2-dimethyltetrahydro-2H-pyran-4-yl)methoxy)pyrimidin-2-yl)amino)-3-methyl-1H-pyrazol-1-yl)cyclobutane-1-carbonitrile |
| 151 | 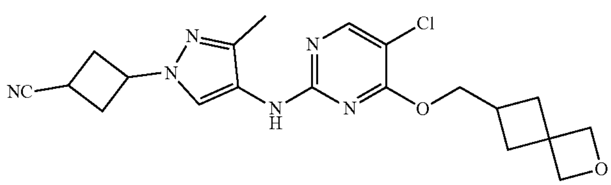 [SMILES: Cc1nn(C2CC(C#N)C2)cc1Nc1ncc(Cl)c(OCC2CC3(COC3)C2)n1] | 3-(4-((4-((2-oxaspiro[3.3]heptan-6-yl)methoxy)-5-chloropyrimidin-2-yl)amino)-3-methyl-1H-pyrazol-1-yl)cyclobutane-1-carbonitrile |
| 152 | 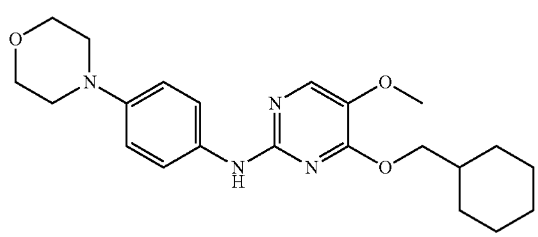 | 4-(cyclohexylmethoxy)-5-methoxy-N-(4-morpholinophenyl)pyrimidin-2-amine |
| 153 | 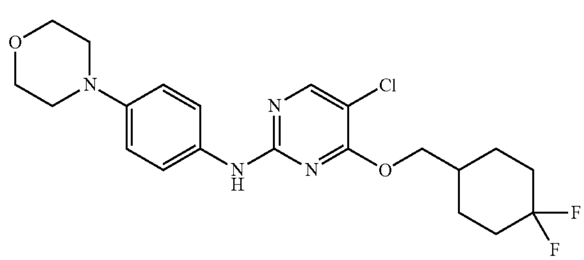 | 5-chloro-4-((4,4-difluorocyclohexyl)methoxy)-N-(4-morpholinophenyl)pyrimidin-2-amine |

TABLE 1-continued

Representative Compounds of Structure (I)

| Example | Structure | Name |
|---|---|---|
| 154 | 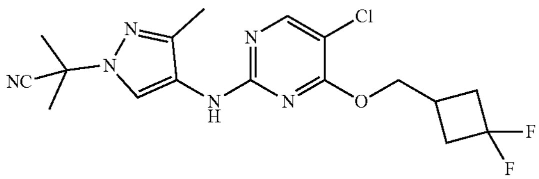 [SMILES: Cc1nn(C(C)(C)C#N)cc1Nc1ncc(Cl)c(OCC2CC(F)(F)C2)n1] | 2-(4-((5-chloro-4-((3,3-difluorocyclobutyl)methoxy)pyrimidin-2-yl)amino)-3-methyl-1H-pyrazol-1-yl)-2-methylpropanenitrile |
| 155 | 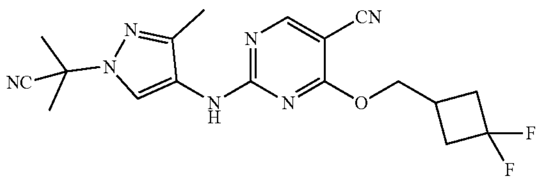 [SMILES: Cc1nn(C(C)(C)C#N)cc1Nc1ncc(C#N)c(OCC2CC(F)(F)C2)n1] | 2-((1-(2-cyanopropan-2-yl)-3-methyl-1H-pyrazol-4-yl)amino)-4-((3,3-difluorocyclobutyl)methoxy)pyrimidine-5-carbonitrile |
| 156 | 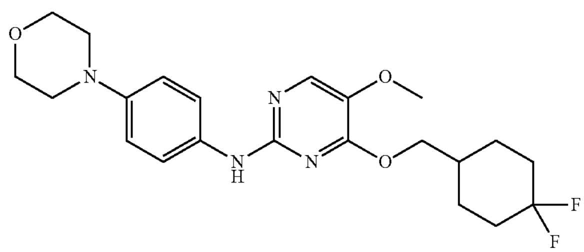 | 4-((4,4-difluorocyclohexyl)methoxy)-5-methoxy-N-(4-morpholinophenyl)pyrimidin-2-amine |
| 157 | 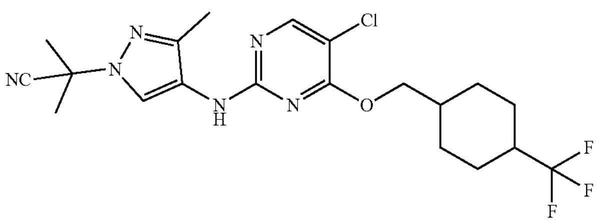 [SMILES: Cc1nn(C(C)(C)C#N)cc1Nc1ncc(Cl)c(OCC2CCC(C(F)(F)F)CC2)n1] | 2-(4-((5-chloro-4-((4-(trifluoromethyl)cyclohexyl)methoxy)pyrimidin-2-yl)amino)-3-methyl-1H-pyrazol-1-yl)-2-methylpropanenitrile |
| 158 | 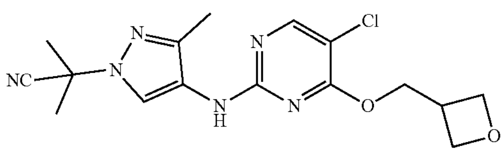 [SMILES: Cc1nn(C(C)(C)C#N)cc1Nc1ncc(Cl)c(OCC2COC2)n1] | 2-(4-((5-chloro-4-(oxetan-3-ylmethoxy)pyrimidin-2-yl)amino)-3-methyl-1H-pyrazol-1-yl)-2-methylpropanenitrile |
| 159 | 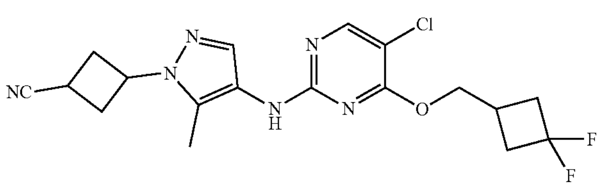 [SMILES: Cc1c(Nc2ncc(Cl)c(OCC3CC(F)(F)C3)n2)cnn1C1CC(C#N)C1] | 3-(4-((5-chloro-4-((3,3-difluorocyclobutyl)methoxy)pyrimidin-2-yl)amino)-5-methyl-1H-pyrazol-1-yl)cyclobutane-1-carbonitrile |
| 160 | 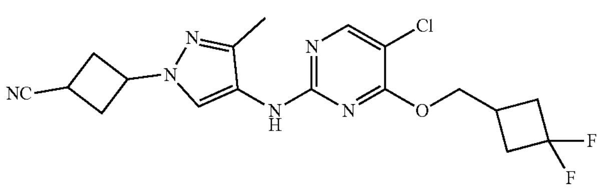 [SMILES: Cc1nn(C2CC(C#N)C2)cc1Nc1ncc(Cl)c(OCC2CC(F)(F)C2)n1] | 3-(4-((5-chloro-4-((3,3-difluorocyclobutyl)methoxy)pyrimidin-2-yl)amino)-3-methyl-1H-pyrazol-1-yl)cyclobutane-1-carbonitrile |

TABLE 1-continued

Representative Compounds of Structure (I)

| Example | Structure | Name |
|---|---|---|
| 161 | 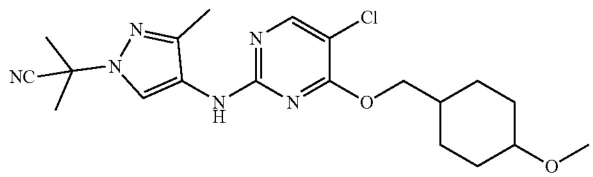 [SMILES: COC1CCC(COc2nc(Nc3cn(C(C)(C)C#N)nc3C)ncc2Cl)CC1] | 2-(4-((5-chloro-4-((4-methoxycyclohexyl)methoxy)pyrimidin-2-yl)amino)-3-methyl-1H-pyrazol-1-yl)-2-methylpropanenitrile |
| 162 | 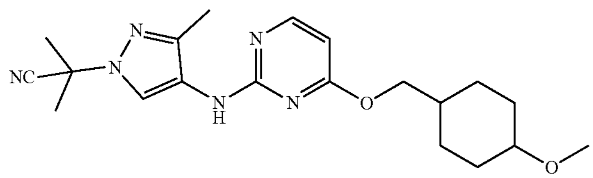 [SMILES: COC1CCC(COc2ccnc(Nc3cn(C(C)(C)C#N)nc3C)n2)CC1] | 2-(4-((4-((4-methoxycyclohexyl)methoxy)pyrimidin-2-yl)amino)-3-methyl-1H-pyrazol-1-yl)-2-methylpropanenitrile |
| 163 | 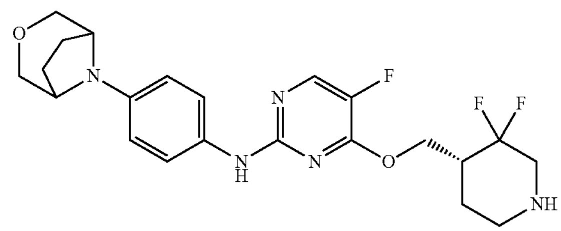 [SMILES: Fc1cnc(Nc2ccc(N3C4CCC3COC4)cc2)nc1OC[C@H]1CCNCC1(F)F] | N-(4-(3-oxa-8-azabicyclo[3.2.1]octan-8-yl)phenyl)-4-((3,3-difluoropiperidin-4-yl)methoxy)-5-fluoropyrimidin-2-amine |
| 164 | 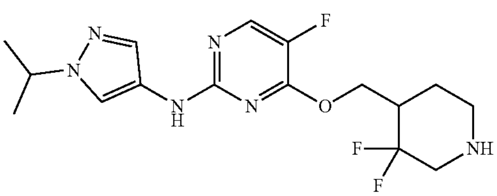 [SMILES: CC(C)n1cc(Nc2ncc(F)c(OCC3CCNCC3(F)F)n2)cn1] | 4-((3,3-difluoropiperidin-4-yl)methoxy)-5-fluoro-N-(1-isopropyl-1H-pyrazol-4-yl)pyrimidin-2-amine |
| 165 | 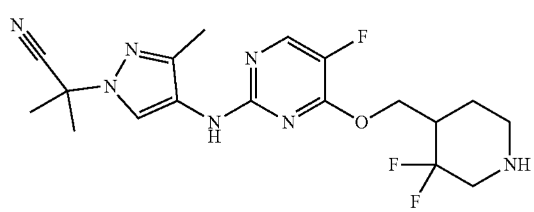 [SMILES: Cc1nn(C(C)(C)C#N)cc1Nc1ncc(F)c(OCC2CCNCC2(F)F)n1] | 2-(4-((4-((3,3-difluoropiperidin-4-yl)methoxy)-5-fluoropyrimidin-2-yl)amino)-3-methyl-1H-pyrazol-1-yl)-2-methylpropanenitrile |
| 166 | 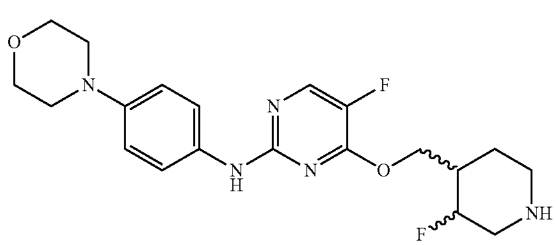 [SMILES: Fc1cnc(Nc2ccc(N3CCOCC3)cc2)nc1OCC1CCNCC1F] | 5-fluoro-4-((3-fluoropiperidin-4-yl)methoxy)-N-(4-morpholinophenyl)pyrimidin-2-amine (1$^{st}$ eluting peak) |
| 167 | 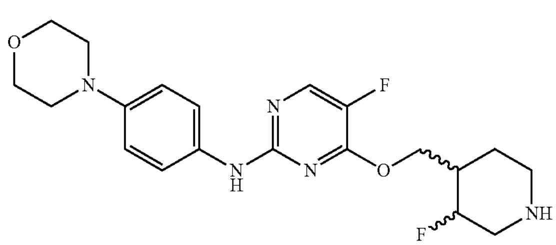 [SMILES: Fc1cnc(Nc2ccc(N3CCOCC3)cc2)nc1OCC1CCNCC1F] | 5-fluoro-4-((3-fluoropiperidin-4-yl)methoxy)-N-(4-morpholinophenyl)pyrimidin-2-amine (2$^{nd}$ eluting peak) |

TABLE 1-continued

Representative Compounds of Structure (I)

| Example | Structure | Name |
|---|---|---|
| 168 | 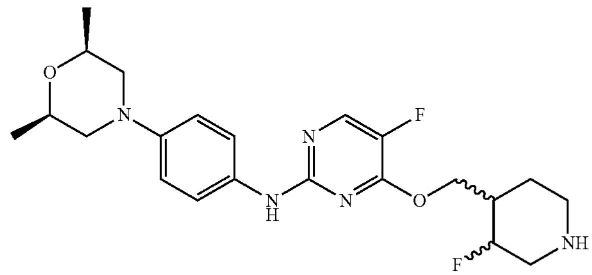 [SMILES: C[C@@H]1CN(c2ccc(Nc3ncc(F)c(OCC4CCNCC4F)n3)cc2)C[C@H](C)O1] | N-(4-((2S,6R)-2,6-dimethylmorpholino)phenyl)-5-fluoro-4-((3-fluoropiperidin-4-yl)methoxy)pyrimidin-2-amine (1st eluting peak) |
| 169 | 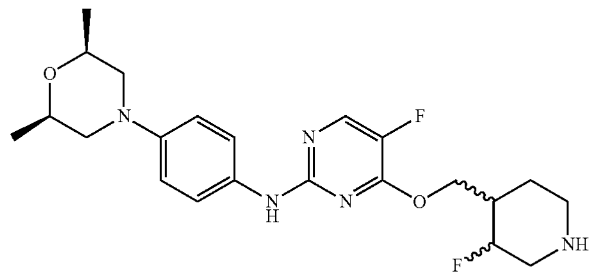 [SMILES: C[C@@H]1CN(c2ccc(Nc3ncc(F)c(OCC4CCNCC4F)n3)cc2)C[C@H](C)O1] | N-(4-((2S,6R)-2,6-dimethylmorpholino)phenyl)-5-fluoro-4-((3-fluoropiperidin-4-yl)methoxy)pyrimidin-2-amine (2nd eluting peak) |
| 170 | 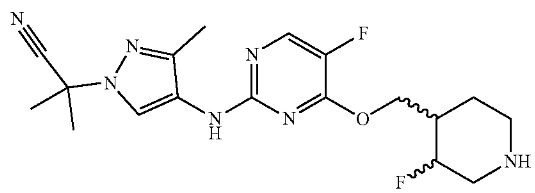 [SMILES: Cc1nn(C(C)(C)C#N)cc1Nc1ncc(F)c(OCC2CCNCC2F)n1] | 2-(4-((5-fluoro-4-((3-fluoropiperidin-4-yl)methoxy)pyrimidin-2-yl)amino)-3-methyl-1H-pyrazol-1-yl)-2-methylpropanenitrile (1st eluting peak) |
| 171 | 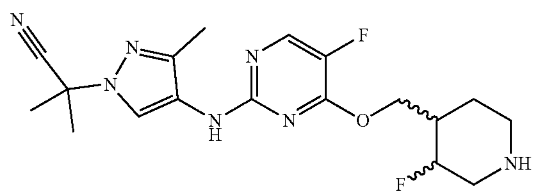 [SMILES: Cc1nn(C(C)(C)C#N)cc1Nc1ncc(F)c(OCC2CCNCC2F)n1] | 2-(4-((5-fluoro-4-((3-fluoropiperidin-4-yl)methoxy)pyrimidin-2-yl)amino)-3-methyl-1H-pyrazol-1-yl)-2-methylpropanenitrile (2nd eluting peak) |
| 172 | 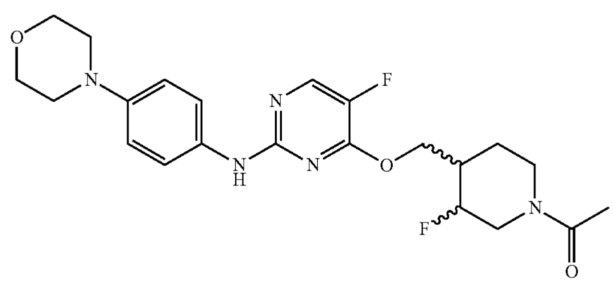 [SMILES: CC(=O)N1CCC(COc2nc(Nc3ccc(N4CCOCC4)cc3)ncc2F)C(F)C1] | 1-(3-fluoro-4-(((5-fluoro-2-((4-morpholinophenyl)amino)pyrimidin-4-yl)oxy)methyl)piperidin-1-yl)ethan-1-one (1st eluting peak) |
| 173 | 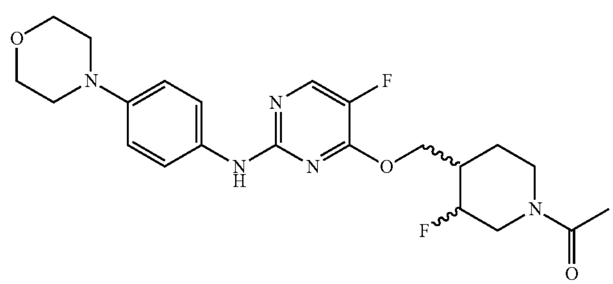 [SMILES: CC(=O)N1CCC(COc2nc(Nc3ccc(N4CCOCC4)cc3)ncc2F)C(F)C1] | 1-(3-fluoro-4-(((5-fluoro-2-((4-morpholinophenyl)amino)pyrimidin-4-yl)oxy)methyl)piperidin-1-yl)ethan-1-one (2nd eluting peak) |

TABLE 1-continued

Representative Compounds of Structure (I)

| Example | Structure | Name |
|---|---|---|
| 174 | 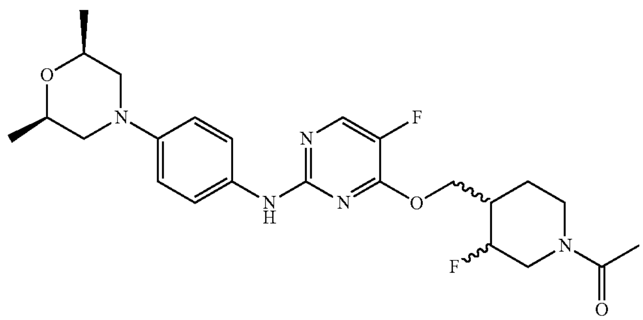 [SMILES: CC(=O)N1CCC(COc2nc(Nc3ccc(N4C[C@@H](C)O[C@@H](C)C4)cc3)ncc2F)C(F)C1] | 1-(4-(((2-((4-((2S,6R)-2,6-dimethylmorpholino)phenyl)amino)-5-fluoropyrimidin-4-yl)oxy)methyl)-3-fluoropiperidin-1-yl)ethan-1-one (1$^{st}$ eluting peak) |
| 175 | 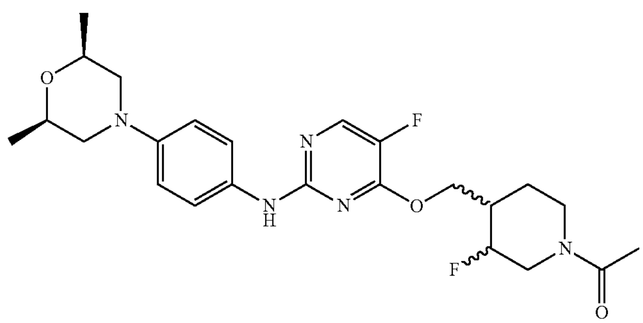 [SMILES: CC(=O)N1CCC(COc2nc(Nc3ccc(N4C[C@@H](C)O[C@@H](C)C4)cc3)ncc2F)C(F)C1] | 1-(4-(((2-((4-((2S,6R)-2,6-dimethylmorpholino)phenyl)amino)-5-fluoropyrimidin-4-yl)oxy)methyl)-3-fluoropiperidin-1-yl)ethan-1-one (2$^{nd}$ eluting peak) |
| 176 | 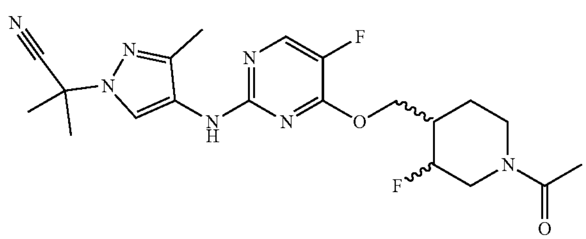 [SMILES: CC(=O)N1CCC(COc2nc(Nc3cn(C(C)(C)C#N)nc3C)ncc2F)C(F)C1] | 2-(4-((4-((1-acetyl-3-fluoropiperidin-4-yl)methoxy)-5-fluoropyrimidin-2-yl)amino)-3-methyl-1H-pyrazol-1-yl)-2-methylpropanenitrile (1$^{st}$ eluting peak) |
| 177 | 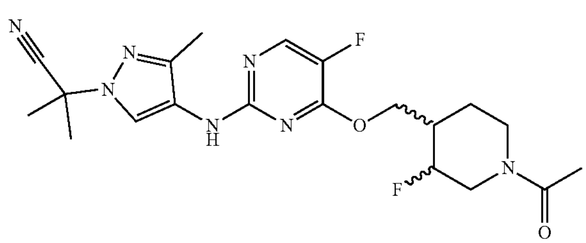 [SMILES: CC(=O)N1CCC(COc2nc(Nc3cn(C(C)(C)C#N)nc3C)ncc2F)C(F)C1] | 2-(4-((4-((1-acetyl-3-fluoropiperidin-4-yl)methoxy)-5-fluoropyrimidin-2-yl)amino)-3-methyl-1H-pyrazol-1-yl)-2-methylpropanenitrile (2$^{nd}$ eluting peak) |
| 178 | 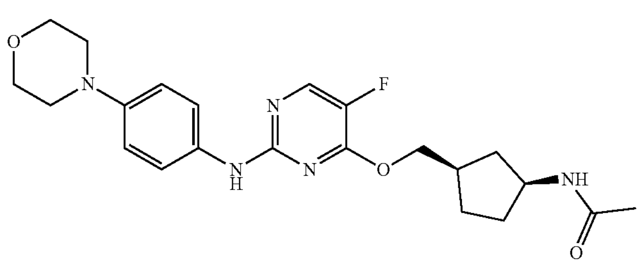 [SMILES: CC(=O)N[C@H]1CC[C@@H](COc2nc(Nc3ccc(N4CCOCC4)cc3)ncc2F)C1] | N-((1S,3R)-3-(((5-fluoro-2-((4-morpholinophenyl)amino)pyrimidin-4-yl)oxy)methyl)cyclopentyl)acetamide |

TABLE 1-continued

Representative Compounds of Structure (I)

| Example | Structure | Name |
|---|---|---|
| 179 | 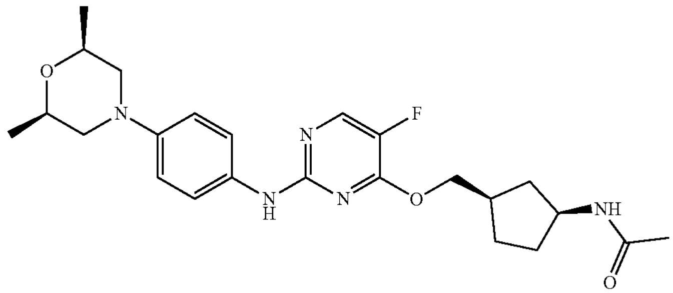 [SMILES: CC(=O)N[C@H]1CC[C@@H](COc2nc(Nc3ccc(N4C[C@@H](C)O[C@@H](C)C4)cc3)ncc2F)C1] | N-((1S,3R)-3-(((2-((4-((2S,6R)-2,6-dimethylmorpholino)phenyl)amino)-5-fluoropyrimidin-4-yl)oxy)methyl)cyclopentyl)acetamide |
| 180 | 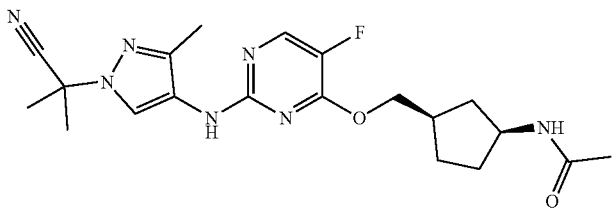 [SMILES: CC(=O)N[C@H]1CC[C@@H](COc2nc(Nc3cn(C(C)(C)C#N)nc3C)ncc2F)C1] | N-((1S,3R)-3-(((2-((1-(2-cyanopropan-2-yl)-3-methyl-1H-pyrazol-4-yl)amino)-5-fluoropyrimidin-4-yl)oxy)methyl)cyclopentyl)acetamide |
| 181 | 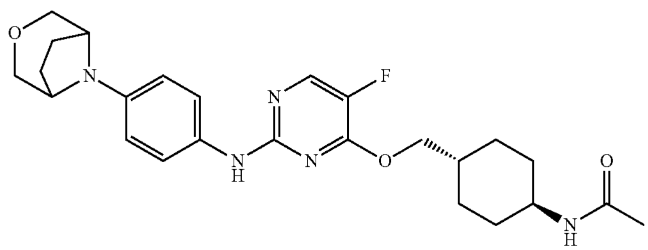 [SMILES: CC(=O)N[C@H]1CC[C@H](COc2nc(Nc3ccc(N4C5CCC4COC5)cc3)ncc2F)CC1] | N-((1R,4R)-4-(((2-((4-(3-oxa-8-azabicyclo[3.2.1]octan-8-yl)phenyl)amino)-5-fluoropyrimidin-4-yl)oxy)methyl)cyclohexyl)acetamide |
| 182 | 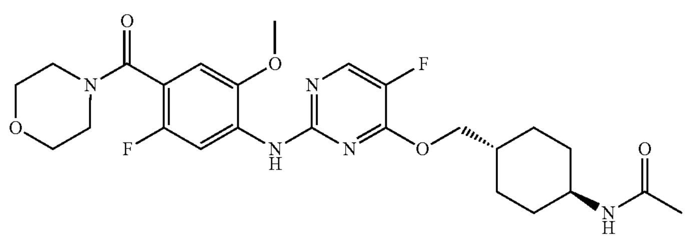 [SMILES: COc1cc(C(=O)N2CCOCC2)c(F)cc1Nc1ncc(F)c(OC[C@H]2CC[C@H](NC(C)=O)CC2)n1] | N-((1R,4R)-4-(((5-fluoro-2-((5-fluoro-2-methoxy-4-(morpholine-4-carbonyl)phenyl)amino)pyrimidin-4-yl)oxy)methyl)cyclohexyl)acetamide |
| 183 | 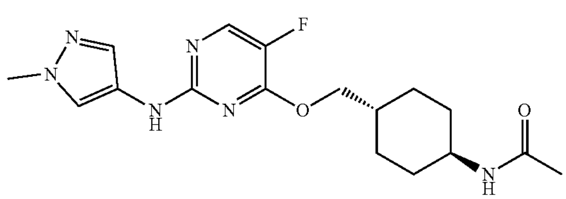 [SMILES: CC(=O)N[C@H]1CC[C@H](COc2nc(Nc3cnn(C)c3)ncc2F)CC1] | N-((1R,4R)-4-(((5-fluoro-2-((1-methyl-1H-pyrazol-4-yl)amino)pyrimidin-4-yl)oxy)methyl)cyclohexyl)acetamide |
| 184 | 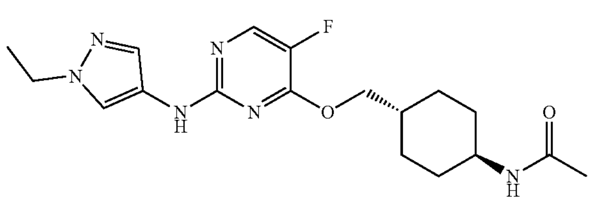 [SMILES: CCn1cc(Nc2ncc(F)c(OC[C@H]3CC[C@H](NC(C)=O)CC3)n2)cn1] | N-((1R,4R)-4-(((2-((1-ethyl-1H-pyrazol-4-yl)amino)-5-fluoropyrimidin-4-yl)oxy)methyl)cyclohexyl)acetamide |

TABLE 1-continued

Representative Compounds of Structure (I)

| Example | Structure | Name |
|---|---|---|
| 185 | 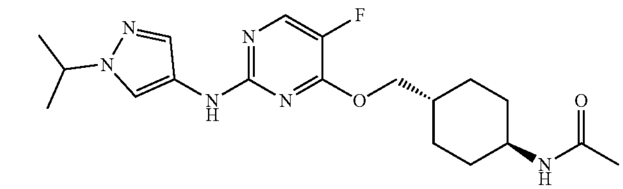 [SMILES: CC(=O)N[C@H]1CC[C@H](COc2nc(Nc3cnn(C(C)C)c3)ncc2F)CC1] | N-((1R,4R)-4-(((5-fluoro-2-((1-isopropyl-1H-pyrazol-4-yl)amino)pyrimidin-4-yl)oxy)methyl)cyclohexyl)acetamide |
| 186 | 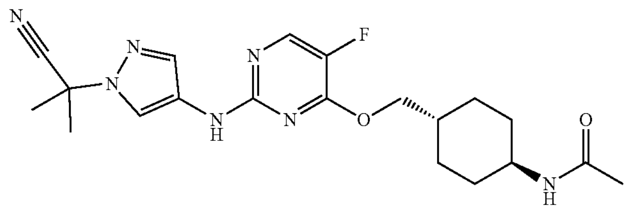 [SMILES: CC(=O)N[C@H]1CC[C@H](COc2nc(Nc3cnn(C(C)(C)C#N)c3)ncc2F)CC1] | N-((1R,4R)-4-(((2-((1-(2-cyanopropan-2-yl)-1H-pyrazol-4-yl)amino)-5-fluoropyrimidin-4-yl)oxy)methyl)cyclohexyl)acetamide |
| 187 | 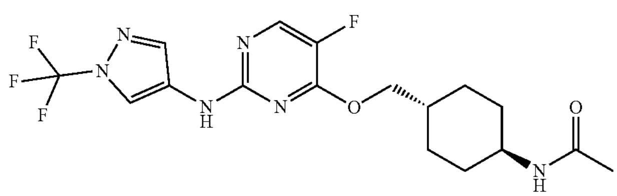 [SMILES: CC(=O)N[C@H]1CC[C@H](COc2nc(Nc3cnn(C(F)(F)F)c3)ncc2F)CC1] | N-((1R,4R)-4-(((5-fluoro-2-((1-(trifluoromethyl)-1H-pyrazol-4-yl)amino)pyrimidin-4-yl)oxy)methyl)cyclohexyl)acetamide |
| 188 | 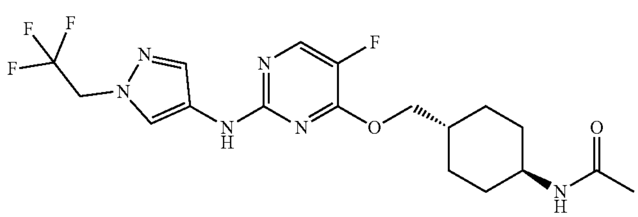 [SMILES: CC(=O)N[C@H]1CC[C@H](COc2nc(Nc3cnn(CC(F)(F)F)c3)ncc2F)CC1] | N-((1R,4R)-4-(((5-fluoro-2-((1-(2,2,2-trifluoroethyl)-1H-pyrazol-4-yl)amino)pyrimidin-4-yl)oxy)methyl)cyclohexyl)acetamide |
| 189 | 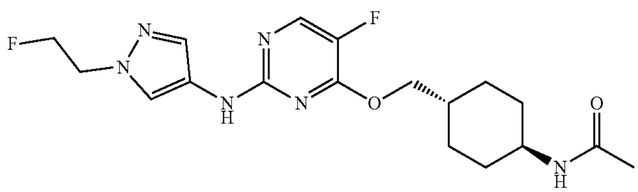 [SMILES: CC(=O)N[C@H]1CC[C@H](COc2nc(Nc3cnn(CCF)c3)ncc2F)CC1] | N-((1R,4R)-4-(((5-fluoro-2-((1-(2-fluoroethyl)-1H-pyrazol-4-yl)amino)pyrimidin-4-yl)oxy)methyl)cyclohexyl)acetamide |
| 190 | 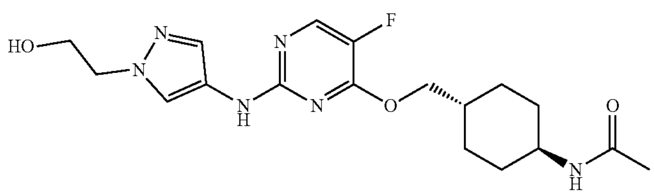 [SMILES: CC(=O)N[C@H]1CC[C@H](COc2nc(Nc3cnn(CCO)c3)ncc2F)CC1] | N-((1R,4R)-4-(((5-fluoro-2-((1-(2-hydroxyethyl)-1H-pyrazol-4-yl)amino)pyrimidin-4-yl)oxy)methyl)cyclohexyl)acetamide |
| 191 | 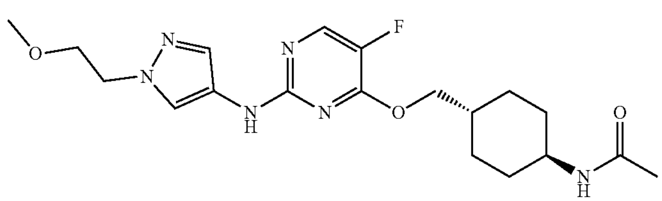 [SMILES: COCCn1cc(Nc2ncc(F)c(OC[C@H]3CC[C@H](NC(C)=O)CC3)n2)cn1] | N-((1R,4R)-4-(((5-fluoro-2-((1-(2-methoxyethyl)-1H-pyrazol-4-yl)amino)pyrimidin-4-yl)oxy)methyl)cyclohexyl)acetamide |

TABLE 1-continued

Representative Compounds of Structure (I)

| Example | Structure | Name |
|---|---|---|
| 192 | 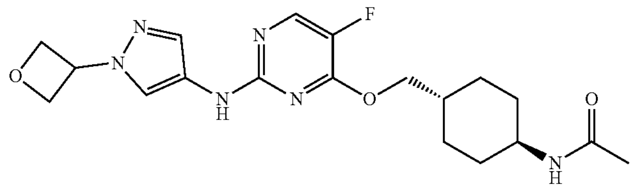 [SMILES: CC(=O)N[C@H]1CC[C@H](COc2nc(Nc3cnn(C4COC4)c3)ncc2F)CC1] | N-((1R,4R)-4-(((5-fluoro-2-((1-(oxetan-3-yl)-1H-pyrazol-4-yl)amino)pyrimidin-4-yl)oxy)methyl)cyclohexyl)acetamide |
| 193 | 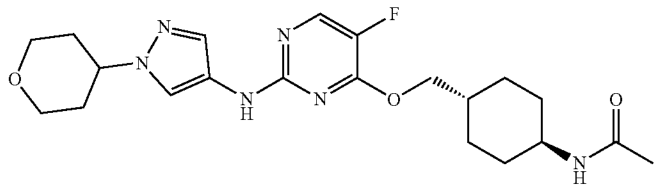 [SMILES: CC(=O)N[C@H]1CC[C@H](COc2nc(Nc3cnn(C4CCOCC4)c3)ncc2F)CC1] | N-((1R,4R)-4-(((5-fluoro-2-((1-(tetrahydro-2H-pyran-4-yl)-1H-pyrazol-4-yl)amino)pyrimidin-4-yl)oxy)methyl)cyclohexyl)acetamide |
| 194 | 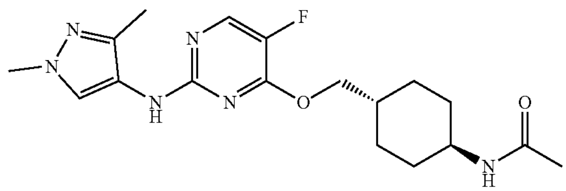 [SMILES: CC(=O)N[C@H]1CC[C@H](COc2nc(Nc3cn(C)nc3C)ncc2F)CC1] | N-((1R,4R)-4-(((2-((1,3-dimethyl-1H-pyrazol-4-yl)amino)-5-fluoropyrimidin-4-yl)oxy)methyl)cyclohexyl)acetamide |
| 195 | 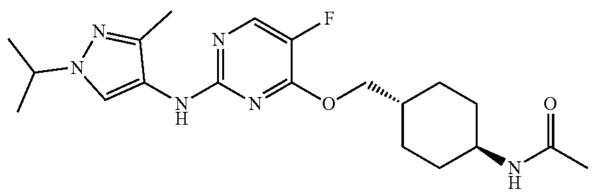 [SMILES: CC(=O)N[C@H]1CC[C@H](COc2nc(Nc3cn(C(C)C)nc3C)ncc2F)CC1] | N-((1R,4R)-4-(((5-fluoro-2-((1-isopropyl-3-methyl-1H-pyrazol-4-yl)amino)pyrimidin-4-yl)oxy)methyl)cyclohexyl)acetamide |
| 196 | 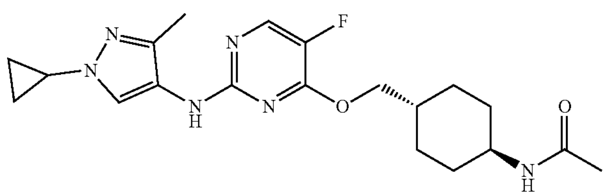 [SMILES: CC(=O)N[C@H]1CC[C@H](COc2nc(Nc3cn(C4CC4)nc3C)ncc2F)CC1] | N-((1R,4R)-4-(((2-((1-cyclopropyl-3-methyl-1H-pyrazol-4-yl)amino)-5-fluoropyrimidin-4-yl)oxy)methyl)cyclohexyl)acetamide |
| 197 | 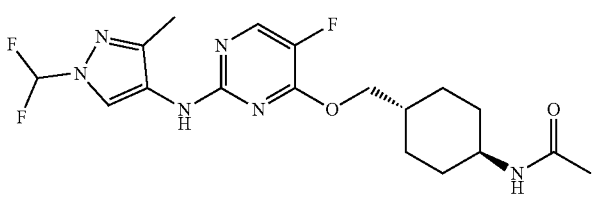 [SMILES: CC(=O)N[C@H]1CC[C@H](COc2nc(Nc3cn(C(F)F)nc3C)ncc2F)CC1] | N-((1R,4R)-4-(((2-((1-(difluoromethyl)-3-methyl-1H-pyrazol-4-yl)amino)-5-fluoropyrimidin-4-yl)oxy)methyl)cyclohexyl)acetamide |
| 198 | 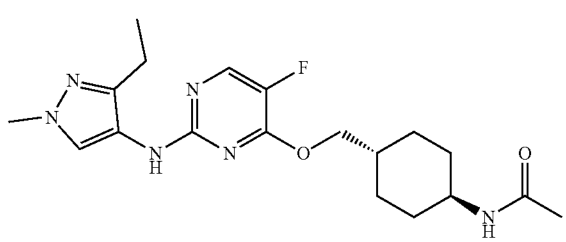 [SMILES: CCc1nn(C)cc1Nc1ncc(F)c(OC[C@H]2CC[C@H](NC(C)=O)CC2)n1] | N-((1R,4R)-4-(((2-((3-ethyl-1-methyl-1H-pyrazol-4-yl)amino)-5-fluoropyrimidin-4-yl)oxy)methyl)cyclohexyl)acetamide |

TABLE 1-continued

Representative Compounds of Structure (I)

| Example | Structure | Name |
|---|---|---|
| 199 | 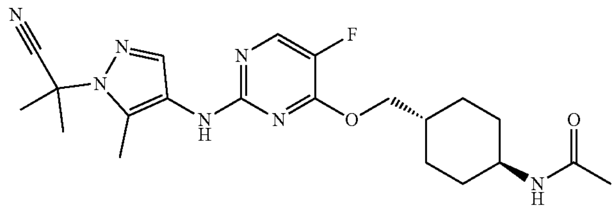 [SMILES: CC(=O)N[C@H]1CC[C@H](COc2nc(Nc3cnn(C(C)(C)C#N)c3C)ncc2F)CC1] | N-((1R,4R)-4-(((2-((1-(2-cyanopropan-2-yl)-5-methyl-1H-pyrazol-4-yl)amino)-5-fluoropyrimidin-4-yl)oxy)methyl)cyclohexyl)acetamide |
| 200 | 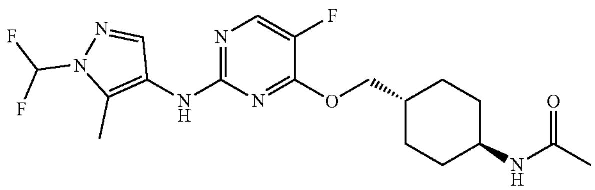 [SMILES: CC(=O)N[C@H]1CC[C@H](COc2nc(Nc3cnn(C(F)F)c3C)ncc2F)CC1] | N-((1R,4R)-4-(((2-((1-(difluoromethyl)-5-methyl-1H-pyrazol-4-yl)amino)-5-fluoropyrimidin-4-yl)oxy)methyl)cyclohexyl)acetamide |
| 201 | 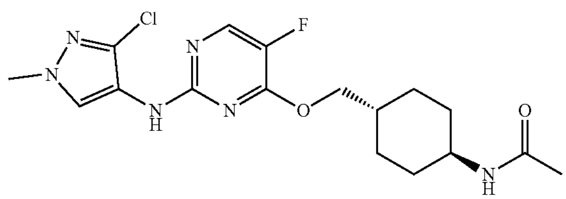 [SMILES: CC(=O)N[C@H]1CC[C@H](COc2nc(Nc3cn(C)nc3Cl)ncc2F)CC1] | N-((1R,4R)-4-(((2-((3-chloro-1-methyl-1H-pyrazol-4-yl)amino)-5-fluoropyrimidin-4-yl)oxy)methyl)cyclohexyl)acetamide |
| 202 | 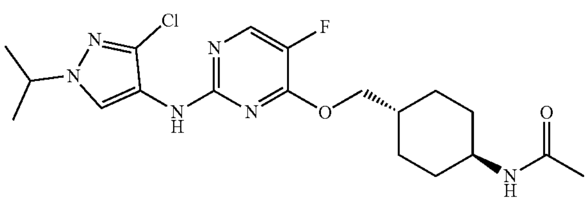 [SMILES: CC(=O)N[C@H]1CC[C@H](COc2nc(Nc3cn(C(C)C)nc3Cl)ncc2F)CC1] | N-((1R,4R)-4-(((2-((3-chloro-1-isopropyl-1H-pyrazol-4-yl)amino)-5-fluoropyrimidin-4-yl)oxy)methyl)cyclohexyl)acetamide |
| 203 | 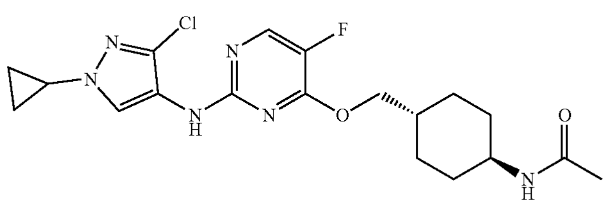 [SMILES: CC(=O)N[C@H]1CC[C@H](COc2nc(Nc3cn(C4CC4)nc3Cl)ncc2F)CC1] | N-((1R,4R)-4-(((2-((3-chloro-1-cyclopropyl-1H-pyrazol-4-yl)amino)-5-fluoropyrimidin-4-yl)oxy)methyl)cyclohexyl)acetamide |
| 204 | 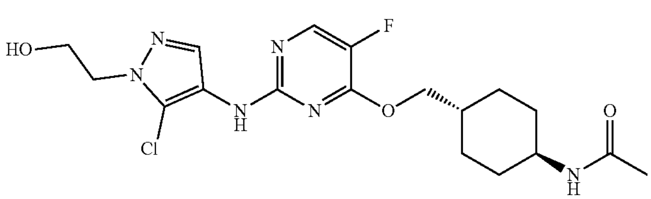 [SMILES: CC(=O)N[C@H]1CC[C@H](COc2nc(Nc3cnn(CCO)c3Cl)ncc2F)CC1] | N-((1R,4R)-4-(((2-((5-chloro-1-(2-hydroxyethyl)-1H-pyrazol-4-yl)amino)-5-fluoropyrimidin-4-yl)oxy)methyl)cyclohexyl)acetamide |
| 205 | 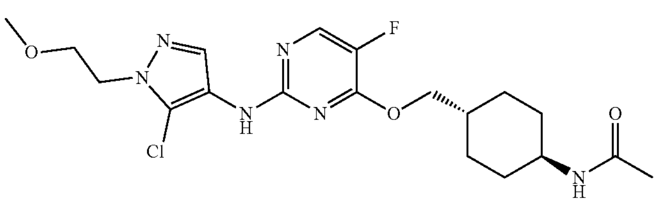 [SMILES: COCCn1ncc(Nc2ncc(F)c(OC[C@H]3CC[C@H](NC(C)=O)CC3)n2)c1Cl] | N-((1R,4R)-4-(((2-((5-chloro-1-(2-methoxyethyl)-1H-pyrazol-4-yl)amino)-5-fluoropyrimidin-4-yl)oxy)methyl)cyclohexyl)acetamide |

TABLE 1-continued

Representative Compounds of Structure (I)

| Example | Structure | Name |
|---|---|---|
| 206 | 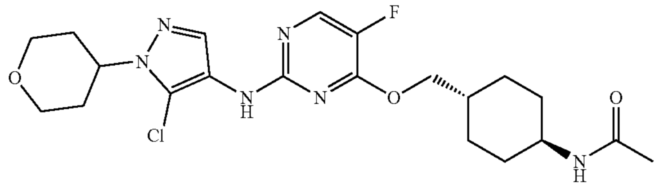 [SMILES: CC(=O)N[C@H]1CC[C@H](COc2nc(Nc3cnn(C4CCOCC4)c3Cl)ncc2F)CC1] | N-((1R,4R)-4-(((2-((5-chloro-1-(tetrahydro-2H-pyran-4-yl)-1H-pyrazol-4-yl)amino)-5-fluoropyrimidin-4-yl)oxy)methyl)cyclohexyl)acetamide |
| 207 | 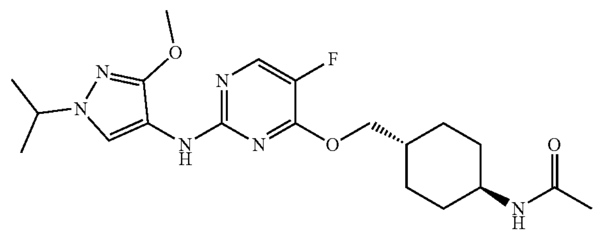 [SMILES: COc1nn(C(C)C)cc1Nc1ncc(F)c(OC[C@H]2CC[C@H](NC(C)=O)CC2)n1] | N-((1R,4R)-4-(((5-fluoro-2-((1-isopropyl-3-methoxy-1H-pyrazol-4-yl)amino)pyrimidin-4-yl)oxy)methyl)cyclohexyl)acetamide |
| 208 | 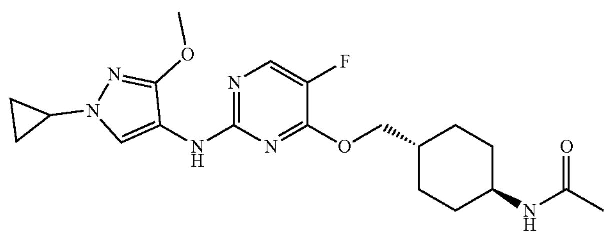 [SMILES: COc1nn(C2CC2)cc1Nc1ncc(F)c(OC[C@H]2CC[C@H](NC(C)=O)CC2)n1] | N-((1R,4R)-4-(((2-((1-cyclopropyl-3-methoxy-1H-pyrazol-4-yl)amino)-5-fluoropyrimidin-4-yl)oxy)methyl)cyclohexyl)acetamide |
| 209 | 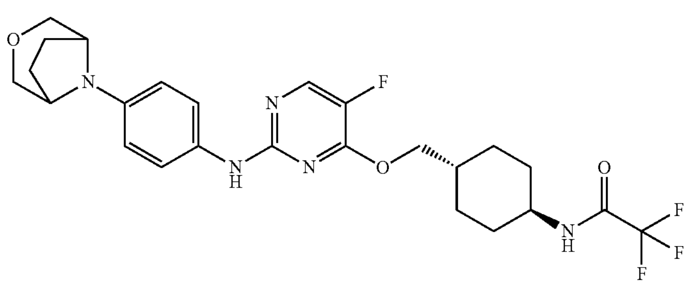 [SMILES: O=C(N[C@H]1CC[C@H](COc2nc(Nc3ccc(N4C5CCC4COC5)cc3)ncc2F)CC1)C(F)(F)F] | N-((1R,4R)-4-(((2-((4-(3-oxa-8-azabicyclo[3.2.1]octan-8-yl)phenyl)amino)-5-fluoropyrimidin-4-yl)oxy)methyl)cyclohexyl)-2,2,2-trifluoroacetamide |
| 210 | 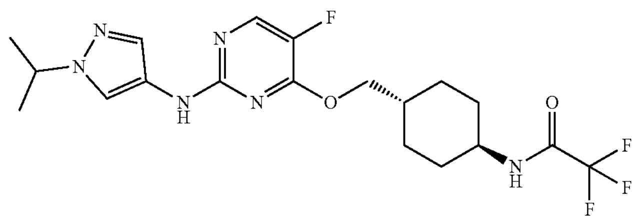 [SMILES: CC(C)n1cc(Nc2ncc(F)c(OC[C@H]3CC[C@H](NC(=O)C(F)(F)F)CC3)n2)cn1] | 2,2,2-trifluoro-N-((1R,4R)-4-(((5-fluoro-2-((1-isopropyl-1H-pyrazol-4-yl)amino)pyrimidin-4-yl)oxy)methyl)cyclohexyl)acetamide |
| 211 | 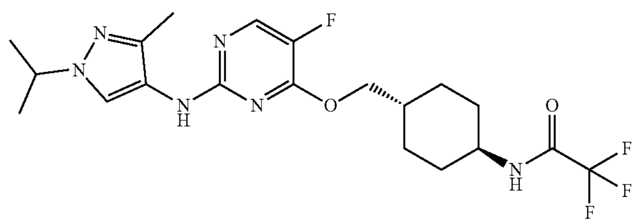 [SMILES: Cc1nn(C(C)C)cc1Nc1ncc(F)c(OC[C@H]2CC[C@H](NC(=O)C(F)(F)F)CC2)n1] | 2,2,2-trifluoro-N-((1R,4R)-4-(((5-fluoro-2-((1-isopropyl-3-methyl-1H-pyrazol-4-yl)amino)pyrimidin-4-yl)oxy)methyl)cyclohexyl)acetamide |

TABLE 1-continued

Representative Compounds of Structure (I)

| Example | Structure | Name |
|---|---|---|
| 212 | 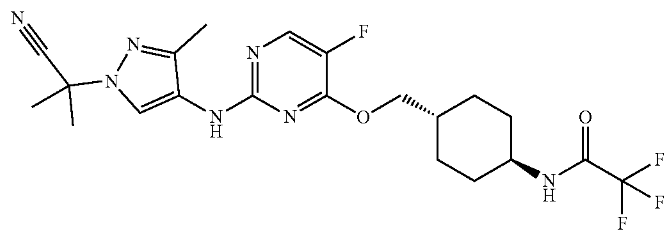 [SMILES: Cc1nn(C(C)(C)C#N)cc1Nc1ncc(F)c(OC[C@H]2CC[C@H](NC(=O)C(F)(F)F)CC2)n1] | N-((1R,4R)-4-(((2-((1-(2-cyanopropan-2-yl)-3-methyl-1H-pyrazol-4-yl)amino)-5-fluoropyrimidin-4-yl)oxy)methyl)cyclohexyl)-2,2,2-trifluoroacetamide |
| 213 | 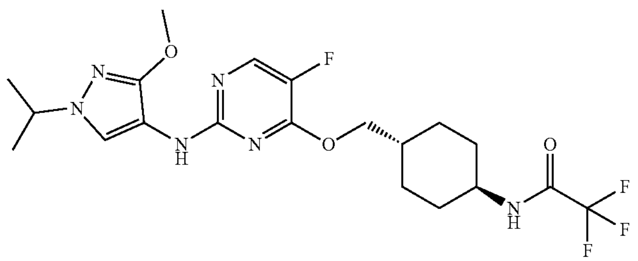 [SMILES: COc1nn(C(C)C)cc1Nc1ncc(F)c(OC[C@H]2CC[C@H](NC(=O)C(F)(F)F)CC2)n1] | 2,2,2-trifluoro-N-((1R,4R)-4-(((5-fluoro-2-((1-isopropyl-3-methoxy-1H-pyrazol-4-yl)amino)pyrimidin-4-yl)oxy)methyl)cyclohexyl)acetamide |
| 214 | 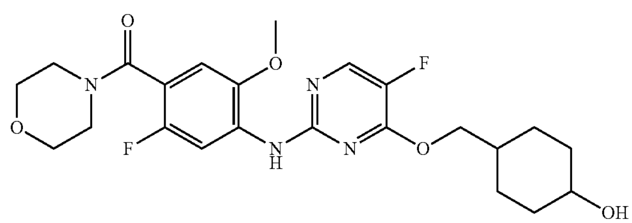 [SMILES: COc1cc(C(=O)N2CCOCC2)c(F)cc1Nc1ncc(F)c(OCC2CCC(O)CC2)n1] | (2-fluoro-4-((5-fluoro-4-((4-hydroxycyclohexyl)methoxy)pyrimidin-2-yl)amino)-5-methoxyphenyl)(morpholino)methanone |
| 215 | 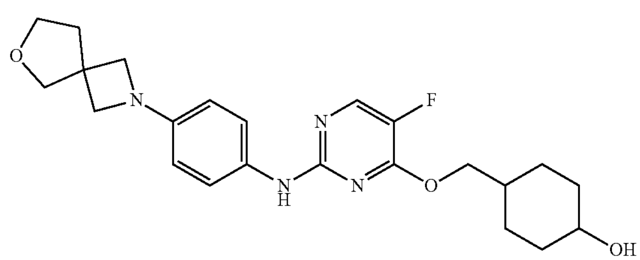 [SMILES: OC1CCC(COc2nc(Nc3ccc(N4CC5(CCOC5)C4)cc3)ncc2F)CC1] | 4-(((2-((4-(6-oxa-2-azaspiro[3.4]octan-2-yl)phenyl)amino)-5-fluoropyrimidin-4-yl)oxy)methyl)cyclohexan-1-ol |
| 216 | 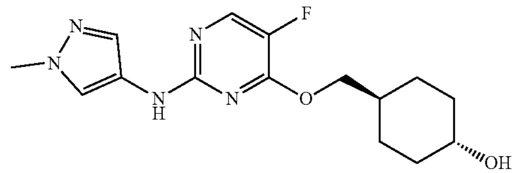 [SMILES: Cn1cc(Nc2ncc(F)c(OC[C@H]3CC[C@H](O)CC3)n2)cn1] | (1R,4R)-4-(((5-fluoro-2-((1-methyl-1H-pyrazol-4-yl)amino)pyrimidin-4-yl)oxy)methyl)cyclohexan-1-ol |
| 217 | 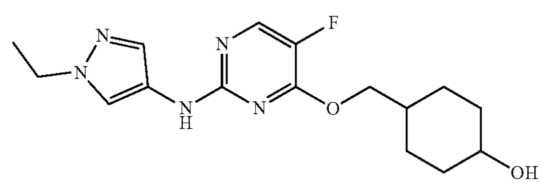 [SMILES: CCn1cc(Nc2ncc(F)c(OCC3CCC(O)CC3)n2)cn1] | 4-(((2-((1-ethyl-1H-pyrazol-4-yl)amino)-5-fluoropyrimidin-4-yl)oxy)methyl)cyclohexan-1-ol |
| 218 | 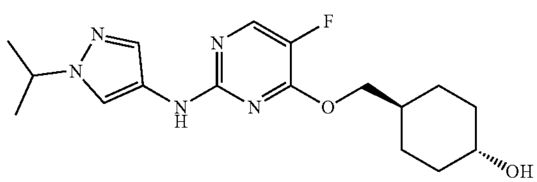 [SMILES: CC(C)n1cc(Nc2ncc(F)c(OC[C@H]3CC[C@H](O)CC3)n2)cn1] | (1R,4R)-4-(((5-fluoro-2-((1-isopropyl-1H-pyrazol-4-yl)amino)pyrimidin-4-yl)oxy)methyl)cyclohexan-1-ol |

TABLE 1-continued

Representative Compounds of Structure (I)

| Example | Structure | Name |
|---|---|---|
| 219 | 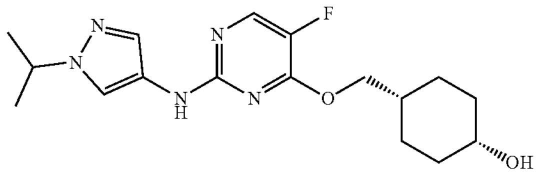 [SMILES: CC(C)n1cc(Nc2ncc(F)c(OC[C@H]3CC[C@@H](O)CC3)n2)cn1] | (1S,4S)-4-(((5-fluoro-2-((1-isopropyl-1H-pyrazol-4-yl)amino)pyrimidin-4-yl)oxy)methyl)cyclohexan-1-ol |
| 220 | 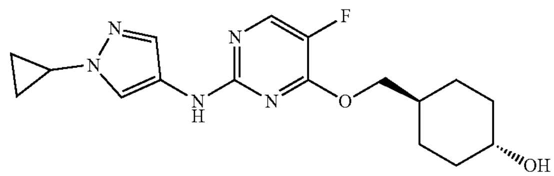 [SMILES: O[C@H]1CC[C@H](COc2nc(Nc3cnn(C4CC4)c3)ncc2F)CC1] | (1R,4R)-4-(((2-((1-cyclopropyl-1H-pyrazol-4-yl)amino)-5-fluoropyrimidin-4-yl)oxy)methyl)cyclohexan-1-ol |
| 221 | 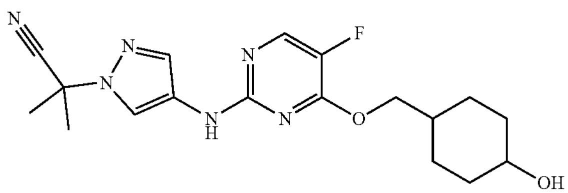 [SMILES: CC(C)(C#N)n1cc(Nc2ncc(F)c(OCC3CCC(O)CC3)n2)cn1] | 2-(4-((5-fluoro-4-((4-hydroxycyclohexyl)methoxy)pyrimidin-2-yl)amino)-1H-pyrazol-1-yl)-2-methylpropanenitrile |
| 222 | 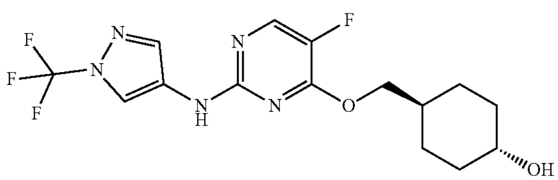 [SMILES: O[C@H]1CC[C@H](COc2nc(Nc3cnn(C(F)(F)F)c3)ncc2F)CC1] | (1R,4R)-4-(((5-fluoro-2-((1-(trifluoromethyl)-1H-pyrazol-4-yl)amino)pyrimidin-4-yl)oxy)methyl)cyclohexan-1-ol |
| 223 | 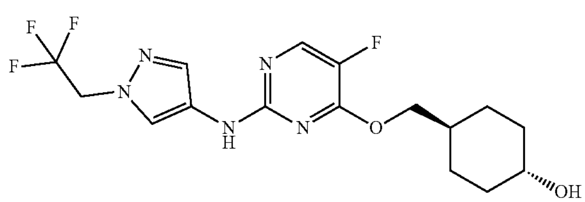 [SMILES: O[C@H]1CC[C@H](COc2nc(Nc3cnn(CC(F)(F)F)c3)ncc2F)CC1] | (1R,4R)-4-(((5-fluoro-2-((1-(2,2,2-trifluoroethyl)-1H-pyrazol-4-yl)amino)pyrimidin-4-yl)oxy)methyl)cyclohexan-1-ol |
| 224 | 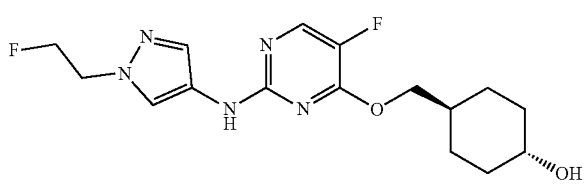 [SMILES: O[C@H]1CC[C@H](COc2nc(Nc3cnn(CCF)c3)ncc2F)CC1] | (1R,4R)-4-(((5-fluoro-2-((1-(2-fluoroethyl)-1H-pyrazol-4-yl)amino)pyrimidin-4-yl)oxy)methyl)cyclohexan-1-ol |
| 225 | 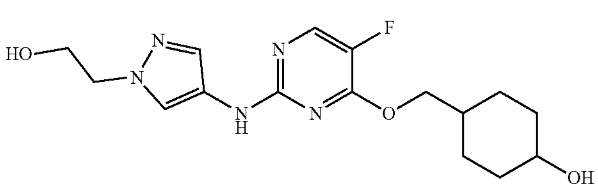 [SMILES: OCCn1cc(Nc2ncc(F)c(OCC3CCC(O)CC3)n2)cn1] | 4-(((5-fluoro-2-((1-(2-hydroxyethyl)-1H-pyrazol-4-yl)amino)pyrimidin-4-yl)oxy)methyl)cyclohexan-1-ol |
| 226 | 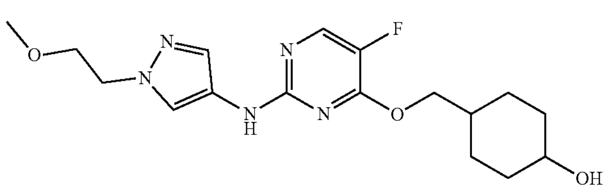 [SMILES: COCCn1cc(Nc2ncc(F)c(OCC3CCC(O)CC3)n2)cn1] | 4-(((5-fluoro-2-((1-(2-methoxyethyl)-1H-pyrazol-4-yl)amino)pyrimidin-4-yl)oxy)methyl)cyclohexan-1-ol |

TABLE 1-continued

Representative Compounds of Structure (I)

| Example | Structure | Name |
|---|---|---|
| 227 | 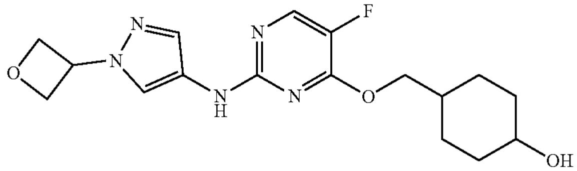 [SMILES: OC1CCC(COc2nc(Nc3cnn(C4COC4)c3)ncc2F)CC1] | 4-(((5-fluoro-2-((1-(oxetan-3-yl)-1H-pyrazol-4-yl)amino)pyrimidin-4-yl)oxy)methyl)cyclohexan-1-ol |
| 228 | 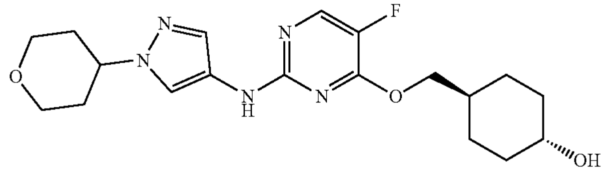 [SMILES: O[C@H]1CC[C@H](COc2nc(Nc3cnn(C4CCOCC4)c3)ncc2F)CC1] | (1R,4R)-4-(((5-fluoro-2-((1-(tetrahydro-2H-pyran-4-yl)-1H-pyrazol-4-yl)amino)pyrimidin-4-yl)oxy)methyl)cyclohexan-1-ol |
| 229 | 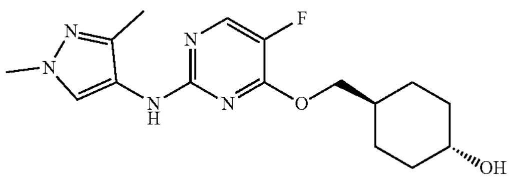 [SMILES: Cc1nn(C)cc1Nc1ncc(F)c(OC[C@H]2CC[C@H](O)CC2)n1] | (1R,4R)-4-(((2-((1,3-dimethyl-1H-pyrazol-4-yl)amino)-5-fluoropyrimidin-4-yl)oxy)methyl)cyclohexan-1-ol |
| 230 | 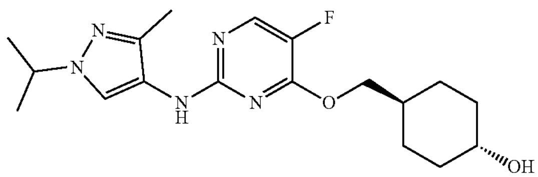 [SMILES: Cc1nn(C(C)C)cc1Nc1ncc(F)c(OC[C@H]2CC[C@H](O)CC2)n1] | (1R,4R)-4-(((5-fluoro-2-((1-isopropyl-3-methyl-1H-pyrazol-4-yl)amino)pyrimidin-4-yl)oxy)methyl)cyclohexan-1-ol |
| 231 | 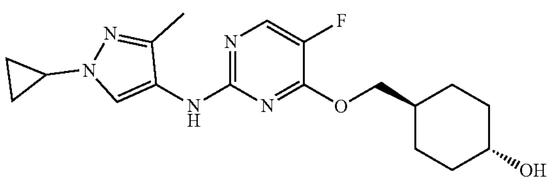 [SMILES: Cc1nn(C2CC2)cc1Nc1ncc(F)c(OC[C@H]2CC[C@H](O)CC2)n1] | (1R,4R)-4-(((2-((1-cyclopropyl-3-methyl-1H-pyrazol-4-yl)amino)-5-fluoropyrimidin-4-yl)oxy)methyl)cyclohexan-1-ol |
| 232 | 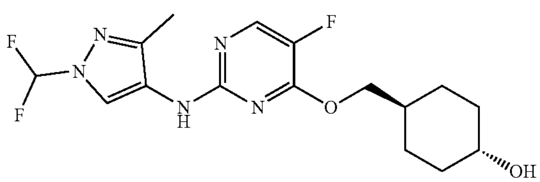 [SMILES: Cc1nn(C(F)F)cc1Nc1ncc(F)c(OC[C@H]2CC[C@H](O)CC2)n1] | (1R,4R)-4-(((2-((1-(difluoromethyl)-3-methyl-1H-pyrazol-4-yl)amino)-5-fluoropyrimidin-4-yl)oxy)methyl)cyclohexan-1-ol |
| 233 | 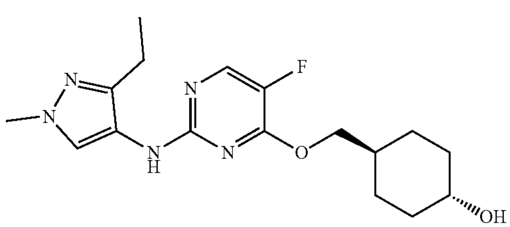 | (1R,4R)-4-(((2-((3-ethyl-1-methyl-1H-pyrazol-4-yl)amino)-5-fluoropyrimidin-4-yl)oxy)methyl)cyclohexan-1-ol |
| 234 | 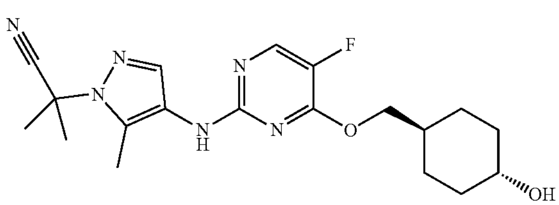 [SMILES: Cc1c(Nc2ncc(F)c(OC[C@H]3CC[C@H](O)CC3)n2)cnn1C(C)(C)C#N] | 2-(4-((5-fluoro-4-(((1R,4R)-4-hydroxycyclohexyl)methoxy)pyrimidin-2-yl)amino)-5-methyl-1H-pyrazol-1-yl)-2-methylpropanenitrile |

TABLE 1-continued

Representative Compounds of Structure (I)

| Example | Structure | Name |
|---|---|---|
| 235 | 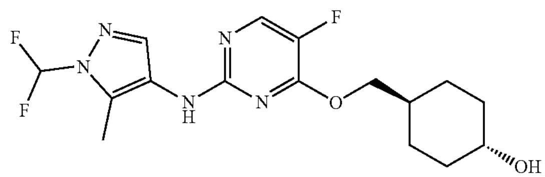 [SMILES: Cc1c(Nc2ncc(F)c(OC[C@H]3CC[C@H](O)CC3)n2)cnn1C(F)F] | (1R,4R)-4-(((2-((1-(difluoromethyl)-5-methyl-1H-pyrazol-4-yl)amino)-5-fluoropyrimidin-4-yl)oxy)methyl)cyclohexan-1-ol |
| 236 | 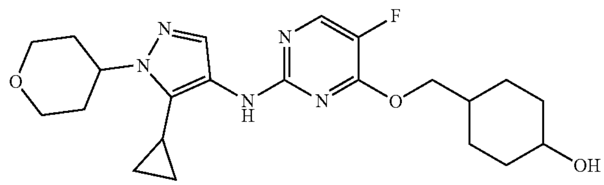 [SMILES: OC1CCC(COc2nc(Nc3cnn(C4CCOCC4)c3C3CC3)ncc2F)CC1] | 4-(((2-((5-cyclopropyl-1-(tetrahydro-2H-pyran-4-yl)-1H-pyrazol-4-yl)amino)-5-fluoropyrimidin-4-yl)oxy)methyl)cyclohexan-1-ol |
| 237 | 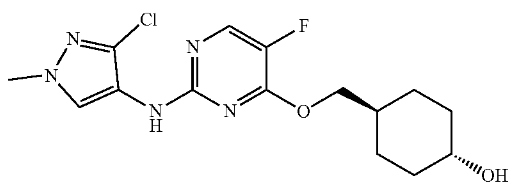 [SMILES: Cn1cc(Nc2ncc(F)c(OC[C@H]3CC[C@H](O)CC3)n2)c(Cl)n1] | (1R,4R)-4-(((2-((3-chloro-1-methyl-1H-pyrazol-4-yl)amino)-5-fluoropyrimidin-4-yl)oxy)methyl)cyclohexan-1-ol |
| 238 | 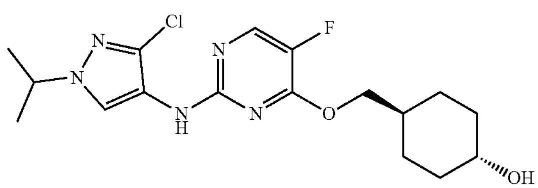 [SMILES: CC(C)n1cc(Nc2ncc(F)c(OC[C@H]3CC[C@H](O)CC3)n2)c(Cl)n1] | (1R,4S)-4-(((2-((3-chloro-1-isopropyl-1H-pyrazol-4-yl)amino)-5-fluoropyrimidin-4-yl)oxy)methyl)cyclohexan-1-ol |
| 239 | 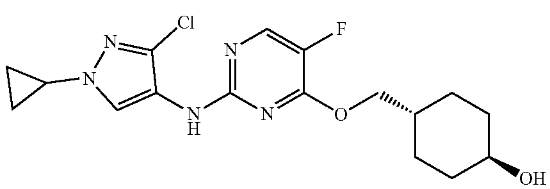 [SMILES: O[C@H]1CC[C@H](COc2nc(Nc3cn(C4CC4)nc3Cl)ncc2F)CC1] | (1R,4R)-4-(((2-((3-chloro-1-cyclopropyl-1H-pyrazol-4-yl)amino)-5-fluoropyrimidin-4-yl)oxy)methyl)cyclohexan-1-ol |
| 240 | 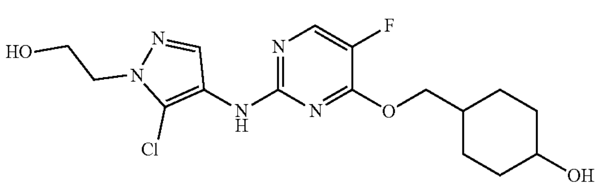 [SMILES: OCCn1ncc(Nc2ncc(F)c(OCC3CCC(O)CC3)n2)c1Cl] | 4-(((2-((5-chloro-1-(2-hydroxyethyl)-1H-pyrazol-4-yl)amino)-5-fluoropyrimidin-4-yl)oxy)methyl)cyclohexan-1-ol |
| 241 | 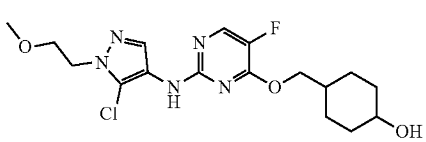 [SMILES: COCCn1ncc(Nc2ncc(F)c(OCC3CCC(O)CC3)n2)c1Cl] | 4-(((2-((5-chloro-1-(2-methoxyethyl)-1H-pyrazol-4-yl)amino)-5-fluoropyrimidin-4-yl)oxy)methyl)cyclohexan-1-ol |
| 242 | 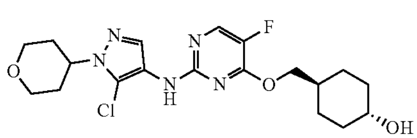 [SMILES: O[C@H]1CC[C@H](COc2nc(Nc3cnn(C4CCOCC4)c3Cl)ncc2F)CC1] | (1R,4R)-4-(((2-((5-chloro-1-(tetrahydro-2H-pyran-4-yl)-1H-pyrazol-4-yl)amino)-5-fluoropyrimidin-4-yl)oxy)methyl)cyclohexan-1-ol |

TABLE 1-continued

Representative Compounds of Structure (I)

| Example | Structure | Name |
|---|---|---|
| 243 | 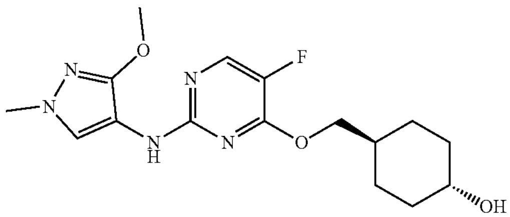 [SMILES: COc1nn(C)cc1Nc1ncc(F)c(OC[C@H]2CC[C@H](O)CC2)n1] | (1R,4R)-4-(((5-fluoro-2-((3-methoxy-1-methyl-1H-pyrazol-4-yl)amino)pyrimidin-4-yl)oxy)methyl)cyclohexan-1-ol |
| 244 | 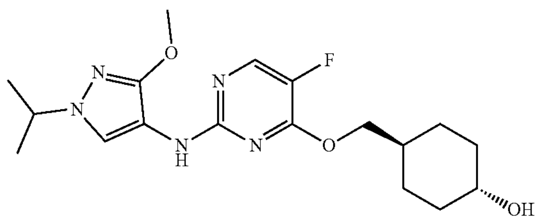 [SMILES: COc1nn(C(C)C)cc1Nc1ncc(F)c(OC[C@H]2CC[C@H](O)CC2)n1] | (1R,4R)-4-(((5-fluoro-2-((1-isopropyl-3-methoxy-1H-pyrazol-4-yl)amino)pyrimidin-4-yl)oxy)methyl)cyclohexan-1-ol |
| 245 | 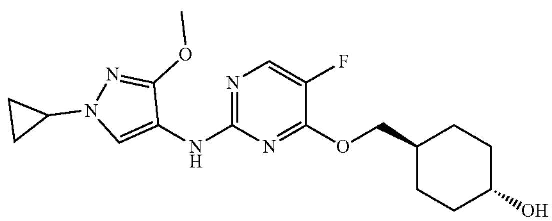 [SMILES: COc1nn(C2CC2)cc1Nc1ncc(F)c(OC[C@H]2CC[C@H](O)CC2)n1] | (1R,4R)-4-(((2-((1-cyclopropyl-3-methoxy-1H-pyrazol-4-yl)amino)-5-fluoropyrimidin-4-yl)oxy)methyl)cyclohexan-1-ol |
| 246 | 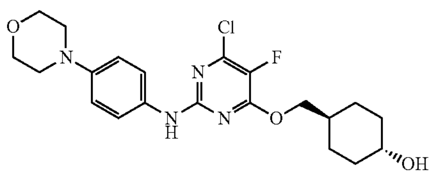 [SMILES: O[C@H]1CC[C@H](COc2nc(Nc3ccc(N4CCOCC4)cc3)nc(Cl)c2F)CC1] | (1R,4R)-4-(((6-chloro-5-fluoro-2-((4-morpholinophenyl)amino)pyrimidin-4-yl)oxy)methyl)cyclohexan-1-ol |
| 247 | 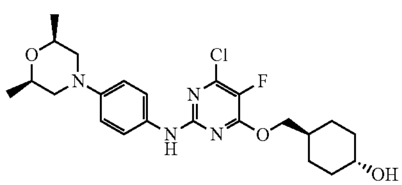 [SMILES: C[C@@H]1CN(c2ccc(Nc3nc(Cl)c(F)c(OC[C@H]4CC[C@H](O)CC4)n3)cc2)C[C@H](C)O1] | (1R,4R)-4-(((6-chloro-2-((4-((2S,6R)-2,6-dimethylmorpholino)phenyl)amino)-5-fluoropyrimidin-4-yl)oxy)methyl)cyclohexan-1-ol |
| 248 | 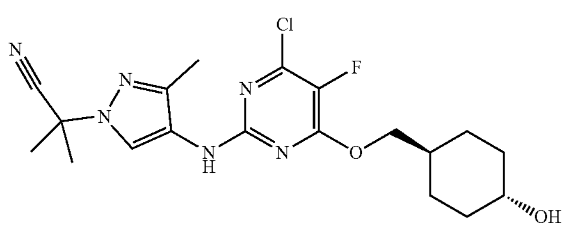 [SMILES: Cc1nn(C(C)(C)C#N)cc1Nc1nc(Cl)c(F)c(OC[C@H]2CC[C@H](O)CC2)n1] | 2-(4-((4-chloro-5-fluoro-6-(((1R,4R)-4-hydroxycyclohexyl)methoxy)pyrimidin-2-yl)amino)-3-methyl-1H-pyrazol-1-yl)-2-methylpropanenitrile |
| 249 | 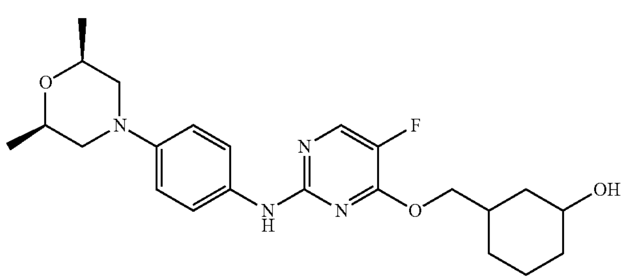 [SMILES: C[C@@H]1CN(c2ccc(Nc3ncc(F)c(OCC4CCCC(O)C4)n3)cc2)C[C@H](C)O1] | 3-(((2-((4-((2S,6R)-2,6-dimethylmorpholino)phenyl)amino)-5-fluoropyrimidin-4-yl)oxy)methyl)cyclohexan-1-ol |

TABLE 1-continued

Representative Compounds of Structure (I)

| Example | Structure | Name |
|---|---|---|
| 250 | 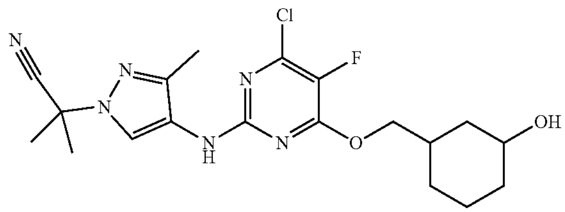 [SMILES: Cc1nn(C(C)(C)C#N)cc1Nc1nc(Cl)c(F)c(OCC2CCCC(O)C2)n1] | 2-(4-((5-fluoro-4-((3-hydroxycyclohexyl)methoxy)pyrimidin-2-yl)amino)-3-methyl-1H-pyrazol-1-yl)-2-methylpropanenitrile |
| 251 | 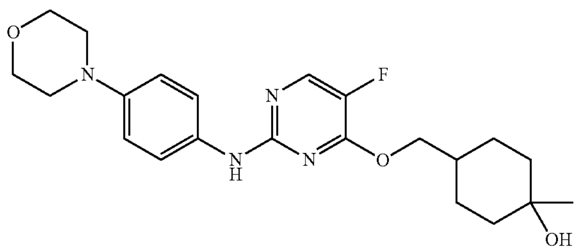 [SMILES: CC1(O)CCC(COc2nc(Nc3ccc(N4CCOCC4)cc3)ncc2F)CC1] | 4-(((5-fluoro-2-((4-morpholinophenyl)amino)pyrimidin-4-yl)oxy)methyl)-1-methylcyclohexan-1-ol |
| 252 | 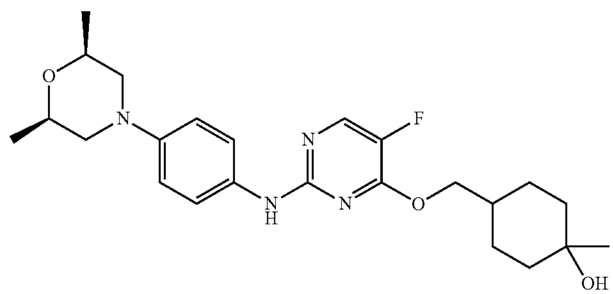 | 4-(((2-((4-((2S,6R)-2,6-dimethylmorpholino)phenyl)amino)-5-fluoropyrimidin-4-yl)oxy)methyl)-1-methylcyclohexan-1-ol |
| 253 | 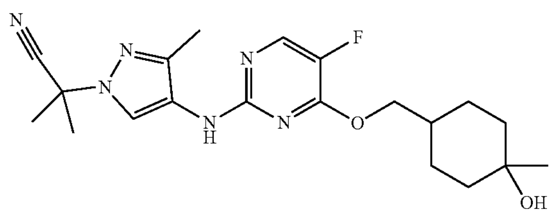 [SMILES: Cc1nn(C(C)(C)C#N)cc1Nc1ncc(F)c(OCC2CCC(C)(O)CC2)n1] | 2-(4-((5-fluoro-4-((4-hydroxy-4-methylcyclohexyl)methoxy)pyrimidin-2-yl)amino)-3-methyl-1H-pyrazol-1-yl)-2-methylpropanenitrile |
| 254 | 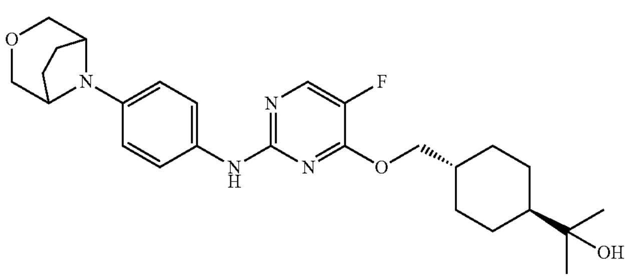 [SMILES: CC(C)(O)[C@H]1CC[C@H](COc2nc(Nc3ccc(N4C5CCC4COC5)cc3)ncc2F)CC1] | 2-((1S,4S)-4-(((2-((4-(3-oxa-8-azabicyclo[3.2.1]octan-8-yl)phenyl)amino)-5-fluoropyrimidin-4-yl)oxy)methyl)cyclohexyl)propan-2-ol |
| 255 | 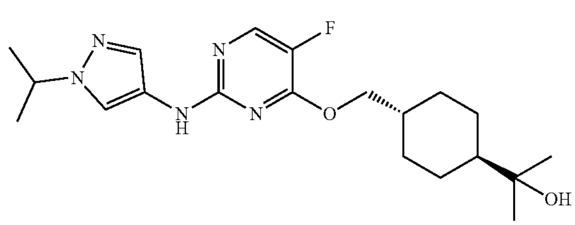 [SMILES: CC(C)n1cc(Nc2ncc(F)c(OC[C@H]3CC[C@H](C(C)(C)O)CC3)n2)cn1] | 2-((1R,4R)-4-(((5-fluoro-2-((1-isopropyl-1H-pyrazol-4-yl)amino)pyrimidin-4-yl)oxy)methyl)cyclohexyl)propan-2-ol |

TABLE 1-continued

Representative Compounds of Structure (I)

| Example | Structure | Name |
|---|---|---|
| 256 | 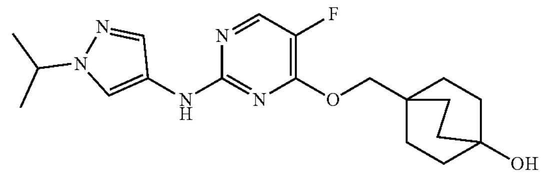 [SMILES: CC(C)n1cc(Nc2ncc(F)c(OCC34CCC(O)(CC3)CC4)n2)cn1] | 4-(((5-fluoro-2-((1-isopropyl-1H-pyrazol-4-yl)amino)pyrimidin-4-yl)oxy)methyl)bicyclo[2.2.2]octan-1-ol |
| 257 | 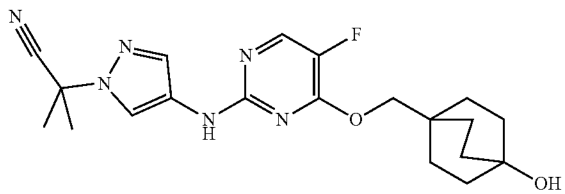 [SMILES: CC(C)(C#N)n1cc(Nc2ncc(F)c(OCC34CCC(O)(CC3)CC4)n2)cn1] | 2-(4-((5-fluoro-4-((4-hydroxybicyclo[2.2.2]octan-1-yl)methoxy)pyrimidin-2-yl)amino)-3-methyl-1H-pyrazol-1-yl)-2-methylpropanenitrile |
| 258 | 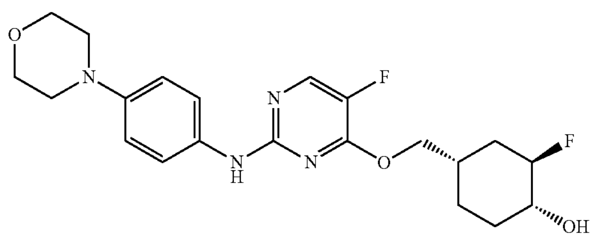 [SMILES: O[C@@H]1CC[C@H](COc2nc(Nc3ccc(N4CCOCC4)cc3)ncc2F)C[C@H]1F] | (1R,2R,4S)-2-fluoro-4-(((5-fluoro-2-((4-morpholinophenyl)amino)pyrimidin-4-yl)oxy)methyl)cyclohexan-1-ol |
| 259 | 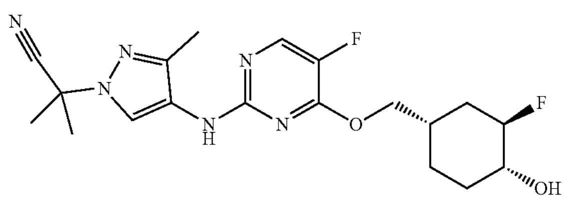 [SMILES: Cc1nn(C(C)(C)C#N)cc1Nc1ncc(F)c(OC[C@H]2CC[C@@H](O)[C@H](F)C2)n1] | 2-(4-((5-fluoro-4-(((1S,3R,4R)-3-fluoro-4-hydroxycyclohexyl)methoxy)pyrimidin-2-yl)amino)-3-methyl-1H-pyrazol-1-yl)-2-methylpropanenitrile |
| 260 | 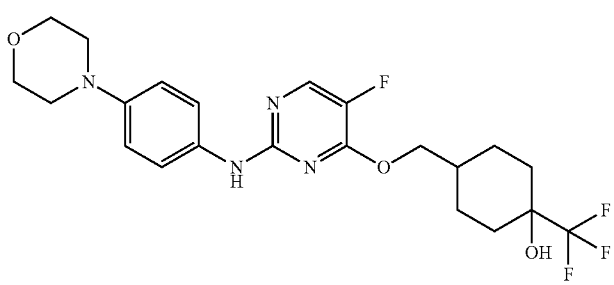 [SMILES: OC1(C(F)(F)F)CCC(COc2nc(Nc3ccc(N4CCOCC4)cc3)ncc2F)CC1] | 4-(((5-fluoro-2-((4-morpholinophenyl)amino)pyrimidin-4-yl)oxy)methyl)-1-(trifluoromethyl)cyclohexan-1-ol |
| 261 | 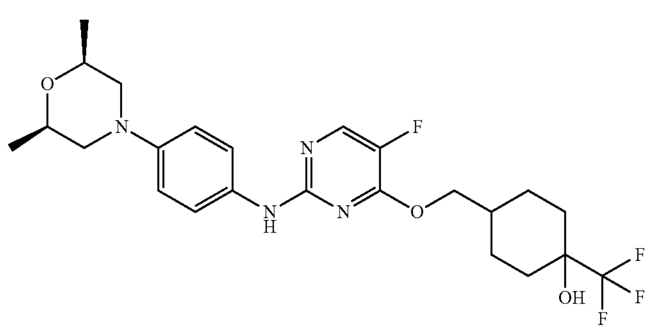 [SMILES: C[C@@H]1CN(c2ccc(Nc3ncc(F)c(OCC4CCC(O)(C(F)(F)F)CC4)n3)cc2)C[C@H](C)O1] | 4-(((2-((4-((2S,6R)-2,6-dimethylmorpholino)phenyl)amino)-5-fluoropyrimidin-4-yl)oxy)methyl)-1-(trifluoromethyl)cyclohexan-1-ol |

TABLE 1-continued

Representative Compounds of Structure (I)

| Example | Structure | Name |
|---|---|---|
| 262 | 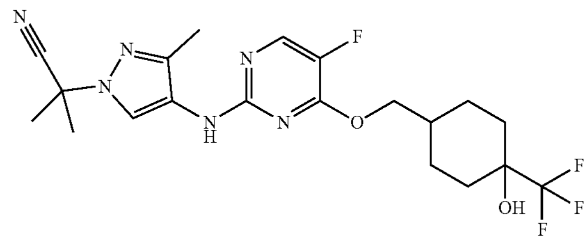 [SMILES: Cc1nn(C(C)(C)C#N)cc1Nc1ncc(F)c(OCC2CCC(O)(C(F)(F)F)CC2)n1] | 2-(4-((5-fluoro-4-((4-hydroxy-4-(trifluoromethyl)cyclohexyl)methoxy)pyrimidin-2-yl)amino)-3-methyl-1H-pyrazol-1-yl)-2-methylpropanenitrile |
| 263 | 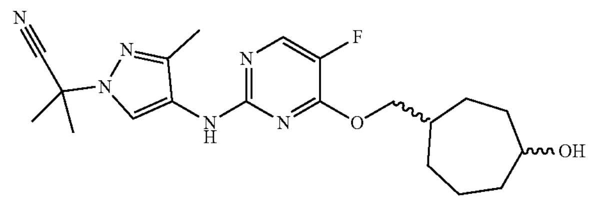 [SMILES: Cc1nn(C(C)(C)C#N)cc1Nc1ncc(F)c(OCC2CCCC(O)CC2)n1] | 2-(4-((5-fluoro-4-((4-hydroxycycloheptyl)methoxy)pyrimidin-2-yl)amino)-3-methyl-1H-pyrazol-1-yl)-2-methylpropanenitrile (1st eluting peak) |
| 264 | 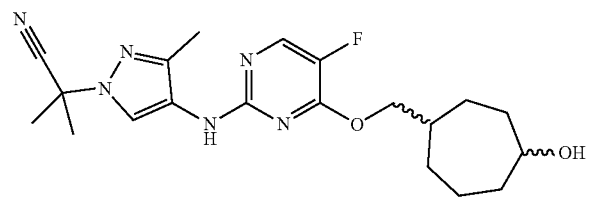 [SMILES: Cc1nn(C(C)(C)C#N)cc1Nc1ncc(F)c(OCC2CCCC(O)CC2)n1] | 2-(4-((5-fluoro-4-((4-hydroxycycloheptyl)methoxy)pyrimidin-2-yl)amino)-3-methyl-1H-pyrazol-1-yl)-2-methylpropanenitrile (2nd eluting peak) |
| 265 | 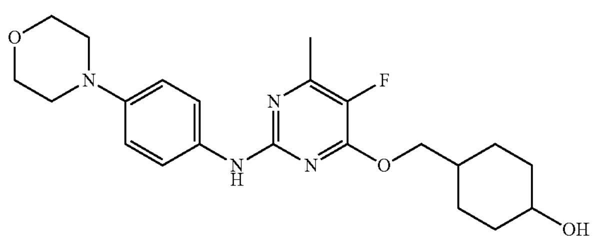 | 4-(((5-fluoro-6-methyl-2-((4-morpholinophenyl)amino)pyrimidin-4-yl)oxy)methyl)cyclohexan-1-ol |
| 266 | 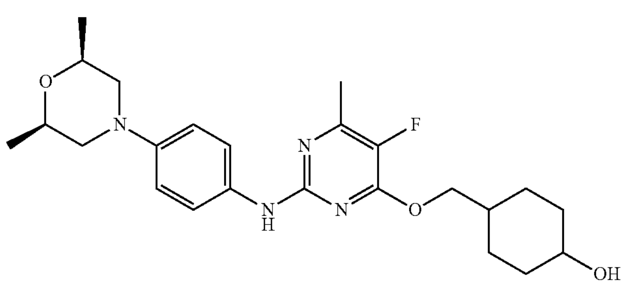 [SMILES: Cc1nc(Nc2ccc(N3C[C@@H](C)O[C@@H](C)C3)cc2)nc(OCC2CCC(O)CC2)c1F] | 4-(((2-((4-((2S,6R)-2,6-dimethylmorpholino)phenyl)amino)-5-fluoro-6-methylpyrimidin-4-yl)oxy)methyl)cyclohexan-1-ol |
| 267 | 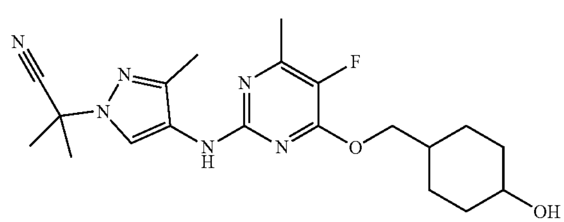 [SMILES: Cc1nn(C(C)(C)C#N)cc1Nc1nc(C)c(F)c(OCC2CCC(O)CC2)n1] | 2-(4-((5-fluoro-4-((4-hydroxycyclohexyl)methoxy)-6-methylpyrimidin-2-yl)amino)-3-methyl-1H-pyrazol-1-yl)-2-methylpropanenitrile |

TABLE 1-continued

Representative Compounds of Structure (I)

| Example | Structure | Name |
|---|---|---|
| 268 | 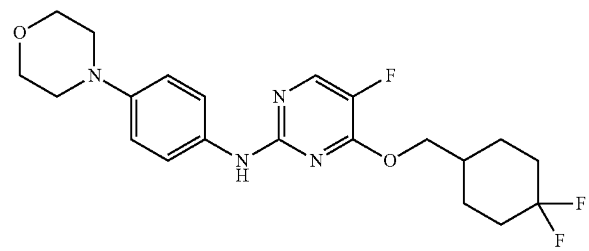 | 4-((4,4-difluorocyclohexyl)methoxy)-5-fluoro-N-(4-morpholinophenyl)pyrimidin-2-amine |
| 269 | 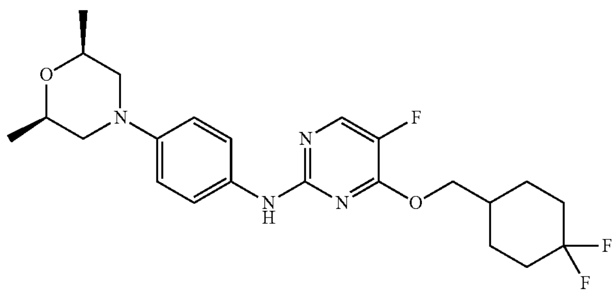 [SMILES: C[C@@H]1CN(c2ccc(Nc3ncc(F)c(OCC4CCC(F)(F)CC4)n3)cc2)C[C@H](C)O1] | 4-((4,4-difluorocyclohexyl)methoxy)-N-(4-((2R,6S)-2,6-dimethylmorpholino)phenyl)-5-fluoropyrimidin-2-amine |
| 270 | 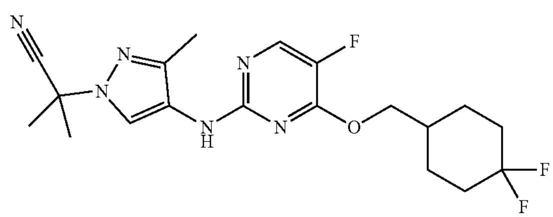 [SMILES: Cc1nn(C(C)(C)C#N)cc1Nc1ncc(F)c(OCC2CCC(F)(F)CC2)n1] | 2-(4-((4-((4,4-difluorocyclohexyl)methoxy)-5-fluoropyrimidin-2-yl)amino)-3-methyl-1H-pyrazol-1-yl)-2-methylpropanenitrile |
| 271 | 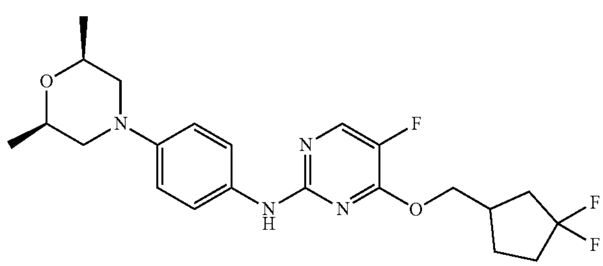 [SMILES: C[C@@H]1CN(c2ccc(Nc3ncc(F)c(OCC4CCC(F)(F)C4)n3)cc2)C[C@H](C)O1] | 4-((3,3-difluorocyclopentyl)methoxy)-N-(4-((2S,6R)-2,6-dimethylmorpholino)phenyl)-5-fluoropyrimidin-2-amine |
| 272 | 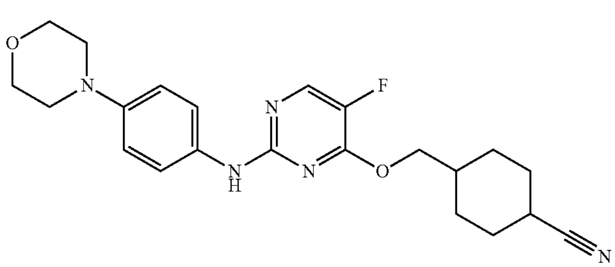 [SMILES: N#CC1CCC(COc2nc(Nc3ccc(N4CCOCC4)cc3)ncc2F)CC1] | 4-(((5-fluoro-2-((4-morpholinophenyl)amino)pyrimidin-4-yl)oxy)methyl)cyclohexane-1-carbonitrile |

TABLE 1-continued

Representative Compounds of Structure (I)

| Example | Structure | Name |
|---|---|---|
| 273 | 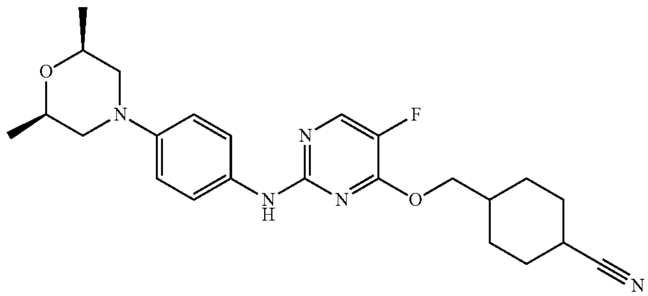 [SMILES: C[C@@H]1CN(c2ccc(Nc3ncc(F)c(OCC4CCC(C#N)CC4)n3)cc2)C[C@H](C)O1] | 4-(((2-((4-((2S,6R)-2,6-dimethylmorpholino)phenyl)amino)-5-fluoropyrimidin-4-yl)oxy)methyl)cyclohexane-1-carbonitrile |
| 274 | 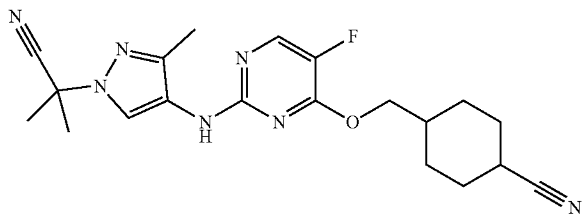 [SMILES: Cc1nn(C(C)(C)C#N)cc1Nc1ncc(F)c(OCC2CCC(C#N)CC2)n1] | 4-(((2-((1-(2-cyanopropan-2-yl)-3-methyl-1H-pyrazol-4-yl)amino)-5-fluoropyrimidin-4-yl)oxy)methyl)cyclohexane-1-carbonitrile |
| 275 | 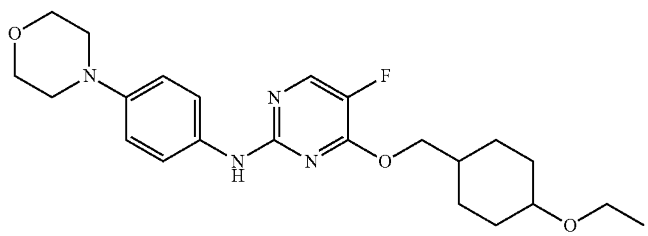 [SMILES: CCOC1CCC(COc2nc(Nc3ccc(N4CCOCC4)cc3)ncc2F)CC1] | 4-((4-ethoxycyclohexyl)methoxy)-5-fluoro-N-(4-morpholinophenyl)pyrimidin-2-amine |
| 276 | 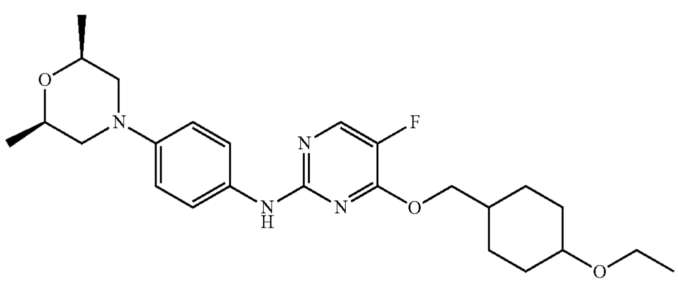 [SMILES: CCOC1CCC(COc2nc(Nc3ccc(N4C[C@@H](C)O[C@@H](C)C4)cc3)ncc2F)CC1] | N-(4-(((2S,6R)-2,6-dimethylmorpholino)phenyl)-4-((4-ethoxycyclohexyl)methoxy)-5-fluoropyrimidin-2-amine |
| 277 | 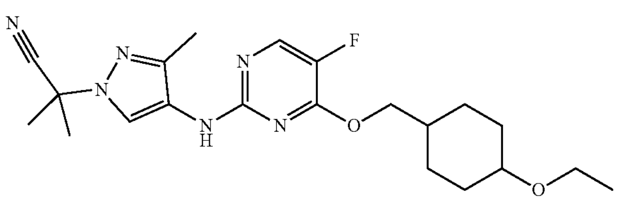 [SMILES: CCOC1CCC(COc2nc(Nc3cn(C(C)(C)C#N)nc3C)ncc2F)CC1] | 2-(4-((4-((4-ethoxycyclohexyl)methoxy)-5-fluoropyrimidin-2-yl)amino)-3-methyl-1H-pyrazol-1-yl)-2-methylpropanenitrile |
| 278 | 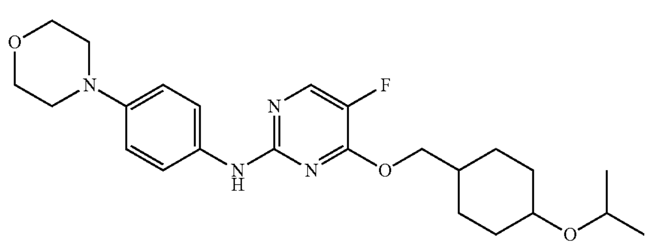 [SMILES: CC(C)OC1CCC(COc2nc(Nc3ccc(N4CCOCC4)cc3)ncc2F)CC1] | 5-fluoro-4-((4-isopropoxycyclohexyl)methoxy)-N-(4-morpholinophenyl)pyrimidin-2-amine |

TABLE 1-continued

Representative Compounds of Structure (I)

| Example | Structure | Name |
|---|---|---|
| 279 | 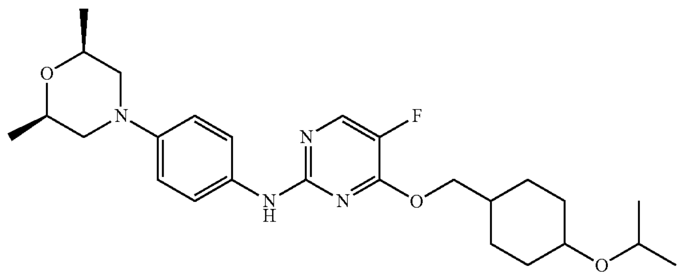 [SMILES: CC(C)OC1CCC(COc2nc(Nc3ccc(N4C[C@@H](C)O[C@@H](C)C4)cc3)ncc2F)CC1] | N-(4-((2S,6R)-2,6-dimethylmorpholino)phenyl)-5-fluoro-4-((4-isopropoxycyclohexyl)methoxy)pyrimidin-2-amine |
| 280 | 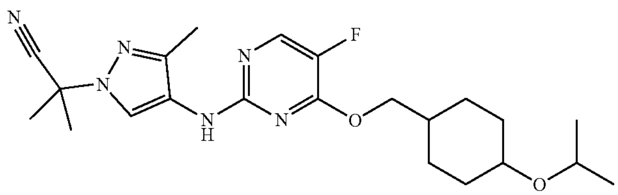 [SMILES: Cc1nn(C(C)(C)C#N)cc1Nc1ncc(F)c(OCC2CCC(OC(C)C)CC2)n1] | 2-(4-((5-fluoro-4-((4-isopropoxycyclohexyl)methoxy)pyrimidin-2-yl)amino)-3-methyl-1H-pyrazol-1-yl)-2-methylpropanenitrile |
| 281 | 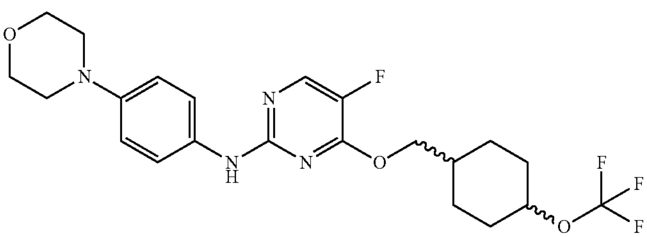 [SMILES: Fc1cnc(Nc2ccc(N3CCOCC3)cc2)nc1OCC1CCC(OC(F)(F)F)CC1] | 5-fluoro-N-(4-morpholinophenyl)-4-((4-(trifluoromethoxy)cyclohexyl)methoxy)pyrimidin-2-amine (1$^{st}$ eluting peak) |
| 282 | 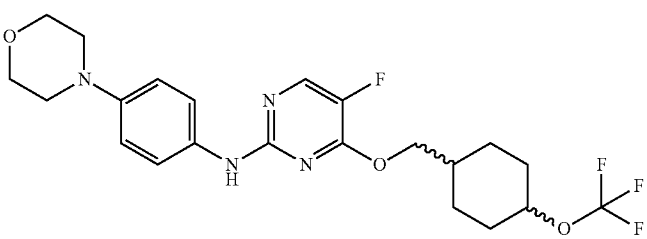 [SMILES: Fc1cnc(Nc2ccc(N3CCOCC3)cc2)nc1OCC1CCC(OC(F)(F)F)CC1] | 5-fluoro-N-(4-morpholinophenyl)-4-((4-(trifluoromethoxy)cyclohexyl)methoxy)pyrimidin-2-amine (2$^{nd}$ eluting peak) |
| 283 | 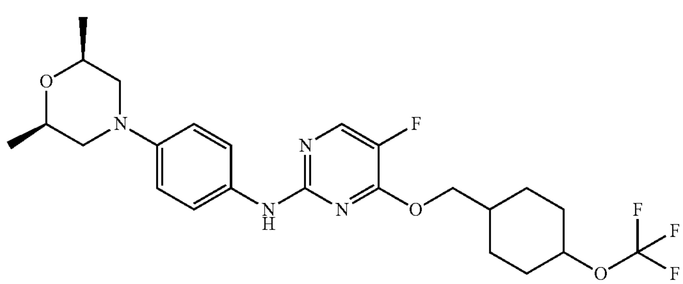 [SMILES: C[C@@H]1CN(c2ccc(Nc3ncc(F)c(OCC4CCC(OC(F)(F)F)CC4)n3)cc2)C[C@H](C)O1] | N-(4-((2S,6R)-2,6-dimethylmorpholino)phenyl)-5-fluoro-4-((4-(trifluoromethoxy)cyclohexyl)methoxy)pyrimidin-2-amine |
| 284 | 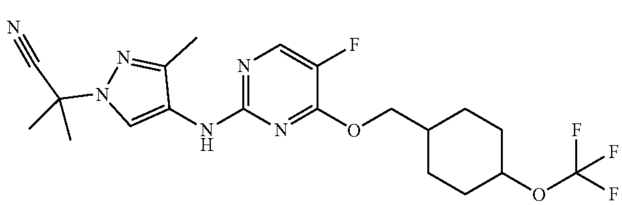 [SMILES: Cc1nn(C(C)(C)C#N)cc1Nc1ncc(F)c(OCC2CCC(OC(F)(F)F)CC2)n1] | 2-(4-((5-fluoro-4-((4-(trifluoromethoxy)cyclohexyl)methoxy)pyrimidin-2-yl)amino)-3-methyl-1H-pyrazol-1-yl)-2-methylpropanenitrile |

TABLE 1-continued

Representative Compounds of Structure (I)

| Example | Structure | Name |
|---|---|---|
| 285 | 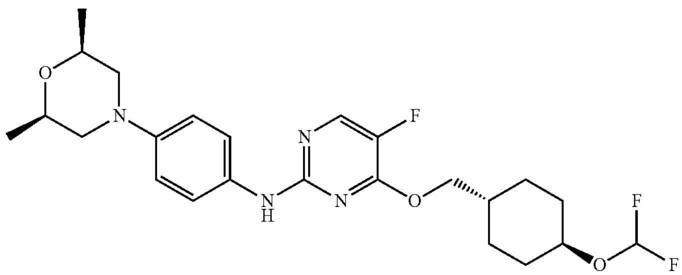 [SMILES: C[C@@H]1CN(c2ccc(Nc3ncc(F)c(OC[C@H]4CC[C@H](OC(F)F)CC4)n3)cc2)C[C@H](C)O1] | 4-(((1R,4R)-4-(difluoromethoxy)cyclohexyl)methoxy)-N-(4-((2S,6R)-2,6-dimethylmorpholino)phenyl)-5-fluoropyrimidin-2-amine |
| 286 | 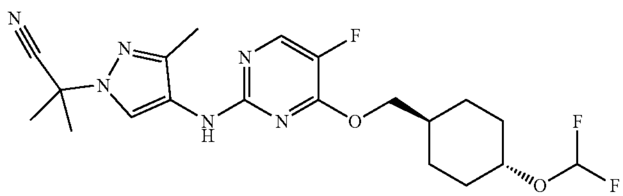 [SMILES: Cc1nn(C(C)(C)C#N)cc1Nc1ncc(F)c(OC[C@H]2CC[C@H](OC(F)F)CC2)n1] | 2-(4-((4-(((1R,4R)-4-(difluoromethoxy)cyclohexyl)methoxy)-5-fluoropyrimidin-2-yl)amino)-3-methyl-1H-pyrazol-1-yl)-2-methylpropanenitrile |
| 287 | 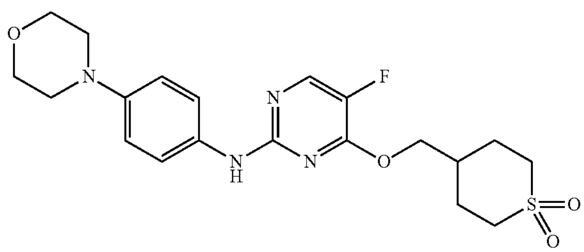 [SMILES: O=S1(=O)CCC(COc2nc(Nc3ccc(N4CCOCC4)cc3)ncc2F)CC1] | 4-(((5-fluoro-2-((4-morpholinophenyl)amino)pyrimidin-4-yl)oxy)methyl)tetrahydro-2H-thiopyran 1,1-dioxide |
| 288 | 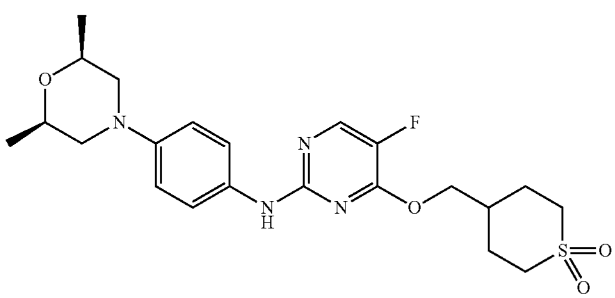 [SMILES: C[C@@H]1CN(c2ccc(Nc3ncc(F)c(OCC4CCS(=O)(=O)CC4)n3)cc2)C[C@H](C)O1] | 4-(((2-((4-((2R,6S)-2,6-dimethylmorpholino)phenyl)amino)-5-fluoropyrimidin-4-yl)oxy)methyl)tetrahydro-2H-thiopyran 1,1-dioxide |
| 289 | 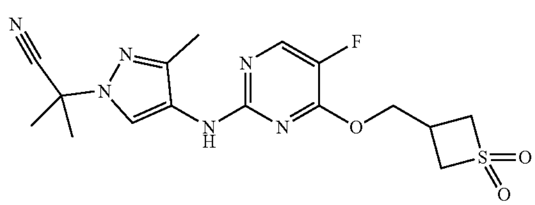 [SMILES: Cc1nn(C(C)(C)C#N)cc1Nc1ncc(F)c(OCC2CS(=O)(=O)C2)n1] | 2-(4-((4-((1,1-dioxidothietan-3-yl)methoxy)-5-fluoropyrimidin-2-yl)amino)-3-methyl-1H-pyrazol-1-yl)-2-methylpropanenitrile |
| 290 | 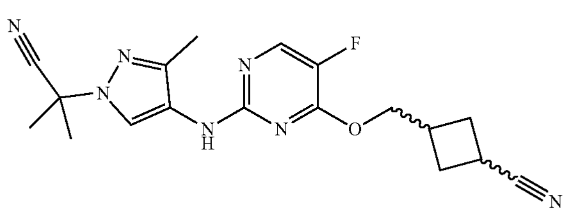 [SMILES: Cc1nn(C(C)(C)C#N)cc1Nc1ncc(F)c(OCC2CC(C#N)C2)n1] | 3-(((2-((1-(2-cyanopropan-2-yl)-3-methyl-1H-pyrazol-4-yl)amino)-5-fluoropyrimidin-4-yl)oxy)methyl)cyclobutane-1-carbonitrile (1$^{st}$ eluting peak) |

TABLE 1-continued

Representative Compounds of Structure (I)

| Example | Structure | Name |
|---|---|---|
| 291 | 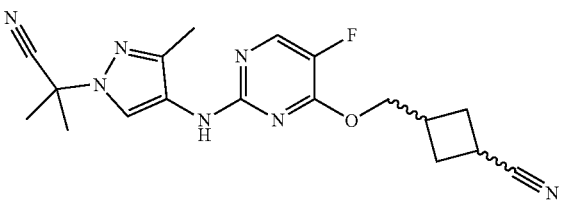 [SMILES: Cc1nn(C(C)(C)C#N)cc1Nc1ncc(F)c(OCC2CC(C#N)C2)n1] | 3-(((2-((1-(2-cyanopropan-2-yl)-3-methyl-1H-pyrazol-4-yl)amino)-5-fluoropyrimidin-4-yl)oxy)methyl)cyclobutane-1-carbonitrile (2$^{nd}$ eluting peak) |

It is understood that in the present description, combinations of substituents and/or variables of the depicted formulae are permissible only if such contributions result in stable compounds.

In an additional embodiment, various compounds of the disclosure which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

Methods for producing the compounds described herein are provided in the Examples that follow. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

Pharmaceutical Compositions

Other embodiments are directed to pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the compound is delivered in a targeted drug delivery system, for example, in a liposome coated with and organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In treatment methods according to embodiments of the disclosure, an effective amount of at least one compound of Structure (I) is administered to a subject suffering from or diagnosed as having such a disease, disorder, or medical condition. Effective amounts or doses may be ascertained by methods such as modeling, dose escalation studies or clinical trials, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician.

The compounds according to the disclosure are effective over a wide dosage range. For example, in the treatment of adult humans, dosages from 10 to 5000 mg, from 100 to 5000 mg, from 1000 mg to 4000 mg per day, and from 1000 to 3000 mg per day are examples of dosages that are used in some embodiments. The exact dosage will depend upon the route of administration, the form in which the compound is administered, the subject to be treated, the body weight of the subject to be treated, and the preference and experience of the attending physician.

In some embodiments, compounds of the disclosure are administered in a single dose. Typically, such administration will be by injection, e.g., intravenous injection, in order to introduce the agent quickly. However, other routes are used as appropriate. A single dose of a compound of the disclosure may also be used for treatment of an acute condition.

In some embodiments, compounds of the disclosure are administered in multiple doses. In some embodiments, dosing is about once, twice, three times, four times, five times, six times, or more than six times per day. In other embodiments, dosing is about once a month, once every two weeks, once a week, or once every other day. In another embodiment compounds of the disclosure and another agent (e.g., anti-cancer agent) are administered together about once per day to about 6 times per day. In another embodiment the administration of compounds of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of compounds of the disclosure may continue as long as necessary. In some embodiments, compounds of the disclosure are administered for more than 1, 2, 3, 4, 5, 6, 7, 14, or 28 days. In some embodiments, compounds of the disclosure are administered for less than 28, 14, 7, 6, 5, 4, 3, 2, or 1 day. In some embodiments, compounds of the disclosure are administered chronically on an ongoing basis, e.g., for the treatment of chronic effects.

In some embodiments, the compounds of the disclosure are administered in individual dosage forms. It is known in the art that due to intersubject variability in compound pharmacokinetics, individualization of dosing regimen is necessary for optimal therapy.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the disclosed compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising one or more compounds of Structure (I), and a pharmaceutically acceptable carrier.

Provided herein are pharmaceutical compositions comprising one or more compounds selected from compounds of Structure (I) and pharmaceutically acceptable diluent(s), excipient(s), and carrier(s). In certain embodiments, the compounds described are administered as pharmaceutical compositions in which one or more compounds selected from compounds of Structure (I) are mixed with other active ingredients, as in combination therapy. Encompassed herein are all combinations of actives set forth in the combination therapies section below and throughout this disclosure. In specific embodiments, the pharmaceutical compositions include one or more compounds of Structure (I).

In a specific embodiment, pharmaceutical compositions of the compounds of Structure (I) inhibit LRRK2 kinase when administered to a patient or a biological sample.

A pharmaceutical composition, as used herein, refers to a mixture of one or more compounds selected from compounds of Structure (I) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, therapeutically effective amounts of one or more compounds selected from compounds of Structure (I) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds selected from compounds of Structure (I) are formulated in aqueous solutions. In specific embodiments, the aqueous solution is selected from, by way of example only, a physiologically compatible buffer, such as Hank's solution, Ringer's solution, or physiological saline buffer. In other embodiments, one or more compounds selected from compounds of Structure (I) are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of one or more compounds selected from compounds of Structure (I) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

Pharmaceutical compositions include at least one pharmaceutically acceptable carrier, diluent or excipient, and one or more compounds selected from compounds of Structure (I), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass un-solvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical compositions comprising one or more compounds selected from compounds of Structure (I) illustratively takes the form of a liquid where the agents are present in solution, in suspension or both. Typically when the composition is administered as a suspension, a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, aqueous suspensions contain one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally, include solubilizing agents to aid in the solubility of one or more compounds selected from compounds of Structure (I). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Compositions may include one or more surfactants to enhance physical stability or for other purposes. Suitable nonionic surfactants include polyoxyethylene fatty acid glycerides and vegetable oils, e.g., polyoxyethylene (60)

hydrogenated castor oil; and polyoxyethylene alkylethers and alkylphenyl ethers, e.g., octoxynol 10, octoxynol 40.

Compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds selected from compounds of Structure (I) provided in the pharmaceutical compositions of the present disclosure is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds selected from compounds of Structure (I) provided in the pharmaceutical compositions of the present disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the amount the one or more compounds selected from compounds of Structure (I) provided in the pharmaceutical compositions of the present disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the one or more compounds selected from compounds of Structure (I) provided in the pharmaceutical compositions of the present disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

Packaging materials for use in packaging pharmaceutical compositions described herein include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

Embodiments of the present disclosure are useful as inhibitors of LRRK2 in a host species. The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

Accordingly, some embodiments include methods of treating, preventing, or managing the symptoms of a disease or disorder, wherein the disease or disorder is selected from neurodegenerative diseases, central nervous system (CNS) disorders, cancer, inflammatory diseases, and combinations thereof.

In some embodiments, the disease or disorder is a neurodegenerative disease. For example, in some more specific embodiments, the neurodegenerative disease is Parkinson's disease, or Lewy body dementia. In certain embodiments, the disease or disorder is a CNS disorder (e.g., Alzheimer's disease or L-DOPA induced dyskinesia). In certain embodiments, the disease or disorder is cancer. In certain more specific embodiments, the cancer is kidney cancer, breast cancer, prostate cancer, a blood cancer, papillary cancer, lung cancer, acute myelogenous leukemia, or multiple myeloma. In some embodiments, the disease or disorder is an inflammatory disease. In some more specific embodiments, the inflammatory disease is leprosy, Crohn's disease, amyotrophic lateral sclerosis, rheumatoid arthritis, or ankylosing spondylitis.

Embodiments of the disclosure also relate to the use of compounds according to Structure (I) and/or physiologically acceptable salts thereof for the prophylactic or therapeutic treatment and/or monitoring of diseases that are caused, mediated and/or modulated by the LRRK2 kinase activity. Furthermore, embodiments of the disclosure relate to the use of compounds according to Structure (I) and/or physiologically acceptable salts thereof for the production of a medicament for the prophylactic or therapeutic treatment and/or monitoring of diseases that are caused, mediated and/or modulated by LRRK2 activity. In certain embodiments, the disclosure provides the use of a compound according to Structure I or physiologically acceptable salts thereof, for the production of a medicament for the prophylactic or therapeutic treatment of a LRRK2-mediated disorder.

In another embodiment, the present disclosure relates to a method of treating inflammatory diseases or conditions mediated by LRRK2 by administering to a patient in need thereof a therapeutically effective amount of the compound of Structure (I).

Also included herein are methods of treatment in which at least one compound of Structure (I) is administered in combination with an anti-inflammatory or a therapeutic agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate. Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine.

Examples of NSAIDs also include COX-2 specific inhibitors such as celecoxib, valdecoxib, lumiracoxib dnd/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The disclosure also includes embodiments in which the anti-inflammatory agent is a metabolic inhibitor such as a dihydrofolate reductase inhibitor, such as methotrexate or a dihydroorotate dehydrogenase inhibitor, such as leflunomide.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, ß-adrenergic agonists, ipratropium, glucocorticoids, methylxanthines, sodium channel blockers, opioid receptor agonists, calcium channel blockers, membrane stabilizers and leukotriene inhibitors.

Other embodiments of the disclosure pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the disclosure pertain to combinations in which at least one active agent is an immunosuppressant compound such as an immunosuppressant compound chosen from methotrexate, leflunomide, cyclosporine, tacrolimus, azathioprine, and mycophenolate mofetil.

In some embodiments, medicaments which are administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatoires, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutaline, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics, e.g., ipratropium, atropine or oxitropium; hormones, e.g., cortisone, hydrocortisone or prednisolone; xanthines, e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts) or as esters (e.g., lower alkyl esters) or as solvates (e.g., hydrates) to optimize the activity and/or stability of the medicament.

The agents disclosed herein or other suitable agents are administered depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

In some embodiments, the compounds of Structure (I) are administered as a mono-therapy.

The methods of embodiments of embodiments of this disclosure can be performed either in vitro or in vivo. The susceptibility of a particular cell to treatment with the compounds of Structure (I) can be particularly determined by in vitro tests, whether in the course of research or clinical application. Typically, a culture of the cell is combined with a compound at various concentrations for a period of time which is sufficient to allow the active agents to inhibit LRRK2 kinase activity, usually between about one hour and one week. In vitro treatment can be carried out using cultivated cells from a biopsy sample or cell line. In some embodiments, the $IC_{50}$ of the compounds of Structure (I) to inhibit LRRK2 kinase was determined by the concentration of the compound required to inhibit 50% of the activity of the LRRK2.

The examples and preparations provided below further illustrate and exemplify the compounds of the present disclosure and methods of preparing and testing such compounds. It is to be understood that the scope of the present disclosure is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers may be obtained by methods known to those skilled in the art.

EXAMPLES

The following examples are provided for exemplary purposes. For examples which result in a compound of Structure (I), General Synthetic Schemes 1-12 are generally used, unless otherwise noted.

The following General Reaction Schemes illustrates exemplary methods for preparation of compounds of Structure (I):

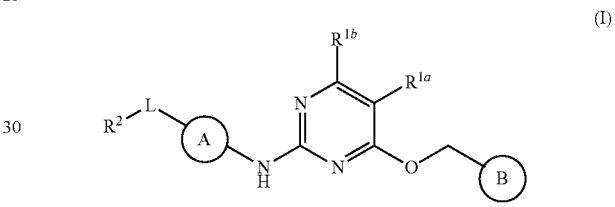

or pharmaceutically acceptable salts, stereoisomers or prodrugs thereof, wherein each of A, B, $R^{1a}$, $R^{1b}$, $R^2$, and L are as defined herein.

Any of the reaction schemes can be modified at any step to add and/or modify a substituent as appropriate during any stage of the overall synthesis of desired compounds.

It will also be appreciated by those skilled in the art that in the processes for preparing the compounds described herein the functional groups of intermediate compounds may need to be protected by suitable protecting groups. Such functional groups include, but are not limited to, hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R″ (where R″ is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". Prodrugs of compounds of this disclosure are included within the scope of embodiments of the disclosure.

General Procedures

All proton NMR experiments were recorded on a Bruker NEO Spectrometer equipped with a BBFO probe at 400 MHz. Deuterated solvents contained less than 0.05% v/v tetramethylsilane which was used as the reference signal (set at 0.00 ppm). When deuterated solvents did not contain tetramethylsilane, the residual nondeuterated solvent peaks were used as a reference signal, as per published guidelines (J. Org. Chem. 1997, 62(21), 7512-7515). Chemical shifts are expressed in parts per million (ppm, δ units).

Coupling constants are in hertz (Hz). Splitting patterns describe apparent multiplicities and are designated as broad singlet (bs), s (singlet), d (doublet), t (triplet), q (quartet), m (multiplet), qt (quintuplet) or brs (broad singlet).

LC/MS analyses were performed on an Agilent Technologies UHPLC 1290 Infinity II with a G6125 MS detector.

Microwave reactions were conducted with a Monowave 300 by Anton Paar GmbH using standard protocols.

Abbreviations

° C. (degree Celsius); 1H NMR (proton Nuclear Magnetic Resonance); ACN (acetonitrile); AcOH (acetic acid); BINAP (2,2'-bis(diphenylphosphino)-1,1'-binaphthyl); DCE (dichloroethane); DCM (dichloromethane); DFAA (difluoroacetic anhydride); DIPEA (N,N-diisopropylethylamine); DPPA (diphenylphosporyl azide); EDC·HCl (N-(3-dimethylaminopropyl)-N'-ethylcarbodiimide hydrochloride); DMF (N,N-dimethylformamide); DMSO-$d_6$ (deuterated dimethylsulfoxide); eq (equivalent); EtOAc (ethyl acetate); g (gram); h (hour); HPLC (High Performance Liquid Chromatography); LC-MS (Liquid Chromatography Mass Spectrometry); MeOH (methanol); mg (milligram); min (minute); mL (milliliter); mmol (millimole); MsCl (methanesulfonyl chloride); Pd(dppf)Cl$_2$·DCM ([1,1'-Bis(diphenylphosphino)ferrocene]dichloropalladium(II), complex with dichloromethane); Pd(OAc)$_2$ (palladium(II) acetate); SFC (Supercritical Fluid Chromatography); tBu (tert-butyl); tBuOH (tert-butanol); TFA (trifluoroacetic acid); TFAA (trifluoroacetic anhydride); THF (tetrahydrofuran); TLC (Thin Layer Chromatography); TTIP (titanium(IV) isopropoxide).

Preparation of Synthetic Intermediates

Pyrimidine Intermediates A

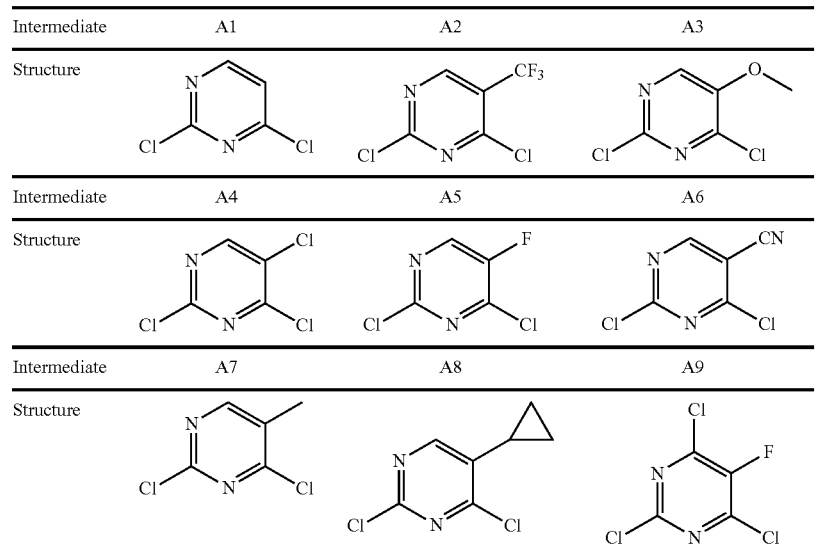

All dichloropyrimidines Intermediates A are commercially available.

Alcohol Intermediates B

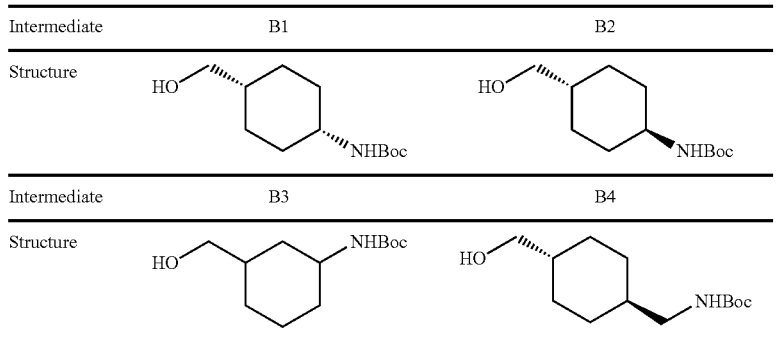

-continued

| Intermediate | B5 | B6 |
|---|---|---|
| Structure | *(cis-3-(hydroxymethyl)cyclopentyl)-NHBoc* | *1-acetyl-3,3-difluoro-4-(hydroxymethyl)piperidine* |
| Intermediate | B7 | B8 |
| Structure | *tert-butyl 4-(hydroxymethyl)piperidine-1-carboxylate* | *tert-butyl 4-fluoro-4-(hydroxymethyl)piperidine-1-carboxylate* |
| Intermediate | B9 | B10 |
| Structure | *tert-butyl 3-fluoro-4-(hydroxymethyl)piperidine-1-carboxylate* | *tert-butyl 3-(hydroxymethyl)azetidine-1-carboxylate* |
| Intermediate | B11 | B12 |
| Structure | *tert-butyl 6-(hydroxymethyl)-2-azaspiro[3.3]heptane-2-carboxylate* | *3,3-difluoro-4-(hydroxymethyl)-1-(trifluoroacetyl)piperidine* |
| Intermediate | B13 | B14 |
| Structure | *(1-(Boc-amino)cyclopropyl)methanol* | *tert-butyl 3-fluoro-3-(hydroxymethyl)azetidine-1-carboxylate* |
| Intermediate | B15 | B16 |
| Structure | *(4-(Boc-amino)bicyclo[2.2.2]octan-1-yl)methanol* | *(4-(Boc-amino)cubane derivative)methanol* |
| Intermediate | B17 | B18 |
| Structure | *(4-(Boc-amino)cycloheptyl)methanol* | *(cis-4-(Boc-amino)-1-methylcyclohexyl)methanol* |
| Intermediate | B19 | B20 |
| Structure | *(cis-3-(Boc-amino)cyclobutyl)methanol* | *4-(hydroxymethyl)cyclohexan-1-one* |

-continued

| Intermediate | B1 | B22 |
|---|---|---|
| Structure | HO–CH₂–(cyclopentanone) | HO–CH₂–(spiro[3.3]heptan-2-one) |

| Intermediate | B23 | B24 |
|---|---|---|
| Structure | trans-4-(hydroxymethyl)-α,α-dimethylcyclohexanemethanol | 1,4-cyclohexanedimethanol |

| Intermediate | B25 | B26 |
|---|---|---|
| Structure | 4-(hydroxymethyl)bicyclo[2.2.2]octan-1-ol | cyclohexylmethanol |

| Intermediate | B27 | B28 |
|---|---|---|
| Structure | (tetrahydro-2H-pyran-4-yl)methanol | (2,6-dimethyltetrahydro-2H-pyran-4-yl)methanol |

| Intermediate | B29 | B30 |
|---|---|---|
| Structure | (2,2-dimethyltetrahydro-2H-pyran-4-yl)methanol | (2-oxaspiro[3.3]heptan-6-yl)methanol |

| Intermediate | B31 | B32 |
|---|---|---|
| Structure | (4,4-difluorocyclohexyl)methanol | (3,3-difluorocyclobutyl)methanol |

| Intermediate | B33 | B34 |
|---|---|---|
| Structure | (4-(trifluoromethyl)cyclohexyl)methanol | oxetan-3-ylmethanol |

| Intermediate | B35 | B36 |
|---|---|---|
| Structure | (4-methoxycyclohexyl)methanol | (4-hydroxy-4-(trifluoromethyl)cyclohexyl)methanol |

| Intermediate | B37 | B38 |
|---|---|---|
| Structure | 4-(hydroxymethyl)cyclohexane-1-carbonitrile | 3-(hydroxymethyl)cyclobutane-1-carbonitrile |

| Intermediate | B39 | B40 |
|---|---|---|
| Structure | 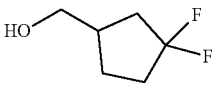 | 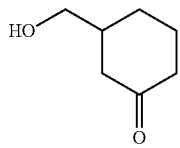 |
| Intermediate | B41 | B42 |
| Structure | 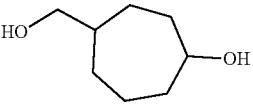 | 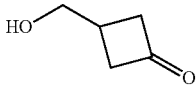 |
| Intermediate | B43 | B44 |
| Structure | 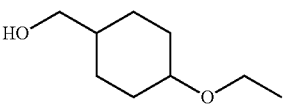 | 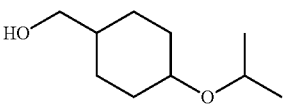 |
| Intermediate | B45 | B46 |
| Structure | 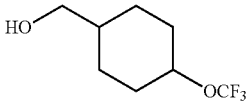 | 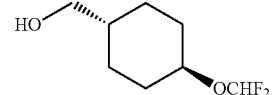 |
| Intermediate | B47 | B48 |
| Structure | 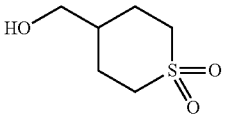 | 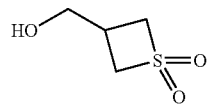 |
| Intermediate | B49 | B50 |
| Structure | 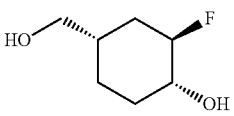 | 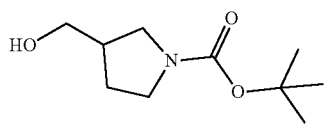 |
| Intermediate | — | — |
| Structure | — | — |

All alcohol Intermediates B are commercially available except for the following:

Intermediate B5 was prepared as reported in PCT Publication No. WO 2020/087024 A1.

Intermediate B8 was prepared as reported in PCT Publication No. WO 2016/191312 A1.

Intermediate B9 was prepared as reported in PCT Publication No. WO 2019/232053 A1.

Intermediate B12 was prepared as reported in J. Org. Chem. 2010, 75, 3, 929-932.

Intermediate B13 was prepared as reported in PCT Publication No. WO 2018/227067 A1.

Intermediate B15 was prepared as reported in PCT Publication No. WO 2018/112382 A1.

Intermediate B36 was prepared as reported in PCT Publication No. US 2016/0122318 A1.

Intermediate B43 was prepared as reported in *Bioorg. Med. Chem. Lett.* 2009, 19, 209-213.

Intermediate B44 was prepared as reported in *Bioorg. Med. Chem. Lett.* 2010, 20, 1830-1833.

Intermediate B47 was prepared as reported in PCT Publication No. WO 2014/154794 A1.

Intermediates B16, B17, B18, B 41, B45, B46, B48, and B49 were prepared as follows:

Intermediate B16

TERT-BUTYL (4-(HYDROXYMETHYL)CUBAN-1-YL) CARBAMATE

Step 1: Synthesis of methyl 4-((tert-butoxycarbonyl)amino)cubane-1-carboxylate

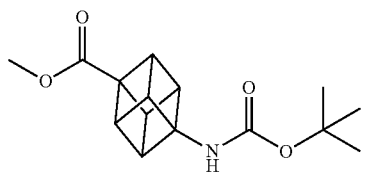 [SMILES: COC(=O)C12C3C4C1C1C2C3C41NC(=O)OC(C)(C)C]

Triethylamine (0.572 g, 5.65 mol) and DPPA (0.960 g, 3.49 mmol) were added to a solution of 4-(methoxycarbonyl)cubane-1-carboxylic acid (0.600 g, 2.91 mmol) in BuOH (4 mL) and the resulting mixture was stirred at 25° C. for 1 h then heated to reflux for 16 h. Following completion of the reaction (as indicated by TLC), the reaction mixture was concentrated under reduced pressure, giving a residue which was dissolved in EtOAc (15 mL), washed with saturated NaHCO$_3$ (5 mL) and brine (5 mL), dried over Na$_2$SO$_4$, filtered, and concentrated under reduced pressure. The resulting crude material was purified by Isolera (silica gel 60-120 mesh, eluting with 20% EtOAc in petroleum ether), affording the title compound as a white solid (0.25 g, 29% yield). 1H NMR (400 MHz, CDCl$_3$) δ=5.10 (bs, 1H), 4.11-4.18 (m, 6H), 3.73 (s, 3H), 1.47 (s, 9H). LCMS: 222.1 [M+H−(Bu].

Step 2: Synthesis of 4-((tert-butoxycarbonyl)amino)cubane-1-carboxylic acid

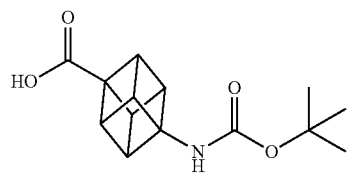 [SMILES: CC(C)(C)OC(=O)NC12C3C4C1C1C2C3C41C(=O)O]

A solution of NaOH (0.04 g, 0.992 mmol) in MeOH (3.4 mL) was added to a solution of methyl 4-((tert-butoxycarbonyl)amino)cubane-1-carboxylate (B17a, 0.25 g, 0.901 mmol) in THF (2.5 mL) at 0° C. and the resulting mixture was stirred at 55° C. for 4 h. Following completion of the reaction (as indicated by TLC), the reaction mixture was concentrated under reduced pressure, giving a residue which was taken in ice water (5 mL), acidified with citric acid (pH=3.0), and extracted with DCM (2×5 mL). The combined organic extracts were dried over Na$_2$SO$_4$, filtered, and concentrated under reduced pressure to yield the title compound as an off-white solid (0.15 g, 62% yield). 1H NMR (400 MHZ, DMSO-d$_6$) δ=12.18 (bs, 1H), 7.72 (bs, 1H), 3.94-3.97 (m, 6H), 1.39 (s, 9H). LCMS: 208.1 [M+H−tBu].

Step 3: Synthesis of tert-butyl (4-(hydroxymethyl)cuban-1-yl)carbamate

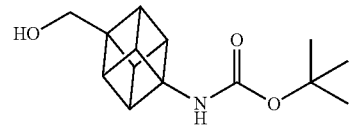 [SMILES: CC(C)(C)OC(=O)NC12C3C4C1C1C2C3C41CO]

Borane-tetrahydrofuran complex (0.712 mL, 1.139 mmol) was added to a solution of 4-((tert-butoxycarbonyl)amino)cubane-1-carboxylic acid (0.150 g, 0.570 mmol) in THF (2.5 mL) 0° C. and the resulting mixture was stirred at 25° C. for 2 h. Following completion of the reaction (as indicated by TLC), the reaction mixture was cooled to 0° C., quenched with ice water (5 mL), and extracted with EtOAc (2×10 mL). The combined organic extracts were dried over Na$_2$SO$_4$, filtered, and concentrated under reduced pressure to afford crude material which was purified by flash chromatography (silica gel 230-400 mesh, eluting with 30% EtOAc in petroleum ether), giving the title compound as an off-white solid (0.13 g, 91% yield). LCMS: 194.1 [M+H−tBu].

Intermediate B17

TERT-BUTYL (4-(HYDROXYMETHYL)CYCLOHEPTYL) CARBAMATE

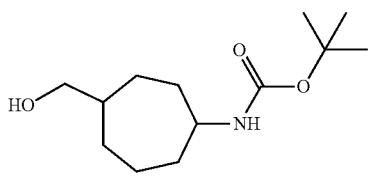 [SMILES: CC(C)(C)OC(=O)NC1CCCC(CO)CC1]

Borane-tetrahydrofuran complex (1M in THF, 1.943 ml, 1.943 mmol) was added dropwise to a solution of 4-((tert-butoxycarbonyl)amino)cycloheptane-1-carboxylic acid (0.250 g, 0.972 mmol) in THF (4 mL) at 0° C. and the resulting mixture was stirred at 25° C. for 2 h. Following completion of the reaction (as indicated by TLC), the reaction mixture was quenched with methanol (10 mL), diluted with ice water (15 mL), and extracted with EtOAc (2×25 mL). The combined organic extracts were dried over Na$_2$SO$_4$, filtered, and concentrated under reduced pressure to afford crude material which was purified by flash chromatography (silica gel 230-400 mesh, eluting with 45% EtOAc in petroleum ether), affording the title compound as a gum (0.20 g, 85% yield). 1H NMR (400 MHZ, DMSO-d$_6$) δ=6.71 (bs, 1H), 4.42 (bs, 1H), 3.14 (bs, 2H), 0.86-1.79 (m, 21H). LCMS: 188.1 [M+H−tBu].

Intermediate B18

TERT-BUTYL (4-(HYDROXYMETHYL)-4-METHYLCYCLOHEXYL)CARBAMATE

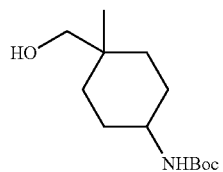 [SMILES: CC1(CO)CCC(NC(=O)OC(C)(C)C)CC1]

Borane-tetrahydrofuran complex (1M in THF, 2.332 ml, 2.332 mmol) was added dropwise to a solution of 4-((tert-butoxycarbonyl)amino)-1-methylcyclohexane-1-carboxylic acid (0.30 g, 1.166 mmol) in THF (2.5 mL) at 0° C. and the resulting mixture was stirred at 25° C. for 2 h. Following completion of the reaction (as indicated by TLC), the reaction mixture was quenched with saturated NaHCO$_3$ (10 mL) and extracted with EtOAc (2×25 mL). The combined organic extracts were dried over Na$_2$SO$_4$, filtered, and concentrated under reduced pressure to afford crude material which was purified by flash chromatography (silica gel 230-400 mesh, eluting with 50% EtOAc in petroleum ether), giving the title compound as an off-white solid (0.18 g) which was used without further purification. LCMS: 144.2 [M+H−Boc].

Intermediate B41

4-(HYDROXYMETHYL)CYCLOHEPTAN-1-OL

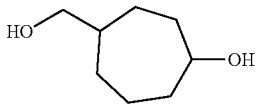

Lithium aluminum hydride (1M in THF, 3.201 mL, 3.20 mmol) was added to a solution of 4-oxocycloheptane-1-carboxylic acid (0.500 g, 3.20 mmol) in THF (5 mL) at 0° C. and the resulting mixture was stirred at 25° C. for 2 h. Following completion of the reaction (as indicated by TLC), the reaction mixture was cooled to 0° C., quenched with ice water (5 mL), and extracted with EtOAc (2×10 mL). The combined organic extracts were dried over Na$_2$SO$_4$, filtered, and concentrated under reduced pressure to afford crude material which was purified by flash chromatography (silica gel 230-400 mesh, eluting with 30% EtOAc in petroleum ether), giving the title compound as an off-white solid (0.07 g, 15% yield). LCMS: 145.1 [M+H].

Intermediate B45

(4-(TRIFLUOROMETHOXY)CYCLOHEXYL)METHANOL

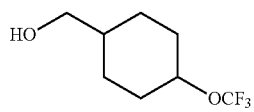

Borane-tetrahydrofuran complex (1M in THF, 0.943 mL, 0.943 mmol) was added to a solution of 4-(trifluoromethoxy)cyclohexane-1-carboxylic acid (0.100 g, 0.471 mmol) in THF (3 mL) at 0° C. and the resulting mixture was stirred at 25° C. for 2 h. Following completion of the reaction (as indicated by TLC), the reaction mixture was cooled to 0° C., quenched with ice water (5 mL), and extracted with EtOAc (2× 10 mL). The combined organic extracts were dried over Na$_2$SO$_4$, filtered, and concentrated under reduced pressure to afford crude material which was purified by flash chromatography (silica gel 230-400 mesh, eluting with 20% EtOAc in petroleum ether), giving the title compound as a colorless gum (0.08 g, 86% yield). LCMS: 199.1 [M+H].

Intermediate B46

TRANS 4-(DIFLUOROMETHOXY)CYCLOHEXYL)METHANOL

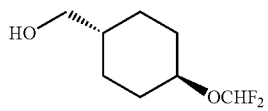

Borane-tetrahydrofuran complex (1M in THF, 0.515 mL, 0.515 mmol) was added to a solution of (1R,4R)-4-(difluoromethoxy)cyclohexane-1-carboxylic acid (0.100 g, 0.515 mmol) in THF (3 mL) at 0° C. and the resulting mixture was stirred at 25° C. for 2 h. Following completion of the reaction (as indicated by TLC), the reaction mixture was cooled to 0° C., quenched with ice water (5 mL), and extracted with EtOAc (2× 10 mL). The combined organic extracts were dried over Na$_2$SO$_4$, filtered, and concentrated under reduced pressure to afford crude material which was purified by flash chromatography (silica gel 230-400 mesh, eluting with 15% EtOAc in petroleum ether), giving the title compound as a colorless gum (0.079 g, 85% yield). LCMS: 181.1 [M+H].

Intermediate B48

3-(HYDROXYMETHYL)THIETANE 1,1-DIOXIDE

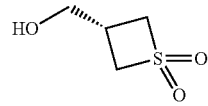

OXONE®, monopersulfate compound (0.590 g, 1.920 mmol) was added to a solution of thietan-3-ylmethanol (0.200 g, 1.920 mmol) in a mixture of MeOH and water (1:1, 2 mL) at 0° C. and the resulting mixture was stirred at 25° C. for 16 h. Following completion of the reaction (as indicated by TLC), the reaction mixture was cooled to 0° C., quenched with ice water (5 mL), and extracted with EtOAc (2×10 mL). The combined organic extracts were washed with brine (5 mL), dried over Na$_2$SO$_4$, filtered, and concentrated under reduced pressure to afford the title compound as a colorless gum (0.060 g, 23% yield) which was used without further purification. LCMS: 137.1 [M+H].

Intermediate B49

3-(HYDROXYMETHYL)THIETANE 1,1-DIOXIDE

Step 1: Synthesis of (1S,3R,4R)-3-fluoro-4-hydroxycyclohexane-1-carboxylic acid

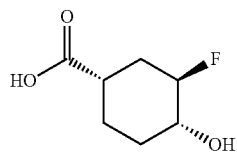

Lithium hydroxide monohydrate (0.106 g, 4.420 mmol) was added to a solution of ethyl (1S,3R,4R)-3-fluoro-4-hydroxycyclohexane-1-carboxylate (0.700 g, 3.680 mmol) in EtOH (7 mL) and water (1 mL) at 0° C. and the resulting mixture was stirred at 25° C. for 3 h. Following completion of the reaction (as indicated by TLC), the reaction mixture was evaporated under reduced pressure to afford a residue which was acidified to pH 2 using 1.5 N HCl then extracted with EtOAc (2×5 mL). The combined organic extracts were dried over $Na_2SO_4$, filtered, and concentrated under reduced pressure to afford the title compound as a colorless gum (0.370 g, 60% yield) which was used without further purification. LCMS: 184.3 [M+Na].

Step 2: Synthesis of (1R,2R,4S)-2-fluoro-4-(hydroxymethyl)cyclohexan-1-ol

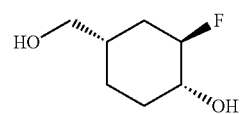

Borane-tetrahydrofuran complex (1M in THF, 2.282 mL, 2.282 mmol) was added to a solution of (1S,3R,4R)-3-fluoro-4-hydroxycyclohexane-1-carboxylic acid (0.370 g, 2.282 mmol) in THF (6 mL) at 0° C. and the resulting mixture was stirred at 25° C. for 2 h. Following completion of the reaction (as indicated by TLC), the reaction mixture was cooled to 0° C., quenched with ice water (5 mL), and extracted with EtOAc (2× 10 mL). The combined organic extracts were dried over $Na_2SO_4$, filtered, and concentrated under reduced pressure to afford the title compound as colorless gum (0.180 g, 43% yield) which was used without further purification. LCMS: 149.1 [M+H].

Amine Intermediates C

| Intermediate | C1 | C2 |
|---|---|---|
| Structure | ![C1 structure: morpholine-phenyl-NH2] | ![C2 structure: N-methylpyrazole-NH2] |

| Intermediate | C3 | C4 |
|---|---|---|
| Structure | ![C3 structure: difluoroethyl-pyrazole-NH2] | ![C4 structure: morpholine-phenyl-NH2 meta] |

| Intermediate | C5 | C6 |
|---|---|---|
| Structure | ![C5 structure: NC-C(CH3)2-pyrazole-NH2] | ![C6 structure: NC-cyclobutyl-pyrazole-NH2] |

| Intermediate | C7 | C8 |
|---|---|---|
| Structure | ![C7 structure: NC-cyclobutyl-dimethylpyrazole-NH2] | ![C8 structure: dimethylmorpholine-phenyl-NH2] |

-continued
| Intermediate | C9 | C10 |
|---|---|---|
| Structure | 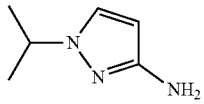 | 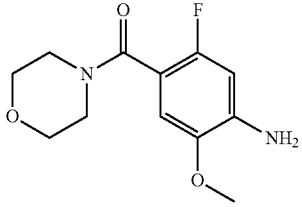 |
| Intermediate | C11 | C12 |
| Structure | 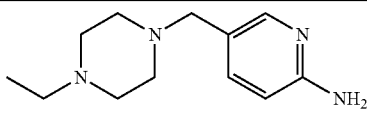 | 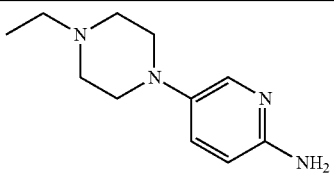 |
| Intermediate | C13 | C14 |
| Structure | 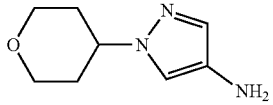 | 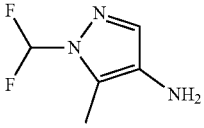 |
| Intermediate | C15 | C16 |
| Structure | 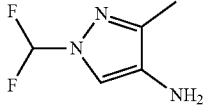 | 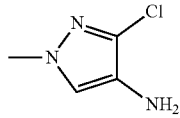 |
| Intermediate | C17 | C18 |
| Structure | 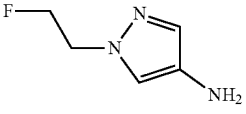 | 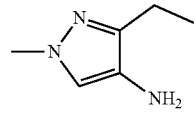 |
| Intermediate | C19 | C20 |
| Structure | 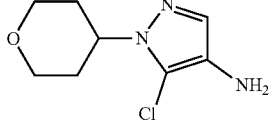 | 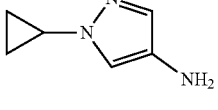 |
| Intermediate | C21 | C22 |
| Structure | 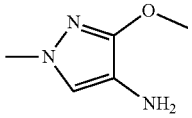 | 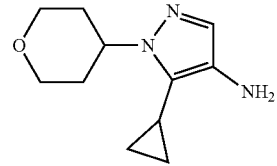 |
| Intermediate | C23 | C24 |
| Structure | 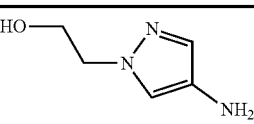 | 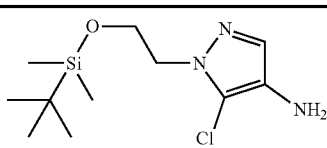 |

-continued
| Intermediate | C25 | C26 |
|---|---|---|
| Structure | 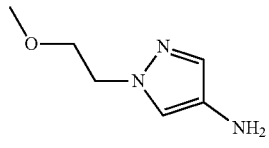 | 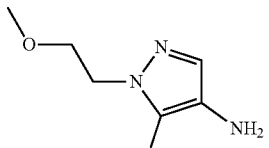 |
| Intermediate | C27 | C28 |
| Structure | 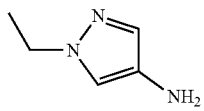 | 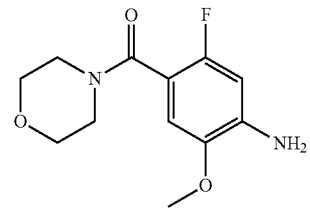 |
| Intermediate | C29 | C30 |
| Structure | 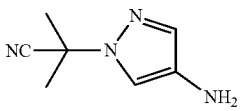 | 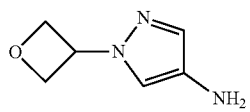 |
| Intermediate | C31 | C32 |
| Structure | 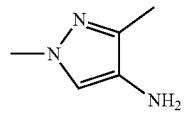 | 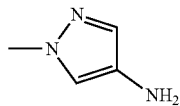 |
| Intermediate | C33 | C34 |
| Structure | 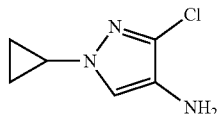 | 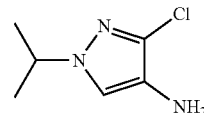 |
| Intermediate | C35 | C36 |
| Structure | 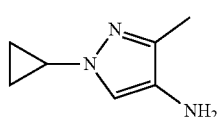 | 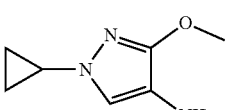 |
| Intermediate | C37 | C38 |
| Structure | 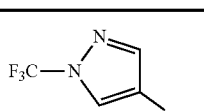 | 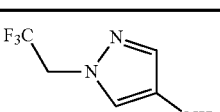 |
| Intermediate | C39 | C40 |
| Structure | 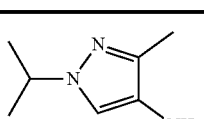 | 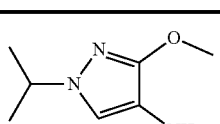 |

| Intermediate | C41 | C42 |
|---|---|---|
| Structure | ![C41 structure] | ![C42 structure] |

| Intermediate | C43 | C44 |
|---|---|---|
| Structure | ![C43 structure] | ![C44 structure] |

| Intermediate | C45 | C46 |
|---|---|---|
| Structure | ![C45 structure] | ![C46 structure] |

| Intermediate | C47 | C48 |
|---|---|---|
| Structure | ![C47 structure] | ![C48 structure] |

| Intermediate | C49 |
|---|---|
| Structure | ![C49 structure] |

All amine Intermediates C are commercially available except for the following:

Intermediate $C_5$ was prepared as reported in PCT Publication No. WO2017/087905 A1.

Intermediate $C_8$ was prepared as reported in PCT Publication No. WO 2006/064189 A1.

Intermediate $C_{10}$ was prepared as reported in J. Med. Chem. 2012, 55, 22, 9416-9433.

Intermediate $C_{19}$ was prepared as reported in PCT Publication No. WO 2012/062783 A1.

Intermediates $C_{22}$ and $C_{24}$ were prepared as reported in PCT Publication No. WO 2020/088390 A1.

Intermediate $C_{26}$ was prepared as reported in PCT Publication No. WO 2020/216371 A1.

Intermediate $C_{28}$ was prepared as reported in J. Med. Chem. 2012, 55(22), 9416-9433.

Intermediate $C_{29}$ was prepared as reported in PCT Publication No. WO 2020/070331 A1.

Intermediate $C_{30}$ was prepared as reported in PCT Publication No. WO 2019/121691 A1.

Intermediates $C_{33}$ and $C_{34}$ were prepared as reported in PCT Publication No. WO2019/112269 A1.

Intermediate $C_{41}$ was prepared as reported in PCT Publication No. CN110467615 A1.

Intermediate $C_{45}$ was prepared as reported in PCT Publication No. WO 2016/049211 A1.

Intermediate $C_{47}$ was prepared as reported in PCT Publication No. WO 2021/005222 A1.

Intermediates $C_6$ and $C_7$ were prepared according to the following synthetic scheme:

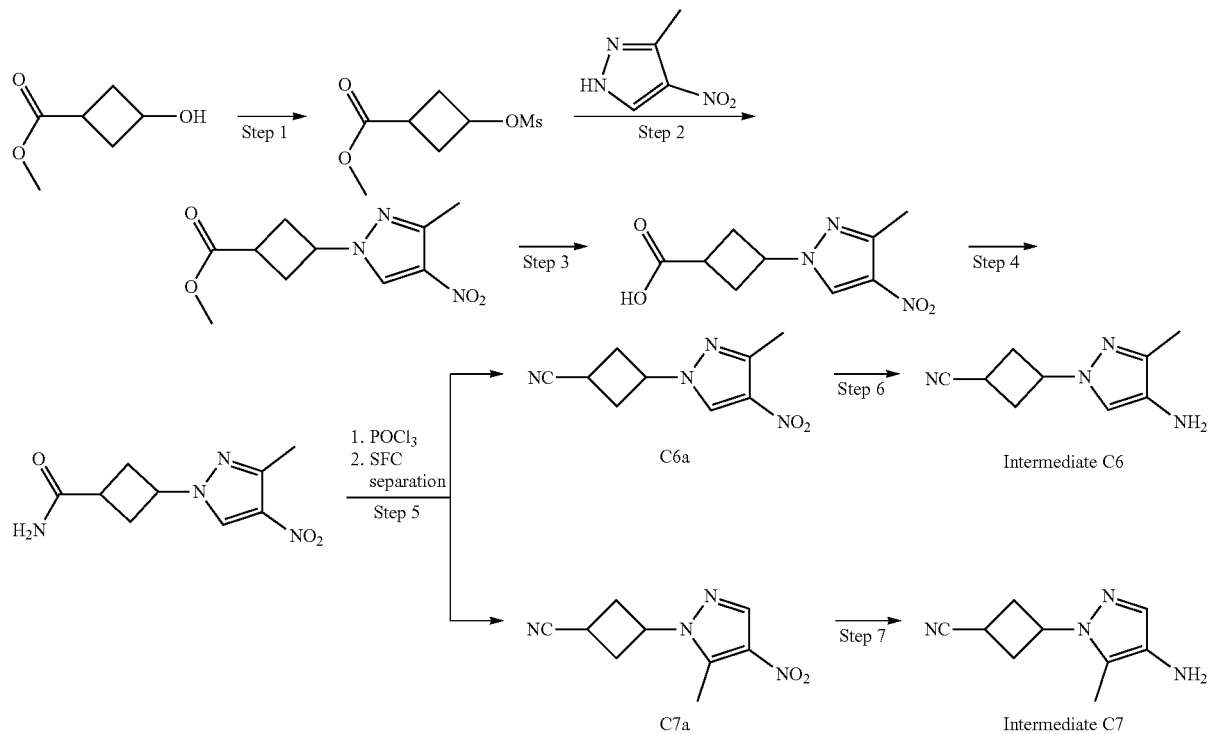

Intermediate C6

3-(4-AMINO-3-METHYL-1H-PYRAZOL-1-YL)CYCLOBUTANE-1-CARBONITRILE

Step 1: Synthesis of methyl 3-((methylsulfonyl)oxy)cyclobutane-1-carboxylate DIPEA (10.43 g, 81.0 mmol) and MsCl (5.03 ml, 64.5 mmol) were added to a solution of methyl 3-hydroxycyclobutane-1-carboxylate (7.00 g, 53.8 mmol) in DCM (70 mL) at 0° C. and the resulting mixture was stirred at 25° C. for 3 h. Following completion of the reaction (as indicated by TLC), the reaction mixture was diluted with DCM (100 mL), washed with brine (50 mL), dried over $Na_2SO_4$, filtered, and concentrated under reduced pressure to give the title compound as a brown solid (10.5 g, 94% yield) which was used without further purification. 1H NMR (400 MHZ, $CDCl_3$) δ=4.91-4.98 (m, 1H), 3.72 (s, 3H), 3.02 (s, 3H), 2.69-2.77 (m, 2H), 2.55-2.64 (m, 2H).

Step 2: Synthesis of methyl 3-(3-methyl-4-nitro-/H-pyrazol-1-yl)cyclobutane-1-carboxylate Methyl 3-((methylsulfonyl)oxy)cyclobutane-1-carboxylate (11.80 g, 56.6 mmol) and $Cs_2CO_3$ (23.07 g, 70.8 mmol) were added to a solution of 3-methyl-4-nitro-1H-pyrazole (6.00 g, 47.2 mmol) in DMF (60 mL) at 25° C. and the resulting mixture was stirred at 80° C. for 16 h. Following completion of the reaction (as indicated by TLC), the reaction mixture was poured into crushed ice (500 g) and extracted with EtOAc (3×100 mL). The combined organic extracts were washed with water (3×100 mL) and brine (200 mL), dried over $Na_2SO_4$, filtered, and concentrated under reduced pressure to yield crude material which was purified by Isolera (silica gel 230-400 mesh, eluting with 40% EtOAc in petroleum ether), giving the title compound as an off-white solid (mixture of regioisomers, 6.5 g, 54% yield). 1H NMR (400 MHZ, $CDCl_3$) δ=8.14 (s, 1H), 4.96-5.00 (m, 1H), 3.74-3.78 (m, 3H), 3.22-3.26 (m, 1H), 2.87-3.02 (m, 2H), 2.64-2.80 (m, 2H), 2.55-2.57 (m, 3H). LCMS: 240.1 [M+H].

Step 3: Synthesis of 3-(3-methyl-4-nitro-/H-pyrazol-1-yl)cyclobutane-1-carboxylic acid Lithium hydroxide monohydrate (1.301 g, 54.3 mmol) was added to a solution of methyl 3-(3-methyl-4-nitro-1H-pyrazol-1-yl)cyclobutane-1-carboxylate (6.500 g, 27.2 mmol) in MeOH:water:THF (1:1:1, 150 mL) at 0° C. and the resulting mixture was stirred at 25° C. for 16 h. Following completion of the reaction (as indicated by TLC), the reaction mixture was concentrated under reduced pressure, giving a residue which was dissolved in water (50 mL) and acidified to pH=2 with HCl (1.5 N). The resulting precipitate was filtered, washed with water (2×10 mL), and dried to give the title compound as an off-white solid (mixture of regioisomers, 4.2 g, 68% yield). 1H NMR (400 MHZ, DMSO-$d_6$) δ=12.45 (bs, 1H), 8.91 (s, 1H), 5.01-5.05 (m, 1H), 3.07-3.14 (m, 1H), 2.72-2.80 (m, 2H), 2.46-2.69 (m, 5H). LCMS: 224.1 [M−H].

Step 4: Synthesis of 3-(3-methyl-4-nitro-/H-pyrazol-1-yl)cyclobutane-1-carboxamide Oxalyl chloride (1.127 ml, 12.88 mmol) and DMF (0.583 mL, 7.49 mmol) were slowly added to a stirred solution of 3-(3-methyl-4-nitro-1H-pyrazol-1-yl)cyclobutane-1-carboxylic acid (2.900 g, 12.88 mmol) with DCM (35 mL) at 0° C. and the resulting mixture was stirred at 25° C. for 1 hr. The reaction mixture was then concentrated under reduced pressure, giving a residue which was taken in THF (46.7 mL). Aqueous ammonia (25% in water, 58.5 mL, 2678 mmol) was slowly added 0° C. and the resulting mixture was stirred at 25° C. for 16 h. Following completion of the reaction (as indicated by TLC), the reaction mixture was concentrated under reduced pressure, giving a residue which was cooled to 0° C. The resulting precipitate was filtered, washed with water (2×5 mL), and dried to give the title compound as an off-white solid (mixture of regioisomers, 2.7 g, 91% yield). LCMS: 225.1 [M+H].

Step 5: Synthesis of 3-(3-methyl-4-nitro-/H-pyra-zol-1-yl)cyclobutane-1-carbonitrile ((6a) and 3-(5-methyl-4-nitro-1H-pyrazol-1-yl)cyclobutane-1-car-bonitrile (C7a)

Phosphoryl chloride (13.90 mL, 149.0 mmol) was added to a solution of 3-(3-methyl-4-nitro-1H-pyrazol-1-yl)cy-clobutane-1-carboxamide (6.70 g, 29.9 mmol) in DCE (40 mL) and the resulting mixture was heated to reflux for 30 min. Following completion of the reaction (as indicated by TLC), the reaction mixture was concentrated under reduced pressure, giving a residue which was slowly poured into crushed ice then neutralized with NaHCO$_3$ and extracted with DCM (3×100 mL). The combined organic extracts were dried over Na$_2$SO$_4$, filtered, and concentrated under reduced pressure to yield crude material which was purified by Isolera (silica gel 230-400 mesh, eluting with 20% EtOAc in petroleum ether), giving the title product as an off-white solid (mixture of regioisomers C$_7$a and C$_8$a, 5.4 g, 87% yield). 1H NMR (400 MHZ, CDCl$_3$) δ=8.15-8.16 (m, 1H), 4.97-5.09 (m, 1H), 3.36-3.42 (m, 1H), 3.05-3.19 (m, 2H), 2.87-2.96 (m, 2H), 2.58-2.67 (m, 3H). LCMS: 207.1 [M+H].

0.90 g of the mixture of regioisomers was purified by SFC (Chiralpak AS-H column, eluting with 0.5% isopropyl amine in IPA: 30% CO$_2$) to afford 0.65 g of the major isomer (second eluting peak) and 0.25 g of the minor isomer (first eluting peak). Based on the reported 1H NMR data of the minor isomer (WO 2017/218843 A1), the first eluting peak was attributed to C$_7$a and the second eluting peak to C6a.

3-(3-methyl-4-nitro-1H-pyrazol-1-yl)cyclobutane-1-car-bonitrile (C$_6$a): 1H NMR (400 MHZ, CDCl$_3$) δ=8.14 (s, 1H), 4.98-5.03 (m, 1H), 3.34-3.42 (m, 1H), 3.04-3.14 (m, 2H), 2.88-2.96 (m, 2H), 2.58 (s, 3H). LCMS: 207.1 [M+H].

3-(5-methyl-4-nitro-1H-pyrazol-1-yl)cyclobutane-1-car-bonitrile (C$_7$a): 1H NMR (400 MHZ, CDCl$_3$) δ=8.16 (s, 1H), 5.06-5.08 (m, 1H), 3.36-3.37 (m, 1H), 3.10-3.13 (m, 2H), 2.87-2.90 (m, 2H), 2.67 (s, 3H). LCMS: 207.1 [M+H].

Step 6: Synthesis of 3-(4-amino-3-methyl-/H-pyra-zol-1-yl)cyclobutane-1-carbonitrile Iron powder (1.600 g, 29.10 mmol) and ammonium chloride (0.156 g, 2.91 mmol) were added to a suspension of 3-(3-methyl-4-nitro-1H-pyrazol-1-yl)cyclobutane-1-carbo-nitrile (C$_6$a, 0.600 g, 2.91 mmol) in a mixture of ethanol (8 mL) and water (2 mL) and the resulting suspension was stirred at 90° C. for 3 h. Following completion of the reaction (as indicated by TLC), the reaction mixture was filtered through a pad of Celite® (i.e., diatomaceous earth) which was then rinsed with EtOAc (10 mL). The combined filtrates were concentrated under reduced pressure to yield crude material which was taken in DCM (20 mL), washed with brine (2 mL), dried over Na$_2$SO$_4$, filtered, and concentrated under reduced pressure to give the title compound (0.48 g) which was used without further purification. LCMS: 177.1 [M+H].

Intermediate C7

3-(4-AMINO-5-METHYL-1H-PYRAZOL-1-YL)CYCLOBUTANE-1-CARBONITRILE

Step 7: Synthesis of 3-(4-amino-3-methyl-1H-pyra-zol-1-yl)cyclobutane-1-carbonitrile Iron powder (0.680 g, 12.120 mmol) and ammonium chloride (0.065 g, 1.212 mmol) were added to a suspension of 3-(5-methyl-4-nitro-1H-pyrazol-1-yl)cyclobutane-1-car-bonitrile (C$_7$a, 0.250 g, 1.212 mmol) in a mixture of ethanol (4 mL) and water (1 mL) and the resulting suspension was stirred at 90° C. for 3 h. Following completion of the reaction (as indicated by TLC), the reaction mixture was filtered through a pad of Celite® (i.e., diatomaceous earth) which was then rinsed with EtOAc (5 mL). The combined filtrates were concentrated under reduced pressure to yield crude material which was taken in DCM (10 mL), washed with brine (2 mL), dried over Na$_2$SO$_4$, filtered, and concentrated under reduced pressure to give the title compound (0.16 g) which was used without further purification. LCMS: 177.1 [M+H].

Intermediate C35

1-CYCLOPROPYL-3-METHYL-1H-PYRAZOL-4-AMINE

Step 1: Synthesis of 1-cyclopropyl-3-methyl-4-nitro-1H-pyrazole

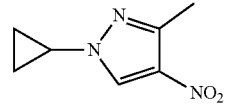

Copper (II) acetate (0.286 g, 1.574 mmol), 2,2'-bipyridine (0.256 g, 1.574 mmol), and NaHCO$_3$ (0.334 g, 3.15 mmol) were added to a stirred solution of 3-methyl-4-nitro-1H-pyrazole (0.200 g, 1.574 mmol) and cyclopropylboronic acid (0.270 g, 3.150 mmol) in dichloroethane (10 mL). The resulting mixture was stirred at 70° C. under oxygen atmosphere for 12 h. Following completion of the reaction (as indicated by TLC), the reaction mixture was filtered through a pad of Celite® (i.e., diatomaceous earth) which was then rinsed with DCM (2×20 mL). The combined filtrates were washed with water (20 mL) and brine (25 mL), the organic layer was separated, dried over Na$_2$SO$_4$, filtered, and concentrated under reduced pressure to yield crude material which was purified by flash chromatography (silica gel 230-400 mesh, eluting with 20% EtOAc in petroleum ether), giving the title compound as a colorless liquid (0.180 g, 68% yield). LCMS: 168.1 [M+H].

Step 2: Synthesis of 1-cyclopropyl-3-methyl-1H-pyrazol-4-amine

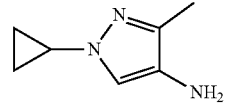

Iron powder (0.334 g, 5.98 mmol) and NH₄Cl (0.032 g, 0.598 mmol) were added to a suspension of 1-cyclopropyl-3-methyl-4-nitro-1H-pyrazole (0.100 g, 0.598 mmol) in a mixture of ethanol (4 mL) and water (1 mL) and the resulting suspension was stirred at 90° C. for 3 h. Following completion of the reaction (as indicated by TLC), the reaction mixture was filtered through a pad of Celite® (i.e., diatomaceous earth) which was then rinsed with EtOAc (5 mL). The combined filtrates were concentrated under reduced pressure to yield crude material which was taken in DCM (10 mL), washed with brine (2 mL), dried over Na₂SO₄, filtered, and concentrated under reduced pressure to give the title compound (0.045 g) which was used without further purification. LCMS: 138.2 [M+H].

Intermediate C36

1-CYCLOPROPYL-3-METHOXY-1H-PYRAZOL-4-AMINE

Step 1: Synthesis of 1-cyclopropyl-3-methoxy-4-nitro-1H-pyrazole

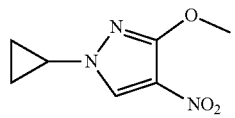

Copper (II) acetate (0.508 g, 2.80 mmol), 2,2'-bipyridine (0.437 g, 2.80 mmol), and NaHCO₃ (0.444 g, 4.19 mmol) were added to a stirred solution of 3-methoxy-4-nitro-1H-pyrazole (0.400 g, 2.80 mmol) and cyclopropylboronic acid (0.480 g, 5.59 mmol) in dichloroethane (20 mL). The resulting mixture was stirred at 70° C. under oxygen atmosphere for 12 h. Following completion of the reaction (as indicated by TLC), the reaction mixture was filtered through a pad of Celite® (i.e., diatomaceous earth) which was then rinsed with DCM (2×20 mL). The combined filtrates were washed with water (20 mL) and brine (25 mL), the organic layer was separated, dried over Na₂SO₄, filtered, and concentrated under reduced pressure to yield crude material which was purified by flash chromatography (silica gel 230-400 mesh, eluting with 20% EtOAc in petroleum ether), giving the title compound as a pale yellow solid (0.30 g, 58% yield). 1H NMR (400 MHZ, CDCl₃) δ=8.06 (s, 1H), 4.06 (s, 3H), 3.53-3.56 (m, 1H), 1.10-1.18 (m, 4H). LCMS: 184.1 [M+H].

Step 2: Synthesis of 1-cyclopropyl-3-methoxy-1H-pyrazol-4-amine

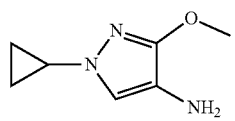

Iron powder (0.457 g, 8.190 mmol) and NH₄Cl (0.438 g, 8.190 mmol) were added to a suspension of 1-cyclopropyl-3-methoxy-4-nitro-1H-pyrazole (0.300 g, 1.638 mmol) in a mixture of ethanol (4 mL) and water (1 mL) and the resulting suspension was stirred at 80° C. for 2 h. Following completion of the reaction (as indicated by TLC), the reaction mixture was filtered through a pad of Celite® (i.e., diatomaceous earth) which was then rinsed with EtOAc (5 mL). The combined filtrates were concentrated under reduced pressure to yield crude material which was taken in DCM (10 mL), washed with brine (2 mL), dried over Na₂SO₄, filtered, and concentrated under reduced pressure to yield crude material which was purified by flash chromatography (silica gel 230-400 mesh, eluting with 50% EtOAc in petroleum ether), giving the title compound as a brown gum (0.170 g, 62% yield). LCMS: 154.2 [M+H].

Intermediate C43

4-(6-OXA-2-AZASPIRO[3.4]OCTAN-2-YL) ANILINE

Step 1: Synthesis of 2-(4-nitrophenyl)-6-oxa-2-azaspiro[3.4]octane

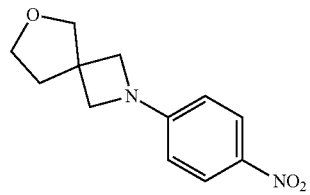

K₂CO₃ (0.366 g, 2.65 mmol) was add to a solution of 6-oxa-2-azaspiro[3.4]octane (0.200 g, 1.767 mmol) and 1-fluoro-4-nitrobenzene (0.188 mL, 1.767 mmol) in dry DMF (1 mL) at 25° C. and the resulting mixture was subjected to microwave irradiation at 80° C. for 2 h. Following completion of the reaction (as indicated by TLC), the reaction mixture was poured into crushed ice (10 g) and extracted with EtOAc (5 mL×3). The combined organic extracts were washed with water (5 mL) and brine (5 mL), dried over Na₂SO₄, filtered, and concentrated under reduced pressure to yield crude material which was purified by flash chromatography (silica gel 230-400 mesh, eluting with 15% EtOAc in petroleum ether), giving the title compound as a yellow solid (0.260 g, 63% yield). 1H NMR (400 MHZ, DMSO-d₆) δ=8.06 (s, 1H), 4.06 (s, 3H), 3.53-3.56 (m, 1H), 1.10-1.18 (m, 4H). LCMS: 235.1 [M+H].

Step 2: Synthesis of 4-(6-oxa-2-azaspiro[3.4]octan-2-yl)aniline

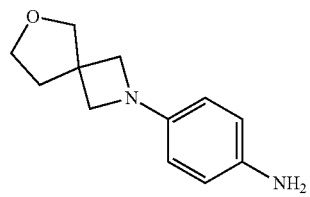 [SMILES: O=[N+]([O-])c1ccc(N2CC3(CCOC3)C2)cc1]

Pd/C (10% w/w, 0.020 g) was added to a solution of 2-(4-nitrophenyl)-6-oxa-2-azaspiro[3.4]octane (0.200 g, 0.854 mmol) in methanol (4 mL) and the resulting mixture was stirred at 25° C. under H₂ atmosphere (bladder pressure) for 4 h. Following completion of the reaction (as indicated by TLC), the reaction mixture was filtered through a pad of Celite® (i.e., diatomaceous earth) which was then rinsed with MeOH (5 mL). The combined filtrates were concentrated under reduced pressure to give the title compound (0.150 g, 86% yield) which was used without further purification. LCMS: 205.1 [M+H].

Intermediate C46

(R)-4-(3-METHYLMORPHOLINO)ANILINE

Step 1: Synthesis of
(R)-3-methyl-4-(4-nitrophenyl)morpholine

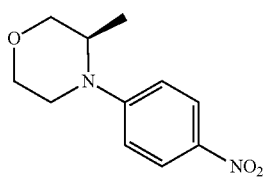

K$_2$CO$_3$ (1.025 g, 7.41 mmol) was added to a solution of (R)-3-methylmorpholine (0.400 g, 4.94 mmol) and 1-fluoro-4-nitrobenzene (1.046, 7.41 mmol) in dry DMF (5 mL) at 25° C. and the reaction mixture was subjected to microwave irradiation at 80° C. for 2 h. Following completion of the reaction (as indicated by TLC), the reaction mixture was poured into crushed ice (50 g) and extracted with EtOAc (15 mL×3). The combined organic extracts were washed with water (5 mL) and brine (5 mL), dried over Na$_2$SO$_4$, filtered, and concentrated under reduced pressure to yield crude material which was triturated with n-hexane (15 mL). The resulting solid was filtered, washed with n-hexane (2×5 mL), and dried under reduced pressure to yield the title compound as a yellow solid (0.800 g, 60% yield). LCMS: 223.1 [M+H].

Step 2: Synthesis of
(R)-4-(3-methylmorpholino)aniline

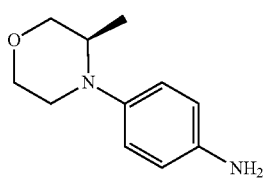 [SMILES: C[C@@H]1COCCN1c1ccc([N+](=O)[O-])cc1]

Iron powder (0.503 g, 9.00 mmol) and NH$_4$Cl (0.048 g, 0.900 mmol) were added to a suspension of (R)-3-methyl-4-(4-nitrophenyl)morpholine (0.200 g, 0.900 mmol) in a mixture of ethanol (8 mL) and water (2 mL) and the resulting suspension was stirred at 80° C. for 2 h. Following completion of the reaction (as indicated by TLC), the reaction mixture was filtered through a pad of Celite® (i.e., diatomaceous earth) which was then rinsed with EtOAc (5 mL). The combined filtrates were concentrated under reduced pressure to give a residue which was taken in DCM (10 mL), washed with brine (2 mL), dried over Na$_2$SO$_4$, filtered, and concentrated under reduced pressure. The resulting crude material was purified by flash chromatography (silica gel 230-400 mesh, eluting with 30% EtOAc in petroleum ether), giving the title compound as an off-white solid (0.110 g, 64% yield). LCMS: 193.2 [M+H].

Intermediate C48

4-(2-(TRIFLUOROMETHYL)
MORPHOLINO)ANILINE

Step 1: Synthesis of
4-(4-nitrophenyl)-2-(trifluoromethyl)morpholine

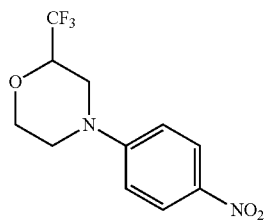

DIPEA (1.360 ml, 7.79 mmol) was added to a solution of 2-(trifluoromethyl)morpholine (0.400 g, 2.60 mmol) and 1-fluoro-4-nitrobenzene (0.366 g, 2.60 mmol) in dry DMF (4 mL) at 25° C. and the resulting mixture was stirred at 100° C. for 16 h. Following completion of the reaction (as indicated by TLC), the reaction mixture was poured into crushed ice (40 g). The resulting precipitate was filtered, washed with water (2×10 mL), and dried under reduced pressure to afford the title compound as a yellow solid (0.500 g, 64% yield). LCMS: 277.1 [M+H]

Step 2: Synthesis of
4-(2-(trifluoromethyl)morpholino)aniline

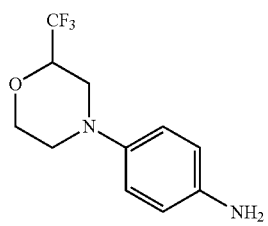 [SMILES: O=[N+]([O-])c1ccc(N2CCOC(C(F)(F)F)C2)cc1]

Pd/C (10% w/w, 0.025 g) was added to a solution of 4-(4-nitrophenyl)-2-(trifluoromethyl)morpholine (0.250 g, 0.905 mmol) in methanol (3 mL) and the resulting suspension was stirred at 25° C. under H$_2$ atmosphere (bladder pressure) for 2 h. Following completion of the reaction (as indicated by TLC), the reaction mixture was filtered through a pad of Celite® (i.e., diatomaceous earth) which was then rinsed with MeOH (5 mL). The combined filtrates were concentrated under reduced pressure to give the title compound (0.130 g, 59% yield) which was used without further purification. LCMS: 247.2 [M+H].

183

Intermediate C49

2-(4-AMINO-5-METHYL-1H-PYRAZOL-1-YL)-2-METHYLPROPANENITRILE

Step 1: Synthesis of 2-methyl-2-(5-methyl-4-nitro-1H-pyrazol-1-yl)propanamide

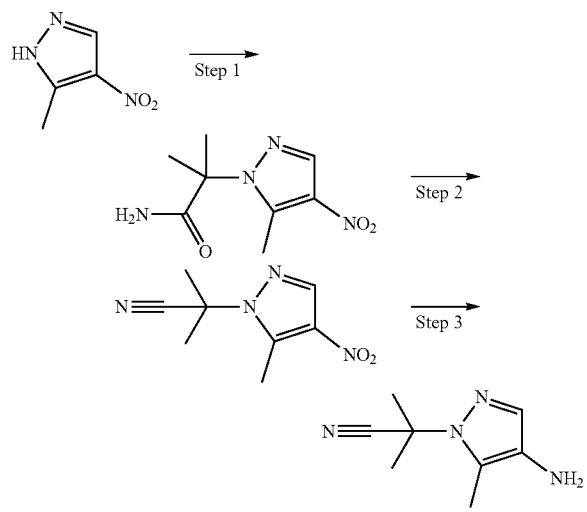

K$_2$CO$_3$ (1.086 g, 7.86 mmol) and 2-bromo-2-methylpropanamide (0.653 g, 3.93 mmol) were added to a stirred solution of 5-methyl-4-nitro-1H-pyrazole (0.500 g, 3.93 mmol) in dry DMF (5 mL) and the reaction mixture was stirred at 25° C. for 16 h. Following completion of the reaction (as indicated by TLC), the reaction mixture was poured into crushed ice (50 g) and extracted with EtOAc (3×10 mL). The combined organic extracts were dried over Na$_2$SO$_4$, filtered, and concentrated under reduced pressure to yield crude material which was purified by flash chromatography (silica gel 230-400 mesh, eluting with 30% EtOAc in petroleum ether), giving the title compound as a yellow gum (0.600 g, 50% yield). LCMS: 213.2 [M+H].

Step 2: Synthesis of 2-methyl-2-(5-methyl-4-nitro-1H-pyrazol-1-yl)propanenitrile POCl$_3$ (3.11 mL, 33.400 mmol) was added to 2-methyl-2-(5-methyl-4-nitro-1H-pyrazol-1-yl)propanamide (0.50 g, 2.356 mmol) at 0° C. and the resulting solution was stirred at 110° C. for 2 h. Following completion of the reaction (as indicated by TLC), the reaction mixture was concentrated under reduced pressure to yield crude material which was taken in EtOAc (10 mL) and neutralized with aqueous NaHCO$_3$ (10%). The resulting aqueous layer was extracted with EtOAc (2×5 mL) and the combined organic extracts were dried over Na$_2$SO$_4$, filtered, and concentrated under reduced pressure to yield crude material which was purified by flash chromatography (silica gel 230-400 mesh, eluting with 15% EtOAc in petroleum ether), giving the title compound as a pale yellow gum (0.300 g, 66% yield). 1H NMR (400 MHZ, CD$_3$OD) δ=8.79 (s, 1H), 2.55 (s, 3H), 2.03 (s, 6H). LCMS: 195.1 [M+H].

Step 3: Synthesis of 2-(4-amino-5-methyl-1H-pyrazol-1-yl)-2-methylpropanenitrile Iron powder (0.575 g, 10.30 mmol) and NH$_4$Cl (0.551 g, 10.30 mmol) were added to a suspension of 2-methyl-2-(5-

184 methyl-4-nitro-1H-pyrazol-1-yl)propanenitrile (0.200 g, 1.030 mmol) in a mixture of ethanol (4 mL) and water (1 mL) and the resulting suspension was stirred at 75° C. for 2 h. Following completion of the reaction (as indicated by TLC), the reaction mixture was filtered through a pad of Celite® (i.e., diatomaceous earth) which was then rinsed with EtOAc (5 mL). The combined filtrates were concentrated under reduced pressure to yield crude material which was taken in DCM (10 mL), washed with brine (2 mL), dried over Na$_2$SO$_4$, filtered, and concentrated under reduced pressure to give crude material which was purified by flash chromatography (silica gel 230-400 mesh, eluting with 30% EtOAc in petroleum ether), giving the title compound as an off-white solid (0.084 g, 46% yield). 1H NMR (400 MHZ, CD$_3$OD) δ=7.34 (s, 1H), 2.19 (s, 3H), 1.93 (s, 6H). LCMS: 165.2 [M+H].

PREPARATION OF EXAMPLES

General Synthetic Scheme 1 for the Synthesis of Examples 1-16

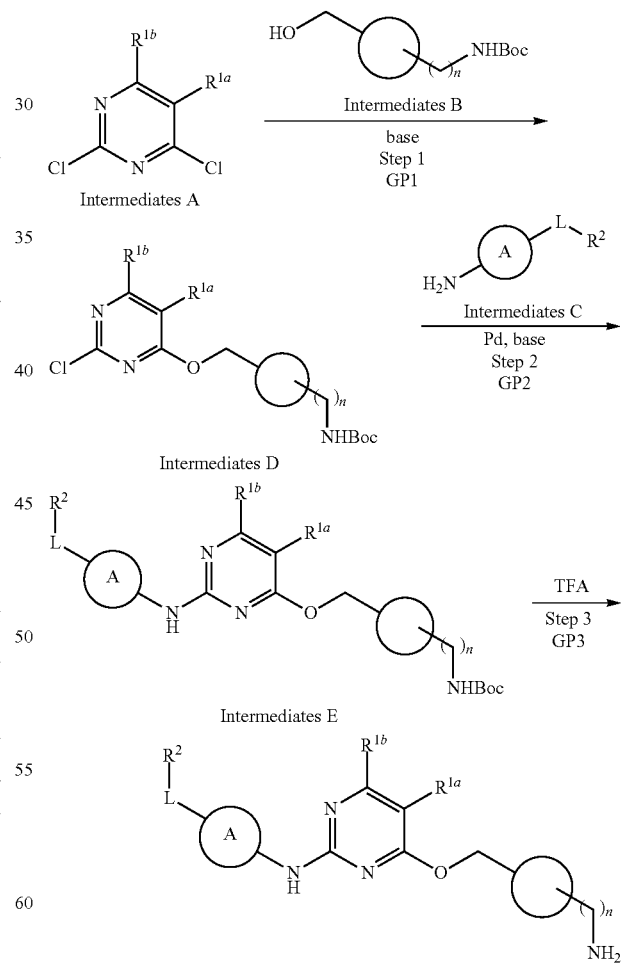

Examples 1-16 wherein each of R$^{1a}$, R$^{1b}$, R$^2$, A, and L are as defined herein and n is 0 or 1.

Step 1: General Procedure GP1 for the Synthesis of Intermediates D

A solution of alcohol Intermediate B (1.0 eq.) in DMF was added to a stirred suspension of NaH (60% in mineral oil, 1.2 eq.) in DMF at 0° C. and the resulting mixture was stirred at 25° C. for 10 min. A solution of dichloropyrimidine Intermediate A (1.0 eq.) in DMF was then added and the resulting mixture was stirred at 25° C. until completion of the reaction (as indicated by TLC). The reaction mixture was then quenched with saturated NH$_4$Cl and diluted with EtAOc. The layers were separated, the organic layer was washed with water and brine, dried over Na$_2$SO$_4$, filtered, and concentrated under reduced pressure to yield crude material which was purified by flash chromatography, giving the desired Intermediate D.

Step 2: General Procedure GP2 (Buchwald-Hartwig Coupling) for the Synthesis of Intermediates E Cs$_2$CO$_3$ (2.0 eq.) was added to a stirred solution of Intermediate D (1.0 eq.) and amine Intermediate C (1.0 eq.) in dioxane and the resulting mixture was purged with N$_2$ for 10 minutes. BINAP (0.2 eq.) and Pd(OAc)$_2$ (0.1 eq.) were then added and the reaction mixture was subjected to microwave irradiation at 100° C. for 2 h. Following completion of the reaction (as indicated by TLC), the reaction mixture was filtered through a pad of Celite® (i.e., diatomaceous earth) and the filtrate was concentrated under reduced pressure to yield crude material which was purified by flash chromatography, giving the desired Intermediate E.

Step 3: General Procedure GP3 (Boc Deprotection) for the Synthesis of Examples 1-16

TFA (5 vol.) was added to a solution of Intermediate E (1 eq.) in dry DCM at 0° C. and the resulting mixture was stirred at 25° C. until completion of the reaction (as indicated by TLC). The reaction mixture was then concentrated under reduced pressure to yield crude material which was purified by preparative HPLC, giving the desired Example 1-16.

The following examples were synthesized following General Synthetic Scheme 1:

| Example | Structure | Name | Spectral data[†] |
|---|---|---|---|
| 1 | 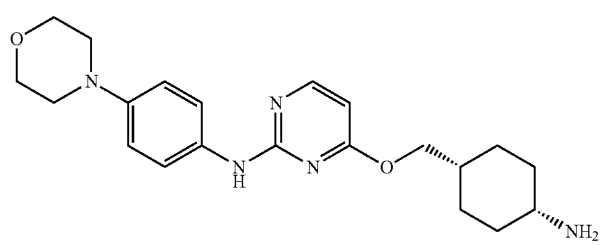 [SMILES: N[C@H]1CC[C@@H](COc2ccnc(Nc3ccc(N4CCOCC4)cc3)n2)CC1] | 4-(((1S,4S)-4-aminocyclohexyl)methoxy)-N-(4-morpholinophenyl)pyrimidin-2-amine | (DMSO-d$_6$) δ = 10.78 (bs, 1H), 8.26 (bs, 2H), 8.11 (d, J = 6.6 Hz, 1H), 7.51 (d, J = 8.8 Hz, 2H), 7.26 (d, J = 8.9 Hz, 2H), 6.48 (d, J = 6.6 Hz, 1H), 4.25-4.27 (m, 2H), 3.82-3.87 (m, 4H), 3.17-3.29 (m, 5H), 1.95-1.97 (m, 1H), 1.53-1.69 (m, 8H). LCMS: 384.4 [M + H] |
| 2 | 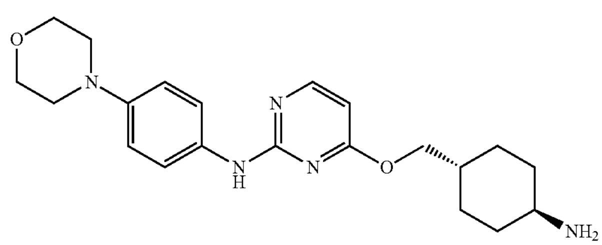 [SMILES: N[C@H]1CC[C@H](COc2ccnc(Nc3ccc(N4CCOCC4)cc3)n2)CC1] | 4-(((1R,4R)-4-aminocyclohexyl)methoxy)-N-(4-morpholinophenyl)pyrimidin-2-amine | (DMSO-d$_6$) δ = 9.23 (s, 1H), 8.12 (d, J = 5.6 Hz, 1H), 7.58 (d, J = 9.2 Hz, 2H), 6.88 (d, J = 9.2 Hz, 2H), 6.18 (d, J = 5.6 Hz, 1H), 4.11 (d, J = 6.4 Hz, 2H), 3.73-3.74 (m, 4H), 3.02-3.03 (m, 4H), 1.62-1.81 (m, 6H), 0.99-1.08 (m, 4H). LCMS: 384.4 [M + H] |
| 3 | 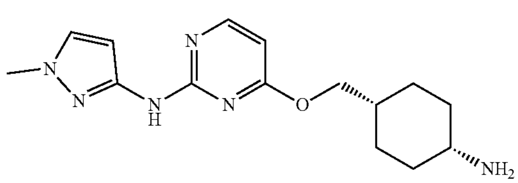 [SMILES: Cn1ccc(Nc2nccc(OC[C@H]3CC[C@@H](N)CC3)n2)n1] | 4-(((1S,4S)-4-aminocyclohexyl)methoxy)-N-(1-methyl-1H-pyrazol-3-yl)pyrimidin-2-amine | (DMSO-d$_6$) δ = 9.57 (bs, 1H), 8.12 (d, J = 5.6 Hz, 1H), 7.54 (d, J = 1.9 Hz, 1H), 6.53 (d, J = 2.0 Hz, 1H), 6.19 (d, J = 5.6 Hz, 1H), 4.18 (d, J = 7.0 Hz, 2H), 3.73 (s, 3H), 1.79-1.89 (m, 1H), 1.42-1.54 (m, 9H). LCMS: 303.2 [M + H] |
| 4 | 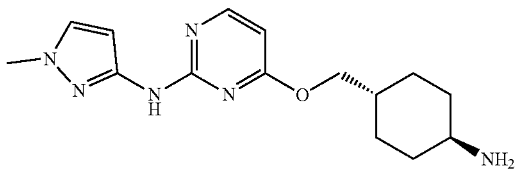 [SMILES: Cn1ccc(Nc2nccc(OC[C@H]3CC[C@H](N)CC3)n2)n1] | 4-(((1R,4R)-4-aminocyclohexyl)methoxy)-N-(1-methyl-1H-pyrazol-3-yl)pyrimidin-2-amine | (CD$_3$OD) δ = 8.09 (d, J = 5.6 Hz, 1H), 7.48 (d, J = 2.0 Hz, 1H), 6.58 (d, J = 2.4 Hz, 1H), 6.21 (d, J = 6.0 Hz, 1H), 4.21 (d, J = 6.4 Hz, 2H), 3.82 (s, 3H), 2.76-2.77 (m, 1H), 1.79-2.01 (m, 5H), 1.28-1.31 (m, 4H). LCMS: 303.3 [M + H] |

| Example | Structure | Name | Spectral data† |
|---|---|---|---|
| 5 | 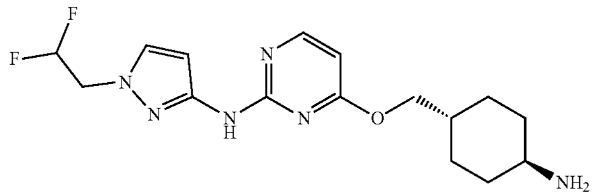 [SMILES: N[C@H]1CC[C@H](COc2ccnc(Nc3ccn(CC(F)F)n3)n2)CC1] | 4-(((1R,4R)-4-aminocyclohexyl)methoxy)-N-(1-(2,2-difluoroethyl)-1H-pyrazol-3-yl)pyrimidin-2-amine | (DMSO-$d_6$) δ = 9.73 (bs, 1H), 8.14 (d, J = 5.6 Hz, 1H), 7.66 (d, J = 2.0 Hz, 1H), 6.65 (d, J = 2.4 Hz, 1H), 6.17-6.44 (m, 2H), 4.46-4.54 (m, 2H), 4.11 (d, J = 6.4 Hz, 2H), 1.66-1.79 (m, 6H), 1.04-1.10 (m, 4H). LCMS: 353.1 [M + H] |
| 6 | 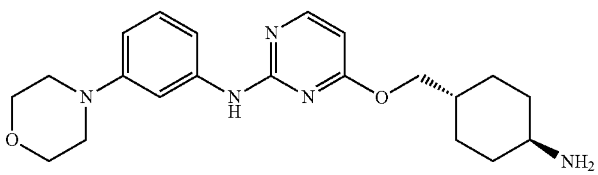 [SMILES: N[C@H]1CC[C@H](COc2ccnc(Nc3cccc(N4CCOCC4)c3)n2)CC1] | 4-(((1R,4R)-4-aminocyclohexyl)methoxy)-N-(3-morpholinophenyl)pyrimidin-2-amine | (DMSO-$d_6$) δ = 9.36 (bs, 1H), 8.18 (d, J = 5.6 Hz, 1H), 7.49 (s, 1H), 7.09-7.17 (m, 2H), 6.55-6.57 (m, 1H), 6.24 (d, J = 5.6 Hz, 1H), 4.15 (d, J = 6.4 Hz, 2H), 3.73-3.76 (m, 4H), 3.07-3.09 (m, 4H), 2.74-2.80 (m, 1H), 1.71-1.91 (m, 5H), 1.07-1.24 (m, 4H). LCMS: 384.4 [M + H] |
| 7 | 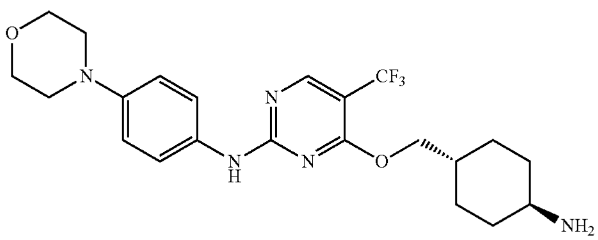 [SMILES: N[C@H]1CC[C@H](COc2nc(Nc3ccc(N4CCOCC4)cc3)ncc2C(F)(F)F)CC1] | 4-(((1R,4R)-4-aminocyclohexyl)methoxy)-N-(4-morpholinophenyl)-5-(trifluoromethyl)pyrimidin-2-amine | (DMSO-$d_6$) δ = 8.88 (bs, 1H), 8.41 (s, 1H), 7.46 (bs, 2H), 7.28 (d, J = 8.8 Hz, 2H), 6.94 (d, J = 9.2 Hz, 2H), 3.98 (d, J = 6.4 Hz, 2H), 3.74-3.75 (m, 4H), 3.09-3.11 (m, 4H), 2.87-2.91 (m, 1H), 1.58-1.91 (m, 5H), 0.99-1.28 (m, 4H). LCMS: 452.3.0 [M + H] |
| 8 | 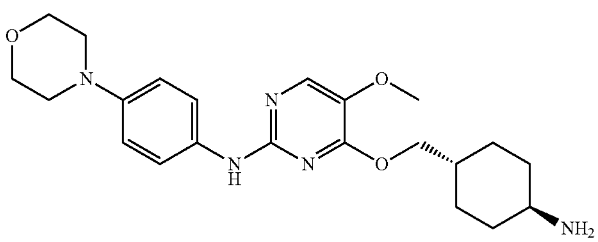 [SMILES: COc1cnc(Nc2ccc(N3CCOCC3)cc2)nc1OC[C@H]1CC[C@H](N)CC1] | 4-(((1R,4R)-4-aminocyclohexyl)methoxy)-5-methoxy-N-(4-morpholinophenyl)pyrimidin-2-amine | (DMSO-$d_6$) δ = 8.97 (bs, 1H), 7.93 (s, 1H), 7.56 (d, J = 9.2 Hz, 2H), 6.86 (d, J = 9.2 Hz, 2H), 4.16 (d, J = 6.4 Hz, 2H), 3.72-3.74 (m, 7H), 3.00-3.02 (m, 4H), 2.67-2.69 (m, 1H), 1.81-1.90 (m, 5H), 1.04-1.24 (m, 4H). LCMS: 414.0 [M + H] |
| 9 | 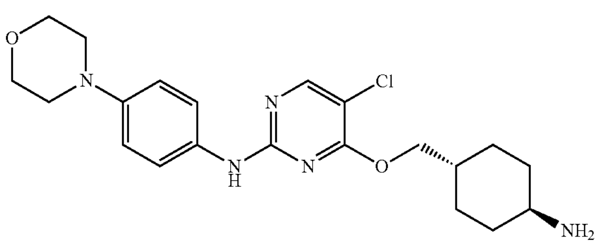 [SMILES: N[C@H]1CC[C@H](COc2nc(Nc3ccc(N4CCOCC4)cc3)ncc2Cl)CC1] | 4-(((1R,4R)-4-aminocyclohexyl)methoxy)-5-chloro-N-(4-morpholinophenyl)pyrimidin-2-amine | (DMSO-$d_6$) δ = 9.46 (bs, 1H), 8.23 (bs, 1H), 7.53 (d, J = 9.2 Hz, 2H), 6.89 (d, J = 8.8 Hz, 2H), 4.21 (d, J = 6.4 Hz, 2H), 3.73-3.75 (m, 7H), 3.02-3.05 (m, 4H), 2.67-2.69 (m, 1H), 1.81-1.88 (m, 5H), 1.04-1.24 (m, 4H). LCMS: 418.0 [M + H] |
| 10 | 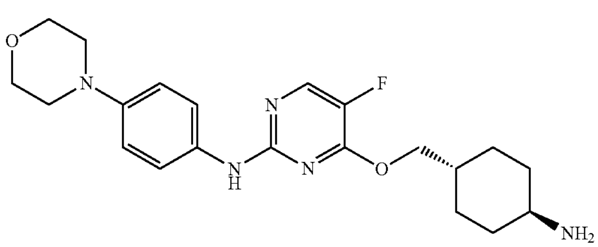 [SMILES: N[C@H]1CC[C@H](COc2nc(Nc3ccc(N4CCOCC4)cc3)ncc2F)CC1] | 4-(((1R,4R)-4-aminocyclohexyl)methoxy)-5-fluoro-N-(4-morpholinophenyl)pyrimidin-2-amine | (DMSO-$d_6$) δ = δ 9.37 (bs, 1H), 8.24 (d, J = 3.2 Hz, 1H), 7.81 (bs, 2H), 7.56 (d, J = 8.8 Hz, 2H), 6.95 (d, J = 8.4 Hz, 2H), 4.23 (d, J = 6.4 Hz, 2H), 3.75-3.77 (m, 4H), 2.98-3.08 (m, 5H), 1.77-1.99 (m, 5H), 1.24-1.37 (m, 4H). LCMS: 402.2 [M + H] |

| Example | Structure | Name | Spectral data† |
|---|---|---|---|
| 11 | 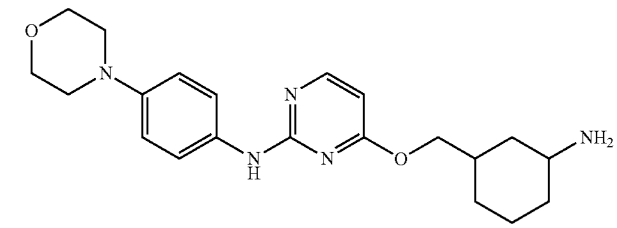 [SMILES: NC1CCCC(COc2ccnc(Nc3ccc(N4CCOCC4)cc3)n2)C1] | 4-((3-aminocyclohexyl)methoxy)-N-(4-morpholinophenyl)pyrimidin-2-amine | (DMSO-$d_6$) δ = 9.23 (bs, 1H), 8.12-8.14 (m, 1H), 7.58 (d, J = 8.8 Hz, 2H), 6.88 (d, J = 9.2 Hz, 2H), 6.18 (d, J = 4.0 Hz, 2H), 4.12-4.15 (m, 2H), 3.73-3.75 (m, 4H), 3.02-3.06 (m, 4H), 2.67-2.68 (m, 1H), 1.24-1.90 (m, 4H), 0.79-1.36 (m, 4H). LCMS: 384.3 [M + H] |
| 12 | 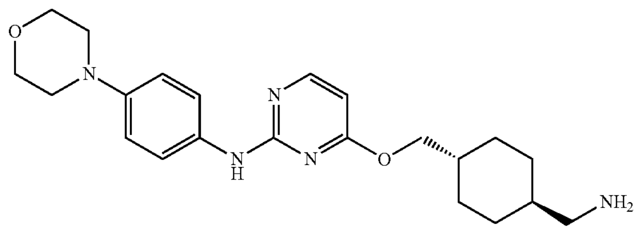 [SMILES: NC[C@H]1CC[C@H](COc2ccnc(Nc3ccc(N4CCOCC4)cc3)n2)CC1] | 4-(((1R,4R)-4-(aminomethyl)cyclohexyl)methoxy)-N-(4-morpholinophenyl)pyrimidin-2-amine | (DMSO-$d_6$) δ = 9.24 (bs, 1H), 8.13 (d, J = 5.6 Hz, 1H), 7.58 (d, J = 9.2 Hz, 2H), 6.88 (d, J = 9.2 Hz, 2H), 6.18 (d, J = 5.6 Hz, 1H), 4.11-4.13 (m, 2H), 3.72-3.75 (m, 4H), 3.01-3.04 (m, 4H), 2.43-2.45 (m, 2H), 1.69-1.83 (m, 5H), 1.25-1.27 (m, 1H), 0.85-1.06 (m, 4H). LCMS: 398.3 [M + H] |
| 13 | 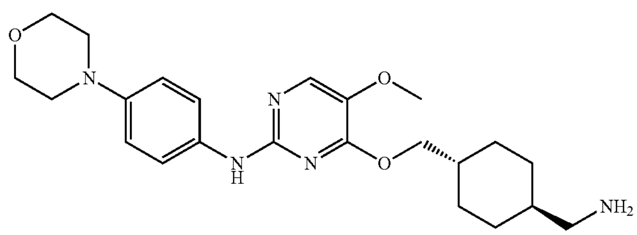 [SMILES: COc1cnc(Nc2ccc(N3CCOCC3)cc2)nc1OC[C@H]1CC[C@H](CN)CC1] | 4-(((1R,4R)-4-(aminomethyl)cyclohexyl)methoxy)-5-methoxy-N-(4-morpholinophenyl)pyrimidin-2-amine | (DMSO-$d_6$) δ = 8.96 (bs, 1H), 7.92 (s, 1H), 7.57 (d, J = 8.8 Hz, 2H), 6.86 (d, J = 9.2 Hz, 2H), 4.16 (d, J = 6.4 Hz, 2H), 3.72-3.74 (m, 7H), 3.00-3.02 (m, 4H), 2.38-2.40 (m, 2H), 1.71-1.85 (m, 5H), 0.81-1.24 (m, 5H). LCMS: 428.4 [M + H] |
| 14 | 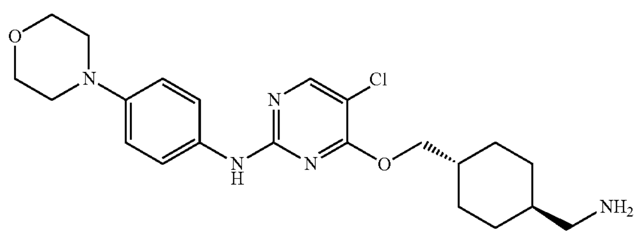 [SMILES: NC[C@H]1CC[C@H](COc2nc(Nc3ccc(N4CCOCC4)cc3)ncc2Cl)CC1] | 4-(((1R,4R)-4-(aminomethyl)cyclohexyl)methoxy)-5-chloro-N-(4-morpholinophenyl)pyrimidin-2-amine | (DMSO-$d_6$) δ = 9.45 (bs, 1H), 8.23 (s, 1H), 7.54 (d, J = 8.8 Hz, 2H), 6.89 (d, J = 8.8 Hz, 2H), 4.22 (d, J = 6.0 Hz, 2H), 3.73-3.75 (m, 4H), 3.02-3.05 (m, 4H), 2.44-2.46 (m, 2H), 1.75-1.85 (m, 5H), 0.89-1.27 (m, 5H). LCMS: 432.2 [M + H] |
| 15 | 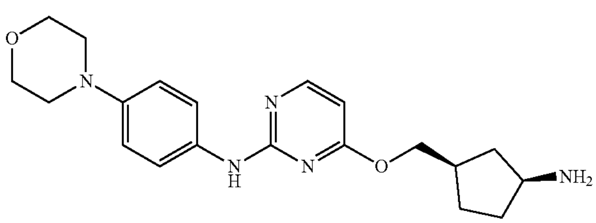 [SMILES: N[C@H]1CC[C@@H](COc2ccnc(Nc3ccc(N4CCOCC4)cc3)n2)C1] | 4-(((1R,3S)-3-aminocyclopentyl)methoxy)-N-(4-morpholinophenyl)pyrimidin-2-amine | (DMSO-$d_6$) δ = 9.26 (bs, 1H), 8.15 (d, J = 5.6 Hz, 1H), 7.58 (d, J = 8.8 Hz, 2H), 6.89 (d, J = 8.8 Hz, 2H), 6.19 (d, J = 5.6 Hz, 1H), 4.24-4.27 (m, 2H), 3.73-3.75 (m, 4H), 3.47-3.51 (m, 1H), 3.02-3.06 (m, 4H), 2.40-2.43 (m, 1H), 2.16-2.19 (m, 1H), 1.91-1.94 (m, 1H), 1.78-1.80 (m, 1H), 1.55-1.60 (m, 2H), 1.24-1.30 (m, 1H). LCMS: 370.0 [M + H] |
| 16 | 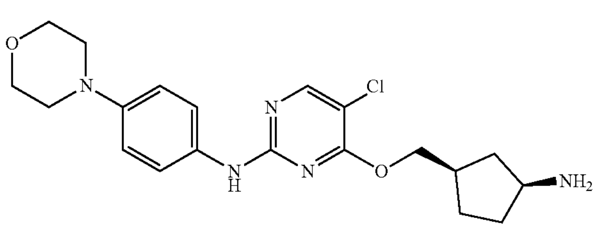 [SMILES: N[C@H]1CC[C@@H](COc2nc(Nc3ccc(N4CCOCC4)cc3)ncc2Cl)C1] | 4-(((1R,3S)-3-aminocyclopentyl)methoxy)-5-chloro-N-(4-morpholinophenyl)pyrimidin-2-amine | (DMSO-$d_6$) δ = 9.44 (bs, 1H), 8.22 (s, 1H), 7.54 (d, J = 9.2 Hz, 2H), 6.90 (d, J = 6.8 Hz, 2H), 4.33 (d, J = 6.4 Hz, 2H), 3.73-3.75 (m, 4H), 3.02-3.05 (m, 4H), 0.99-2.02 (m, 8H). LCMS: 404.0 [M + H] |

†All $^1$H NMR recorded at 400 MHz

General Synthetic Scheme 2 for the Synthesis of Examples 17-30, 95-96 and 163-177

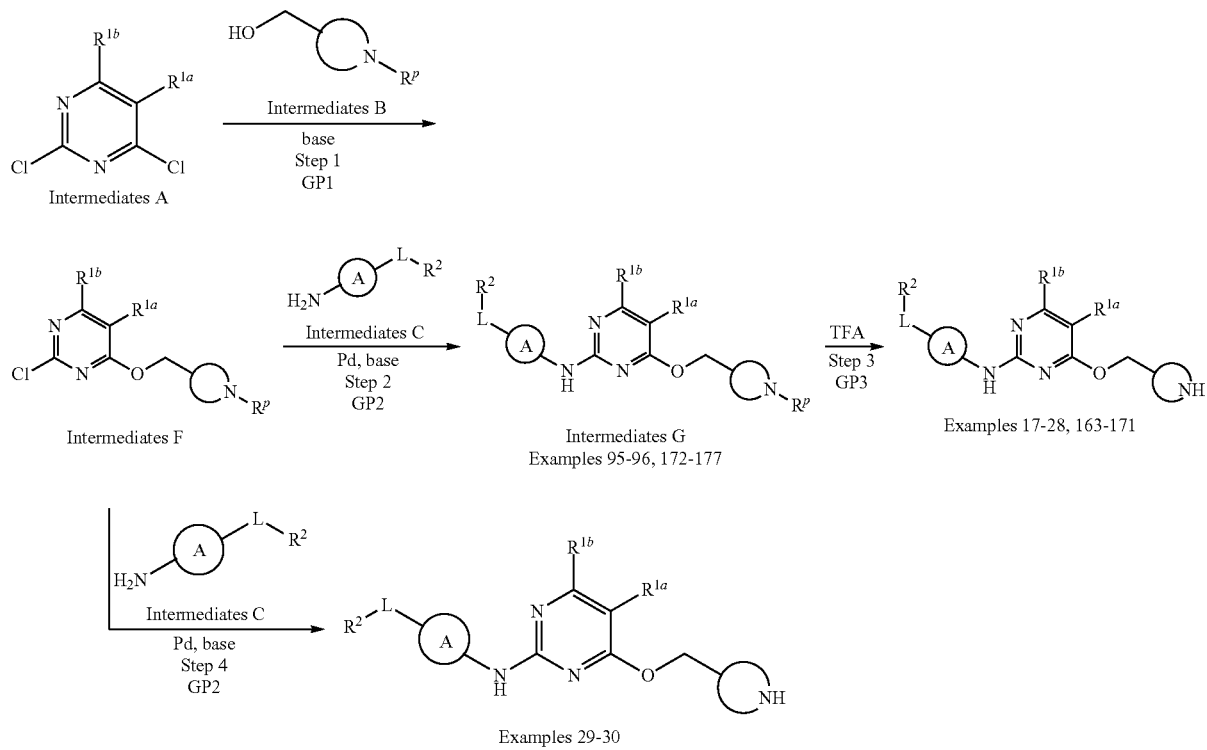

wherein $R^P$ is C(O)OtBu (Examples 17-28, 163-171) or C(O)CF$_3$ (Examples 29-30) or C(O)CH$_3$ (examples 95-96, 172-177).

Step 1: Synthesis of Intermediates F

Intermediates F were synthesized by following General Procedure GP1 described above.

Step 2: Synthesis of Intermediates G (including Examples 95-96 and 172-177)

Intermediates G (including Examples 95-96 and 172-177 wherein $R^P$ is C(O)CH$_3$) were synthesized by following General Procedure GP2 described above. In the case of Examples 95-96 and 172-177 the crude materials were purified by preparative HPLC.

Step 3: Synthesis of Examples 17-28 and 163-171

Examples 17-28 and 163-171 were synthesized by following General Procedure GP3 described above.

Step 4: Synthesis of Examples 29-30

Examples 29-30 (wherein $R^P$ is C(O)CF$_3$) were synthesized by following General Procedure GP2 described above. The trifluoroacetamide protecting group was found to be unstable under the Buchwald-Hartwig coupling conditions, yielding the desired Examples 29-30 (which were purified by preparative HPLC) without a dedicated deprotection step.

The following examples were synthesized following General Synthetic Scheme 2:

| Example | Structure | Name | †Spectral data |
|---|---|---|---|
| 95 | 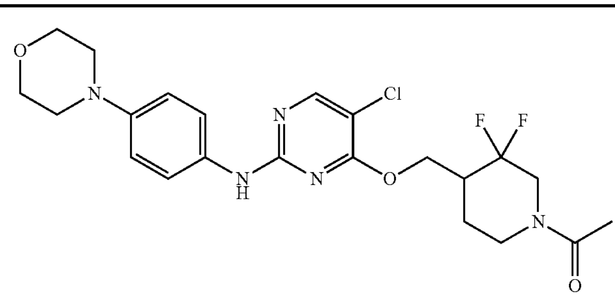 | 1-(4-(((5-chloro-2-((4-morpholinophenyl)amino)pyrimidin-4-yl)oxy)methyl)-3,3-difluoropiperidin-1-yl)ethan-1-one | (DMSO-d$_6$) δ = 9.56 (bs, 1H), 8.27 (bs, 1H), 7.56 (d, J = 8.8 Hz, 2H), 6.93-6.96 (m, 2H), 4.53-4.71 (m, 2H), 4.34-4.41 (m, 1H), 3.75-3.77 (m, 4H), 3.51-3.61 (m, 1H), 3.05-3.23 (m, 5H), 2.67-2.78 (m, 1H), 2.03-2.09 (m, 3H), 1.89-1.99 (m, 1H), 1.39-1.57 (m, 2H). LCMS: 481.8 [M + H] |

| Example | Structure | Name | †Spectral data |
|---|---|---|---|
| 96 | 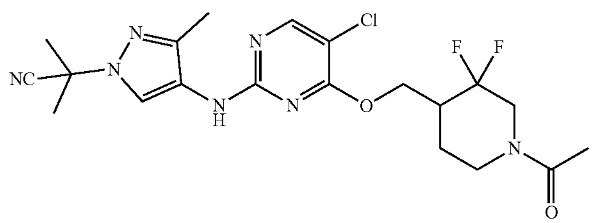 [SMILES: CC(=O)N1CCC(COc2nc(Nc3cn(C(C)(C)C#N)nc3C)ncc2Cl)C(F)(F)C1] | 2-(4-((4-((1-acetyl-3,3-difluoropiperidin-4-yl)methoxy)-5-chloropyrimidin-2-yl)amino)-3-methyl-1H-pyrazol-1-yl)-2-methylpropanenitrile | (CD$_3$OD) δ = 8.14 (s, 1H), 8.09 (s, 1H), 4.54-4.66 (m, 2H), 3.95-3.99 (m, 1H), 3.33-3.57 (m, 2H), 3.13-3.20 (m, 1H), 2.25-2.32 (m, 3H), 2.00-2.17 (m, 4H), 1.99-2.00 (m, 6H), 1.39-1.57 (m, 2H). LCMS: 468.1 [M + H] |
| 172 | 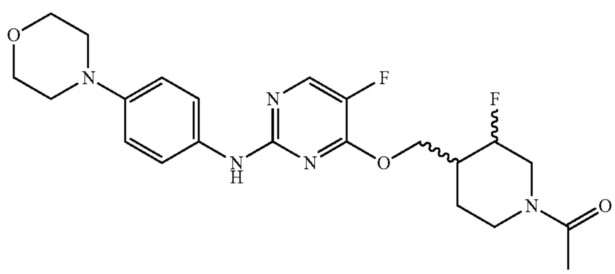 [SMILES: CC(=O)N1CCC(COc2nc(Nc3ccc(N4CCOCC4)cc3)ncc2F)C(F)C1] | 1-(3-fluoro-4-(((5-fluoro-2-((4-morpholinophenyl)amino)pyrimidin-4-yl)oxy)methyl)piperidin-1-yl)ethan-1-one | LCMS: 448.3 [M + H] (second eluting peak) |
| 173 | 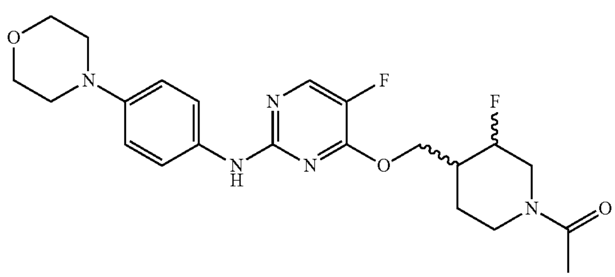 [SMILES: CC(=O)N1CCC(COc2nc(Nc3ccc(N4CCOCC4)cc3)ncc2F)C(F)C1] | 1-(3-fluoro-4-(((5-fluoro-2-((4-morpholinophenyl)amino)pyrimidin-4-yl)oxy)methyl)piperidin-1-yl)ethan-1-one | LCMS: 448.2 [M + H] (first eluting peak) |
| 174 | 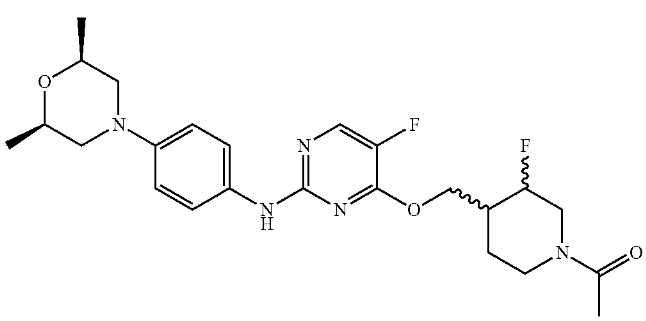 [SMILES: CC(=O)N1CCC(COc2nc(Nc3ccc(N4C[C@@H](C)O[C@@H](C)C4)cc3)ncc2F)C(F)C1] | 1-(4-(((2-((4-((2S,6R)-2,6-dimethylmorpholino)phenyl)amino)-5-fluoropyrimidin-4-yl)oxy)methyl)-3-fluoropiperidin-1-yl)ethan-1-one | LCMS: 476.3 [M + H] (first eluting peak) |
| 175 | 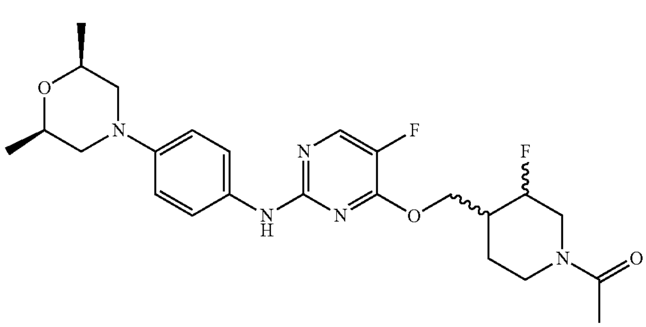 [SMILES: CC(=O)N1CCC(COc2nc(Nc3ccc(N4C[C@@H](C)O[C@@H](C)C4)cc3)ncc2F)C(F)C1] | 1-(4-(((2-((4-((2S,6R)-2,6-dimethylmorpholino)phenyl)amino)-5-fluoropyrimidin-4-yl)oxy)methyl)-3-fluoropiperidin-1-yl)ethan-1-one | LCMS: 476.3 [M + H] (second eluting peak) |

-continued

| Example | Structure | Name | †Spectral data |
|---|---|---|---|
| 176 | 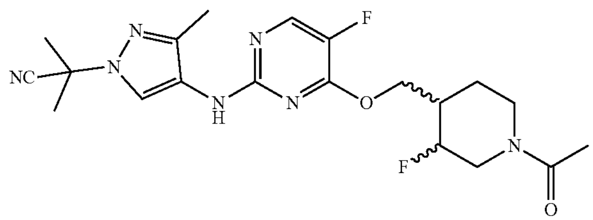 [SMILES: CC(=O)N1CCC(COc2nc(Nc3cn(C(C)(C)C#N)nc3C)ncc2F)C(F)C1] | 2-(4-((4-((1-acetyl-3-fluoropiperidin-4-yl)methoxy)-5-fluoropyrimidin-2-yl)amino)-3-methyl-1H-pyrazol-1-yl)-2-methylpropanenitrile | LCMS: 434.4 [M + H] (second eluting peak) |
| 177 | 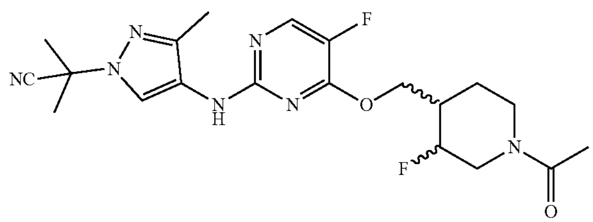 [SMILES: CC(=O)N1CCC(COc2nc(Nc3cn(C(C)(C)C#N)nc3C)ncc2F)C(F)C1] | 2-(4-((4-((1-acetyl-3-fluoropiperidin-4-yl)methoxy)-5-fluoropyrimidin-2-yl)amino)-3-methyl-1H-pyrazol-1-yl)-2-methylpropanenitrile | LCMS: 434.4 [M + H] (first eluting peak) |
| 17 | 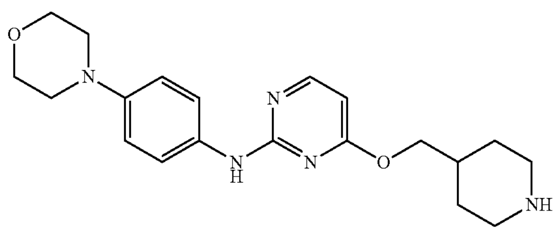 [SMILES: c1cc(OCC2CCNCC2)nc(Nc2ccc(N3CCOCC3)cc2)n1] | N-(4-morpholinophenyl)-4-(piperidin-4-ylmethoxy)pyrimidin-2-amine | (DMSO-d$_6$) δ = 9.26 (bs, 1H), 8.14 (d, J = 7.6 Hz, 1H), 7.56 (d, J = 12.0 Hz, 2H), 6.88 (d, J = 12.0 Hz, 2H), 6.17 (d, J = 7.6 Hz, 2H), 4.19 (d, J = 8.4 Hz, 1H), 3.71-3.74 (m, 4H), 3.00-3.03 (m, 4H), 2.73-2.88 (m, 3H), 1.74-2.15 (m, 4H), 1.32-1.48 (m, 2H). LCMS: 370.0 [M + H] |
| 18 | 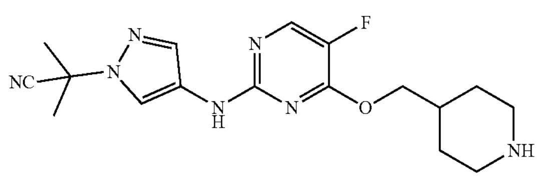 | 2-(4-((5-fluoro-4-(piperidin-4-ylmethoxy)pyrimidin-2-yl)amino)-3-methyl-1H-pyrazol-1-yl)-2-methylpropanenitrile | (CD$_3$OD) δ = 8.11 (s, 1H), 8.04 (d, J = 3.2 Hz, 1H), 4.32 (d, J = 6.4 Hz, 2H), 3.22-3.25 (m, 2H), 2.77-2.83 (m, 2H), 2.25 (s, 3H), 2.05-2.11 (m, 1H), 1.99 (s, 6H), 1.91-1.94 (m, 2H), 1.31-1.49 (m, 2H). LCMS: 374.1 [M + H] |
| 19 | 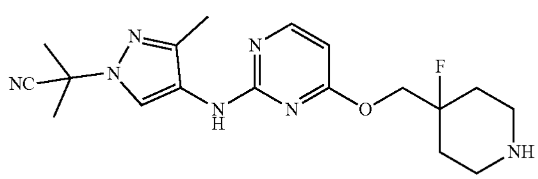 [SMILES: Cc1nn(C(C)(C)C#N)cc1Nc1nccc(OCC2(F)CCNCC2)n1] | 2-(4-((4-((4-fluoropiperidin-4-yl)methoxy)pyrimidin-2-yl)amino)-3-methyl-1H-pyrazol-1-yl)-2-methylpropanenitrile | (CD$_3$OD) δ = 8.40 (s, 1H), 8.13 (d, J = 5.6 Hz, 1H), 6.25 (d, J = 6.0 Hz, 1H), 4.52 (d, J = 19.6 Hz, 2H), 3.24-3.50 (m, 4H), 2.25-2.27 (m, 5H), 1.95-2.12 (m, 8H). LCMS: 374.0 [M + H] |
| 20 | 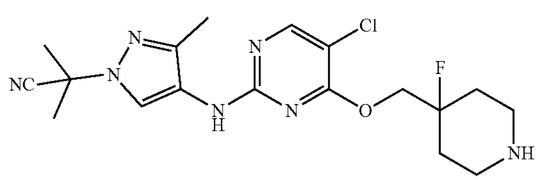 [SMILES: Cc1nn(C(C)(C)C#N)cc1Nc1ncc(Cl)c(OCC2(F)CCNCC2)n1] | 2-(4-((5-chloro-4-((4-fluoropiperidin-4-yl)methoxy)pyrimidin-2-yl)amino)-3-methyl-1H-pyrazol-1-yl)-2-methylpropanenitrile | (CD$_3$OD) δ = 8.18 (s, 1H), 8.14 (s, 1H), 4.56-4.61 (m, 2H), 3.43-3.50 (m, 2H), 2.30-2.36 (m, 2H), 2.25 (s, 3H), 2.02-2.16 (m, 4H), 2.00 (s, 6H). LCMS: 408.1 [M + H] |
| 21 | 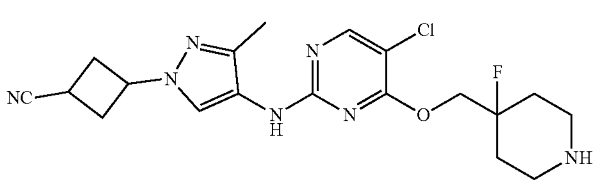 [SMILES: Cc1nn(C2CC(C#N)C2)cc1Nc1ncc(Cl)c(OCC2(F)CCNCC2)n1] | 3-(4-((5-chloro-4-((4-fluoropiperidin-4-yl)methoxy)pyrimidin-2-yl)amino)-3-methyl-1H-pyrazol-1-yl)cyclobutane-1-carbonitrile | (CD$_3$OD) δ = 8.12 (s, 1H), 7.89 (s, 1H), 5.10-5.10 (m, 1H), 4.54 (d, J = 19.2 Hz, 2H), 3.36-3.40 (m, 2H), 3.21-3.25 (m, 2H), 2.96-3.01 (m, 2H), 2.80-2.86 (m, 2H), 2.20-2.22 (m, 6H), 1.94-2.07 (m, 2H). LCMS: 420.1 [M + H] |

-continued

| Example | Structure | Name | †Spectral data |
|---|---|---|---|
| 22 | 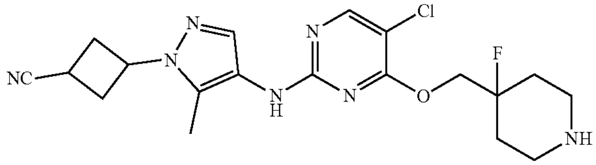 [SMILES: Cc1c(Nc2ncc(Cl)c(OCC3(F)CCNCC3)n2)cnn1C1CC(C#N)C1] | 3-(4-((5-chloro-4-((4-fluoropiperidin-4-yl)methoxy)pyrimidin-2-yl)amino)-5-methyl-1H-pyrazol-1-yl)cyclobutane-1-carbonitrile | (CD$_3$OD) δ = 8.10 (s, 1H), 7.66 (s, 1H), 5.18-5.22 (m, 1H), 4.55 (d, J = 18.4 Hz, 2H), 3.36-3.32 (m, 5H), 3.01-3.09 (m, 2H), 2.82-2.88 (m, 2H), 2.12-2.82 (m, 7H). LCMS: 420.1 [M + H] |
| 23 | 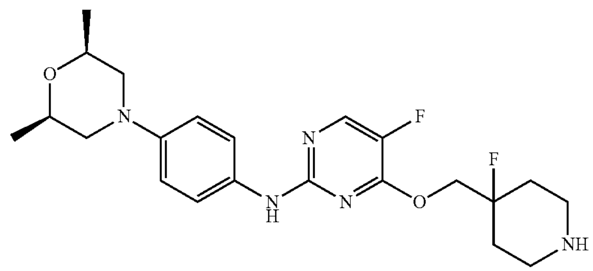 [SMILES: C[C@@H]1CN(c2ccc(Nc3ncc(F)c(OCC4(F)CCNCC4)n3)cc2)C[C@H](C)O1] | N-(4-((2R,6S)-2,6-dimethylmorpholino)phenyl)-5-fluoro-4-((4-fluoropiperidin-4-yl)methoxy)pyrimidin-2-amine | (CD$_3$OD) δ = 8.19 (d, J = 2.8 Hz, 1H), 7.80 (d, J = 9.2 Hz, 2H), 7.41 (d, J = 9.2 Hz, 2H), 4.63 (d, J = 18.4 Hz, 2H), 3.99-4.03 (m, 2H), 3.58-3.61 (m, 2H), 3.44-3.48 (m, 2H), 3.01-3.07 (m, 2H), 2.30-2.34 (m, 3H), 2.05-2.28 (m, 3H), 1.27-1.31 (m, 6H). LCMS: 434.2 [M + H] |
| 24 | 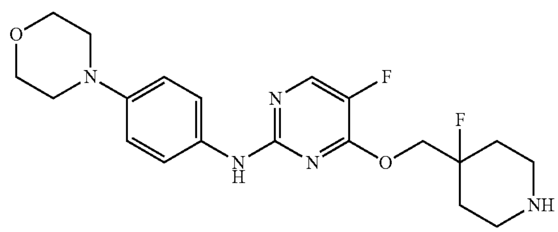 [SMILES: Fc1cnc(Nc2ccc(N3CCOCC3)cc2)nc1OCC1(F)CCNCC1] | 5-fluoro-4-((4-fluoropiperidin-4-yl)methoxy)-N-(4-morpholinophenyl)pyrimidin-2-amine | (CD$_3$OD) δ = 8.19 (d, J = 2.8 Hz, 1H), 7.76-7.77 (m, 2H), 7.37-7.38 (m, 2H), 4.63 (d, J = 18.4 Hz, 2H), 4.00-4.01 (m, 4H), 3.44-3.52 (m, 6H), 3.27-3.28 (m, 2H), 2.30-2.34 (m, 2H), 2.05-2.28 (m, 2H). LCMS: 406.2.2 [M + H] |
| 25 | 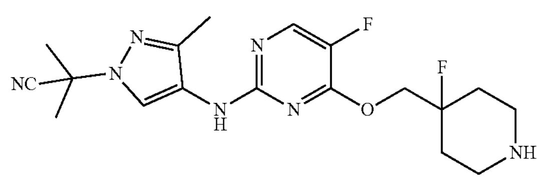 | 2-(4-((5-fluoro-4-((4-fluoropiperidin-4-yl)methoxy)pyrimidin-2-yl)amino)-3-methyl-1H-pyrazol-1-yl)-2-methylpropanenitrile | (CD$_3$OD) δ = 8.11 (s, 1H), 8.04 (d, J = 3.2 Hz, 1H), 4.59 (d, J = 18.4 Hz, 2H), 3.27-3.46 (m, 4H), 2.28-2.33 (m, 2H), 2.25 (s, 3H), 1.96-2.16 (m, 8H). LCMS: 392.2 [M + H] |
| 26 | 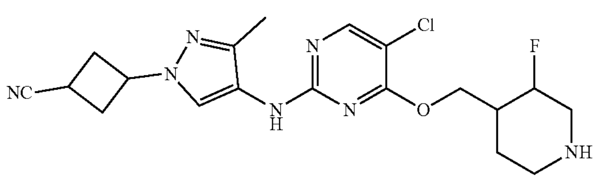 [SMILES: Cc1nn(C2CC(C#N)C2)cc1Nc1ncc(Cl)c(OCC2CCNCC2F)n1] | 3-(4-((5-chloro-4-((3-fluoropiperidin-4-yl)methoxy)pyrimidin-2-yl)amino)-3-methyl-1H-pyrazol-1-yl)cyclobutane-1-carbonitrile | (DMSO-d$_6$) δ = 9.01 (bs, 1H), 8.65 (bs, 1H), 8.23 (s, 1H), 7.91 (s, 1H), 5.01-5.11 (m, 1H), 5.01-5.11 (m, 2H), 3.56-3.65 (m, 1H), 2.89-3.46 (m, 4H), 2.65-2.82 (m, 4H), 2.24-2.51 (m, 2H), 2.07-2.20 (m, 3H), 1.66-1.78 (m, 2H). LCMS: 420.1 [M + H] |
| 27 | 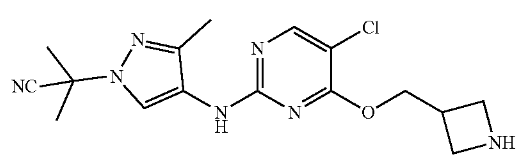 [SMILES: Cc1nn(C(C)(C)C#N)cc1Nc1ncc(Cl)c(OCC2CNC2)n1] | 2-(4-((4-(azetidin-3-ylmethoxy)-5-chloropyrimidin-2-yl)amino)-3-methyl-1H-pyrazol-1-yl)-2-methylpropanenitrile | (DMSO-d$_6$) δ = 9.22 (bs, 1H), 8.74 (bs, 1H), 8.29 (s, 1H), 8.12 (s, 2H), 4.54 (d, J = 6.4 Hz, 1H), 3.85-4.08 (m, 4H), 3.24-3.32 (m, 1H), 2.18 (s, 3H), 1.94 (s, 6H). LCMS: 362.1 [M + H] |
| 28 | 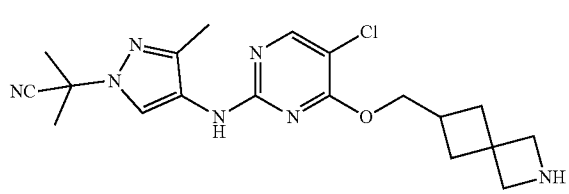 [SMILES: Cc1nn(C(C)(C)C#N)cc1Nc1ncc(Cl)c(OCC2CC3(CNC3)C2)n1] | 2-(4-((4-((2-azaspiro[3.3]heptan-6-yl)methoxy)-5-chloropyrimidin-2-yl)amino)-3-methyl-1H-pyrazol-1-yl)-2-methylpropanenitrile | (DMSO-d$_6$) δ = 9.19 (bs, 1H), 8.51 (bs, 1H), 8.25 (s, 1H), 8.13 (s, 1H), 4.32-4.34 (m, 3H), 3.99 (t, J = 6.0 Hz, 2H), 3.90 (t, J = 6.4 Hz, 2H), 2.51-2.61 (m, 1H), 2.34-2.40 (m, 1H), 2.18 (s, 3H), 2.04-2.09 (m, 2H), 1.94 (s, 6H). LCMS: 402.0 [M + H] |

| Example | Name | †Spectral data |
|---|---|---|
| 163 | N-(4-(3-oxa-8-azabicyclo[3.2.1]octan-8-yl)phenyl)-4-((3,3-difluoropiperidin-4-yl)methoxy)-5-fluoropyrimidin-2-amine | (CD₃OD) δ = 7.90 (d, J = 8.0 Hz, 1H), 7.30 (d, J = 8.8 Hz, 2H), 7.00 (d, J = 8.8 Hz, 2H), 4.69-4.84 (m, 2H), 4.19 (bs, 2H), 3.89-3.98 (m, 3H), 3.51-3.67 (m, 5H), 2.02-2.39 (m, 6H), 1.66-1.70 (m, 1H). LCMS 450.3 [M + H] |
| 164 | 4-((3,3-difluoropiperidin-4-yl)methoxy)-5-fluoro-N-(1-isopropyl-1H-pyrazol-4-yl)pyrimidin-2-amine | (DMSO-d₆) δ = 9.24 (bs, 1H), 8.05 (d, J = 6.8 Hz, 1H), 7.81 (s, 1H), 7.44 (s, 1H), 4.38-4.44 (m, 3H), 3.75-3.78 (m, 1H), 3.24-3.39 (m, 2H), 2.03-2.34 (m, 2H), 1.54-1.55 (m, 8H). LCMS: 371.2 [M + H] |
| 165 | 2-(4-((4-((3,3-difluoropiperidin-4-yl)methoxy)-5-fluoropyrimidin-2-yl)amino)-3-methyl-1H-pyrazol-1-yl-2-methylpropanenitrile | (CD₃OD) δ = 8.01 (s, 1H), 7.85 (d, J = 6.8 Hz, 1H), 4.54-4.66 (m, 2H), 3.89-3.92 (m, 1H), 3.37-3.57 (m, 2H), 3.13-3.20 (m, 1H), 2.21-2.26 (m, 4H), 1.96-2.16 (m, 7H), 1.63-1.67 (m, 1H). LCMS: 410.2 [M + H] |
| 166 | 5-fluoro-4-((3-fluoropiperidin-4-yl)methoxy)-N-(4-morpholinophenyl)pyrimidin-2-amine | (CD₃OD) δ = 8.18 (d, J = 2.8 Hz, 1H), 7.80 (d, J = 9.2 Hz, 2H), 7.42 (d, J = 8.8 Hz, 2H), 4.61-4.71 (m, 2H), 4.01-4.04 (m, 4H), 3.64-3.68 (m, 1H), 3.50-3.56 (m, 4H), 3.41-3.44 (m, 1H), 3.12-3.29 (m, 2H), 2.52-2.57 (m, 1H), 2.26-2.27 (m, 1H), 1.90-2.03 (m, 1H). LCMS: 406.3 [M + H] (second eluting peak) |
| 167 | 5-fluoro-4-((3-fluoropiperidin-4-yl)methoxy)-N-(4-morpholinophenyl)pyrimidin-2-amine | (DMSO-d₆) δ = 9.38 (bs, 1H), 8.98 (bs, 1H), 8.64 (bs, 1H), 8.27 (d, J = 2.8 Hz, 1H), 7.55 (d, J = 8.8 Hz, 2H), 6.94 (d, J = 8.8 Hz, 2H), 5.05-5.17 (m, 2H), 4.39-4.40 (m, 2H), 3.75-3.77 (m, 4H), 3.57-3.63 (m, 1H), 3.29-3.32 (m, 2H), 3.01-3.08 (m, 5H), 1.68-1.85 (m, 2H). LCMS: 406.3 [M + H] (first eluting peak) |
| 168 | N-(4-((2S,6R)-2,6-dimethylmorpholino)phenyl)-5-fluoro-4-((3-fluoropiperidin-4-yl)methoxy)pyrimidin-2-amine | LCMS: 434.2 [M + H] (second eluting peak) |

-continued

| Example | Name | †Spectral data |
|---|---|---|
| 169 | N-(4-((2S,6R)-2,6-dimethylmorpholino)phenyl)-5-fluoro-4-((3-fluoropiperidin-4-yl)methoxy)pyrimidin-2-amine | (DMSO-d$_6$) δ = 9.29 (bs, 1H), 8.23-8.24 (m, 1H), 7.50-7.53 (m, 2H), 6.86-6.89 (m, 2H), 4.71 (d, J = 49.2 Hz, 1H), 4.31-4.35 (m, 2H), 3.68-3.72 (m, 2H), 3.47-3.49 (m, 2H), 3.14-3.18 (m, 1H), 2.96-2.99 (m, 1H), 2.58-2.78 (m, 2H), 2.16-2.21 (m, 3H), 1.41-1.51 (m, 2H), 1.11-1.16 (m, 6H). LCMS: 434.2 [M + H] (first eluting peak) |
| 170 | 2-(4-((5-fluoro-4-((3-fluoropiperidin-4-yl)methoxy)pyrimidin-2-yl)amino)-3-methyl-1H-pyrazol-1-yl)-2-methylpropanenitrile | LCMS: 392.2 [M + H] (first eluting peak) |
| 171 | 2-(4-((5-fluoro-4-((3-fluoropiperidin-4-yl)methoxy)pyrimidin-2-yl)amino)-3-methyl-1H-pyrazol-1-yl)-2-methylpropanenitrile | (CD$_3$OD) δ = 8.09 (s, 1H), 8.03 (d, J = 3.2 Hz, 1H), 4.59-4.87 (m, 2H), 4.45-4.49 (m, 2H), 3.33-3.38 (m, 1H), 3.06-3.09 (m, 1H), 2.71-2.78 (m, 2H), 2.22 (s, 3H), 2.01-2.08 (m, 1H), 1.92 (s, 6H), 1.57-1.66 (m, 1H). LCMS: 392.2 [M + H] (second eluting peak) |
| 29 | 4-((3,3-difluoropiperidin-4-yl)methoxy)-5-fluoro-N-(4-morpholinophenyl)pyrimidin-2-amine | (CD$_3$OD) δ = 7.92 (d, J = 8.0 Hz, 1H), 7.36 (d, J = 9.2 Hz, 2H), 7.09 (d, J = 8.8 Hz, 2H), 4.71-4.92 (m, 2H), 3.94-3.98 (m, 1H), 3.87-3.89 (m, 4H), 3.55-3.60 (m, 2H), 3.21-3.24 (m, 4H), 2.14-2.19 (m, 2H), 1.67-1.70 (m, 2H). LCMS: 424.2 [M + H] |
| 30 | 4-((3,3-difluoropiperidin-4-yl)methoxy)-N-(4-((2S,6R)-2,6-dimethylmorpholino)phenyl)-5-fluoropyrimidin-2-amine | (CD$_3$OD) δ = 7.94 (d, J = 10.4 Hz, 1H), 7.38 (d, J = 11.2 Hz, 2H), 7.15 (d, J = 11.6 Hz, 2H), 4.70-4.80 (m, 2H), 3.95-3.99 (m, 1H), 3.84-3.88 (m, 2H), 3.34-3.69 (m, 5H), 2.51-2.56 (m, 2H), 2.16-2.38 (m, 2H), 1.67-1.73 (m, 1H), 1.26-1.28 (m, 6H). LCMS: 452.2 [M + H] |

†All $^1$H NMR recorded at 400 MHz

General Synthetic Scheme 3 for the Synthesis of Examples 31-55

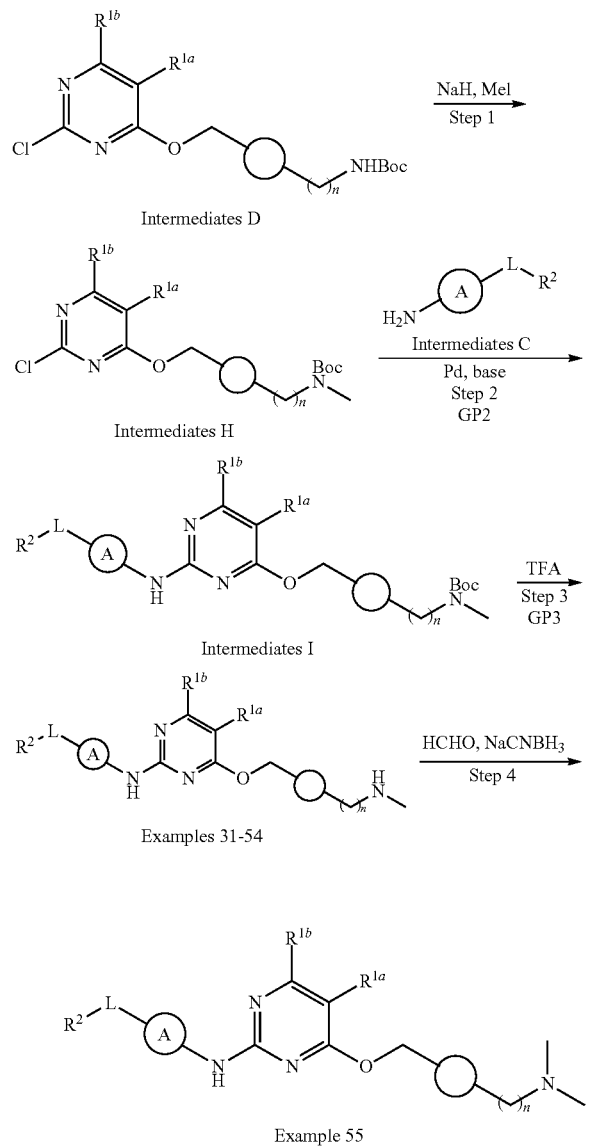

wherein n is 0 or 1.

Step 1: Synthesis of Intermediates H

A solution of Boc-protected amine (Intermediate D, 1.0 eq.) in DMF was added to a stirred suspension of NaH (60% in mineral oil, 2.0 eq.) in DMF at 0° C. and the resulting mixture was stirred at 25° C. for 10 min. Iodomethane (2.0 eq.) was then added and the resulting mixture was stirred at 25° C. until completion of the reaction (as indicated by TLC). The reaction mixture was then quenched with saturated $NH_4Cl$ and diluted with EtOAc. Layers were separated and the organic layer was washed with water and brine. The layers were separated, the organic layer was washed with water and brine, dried over $Na_2SO_4$, filtered, and concentrated under reduced pressure to yield crude material which was purified by flash chromatography, giving the desired Intermediate H.

Step 2: Synthesis of Intermediates I

Intermediates I were synthesized by following General Procedure GP2 described above.

Step 3: Synthesis of Examples 31-54

Examples 31-54 were synthesized by following General Procedure GP3 described above.

Step 4: Synthesis of Examples 55

Formaldehyde (37% in water, 2.0 eq.) AcOH (0.2 eq.), and MP-cyanoborohydride resin (2.5 eq.) were added to a solution of 5-methoxy-4-(((1R,4R)-4-(methylamino)cyclohexyl)methoxy)-N-(4-morpholinophenyl)pyrimidin-2-amine (Example 35, 1.0 eq.) in MeOH at 0° C. and the resulting mixture was stirred at 25° C. for 16 h. Following completion of the reaction (as indicated by LCMS), the reaction mixture was filtered through a pad of Celite® (i.e., diatomaceous earth) which was rinsed with MeOH (2×5 mL). The combined filtrates were concentrated under reduced pressure to afford crude material which was purified by preparative HPLC, giving Example 55 as an off-white solid.

The following examples were synthesized following General Synthetic Scheme 3:

| Example | Structure | Name | †Spectral data |
|---|---|---|---|
| 31 | 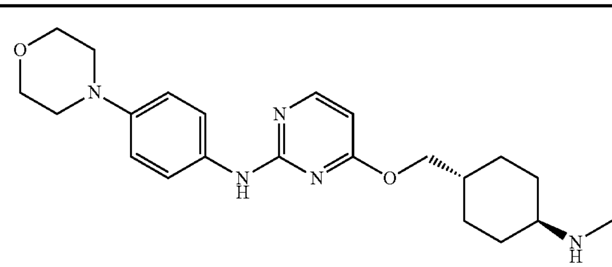 | 4-(((1R,4R)-4-(methylamino)cyclohexyl)methoxy)-N-(4-morpholinophenyl)pyrimidin-2-amine | (DMSO-$d_6$) δ = 9.26 (bs, 1H), 8.14 (d, J = 5.6 Hz, 1H), 7.58 (d, J = 9.2 Hz, 2H), 6.88 (d, J = 9.2 Hz, 2H), 6.18 (d, J = 5.6 Hz, 1H), 4.13 (d, J = 6.4 Hz, 2H), 3.73-3.75 (m, 4H), 3.02-3.04 (m, 4H), 2.49 (s, 3H), 2.77-2.93 (m, 1H), 1.75-2.07 (m, 5H), 1.08-1.28 (m, 4H). LCMS: 398.0 [M + H] |

| Example | Name | †Spectral data |
|---|---|---|
| 32 | 2-methyl-2-(3-methyl-4-((4-(((1R,4R)-4-(methylamino)cyclohexyl)methoxy)pyrimidin-2-yl)amino)-1H-pyrazol-1-yl)propanenitrile | (CD₃OD) δ = 8.10 (s, 1H), 8.05 (d, J = 5.6 Hz, 1H), 6.17 (d, J = 6.0 Hz, 1H), 4.18 (d, J = 6.4 Hz, 2H), 2.37-2.39 (m, 4H), 2.25 (s, 3H), 2.04-2.05 (m, 2H), 2.00 (s, 6H), 1.91-1.93 (m, 2H), 1.77-1.79 (m, 1H), 1.12-1.15 (m, 4H). LCMS: 384.0 [M + H] |
| 33 | N-(1-isopropyl-1H-pyrazol-4-yl)-4-(methylamino)cyclohexyl)methoxy)pyrimidin-2-amine | (CD₃OD) δ = 8.05 (s, 1H), 7.94 (s, 1H), 7.67 (s, 1H), 6.42 (d, J = 6.8 Hz, 1H), 4.54 (s, 1H), 4.35-4.36 (m, 2H), 3.02-3.06 (m, 1H), 2.70 (s, 3H), 2.22 (s, 2H), 2.05-2.09 (m, 2H), 1.90-1.94 (m, 1H), 1.52-1.54 (m, 6H), 1.39-1.50 (m, 4H). LCMS: 345.3 [M + H] |
| 34 | (2-fluoro-5-methoxy-4-((4-(((1R,4R)-4-(methylamino)cyclohexyl)methoxy)pyrimidin-2-yl)amino)phenyl)(morpholino)methanone | (DMSO-d₆) δ = 8.27-8.31 (m, 2H), 8.07 (s, 1H), 7.03 (d, J = 6.4 Hz, 1H), 6.42 (d, J = 5.6 Hz, 1H), 4.16 (d, J = 6.8 Hz, 2H), 3.90 (s, 3H), 3.56-3.65 (m, 6H), 2.30 (s, 3H), 1.81-1.94 (m, 6H), 0.99-1.09 (m, 4H). LCMS: 473.9 [M + H] |
| 35 | 5-methoxy-4-(((1R,4R)-4-(methylamino)cyclohexyl)methoxy)-N-(4-morpholinophenyl)pyrimidin-2-amine | (DMSO-d₆) δ = 7.81 (bs, 1H), 7.48 (d, J = 9.2 Hz, 2H), 6.94-6.97 (m, 2H), 4.26 (d, J = 6.4 Hz, 2H), 3.81-3.87 (m, 7H), 3.09-3.11 (m, 4H), 2.78-2.80 (m, 1H), 2.60 (s, 3H), 1.87-2.16 (m, 5H), 1.22-1.33 (m, 4H). LCMS: 428.3 [M + H] |
| 36 | (2-fluoro-5-methoxy-4-((5-methoxy-4-(methylamino)cyclohexyl)methoxy)pyrimidin-2-yl)amino)phenyl)(morpholino)methanone | (CD₃OD) δ = 8.42 (d, J = 12.4 Hz, 1H), 7.97 (s, 1H), 6.98 (d, J = 6.0 Hz, 1H), 4.29 (d, J = 6.4 Hz, 2H), 3.98 (s, 3H), 3.87 (s, 3H), 3.68-3.78 (m, 6H), 3.44-3.47 (m, 2H), 2.41 (s, 3H), 1.91-2.08 (m, 5H), 1.15-1.23 (m, 4H). LCMS: 504.3 [M + H] |
| 37 | 2-(4-((5-methoxy-4-(((1R,4R)-4-(methylamino)cyclohexyl)methoxy)pyrimidin-2-yl)amino)-3-methyl-1H-pyrazol-1-yl)-2-methylpropanenitrile | (CD₃OD) δ = 8.09 (s, 1H), 7.81 (s, 1H), 4.23 (d, J = 6.8 Hz, 2H), 3.81 (s, 3H), 2.45 (s, 3H), 2.24 (s, 3H), 1.93-2.16 (m, 12H), 1.16-1.31 (m, 4H). LCMS: 414.3 [M + H] |

| Example | Structure | Name | †Spectral data |
|---|---|---|---|
| 38 | 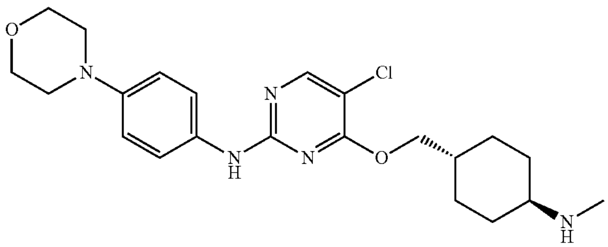 [SMILES: CN[C@H]1CC[C@H](COc2nc(Nc3ccc(N4CCOCC4)cc3)ncc2Cl)CC1] | 5-chloro-4-(((1R,4R)-4-(methylamino)cyclohexyl)methoxy)-N-(4-morpholinophenyl)pyrimidin-2-amine | (CD$_3$OD) δ = 8.08 (s, 1H), 7.50 (d, J = 8.8 Hz, 2H), 6.96 (d, J = 9.2 Hz, 2H), 4.27 (d, J = 6.4 Hz, 2H), 3.84-3.87 (m, 4H), 3.10-3.12 (m, 4H), 2.44 (s, 3H), 1.95-2.09 (m, 5H), 1.17-1.26 (m, 4H). LCMS: 432.2 [M + H] |
| 39 | 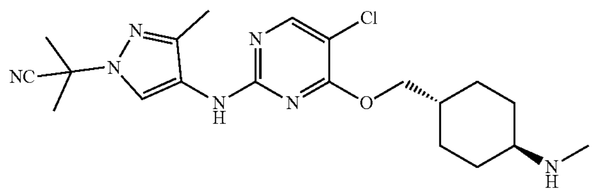 [SMILES: CN[C@H]1CC[C@H](COc2nc(Nc3cn(C(C)(C)C#N)nc3C)ncc2Cl)CC1] | 2-(4-((5-chloro-4-(((1R,4R)-4-(methylamino)cyclohexyl)methoxy)pyrimidin-2-yl)amino)-3-methyl-1H-pyrazol-1-yl)-2-methylpropanenitrile | (CD$_3$OD) δ = 8.11 (s, 1H), 8.10 (s, 1H), 4.26 (d, J = 6.4 Hz, 2H), 2.38 (s, 3H), 2.25 (s, 3H), 1.81-2.06 (m, 11H), 1.15-1.17 (m, 4H). LCMS: 418.0 [M + H] |
| 40 | 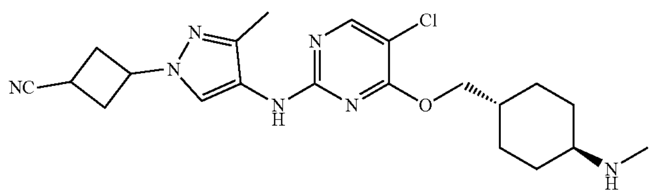 [SMILES: CN[C@H]1CC[C@H](COc2nc(Nc3cn(C4CC(C#N)C4)nc3C)ncc2Cl)CC1] | 3-(4-((5-chloro-4-(((1R,4R)-4-(methylamino)cyclohexyl)methoxy)pyrimidin-2-yl)amino)-3-methyl-1H-pyrazol-1-yl)cyclobutane-1-carbonitrile | (CD$_3$OD) δ = 8.07 (s, 1H), 7.88 (m, 1H), 4.24-4.27 (m, 2H), 3.38-3.43 (m, 1H), 2.95-3.06 (m, 2H), 2.80-2.87 (m, 2H), 2.68 (s, 3H), 2.18-2.22 (m, 5H), 1.88-2.07 (m, 4H), 1.24-1.41 (m, 5H). LCMS: 430.0 [M + H] |
| 41 | 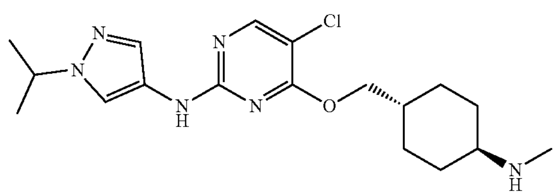 [SMILES: CN[C@H]1CC[C@H](COc2nc(Nc3cnn(C(C)C)c3)ncc2Cl)CC1] | 5-chloro-N-(1-isopropyl-1H-pyrazol-4-yl)-4-(((1R,4R)-4-(methylamino)cyclohexyl)methoxy)pyrimidin-2-amine | (DMSO-d$_6$) δ = 9.61 (bs, 1H), 8.38 (bs, 1H), 8.23 (s, 1H), 7.85 (s, 1H), 7.49 (s, 1H), 4.41-4.48 (m, 2H), 4.07-4.26 (m, 1H), 2.92-2.94 (m, 1H), 2.58 (s, 3H), 1.81-2.10 (m, 5H), 1.39-1.41 (m, 6H), 1.14-1.37 (m, 4H). LCMS: 379.2 [M + H] |
| 42 | 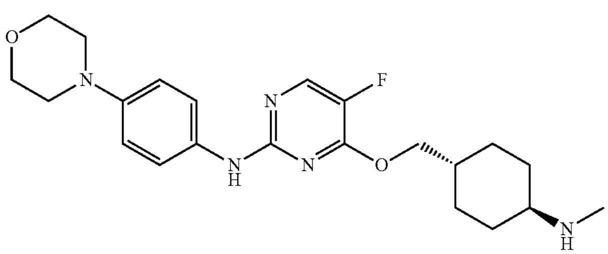 | 5-fluoro-4-(((1R,4R)-4-(methylamino)cyclohexyl)methoxy)-N-(4-morpholinophenyl)pyrimidin-2-amine | (CD$_3$OD) δ = 8.13 (d, J = 3.2 Hz, 1H), 7.74 (d, J = 8.8 Hz, 2H), 7.37 (d, J = 8.8 Hz, 2H), 4.35 (d, J = 6.0 Hz, 2H), 3.99-4.02 (m, 4H), 3.35-3.50 (m, 4H), 3.03-3.08 (m, 1H), 2.72 (s, 3H), 2.21-2.24 (m, 2H), 2.05-2.09 (m, 2H), 1.92-1.94 (m, 1H), 1.24-1.48 (m, 4H). LCMS: 416.2 [M + H] |
| 43 | 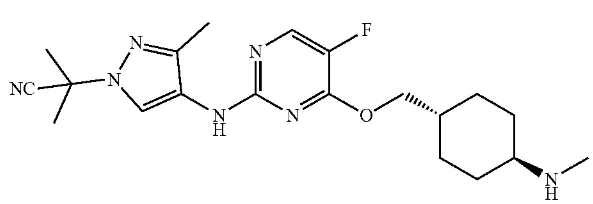 | 2-(4-((5-fluoro-4-(((1R,4R)-4-(methylamino)cyclohexyl)methoxy)pyrimidin-2-yl)amino)-3-methyl-1H-pyrazol-1-yl)-2-methylpropanenitrile | (CD$_3$OD) δ = 8.11 (s, 1H), 8.08 (d, J = 3.6 Hz, 1H), 4.33 (d, J = 6.4 Hz, 2H), 3.01-3.08 (m, 1H), 2.72 (s, 3H), 2.20-2.24 (m, 5H), 1.91-2.07 (m, 9H), 1.30-1.48 (m, 4H). LCMS: 402.3 [M + H] |
| 44 | 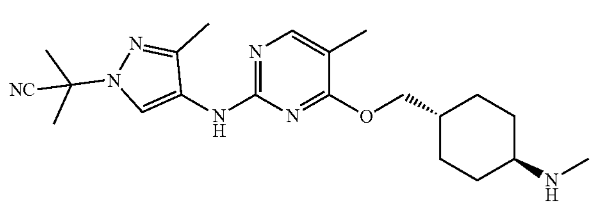 | 2-methyl-2-(3-methyl-4-((5-methyl-4-(((1R,4R)-4-(methylamino)cyclohexyl)methoxy)pyrimidin-2-yl)amino)-1H-pyrazol-1-yl)propanenitrile | (CD$_3$OD) δ = 8.12 (s, 1H), 7.88 (s, 1H), 4.36 (d, J = 6.4 Hz, 2H), 3.04-3.05 (m, 1H), 2.72 (s,3H), 2.19-2.21 (m, 5H), 1.91-2.11 (m, 11H), 1.37 (s, 5H). LCMS: 398.2 [M + H] |

| Example | Structure | Name | †Spectral data |
|---|---|---|---|
| 45 | 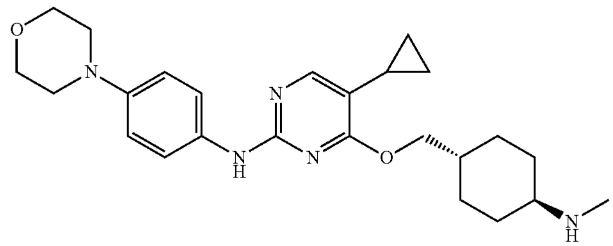 [SMILES: CN[C@H]1CC[C@H](COc2nc(Nc3ccc(N4CCOCC4)cc3)ncc2C2CC2)CC1] | 5-cyclopropyl-4-(((1R,4R)-4-(methylamino)cyclohexyl)methoxy)-N-(4-morpholinophenyl)pyrimidin-2-amine | (CD$_3$OD) δ = 7.65 (s, 1H), 7.39 (d, J = 8.8 Hz, 2H), 7.13 (d, J = 9.2 Hz, 2H), 4.38 (d, J = 6.0 Hz, 2H), 3.87-3.89 (m, 4H), 3.23-3.26 (m, 4H), 3.02-3.08 (m, 1H), 2.73 (s, 3H), 2.21-2.24 (m, 2H), 2.04-2.07 (m, 2H), 1.95-1.96 (m, 1H), 1.79-1.84 (m, 1H), 1.27-1.49 (m, 4H), 0.97-0.99 (m, 2H), 0.67-0.71 (m, 2H). LCMS: 438.0 [M + H] |
| 46 | 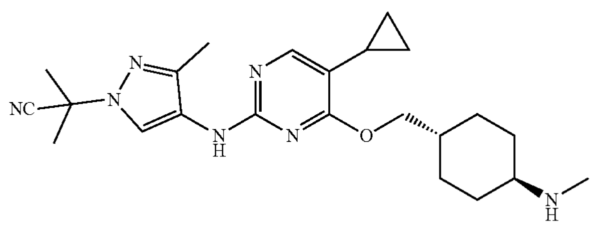 [SMILES: CN[C@H]1CC[C@H](COc2nc(Nc3cn(C(C)(C)C#N)nc3C)ncc2C2CC2)CC1] | 2-(4-((5-cyclopropyl-4-(((1R,4R)-4-(methylamino)cyclohexyl)methoxy)pyrimidin-2-yl)amino)-3-methyl-1H-pyrazol-1-yl)-2-methylpropanenitrile | (CD$_3$OD) δ = 8.13 (s, 1H), 7.78 (s, 1H), 4.40 (d, J = 5.6 Hz, 2H), 3.05-3.07 (m, 1H), 2.21-2.24 (m, 5H), 1.81-2.08 (m, 11H), 1.31-1.47 (m, 6H), 0.94-0.99 (m, 2H), 0.67-0.71 (m, 2H). LCMS: 423.5 [M + H] |
| 47 | 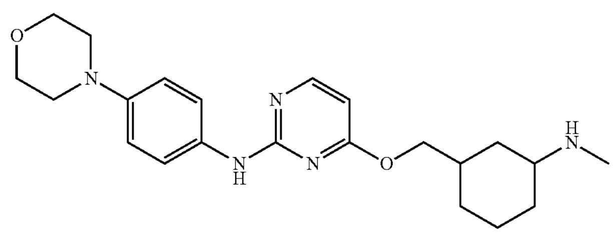 [SMILES: CNC1CCCC(COc2ccnc(Nc3ccc(N4CCOCC4)cc3)n2)C1] | 4-((3-(methylamino)cyclohexyl)methoxy)-N-(4-morpholinophenyl)pyrimidin-2-amine | (CD$_3$OD) δ = 8.05-8.07 (m, 1H), 7.50 (d, J = 8.8 Hz, 2H), 6.96-6.99 (m, 2H), 6.63 (s, 1H), 6.16-6.18 (m, 2H), 4.19-4.32 (m, 2H), 3.84-3.87 (m, 4H), 3.10-3.12 (m, 4H), 2.80-2.83 (m, 1H), 2.50-2.59 (m, 3H), 1.63-2.23 (m, 5H), 1.06-1.45 (m, 4H). LCMS: 398.3 [M + H] |
| 48 | 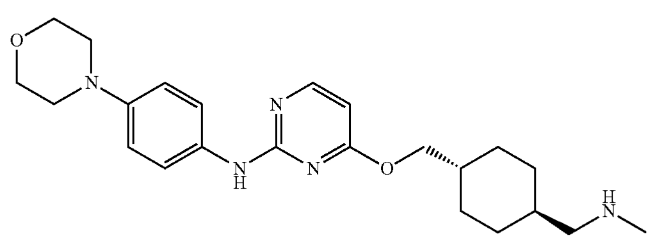 [SMILES: CNC[C@H]1CC[C@H](COc2ccnc(Nc3ccc(N4CCOCC4)cc3)n2)CC1] | 4-(((1R,4R)-4-((methylamino)methyl)cyclohexyl)methoxy)-N-(4-morpholinophenyl)pyrimidin-2-amine | (DMSO-d$_6$) δ = 9.23 (bs, 1H), 8.12 (d, J = 5.6 Hz, 1H), 7.58 (d, J = 9.2 Hz, 2H), 6.87-6.89 (m, 2H), 6.18 (d, J = 5.6 Hz, 1H), 4.11-4.13 (m, 2H), 3.73-3.75 (m, 4H), 3.02-3.04 (m, 4H), 2.29-2.34 (m, 2H), 2.25 (s, 3H), 1.69-1.84 (m, 5H), 1.24-1.36 (m, 1H), 0.88-1.04 (m, 4H). LCMS: 412.4 [M + H] |
| 49 | 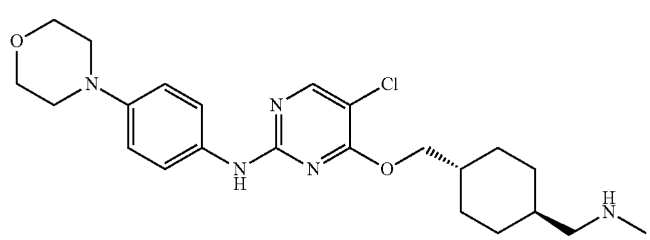 [SMILES: CNC[C@H]1CC[C@H](COc2nc(Nc3ccc(N4CCOCC4)cc3)ncc2Cl)CC1] | 5-chloro-4-(((1R,4R)-4-((methylamino)methyl)cyclohexyl)methoxy)-N-(4-morpholinophenyl)pyrimidin-2-amine | (DMSO-d$_6$) δ = 9.44 (bs, 1H), 8.22 (s, 1H), 7.54 (d, J = 8.8 Hz, 2H), 6.89 (d, J = 9.2 Hz, 2H), 4.20-4.22 (m, 2H), 3.73-3.75 (m, 4H), 3.02-3.05 (m, 4H), 2.29-2.34 (m, 2H), 2.25 (s, 3H), 1.75-1.83 (m, 5H), 0.86-1.36 (m, 5H). LCMS: 446.2 [M + H] |
| 50 | 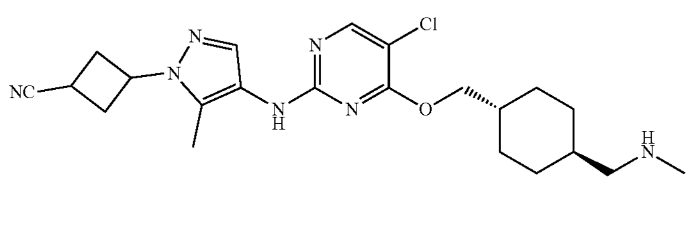 [SMILES: CNC[C@H]1CC[C@H](COc2nc(Nc3cnn(C4CC(C#N)C4)c3C)ncc2Cl)CC1] | 3-(4-((5-chloro-4-(((1R,4R)-4-((methylamino)methyl)cyclohexyl)methoxy)pyrimidin-2-yl)amino)-5-methyl-1H-pyrazol-1-yl)cyclobutane-1-carbonitrile | (CD$_3$OD) δ = 8.03 (s, 1H), 7.64 (s, 1H), 5.17-5.21 (m, 1H), 4.23-4.24 (m, 2H), 3.43-3.44 (m, 1H), 3.01-3.09 (m, 2H), 2.81-2.91 (m, 4H), 2.73 (s, 3H), 2.21 (s, 3H), 1.65-1.97 (m, 6H), 1.11-1.21 (m, 4H). LCMS: 444.2 [M + H] |

-continued

| Example | Structure | Name | †Spectral data |
|---|---|---|---|
| 51 | 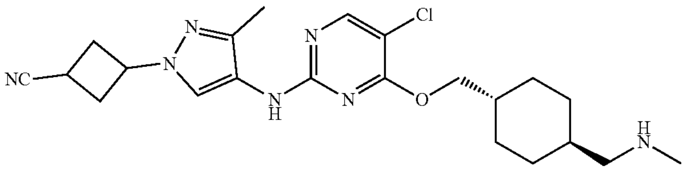 [SMILES: CNC[C@H]1CC[C@H](COc2nc(Nc3cn(C4CC(C#N)C4)nc3C)ncc2Cl)CC1] | 3-(4-((5-chloro-4-(((1R,4R)-4-((methylamino)methyl)cyclohexyl)methoxy)pyrimidin-2-yl)amino)-3-methyl-1H-pyrazol-1-yl)cyclobutane-1-carbonitrile | (CD$_3$OD) δ = 8.08 (s, 1H), 7.88 (s, 1H), 5.07-5.12 (m, 1H), 4.26-4.28 (m, 2H), 3.34-3.40 (m, 1H), 2.79-3.01 (m, 6H), 2.73 (s, 3H), 2.22 (s, 3H), 1.65-1.99 (m, 6H), 1.16-1.24 (m, 4H). LCMS: 444.2 [M + H] |
| 52 | 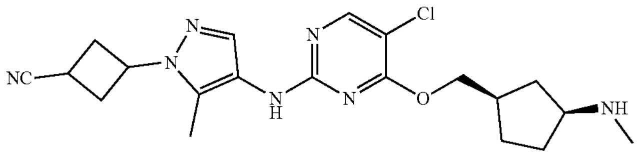 [SMILES: CN[C@H]1CC[C@@H](COc2nc(Nc3cnn(C4CC(C#N)C4)c3C)ncc2Cl)C1] | 3-(4-((5-chloro-4-(((1R,3S)-3-(methylamino)cyclopentyl)methoxy)pyrimidin-2-yl)amino)-5-methyl-1H-pyrazol-1-yl)cyclobutane-1-carbonitrile | (CD$_3$OD) δ = 8.04 (s, 1H), 7.65 (s, 1H), 5.17-5.21 (m, 1H), 4.30-4.48 (m, 2H), 3.42-3.59 (m, 2H), 2.81-3.09 (m, 4H), 2.73 (s, 3H), 2.41-2.59 (m, 2H), 2.17-2.22 (m, 4H), 1.46-1.99 (m, 4H). LCMS: 416.1 [M + H] |
| 53 | 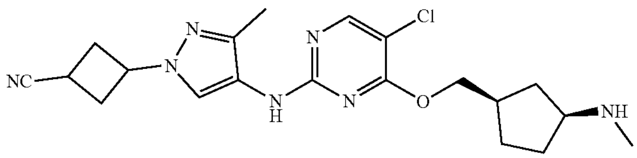 [SMILES: CN[C@H]1CC[C@@H](COc2nc(Nc3cn(C4CC(C#N)C4)nc3C)ncc2Cl)C1] | 3-(4-((5-chloro-4-(((1R,3S)-3-(methylamino)cyclopentyl)methoxy)pyrimidin-2-yl)amino)-3-methyl-1H-pyrazol-1-yl)cyclobutane-1-carbonitrile | (CD$_3$OD) δ = 8.09 (s, 1H), 7.88 (s, 1H), 5.08-5.10 (m, 1H), 4.38-4.46 (m, 2H), 3.57-3.71 (m, 2H), 2.96-3.02 (m, 2H), 2.79-2.86 (m, 2H), 2.73 (s, 3H), 2.42-2.59 (m, 2H), 1.48-2.22 (m, 8H). LCMS: 416.1 [M + H] |
| 54 | 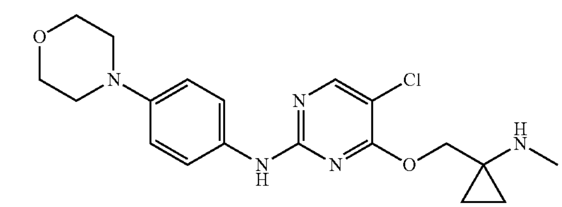 [SMILES: CNC1(COc2nc(Nc3ccc(N4CCOCC4)cc3)ncc2Cl)CC1] | 5-chloro-4-((1-(methylamino)cyclopropyl)methoxy)-N-(4-morpholinophenyl)pyrimidin-2-amine | (DMO-d$_6$) δ = 9.55 (bs, 1H), 8.98 (bs, 1H), 8.31 (s, 1H), 7.52 (d, J = 8.8 Hz, 2H), 6.93 (d, J = 8.8 Hz, 2H), 4.61 (bs, 2H), 3.74-3.76 (m, 4H), 3.05-3.06 (m, 4H), 2.75 (s, 3H), 1.09-1.20 (m, 4H). LCMS: 390.2[M + H] |
| 55 | 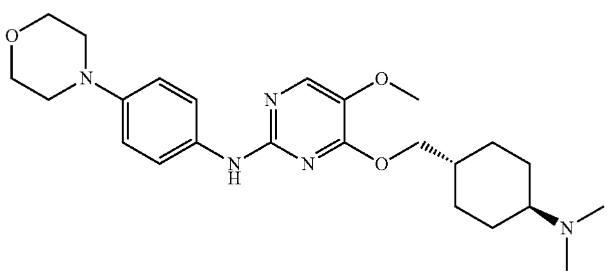 [SMILES: COc1cnc(Nc2ccc(N3CCOCC3)cc2)nc1OC[C@H]1CC[C@H](N(C)C)CC1] | 4-(((1R,4R)-4-(dimethylamino)cyclohexyl)methoxy)-5-methoxy-N-(4-morpholinophenyl)pyrimidin-2-amine | (, CD$_3$OD) δ = 7.81 (s, 1H), 7.47-7.49 (m, 2H), 6.94-6.97 (m, 2H), 4.24 (d, J = 6.4 Hz, 2H), 3.81-3.87 (m, 7H), 3.09-3.11 (m, 4H), 2.39-2.41 (m, 7H), 1.84-2.04 (m, 5H), 1.23-1.36 (m, 4H). LCMS: 442.3[M + H] |

†All $^1$H NMR recorded at 400 MHz

General Synthetic Scheme 4 for the Synthesis of Examples 56-70

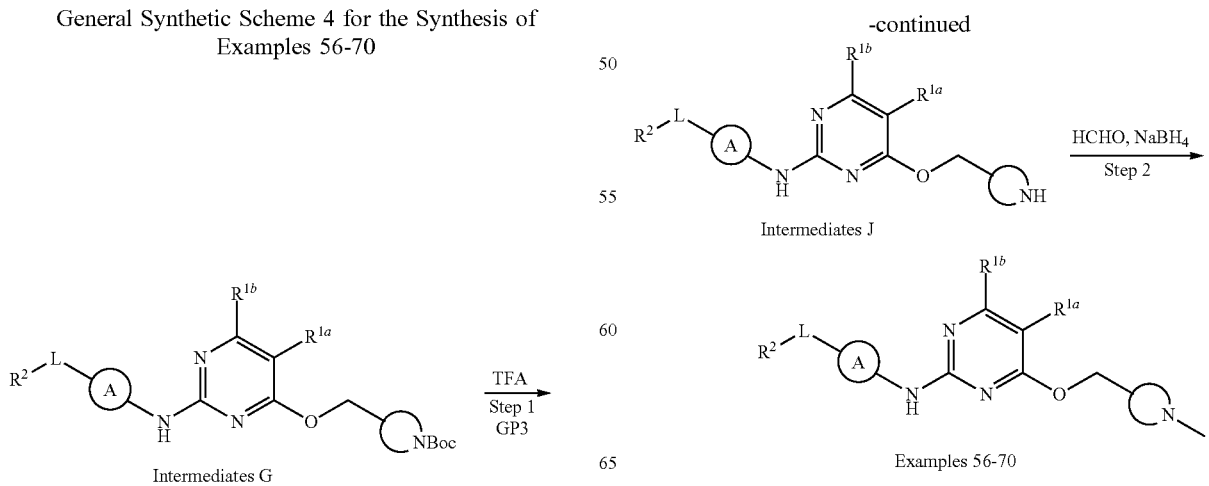

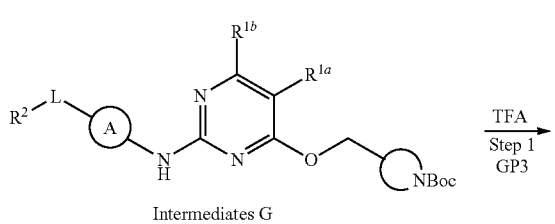

Intermediates G

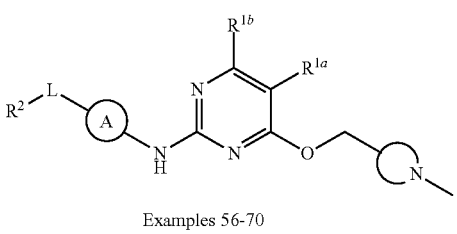

Examples 56-70

Step 1: Synthesis of Intermediates J

Intermediates J were synthesized by following General Procedure GP3 described above. Crude materials were purified by flash chromatography.

Step 2: Synthesis of Examples 56-70

Formaldehyde (37% in water, 2.0 eq.), AcOH (0.2 eq.), and NaBH$_4$ (1.5 eq.) were added to a solution of amine Intermediate J (1.0 eq.) DCM at 0° C. and the resulting mixture was and stirred at 45° C. until completion of the reaction (as indicated by LCMS). The reaction mixture was then cooled to 0° C., quenched with ice water, and extracted with DCM (2×50). The combined organic extracts were dried over Na$_2$SO$_4$, filtered, and concentrated under reduced pressure to give yield crude material which was purified by preparative HPLC, giving the desired Examples 56-70.

The following examples were synthesized following General Synthetic Scheme 4:

| Example | Structure | Name | †Spectral data |
|---|---|---|---|
| 56 | 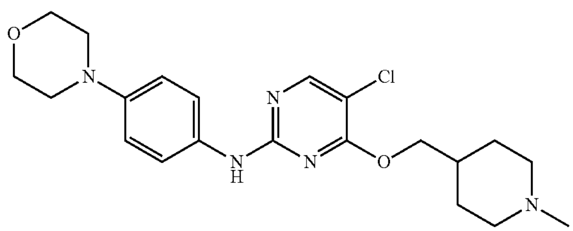 [SMILES: CN1CCC(COc2nc(Nc3ccc(N4CCOCC4)cc3)ncc2Cl)CC1] | 5-chloro-4-((1-methylpiperidin-4-yl)methoxy)-N-(4-morpholinophenyl)pyrimidin-2-amine | (CD$_3$OD) δ = 8.09 (s, 1H), 7.49-7.51 (m, 2H), 6.96-6.98 (m, 2H), 4.32 (d, J = 6.4 Hz, 2H), 3.84-3.87 (m, 4H), 3.10-3.16 (m, 4H), 2.96-2.99 (m, 2H), 2.34 (s, 3H), 2.11-2.17 (m, 2H), 1.85-1.92 (m, 2H), 1.46-1.49 (m, 2H). LCMS: 417.8 [M + H] |
| 57 | 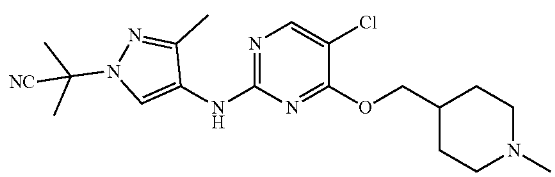 | 2-(4-((5-chloro-4-((1-methylpiperidin-4-yl)methoxy)pyrimidin-2-yl)amino)-3-methyl-1H-pyrazol-1-yl)-2-methylpropanenitrile | (CD$_3$OD) δ = 8.15 (s, 1H), 8.12 (s, 1H), 4.36-4.38 (m, 2H), 3.58-3.61 (m, 2H), 3.04-3.10 (m, 2H), 2.90 (s, 3H), 2.25 (s, 3H), 2.12-2.20 (m, 3H), 2.00 (s, 6H), 1.66-1.70 (m, 2H). LCMS: 404.2 [M + H] |
| 58 | 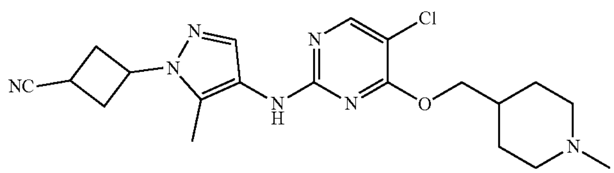 [SMILES: Cc1c(Nc2ncc(Cl)c(OCC3CCN(C)CC3)n2)cnn1C1CC(C#N)C1] | 3-(4-((5-chloro-4-((1-methylpiperidin-4-yl)methoxy)pyrimidin-2-yl)amino)-5-methyl-1H-pyrazol-1-yl)cyclobutane-1-carbonitrile | (CD$_3$OD) δ = 8.05 (s, 1H), 7.87 (s, 1H), 5.08-5.10 (m, 1H), 4.33-4.36 (m, 2H), 3.35-3.61 (m, 4H), 2.81-3.10 (m, 9H), 2.22 (s, 3H), 1.68-2.12 (m, 4H). LCMS: 416.2[M + H] |
| 59 | 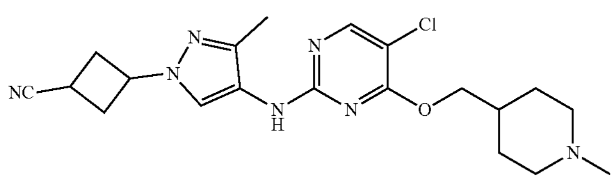 [SMILES: Cc1nn(C2CC(C#N)C2)cc1Nc1ncc(Cl)c(OCC2CCN(C)CC2)n1] | 3-(4-((5-chloro-4-((1-methylpiperidin-4-yl)methoxy)pyrimidin-2-yl)amino)-3-methyl-1H-pyrazol-1-yl)cyclobutane-1-carbonitrile | (CD$_3$OD) δ = 8.09 (s, 1H), 7.88 (s, 1H), 4.91-5.12 (m, 1H), 4.35 (d, J = 5.6 Hz, 2H), 3.42-3.61 (m, 4H), 2.98-3.10 (m, 4H), 2.96 (s, 3H), 2.79-2.90 (m, 2H), 2.22 (s, 3H), 2.10-2.13 (m, 2H), 1.68-1.72 (m, 2H). LCMS: 416.2[M + H] |
| 60 | 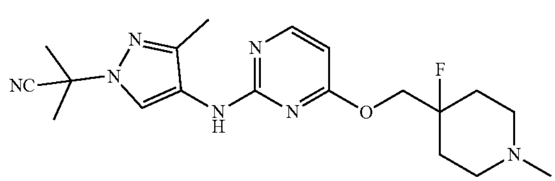 [SMILES: Cc1nn(C(C)(C)C#N)cc1Nc1nccc(OCC2(F)CCN(C)CC2)n1] | 2-(4-((4-((4-fluoro-1-methylpiperidin-4-yl)methoxy)pyrimidin-2-yl)amino)-3-methyl-1H-pyrazol-1-yl)-2-methylpropanenitrile | (CD$_3$OD) δ = 8.15 (s, 1H), 8.12 (d, J = 5.2 Hz, 1H), 6.45 (d, J = 6.4 Hz, 1H), 4.61 (d, J = 19.20 Hz, 2H), 3.55-3.57 (m, 2H), 2.96 (s, 3H), 2.33-2.35 (m, 2H), 2.25 (s, 3H), 2.10-2.22 (m, 4H), 2.02 (s, 6H). LCMS: 388.2[M + H] |

| Example | Structure | Name | †Spectral data |
|---|---|---|---|
| 61 | 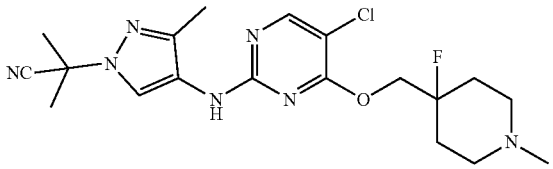 [SMILES: Cc1nn(C(C)(C)C#N)cc1Nc1ncc(Cl)c(OCC2(F)CCN(C)CC2)n1] | 2-(4-((5-chloro-4-((4-fluoro-1-methylpiperidin-4-yl)methoxy)pyrimidin-2-yl)amino)-3-methyl-1H-pyrazol-1-yl)-2-methylpropanenitrile | (CD₃OD) δ = 8.15 (s, 1H), 8.13 (s, 1H), 4.52 (d, J = 19.6 Hz, 2H), 2.91-2.94 (m, 2H), 2.55-2.59 (m, 2H), 2.47 (s, 3H), 2.25 (s, 3H), 1.83-2.13 (m, 10H). LCMS: 422.1[M + H] |
| 62 | 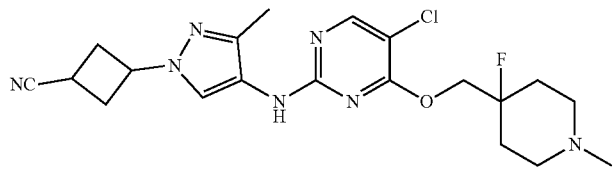 [SMILES: Cc1nn(C2CC(C#N)C2)cc1Nc1ncc(Cl)c(OCC2(F)CCN(C)CC2)n1] | 3-(4-((5-chloro-4-((4-fluoro-1-methylpiperidin-4-yl)methoxy)pyrimidin-2-yl)amino)-3-methyl-1H-pyrazol-1-yl)cyclobutane-1-carbonitrile | (CD₃OD) δ = 8.14 (s, 1H), 7.89 (s, 1H), 5.08-5.10 (m, 1H), 4.57 (d, J = 18.4 Hz, 2H), 3.38-3.39 (m, 5H), 2.96-3.04 (m, 5H), 2.79-2.86 (m, 2H), 2.34-2.39 (m, 2H), 2.22-2.22 (m, 3H), 2.09-2.20 (m, 2H). LCMS: 434.1[M + H] |
| 63 | 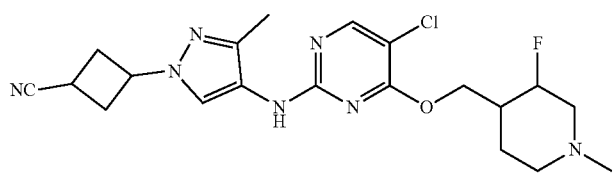 [SMILES: Cc1nn(C2CC(C#N)C2)cc1Nc1ncc(Cl)c(OCC2CCN(C)CC2F)n1] | 3-(4-((5-chloro-4-((3-fluoro-1-methylpiperidin-4-yl)methoxy)pyrimidin-2-yl)amino)-3-methyl-1H-pyrazol-1-yl)cyclobutane-1-carbonitrile | (CD₃OD) δ = 8.13 (s, 1H), 7.83 (s, 1H), 5.08-5.27 (m, 2H), 4.47-4.90 (m, 2H), 3.86-3.92 (m, 1H), 3.60-3.63 (m, 1H), 3.37-3.44 (m, 1H), 2.80-3.21 (m, 9H), 1.90-2.47 (m, 6H). LCMS: 434.0[M + H] |
| 64 | 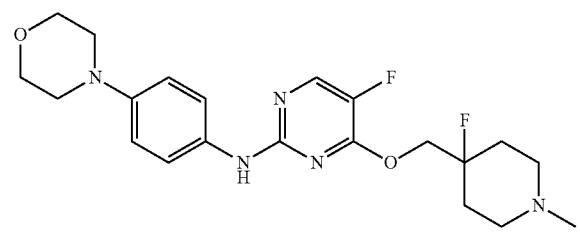 [SMILES: CN1CCC(F)(COc2nc(Nc3ccc(N4CCOCC4)cc3)ncc2F)CC1] | 5-fluoro-4-((4-fluoro-1-methylpiperidin-4-yl)methoxy)-N-(4-morpholinophenyl)pyrimidin-2-amine | (CD₃OD) δ = 8.18 (d, J = 2.8 Hz, 1H), 7.76 (d, J = 8.8 Hz, 2H), 7.37 (d, J = 6.0 Hz, 2H), 4.63 (d, J = 18.4 Hz, 2H), 3.99-4.02 (m, 4H), 3.49-3.59 (m, 6H), 3.34-3.37 (m, 2H), 2.96 (s, 3H), 2.09-2.39 (m, 4H). LCMS: 420.2[M + H] |
| 65 | 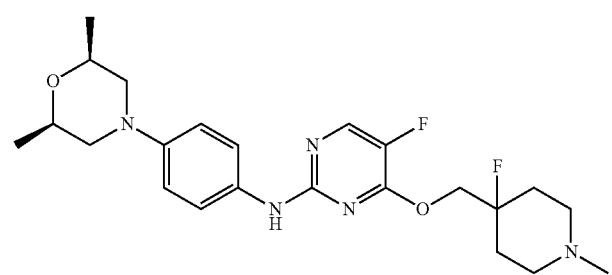 | N-(4-((2R,6S)-2,6-dimethylmorpholino)phenyl)-5-fluoro-4-((4-fluoro-1-methylpiperidin-4-yl)methoxy)pyrimidin-2-amine | (CD₃OD) δ = 8.18 (d, J = 2.8 Hz, 1H), 7.76 (d, J = 8.8 Hz, 2H), 7.37 (d, J = 6.0 Hz, 2H), 4.60-4.67 (m, 2H), 3.97-4.02 (m, 2H), 3.50-3.58 (m, 4H), 2.88-2.97 (m, 5H), 2.08-2.39 (m, 2H), 1.26-1.32 (m, 6H). LCMS: 448.2[M + H] |
| 66 | 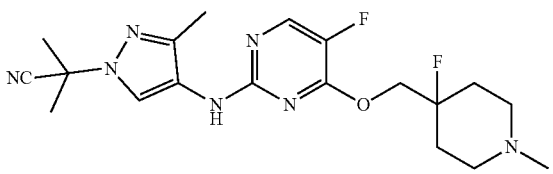 [SMILES: Cc1nn(C(C)(C)C#N)cc1Nc1ncc(F)c(OCC2(F)CCN(C)CC2)n1] | 2-(4-((5-fluoro-4-((4-fluoro-1-methylpiperidin-4-yl)methoxy)pyrimidin-2-yl)amino)-3-methyl-1H-pyrazol-1-yl)-2-methylpropanenitrile | (CD₃OD) δ = 8.14 (s, 1H), 8.12 (d, J = 2.8 Hz, 1H), 4.60 (d, J = 18.8 Hz, 2H), 3.54-3.58 (m, 2H), 3.33-3.34 (m, 2H), 2.96 (s, 3H), 2.34-2.40 (m, 2H), 2.25 (s, 3H), 2.12 (s, 2H), 2.02 (s, 6H). LCMS: 406.2[M + H] |

| Example | Structure | Name | †Spectral data |
|---|---|---|---|
| 67 | 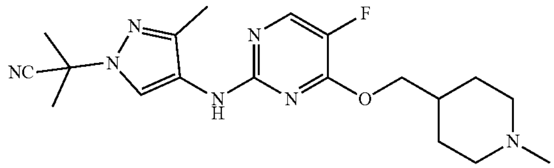 [SMILES: Cc1nn(C(C)(C)C#N)cc1Nc1ncc(F)c(OCC2CCN(C)CC2)n1] | 2-(4-((5-fluoro-4-((1-methylpiperidin-4-yl)methoxy)pyrimidin-2-yl)amino)-3-methyl-1H-pyrazol-1-yl)-2-methylpropanenitrile | (CD$_3$OD) δ = 8.12 (s, 1H), 8.07 (d, J = 3.2 Hz, 1H), 4.38 (d, J = 6.0 Hz, 2H), 3.57-3.60 (m, 2H), 3.03-3.06 (m, 2H), 2.89-2.93 (m, 3H), 2.00-2.24 (m, 12H), 1.67 (s, 2H). LCMS: 388.3[M + H] |
| 68 | 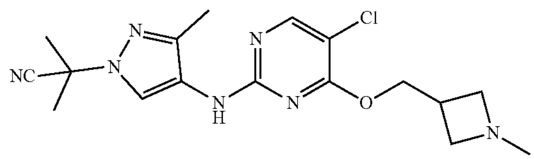 [SMILES: Cc1nn(C(C)(C)C#N)cc1Nc1ncc(Cl)c(OCC2CN(C)C2)n1] | 2-(4-((5-chloro-4-((1-methylazetidin-3-yl)methoxy)pyrimidin-2-yl)amino)-3-methyl-1H-pyrazol-1-yl)-2-methylpropanenitrile | (CD$_3$OD) δ = 8.18 (s, 1H), 8.13 (s, 1H), 4.46-4.67 (m, 4H), 4.04-4.09 (m, 2H), 3.50-3.58 (m, 1H), 3.01 (s, 3H), 2.25 (s, 3H), 1.99 (s, 6H). LCMS: 376.1[M + H] |
| 69 | 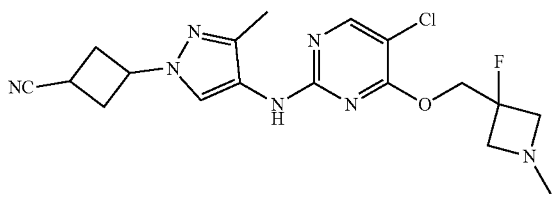 [SMILES: Cc1nn(C2CC(C#N)C2)cc1Nc1ncc(Cl)c(OCC2(F)CN(C)C2)n1] | 3-(4-((5-chloro-4-((3-fluoro-1-methylazetidin-3-yl)methoxy)pyrimidin-2-yl)amino)-3-methyl-1H-pyrazol-1-yl)cyclobutane-1-carbonitrile | (CD$_3$OD) δ = 8.17 (s, 1H), 7.83 (s, 1H), 5.06-5.10 (m, 1H), 4.71-4.75 (m, 6H), 3.10 (s, 3H), 2.96-3.03 (m, 3H), 2.79-2.86 (m, 2H), 2.21 (s, 3H). LCMS: 406.2 [M + H] |
| 70 | 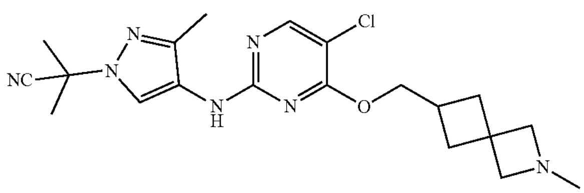 [SMILES: Cc1nn(C(C)(C)C#N)cc1Nc1ncc(Cl)c(OCC2CC3(C2)CN(C)C3)n1] | 2-(4-((5-chloro-4-((2-methyl-2-azaspiro[3.3]heptan-6-yl)methoxy)pyrimidin-2-yl)amino)-3-methyl-1H-pyrazol-1-yl)-2-methylpropanenitrile | (CD$_3$OD) δ = 8.12 (bs, 2H), 4.38 (d, J = 6.0 Hz, 2H), 3.89-3.95 (m, 4H), 2.73 (s, 3H), 2.43-2.49 (m, 2H), 2.20-2.25 (m, 5H), 1.99 (s, 6H), 1.94-1.96 (m, 1H). LCMS: 416.1[M + H] |

†All $^1$H NMR recorded at 400 MHz

General Synthetic Scheme 5 for the Synthesis of Examples 71-94 and 178-208

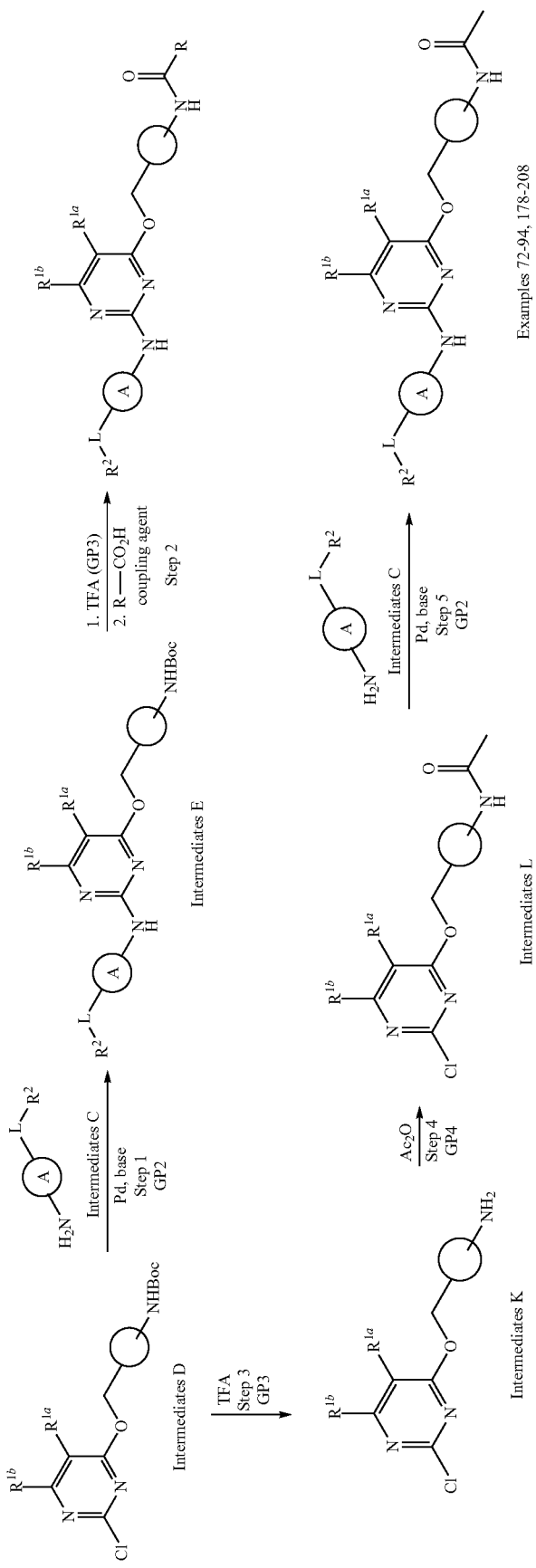

wherein R is C(cPr)(Me).

Step 1: Synthesis of Intermediates E

Intermediates E were synthesized by following General Procedure GP2 described above.

Step 2: Synthesis of Example 71

Boc deprotection of tert-butyl ((1R,4R)-4-(((2-((4-morpholinophenyl)amino)pyrimidin-4-yl)oxy)methyl)cyclohexyl)carbamate was done according to General Procedure GP3 described above, giving 4-(((1R,4R)-4-aminocyclohexyl)methoxy)-N-(4-morpholinophenyl)pyrimidin-2-amine (Example 2, 1.0 eq.) which was dissolved in DCM (10 vol.) with 1-methylcyclopropane-1-carboxylic acid (1.0 eq.). HOBt (1.2 eq.) and EDC.HCl (1.5 eq.) were added and the resulting mixture was stirred at 25° C. for 16 h. Following completion of the reaction (as indicated by LCMS), the reaction mixture was diluted with DCM (10 mL), washed with aqueous NaHCO$_3$ (2 mL) and brine (2 mL), dried over Na$_2$SO$_4$, filtered, and concentrated under reduced pressure. The resulting crude material was purified by preparative HPLC, affording Example 71 as a pale yellow solid.

Step 3: Synthesis of Intermediates K

Intermediates K were synthesized by following General Procedure GP3 described above. Crude materials were purified by flash chromatography.

Step 4: General Procedure GP4 (Acetamide Formation) for the Synthesis of Intermediates L Triethylamine (3.0 eq.) and acetic anhydride (1.5 eq.) were added to a solution of amine Intermediate K (1.0 eq.) in DCM (10 vol) at 0° C. and the resulting mixture was stirred at 0° C. for 2 h. Following completion of the reaction (as indicated by TLC), the reaction mixture was quenched with ice water and extracted with DCM. The combined organic layers were washed with brine, dried over Na$_2$SO$_4$, filtered, and concentrated under reduced pressure to yield crude material which was purified by flash chromatography (silica gel 230-400 mesh), affording the desired Intermediate L.

Step 5: Synthesis of Examples 72 to 89 and 178-208

Examples 72-89 and 178-208 were synthesized by following General Procedure GP2 described above; crude materials were purified by preparative HPLC.

The following examples were synthesized following General Synthetic Scheme 5:

| Example | Structure | Name | †Spectral data |
|---|---|---|---|
| 71 | 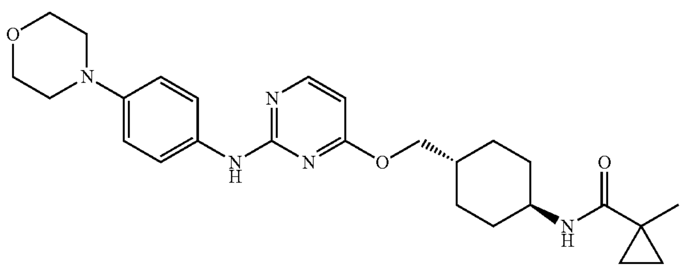 [SMILES: CC1(C(=O)N[C@H]2CC[C@H](COc3ccnc(Nc4ccc(N5CCOCC5)cc4)n3)CC2)CC1] | 1-methyl-N-((1R,4R)-4-(((2-((4-morpholinophenyl)amino)pyrimidin-4-yl)oxy)methyl)cyclohexyl)cyclopropane-1-carboxamide | (DMSO-d$_6$) δ = 9.25 (bs, 1H), 8.13 (d, J = 5.6 Hz, 1H), 7.57-7.60 (m, 2H), 7.15-7.17 (m, 1H), 6.88 (d, J = 9.2 Hz, 2H), 6.19 (d, J = 5.6 Hz, 1H), 4.12 (d, J = 6.8 Hz, 2H), 3.73-3.75 (m, 4H), 3.54-3.56 (m, 1H), 3.02-3.04 (m, 4H), 1.71-1.84 (m, 5H), 0.87-1.33 (m, 9H), 0.45-0.48 (m, 2H). LCMS: 466.0 [M + H] |
| 72 | 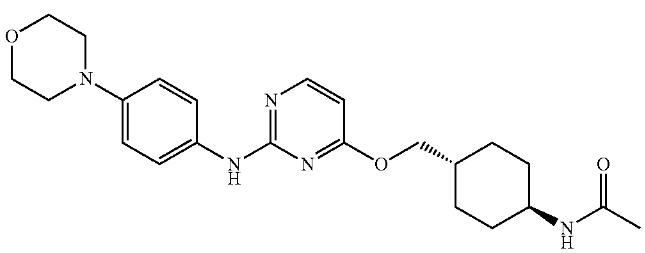 [SMILES: CC(=O)N[C@H]1CC[C@H](COc2ccnc(Nc3ccc(N4CCOCC4)cc3)n2)CC1] | N-((1R,4R)-4-(((2-((4-morpholinophenyl)amino)pyrimidin-4-yl)oxy)methyl)cyclohexyl)acetamide | (DMSO-d$_6$) δ = 9.24 (bs, 1H), 8.14 (d, J = 5.6 Hz, 1H), 7.72 (d, J = 8.0 Hz, 1H), 7.58 (d, J = 8.8 Hz, 2H), 6.88 (d, J = 8.8 Hz, 2H), 6.18 (d, J = 5.6 Hz, 1H), 4.11-4.13 (m, 2H), 3.73-3.75 (m, 4H), 3.02-3.04 (m, 4H), 1.77-1.83 (m, 9H), 1.05-1.24 (m, 4H). LCMS: 426.2 [M + H] |
| 73 | 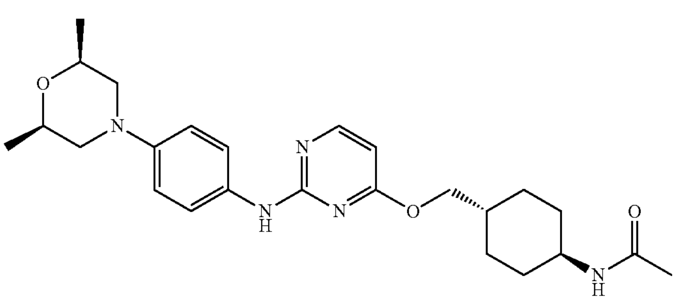 [SMILES: CC(=O)N[C@H]1CC[C@H](COc2ccnc(Nc3ccc(N4C[C@@H](C)O[C@@H](C)C4)cc3)n2)CC1] | N-((1R,4R)-4-(((2-((2R,6S)-2,6-dimethylmorpholino)phenyl)amino)pyrimidin-4-yl)oxy)methyl)cyclohexyl)acetamide | (DMSO-d$_6$) δ = 9.24 (bs, 1H), 8.13 (d, J = 5.6 Hz, 1H), 7.73 (d, J = 7.6 Hz, 1H), 7.57 (d, J = 9.2 Hz, 2H), 6.88 (d, J = 9.2 Hz, 2H), 6.18 (d, J = 5.6 Hz, 1H), 4.12 (d, J = 6.4 Hz, 2H), 3.67-3.72 (m, 2H), 3.46-3.49 (m, 3H), 2.16-2.22 (m, 2H), 1.77-1.83 (m, 8H), 1.11-1.16 (m, 10H). LCMS: 454.2 [M + H] |

-continued

| Example | Structure | Name | †Spectral data |
|---|---|---|---|
| 74 | 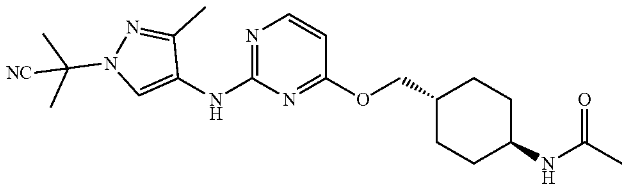 [SMILES: CC(=O)N[C@H]1CC[C@H](COc2ccnc(Nc3cn(C(C)(C)C#N)nc3C)n2)CC1] | N-((1R,4R)-4-(((2-((1-(2-cyanopropan-2-yl)-3-methyl-1H-pyrazol-4-yl)amino)pyrimidin-4-yl)oxy)methyl)cyclohexyl)acetamide | (CD$_3$OD) δ = 8.14 (s, 1H), 7.97 (d, J = 17.6 Hz, 1H), 6.54 (d, J = 6.8 Hz, 1H), 4.40 (d, J = 5.6 Hz, 2H), 3.53-3.62 (m, 1H), 2.25 (s, 3H), 1.94-2.03 (m, 14H), 1.25-1.27 (m, 4H). LCMS: 412.2 [M + H] |
| 75 | 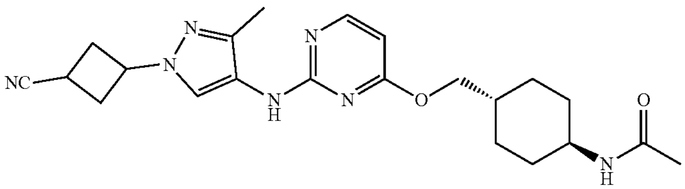 [SMILES: CC(=O)N[C@H]1CC[C@H](COc2ccnc(Nc3cn(C4CC(C#N)C4)nc3C)n2)CC1] | N-((1R,4R)-4-(((2-((1-(3-cyanocyclobutyl)-3-methyl-1H-pyrazol-4-yl)amino)pyrimidin-4-yl)oxy)methyl)cyclohexyl)acetamide | (DMSO-d$_6$) δ = 9.59 (bs, 1H), 8.10 (bs, 1H), 7.95 (s, 1H), 7.74 (d, J = 7.6 Hz, 1H), 6.34 (bs, 1H), 5.07-5.11 (m, 1H), 4.16 (d, J = 4.8 Hz, 2H), 3.42-3.48 (m, 3H), 2.82-2.89 (m, 2H), 2.68-2.75 (m, 2H), 2.17 (s, 3H), 1.72-1.81 (m, 7H), 1.05-1.19 (m, 4H). LCMS: 424.1 [M + H] |
| 76 | 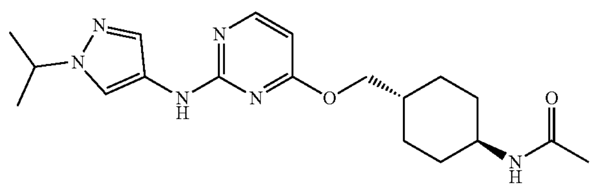 [SMILES: CC(=O)N[C@H]1CC[C@H](COc2ccnc(Nc3cnn(C(C)C)c3)n2)CC1] | N-((1R,4R)-4-(((2-((1-isopropyl-1H-pyrazol-4-yl)amino)pyrimidin-4-yl)oxy)methyl)cyclohexyl)acetamide | (DMSO-d$_6$) δ = 9.36 (bs, 1H), 8.12 (d, J = 5.2 Hz, 1H), 7.88 (s, 1H), 7.74 (d, J = 7.6 Hz, 1H), 7.47 (s, 1H), 6.13 (d, J = 5.6 Hz, 1H), 4.40-4.47 (m, 1H), 4.14 (bs, 2H), 3.47-3.49 (m, 1H), 1.72-1.88 (m, 8H), 1.40 (d, J = 6.8 Hz, 6H), 1.12-1.39 (m, 4H). LCMS: 373.1 [M + H] |
| 77 | 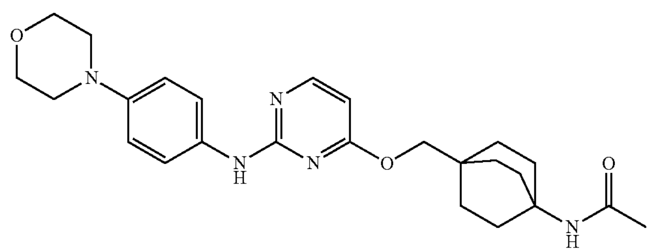 [SMILES: CC(=O)NC12CCC(COc3ccnc(Nc4ccc(N5CCOCC5)cc4)n3)(CC1)CC2] | N-(4-(((2-((4-morpholinophenyl)amino)pyrimidin-4-yl)oxy)methyl)bicyclo[2.2.2]octan-1-yl)acetamide | (CD$_3$OD) δ = 7.95 (s, 1H), 7.37 (d, J = 8.8 Hz, 2H), 7.12-7.15 (m, 2H), 6.49 (d, J = 7.2 Hz, 1H), 4.15 (bs, 2H), 3.88 (s, 4H), 3.24-3.26 (m, 4H), 1.94-1.98 (m, 6H), 1.88 (s, 3H), 1.64-1.68 (m, 6H). LCMS: 452.2 [M + H] |
| 78 | 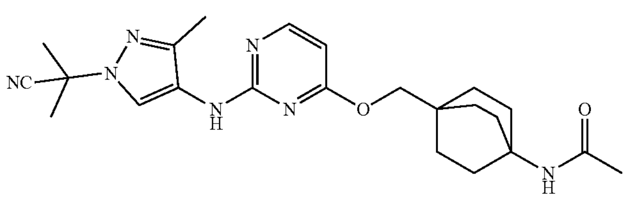 | N-(4-(((2-((1-(2-cyanopropan-2-yl)-3-methyl-1H-pyrazol-4-yl)amino)pyrimidin-4-yl)oxy)methyl)bicyclo[2.2.2]octan-1-yl)acetamide | (CD$_3$OD) δ = 8.11 (s, 1H), 8.05 (d, J = 5.6 Hz, 1H), 7.45 (s, 1H), 6.18 (d, J = 6.0 Hz, 1H), 4.01 (bs, 2H), 2.25 (s, 3H), 1.88-2.01 (m, 14H), 1.63-1.67 (m, 6H). LCMS: 412.1 [M + H] |
| 79 | 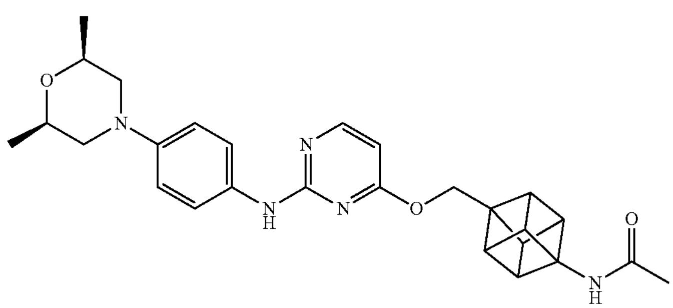 [SMILES: CC(=O)NC12C3C4C1C1C2C3C41COc1ccnc(Nc2ccc(N3C[C@@H](C)O[C@@H](C)C3)cc2)n1] | N-(4-(((2-((4-((2S,6R)-2,6-dimethylmorpholino)phenyl)amino)pyrimidin-4-yl)oxy)methyl)cuban-1-yl)acetamide | (CD$_3$OD) δ = 7.94-7.96 (m, 1H), 7.36-7.38 (m, 2H), 7.11-7.14 (m, 2H), 6.47-6.50 (m, 1H), 4.68 (s, 2H), 4.04-4.06 (m, 2H), 3.81-3.88 (m, 4H), 3.60-3.63 (m, 2H), 2.42-2.47 (m, 2H), 1.97-2.00 (m, 5H), 1.26-1.27 (m, 6H). LCMS: 474.3 [M + H] |

| Example | Structure | Name | †Spectral data |
|---|---|---|---|
| 80 | 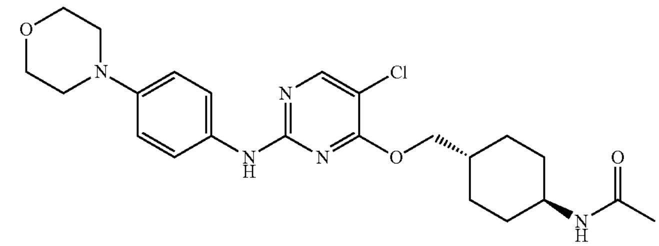 [SMILES: CC(=O)N[C@H]1CC[C@H](COc2nc(Nc3ccc(N4CCOCC4)cc3)ncc2Cl)CC1] | N-((1R,4R)-4-(((5-chloro-2-((4-morpholinophenyl)amino)pyrimidin-4-yl)oxy)methyl)cyclohexyl)acetamide | (DMSO-$d_6$) δ = 9.46 (bs, 1H), 8.23 (s, 1H), 7.73 (d, J = 8.0 Hz, 1H), 7.52-7.55 (m, 2H), 6.87-6.91 (m, 2H), 4.21 (d, J = 6.4 Hz, 2H), 3.73-3.75 (m, 4H), 3.48-3.49 (m, 1H), 3.02-3.05 (m, 4H), 1.77-1.81 (m, 8H), 1.12-1.13 (m, 4H). LCMS: 460.0 [M + H] |
| 81 | 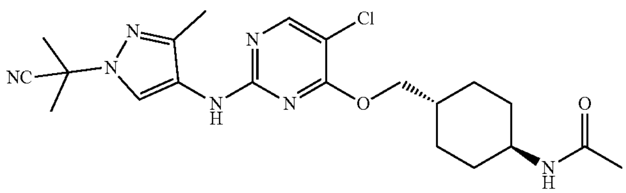 | N-((1R,4R)-4-(((5-chloro-2-((1-(2-cyanopropan-2-yl)-3-methyl-1H-pyrazol-4-yl)amino)pyrimidin-4-yl)oxy)methyl)cyclohexyl)acetamide | (DMSO-$d_6$) δ = 9.15 (bs, 1H), 8.24 (s, 1H), 8.13 (bs, 1H), 7.74 (d, J = 8.0 Hz, 2H), 4.20 (d, J = 6.4 Hz, 2H), 3.47-3.48 (m, 1H), 2.18 (s, 3H), 1.73-1.97 (m, 13H), 1.15-1.24 (m, 4H). LCMS: 446.0 [M + H] |
| 82 | 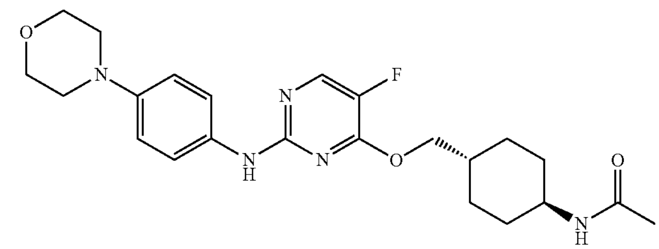 [SMILES: CC(=O)N[C@H]1CC[C@H](COc2nc(Nc3ccc(N4CCOCC4)cc3)ncc2F)CC1] | N-((1R,4R)-4-(((5-fluoro-2-((4-morpholinophenyl)amino)pyrimidin-4-yl)oxy)methyl)cyclohexyl)acetamide | (CD$_3$OD) δ = 8.01 (d, J = 3.2 Hz, 1H), 7.48-7.51 (m, 2H), 6.95-6.97 (m, 2H), 4.27 (d, J = 6.4 Hz, 2H), 3.84-3.87 (m, 4H), 3.63-3.64 (m, 1H), 3.09-3.12 (m, 4H), 1.85-1.99 (m, 8H), 1.18-1.33 (m, 4H). LCMS: 444.1 [M + H] |
| 83 | 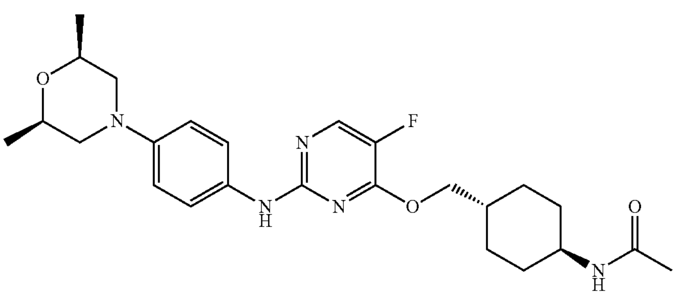 [SMILES: CC(=O)N[C@H]1CC[C@H](COc2nc(Nc3ccc(N4C[C@@H](C)O[C@@H](C)C4)cc3)ncc2F)CC1] | N-((1R,4R)-4-(((2-((4-((2R,6S)-2,6-dimethylmorpholino)phenyl)amino)-5-fluoropyrimidin-4-yl)oxy)methyl)cyclohexyl)acetamide yl)oxy)methyl)cyclohexyl)acetamide | (CD$_3$OD) δ = 8.00 (d, J = 3.2 Hz, 1H), 7.48 (d, J = 12.0 Hz, 2H), 6.94-6.97 (m, 2H), 4.27 (d, J = 6.8 Hz, 1H), 3.80-3.85 (m, 2H), 3.63-3.64 (m, 2H), 3.45-3.47 (m, 2H), 2.32 (s, 3H), 1.85-1.99 (m, 8H), 1.21-1.26 (m, 12H). LCMS: 472.2 [M + H] |
| 84 | 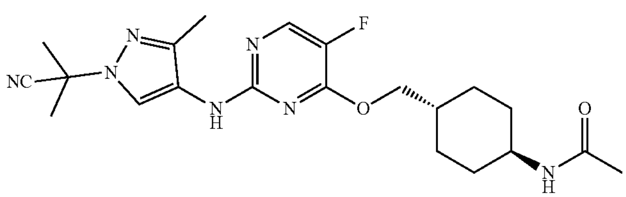 [SMILES: CC(=O)N[C@H]1CC[C@H](COc2nc(Nc3cn(C(C)(C)C#N)nc3C)ncc2F)CC1] | N-((1R,4R)-4-(((2-((1-(2-cyanopropan-2-yl)-3-methyl-1H-pyrazol-4-yl)amino)-5-fluoropyrimidin-4-yl)oxy)methyl)cyclohexyl)acetamide | (DMSO-$d_6$) δ = 8.92 (bs, 1H), 8.22 (d, J = 3.2 Hz, 1H), 8.12 (s, 1H), 7.74 (d, J = 7.6 Hz, 1H), 4.21 (d, J = 6.8 Hz, 2H), 3.47-3.49 (m, 1H), 2.18 (s, 3H), 1.93 (s, 6H), 1.77-1.83 (m, 8H), 1.07-1.18 (m, 4H). LCMS: 430.2 [M + H] |
| 85 | 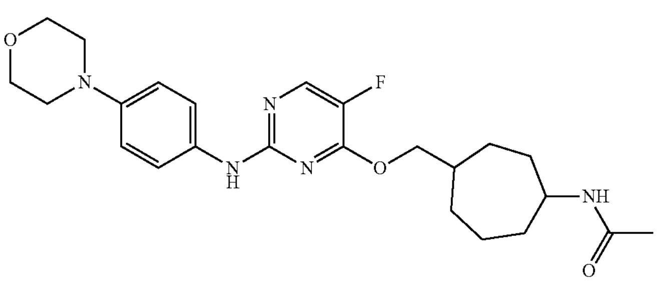 [SMILES: CC(=O)NC1CCCC(COc2nc(Nc3ccc(N4CCOCC4)cc3)ncc2F)CC1] | N-(4-(((5-fluoro-2-((4-morpholinophenyl)amino)pyrimidin-4-yl)oxy)methyl)cycloheptyl)acetamide | (DMSO-$d_6$) δ = 9.38 (bs, 1H), 8.23 (d, J = 2.8 Hz, 1H), 7.75-7.77 (m, 1H), 7.57-7.59 (m, 2H), 6.97-6.99 (m, 2H), 4.20-4.21 (m, 2H), 3.71-3.72 (m, 5H), 3.10 (bs, 4H), 1.19-2.01 (m, 14H). LCMS: 458.3 [M + H] |

-continued

| Example | Structure | Name | †Spectral data |
|---|---|---|---|
| 86 | 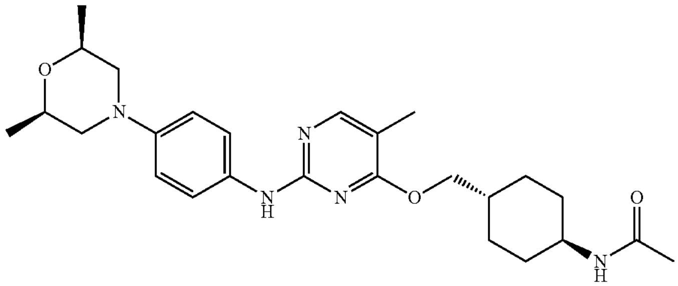 [SMILES: CC(=O)N[C@H]1CC[C@H](COc2nc(Nc3ccc(N4C[C@@H](C)O[C@@H](C)C4)cc3)ncc2C)CC1] | N-((1R,4R)-4-(((2-((4-((2S,6R)-2,6-dimethylmorpholino)phenyl)amino)-5-methylpyrimidin-4-yl)oxy)methyl)cyclohexyl)acetamide | (CD₃OD) δ = 7.78 (s, 1H), 7.33 (d, J = 9.2 Hz, 2H), 7.09-7.11 (m, 2H), 4.36 (d, J = 6.0 Hz, 1H), 3.79-3.89 (m, 2H), 3.59-3.62 (m, 2H), 2.39-2.45 (m, 2H), 2.11 (s, 3H), 1.92-1.94 (m, 8H), 1.24-1.27 (m, 12H). LCMS: 467.9 [M + H] |
| 87 | 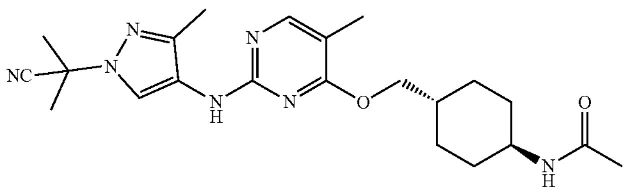 [SMILES: CC(=O)N[C@H]1CC[C@H](COc2nc(Nc3cn(C(C)(C)C#N)nc3C)ncc2C)CC1] | N-((1R,4R)-4-(((2-((1-(2-cyanopropan-2-yl)-3-methyl-1H-pyrazol-4-yl)amino)-5-methylpyrimidin-4-yl)oxy)methyl)cyclohexyl)acetamide | (CD₃OD) δ = 8.12 (s, 1H), 7.83 (s, 1H), 4.38 (d, J = 4.4 Hz, 2H), 3.61-3.64 (m, 1H), 2.24 (s, 3H), 2.12 (s, 3H), 1.98-2.06 (m, 8H), 1.94 (s, 6H), 1.27-1.31 (m, 4H). LCMS: 426.3 [M + H] |
| 88 | 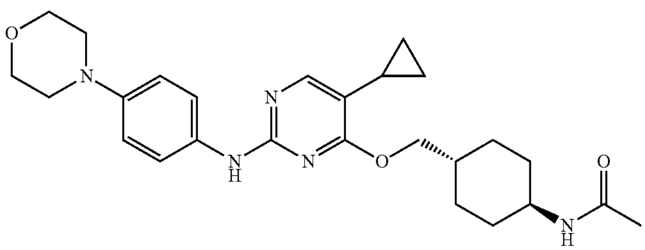 [SMILES: CC(=O)N[C@H]1CC[C@H](COc2nc(Nc3ccc(N4CCOCC4)cc3)ncc2C2CC2)CC1] | N-((1R,4R)-4-(((5-cyclopropyl-2-((4-morpholinophenyl)amino)pyrimidin-4-yl)oxy)methyl)cyclohexyl)acetamide | (DMSO-d₆) δ = 7.60 (s, 1H), 7.35 (d, J = 9.2 Hz, 2H), 7.11 (d, J = 9.2 Hz, 2H), 4.38 (d, J = 6.0 Hz, 2H), 3.86-3.88 (m, 4H), 3.64-3.70 (m, 1H), 3.22-3.24 (m, 4H), 1.82-1.99 (m, 9H), 1.27-1.34 (m, 4H), 0.95-0.99 (m, 2H), 0.67-0.70 (m, 2H). LCMS: 466.0 [M + H] |
| 89 | 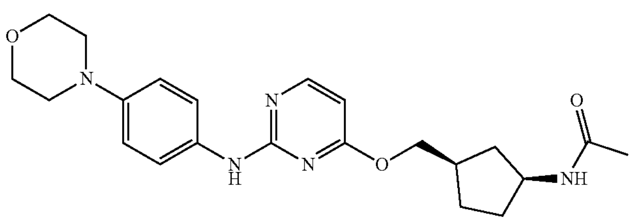 [SMILES: CC(=O)N[C@H]1CC[C@@H](COc2ccnc(Nc3ccc(N4CCOCC4)cc3)n2)C1] | N-((1S,3R)-3-(((2-((4-morpholinophenyl)amino)pyrimidin-4-yl)oxy)methyl)cyclopentyl)acetamide | (CD₃OD) δ = 7.97 (s, 1H), 7.38 (d, J = 8.8 Hz, 2H), 7.11-7.15 (m, 2H), 6.48 (d, J = 6.8 Hz, 1H), 4.44 (d, J = 6.8 Hz, 2H), 4.13-4.17 (m, 1H), 3.87-3.89 (m, 4H), 3.23-3.26 (m, 4H), 2.47-2.51 (m, 1H), 2.24-2.29 (m, 1H), 1.96 (d, J = 10.4 Hz, 5H), 1.55-1.60 (m, 2H), 1.21-1.29 (m, 1H). LCMS: 412.1 [M + H] |
| 90 | 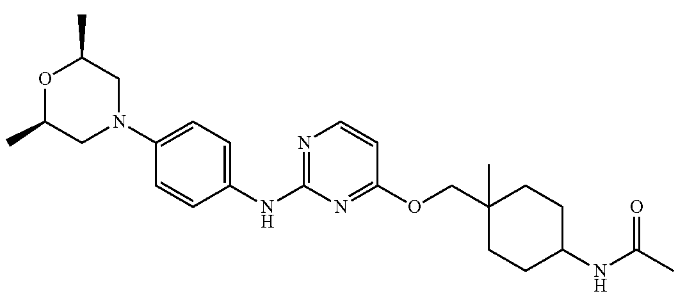 [SMILES: CC(=O)NC1CCC(C)(COc2ccnc(Nc3ccc(N4C[C@@H](C)O[C@@H](C)C4)cc3)n2)CC1] | N-(4-(((2-((4-((2S,6R)-2,6-dimethylmorpholino)phenyl)amino)pyrimidin-4-yl)oxy)methyl)-4-methylcyclohexyl)acetamide | (CD₃OD) δ = 7.96 (d, J = 6.8 Hz, 1H), 7.39 (d, J = 8.8 Hz, 2H), 7.13-7.16 (m, 2H), 6.52 (d, J = 6.8 Hz, 1H), 4.42 (s, 2H), 3.81-3.85 (m, 2H), 3.61-3.63 (m, 3H), 2.43-2.49 (m, 2H), 1.94 (s, 3H), 1.77-1.80 (m, 4H), 1.41-1.45 (m, 4H), 1.26-1.28 (m, 6H), 1.07 (s, 3H). LCMS: 468.3 [M + H] |
| 91 | 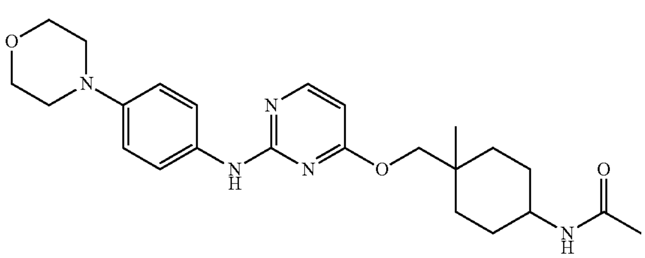 [SMILES: CC(=O)NC1CCC(C)(COc2ccnc(Nc3ccc(N4CCOCC4)cc3)n2)CC1] | N-(4-methyl-4-(((2-((4-morpholinophenyl)amino)pyrimidin-4-yl)oxy)methyl)cyclohexyl)acetamide | (CD₃OD) δ = 7.97 (d, J = 6.8 Hz, 1H), 7.40 (d, J = 8.8 Hz, 2H), 7.12-7.16 (m, 2H), 6.53 (d, J = 6.8 Hz, 1H), 4.47 (s, 2H), 3.85-3.89 (m, 4H), 3.68-3.71 (m, 1H), 3.24-3.27 (m, 4H), 1.94 (s, 3H), 1.77-1.80 (m, 4H), 1.40-1.45 (m, 4H), 1.07 (s, 3H). LCMS: 440.2 [M + H] |

-continued

| Example | Structure | Name | †Spectral data |
|---|---|---|---|
| 92 | 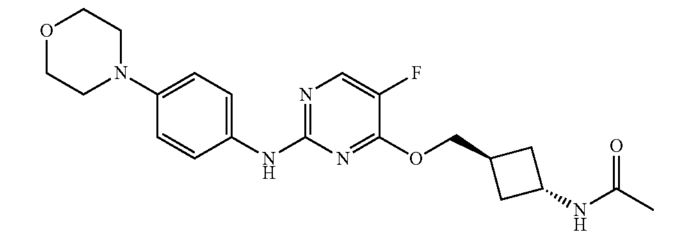 [SMILES: CC(=O)N[C@H]1C[C@H](COc2nc(Nc3ccc(N4CCOCC4)cc3)ncc2F)C1] | N-((1R,3R)-3-(((5-fluoro-2-((4-morpholinophenyl)amino)pyrimidin-4-yl)oxy)methyl)cyclobutyl)acetamide | (CD$_3$OD) δ = 8.15 (d, J = 3.2 Hz, 1H), 7.79 (d, J = 9.2 Hz, 2H), 7.47 (d, J = 9.2 Hz, 2H), 4.58 (d, J = 7.2 Hz, 2H), 4.43-4.47 (m, 1H), 4.03-4.05 (m, 4H), 3.57-3.59 (m, 4H), 2.74-2.79 (m, 1H), 2.19-2.34 (m, 4H), 1.95 (s, 3H). LCMS: 416.0 [M + H] |
| 93 | 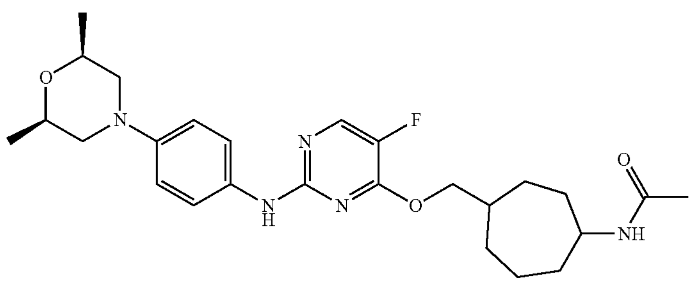 [SMILES: CC(=O)NC1CCCC(COc2nc(Nc3ccc(N4C[C@@H](C)O[C@@H](C)C4)cc3)ncc2F)CC1] | N-(4-(((2-((4-((2S,6R)-2,6-dimethylmorpholino)phenyl)amino)-5-fluoropyrimidin-4-yl)oxy)methyl)cycloheptyl)acetamide | (DMSO-d$_6$) δ = δ 9.36 (bs, 1H), 8.23 (d, J = 3.2 Hz, 1H), 7.75-7.77 (m, 1H), 7.55-7.57 (m, 2H), 4.19 (d, J = 6.4 Hz, 2H), 3.71-3.75 (m, 2H), 3.48-3.50 (m, 2H), 2.31-2.33 (m, 2H), 2.01 (bs, 2H), 1.54-1.87 (m, 10H), 1.31-1.43 (m, 2H), 1.15-1.16 (m, 6H). LCMS: 486.3 [M + H] |
| 94 | 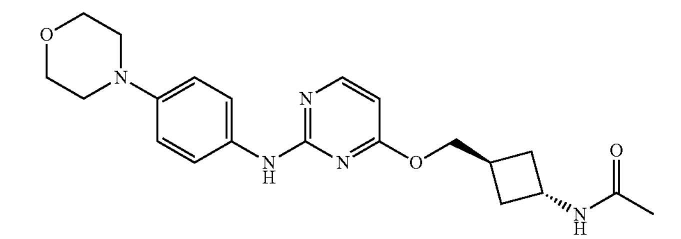 [SMILES: CC(=O)N[C@H]1C[C@H](COc2ccnc(Nc3ccc(N4CCOCC4)cc3)n2)C1] | N-((1R,3R)-3-(((2-((4-morpholinophenyl)amino)pyrimidin-4-yl)oxy)methyl)cyclobutyl)acetamide | (CD$_3$OD) δ = 8.00 (d, J = 7.2 Hz, 1H), 7.44 (d, J = 8.8 Hz, 2H), 7.17-7.21 (m, 2H), 6.50-6.52 (m, 1H), 4.57 (d, J= 7.2 Hz, 2H), 4.40-4.44 (m, 1H), 3.87-3.91 (m, 4H), 3.27-3.30 (m, 4H), 2.71-2.75 (m, 1H), 2.16-2.31 (m, 4H), 1.95 (s, 3H). LCMS: 398.2 [M + H] |
| 178 | 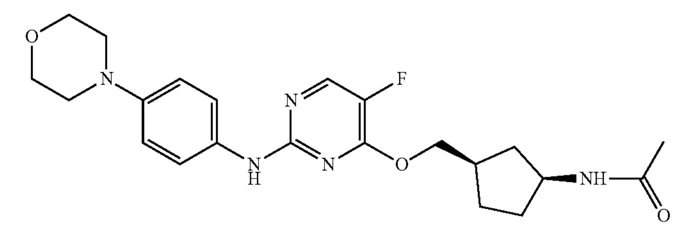 [SMILES: CC(=O)N[C@H]1CC[C@@H](COc2nc(Nc3ccc(N4CCOCC4)cc3)ncc2F)C1] | N-((1S,3R)-3-(((5-fluoro-2-((4-morpholinophenyl)amino)pyrimidin-4-yl)oxy)methyl)cyclopentyl)acetamide | (CD$_3$OD) δ = 8.16 (d, J = 3.2 Hz, 1H), 7.79 (d, J = 9.2 Hz, 2H), 7.49 (d, J = 8.8 Hz, 2H), 4.44-4.46 (m, 2H), 4.14-4.18 (m, 1H), 4.03-4.05 (m, 4H), 3.59 (s, 4H), 2.50-2.54 (m, 1H), 2.25-2.30 (m, 1H), 1.89-2.04 (m, 5H), 1.58-1.65 (m, 2H), 1.27-1.35 (m, 1H). LCMS: 430.2 [M + H] |
| 179 | 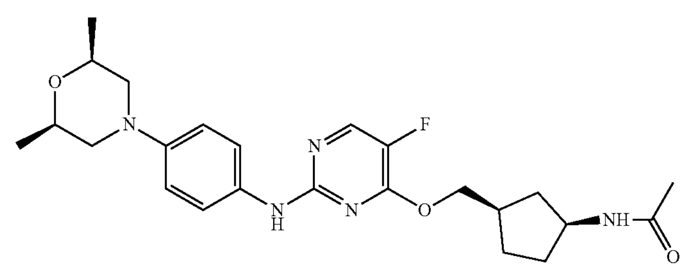 [SMILES: CC(=O)N[C@H]1CC[C@@H](COc2nc(Nc3ccc(N4C[C@@H](C)O[C@@H](C)C4)cc3)ncc2F)C1] | N-((1S,3R)-3-(((2-((4-((2S,6R)-2,6-dimethylmorpholino)phenyl)amino)-5-fluoropyrimidin-4-yl)oxy)methyl)cyclopentyl)acetamide | (CD$_3$OD) δ = 8.13 (d, J = 3.2 Hz, 1H), 7.76 (d, J = 8.8 Hz, 2H), 7.39 (d, J = 8.8 Hz, 2H), 4.43-4.46 (m, 2H), 4.14-4.18 (m, 1H), 3.97-4.01 (m, 2H), 3.59-3.62 (m, 2H), 2.98-3.04 (m, 2H), 2.51-2.55 (m, 1H), 2.26-2.31 (m, 1H), 1.89-2.04 (m, 5H), 1.58-1.66 (m, 2H), 1.30-1.33 (m, 7H). LCMS: 459.0 [M + H] |
| 180 | 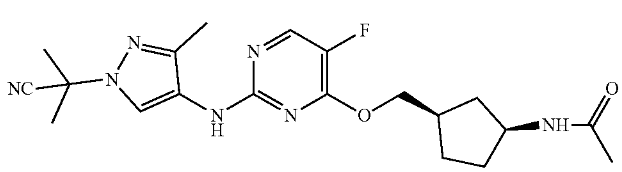 [SMILES: CC(=O)N[C@H]1CC[C@@H](COc2nc(Nc3cn(C(C)(C)C#N)nc3C)ncc2F)C1] | N-((1S,3R)-3-(((2-((1-(2-cyanopropan-2-yl)-3-methyl-1H-pyrazol-4-yl)amino)-5-fluoropyrimidin-4-yl)oxy)methyl)cyclopentyl)acetamide | (CD$_3$OD) δ = 8.10-8.12 (m, 2H), 4.46 (d, J = 6.8 Hz, 2H), 4.14-4.18 (m, 1H), 2.49-2.53 (m, 1H), 2.25-2.31 (m, 4H), 1.87-2.05 (m, 11H), 1.56-1.64 (m, 2H), 1.30-1.33 (m, 1H). LCMS: 416.3 [M + H] |

-continued

| Example | Structure | Name | †Spectral data |
|---|---|---|---|
| 181 | 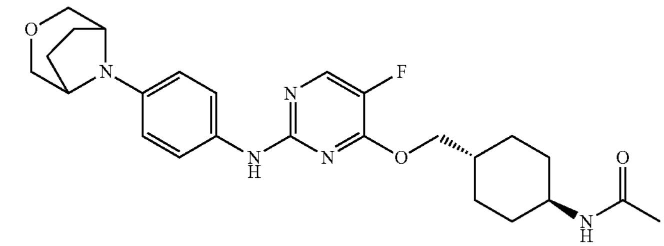 [SMILES: CC(=O)N[C@H]1CC[C@H](COc2nc(Nc3ccc(N4C5CCC4COC5)cc3)ncc2F)CC1] | N-((1R,4R)-4-(((2-((4-(3-oxa-8-azabicyclo[3.2.1]octan-8-yl)phenyl)amino)-5-fluoropyrimidin-4-yl)oxy)methyl)cyclohexyl)acetamide | (CD$_3$OD) δ = 8.08 (s, 1H), 7.61-7.62 (m, 2H), 7.19-7.21 (m, 2H), 4.32-4.34 (m, 4H), 4.02 (bs, 2H), 3.67-3.71 (m, 3H), 3.57-3.59 (m, 2H), 2.17 (bs, 2H), 1.93-1.99 (m, 8H), 1.25-1.31 (m, 4H). LCMS: 470.2 [M + H] |
| 182 | 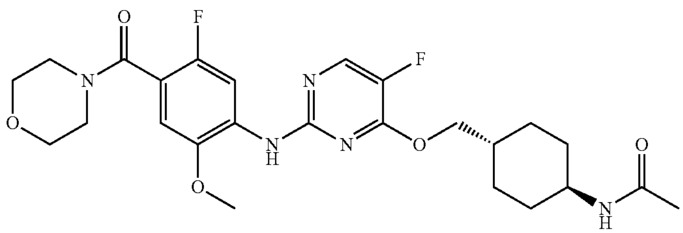 [SMILES: COc1cc(C(=O)N2CCOCC2)c(F)cc1Nc1ncc(F)c(OC[C@H]2CC[C@H](NC(C)=O)CC2)n1] | N-((1R,4R)-4-(((5-fluoro-2-((5-fluoro-2-methoxy-4-(morpholine-4-carbonyl)phenyl)amino)pyrimidin-4-yl)oxy)methyl)cyclohexyl)acetamide | (CD$_3$OD) δ = 8.39 (d, J = 12.4 Hz, 1H), 8.20 (d, J = 3.2 Hz, 1H), 7.00 (d, J = 6.0 Hz, 1H), 4.34 (d, J = 6.8 Hz, 2H), 3.98 (s, 3H), 3.78 (bs, 4H), 3.67-3.68 (m, 4H), 3.46 (bs, 1H), 1.90-2.00 (m, 8H), 1.24-1.31 (m, 4H). LCMS: 520.2 [M + H] |
| 183 | 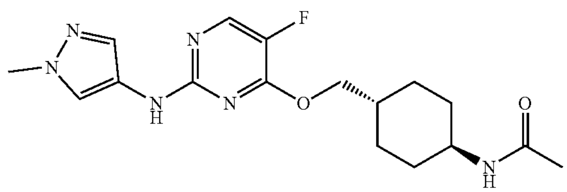 [SMILES: CC(=O)N[C@H]1CC[C@H](COc2nc(Nc3cnn(C)c3)ncc2F)CC1] | N-((1R,4R)-4-(((5-fluoro-2-((1-methyl-1H-pyrazol-4-yl)amino)pyrimidin-4-yl)oxy)methyl)cyclohexyl)acetamide | (CD$_3$OD) δ = 8.10 (d, J = 3.60 Hz, 1H), 7.87 (s, 1H), 7.59 (s, 1H), 4.36 (d, J = 6.40 Hz, 2H), 3.91 (s, 3H), 3.62-3.65 (m, 1H), 1.93-2.00 (m, 8H), 1.24-1.31 (m, 4H). LCMS: 363.2 [M + H] |
| 184 | 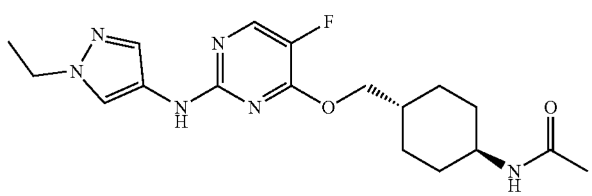 [SMILES: CCn1cc(Nc2ncc(F)c(OC[C@H]3CC[C@H](NC(C)=O)CC3)n2)cn1] | N-((1R,4R)-4-(((2-((1-ethyl-1H-pyrazol-4-yl)amino)-5-fluoropyrimidin-4-yl)oxy)methyl)cyclohexyl)acetamide | (CD$_3$OD) δ = 8.10 (d, J = 2.0 Hz, 1H), 7.91 (s, 1H), 7.60 (s, 1H), 4.35 (d, J = 5.6 Hz, 2H), 4.16-4.22 (m, 2H), 3.62-3.68 (m, 1H), 1.93-1.97 (m, 8H), 1.46-1.50 (m, 3H), 1.24-1.31 (m, 4H). LCMS: 377.3 [M + H] |
| 185 | 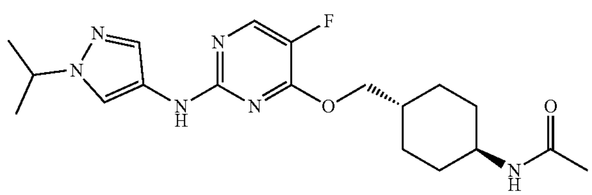 [SMILES: CC(=O)N[C@H]1CC[C@H](COc2nc(Nc3cnn(C(C)C)c3)ncc2F)CC1] | N-((1R,4R)-4-(((5-fluoro-2-((1-isopropyl-1H-pyrazol-4-yl)amino)pyrimidin-4-yl)oxy)methyl)cyclohexyl)acetamide | (CD$_3$OD) δ = 8.09 (d, J = 3.6 Hz, 1H), 7.93 (s, 1H), 7.60 (s, 1H), 4.50-4.53 (m, 1H), 4.35 (d, J = 6.4 Hz, 2H), 3.64-3.64 (m, 1H), 1.86-2.00 (m, 8H), 1.52 (d, J = 6.8 Hz, 6H), 1.23-1.35 (m, 4H). LCMS: 391.3 [M + H] |
| 186 | 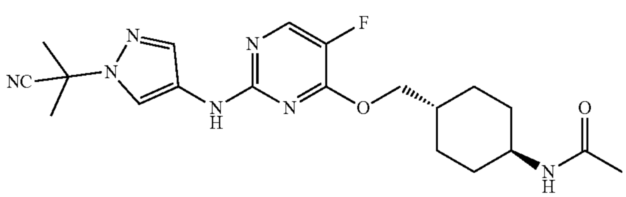 [SMILES: CC(=O)N[C@H]1CC[C@H](COc2nc(Nc3cnn(C(C)(C)C#N)c3)ncc2F)CC1] | N-((1R,4R)-4-(((2-((1-(2-cyanopropan-2-yl)-1H-pyrazol-4-yl)amino)-5-fluoropyrimidin-4-yl)oxy)methyl)cyclohexyl)acetamide | (CD$_3$OD) δ = 8.21 (s, 1H), 8.10 (d, J = 3.2 Hz, 1H), 7.68 (s, 1H), 4.33 (d, J = 6.4 Hz, 2H), 3.64-3.65 (m, 1H), 1.85-2.05 (m, 14H), 1.23-1.31 (m, 4H). LCMS: 416.3 [M + H] |
| 187 | 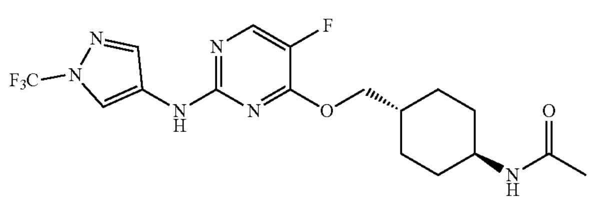 [SMILES: CC(=O)N[C@H]1CC[C@H](COc2nc(Nc3cnn(C(F)(F)F)c3)ncc2F)CC1] | N-((1R,4R)-4-(((5-fluoro-2-((1-(trifluoromethyl)-1H-pyrazol-4-yl)amino)pyrimidin-4-yl)oxy)methyl)cyclohexyl)acetamide | (CD$_3$OD) δ = 8.38 (s, 1H), 8.13 (d, J = 3.2 Hz, 1H), 7.88 (s, 1H), 4.30 (d, J = 6.4 Hz, 2H), 3.61-3.68 (m, 1H), 1.74-2.09 (m, 8H), 1.20-1.33 (m, 4H). LCMS: 417.2 [M + H] |

| Example | Name | †Spectral data |
|---|---|---|
| 188 | N-((1R,4R)-4-(((5-fluoro-2-((1-(2,2,2-trifluoroethyl)-1H-pyrazol-4-yl)amino)pyrimidin-4-yl)oxy)methyl)cyclohexyl)acetamide | (CD$_3$OD) δ = 8.06-8.08 (m, 2H), 7.65 (s, 1H), 4.90-4.96 (m, 2H), 4.30 (d, J = 6.4 Hz, 2H), 3.64-3.66 (m, 1H), 1.74-1.93 (m, 8H), 1.20-1.33 (m, 4H). LCMS: 431.2 [M + H] |
| 189 | N-((1R,4R)-4-(((5-fluoro-2-((1-(2-fluoroethyl)-1H-pyrazol-4-yl)amino)pyrimidin-4-yl)oxy)methyl)cyclohexyl)acetamide | (CD$_3$OD) δ = 8.04 (d, J = 2.8 Hz, 1H), 7.97 (s, 1H), 7.59 (s, 1H), 4.80 (t, J = 4.8 Hz, 1H), 4.68 (t, J = 4.4 Hz, 1H), 4.44 (t, J = 4.4 Hz, 1H), 4.38 (t, J = 4.4 Hz, 1H), 4.29 (d, J = 6.4 Hz, 2H), 3.62-3.64 (m, 1H), 1.85-1.99 (m, 8H), 1.19-1.34 (m, 4H). LCMS: 395.2 [M + H] |
| 190 | N-((1R,4R)-4-(((5-fluoro-2-((1-(2-hydroxyethyl)-1H-pyrazol-4-yl)amino)pyrimidin-4-yl)oxy)methyl)cyclohexyl)acetamide | (CD$_3$OD) δ = 8.03 (d, J = 3.2 Hz, 1H), 7.96 (s, 1H), 7.57 (s, 1H), 4.30 (d, J = 6.4 Hz, 2H), 4.18-4.21 (m, 2H), 3.88-3.90 (m, 2H), 3.64-3.65 (m, 1H), 1.86-2.00 (m, 8H), 1.23-1.31 (m, 4H). LCMS: 393.3 [M + H] |
| 191 | N-((1R,4R)-4-(((5-fluoro-2-((1-(2-methoxyethyl)-1H-pyrazol-4-yl)amino)pyrimidin-4-yl)oxy)methyl)cyclohexyl)acetamide | (CD$_3$OD) δ = 8.10 (d, J = 3.6 Hz, 1H), 7.94 (s, 1H), 7.61 (s, 1H), 4.29-4.37 (m, 4H), 3.67-3.77 (m, 3H), 3.35 (s, 3H), 1.88-2.00 (m, 8H), 1.21-1.35 (m, 4H). LCMS: 407.3 [M + H] |
| 192 | N-((1R,4R)-4-(((5-fluoro-2-((1-(oxetan-3-yl)-1H-pyrazol-4-yl)amino)pyrimidin-4-yl)oxy)methyl)cyclohexyl)acetamide | (CD$_3$OD) δ = 8.10 (s, 1H), 8.09 (s, 1H), 7.70 (s, 1H), 5.52-5.58 (m, 1H), 5.01-5.10 (m, 4H), 4.35 (d, J = 6.4 Hz, 2H), 3.35 (s, 1H), 1.93-2.00 (m, 8H), 1.26-1.32 (m, 4H). LCMS: 405.3 [M + H] |
| 193 | N-((1R,4R)-4-(((5-fluoro-2-((1-(tetrahydro-2H-pyran-4-yl)-1H-pyrazol-4-yl)amino)pyrimidin-4-yl)oxy)methyl)cyclohexyl)acetamide | (CD$_3$OD) δ = 8.04 (d, J = 3.6 Hz, 1H), 7.97 (s, 1H), 7.58 (s, 1H), 4.27-4.37 (m, 3H), 4.06-4.10 (m, 2H), 3.56-3.62 (m, 3H), 2.04-2.10 (m, 4H), 1.93-2.00 (m, 8H), 1.23-1.31 (m, 4H). LCMS: 433.2 [M + H] |
| 194 | N-((1R,4R)-4-(((2-((1,3-dimethyl-1H-pyrazol-4-yl)amino)-5-fluoropyrimidin-4-yl)oxy)methyl)cyclohexyl)acetamide | (CD$_3$OD) δ = 8.07 (d, J = 3.6 Hz, 1H), 7.79 (s, 1H), 4.36 (d, J = 6.0 Hz, 2H), 3.86 (s, 3H), 3.61-3.69 (m, 1H), 2.19 (s, 3H), 1.92-2.00 (m, 8H), 1.23-1.34 (m, 4H). LCMS: 377.3 [M + H] |

| Example | Name | †Spectral data |
|---|---|---|
| 195 | N-((1R,4R)-4-(((5-fluoro-2-((1-isopropyl-3-methyl-1H-pyrazol-4-yl)amino)pyrimidin-4-yl)oxy)methyl)cyclohexyl)acetamide | (CD$_3$OD) δ = 8.05 (d, J = 3.6 Hz, 1H), 7.85 (s, 1H), 4.43-4.48 (m, 1H), 4.34 (d, J = 6.4 Hz, 2H), 3.61-3.66 (m, 1H), 2.21 (s, 3H), 1.89-2.00 (m, 8H), 1.51 (d, J = 6.4 Hz, 6H), 1.22-1.33 (m, 4H). LCMS: 405.2 [M + H] |
| 196 | N-((1R,4R)-4-(((2-((1-cyclopropyl-3-methyl-1H-pyrazol-4-yl)amino)-5-fluoropyrimidin-4-yl)oxy)methyl)cyclohexyl)acetamide | (CD$_3$OD) δ = 8.07 (d, J = 3.6 Hz, 1H), 7.87 (s, 1H), 4.35 (d, J = 6.4 Hz, 2H), 3.59-3.64 (m, 2H), 2.19 (s, 3H), 1.94-2.00 (m, 8H), 1.22-1.31 (m, 4H), 1.05-1.10 (m, 4H). LCMS: 403.6 [M + H] |
| 197 | N-((1R,4R)-4-(((2-((1-(difluoromethyl)-3-methyl-1H-pyrazol-4-yl)amino)-5-fluoropyrimidin-4-yl)oxy)methyl)cyclohexyl)acetamide | (CD$_3$OD) δ = 8.28 (s, 1H), 8.09 (d, J = 3.2 Hz, 1H), 7.34 (t, J = 60.0 Hz, 1H), 4.29-4.31 (m, 2H), 3.63-3.64 (m, 1H), 2.29 (s, 3H), 1.84-2.05 (m, 8H), 1.21-1.30 (m, 4H). LCMS: 413.2 [M + H] |
| 198 | N-((1R,4R)-4-(((2-((3-ethyl-1-methyl-1H-pyrazol-4-yl)amino)-5-fluoropyrimidin-4-yl)oxy)methyl)cyclohexyl)acetamide | (CD$_3$OD) δ = 7.96 (d, J = 3.2 Hz, 1H), 7.71 (s, 1H), 4.24 (d, J = 6.4 Hz, 2H), 3.83 (s, 3H), 3.60-3.66 (m, 1H), 2.61 (t, J = 7.6 Hz, 2H), 1.80-1.99 (m, 8H), 1.16-1.32 (m, 7H). LCMS: 391.2 [M + H] |
| 199 | N-((1R,4R)-4-(((2-((1-(2-cyanopropan-2-yl)-5-methyl-1H-pyrazol-4-yl)amino)-5-fluoropyrimidin-4-yl)oxy)methyl)cyclohexyl)acetamide | (CD$_3$OD) δ = 8.09-8.11 (m, 2H), 4.34 (d, J = 6.4 Hz, 2H), 3.61-3.66 (m, 1H), 2.25 (s, 3H), 1.84-2.05 (m, 14H), 1.19-1.34 (m, 4H). LCMS: 430.3 [M + H] |
| 200 | N-((1R,4R)-4-(((2-((1-(difluoromethyl)-5-methyl-1H-pyrazol-4-yl)amino)-5-fluoropyrimidin-4-yl)oxy)methyl)cyclohexyl)acetamide | (CD$_3$OD) δ = 8.05 (d, J = 3.6 Hz, 1H), 7.81 (s, 1H), 7.47 (t, J = 58.4 Hz, 1H), 4.27-4.29 (m, 2H), 3.60-3.66 (m, 1H), 2.41 (s, 3H), 1.83-2.06 (m, 8H), 1.20-1.33 (m, 4H). LCMS: 413.2 [M + H] |
| 201 | N-((1R,4R)-4-(((2-((3-chloro-1-methyl-1H-pyrazol-4-yl)amino)-5-fluoropyrimidin-4-yl)oxy)methyl)cyclohexyl)acetamide | (CD$_3$OD) δ = 8.08 (d, J = 3.6 Hz, 1H), 7.91 (s, 1H), 4.31 (d, J = 6.4 Hz, 2H), 3.87 (s, 3H), 3.63-3.65 (m, 1H), 1.84-1.99 (m, 8H), 1.22-1.30 (m, 4H). LCMS: 397.2 [M + H] |

| Example | Structure | Name | †Spectral data |
|---|---|---|---|
| 202 | 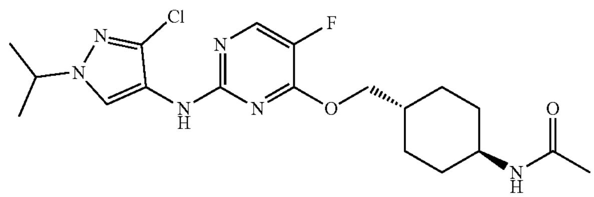 [SMILES: CC(=O)N[C@H]1CC[C@H](COc2nc(Nc3cn(C(C)C)nc3Cl)ncc2F)CC1] | N-((1R,4R)-4-(((2-((3-chloro-1-isopropyl-1H-pyrazol-4-yl)amino)-5-fluoropyrimidin-4-yl)oxy)methyl)cyclohexyl)acetamide | (CD$_3$OD) δ = 8.09 (d, J = 3.6 Hz, 1H), 7.97 (s, 1H), 4.46-4.49 (m, 1H), 4.32 (d, J = 6.4 Hz, 2H), 3.62-3.63 (m, 1H), 1.86-1.99 (m, 8H), 1.50-1.54 (m, 6H), 1.21-1.31 (m, 4H). LCMS: 425.6 [M + H] |
| 203 | 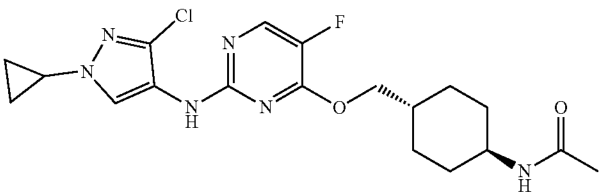 [SMILES: CC(=O)N[C@H]1CC[C@H](COc2nc(Nc3cn(C4CC4)nc3Cl)ncc2F)CC1] | N-((1R,4R)-4-(((2-((3-chloro-1-cyclopropyl-1H-pyrazol-4-yl)amino)-5-fluoropyrimidin-4-yl)oxy)methyl)cyclohexyl)acetamide | (CD$_3$OD) δ = 8.07 (d, J = 3.2 Hz, 1H), 8.00 (s, 1H), 4.30 (d, J = 6.8 Hz, 2H), 3.62-3.68 (m, 2H), 1.85-1.99 (m, 8H), 1.10-1.34 (m, 8H). LCMS: 423.2 [M + H] |
| 204 | 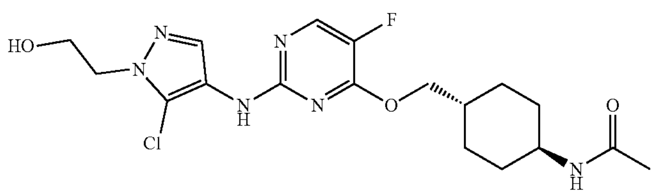 [SMILES: CC(=O)N[C@H]1CC[C@H](COc2nc(Nc3cnn(CCO)c3Cl)ncc2F)CC1] | N-((1R,4R)-4-(((2-((5-chloro-1-(2-hydroxyethyl)-1H-pyrazol-4-yl)amino)-5-fluoropyrimidin-4-yl)oxy)methyl)cyclohexyl)acetamide | (CD$_3$OD) δ = 8.05 (d, J = 3.6 Hz, 1H), 7.78 (s, 1H), 4.27-4.31 (m, 4H), 3.93 (d, J = 10.8 Hz, 2H), 3.62-3.63 (m, 1H), 1.91-1.97 (m, 8H), 1.21-1.30 (m, 4H). LCMS: 427.2 [M + H] |
| 205 | 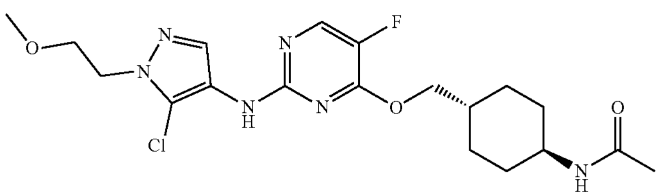 [SMILES: COCCn1ncc(Nc2ncc(F)c(OC[C@H]3CC[C@H](NC(C)=O)CC3)n2)c1Cl] | N-((1R,4R)-4-(((2-((5-chloro-1-(2-methoxyethyl)-1H-pyrazol-4-yl)amino)-5-fluoropyrimidin-4-yl)oxy)methyl)cyclohexyl)acetamide | (CD$_3$OD) δ = 7.99 (d, J = 3.2 Hz, 1H), 7.81 (s, 1H), 4.31-4.63 (m, 2H), 4.22 (d, J = 6.4 Hz, 2H), 3.77 (t, J = 10.8 Hz, 2H), 3.60-3.65 (m, 1H), 3.32 (s, 3H), 1.79-1.98 (m, 8H), 1.18-1.29 (m, 4H). LCMS: 441.2 [M + H] |
| 206 | 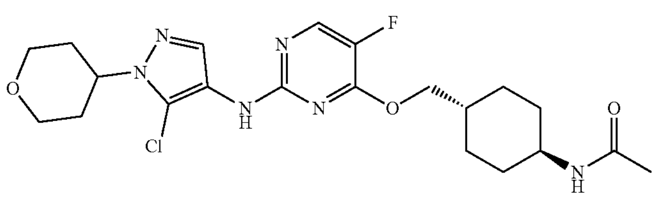 [SMILES: CC(=O)N[C@H]1CC[C@H](COc2nc(Nc3cnn(C4CCOCC4)c3Cl)ncc2F)CC1] | N-((1R,4R)-4-(((2-((5-chloro-1-(tetrahydro-2H-pyran-4-yl)-1H-pyrazol-4-yl)amino)-5-fluoropyrimidin-4-yl)oxy)methyl)cyclohexyl)acetamide | (CD$_3$OD) δ = 7.99 (d, J = 3.2 Hz, 1H), 7.81 (s, 1H), 4.57-4.61 (m, 1H), 4.23 (d, J = 6.8 Hz, 2H), 4.08-4.12 (m, 2H), 3.58-3.65 (m, 3H), 2.17-2.23 (m, 2H), 1.89-1.98 (m, 10H), 1.18-1.31 (m, 4H). LCMS: 467.3 [M + H] |
| 207 | 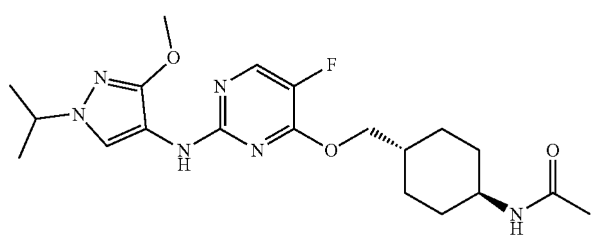 [SMILES: COc1nn(C(C)C)cc1Nc1ncc(F)c(OC[C@H]2CC[C@H](NC(C)=O)CC2)n1] | N-((1R,4R)-4-(((5-fluoro-2-((1-isopropyl-3-methoxy-1H-pyrazol-4-yl)amino)pyrimidin-4-yl)oxy)methyl)cyclohexyl)acetamide | (CD$_3$OD) δ = 8.07 (d, J = 4.0 Hz, 1H), 7.72 (s, 1H), 4.32-4.38 (m, 3H), 3.93 (s, 3H), 3.62-3.67 (m, 1H), 1.87-2.00 (m, 8H), 1.45-1.49 (m, 6H), 1.28-1.31 (m, 4H). LCMS: 421.3 [M + H] |
| 208 | 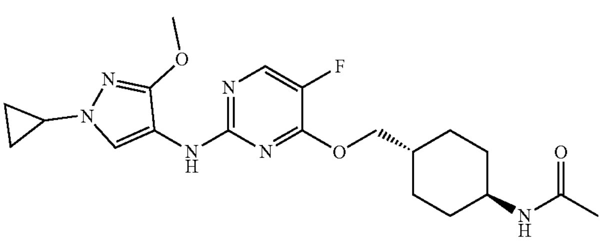 [SMILES: COc1nn(C2CC2)cc1Nc1ncc(F)c(OC[C@H]2CC[C@H](NC(C)=O)CC2)n1] | N-((1R,4R)-4-(((2-((1-cyclopropyl-3-methoxy-1H-pyrazol-4-yl)amino)-5-fluoropyrimidin-4-yl)oxy)methyl)cyclohexyl)acetamide | (DMSO-d$_6$) δ = 8.41 (bs, 1H), 8.14 (d, J = 3.2 Hz, 1H), 7.72 (d, J = 7.6 Hz, 1H), 7.68 (s, 1H), 4.16 (d, J = 6.4 Hz, 2H), 3.79 (s, 3H), 3.45-3.50 (m, 2H), 1.77-1.83 (m, 8H), 1.03-1.24 (m, 4H), 0.93-0.96 (m, 4H). LCMS: 419.3 [M + H] |

†All $^1$H NMR recorded at 400 MHz

Synthetic Scheme 6 for the Synthesis of Example 97

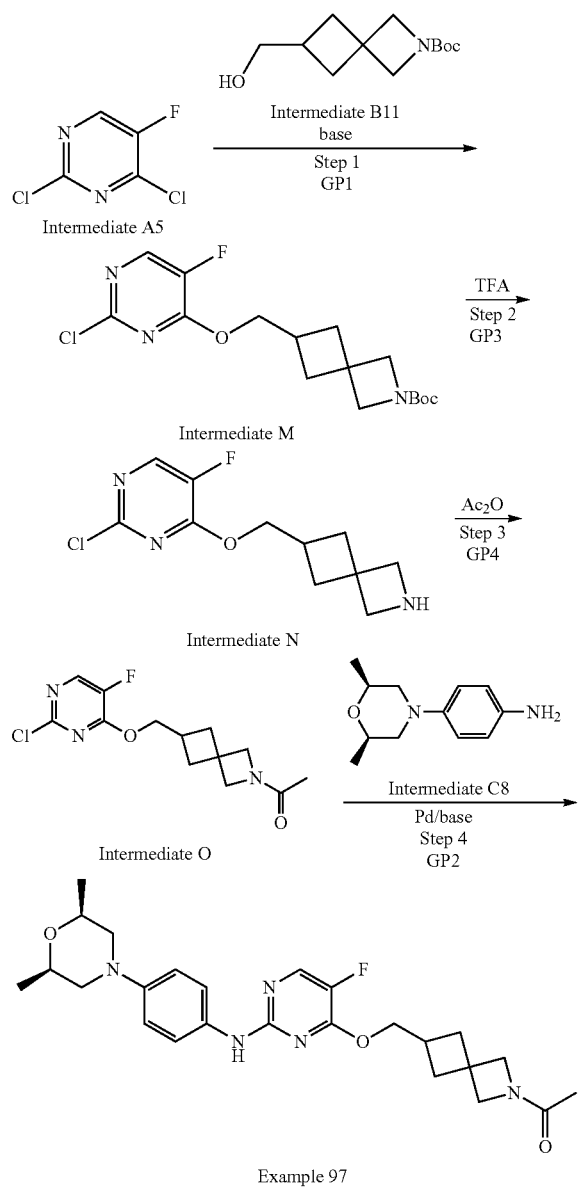

Step 1: Synthesis of Intermediate M

Intermediate M was synthesized by following General Procedure GP1 described above.

Step 2: Synthesis of Intermediate N

Intermediate N was synthesized by following General Procedure GP3 described above. The crude material was purified by flash chromatography.

Step 3: Synthesis of Intermediate O

Intermediate O was synthesized by following General Procedure GP4 described above.

Step 4: Synthesis of Example 97

1-(6-(((2-((4-((2S,6R)-2,6-dimethylmorpholino)phenyl)amino)-5-fluoropyrimidin-4-yl)oxy)methyl)-2-azaspiro[3.3]heptan-2-yl)ethan-1-one (Example 97) was synthesized by following General Procedure GP2 described above and was purified by preparative HPLC. 1H NMR (400 MHz, CD$_3$OD) δ=δ 8.11 (d, J=2.0 Hz, 1H), 7.72 (d, J=8.8 Hz, 2H), 7.34-7.37 (m, 2H), 4.43-4.44 (m, 2H), 4.25 (s, 1H), 4.17 (s, 1H), 3.93-4.01 (m, 4H), 3.56-3.59 (m, 2H), 2.88-2.95 (m, 2H), 2.72-2.75 (m, 1H), 2.42-2.47 (m, 2H), 2.14-2.40 (m, 2H), 1.85-1.86 (m, 3H), 1.24-1.29 (m, 6H). LCMS: 470.2 [M+H]

General Synthetic Scheme 7 for the Synthesis of Examples 98-108 and 209-213

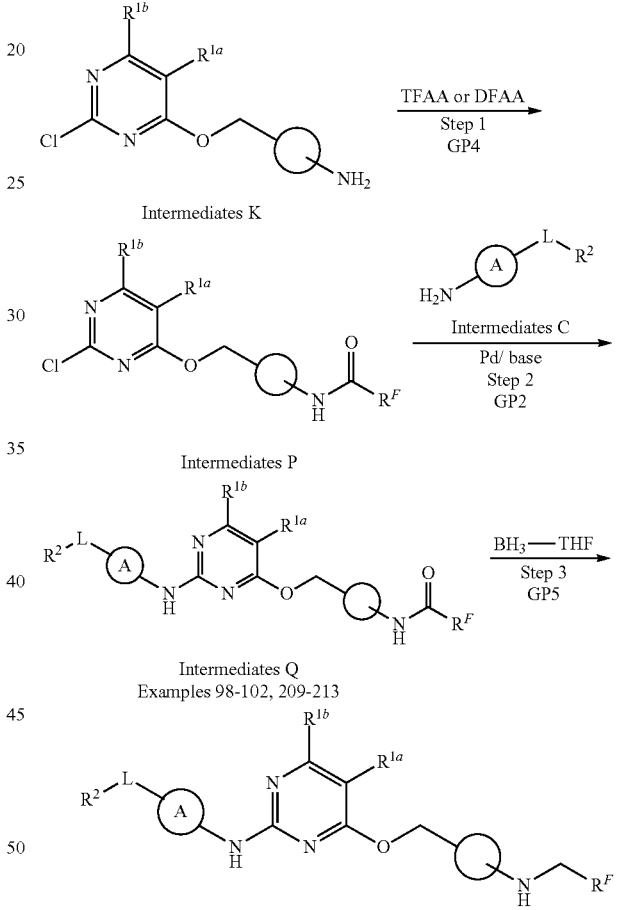

wherein R$^F$ is CF$_3$ or CHF$_2$.

Step 1: Synthesis of Intermediates P

Intermediates P were synthesized by following a modified General Procedure GP4 described above where acetic anhydride is replaced by trifluoroacetic anhydride (if R$^F$ is CF$_3$) or difluoroacetic anhydride (if R$^F$ is CHF$_2$).

Step 2: Synthesis of Intermediates Q (Including Examples 98-102 and 209-213)

Intermediates Q (Including Examples 98-102 and 209-213) were synthesized by following General Procedure GP2 described above. Crude materials were purified by preparative HPLC in the case of Examples 98-102 and 209-213.

Step 3: General Procedure GP5 (Amide Reduction) for the Synthesis of Examples 103-108

Borane-tetrahydrofuran complex (1M in THF, 1.0 eq.) was added dropwise to a solution of amide (Examples 98-102, 1.0 eq.) in THF (10 vol.) at 0° C. and the resulting mixture was stirred at 25° C. for 2 h. Following completion of the reaction (as indicated by TLC), the reaction mixture was quenched with saturated $NH_4Cl$ and extracted twice with EtOAc. The combined organic extracts were dried over $Na_2SO_4$, filtered, and concentrated under reduced pressure to give crude material which was purified by preparative HPLC, affording Examples 99 to 106.

The following examples were synthesized following General Synthetic Scheme 7:

| Example | Structure | Name | †Spectral data |
|---|---|---|---|
| 98 | 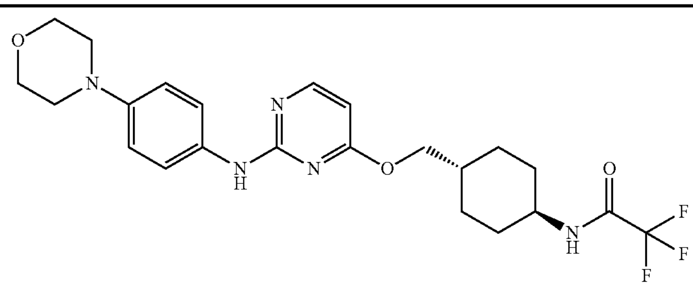 | 2,2,2-trifluoro-N-((1R,4R)-4-(((2-((4-morpholino-phenyl)amino)pyrimidin-4-yl)oxy)methyl)cyclohexyl)acetamide | (CD$_3$OD) δ = 7.96 (d, J = 6.4 Hz, 1H), 7.38 (d, J = 8.8 Hz, 2H), 7.13 (d, J = 9.2 Hz, 2H), 6.49 (d, J = 7.2 Hz, 1H), 4.34 (d, J = 6.4 Hz, 2H), 3.87-3.89 (m, 4H), 3.70-3.77 (m, 1H), 3.23-3.25 (m, 4H), 1.82-2.00 (m, 5H), 1.39-1.48 (m, 2H), 1.21-1.30 (m, 2H). LCMS: 480.2 [M + H] |
| 99 | 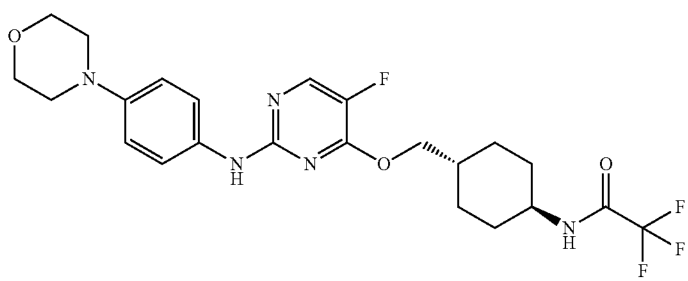 [SMILES: O=C(N[C@H]1CC[C@H](COc2nc(Nc3ccc(N4CCOCC4)cc3)ncc2F)CC1)C(F)(F)F] | 2,2,2-trifluoro-N-((1R,4R)-4-(((5-fluoro-2-((4-morpholino-phenyl)amino)pyrimidin-4-yl)oxy)methyl)cyclohexyl)acetamide | (DMSO-d$_6$) δ = 9.41 (bs, 1H), 9.32 (d, J = 8.0 Hz, 1H), 8.24 (d, J = 3.2 Hz, 1H), 7.59 (d, J = 9.2 Hz, 2H), 6.99-7.01 (m, 2H), 4.23 (d, J = 6.4 Hz, 2H), 3.76-3.79 (m, 4H), 3.62-3.65 (m, 1H), 3.12 (bs, 4H), 1.79-1.87 (m, 5H), 1.34-1.42 (m, 2H), 1.15-1.20 (m, 2H). LCMS: 498.1 [M + H] |
| 100 | 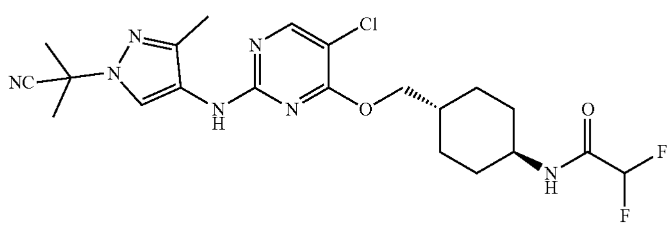 [SMILES: Cc1nn(C(C)(C)C#N)cc1Nc1ncc(Cl)c(OC[C@H]2CC[C@H](NC(=O)C(F)F)CC2)n1] | N-((1R,4R)-4-(((5-chloro-2-((1-(2-cyano-propan-2-yl)-3-methyl-1H-pyrazol-4-yl)amino)pyrimidin-4-yl)oxy)methyl)cyclohexyl)-2,2-difluoro-acetamide | (CD$_3$OD) δ = 8.12 (s, 1H), 8.10 (s, 1H), 5.87-6.14 (m, 1H), 4.27 (d, J = 6.4 Hz, 2H), 3.71-3.77 (m, 1H), 2.25 (s, 3H), 1.82-2.01 (m, 11H), 1.31-1.46 (m, 4H). LCMS: 482.2 [M + H] |
| 101 | 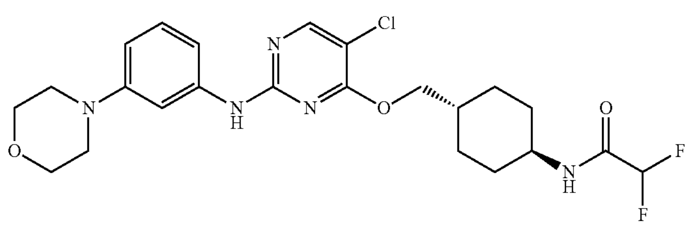 [SMILES: O=C(N[C@H]1CC[C@H](COc2nc(Nc3cccc(N4CCOCC4)c3)ncc2Cl)CC1)C(F)F] | N-((1R,4R)-4-(((5-chloro-2-((3-morpholino-phenyl)amino)pyrimidin-4-yl)oxy)methyl)cyclohexyl)-2,2-difluoro-acetamide | (CD$_3$OD) δ = 8.14 (s, 1H), 7.37-7.38 (m, 1H), 7.11-7.21 (m, 2H), 6.66-6.69 (m, 1H), 5.87-6.14 (m, 1H), 4.31 (d, J = 6.4 Hz, 2H), 3.84-3.87 (m, 4H), 3.15-3.17 (m, 4H), 1.85-2.25 (m, 5H), 1.22-1.46 (m, 5H). LCMS: 495.9 [M + H] |
| 102 | 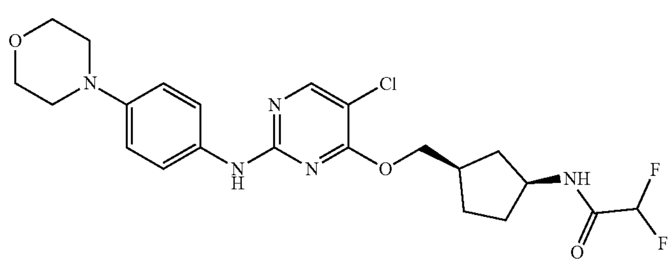 [SMILES: O=C(N[C@H]1CC[C@@H](COc2nc(Nc3ccc(N4CCOCC4)cc3)ncc2Cl)C1)C(F)F] | N-((1S,3R)-3-(((5-chloro-2-((4-morpholino-phenyl)amino)pyrimidin-4-yl)oxy)methyl)cyclopentyl)-2,2-difluoro-acetamide | (DMSO-d$_6$) δ = 9.47 (bs, 1H), 8.82 (d, J = 7.2 Hz, 1H), 8.24 (s, 1H), 7.52-7.55 (m, 2H), 6.90 (d, J = 9.2 Hz, 2H), 6.03-6.30 (m, 1H), 4.32-4.34 (m, 2H), 4.10-4.12 (m, 1H), 3.72-3.75 (m, 4H), 3.02-3.05 (m, 4H), 2.41-2.43 (m, 1H), 2.13-2.16 (m, 1H), 1.90-1.91 (m, 1H), 1.77-1.80 (m, 1H), 1.53-1.61 (m, 2H), 1.31-1.36 (m, 1H). LCMS: 482.0 |

| Example | Structure | Name | †Spectral data |
|---|---|---|---|
| | | | [M + H] |
| 103 | 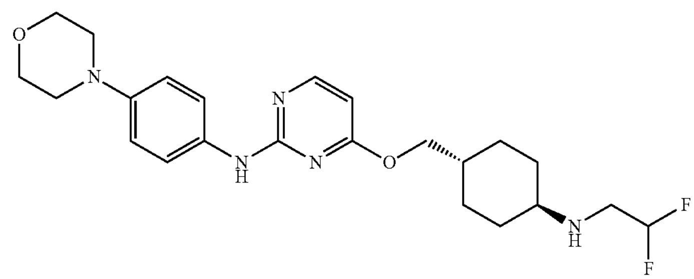 [SMILES: FC(F)CN[C@H]1CC[C@H](COc2ccnc(Nc3ccc(N4CCOCC4)cc3)n2)CC1] | 4-(((1R,4R)-4-((2,2-difluoro-ethyl)amino)cyclohexyl)methoxy)-N-(4-morpholinophenyl)pyrimidin-2-amine | (DMSO-$d_6$) δ = 9.21 (bs, 1H), 8.11 (s, 1H), 7.56 (d, J = 7.6 Hz, 2H), 6.86 (d, J = 7.2 Hz, 2H), 6.13 (m, 1H), 5.73-5.92 (m, 1H), 4.10 (d, J = 6.4 Hz, 2H), 3.72-3.74 (m, 4H), 3.56-3.58 (m, 2H), 2.83-3.03 (m, 6H), 1.69-1.92 (m, 4H), 0.97-1.05 (m, 4H). LCMS: 448.0 [M + H] |
| 209 | 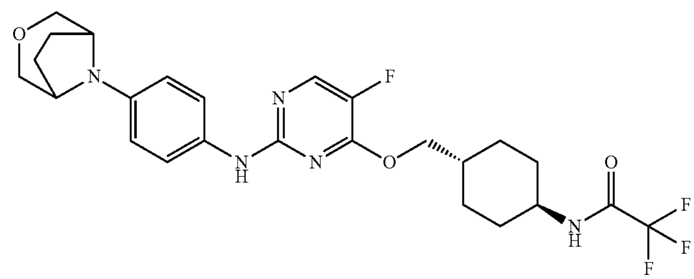 [SMILES: O=C(N[C@H]1CC[C@H](COc2nc(Nc3ccc(N4C5CCC4COC5)cc3)ncc2F)CC1)C(F)(F)F] | N-((1R,4R)-4-(((2-((4-(3-oxa-8-aza-bicyclo[3.2.1]octan-8-yl)phenyl)amino)-5-fluoro-pyrimidin-4-yl)oxy)methyl)cyclohexyl)-2,2,2-trifluoro-acetamide | (CD$_3$OD) δ = 8.07 (s, 1H), 7.52-7.59 (m, 2H), 7.07-7.14 (m, 2H), 4.27-4.33 (m, 4H), 3.98-4.00 (m, 2H), 3.68-3.78 (m, 3H), 1.88-2.15 (m, 9H), 1.39-1.45 (m, 2H), 1.24-1.31 (m, 2H). LCMS: 524.3 [M + H] |
| 210 | 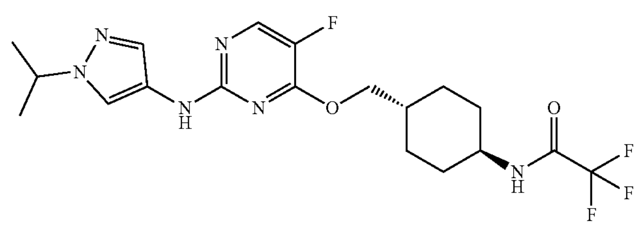 [SMILES: CC(C)n1cc(Nc2ncc(F)c(OC[C@H]3CC[C@H](NC(=O)C(F)(F)F)CC3)n2)cn1] | 2,2,2-trifluoro-N-((1R,4R)-4-(((5-fluoro-2-((1-isopropyl-1H-pyrazol-4-yl)amino)pyrimidin-4-yl)oxy)methyl)cyclohexyl)acetamide | (CD$_3$OD) δ = 8.09 (d, J = 3.6 Hz, 1H), 7.93 (s, 1H), 7.60 (s, 1H), 4.49-4.55 (m, 1H), 4.36 (d, J = 6.4 Hz, 2H), 3.72-3.79 (m, 1H), 1.91-2.01 (m, 5H), 1.52 (d, J = 6.4 Hz, 6H), 1.40-1.50 (m, 2H), 1.26-1.32 (m, 2H). LCMS: 445.2 [M + H] |
| 211 | 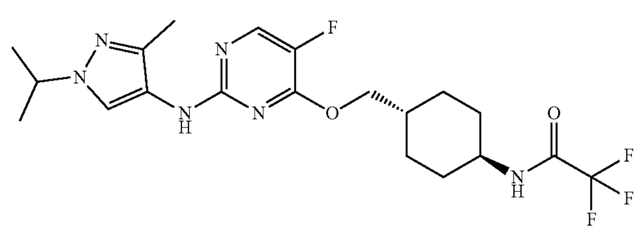 [SMILES: Cc1nn(C(C)C)cc1Nc1ncc(F)c(OC[C@H]2CC[C@H](NC(=O)C(F)(F)F)CC2)n1] | 2,2,2-trifluoro-N-((1R,4R)-4-(((5-fluoro-2-((1-isopropyl-3-methyl-1H-pyrazol-4-yl)amino)pyrimidin-4-yl)oxy)methyl)cyclohexyl)acetamide | (CD$_3$OD) δ = 8.07 (d, J = 3.6 Hz, 1H), 7.86 (s, 1H), 4.44-4.50 (m, 1H), 4.35 (d, J = 6.0 Hz, 2H), 3.72-3.78 (m, 1H), 2.21 (s, 3H), 1.88-2.01 (m, 5H), 1.51 (d, J = 6.8 Hz, 6H), 1.40-1.46 (m, 2H), 1.22-1.31 (m, 2H). LCMS: 459.3 [M + H] |
| 212 | 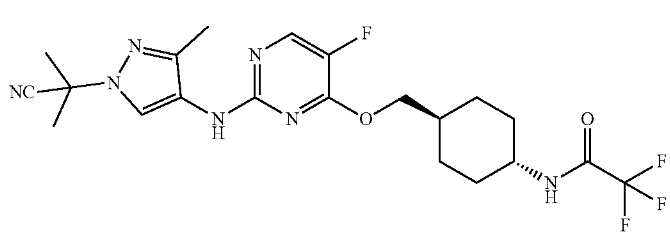 [SMILES: Cc1nn(C(C)(C)C#N)cc1Nc1ncc(F)c(OC[C@H]2CC[C@H](NC(=O)C(F)(F)F)CC2)n1] | N-((1R,4R)-4-(((2-((1-(2-cyanopropan-2-yl)-3-methyl-1H-pyrazol-4-yl)amino)-5-fluoro-pyrimidin-4-yl)oxy)methyl)cyclohexyl)-2,2,2-trifluoro-acetamide | (CD$_3$OD) δ = 8.11 (s, 1H), 8.08 (d, J = 3.6 Hz, 1H), 4.33 (d, J = 6.4 Hz, 2H), 3.72-3.77 (m, 1H), 2.25 (s, 3H), 1.84-2.00 (m, 11H), 1.39-1.49 (m, 2H), 1.24-1.27 (m, 2H). LCMS: 484.1 [M + H] |

| Example | Name | †Spectral data |
|---|---|---|
| 213 | 2,2,2-trifluoro-N-((1R,4R)-4-(((5-fluoro-2-((1-isopropyl-3-methoxy-1H-pyrazol-4-yl)amino)pyrimidin-4-yl)oxy)methyl)cyclohexyl)acetamide | (CD$_3$OD) δ = 8.00 (d, J = 3.6 Hz, 1H), 7.69 (s, 1H), 4.29-4.35 (m, 3H), 3.93 (s, 3H), 3.71-3.77 (m, 1H), 1.86-2.04 (m, 5H), 1.47 (d, J = 6.8 Hz, 6H), 1.40-1.46 (m, 2H), 1.22-1.31 (m, 2H). LCMS: 475.2 [M + H] |
| 104 | N-(4-morpholinophenyl)-4-(((1R,4R)-4-((2,2,2-trifluoroethyl)amino)cyclohexyl)methoxy)pyrimidin-2-amine | (DMSO-d$_6$) δ = 9.23 (s, 1H), 8.13 (d, J = 5.6 Hz, 1H), 7.57-7.59 (m, 2H), 6.87-6.89 (m, 2H), 6.18 (d, J = 5.6 Hz, 1H), 4.12 (d, J = 6.4 Hz, 2H), 3.73-3.75 (m, 4H), 3.21-3.24 (m, 2H), 3.02-3.04 (m, 4H), 2.36-2.38 (m, 1H), 2.15-2.18 (m, 1H), 1.71-1.94 (m, 5H), 1.00-1.06 (m, 4H). LCMS: 466.0 [M + H] |
| 105 | 5-methoxy-N-(4-morpholinophenyl)-4-(((1R,4R)-4-((2,2,2-trifluoroethyl)amino)cyclohexyl)methoxy)pyrimidin-2-amine | (DMSO-d$_6$) δ = 8.96 (bs, 1H), 7.92 (s, 1H), 7.56 (d, J = 8.8 Hz, 2H), 6.85-6.87 (m, 2H), 4.16 (d, J = 6.4 Hz, 2H), 3.72-3.74 (m, 7H), 3.23-3.25 (m, 2H), 3.00-3.02 (m, 4H), 2.40-2.42 (m, 2H), 1.80-1.94 (m, 4H), 1.01-1.07 (m, 4H). LCMS: 496.0 [M + H] |
| 106 | 5-chloro-4-(((1R,4R)-4-((2,2-difluoroethyl)amino)cyclohexyl)methoxy)-N-(4-morpholinophenyl)pyrimidin-2-amine | (CD$_3$OD) δ = 8.08 (s, 1H), 7.48-7.52 (m, 2H), 6.95-6.99 (m, 2H), 5.76-6.06 (m, 1H), 4.26 (d, J = 6.4 Hz, 2H), 3.84-3.87 (m, 4H), 3.10-3.12 (m, 4H), 2.95-3.04 (m, 2H), 2.51-2.53 (m, 1H), 1.85-2.06 (m, 5H), 1.15-1.21 (m, 4H). LCMS: 481.9 [M + H] |
| 107 | 5-chloro-4-(((1R,4R)-4-((2,2-difluoroethyl)amino)cyclohexyl)methoxy)-N-(3-morpholinophenyl)pyrimidin-2-amine | (CD$_3$OD) δ = 8.14 (s, 1H), 7.38-7.38 (m, 1H), 7.11-7.21 (m, 2H), 6.66-6.68 (m, 1H), 5.76-6.07 (m, 1H), 4.29-4.30 (m, 2H), 3.84-3.87 (m, 4H), 3.15-3.17 (m, 4H), 2.96-2.97 (m, 2H), 2.50-2.53 (m, 1H), 1.85-1.96 (m, 5H), 1.19-1.22 (m, 4H). LCMS: 481.9 [M + H] |

| Example | Structure | Name | †Spectral data |
|---|---|---|---|
| 108 | 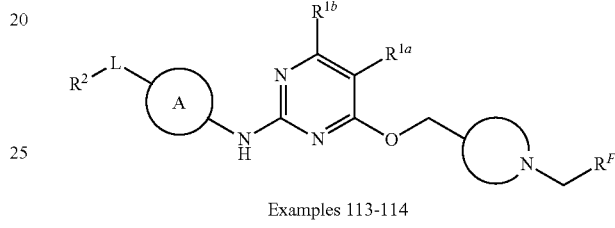 | 5-chloro-N-(4-morpholino-phenyl)-4-(((1R,4R)-4-((2,2,2-trifluoroethyl)amino)cyclohexyl)methoxy)pyrimidin-2-amine | (CD$_3$OD) δ = 8.08 (s, 1H), 7.48-7.52 (m, 2H), 6.94-6.98 (m, 2H), 4.26 (d, J = 6.4 Hz, 2H), 3.84-3.87 (m, 4H), 3.23-3.28 (m, 2H), 3.10-3.16 (m, 4H), 2.53-2.54 (m, 1H), 1.84-2.05 (m, 5H), 1.15-1.23 (m, 4H). LCMS: 499.9 [M + H] |

†All $^1$H NMR recorded at 400 MHz

General Synthetic Scheme 8 for the Synthesis of Examples 109-114

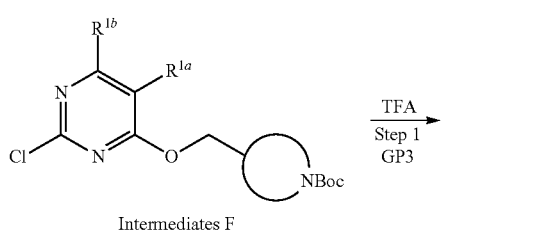

Intermediates F

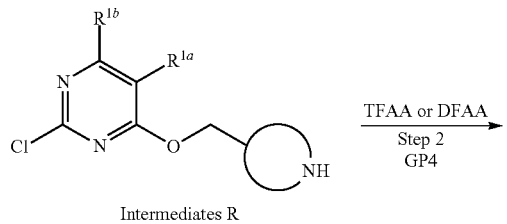

Intermediates R

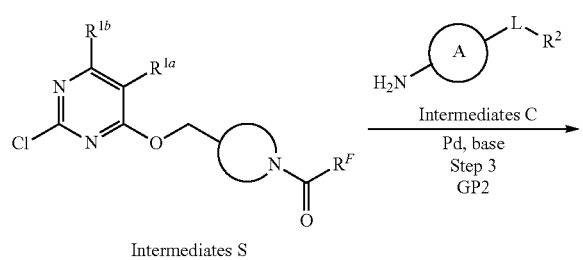

Intermediates S

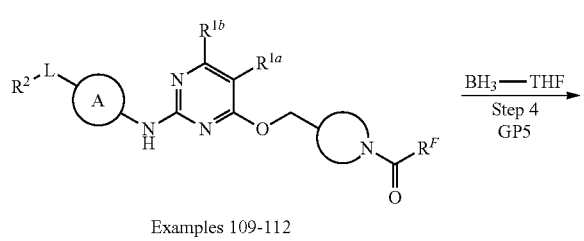

Examples 109-112

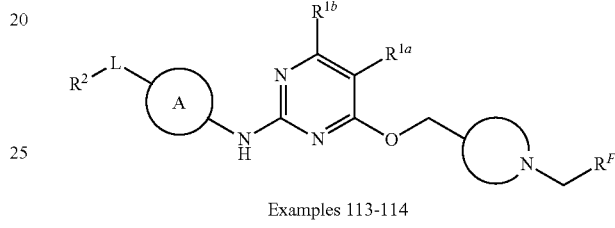

Examples 113-114 wherein $R^F$ is $CF_3$ or $CHF_2$.

Step 1: Synthesis of Intermediates R

Intermediates R were synthesized by following General Procedure GP3 described above. Crude materials were purified by flash chromatography.

Step 2: Synthesis of Intermediates S

Intermediates S were synthesized by following a modified General Procedure GP4 described above where acetic anhydride is replaced by trifluoroacetic anhydride (if $R^F$ is $CF_3$) or difluoroacetic anhydride (if $R^F$ is $CHF_2$).

Step 3: Synthesis of Examples 109-112

Examples 109-112 were synthesized by following General Procedure GP2 described above. Crude materials were purified by preparative HPLC.

Step 4: Synthesis of Examples 113-114

Examples 113-114 were synthesized by following General Procedure GP5 described above.

The following examples were synthesized following General Synthetic Scheme 8

| Example | Structure | Name | †Spectral data |
|---|---|---|---|
| 109 | 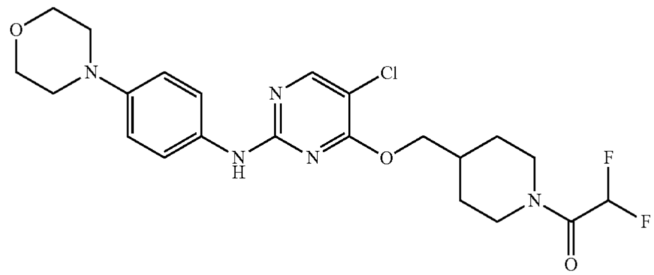 [SMILES: O=C(C(F)F)N1CCC(COc2nc(Nc3ccc(N4CCOCC4)cc3)ncc2Cl)CC1] | 1-(4-(((5-chloro-2-((4-morpholino-phenyl)amino)pyrimidin-4-yl)oxy)methyl)piperidin-1-yl)-2,2-difluoro-ethan-1-one | (DMSO-d$_6$) δ = 9.48 (bs, 1H), 8.24 (s, 1H), 7.53 (d, J = 8.8 Hz, 2H), 6.62-6.91 (m, 3H), 4.27-4.37 (m, 3H), 3.91-3.94 (m, 1H), 3.72-3.75 (m, 4H), 3.12-3.15 (m, 1H), 3.02-3.05 (m, 4H), 2.74-2.81 (m, 1H), 2.12-2.16 (m, 1H), 1.81-1.84 (m, 2H), 1.20-1.32 (m, 2H). LCMS: 481.8 [M + H] |
| 110 | 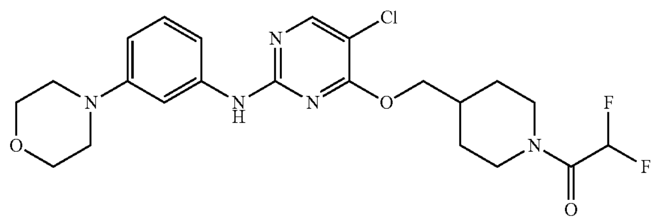 [SMILES: O=C(C(F)F)N1CCC(COc2nc(Nc3cccc(N4CCOCC4)c3)ncc2Cl)CC1] | 1-(4-(((5-chloro-2-((3-morpholino-phenyl)amino)pyrimidin-4-yl)oxy)methyl)piperidin-1-yl)-2,2-difluoro-ethan-1-one | (DMSO-d$_6$) δ = 9.59 (bs, 1H), 8.30 (s, 1H), 7.41 (s, 1H), 7.12-7.13 (m, 2H), 6.58-6.89 (m, 2H), 4.29-4.38 (m, 3H), 3.92-3.96 (m, 1H), 3.73-3.75 (m, 4H), 3.07-3.16 (m, 5H), 2.75-2.81 (m, 1H), 2.14-2.16 (m, 1H), 1.83-1.86 (m, 2H), 1.19-1.31 (m, 2H). LCMS: 482.0 [M + H] |
| 111 | 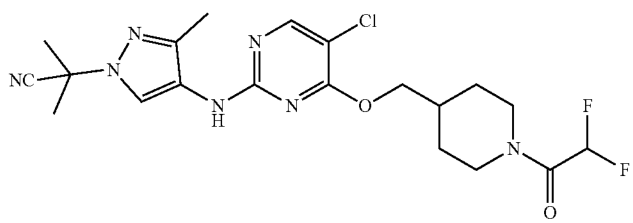 [SMILES: Cc1nn(C(C)(C)C#N)cc1Nc1ncc(Cl)c(OCC2CCN(C(=O)C(F)F)CC2)n1] | 2-(4-((5-chloro-4-((1-(2,2-difluoro-acetyl)piperidin-4-yl)methoxy)pyrimidin-2-yl)amino)-3-methyl-1H-pyrazol-1-yl)-2-methyl-propanenitrile | (DMSO-d$_6$) δ = 9.14 (bs, 1H), 8.25 (s, 1H), 8.14 (s, 1H), 6.62-6.88 (m, 1H), 4.26-4.36 (m, 3H), 3.90-3.94 (m, 1H), 3.12-3.18 (m, 1H), 2.75-2.81 (m, 1H), 2.18 (s, 3H), 2.06-2.08 (m, 1H), 1.93 (s, 6H), 1.80-1.83 (m, 2H), 1.18-1.30 (m, 2H). LCMS: 467.8 [M + H] |
| 112 | 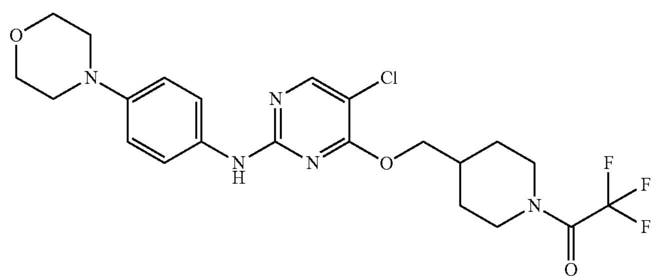 [SMILES: O=C(N1CCC(COc2nc(Nc3ccc(N4CCOCC4)cc3)ncc2Cl)CC1)C(F)(F)F] | 1-(4-(((5-chloro-2-((4-morpholino-phenyl)amino)pyrimidin-4-yl)oxy)methyl)piperidin-1-yl)-2,2,2-trifluoro-ethan-1-one | (DMSO-d$_6$) δ = 9.48 (bs, 1H), 8.24 (s, 1H), 7.53 (d, J = 8.8 Hz, 2H), 6.90 (d, J = 9.2 Hz, 2H), 4.28-4.29 (m, 3H), 3.90-3.94 (m, 1H), 3.73-3.75 (m, 4H), 3.28-3.31 (m, 1H), 3.02-3.05 (m, 4H), 2.92-2.98 (m, 1H), 2.33-2.34 (m, 1H), 1.86-1.92 (m, 2H), 1.24-1.34 (m, 2H). LCMS: 499.9 [M + H] |
| 113 | 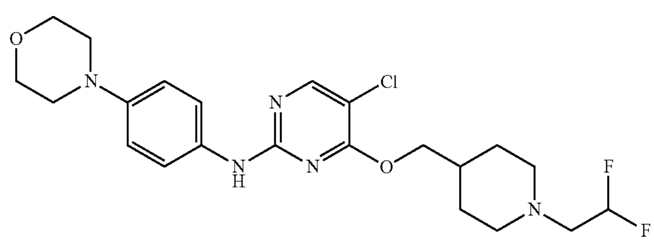 [SMILES: FC(F)CN1CCC(COc2nc(Nc3ccc(N4CCOCC4)cc3)ncc2Cl)CC1] | 5-chloro-4-((1-(2,2-difluoroethyl)piperidin-4-yl)methoxy)-N-(4-morpholino-phenyl)pyrimidin-2-amine | (DMSO-d$_6$) δ = 9.46 (bs, 1H), 8.23 (s, 1H), 7.53 (d, J = 8.8 Hz, 2H), 6.89 (d, J = 8.8 Hz, 2H), 5.99-6.26 (m, 1H), 4.25 (d, J = 6.4 Hz, 2H), 3.72-3.75 (m, 4H), 3.02-3.05 (m, 4H), 2.90-2.94 (m, 2H), 2.67-2.75 (m, 2H), 2.13-2.19 (m, 2H), 1.69-1.82 (m, 3H), 1.24-1.37 (m, 2H). LCMS: 468.2 [M + H] |
| 114 | 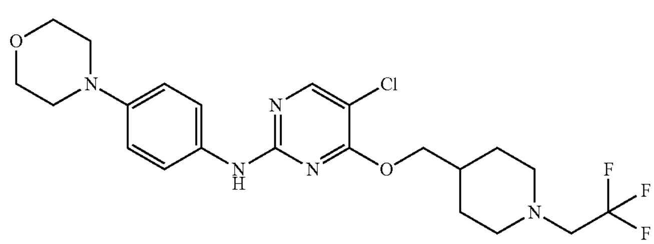 [SMILES: FC(F)(F)CN1CCC(COc2nc(Nc3ccc(N4CCOCC4)cc3)ncc2Cl)CC1] | 5-chloro-N-(4-morpholino-phenyl)-4-((1-(2,2,2-trifluoroethyl)piperidin-4-yl)methoxy)pyrimidin-2-amine | (CD$_3$OD) δ = 7.81 (s, 1H), 7.64-7.66 (m, 2H), 6.92-6.95 (m, 2H), 3.88-3.94 (m, 6H), 3.12-3.15 (m, 4H), 2.99-3.06 (m, 2H), 2.89-2.92 (m, 1H), 2.79 (s, 2H), 2.23-2.79 (m, 1H), 1.55-1.58 (m, 1H), 0.92-1.48 (m, 4H). LCMS: 485.9 [M + H] |

†All $^1$H NMR recorded at 400 MHz

General Synthetic Scheme 9 for the Synthesis of Examples 115-116

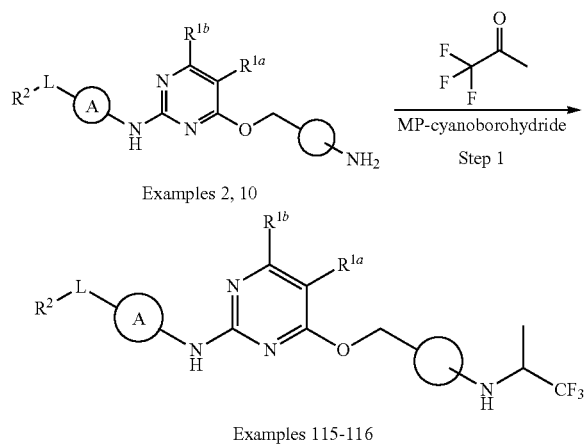

Examples 115-116

Step 1: Synthesis of Examples 115 & 116

1,1,1-Trifluoropropan-2-one (1.5 eq.) was added to a solution of amine (Example 2, 10, 1.0 eq.) in MeOH (10 vol.) and the resulting mixture was stirred at 25° C. for 2 h. MP-cyanoborohydride resin (1.0 eq.) was then added and the reaction mixture was stirred at 60° C. for 48 h. Following completion of the reaction (as indicated by LCMS), the reaction mixture was filtered through a pad of Celite® (i.e., diatomaceous earth) which was then washed with MeOH (2×5 mL). The combined filtrates were concentrated under reduced pressure to yield crude material which was purified by preparative HPLC, affording Examples 115-116 as pale-yellow solids.

The following examples were synthesized following General Synthetic Scheme 9:

| Example | Structure | Name | †Spectral data |
|---|---|---|---|
| 115 | (structure) | N-(4-morpholinophenyl)-4-(((1R,4R)-4-((1,1,1-trifluoropropan-2-yl)amino)cyclohexyl)methoxy)pyrimidin-2-amine | (CD₃OD) δ = 8.00 (d, J = 7.2 Hz, 1H), 7.40 (d, J = 8.8 Hz, 2H), 7.13 (d, J = 8.8 Hz, 2H), 6.48 (d, J = 7.2 Hz, 1H), 4.33-4.43 (m, 3H), 3.87-3.89 (m, 4H), 3.38-3.40 (m, 1H), 3.23-3.25 (m, 4H), 2.18-2.28 (m, 2H), 1.90-2.06 (m, 3H), 1.26-1.61 (m, 7H). LCMS: 480.2 [M + H] |
| 116 | (structure) | 5-fluoro-N-(4-morpholinophenyl)-4-(((1R,4R)-4-((1,1,1-trifluoropropan-2-yl)amino)cyclohexyl)methoxy)pyrimidin-2-amine | (CD₃OD) δ = 8.13 (bs, 1H), 7.74 (bs, 2H), 7.39 (bs, 2H), 4.35-4.43 (m, 3H), 4.01 (bs, 4H), 3.37-3.50 (m, 5H), 1.96-2.30 (m, 5H), 1.33-1.64 (m, 7H). LCMS: 498.2 [M + H] |

†All ¹H NMR recorded at 400 MHz

General Synthetic Scheme 10 for the Synthesis of Examples 117-144 and 214-264

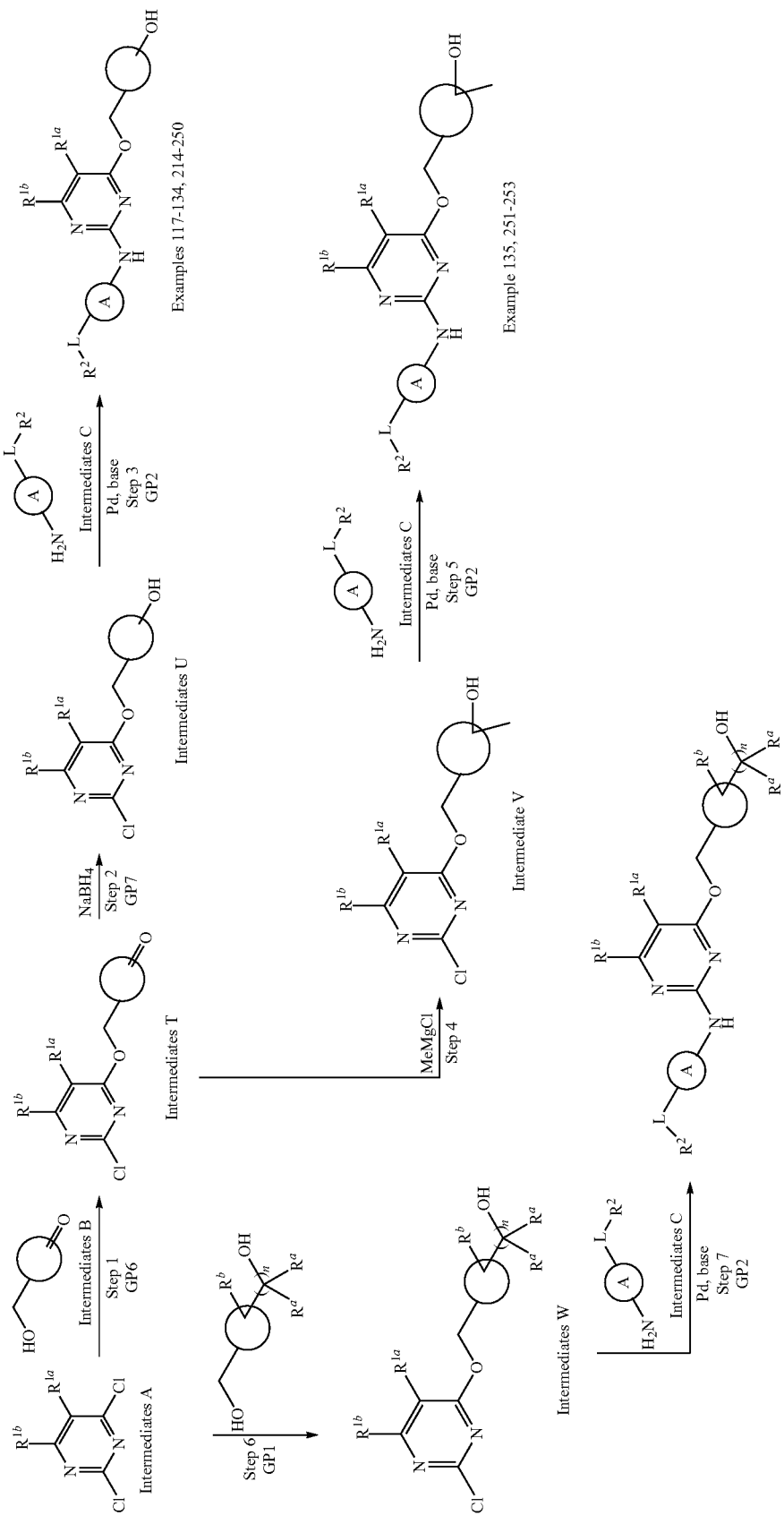

wherein $R^a$ is H or $CH_3$, $R^b$ is $CF_3$ or bridged alkyl connected to two carbons of the ring, and n is 0 or 1

Step 1, General Procedure GP6 for the Synthesis of Intermediates T

Alcohol Intermediate B (1.2 eq.) and $K_2CO_3$ (2.0 eq.) was added to a solution of dichloropyrimidine Intermediate A (1.0 eq.) in ACN (10 vol.) and the resulting mixture was stirred at 85° C. for 18 h. Following completion of the reaction (as indicated by TLC), the reaction mixture was quenched with ice water and extracted twice with EtOAc. The combined organic extracts were dried over $Na_2SO_4$, filtered, and concentrated under reduced pressure to yield crude material which was purified by flash chromatography (silica gel 230-400 mesh, eluting with 15% EtOAc in petroleum), affording the desired Intermediate T.

Step 2, General Procedure GP7 for the Synthesis of Intermediates U $NaBH_4$ (1.5 eq.) was added in portions to a solution of Intermediate T (1.0 eq.) in MeOH (5 vol) at 0° C. and the resulting mixture was stirred at 25° C. for 2 h. Following completion of the reaction (as indicated by TLC), the reaction mixture was quenched with saturated $NH_4Cl$ and extracted twice with DCM. The combined organic extracts were dried over $Na_2SO_4$, filtered, and concentrated under reduced pressure to give crude material which was purified by flash chromatography (silica gel 230-400 mesh, eluting with 30% EtOAc in petroleum ether), affording the desired Intermediate U.

Step 3, Synthesis of Examples 117-134 and 214-250

Examples 117-134 and 214-250 were synthesized by following General Procedure GP2 described above. Crude materials were purified by preparative HPLC.

Step 4, Synthesis of 4-(((2,5-dichloropyrimidin-4-yl)oxy)methyl)-1-methylcyclohexan-1-ol (Intermediate V)

Methylmagnesium chloride (3 M in THF, 1.56 mL, 4.68 mmol) was slowly added to a solution of 4-(((2,5-dichloropyrimidin-4-yl)oxy)methyl)cyclohexan-1-one (0.20 g, 0.73 mmol) in tetrahydrofuran (5 mL) at 0° C. and the resulting mixture was stirred at 25° C. for 2 h. Following completion of the reaction (as indicated by TLC), the reaction mixture was quenched with water (2 mL), filtered to remove insoluble materials, and extracted with EtOAc (2×10 mL). The combined organic extracts were dried over $Na_2SO_4$, filtered, and concentrated under reduced pressure to give crude material which was purified by flash chromatography (silica gel 230-400 mesh, eluting with 25% EtOAc in petroleum ether), affording the title compound (Intermediate V, 100 mg, 50% yield) as a colorless gum. LCMS: 277.2 [M+H].

Step 5, Synthesis of Examples 135 and 251-253

Examples 135 and 251-253 were synthesized by following General Procedure GP2 described above and was purified by preparative HPLC.

Step 6, Synthesis of Intermediates W

Intermediates W were synthesized by following General Procedure GP1 described above.

Step 7, Synthesis of Example 136-144 and 254-264

Examples 136-144 and 254-264 were synthesized by following General Procedure GP2 described above. Crude materials were purified by preparative HPLC.

The following examples were synthesized following General Synthetic Scheme 10:

| Example | Structure | Name | †Spectral data |
|---|---|---|---|
| 117 | 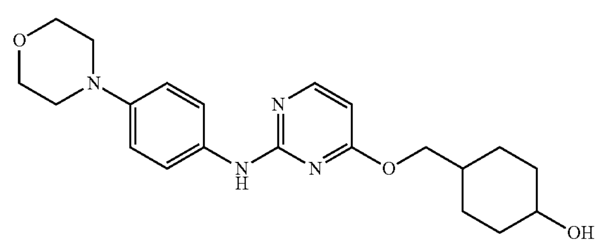 [SMILES: OC1CCC(COc2ccnc(Nc3ccc(N4CCOCC4)cc3)n2)CC1] | 4-(((2-((4-morpholinophenyl)amino)pyrimidin-4-yl)oxy)methyl)cyclohexanol | ($CD_3OD$) δ = 7.98 (d, J = 6.8 Hz, 1H), 7.40 (d, J = 8.8 Hz, 2H), 7.11-7.13 (m, 2H), 6.47 (d, J = 6.8 Hz, 1H), 4.30 (d, J = 6.4 Hz, 2H), 3.86-3.88 (m, 4H), 3.52-3.54 (m, 1H), 3.21-3.25 (m, 4H), 1.99-2.02 (m, 2H), 1.77-1.88 (m, 3H), 1.59-1.61 (m, 2H), 1.14-1.34 (m, 2H). LCMS: 385.2 [M + H] |
| 118 | 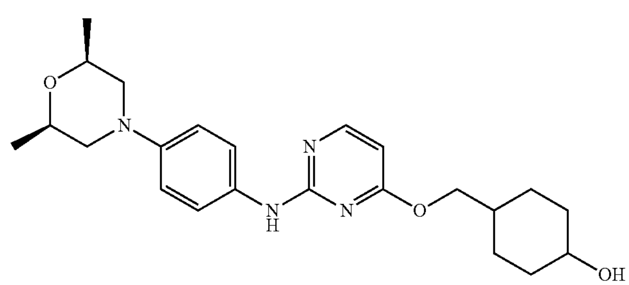 [SMILES: C[C@@H]1CN(c2ccc(Nc3nccc(OCC4CCC(O)CC4)n3)cc2)C[C@H](C)O1] | 4-(((2-((4-((2S,6R)-2,6-dimethylmorpholino)phenyl)amino)pyrimidin-4-yl)oxy)methyl)cyclohexan-1-ol | ($CD_3OD$) δ = 7.97 (d, J = 7.2 Hz, 1H), 7.38 (d, J = 9.2 Hz, 2H), 7.12-7.16 (m, 2H), 6.48 (d, J = 7.2 Hz, 1H), 4.31 (d, J = 6.4 Hz, 2H), 3.82-3.86 (m, 2H), 3.50-3.63 (m, 3H), 2.44-2.50 (m, 2H), 1.99-2.02 (m, 2H), 1.81-1.89 (m, 3H), 1.15-1.31 (m, 10H). LCMS: 413.2 [M + H] |

| Example | Structure | Name | †Spectral data |
|---|---|---|---|
| 119 | 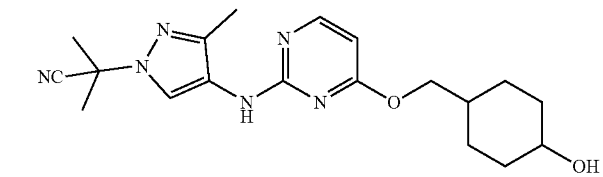 [SMILES: Cc1nn(C(C)(C)C#N)cc1Nc1nccc(OCC2CCC(O)CC2)n1] | 2-(4-((4-((4-hydroxy-cyclohexyl)methoxy)pyrimidin-2-yl)amino)-3-methyl-1H-pyrazol-1-yl)-2-methyl-propanenitrile | (CD$_3$OD) δ = 8.13 (s, 1H), 8.03 (d, J = 24.4 Hz, 1H), 6.48 (d, J = 6.8 Hz, 1H), 4.32 (bs, 2H), 3.43-3.56 (m, 1H), 2.19 (s, 3H), 1.81-2.02 (m, 11H), 1.29-1.34 (m, 4H). LCMS: 371.3 [M + H] |
| 120 | 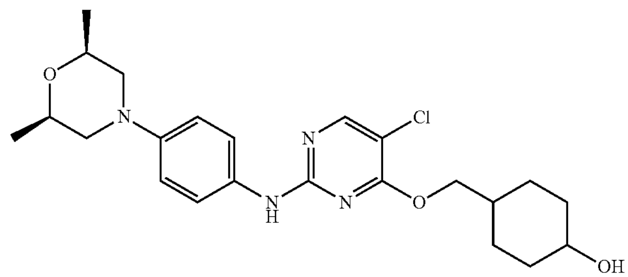 | 4-(((5-chloro-2-((4-((2S,6R)-2,6-dimethylmorpholino)phenyl)amino)pyrimidin-4-yl)oxy)methyl)cyclohexan-1-ol | (DMSO-d$_6$) δ = 9.46 (bs, 1H), 8.23 (d, J = 1.2 Hz, 1H), 7.53 (d, J = 8.4 Hz, 2H), 6.91 (d, J = 8.0 Hz, 2H), 4.20 (d, J = 6.0 Hz, 2H), 3.38-3.73 (m, 6H), 2.19-2.25 (m, 2H), 1.72-1.88 (m, 5H), 1.09-1.16 (m, 10H). LCMS: 447.0 [M + H] |
| 121 | 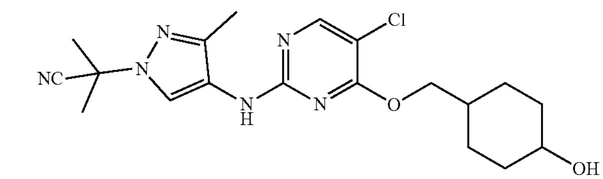 | 2-(4-((5-chloro-4-((4-hydroxycyclohexyl)methoxy)pyrimidin-2-yl)amino)-3-methyl-1H-pyrazol-1-yl)-2-methyl-propanenitrile | (CD$_3$OD) δ = 8.08 (s, 1H), 8.07 (s, 1H), 4.25 (d, J = 6.4 Hz, 2H), 3.49-3.56 (m, 1H), 2.24 (s, 3H), 1.91-2.03 (m, 10H), 1.75-1.82 (m, 2H), 1.13-1.36 (m, 4H). LCMS: 405.2 [M + H] |
| 122 | 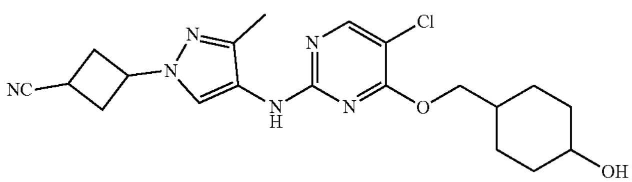 [SMILES: Cc1nn(C2CC(C#N)C2)cc1Nc1ncc(Cl)c(OCC2CCC(O)CC2)n1] | 3-(4-((5-chloro-4-((4-hydroxycyclohexyl)methoxy)pyrimidin-2-yl)amino)-3-methyl-1H-pyrazol-1-yl)cyclobutane-1-carbonitrile | (CD$_3$OD) δ = 8.07 (s, 1H), 7.83 (s, 1H), 5.06-5.10 (m, 1H), 4.26 (d, J = 6.4 Hz, 2H), 3.40-3.53 (m, 1H), 3.32-3.39 (m, 1H), 2.96-3.03 (m, 2H), 2.81-2.87 (m, 2H), 2.21 (s, 3H), 2.00-2.21 (m, 2H), 1.77-1.99 (m, 3H), 1.16-1.32 (m, 4H). LCMS: 417.2 [M + H] |
| 123 | 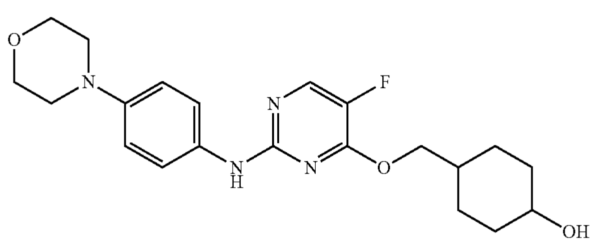 [SMILES: OC1CCC(COc2nc(Nc3ccc(N4CCOCC4)cc3)ncc2F)CC1] | 4-(((5-fluoro-2-((4-morpholinophenyl)amino)pyrimidin-4-yl)oxy)methyl)cyclohexan-1-ol | (CD$_3$OD) δ = 8.00 (d, J = 3.2 Hz, 1H), 7.49 (d, J = 8.8 Hz, 2H), 6.96 (d, J = 8.8 Hz, 2H), 4.26 (d, J = 6.4 Hz, 2H), 3.84-3.87 (m, 4H), 3.51-3.56 (m, 1H), 3.09-3.12 (m, 4H), 1.83-2.03 (m, 5H), 1.26-1.32 (m, 4H). LCMS: 403.0 [M + H] |
| 124 | 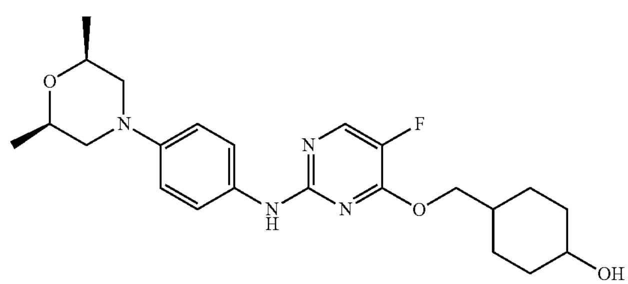 | 4-(((2-((4-((2S,6R)-2,6-dimethylmorpholino)phenyl)amino)-5-fluoropyrimidin-4-yl)oxy)methyl)cyclohexan-1-ol | (CD$_3$OD) δ = 8.08 (s, 1H), 7.67 (d, J = 6.4 Hz, 2H), 7.25 (s, 2H), 4.30 (d, J = 6.8 Hz, 2H), 3.92-3.97 (m, 2H), 3.50-3.58 (m, 3H), 2.79 (s, 2H), 1.80-2.03 (m, 5H), 1.17-1.33 (m, 10H). LCMS: 431.2 [M + H] |

| Example | Structure | Name | †Spectral data |
|---|---|---|---|
| 125 (pure diastereomer obtained by chromatographic purification) | 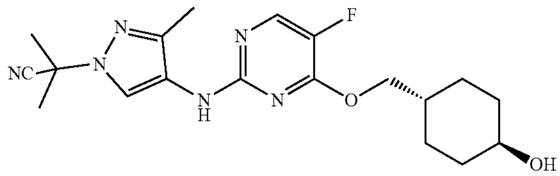 | 2-(4-((5-fluoro-4-(((1R,4R)-4-hydroxycyclohexyl)methoxy)pyrimidin-2-yl)amino)-3-methyl-1H-pyrazol-1-yl)-2-methylpropanenitrile | (CD$_3$OD) δ = 8.10 (s, 1H), 8.02 (d, J = 3.2 Hz, 1H), 4.25 (d, J = 6.4 Hz, 2H), 3.51-3.56 (m, 1H), 2.24 (s, 3H), 1.77-2.02 (m, 11H), 1.26-1.36 (m, 4H). LCMS: 389.2 [M + H] |
| 126 (pure diastereomer obtained by chromatographic purification) | 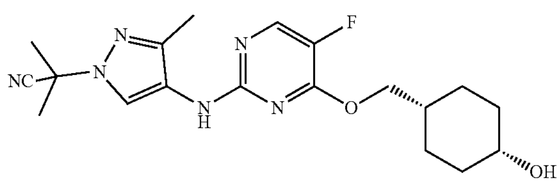 | 2-(4-((5-fluoro-4-(((1S,4S)-4-hydroxycyclohexyl)methoxy)pyrimidin-2-yl)amino)-3-methyl-1H-pyrazol-1-yl)-2-methylpropanenitrile | (CD$_3$OD) δ = 8.10 (s, 1H), 8.01 (d, J = 3.2 Hz, 1H), 4.30 (d, J = 6.8 Hz, 2H), 3.94-3.96 (m, 1H), 2.25 (s, 3H), 1.95-2.01 (m, 7H), 1.60-1.80 (m, 8H). LCMS: 389.2 [M + H] |
| 127 | 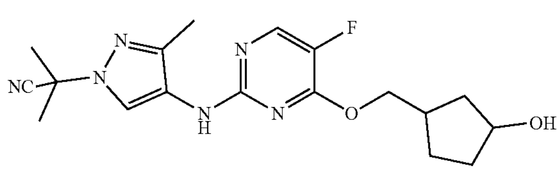 | 2-(4-((5-fluoro-4-((3-hydroxycyclopentyl)methoxy)pyrimidin-2-yl)amino)-3-methyl-1H-pyrazol-1-yl)-2-methylpropanenitrile | (CD$_3$OD) δ = 8.11 (s, 1H), 8.07 (d, J = 3.6 Hz, 1H), 4.33-4.41 (m, 3H), 2.69-2.73 (m, 1H), 2.25 (s, 3H), 1.85-2.05 (m, 9H), 1.45-1.64 (m, 3H). LCMS: 375.1 [M + H] |

-continued

| Example | Structure | Name | †Spectral data |
|---|---|---|---|
| 128 | 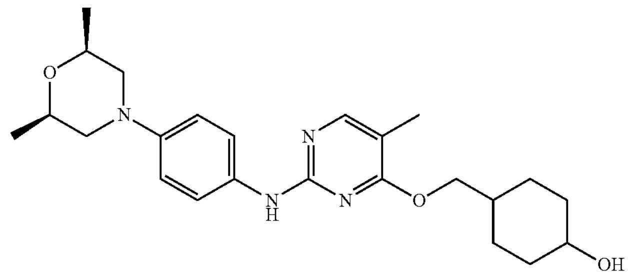 | 4-(((2-((4-((2S,6R)-2,6-dimethyl-morpholino)phenyl)amino)-5-methyl-pyrimidin-4-yl)oxy)methyl)cyclohexan-1-ol | (DMSO-d$_6$) δ = 10.10 (bs, 1H), 8.01 (s, 1H), 7.43 (d, J = 8.8 Hz, 2H), 7.01 (d, J = 8.8 Hz, 2H), 4.20 (d, J = 6.4 Hz, 2H), 3.68-3.75 (m, 2H), 3.55-3.58 (m, 2H), 3.33-3.38 (m, 1H), 2.31-2.34 (m, 2H), 2.00 (s, 3H), 1.85-1.88 (m, 2H), 1.70-1.78 (m, 3H), 1.06-1.20 (m, 10H). LCMS: 427.3 [M + H] |
| 129 | 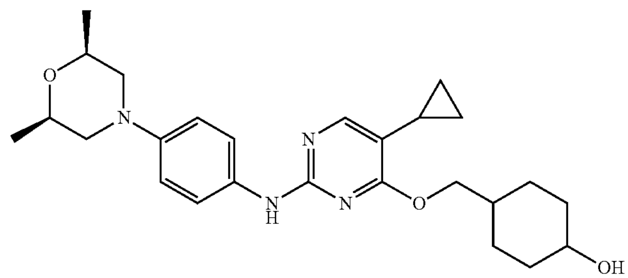 [SMILES: C[C@@H]1CN(c2ccc(Nc3ncc(C4CC4)c(OCC4CCC(O)CC4)n3)cc2)C[C@H](C)O1] | 4-(((5-cyclopropyl-2-((4-((2S,6R)-2,6-dimethyl-morpholino)phenyl)amino)pyrimidin-4-yl)oxy)methyl)cyclohexan-1-ol | (CD$_3$OD) δ = 7.72 (s, 1H), 7.45 (d, J = 8.8 Hz, 2H), 6.97 (d, J = 8.8 Hz, 2H), 4.24 (d, J = 6.4 Hz, 2H), 3.80-3.85 (m, 2H), 3.47-3.53 (m, 3H), 2.30-2.36 (m, 2H), 2.01-2.03 (m, 2H), 1.91-1.94 (m, 2H), 1.71-1.77 (m, 2H), 1.19-1.29 (m, 10H), 0.86-0.89 (m, 2H), 0.60-0.64 (m, 2H). LCMS: 453.3 [M + H] |
| 130 | 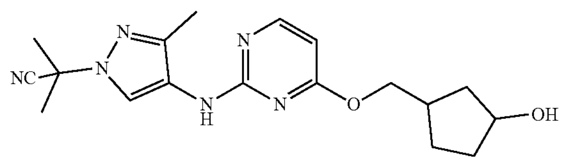 | 2-(4-((4-((3-hydroxy-cyclopentyl)methoxy)pyrimidin-2-yl)amino)-3-methyl-1H-pyrazol-1-yl)-2-methyl-propanenitrile | (DMSO-d$_6$) δ = 9.24 (s, 1H), 8.06 (s, 1H), 8.01 (d, J = 6.8 Hz, 1H), 6.22 (d, J = 5.2 Hz, 1H), 4.14-4.33 (m, 2H), 4.03-4.08 (m, 1H), 2.23-2.26 (m, 1H), 2.11 (s, 3H), 1.83-1.90 (m, 7H), 1.57-1.67 (m, 2H), 1.38-1.49 (m, 2H), 1.17-1.23 (m, 1H). LCMS: 357.2 [M + H] |
| 131 | 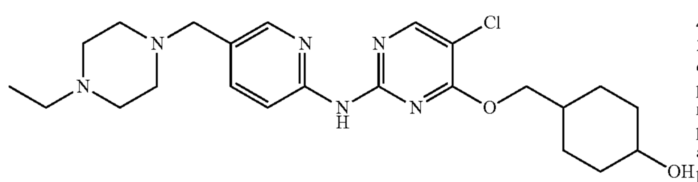 | 4-(((5-chloro-2-((5-((4-ethyl-piperazin-1-yl)methyl)pyridin-2-yl)amino)pyrimidin-4-yl)oxy)methyl)cyclohexan-1-ol | (CD$_3$OD) δ = 8.22-8.26 (m, 3H), 7.77 (d, J = 8.8 Hz, 1H), 4.32 (d, J = 6.0 Hz, 2H), 3.55 (s, 2H), 2.47-2.57 (m, 10H), 1.85-2.05 (m, 5H), 1.21-1.34 (m, 4H), 1.13 (t, J = 7.20 Hz, 3H). LCMS: 461.2 [M + H] |
| 132 | 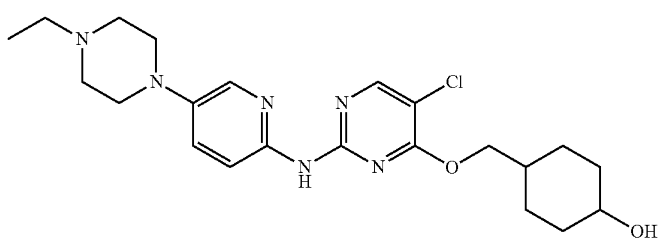 [SMILES: CCN1CCN(c2ccc(Nc3ncc(Cl)c(OCC4CCC(O)CC4)n3)nc2)CC1] | 4-(((5-chloro-2-((5-(4-ethyl-piperazin-1-yl)pyridin-2-yl)amino)pyrimidin-4-yl)oxy)methyl)cyclohexan-1-ol | (CD$_3$OD) δ = 8.48 (s, 1H), 8.18-8.21 (m, 1H), 7.94 (d, J = 2.8 Hz, 1H), 7.50 (d, J = 9.6 Hz, 1H), 4.37 (d, J = 6.4 Hz, 2H), 3.74-3.91 (m, 4H), 3.51-3.59 (m, 1H), 3.32 (3, 6H), 1.85-2.06 (m, 5H), 1.21-1.45 (m, 7H). LCMS: 447.2 [M + H] |
| 133 | 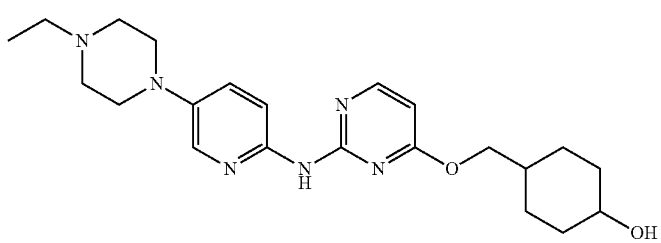 [SMILES: CCN1CCN(c2ccc(Nc3nccc(OCC4CCC(O)CC4)n3)nc2)CC1] | 4-(((2-((5-(4-ethyl-piperazin-1-yl)pyridin-2-yl)amino)pyrimidin-4-yl)oxy)methyl)cyclohexan-1-ol | (CD$_3$OD) δ = 8.33 (d, J = 6.8 Hz, 1H), 8.12 (d, J = 2.8 Hz, 1H), 7.87-7.90 (m, 1H), 7.31 (d, J = 9.2 Hz, 1H), 6.71 (d, J = 6.8 Hz, 1H), 4.37 (d, J = 6.4 Hz, 2H), 3.74-3.92 (m, 4H), 3.51-3.58 (m, 1H), 3.32-3.33 (m, 6H), 1.81-2.04 (m, 5H), 1.19-1.45 (m, 7H). LCMS: 413.1 [M + H] |

| Example | Structure | Name | †Spectral data |
|---|---|---|---|
| 134 | 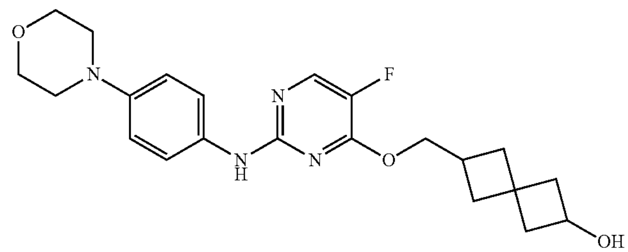 [SMILES: OC1CC2(C1)CC(COc1nc(Nc3ccc(N4CCOCC4)cc3)ncc1F)C2] | 6-(((5-fluoro-2-((4-morpholinophenyl)amino)pyrimidin-4-yl)oxy)methyl)spiro[3.3]heptan-2-ol | (DMSO-d₆) δ = 9.37 (bs, 1H), 8.16 (d, J = 2.8 Hz, 1H), 7.53 (d, J = 8.8 Hz, 2H), 6.98 (d, J = 8.4 Hz, 2H), 4.27 (d, J = 7.2 Hz, 2H), 3.85-3.88 (m, 1H), 3.71-3.73 (m, 4H), 2.54-2.58 (m, 2H), 1.95-2.28 (m, 6H), 1.73-1.78 (m, 5H). LCMS: 415.2 [M + H] |
| 214 | 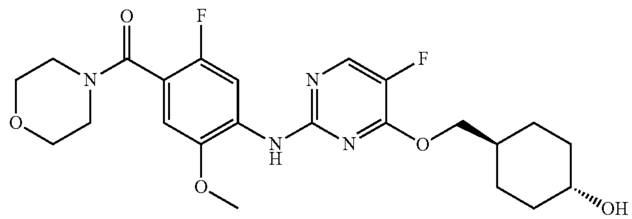 [SMILES: COc1cc(C(=O)N2CCOCC2)c(F)cc1Nc1ncc(F)c(OC[C@H]2CC[C@H](O)CC2)n1] | (2-fluoro-4-((5-fluoro-4-(((1R,4R)-4-hydroxycyclohexyl)methoxy)pyrimidin-2-yl)amino)-5-methoxyphenyl)(morpholino)methanone | (CD₃OD) δ = 8.37 (d, J = 12.4 Hz, 1H), 8.20 (d, J = 2.8 Hz, 1H), 7.01 (d, J = 6.0 Hz, 1H), 4.33 (d, J = 6.4 Hz, 2H), 3.98 (s, 3H), 3.79 (bs, 4H), 3.67-3.70 (m, 2H), 3.54-3.55 (m, 1H), 3.46 (bs, 2H), 1.88-2.06 (m, 5H), 1.20-1.33 (m, 4H). LCMS: 479.3 [M + H] |
| 215 | 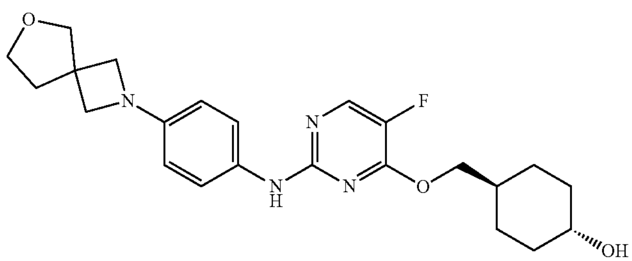 [SMILES: O[C@H]1CC[C@H](COc2nc(Nc3ccc(N4CC5(CCOC5)C4)cc3)ncc2F)CC1] | (1R,4R)-4-(((2-((4-(6-oxa-2-azaspiro[3.4]octan-2-yl)phenyl)amino)-5-fluoropyrimidin-4-yl)oxy)methyl)cyclohexan-1-ol | (CD₃OD) δ = 7.97 (d, J = 3.2 Hz, 1H), 7.40 (dd, J = 2.0, 6.8 Hz, 2H), 6.52 (dd, J = 2.4, 6.8 Hz, 2H), 4.24 (d, J = 6.4 Hz, 2H), 3.92 (bs, 2H), 3.85-3.89 (m, 2H), 3.83 (bs, 4H), 3.49-3.56 (m, 1H), 2.21-2.25 (m, 2H), 1.78-2.05 (m, 5H), 1.12-1.35 (m, 4H). LCMS: 429.5 [M + H] |
| 216 | 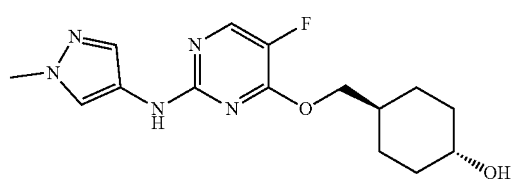 [SMILES: Cn1cc(Nc2ncc(F)c(OC[C@H]3CC[C@H](O)CC3)n2)cn1] | (1R,4R)-4-(((5-fluoro-2-((1-methyl-1H-pyrazol-4-yl)amino)pyrimidin-4-yl)oxy)methyl)cyclohexan-1-ol | (CD₃OD) δ = 8.03 (d, J = 3.2 Hz, 1H), 4.28 (d, J = 6.4 Hz, 2H), 3.87 (s, 3H), 3.50-3.57 (m, 1H), 2.00-3.28 (m, 2H), 1.91-1.94 (m, 2H), 1.83-1.84 (m, 1H), 1.18-1.30 (m, 4H). LCMS: 322.3 [M + H] |
| 217 | 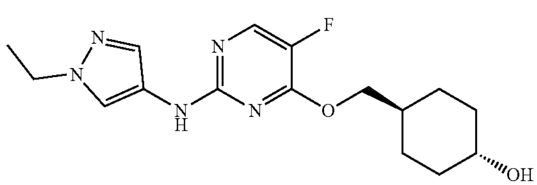 [SMILES: CCn1cc(Nc2ncc(F)c(OC[C@H]3CC[C@H](O)CC3)n2)cn1] | (1R,4R)-4-(((2-((1-ethyl-1H-pyrazol-4-yl)amino)-5-fluoropyrimidin-4-yl)oxy)methyl)cyclohexan-1-ol | (CD₃OD) δ = 8.09 (d, J = 3.6 Hz, 1H), 7.91 (s, 1H), 7.60 (s, 1H), 4.33 (d, J = 6.4 Hz, 2H), 4.16-4.21 (m, 2H), 3.51-3.57 (m, 1H), 1.83-2.06 (m, 5H), 1.48 (t, J = 7.6 Hz, 3H), 1.15-1.37 (m, 4H). LCMS: 336.2 |
| 218 | 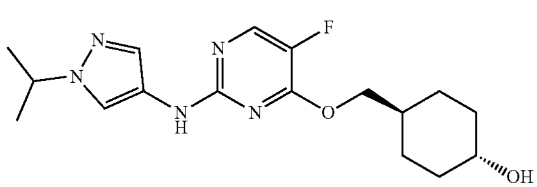 [SMILES: CC(C)n1cc(Nc2ncc(F)c(OC[C@H]3CC[C@H](O)CC3)n2)cn1] | (1R,4R)-4-(((5-fluoro-2-((1-isopropyl-1H-pyrazol-4-yl)amino)pyrimidin-4-yl)oxy)methyl)cyclohexan-1-ol | (CD₃OD) δ = 8.07 (d, J = 3.6 Hz, 1H), 7.92 (s, 1H), 7.59 (s, 1H), 4.48-4.54 (m, 1H), 4.32 (d, J = 6.4 Hz, 2H), 3.51-3.57 (m, 1H), 2.00-2.04 (m, 2H), 1.91-1.95 (m, 2H), 1.83-1.87 (m, 1H), 1.51 (d, J = 6.8 Hz, 6H), 1.18-1.37 (m, 4H). LCMS: 350.1 [M + H] (pure diastereomer obtained by chromatographic purification) |

| Example | Name | †Spectral data |
|---|---|---|
| 219 | (1S,4S)-4-(((5-fluoro-2-((1-isopropyl-1H-pyrazol-4-yl)amino)pyrimidin-4-yl)oxy)methyl)cyclohexan-1-ol | (CD$_3$OD) δ = 8.03 (d, J = 3.2 Hz, 1H), 7.92 (s, 1H), 7.56 (s, 1H), 4.45-4.52 (m, 1H), 4.33 (d, J = 6.8 Hz, 2H), 3.95-3.96 (m, 1H), 1.58-1.97 (m, 9H), 1.51 (d, J = 6.4 Hz, 6H). LCMS: 350.2 [M + H] (pure diastereomer obtained by chromatographic purification) |
| 220 | (1R,4R)-4-(((2-((1-cyclopropyl-1H-pyrazol-4-yl)amino)-5-fluoro-pyrimidin-4-yl)oxy)methyl)cyclohexan-1-ol | (CD$_3$OD) δ = δ 7.27 (s, 1H), 7.12 (s, 1H), 6.76 (s, 1H), 3.51-3.52 (m, 2H), 2.84 (bs, 1H), 2.73 (bs, 1H), 1.04-1.22 (m, 5H), 0.28-0.52 (m, 8H). LCMS: 348.1 [M + H] |
| 221 | 2-(4-((5-fluoro-4-hydroxy-cyclohexyl)methoxy)pyrimidin-2-yl)amino)-1H-pyrazol-1-yl)-2-methyl-propanenitrile | (CD$_3$OD) δ = 8.20 (s, 1H), 8.09 (d, J = 3.6 Hz, 1H), 7.68 (s, 1H), 4.31 (d, J = 6.4 Hz, 2H), 3.52-3.54 (m, 1H), 1.81-2.02 (m, 11H), 1.25-1.37 (m, 4H). LCMS: 375.2 [M + H] |
| 222 | (1R,4R)-4-(((5-fluoro-2-((1-(trifluoro-methyl)-1H-pyrazol-4-yl)amino)pyrimidin-4-yl)oxy)methyl)cyclohexan-1-ol | (CD$_3$OD) δ = 8.38 (s, 1H), 8.14 (d, J = 3.2 Hz, 1H), 7.89 (s, 1H), 4.29 (d, J = 6.4 Hz, 2H), 3.50-3.57 (m, 1H), 1.82-2.05 (m, 5H), 1.14-1.36 (m, 4H). LCMS: 376.1 [M + H] |
| 223 | (1R,4R)-4-(((5-fluoro-2-((1-(2,2,2-trifluoroethyl)-1H-pyrazol-4-yl)amino)pyrimidin-4-yl)oxy)methyl)cyclohexan-1-ol | (CD$_3$OD) δ = 8.10 (s, 1H), 8.06 (s, 1H), 7.67 (s, 1H), 4.89-4.93 (m, 2H), 4.31 (d, J = 6.4 Hz, 2H), 3.52-3.57 (m, 1H), 1.83-2.04 (m, 5H), 1.18-1.36 (m, 4H). LCMS: 390.2 [M + H] |
| 224 | (1R,4R)-4-(((5-fluoro-2-((1-(2-fluoro-ethyl)-1H-pyrazol-4-yl)amino)pyrimidin-4-yl)oxy)methyl)cyclohexan-1-ol | (CD$_3$OD) δ = 8.04 (d, J = 3.2 Hz, 1H), 7.97 (s, 1H), 7.59 (d, J = 0.4 Hz, 1H), 4.80 (t, J = 4.8 Hz, 1H), 4.68 (t, J = 4.8 Hz, 1H), 4.44 (t, J = 4.8 Hz, 1H), 4.38 (t, J = 4.4 Hz, 1H), 4.28 (d, J = 6.4 Hz, 2H), 3.51-3.56 (m, 1H), 1.82-2.04 (m, 5H), 1.24-1.33 (m, 4H). LCMS: 354.2 [M + H] |
| 225 | (1R,4R)-4-(((5-fluoro-2-((1-(2-hydroxy-ethyl)-1H-pyrazol-4-yl)amino)pyrimidin-4-yl)oxy)methyl) | (CD$_3$OD) δ = 8.03 (d, J = 3.2 Hz, 1H), 7.95 (s, 1H), 7.57 (s, 1H), 4.28 (d, J = 6.4 Hz, 2H), 4.18-4.21 (m, 2H), 3.87-3.90 (m, 2H), 3.52-3.58 (m, 1H), 1.82-2.04 (m, 5H), 1.23-1.33 (m, 4H). LCMS: 352.2 [M + H] |

| Example | Name | †Spectral data |
|---|---|---|
| 226 | (1R,4R)-4-(((5-fluoro-2-((1-(2-methoxyethyl)-1H-pyrazol-4-yl)amino)pyrimidin-4-yl)oxy)methyl)cyclohexan-1-ol | (DMSO-d$_6$) δ = 9.37 (bs, 1H), 8.21 (d, J = 3.2 Hz, 1H), 7.83 (s, 1H), 7.47 (s, 1H), 4.18-4.22 (m, 4H), 3.65 (t, J = 5.6 Hz, 2H), 3.32-3.48 (m, 1H), 3.23 (s, 3H), 1.77-1.81 (m, 5H), 1.07-1.10 (m, 4H). LCMS: 366.2 [M + H] |
| 227 | (1R,4R)-4-(((5-fluoro-2-((1-(oxetan-3-yl)-1H-pyrazol-4-yl)amino)pyrimidin-4-yl)oxy)methyl)cyclohexan-1-ol | (DMSO-d$_6$) δ = 9.38 (bs, 1H), 8.15 (d, J = 3.2 Hz, 1H), 7.92 (s, 1H), 7.54 (s, 1H), 5.43-5.48 (m, 1H), 4.76-4.85 (m, 4H), 4.48 (d, J = 4.4 Hz, 1H), 4.15 (d, J = 5.6 Hz, 2H), 3.28-3.31 (m, 1H), 1.65-1.83 (m, 5H), 1.05-1.14 (m, 4H). LCMS: 364.4 |
| 228 | (1R,4R)-4-(((5-fluoro-2-((1-(tetrahydro-2H-pyran-4-yl)-1H-pyrazol-4-yl)amino)pyrimidin-4-yl)oxy)methyl)cyclohexan-1-ol | (CD$_3$OD) δ = 8.04 (d, J = 3.2 Hz, 1H), 7.96 (s, 1H), 7.58 (s, 1H), 4.37-4.38 (m, 1H), 4.27-4.29 (m, 2H), 4.06-4.09 (m, 2H), 3.52-3.62 (m, 3H), 2.04-2.09 (m, 6H), 1.84-1.95 (m, 3H), 1.18-1.33 (m, 4H). LCMS: 392.2 [M + H] |
| 229 | (1R,4R)-4-(((2-((1,3-dimethyl-1H-pyrazol-4-yl)amino)-5-fluoropyrimidin-4-yl)oxy)methyl)cyclohexan-1-ol | CD$_3$OD δ = 7.96 (d, J = 3.2 Hz, 1H), 4.23 (d, J = 6.4 Hz, 2H), 3.81 (s, 3H), 3.50-3.56 (m, 1H), 2.18 (s, 3H), 1.99-2.02 (m, 2H), 1.88-1.91 (m, 2H), 1.77-1.81 (m, 1H), 1.15-1.34 (m, 4H). LCMS: 336.2 |
| 230 | (1R,4R)-4-(((5-fluoro-2-((1-isopropyl-3-methyl-1H-pyrazol-4-yl)amino)pyrimidin-4-yl)oxy)methyl)cyclohexan-1-ol | (CD$_3$OD) δ = 8.02 (d, J = 3.6 Hz, 1H), 7.82 (s, 1H), 4.41-4.48 (m, 1H), 4.29 (d, J = 6.4 Hz, 2H), 3.49-3.56 (m, 1H), 2.20 (s, 3H), 1.79-2.03 (m, 5H), 1.50 (d, J = 6.4 Hz, 6H), 1.13-1.36 (m, 4H). LCMS: 364.2 [M + H] |
| 231 | (1R,4R)-4-(((2-((1-cyclopropyl-3-methyl-1H-pyrazol-4-yl)amino)-5-fluoropyrimidin-4-yl)oxy)methyl)cyclohexan-1-ol | (CD$_3$OD) δ = 8.04 (d, J = 3.6 Hz, 1H), 7.84 (s, 1H), 4.31 (d, J = 6.4 Hz, 2H), 3.51-3.61 (m, 2H), 2.19 (s, 3H), 1.81-2.03 (m, 5H), 1.04-1.36 (m, 8H). LCMS: 362.3 [M + H] |

-continued

| Example | Structure | Name | †Spectral data |
|---|---|---|---|
| 232 | 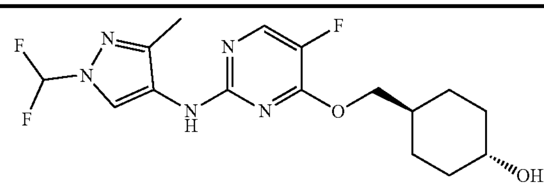 | (1R,4R)-4-(((2-((1-(difluoromethyl)-3-methyl-1H-pyrazol-4-yl)amino)-5-fluoropyrimidin-4-yl)oxy)methyl)cyclohexan-1-ol | (CD$_3$OD) δ = 8.27 (s, 1H), 8.07 (d, J = 3.2 Hz, 1H), 7.33 (t, J = 60.00 Hz, 1H), 4.27 (d, J = 6.8 Hz, 2H), 3.51-3.56 (m, 1H), 2.29 (s, 3H), 1.79-2.05 (m, 5H), 1.13-1.36 (m, 4H). LCMS: 372.2 [M + H] |
| 233 | 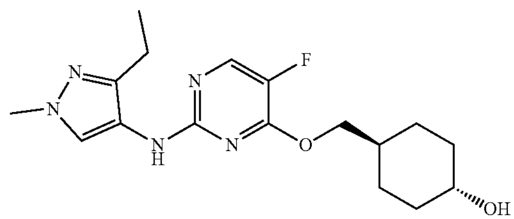 | (1R,4R)-4-(((2-((3-ethyl-1-methyl-1H-pyrazol-4-yl)amino)-5-fluoropyrimidin-4-yl)oxy)methyl)cyclohexan-1-ol | (CD$_3$OD) δ = 8.03 (d, J = 2.4 Hz, 1H), 7.76 (d, J = 2.4 Hz, 1H), 4.32 (d, J = 5.6 Hz, 2H), 3.87 (s, 3H), 3.51-3.56 (m, 1H), 2.58-2.64 (m, 2H), 1.83-2.04 (m, 5H), 1.22-1.36 (m, 7H). LCMS: 350.1 [M + H] |
| 234 | 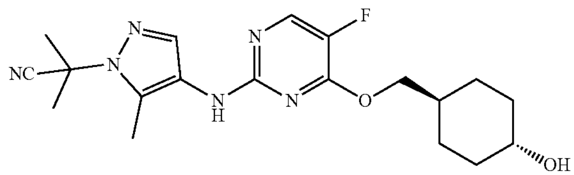 [SMILES: Cc1c(Nc2ncc(F)c(OC[C@H]3CC[C@H](O)CC3)n2)cnn1C(C)(C)C#N] | 2-(4-((5-fluoro-4-(((1R,4R)-4-hydroxycyclohexyl)methoxy)pyrimidin-2-yl)amino)-5-methyl-1H-pyrazol-1-yl)-2-methylpropanenitrile | (CD$_3$OD) δ = 8.07-8.10 (m, 2H), 4.32 (d, J = 6.4 Hz, 2H), 3.50-3.57 (m, 1H), 2.24 (s, 3H), 1.79-2.03 (m, 11H), 1.13-1.36 (m, 4H). LCMS: 389.2 [M + H] |
| 235 | 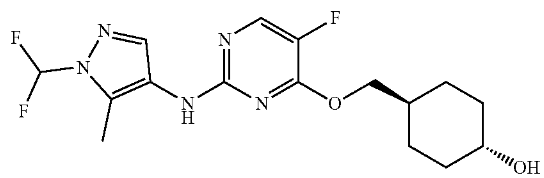 [SMILES: Cc1c(Nc2ncc(F)c(OC[C@H]3CC[C@H](O)CC3)n2)cnn1C(F)F] | (1R,4R)-4-(((2-((1-(difluoromethyl)-5-methyl-1H-pyrazol-4-yl)amino)-5-fluoropyrimidin-4-yl)oxy)methyl)cyclohexan-1-ol | (CD$_3$OD) δ = 8.05 (d, J = 3.2 Hz, 1H), 7.80 (s, 1H), 7.47 (t, J = 58.4 Hz, 1H), 4.26-4.28 (m, 2H), 3.49-3.56 (m, 1H), 2.40 (s, 3H), 1.77-2.02 (m, 5H), 1.12-1.35 (m, 4H). LCMS: 372.1 [M + H] |
| 236 | 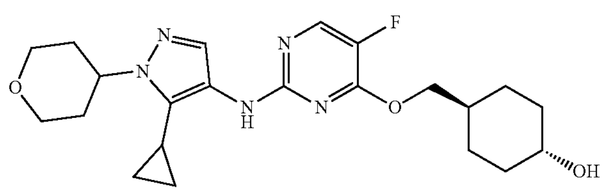 [SMILES: O[C@H]1CC[C@H](COc2nc(Nc3cnn(C4CCOCC4)c3C3CC3)ncc2F)CC1] | (1R,4R)-4-(((2-((5-cyclopropyl-1-(tetrahydro-2H-pyran-4-yl)-1H-pyrazol-4-yl)amino)-5-fluoropyrimidin-4-yl)oxy)methyl)cyclohexan-1-ol | (CD$_3$OD) δ = 8.08 (d, J = 3.6 Hz, 1H), 7.56 (s, 1H), 4.20-4.78 (m, 1H), 4.36 (d, J = 5.2 Hz, 2H), 4.09-4.13 (m, 2H), 3.54-3.66 (m, 3H), 2.24-2.28 (m, 2H), 1.77-2.05 (m, 8H), 1.20-1.33 (m, 4H), 1.00-1.04 (m, 2H), 0.73-0.75 (m, 2H). LCMS: 432.2 [M + H] |
| 237 | 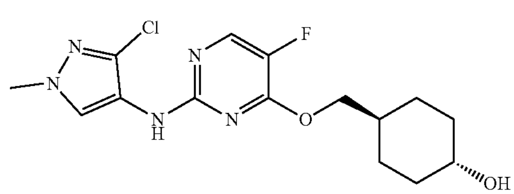 [SMILES: Cn1cc(Nc2ncc(F)c(OC[C@H]3CC[C@H](O)CC3)n2)c(Cl)n1] | (1R,4R)-4-(((2-((3-chloro-1-methyl-1H-pyrazol-4-yl)amino)-5-fluoropyrimidin-4-yl)oxy)methyl)cyclohexan-1-ol | (CD$_3$OD) δ = 8.06 (d, J = 3.6 Hz, 1H), 7.91 (s, 1H), 4.29 (d, J = 6.4 Hz, 2H), 3.87 (s, 3H), 3.51-3.56 (m, 1H), 1.82-2.03 (m, 5H), 1.17-1.32 (m, 4H). LCMS: 356.1 [M + H] |

-continued

| Example | Structure | Name | †Spectral data |
|---|---|---|---|
| 238 | 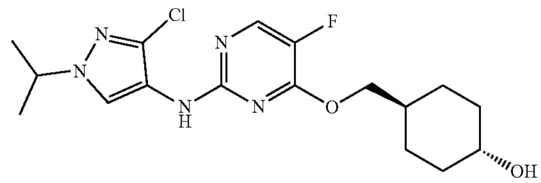 [SMILES: CC(C)n1cc(Nc2ncc(F)c(OC[C@H]3CC[C@H](O)CC3)n2)c(Cl)n1] | (1R,4R)-4-(((2-((3-chloro-1-isopropyl-1H-pyrazol-4-yl)amino)-5-fluoropyrimidin-4-yl)oxy)methyl)cyclohexan-1-ol | (CD$_3$OD) δ = 8.02 (d, J = 3.2 Hz, 1H), 7.96 (s, 1H), 4.41-4.48 (m, 1H), 4.23 (d, J = 6.4 Hz, 2H), 3.50-3.55 (m, 1H), 1.79-2.03 (m, 5H), 1.50 (d, J = 6.8 Hz, 6H), 1.14-1.35 (m, 4H). LCMS: 384.1 [M + H] |
| 239 | 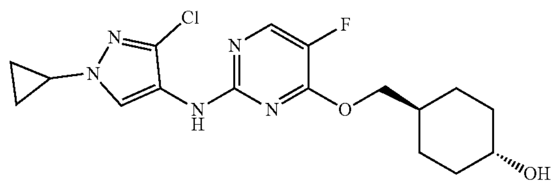 [SMILES: O[C@H]1CC[C@H](COc2nc(Nc3cn(C4CC4)nc3Cl)ncc2F)CC1] | (1R,4R)-4-(((2-((3-chloro-1-cyclopropyl-1H-pyrazol-4-yl)amino)-5-fluoropyrimidin-4-yl)oxy)methyl)cyclohexan-1-ol | (CD$_3$OD) δ = 8.03 (d, J = 3.2 Hz, 1H), 7.99 (s, 1H), 4.25 (d, J = 6.8 Hz, 2H), 3.61-3.65 (m, 1H), 3.50-3.54 (m, 1H), 1.79-2.03 (m, 5H), 1.01-1.36 (m, 8H). LCMS: 382.1 [M + H] |
| 240 | 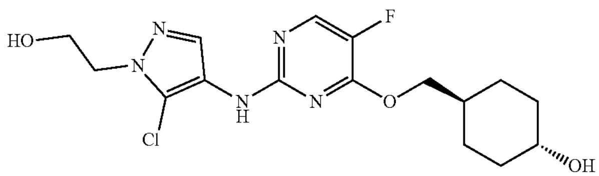 [SMILES: OCCn1ncc(Nc2ncc(F)c(OC[C@H]3CC[C@H](O)CC3)n2)c1Cl] | (1R,4R)-4-(((2-((5-chloro-1-(2-hydroxyethyl)-1H-pyrazol-4-yl)amino)-5-fluoropyrimidin-4-yl)oxy)methyl)cyclohexan-1-ol | (CD$_3$OD) δ = 7.98 (d, J = 3.6 Hz, 1H), 7.78 (s, 1H), 4.23-4.28 (m, 4H), 3.90-3.93 (m, 2H), 3.50-3.56 (m, 1H), 1.99-2.03 (m, 2H), 1.88-1.91 (m, 2H), 1.79-1.81 (m, 1H), 1.15-1.32 (m, 4H). LCMS: 386.2 [M + H] |
| 241 | 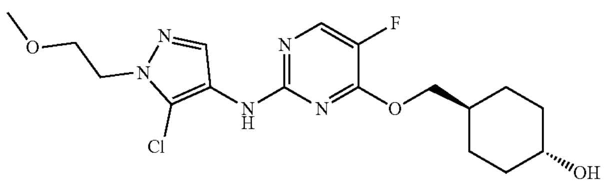 [SMILES: COCCn1ncc(Nc2ncc(F)c(OC[C@H]3CC[C@H](O)CC3)n2)c1Cl] | (1R,4R)-4-(((2-((5-chloro-1-(2-methoxyethyl)-1H-pyrazol-4-yl)amino)-5-fluoropyrimidin-4-yl)oxy)methyl)cyclohexan-1-ol | (CD$_3$OD) δ = 8.06 (d, J = 3.60 Hz, 1H), 7.80 (s, 1H), 4.34 (t, J = 5.20 Hz, 2H), 4.28 (d, J = 6.40 Hz, 2H), 3.79 (t, J = 5.20 Hz, 2H), 3.50-3.57 (m, 1H), 3.33 (s, 3H), 1.78-2.03 (m, 5H), 1.13-1.35 (m, 4H). LCMS: 400.2 [M + H] |
| 242 | 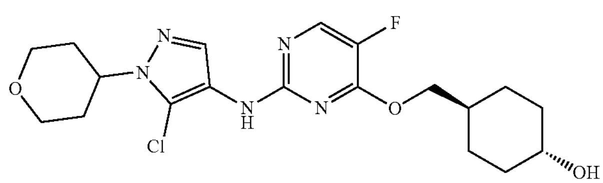 [SMILES: O[C@H]1CC[C@H](COc2nc(Nc3cnn(C4CCOCC4)c3Cl)ncc2F)CC1] | (1R,4R)-4-(((2-((5-chloro-1-(tetrahydro-2H-pyran-4-yl)-1H-pyrazol-4-yl)amino)-5-fluoropyrimidin-4-yl)oxy)methyl)cyclohexan-1-ol | (CD$_3$OD) δ = 8.05 (d, J = 3.6 Hz, 1H), 7.80 (s, 1H), 4.58-4.63 (m, 1H), 4.27 (d, J = 6.4 Hz, 2H), 4.08-4.12 (m, 2H), 3.58-3.65 (m, 3H), 1.87-2.24 (m, 9H), 1.18-1.28 (m, 4H). LCMS: 426.3 [M + H] |
| 243 | 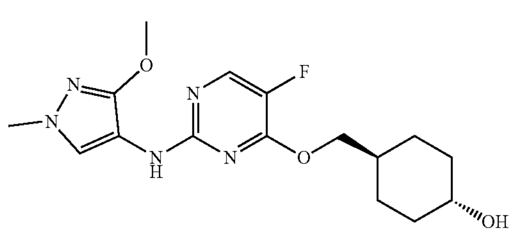 [SMILES: COc1nn(C)cc1Nc1ncc(F)c(OC[C@H]2CC[C@H](O)CC2)n1] | (1R,4R)-4-(((5-fluoro-2-((3-methoxy-1-methyl-1H-pyrazol-4-yl)amino)pyrimidin-4-yl)oxy)methyl)cyclohexan-1-ol | (CD$_3$OD) δ = 8.05 (d, J = 4.0 Hz, 1H), 7.65 (s, 1H), 4.34 (d, J = 6.4 Hz, 2H), 3.92 (s, 3H), 3.76 (s, 3H), 3.51-3.56 (m, 1H), 1.84-2.03 (m, 5H), 1.18-1.33 (m, 4H). LCMS: 352.3 [M + H] |

-continued

| Example | Structure | Name | †Spectral data |
|---|---|---|---|
| 244 | 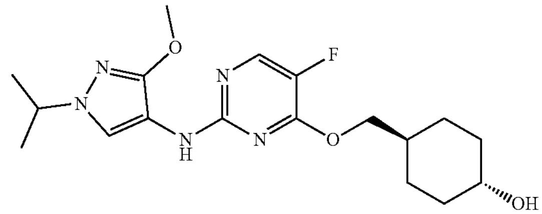 [SMILES: COc1nn(C(C)C)cc1Nc1ncc(F)c(OC[C@H]2CC[C@H](O)CC2)n1] | (1R,4R)-4-(((5-fluoro-2-((1-isopropyl-3-methoxy-1H-pyrazol-4-yl)amino)pyrimidin-4-yl)oxy)methyl)cyclohexan-1-ol | (DMSO-$d_6$) δ = 8.38 (s, 1H), 8.14 (d, J = 3.2 Hz, 1H), 7.69 (s, 1H), 4.23-4.30 (m, 1H), 4.15 (d, J = 6.4 Hz, 2H), 3.37 (s, 3H), 3.32-3.36 (m, 1H), 1.68-1.86 (m, 5H), 1.33-1.37 (m, 6H), 1.00-1.19 (m, 4H). LCMS: 380.3 [M + H] |
| 245 | 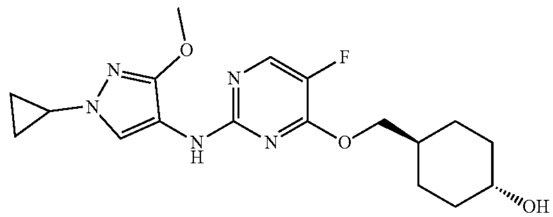 [SMILES: COc1nn(C2CC2)cc1Nc1ncc(F)c(OC[C@H]2CC[C@H](O)CC2)n1] | (1R,4R)-4-(((2-((1-cyclopropyl-3-methoxy-1H-pyrazol-4-yl)amino)-5-fluoropyrimidin-4-yl)oxy)methyl)cyclohexan-1-ol | (DMSO-$d_6$) δ = 8.42 (bs, 1H), 8.14 (d, J = 3.2 Hz, 1H), 7.68 (s, 1H), 4.15 (d, J = 6.4 Hz, 2H), 3.78 (s, 3H), 3.45-3.49 (m, 1H), 3.32-3.38 (m, 1H), 1.69-1.86 (m, 5H), 1.01-1.16 (m, 4H), 0.85-0.94 (m, 4H). LCMS: 378.1 [M + H] |
| 246 | 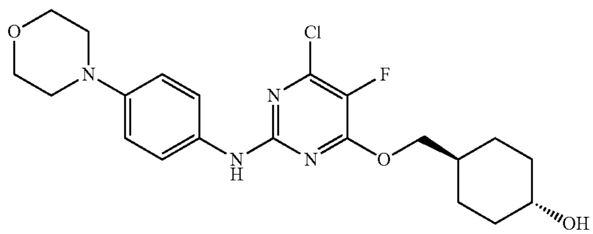 [SMILES: O[C@H]1CC[C@H](COc2nc(Nc3ccc(N4CCOCC4)cc3)nc(Cl)c2F)CC1] | (1R,4R)-4-(((6-chloro-5-fluoro-2-((4-morpholinophenyl)amino)pyrimidin-4-yl)oxy)methyl)cyclohexan-1-ol | (CD$_3$OD) δ = 7.47 (d, J = 9.2 Hz, 2H), 6.98 (d, J = 9.2 Hz, 2H), 4.20 (d, J = 6.4 Hz, 2H), 3.85-3.87 (m, 4H), 3.50-3.56 (m, 1H), 3.13-3.15 (m, 4H), 2.01-2.03 (m, 2H), 1.90-1.93 (m, 2H), 1.77-1.78 (m, 1H), 1.19-1.36 (m, 4H). LCMS: 437.1 [M + H] |
| 247 | 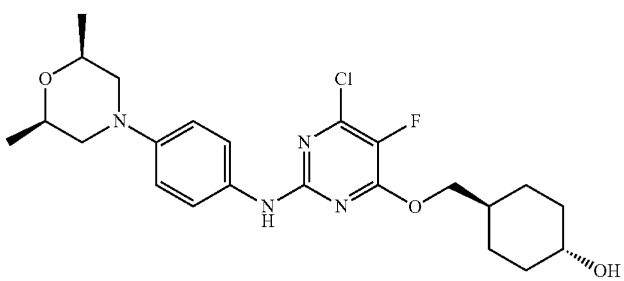 [SMILES: C[C@@H]1CN(c2ccc(Nc3nc(Cl)c(F)c(OC[C@H]4CC[C@H](O)CC4)n3)cc2)C[C@H](C)O1] | (1R,4R)-4-(((6-chloro-2-((4-((2S,6R)-2,6-dimethylmorpholino)phenyl)amino)-5-fluoropyrimidin-4-yl)oxy)methyl)cyclohexan-1-ol | (CD$_3$OD) δ = 7.44-7.48 (m, 2H), 6.95-6.99 (m, 2H), 4.20 (d, J = 6.8 Hz, 2H), 3.80-3.85 (m, 2H), 3.49-3.56 (m, 3H), 2.31-2.37 (m, 2H), 2.00-2.05 (m, 2H), 1.90-1.93 (m, 2H), 1.77-1.78 (m, 1H), 1.22-1.33 (m, 10H). LCMS: 465.3 [M + H] |
| 248 | 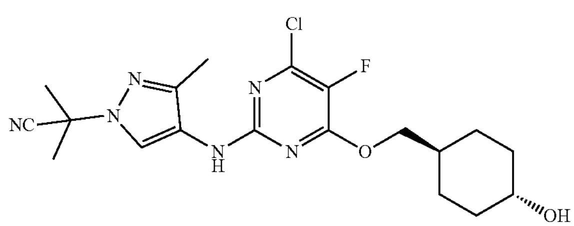 [SMILES: Cc1nn(C(C)(C)C#N)cc1Nc1nc(Cl)c(F)c(OC[C@H]2CC[C@H](O)CC2)n1] | 2-(4-((4-chloro-5-fluoro-6-(((1R,4R)-4-hydroxycyclohexyl)methoxy)pyrimidin-2-yl)amino)-3-methyl-1H-pyrazol-1-yl)-2-methylpropanenitrile | (CD$_3$OD) δ = 7.98 (s, 1H), 4.21 (d, J = 6.4 Hz, 2H), 3.50-3.56 (m, 1H), 2.22 (s, 3H), 1.90-2.03 (m, 10H), 1.76-1.80 (m, 1H), 1.22-1.36 (m, 4H). LCMS: 423.1 [M + H] |
| 249 | 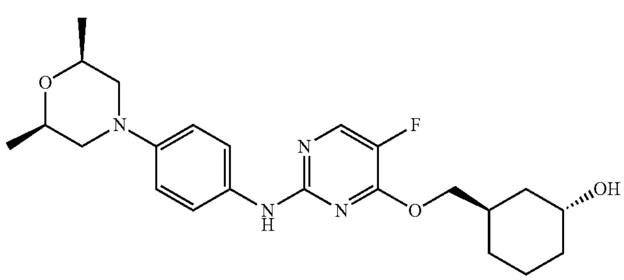 [SMILES: C[C@@H]1CN(c2ccc(Nc3ncc(F)c(OC[C@@H]4CCC[C@@H](O)C4)n3)cc2)C[C@H](C)O1] | (1R,3R)-3-(((2-((4-((2S,6R)-2,6-dimethylmorpholino)phenyl)amino)-5-fluoropyrimidin-4-yl)oxy)methyl)cyclohexan-1-ol | (CD$_3$OD) δ = 8.13 (s, 1H), 7.78 (d, J = 9.2 Hz, 2H), 7.43 (d, J = 9.2 Hz, 2H), 4.36 (d, J = 6.4 Hz, 2H), 3.98-4.03 (m, 2H), 3.58-3.63 (m, 3H), 3.04-3.09 (m, 2H), 1.81-2.09 (m, 5H), 1.23-1.41 (m, 8H), 1.03-1.10 (m, 2H). LCMS: 431.2 [M + H] |

| Example | Structure | Name | †Spectral data |
|---|---|---|---|
| 250 | 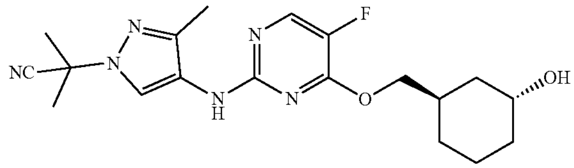 [SMILES: Cc1nn(C(C)(C)C#N)cc1Nc1ncc(F)c(OC[C@@H]2CCC[C@@H](O)C2)n1] | 2-(4-((5-fluoro-4-(((1R,3R)-3-hydroxy-cyclohexyl)methoxy)pyrimidin-2-yl)amino)-3-methyl-1H-pyrazol-1-yl)-2-methyl-propanenitrile | (CD$_3$OD) δ = 8.07-8.11 (m, 2H), 4.34-4.36 (m, 2H), 3.56-3.60 (m, 1H), 2.25 (s, 3H), 1.79-2.11 (m, 11H), 1.02-1.41 (m, 4H). LCMS: 389.2 [M + H] |
| 135 | 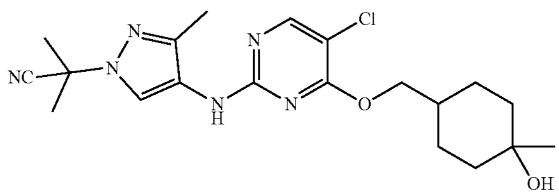 [SMILES: Cc1nn(C(C)(C)C#N)cc1Nc1ncc(Cl)c(OCC2CCC(C)(O)CC2)n1] | 2-(4-((5-chloro-4-((4-hydroxy-4-methyl-cyclohexyl)methoxy)pyrimidin-2-yl)amino)-3-methyl-1H-pyrazol-1-yl)-2-methyl-propanenitrile | (CD$_3$OD) δ = 8.10 (s, 1H), 8.08 (s, 1H), 4.30 (d, J = 6.8 Hz, 2H), 2.24 (s, 3H), 1.99 (s, 6H), 1.65-1.83 (m, 5H), 1.42-1.56 (m, 4H), 1.22 (s, 3H). LCMS: 419.1 [M + H] |
| 251 | 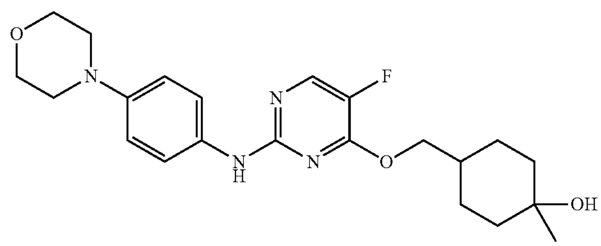 [SMILES: CC1(O)CCC(COc2nc(Nc3ccc(N4CCOCC4)cc3)ncc2F)CC1] | 4-(((5-fluoro-2-((4-morpholino-phenyl)amino)pyrimidin-4-yl)oxy)methyl)-1-methyl cyclohexan-1-ol | (CD$_3$OD) δ = 8.12 (d, J = 3.2 Hz, 1H), 7.72 (d, J = 8.8 Hz, 2H), 7.37 (d, J = 9.2 Hz, 2H), 4.37 (d, J = 6.4 Hz, 2H), 3.99-4.01 (m, 4H), 3.49-3.51 (m, 4H), 1.84-1.92 (m, 3H), 1.71-1.74 (m, 2H), 1.49-1.56 (m, 2H), 1.26-1.35 (m, 2H), 1.25 (s, 3H). LCMS: 417.5 [M + H] |
| 252 | 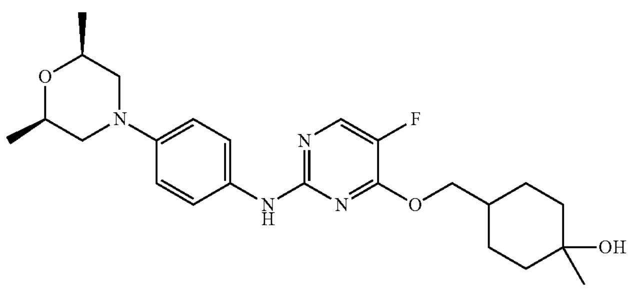 [SMILES: C[C@@H]1CN(c2ccc(Nc3ncc(F)c(OCC4CCC(C)(O)CC4)n3)cc2)C[C@H](C)O1] | 4-(((2-((4-((2S,6R)-2,6-dimethyl-morpholino)phenyl)amino)-5-fluoro-pyrimidin-4-yl)oxy)methyl)-1-methyl-cyclohexan-1-ol | (DMSO-d$_6$) δ = 9.34 (bs, 1H), 8.22 (d, J = 2.8 Hz, 1H), 7.55 (d, J = 8.8 Hz, 2H), 6.94 (d, J = 8.0 Hz, 2H), 4.26 (d, J = 6.8 Hz, 2H), 3.71-3.74 (m, 2H), 3.47-3.50 (m, 2H), 2.28-2.34 (m, 2H), 1.71-1.80 (m, 3H), 1.54-1.58 (m, 2H), 1.34-1.41 (m, 2H), 1.19-1.21 (m, 11H). LCMS: 445.2 [M + H] |
| 253 | 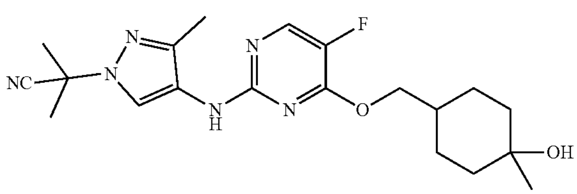 [SMILES: Cc1nn(C(C)(C)C#N)cc1Nc1ncc(F)c(OCC2CCC(C)(O)CC2)n1] | 2-(4-((5-fluoro-4-((4-hydroxy-4-methyl-cyclohexyl)methoxy)pyrimidin-2-yl)amino)-3-methyl-1H-pyrazol-1-yl)-2-methyl-propanenitrile | (CD$_3$OD) δ = 8.11 (s, 1H), 8.07 (d, J = 3.6 Hz, 1H), 4.36 (d, J = 6.4 Hz, 2H), 2.25 (s, 3H), 2.00 (s, 6H), 1.83-1.92 (m, 3H), 1.71-1.75 (m, 2H), 1.49-1.57 (m, 2H), 1.24-1.34 (m, 5H). LCMS: 403.5 [M + H] |
| 136 | 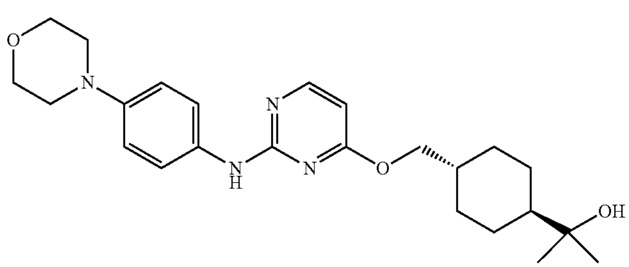 [SMILES: CC(C)(O)[C@H]1CC[C@H](COc2ccnc(Nc3ccc(N4CCOCC4)cc3)n2)CC1] | 2-((1R,4R)-4-(((2-((4-morpholino-phenyl)amino)pyrimidin-4-yl)oxy)methyl)cyclohexyl)propan-2-ol | (DMSO-d$_6$) δ = 9.23 (bs, 1H), 8.12 (d, J = 5.6 Hz, 1H), 7.59 (d, J = 8.8 Hz, 2H), 6.88 (d, J = 9.2 Hz, 2H), 6.18 (d, J = 5.6 Hz, 1H), 4.01-4.12 (m, 3H), 3.72-3.75 (m, 4H), 3.01-3.04 (m, 4H), 1.68-1.85 (m, 4H), 0.97-1.03 (m, 11H). LCMS: 427.2 [M + H] |

| Example | Structure | Name | †Spectral data |
|---|---|---|---|
| 137 | 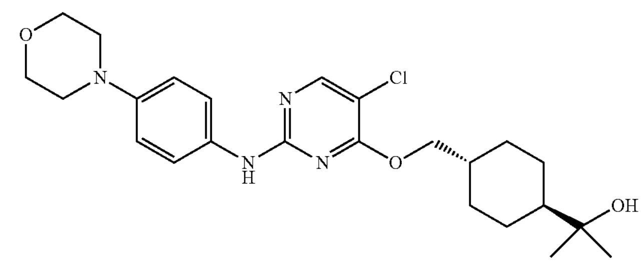 | 2-((1R,4R)-4-(((5-chloro-2-((4-morpholinophenyl)amino)pyrimidin-4-yl)oxy)methyl)cyclohexyl)propan-2-ol | (DMSO-d$_6$) δ = 9.45 (bs, 1H), 8.22 (s, 1H), 7.54 (d, J = 8.8 Hz, 2H), 6.89 (d, J = 9.2 Hz, 2H), 4.21 (d, J = 6.8 Hz, 2H), 4.02 (s, 1H), 3.73-3.74 (m, 4H), 3.02-3.04 (m, 4H), 1.68-1.85 (m, 4H), 0.91-1.30 (m, 11H). LCMS: 461.3 [M + H] |
| 138 | 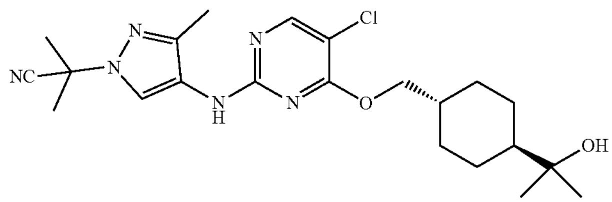 [SMILES: Cc1nn(C(C)(C)C#N)cc1Nc1ncc(Cl)c(OC[C@H]2CC[C@H](C(C)(C)O)CC2)n1] | 2-(4-((5-chloro-4-(((1R,4R)-4-(2-hydroxypropan-2-yl)cyclohexyl)methoxy)pyrimidin-2-yl)amino)-3-methyl-1H-pyrazol-1-yl)-2-methylpropanenitrile | (CDCl$_3$) δ = 8.16 (s, 1H), 8.12 (s, 1H), 4.25 (d, J = 6.4 Hz, 2H), 2.31 (s, 3H), 1.84-2.07 (m, 10H), 1.12-1.25 (m, 12H). LCMS: 447.2 [M + H] |
| 139 | 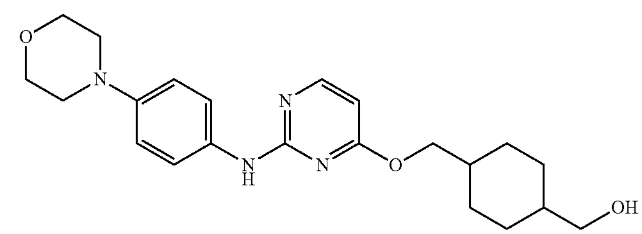 [SMILES: OCC1CCC(COc2ccnc(Nc3ccc(N4CCOCC4)cc3)n2)CC1] | (4-(((2-((4-morpholinophenyl)amino)pyrimidin-4-yl)oxy)methyl)cyclohexyl)methanol22 | (CD$_3$OD) δ = 7.95 (d, J = 6.8 Hz, 1H), 7.38 (d, J = 8.8 Hz, 2H), 7.12 (d, J = 8.8 Hz, 2H), 6.48 (d, J = 7.2 Hz, 1H), 4.32-4.46 (m, 3H), 3.86-3.89 (m, 4H), 3.39-3.49 (m, 2H), 3.23-3.25 (m, 4H), 1.82-1.91 (m, 4H), 1.45-1.63 (m, 2H), 1.00-1.32 (m, 3H). LCMS: 398.9 [M + H] |
| 140 | 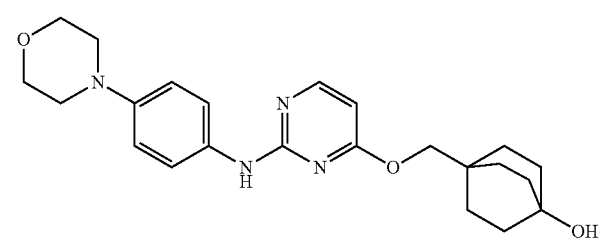 [SMILES: OC12CCC(COc3ccnc(Nc4ccc(N5CCOCC5)cc4)n3)(CC1)CC2] | 4-(((2-((4-morpholinophenyl)amino)pyrimidin-4-yl)oxy)methyl)bicyclo[2.2.2]octan-1-ol | (CD$_3$OD) δ = 7.95 (d, J = 7.2 Hz, 1H), 7.37 (d, J = 8.8 Hz, 2H), 7.13 (d, J = 15.6 Hz, 2H), 6.48 (d, J = 6.8 Hz, 1H), 4.15 (bs, 2H), 3.87-3.89 (m, 4H), 3.23-3.26 (m, 4H), 1.69 (bs, 12H). LCMS: 411.1 [M + H] |
| 141 | 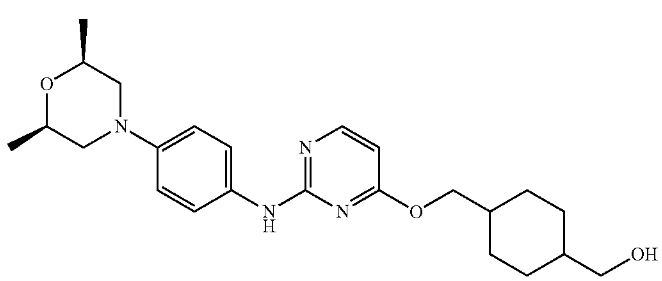 [SMILES: C[C@@H]1CN(c2ccc(Nc3nccc(OCC4CCC(CO)CC4)n3)cc2)C[C@H](C)O1] | (4-(((2-((4-((2R,6S)-2,6-dimethylmorpholino)phenyl)amino)pyrimidin-4-yl)oxy)methyl)cyclohexyl)methanol | (CD$_3$OD) δ = 8.03 (d, J = 5.6 Hz, 1H), 7.48-7.51 (m, 2H), 6.95-6.97 (m, 2H), 6.16 (d, J = 5.6 Hz, 1H), 4.18 (d, J = 6.4 Hz, 2H), 3.80-3.85 (m, 2H), 3.37-3.49 (m, 5H), 2.30-2.35 (m, 2H), 1.46-1.93 (m, 5H), 1.24-1.26 (m, 6H), 0.99-1.14 (m, 4H). LCMS: 427.1 [M + H] |

| Example | Structure | Name | †Spectral data |
|---|---|---|---|
| 142 | 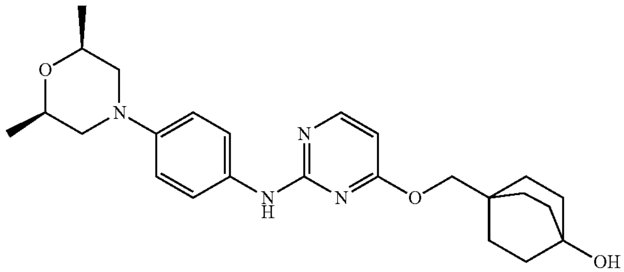 [SMILES: C[C@@H]1CN(c2ccc(Nc3nccc(OCC45CCC(O)(CC4)CC5)n3)cc2)C[C@H](C)O1] | 4-(((2-((4-((2S,6R)-2,6-dimethyl-morpholino)phenyl)amino)pyrimidin-4-yl)oxy)methyl)bicyclo[2.2.2]octan-1-ol | (CD$_3$OD) δ = 7.94 (d, J = 7.2 Hz, 1H), 7.35-7.38 (m, 2H), 7.12-7.15 (m, 2H), 6.48 (d, J = 6.8 Hz, 1H), 4.15 (s, 2H), 3.80-3.88 (m, 2H), 3.61-3.63 (m, 2H), 2.43-2.49 (m, 2H), 1.70 (bs, 12H), 1.27 (d, J = 6.40 Hz, 6H). LCMS: 439.3 [M + H] |
| 143 | 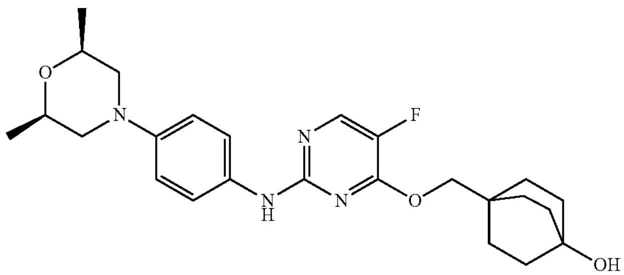 [SMILES: C[C@@H]1CN(c2ccc(Nc3ncc(F)c(OCC45CCC(O)(CC4)CC5)n3)cc2)C[C@H](C)O1] | 4-(((2-((4-((2S,6R)-2,6-dimethyl-morpholino)phenyl)amino)-5-fluoro-pyrimidin-4-yl)oxy)methyl)bicyclo[2.2.2]octan-1-ol | (CD$_3$OD) δ = 8.12 (d, J = 2.8 Hz, 1H), 7.77 (d, J = 8.8 Hz, 2H), 7.42 (d, J = 7.6 Hz, 2H), 4.14 (s, 2H), 3.97-4.04 (m, 2H), 3.60-3.63 (m, 2H), 3.03-3.06 (m, 2H), 1.69-1.72 (m, 12H), 1.31 (d, J = 6.4 Hz, 6H). LCMS: 457.0 [M + H] |
| 144 | 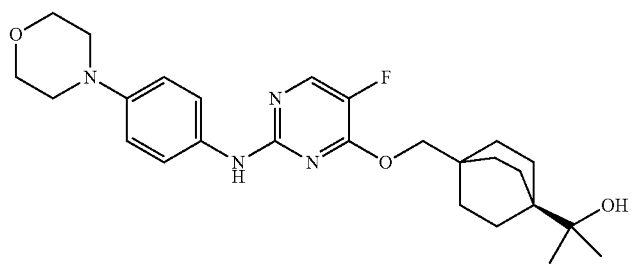 | 2-((1R,4R)-4-(((5-fluoro-2-((4-morpholino-phenyl)amino)pyrimidin-4-yl)oxy)methyl)cyclohexyl)propan-2-ol | (CD$_3$OD) δ = 8.11 (d, J = 3.2 Hz, 1H), 7.71 (d, J = 8.4 Hz, 2H), 7.34 (d, J = 7.6 Hz, 2H), 4.32 (d, J = 6.4 Hz, 2H), 3.98-4.00 (m, 4H), 3.48 (bs, 4H), 1.84-2.05 (m, 5H), 1.12-1.33 (m, 11H). LCMS: 445.4 [M + H] |
| 254 | 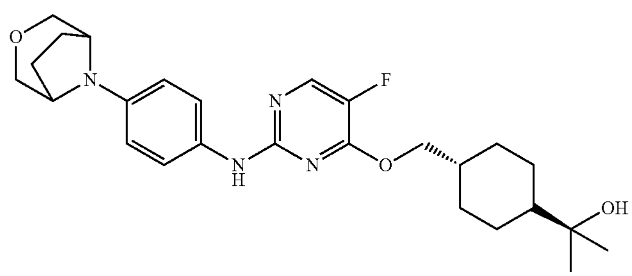 | 2-((1S,4S)-4-(((2-((4-(3-oxa-8-azabicyclo[3.2.1]octan-8-yl)phenyl)amino)-5-fluoro-pyrimidin-4-yl)oxy)methyl)cyclohexyl)propan-2-ol | (CD$_3$OD) δ = 7.98 (d, J = 3.2 Hz, 1H), 7.44 (d, J = 9.2 Hz, 2H), 6.87 (d, J = 8.8 Hz, 2H), 4.24 (d, J = 6.4 Hz, 2H), 4.07 (bs, 2H), 3.90-3.92 (m, 2H), 3.53-3.55 (m, 2H), 1.93-2.05 (m, 8H), 1.80-1.80 (m, 1H), 1.29-1.31 (m, 1H), 1.05-1.15 (m, 10H). LCMS: 471.3 [M + H] |
| 255 | 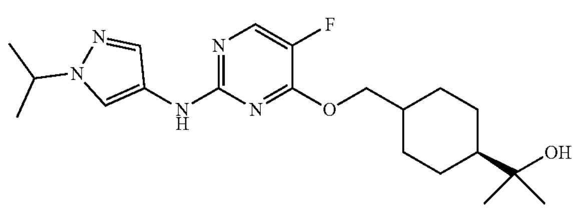 | 2-((1R,4R)-4-(((5-fluoro-2-((1-isopropyl-1H-pyrazol-4-yl)amino)pyrimidin-4-yl)oxy)methyl)cyclohexyl)propan-2-ol | (CD$_3$OD) δ = 8.06 (d, J = 3.6 Hz, 1H), 7.92 (s, 1H), 7.58 (s, 1H), 4.47-4.52 (m, 1H), 4.31 (d, J = 6.4 Hz, 2H), 1.94 (s, 5H), 1.50-1.52 (m, 6H), 1.30-1.33 (m, 1H), 1.11-1.16 (m, 10H). LCMS: 392.2 [M + H] |
| 256 | 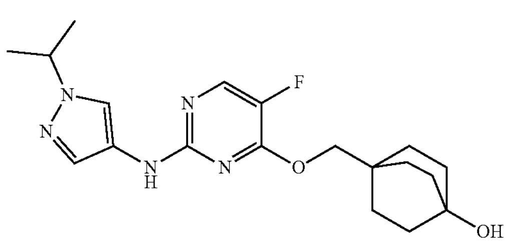 [SMILES: CC(C)n1cc(Nc2ncc(F)c(OCC34CCC(O)(CC3)CC4)n2)cn1] | 4-(((5-fluoro-2-((1-isopropyl-1H-pyrazol-4-yl)amino)pyrimidin-4-yl)oxy)methyl)bicyclo[2.2.2]octan-1-ol | (CD$_3$OD) δ = 8.07 (d, J = 3.6 Hz, 1H), 7.93 (s, 1H), 7.57 (s, 1H), 4.47-4.54 (m, 1H), 4.15 (s, 2H), 1.69-1.74 (m, 12H), 1.51 (d, J = 6.8 Hz, 6H). LCMS: 376.2 [M + H] |

| Example | Name | †Spectral data |
|---|---|---|
| 257 | 2-(4-((5-fluoro-4-((4-hydroxy-bicyclo[2.2.2]octan-1-yl)methoxy)pyrimidin-2-yl)amino)-3-methyl-1H-pyrazol-1-yl)-2-methyl-propanenitrile | (CD₃OD) δ = 8.11 (s, 1H), 8.07 (d, J = 3.6 Hz, 1H), 4.14 (s, 2H), 2.24 (s, 3H), 2.00 (s, 6H), 1.71 (bs, 12H). LCMS: 415.2 [M + H] |
| 258 | (1R,2R,4S)-2-fluoro-4-(((5-fluoro-2-((4-morpholino-phenyl)amino)pyrimidin-4-yl)oxy)methyl)cyclohexan-1-ol | (CD₃OD) δ = 8.15 (d, J = 2.8 Hz, 1H), 7.76 (d, J = 8.4 Hz, 2H), 7.40 (bs, 2H), 5.42-5.45 (m, 1H), 5.00-5.01 (m, 1H), 4.00-4.03 (m, 4H), 3.47-3.53 (m, 6H), 1.95-2.02 (m, 4H), 1.47-1.71 (m, 3H). LCMS: 421.2 [M + H] |
| 259 | 2-(4-((5-fluoro-4-((1S,3R,4R)-3-fluoro-4-hydroxy-cyclohexyl)methoxy)pyrimidin-2-yl)amino)-3-methyl-1H-pyrazol-1-yl)-2-methyl-propanenitrile | LCMS: 407.5 [M + H] |
| 260 | 4-(((5-fluoro-2-((4-morpholino-phenyl)amino)pyrimidin-4-yl)oxy)methyl)-1-(trifluoro-methyl)cyclohexan-1-ol | (CD₃OD) δ = 8.01 (d, J = 3.2 Hz, 1H), 7.49 (d, J = 8.8 Hz, 2H), 6.96 (d, J = 8.8 Hz, 2H), 4.30 (d, J = 6.4 Hz, 2H), 3.84-3.87 (m, 4H), 3.09-3.12 (m, 4H), 1.77-1.90 (m, 5H), 1.51-1.68 (m, 4H). LCMS: 471.5 [M + H] |
| 261 | 4-(((2-((4-((2S,6R)-2,6-dimethyl-morpholino)phenyl)amino)-5-fluoro-pyrimidin-4-yl)oxy)methyl)-1-(trifluoro-methyl)cyclohexan-1-ol | (CD₃OD) δ = 8.01 (d, J = 3.2 Hz, 1H), 7.47-7.49 (m, 2H), 6.94-6.96 (m, 2H), 4.30 (d, J = 6.8 Hz, 2H), 3.80-3.85 (m, 2H), 3.45-3.47 (m, 2H), 2.29-2.35 (m, 2H), 1.87-1.90 (m, 3H), 1.77-1.80 (m, 2H), 1.50-1.67 (m, 4H), 1.23-1.25 (m, 6H). LCMS: 499.2 [M + H] |
| 262 | 2-(4-((5-fluoro-4-((4-hydroxy-4-(trifluoro-methyl)cyclohexyl)methoxy)pyrimidin-2-yl)amino)-3-methyl-1H-pyrazol-1-yl)- | (CD₃OD) δ = 8.11 (s, 1H), 8.07 (d, J = 3.6 Hz, 1H), 4.35 (d, J = 6.8 Hz, 2H), 2.25 (s, 3H), 2.00 (s, 6H), 1.78-1.91 (m, 5H), 1.51-1.69 (m, 4H). LCMS: 457.5 [M + H] |

| Example | Structure | Name | †Spectral data |
|---|---|---|---|
| 263 | 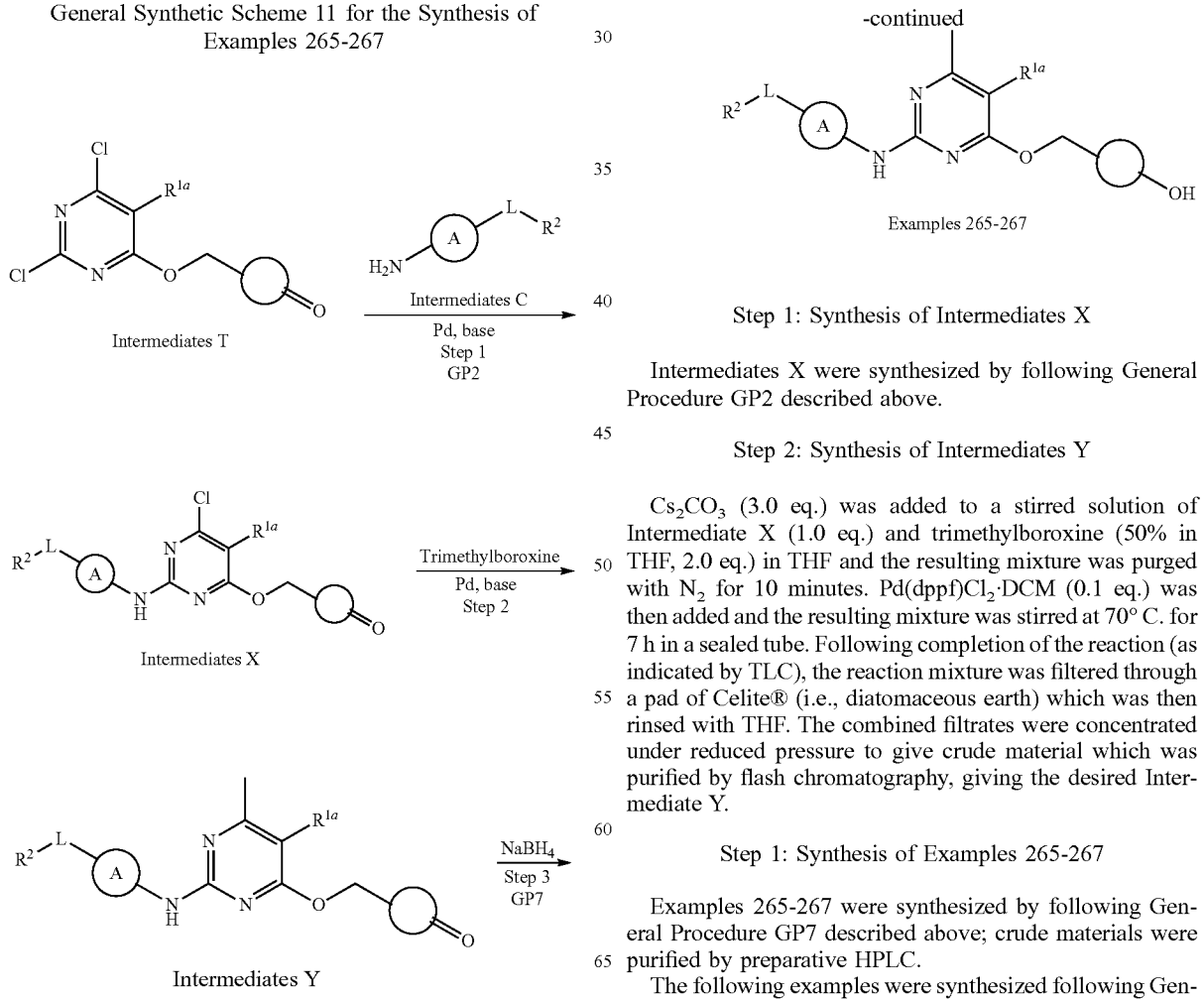 | 2-(4-((5-fluoro-4-((4-hydroxycycloheptyl)methoxy)pyrimidin-2-yl)amino)-3-methyl-1H-pyrazol-1-yl)-2-methylpropanenitrile | LCMS: 403.3 [M + H] (first eluting peak) |
| 264 | 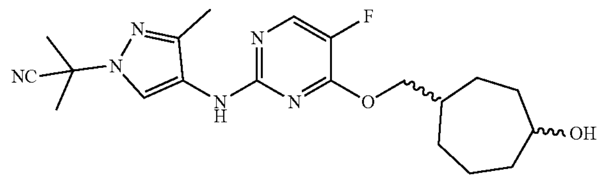 [SMILES: Cc1nn(C(C)(C)C#N)cc1Nc1ncc(F)c(OCC2CCCC(O)CC2)n1] | 2-(4-((5-fluoro-4-((4-hydroxycycloheptyl)methoxy)pyrimidin-2-yl)amino)-3-methyl-1H-pyrazol-1-yl)-2-methylpropanenitrile | LCMS: 403.2 [M + H] (Second eluting peak) |

†All ¹H NMR recorded at 400 MHz

General Synthetic Scheme 11 for the Synthesis of Examples 265-267

Step 1: Synthesis of Intermediates X

Intermediates X were synthesized by following General Procedure GP2 described above.

Step 2: Synthesis of Intermediates Y $Cs_2CO_3$ (3.0 eq.) was added to a stirred solution of Intermediate X (1.0 eq.) and trimethylboroxine (50% in THF, 2.0 eq.) in THF and the resulting mixture was purged with $N_2$ for 10 minutes. $Pd(dppf)Cl_2 \cdot DCM$ (0.1 eq.) was then added and the resulting mixture was stirred at 70° C. for 7 h in a sealed tube. Following completion of the reaction (as indicated by TLC), the reaction mixture was filtered through a pad of Celite® (i.e., diatomaceous earth) which was then rinsed with THF. The combined filtrates were concentrated under reduced pressure to give crude material which was purified by flash chromatography, giving the desired Intermediate Y.

Step 1: Synthesis of Examples 265-267

Examples 265-267 were synthesized by following General Procedure GP7 described above; crude materials were purified by preparative HPLC.

The following examples were synthesized following General Synthetic Scheme 11:

| Example | Structure | Name | †Spectral data |
|---|---|---|---|
| 265 | 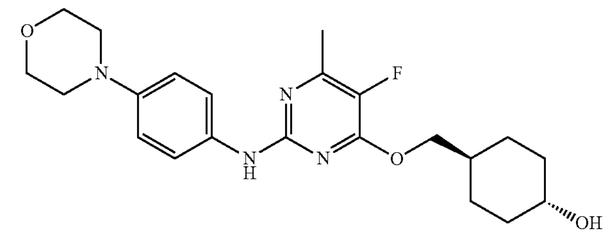 [SMILES: Cc1nc(Nc2ccc(N3CCOCC3)cc2)nc(OC[C@H]2CC[C@H](O)CC2)c1F] | (1R,4R)-4-(((5-fluoro-6-methyl-2-((4-morpholinophenyl)amino)pyrimidin-4-yl)oxy)methyl)cyclohexan-1-ol | (DMSO-$d_6$) δ = 9.28 (bs, 1H), 7.58 (d, J = 8.8 Hz, 2H), 6.95 (d, J = 8.0 Hz, 2H), 4.21 (d, J = 6.0 Hz, 2H), 3.76 (bs, 4H), 3.06 (bs, 4H), 3.50-3.56 (m, 1H), 2.28 (s, 3H), 1.73-1.90 (m, 5H), 1.14-1.23 (m, 4H). LCMS: 417.2 [M + H] |
| 266 | 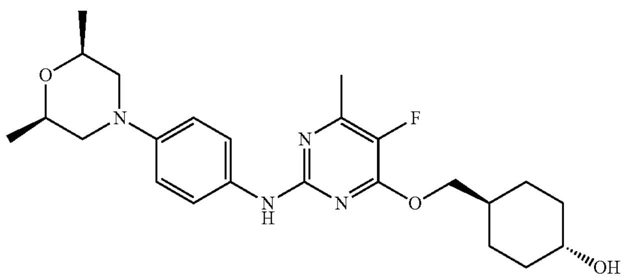 [SMILES: Cc1nc(Nc2ccc(N3C[C@@H](C)O[C@@H](C)C3)cc2)nc(OC[C@H]2CC[C@H](O)CC2)c1F] | (1R,4R)-4-(((2-((2S,6R)-2,6-dimethylmorpholino)phenyl)amino)-5-fluoro-6-methylpyrimidin-4-yl)oxy)methyl)cyclohexan-1-ol | (DMSO-$d_6$) δ = 9.24 (bs, 1H), 7.56 (d, J = 8.4 Hz, 2H), 6.93 (d, J = 9.2 Hz, 2H), 4.18 (d, J = 6.4 Hz, 2H), 3.42-3.49 (m, 5H), 2.27-2.34 (m, 4H), 1.76-1.88 (m, 5H), 1.08-0.00 (m, 10H). LCMS: 445.2 [M + H] |
| 267 | 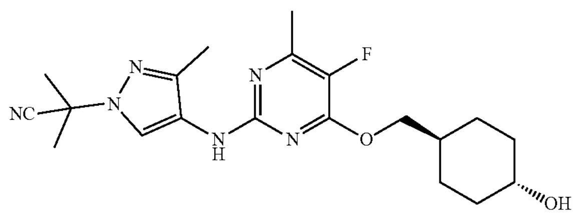 [SMILES: Cc1nn(C(C)(C)C#N)cc1Nc1nc(C)c(F)c(OC[C@H]2CC[C@H](O)CC2)n1] | 2-(4-((5-fluoro-4-(((1R,4R)-4-hydroxycyclohexyl)methoxy)-6-methylpyrimidin-2-yl)amino)-3-methyl-1H-pyrazol-1-yl)-2-methylpropanenitrile | (CD$_3$OD) δ = 8.13 (s, 1H), 4.26 (d, J = 6.4 Hz, 2H), 3.50-3.59 (m, 1H), 2.35 (s, 3H), 2.25 (s, 3H), 1.77-2.02 (m, 11H), 1.15-1.35 (m, 4H). LCMS: 403.2 [M + H] |

†All ¹H NMR recorded at 400 MHz

General Synthetic Scheme 12 for the Synthesis of Examples 145-146

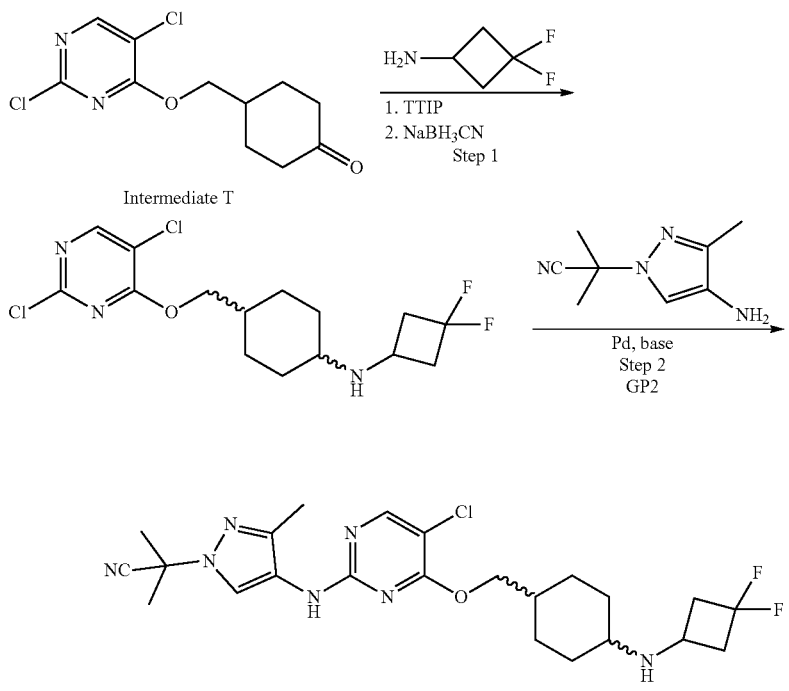

Examples 145-146

Step 1: Synthesis of 4-(((2,5-dichloropyrimidin-4-yl)oxy)methyl)-N-(3,3-difluorocyclobutyl)cyclohexan-1-amine Titanium(IV) isopropoxide (TTIP, 0.639 mL 2.181 mmol) was added to a suspension of 4-(((2,5-dichloropyrimidin-4-yl)oxy)methyl)cyclohexan-1-one (Intermediate T, 0.150 g, 0.545 mmol) and 3,3-difluorocyclobutan-1-amine (0.070 g, 0.654 mmol) in a mixture of THF (10 mL), DCM (3 mL), and DMF (1 mL) and the resulting mixture was stirred at 25° C. for 16 h the heated at 55° C. for 16 h. The reaction mixture was then cooled to 0° C., sodium cyanoborohydride (0.051 g, 0.818 mmol) was added at 0° C., and the reaction mixture was stirred at 25° C. for another 16 h. Following completion of the reaction (as indicated by TLC), the reaction mixture was filtered through a pad of Celite® (i.e., diatomaceous earth) which was then washed with EtOAc (15 mL). The combined filtrates were concentrated under reduced pressure, giving a residue which was dissolved in DCM (20 mL), washed with water (5 mL) and brine (5 mL), dried over $Na_2SO_4$, filtered, and concentrated under reduced pressure to afford crude material which was used without further purification. LCMS: 365.9 [M+H].

Step 2: Synthesis of Examples 145-146

Examples 145-146 were synthesized by following General Procedure GP2 described above. Crude materials were purified by preparative HPLC.

The following examples were synthesized following General Synthetic Scheme 12:

General Synthetic Scheme 13 for the Synthesis of Examples 147-162

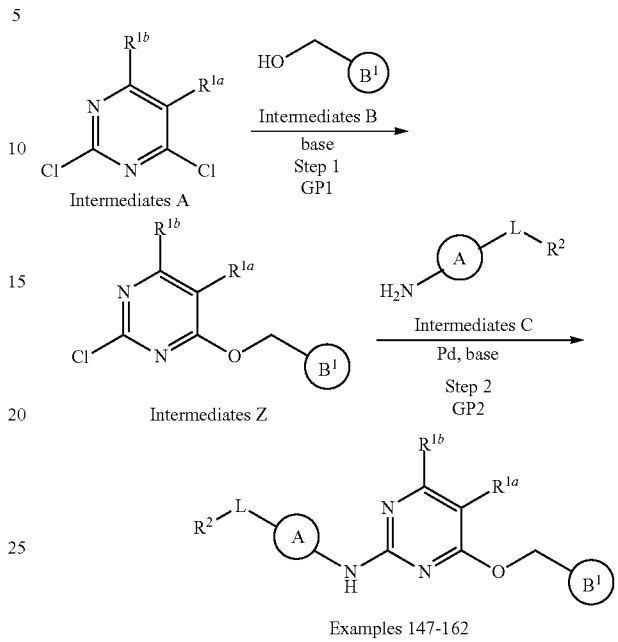

Examples 147-162

Wherein B1 is a subset of B comprised of cycloalkyl and heterocycloalkyl groups.

Step 1: Synthesis of Intermediates Z

Intermediates Z were synthesized by following General Procedure GP1 described above.

Step 2: Synthesis of Examples 147-162 and 268-291

Examples 147-162 and 268-291 were synthesized by following General Procedure GP2 described above. Crude materials were purified by preparative HPLC.

| Example | Structure | Name | †Spectral data |
|---|---|---|---|
| 145 | (pyrazole-pyrimidine-cyclohexyl-cyclobutyl structure) | 2-(4-((5-chloro-4-((4-((3,3-difluoro-cyclobutyl)amino)cyclohexyl)methoxy)pyrimidin-2-yl)amino)-3-methyl-1H-pyrazol-1-yl)-2-methylpropanenitrile (1st eluting peak) | (DMSO-$d_6$) δ = 9.01 (bs, 1H), 8.25 (s, 1H), 8.14 (s, 1H), 4.21 (d, J = 6.4 Hz, 2H), 3.83-3.85 (m, 1H), 2.88-3.02 (m, 5H), 2.21 (s, 3H), 2.04-2.18 (m, 2H), 1.93 (s, 6H), 1.77-1.90 (m, 4H), 1.08-1.38 (m, 4H). LCMS: 494.1 [M + H] |
| 146 | (pyrazole-pyrimidine-cyclohexyl-cyclobutyl structure) | 2-(4-((5-chloro-4-((4-((3,3-difluoro-cyclobutyl)amino)cyclohexyl)methoxy)pyrimidin-2-yl)amino)-3-methyl-1H-pyrazol-1-yl)-2-methylpropanenitrile (2nd eluting peak) | (DMSO-$d_6$) δ = 8.87 (bs, 1H), 8.26 (s, 1H), 8.15 (s, 1H), 4.30 (d, J = 7.6 Hz, 2H), 3.85-3.86 (m, 1H), 2.91-3.23 (m, 5H), 2.19 (s, 3H), 2.06-2.09 (m, 2H), 1.94 (s, 6H), 1.62-1.75 (m, 6H). LCMS: 494.2 [M + H] |

†All $^1$H NMR recorded at 400 MHz

The following examples were synthesized following General Synthetic Scheme 13:

| Example | Structure | Name | †Spectral data |
|---|---|---|---|
| 147 | 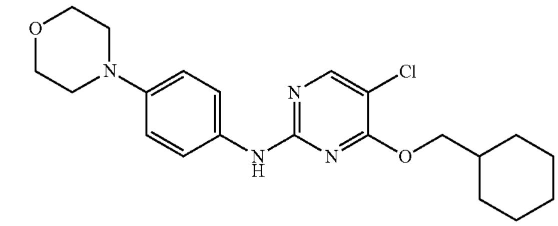 [SMILES: Clc1cnc(Nc2ccc(N3CCOCC3)cc2)nc1OCC1CCCCC1] | 5-chloro-4-(cyclohexyl-methoxy)-N-(4-morpholinophenyl)pyrimidin-2-amine | (DMSO-d$_6$) δ = 9.44 (bs, 1H), 8.22 (s, 1H), 7.54 (d, J = 9.2 Hz, 2H), 6.89 (d, J = 9.2 Hz, 2H), 4.21 (d, J = 6.0 Hz, 2H), 3.73-3.75 (m, 4H), 3.02-3.05 (m, 4H), 1.64-1.84 (m, 5H), 1.01-1.27 (m, 6H). LCMS: 403.2 [M + H] |
| 148 | 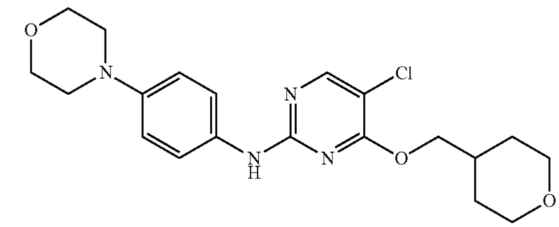 [SMILES: Clc1cnc(Nc2ccc(N3CCOCC3)cc2)nc1OCC1CCOCC1] | 5-chloro-N-(4-morpholinophenyl)-4-((tetrahydro-2H-pyran-4-yl)methoxy)pyrimidin-2-amine | (DMSO-d$_6$) δ = 9.46 (bs, 1H), 8.23 (s, 1H), 7.54 (d, J = 9.2 Hz, 2H), 6.89 (d, J = 9.2 Hz, 2H), 4.26 (d, J = 6.4 Hz, 2H), 3.87-3.90 (m, 2H), 3.73-3.75 (m, 4H), 3.31-3.33 (m, 2H), 3.02-3.05 (m, 4H), 2.04-2.10 (m, 1H), 1.64-1.66 (m, 2H), 1.30-1.40 (m, 2H). LCMS: 405.2 [M + H] |
| 149 | 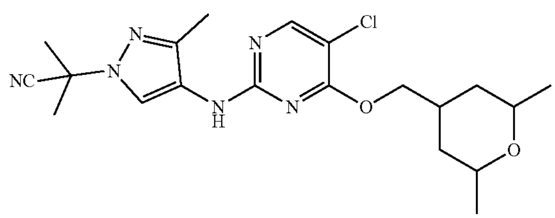 [SMILES: Cc1nn(C(C)(C)C#N)cc1Nc1ncc(Cl)c(OCC2CC(C)OC(C)C2)n1] | 2-(4-((5-chloro-4-((2,6-dimethyl-tetrahydro-2H-pyran-4-yl)methoxy)pyrimidin-2-yl)amino)-3-methyl-1H-pyrazol-1-yl)-2-methylpropane-nitrile | (CDCl$_3$) δ = 8.14-8.16 (m, 2H), 4.25 (d, J = 6.4 Hz, 2H), 3.54-3.58 (m, 2H), 2.30 (s, 3H), 2.12-2.19 (m, 1H), 2.00 (s, 6H), 1.78-1.82 (m, 2H), 1.27 (s, 3H), 1.25 (s, 3H), 1.01-1.10 (m, 2H). LCMS: 419.1 [M + H] |
| 150 | 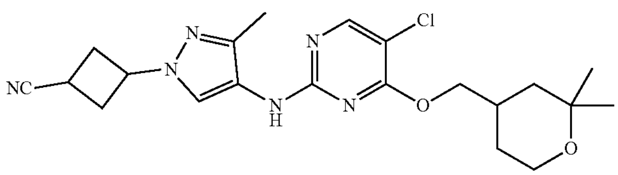 [SMILES: Cc1nn(C2CC(C#N)C2)cc1Nc1ncc(Cl)c(OCC2CCOC(C)(C)C2)n1] | 3-(4-((5-chloro-4-((2,2-dimethyltetra-hydro-2H-pyran-4-yl)methoxy)pyrimidin-2-yl)amino)-3-methyl-1H-pyrazol-1-yl)cyclobutane-1-carbonitrile | (DMSO-d$_6$) δ = 8.90 (bs, 1H), 8.19 (s, 1H), 7.90 (s, 1H), 5.04-5.08 (m, 1H), 4.17-4.22 (m, 2H), 3.58-3.63 (m, 2H), 3.42-3.44 (m, 1H), 2.80-2.86 (m, 2H), 2.68-2.74 (m, 2H), 2.14-2.22 (m, 4H), 1.54-1.61 (m, 2H), 1.10-1.22 (m, 8H). LCMS: 431.1 [M + H] |
| 151 | 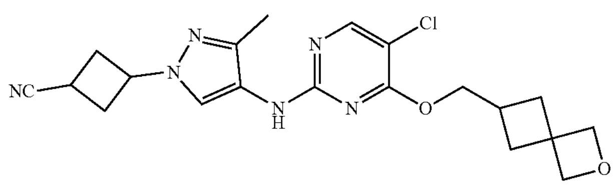 [SMILES: Cc1nn(C2CC(C#N)C2)cc1Nc1ncc(Cl)c(OCC2CC3(COC3)C2)n1] | 3-(4-((4-((2-oxaspiro[3.3]heptan-6-yl)methoxy)-5-chloropyrimidin-2-yl)amino)-3-methyl-1H-pyrazol-1-yl)cyclobutane-1-carbonitrile | (DMSO-6$_d$) δ = 8.09 (s, 1H), 7.87 (s, 1H), 5.11-5.11 (m, 1H), 4.75 (s, 2H), 4.66 (s, 2H), 4.37-4.38 (m, 2H), 3.38-3.41 (m, 1H), 2.98-3.02 (m, 2H), 2.83-2.86 (m, 2H), 2.61-2.66 (m, 1H), 2.42-2.48 (m, 2H), 2.15-2.22 (m, 5H). LCMS: 415.2 [M + H] |
| 152 | 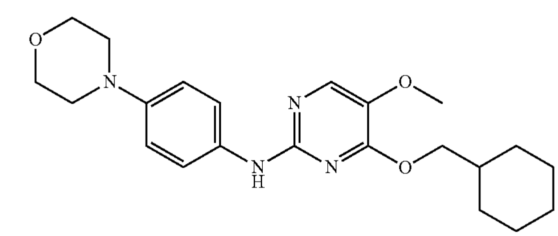 [SMILES: COc1cnc(Nc2ccc(N3CCOCC3)cc2)nc1OCC1CCCCC1] | 4-(cyclo-hexylmethoxy)-5-methoxy-N-(4-morpholino-phenyl)pyrimidin-2-amine | (DMSO-d$_6$) δ = 8.96 (bs, 1H), 7.92 (s, 1H), 7.55-7.58 (m, 2H), 6.86 (d, J = 9.2 Hz, 2H), 4.16 (d, J = 6.0 Hz, 2H), 3.72-3.74 (m, 7H), 3.00-3.02 (m, 4H), 1.70-1.80 (m, 6H), 1.18-1.24 (m, 3H), 1.02-1.05 (m, 2H). LCMS: 399.3 [M + H] |

| Example | Name | †Spectral data |
|---|---|---|
| 153 | 5-chloro-4-((4,4-difluorocyclohexyl)methoxy)-N-(4-morpholinophenyl)pyrimidin-2-amine | (CD$_3$OD) δ = 8.09 (s, 1H), 7.48-7.51 (m, 2H), 6.97 (d, J = 8.8 Hz, 2H), 4.32 (d, J = 6.4 Hz, 2H), 3.84-3.87 (m, 4H), 3.10-3.15 (m, 4H), 1.74-2.09 (m, 7H), 1.24-1.49 (m, 2H). LCMS: 439.2 [M + H] |
| 154 | 2-(4-((5-chloro-4-((3,3-difluorocyclobutyl)methoxy)pyrimidin-2-yl)amino)-3-methyl-1H-pyrazol-1-yl)-2-methylpropanenitrile | (DMSO-d$_6$) δ = 9.18 (bs, 1H), 8.26 (s, 1H), 8.13 (s, 1H), 4.46 (d, J = 6.4 Hz, 2H), 2.62-2.76 (m, 4H), 2.50-2.51 (m, 1H), 2.18 (s, 3H), 1.92 (s, 6H). LCMS: 397.1 [M + H] |
| 155 | 2-((1-(2-cyanopropan-2-yl)-3-methyl-1H-pyrazol-4-yl)amino)-4-((3,3-difluorocyclobutyl)methoxy)pyrimidine-5-carbonitrile | (CDCl$_3$) δ = 8.44 (s, 1H), 8.18 (s, 1H), 4.55 (d, J = 4.8 Hz, 2H), 2.70-2.83 (m, 3H), 2.45-2.56 (m, 2H), 2.30 (s, 3H), 2.01 (s, 6H). LCMS: 388.1 [M + H] |
| 156 | 4-((4,4-difluorocyclohexyl)methoxy)-5-methoxy-N-(4-morpholinophenyl)pyrimidin-2-amine | (DMSO-d$_6$) δ = 8.98 (bs, 1H), 7.94 (s, 1H), 7.56 (d, J = 9.2 Hz, 2H), 6.86 (d, J = 8.8 Hz, 2H), 4.23 (d, J = 6.4 Hz, 2H), 3.72-3.75 (m, 7H), 3.00-3.02 (m, 4H), 1.81-2.06 (m, 7H), 1.31-1.34 (m, 2H). LCMS: 435.2 [M + H] |
| 157 | 2-(4-((5-chloro-4-((4-(trifluoromethyl)cyclohexyl)methoxy)pyrimidin-2-yl)amino)-3-methyl-1H-pyrazol-1-yl)-2-methylpropanenitrile | (DMSO-d$_6$) δ = 9.18 (bs, 1H), 8.24 (s, 1H), 8.13 (s, 1H), 4.22 (d, J = 6.8 Hz, 2H), 2.19-2.31 (m, 1H), 2.18 (s, 3H), 1.90-1.94 (m, 10H), 1.77-1.89 (m, 1H), 1.24-1.32 (m, 2H), 1.11-1.14 (m, 2H). LCMS: 457.1 [M + H] |
| 158 | 2-(4-((5-chloro-4-(oxetan-3-ylmethoxy)pyrimidin-2-yl)amino)-3-methyl-1H-pyrazol-1-yl)-2-methylpropanenitrile | (DMSO-d$_6$) δ = 9.18 (bs, 1H), 8.25 (s, 1H), 8.15 (s, 1H), 4.68-4.72 (m, 2H), 4.63 (d, J = 6.8 Hz, 2H), 4.39-4.42 (m, 2H), 3.40-3.43 (m, 1H), 2.19 (s, 3H), 1.94 (s, 6H). LCMS: 363.0 [M + H] |
| 159 | 3-(4-((5-chloro-4-((3,3-difluorocyclobutyl)methoxy)pyrimidin-2-yl)amino)-5-methyl-1H-pyrazol-1-yl)cyclobutane-1-carbonitrile | (CD$_3$OD) δ = 8.08 (s, 1H), 7.64 (s, 1H), 5.18-5.22 (m, 1H), 4.50 (bs, 2H), 3.40-3.80 (m, 1H), 3.05-3.08 (m, 2H), 2.84-2.88 (m, 2H), 2.61 (s, 5H), 2.20 (s, 3H). LCMS: 409.1 [M + H] |

| Example | Structure | Name | †Spectral data |
|---|---|---|---|
| 160 | 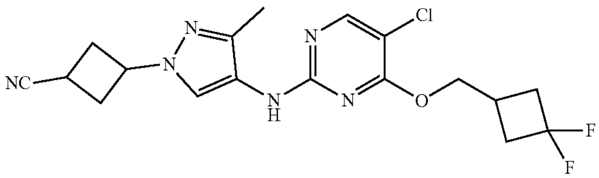 [SMILES: Cc1nn(C2CC(C#N)C2)cc1Nc1ncc(Cl)c(OCC2CC(F)(F)C2)n1] | 3-(4-((5-chloro-4-((3,3-difluorocyclo-butyl)methoxy)pyrimidin-2-yl)amino)-3-methyl-1H-pyrazol-1-yl)cyclobutane-1-carbonitrile | (CD$_3$OD) δ = 8.12 (s, 1H), 7.88 (s, 1H), 5.09-5.14 (m, 1H), 4.51-4.52 (m, 2H), 3.34-3.41 (m, 1H), 2.97-3.02 (m, 2H), 2.73-2.86 (m, 2H), 2.71 (s, 3H), 2.52 (s, 2H), 2.22 (s, 3H). LCMS: 409.2 [M + H] |
| 161 | 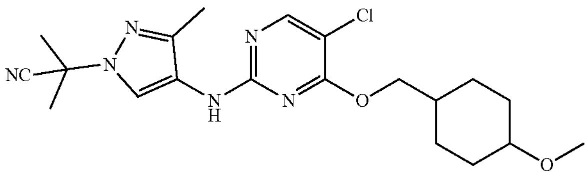 [SMILES: COC1CCC(COc2nc(Nc3cn(C(C)(C)C#N)nc3C)ncc2Cl)CC1] | 2-(4-((5-chloro-4-((4-methoxycyclo-hexyl)methoxy)pyrimidin-2-yl)amino)-3-methyl-1H-pyrazol-1-yl)-2-methylpropanenitrile | (CD$_3$OD) δ = 8.08 (s, 1H), 8.07 (s, 1H), 4.22 (d, J = 6.4 Hz, 2H), 3.35 (s, 3H), 3.14-3.19 (m, 1H), 2.22 (s, 3H), 2.11-2.15 (m, 2H), 1.79-1.97 (m, 9H), 1.13-1.22 (m, 4H). LCMS: 419.1 [M + H] |
| 162 | 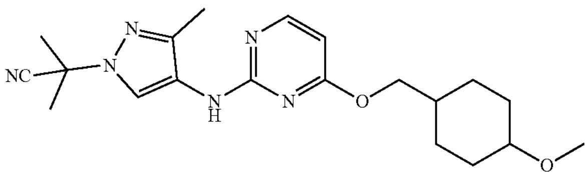 [SMILES: COC1CCC(COc2ccnc(Nc3cn(C(C)(C)C#N)nc3C)n2)CC1] | 2-(4-((4-((4-methoxycyclohexyl)methoxy)pyrimidin-2-yl)amino)-3-methyl-1H-pyrazol-1-yl)-2-methylpropanenitrile | (DMSO-d$_6$) δ = 9.25 (s, 1H), 8.16 (s, 1H), 8.14 (d, J = 6.4 Hz, 1H), 6.28 (d, J = 5.6 Hz, 1H), 4.15 (d, J = 6.4 Hz, 2H), 3.24 (s, 3H), 3.05-3.09 (m, 1H), 2.18 (s, 3H), 2.01-2.04 (m, 2H), 1.94 (s, 6H), 1.70-1.83 (m, 3H), 1.03-1.13 (m, 4H). LCMS: 385.2 [M + H] |
| 268 | 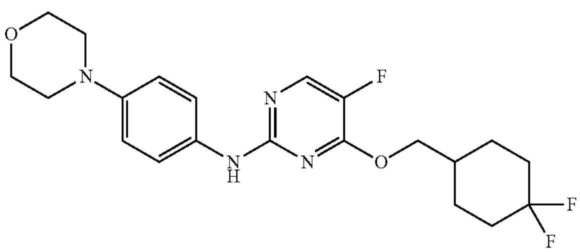 | 4-((4,4-difluorocyclohexyl)methoxy)-5-fluoro-N-(4-morpholinophenyl)pyrimidin-2-amine | (DMSO-d$_6$) δ = 9.35 (bs, 1H), 8.24 (d, J = 3.2 Hz, 1H), 7.57 (d, J = 8.8 Hz, 2H), 6.95 (d, J = 8.4 Hz, 2H), 4.29 (d, J = 6.4 Hz, 2H), 3.75-3.77 (m, 4H), 3.09 (bs, 4H), 1.78-2.06 (m, 7H), 1.29-1.39 (m, 2H). LCMS: 423.1 [M + H] |
| 269 | 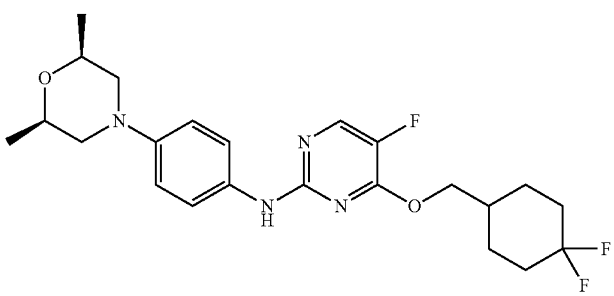 [SMILES: C[C@@H]1CN(c2ccc(Nc3ncc(F)c(OCC4CCC(F)(F)CC4)n3)cc2)C[C@H](C)O1] | 4-((4,4-difluorocyclohexyl)methoxy)-N-(4-((2R,6S)-2,6-dimethylmorpholino)phenyl)-5-fluoropyrimidin-2-amine | (DMSO-d$_6$) δ = 9.35 (bs, 1H), 8.24 (d, J = 3.2 Hz, 1H), 7.56 (d, J = 8.8 Hz, 2H), 6.95 (d, J = 7.6 Hz, 2H), 4.29 (d, J = 6.4 Hz, 2H), 3.71-3.75 (m, 2H), 3.47-3.50 (m, 2H), 2.30-2.33 (m, 2H), 1.78-2.09 (m, 7H), 1.29-1.39 (m, 2H), 1.16 (d, J = 6.4 Hz, 6H). LCMS: 451.2 [M + H] |
| 270 | 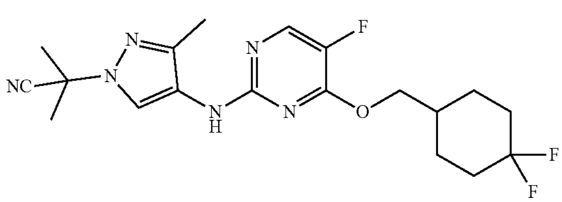 [SMILES: Cc1nn(C(C)(C)C#N)cc1Nc1ncc(F)c(OCC2CCC(F)(F)CC2)n1] | 2-(4-((4-((4,4-difluorocyclohexyl)methoxy)-5-fluoropyrimidin-2-yl)amino)-3-methyl-1H-pyrazol-1-yl)-2-methylpropanenitrile | (DMSO-d$_6$) δ = 8.92 (bs, 1H), 8.23 (d, J = 3.2 Hz, 1H), 8.13 (s, 1H), 4.28 (d, J = 6.8 Hz, 2H), 2.18 (s, 3H), 2.00-2.08 (m, 2H), 1.81-1.93 (m, 11H), 1.24-1.36 (m, 2H). LCMS: 409.1 [M + H] |
| 271 | 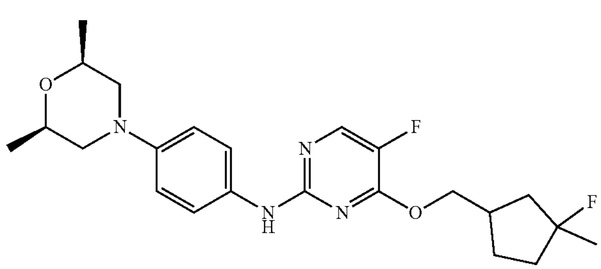 | 4-((3,3-difluorocyclopentyl)methoxy)-N-(4-((2S,6R)-2,6-dimethylmorpholino)phenyl)-5-fluoropyrimidin-2-amine | (CD$_3$OD) δ = 8.15 (d, J = 4.0 Hz, 1H), 7.80 (d, J = 8.0 Hz, 2H), 7.45 (d, J = 8.0 Hz, 2H), 4.44-4.47 (m, 2H), 3.99-4.04 (m, 2H), 3.60-3.63 (m, 2H), 3.07-3.13 (m, 2H), 2.72-2.76 (m, 1H), 1.98-2.39 (m, 5H), 1.68-1.74 (m, 1H), 1.30-1.32 (m, 6H). LCMS: 437.2 [M + H] |

| Example | Name | †Spectral data |
|---|---|---|
| 272 | 4-(((5-fluoro-2-((4-morpholinophenyl)amino)pyrimidin-4-yl)oxy)methyl)cyclohexane-1-carbonitrile | (CDCl$_3$) δ = 8.03 (s, 1H), 7.44-7.48 (m, 2H), 6.96-7.05 (m, 2H), 4.22-4.28 (m, 2H), 3.91-3.93 (m, 4H), 3.15-3.18 (m, 4H), 2.43-2.47 (m, 1H), 1.91-2.23 (m, 5H), 1.49-1.70 (m, 3H), 1.16-1.28 (m, 1H). LCMS: 412.2 [M + H] (racemic mixture) |
| 273 | 4-(((2-((4-((2S,6R)-2,6-dimethylmorpholino)phenyl)amino)-5-fluoropyrimidin-4-yl)oxy)methyl)cyclohexane-1-carbonitrile | (CD$_3$OD) δ = 8.08-8.10 (m, 1H), 7.66-7.71 (m, 2H), 7.28-7.32 (m, 2H), 4.30-4.37 (m, 2H), 3.93-3.97 (m, 2H), 3.55-3.58 (m, 2H), 2.90 (bs, 2H), 2.59-2.65 (m, 1H), 2.15-2.19 (m, 1H), 1.87-2.01 (m, 4H), 1.50-1.72 (m, 3H), 1.20-1.31 (m, 7H). LCMS: 440.2 [M + H] (racemic mixture) |
| 274 | 4-(((2-((1-(2-cyanopropan-2-yl)-3-methyl-1H-pyrazol-4-yl)amino)-5-fluoropyrimidin-4-yl)oxy)methyl)cyclohexane-1-carbonitrile | (CD$_3$OD) δ = 8.11 (d, J = 3.2 Hz, 1H), 7.66-7.71 (m, 1H), 4.24-4.31 (m, 2H), 2.60 (bs, 1H), 2.24 (s, 3H), 2.14-2.17 (m, 1H), 1.86-2.05 (m, 10H), 1.60-1.72 (m, 2H), 1.44-1.47 (m, 1H), 1.18-1.21 (m, 1H). LCMS: 398.1 [M + H] (racemic mixture) |
| 275 | 4-(((1S,4S)-4-ethoxycyclohexyl)methoxy)-5-fluoro-N-(4-morpholinophenyl)pyrimidin-2-amine | (CD$_3$OD) δ = 8.10 (d, J = 3.2 Hz, 1H), 7.69 (d, J = 8.8 Hz, 2H), 7.31 (d, J = 9.2 Hz, 2H), 4.34 (d, J = 6.8 Hz, 2H), 3.97-3.99 (m, 4H), 3.60-3.61 (m, 1H), 3.49-3.54 (m, 2H), 3.43-3.45 (m, 4H), 1.91-1.94 (m, 3H), 1.49-1.65 (m, 6H), 1.21 (t, J = 7.2 Hz, 3H). LCMS: 431.5 [M + H] (pure diastereomer obtained by chromatographic purification) |
| 276 | N-(4-((2S,6R)-2,6-dimethylmorpholino)phenyl)-4-(((1S,4S)-4-ethoxycyclohexyl)methoxy)-5-fluoropyrimidin-2-amine | (CD$_3$OD) δ = 8.07 (bs, 1H), 7.65 (bs, 2H), 7.23 (bs, 2H), 4.32 (d, J = 6.8 Hz, 2H), 3.87 (bs, 2H), 3.49-3.58 (m, 5H), 2.52 (bs, 2H), 1.89-1.92 (m, 3H), 1.52-1.63 (m, 6H), 1.19-1.31 (m, 9H) (pure diastereomer obtained by chromatographic purification) |
| 277 | 2-(4-((4-(((1s,4s)-4-ethoxycyclohexyl)methoxy)-5-fluoropyrimidin-2-yl)amino)-3-methyl-1H-pyrazol-1-yl)-2-methylpropanenitrile | (DMSO-d$_6$) δ = 8.92 (bs, 1H), 8.22 (d, J = 3.2 Hz, 1H), 8.12 (s, 1H), 4.23 (d, J = 7.2 Hz, 2H), 3.50 (bs, 1H), 3.40 (q, J = 6.8 Hz, 2H), 2.18 (s, 3H), 1.93 (s, 6H), 1.77-1.84 (m, 3H), 1.34-1.54 (m, 6H), 1.12 (t, J = 7.2 Hz, 3H). LCMS: 417.3 [M + H] (pure diastereomer obtained by chromatographic purification) |

| Example | Structure | Name | †Spectral data |
|---|---|---|---|
| 278 | 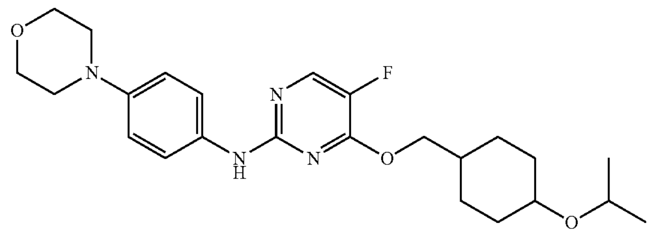 [SMILES: CC(C)OC1CCC(COc2nc(Nc3ccc(N4CCOCC4)cc3)ncc2F)CC1] | 5-fluoro-4-((4-isopropoxycyclohexyl)methoxy)-N-(4-morpholinophenyl)pyrimidin-2-amine | (CD$_3$OD) δ = 8.00 (d, J = 3.2 Hz, 1H), 7.48-7.52 (m, 2H), 6.94-6.98 (m, 2H), 4.29 (d, J = 7.2 Hz, 2H), 3.84-3.87 (m, 4H), 3.68-3.76 (m, 2H), 3.09-3.12 (m, 4H), 1.82-1.95 (m, 3H), 1.51-1.62 (m, 6H), 1.15-1.17 (m, 6H). LCMS: 445.3 [M + H] (racemic mixture) |
| 279 | 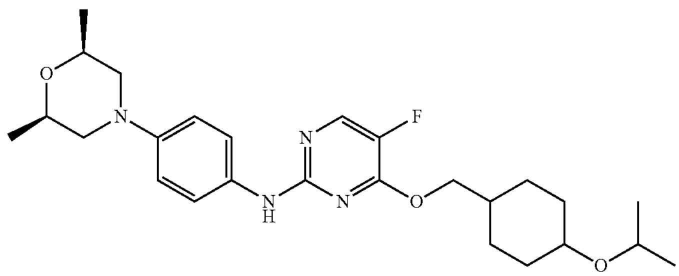 [SMILES: CC(C)OC1CCC(COc2nc(Nc3ccc(N4C[C@@H](C)O[C@@H](C)C4)cc3)ncc2F)CC1] | N-(4-((2S,6R)-2,6-dimethylmorpholino)phenyl)-5-fluoro-4-((4-isopropoxycyclohexyl)methoxy)pyrimidin-2-amine | (CD$_3$OD) δ = 8.10 (d, J = 3.2 Hz, 1H), 7.72 (d, J = 9.2 Hz, 2H), 7.33 (d, J = 8.8 Hz, 2H), 4.34 (d, J = 6.8 Hz, 2H), 3.94-3.99 (m, 2H), 3.70-3.74 (m, 2H), 3.57-3.60 (m, 2H), 2.89-2.95 (m, 2H), 1.83-1.86 (m, 3H), 1.53-1.63 (m, 6H), 1.30 (d, J = 6.40 Hz, 6H), 1.16 (d, J = 6.0 Hz, 6H). LCMS: 473.2 [M + H] (Racemic mixture) |
| 280 | 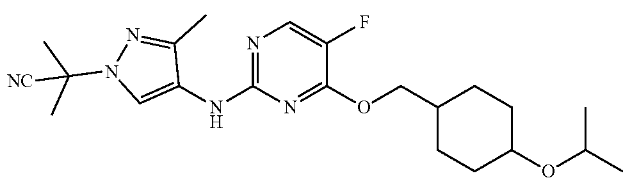 [SMILES: Cc1nn(C(C)(C)C#N)cc1Nc1ncc(F)c(OCC2CCC(OC(C)C)CC2)n1] | 2-(4-((5-fluoro-4-((4-isopropoxycyclohexyl)methoxy)pyrimidin-2-yl)amino)-3-methyl-1H-pyrazol-1-yl)-2-methylpropanenitrile | (CD$_3$OD) δ = 8.10 (s, 1H), 8.05 (d, J = 3.6 Hz, 1H), 4.32 (d, J = 6.8 Hz, 2H), 3.69-3.74 (m, 2H), 2.24 (s, 3H), 1.82-2.00 (m, 9H), 1.53-1.62 (m, 6H), 1.16 (d, J = 6.00 Hz, 6H). LCMS: 431.4 [M + H] (racemic mixture) |
| 281 | 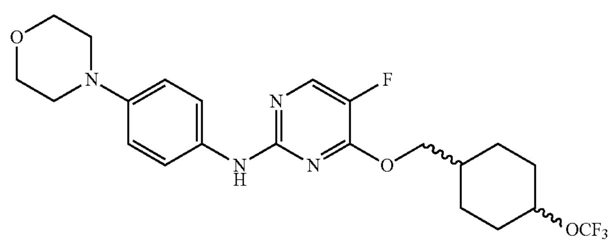 [SMILES: Fc1cnc(Nc2ccc(N3CCOCC3)cc2)nc1OCC1CCC(OC(F)(F)F)CC1] | 5-fluoro-N-(4-morpholinophenyl)-4-((4-(trifluoromethoxy)cyclohexyl)methoxy)pyrimidin-2-amine | LCMS: 471.2 [M + H]. Enantiomer separated by SFC chiral purification (first eluting peak, SFC chiral purity = 100% ee) |
| 282 | 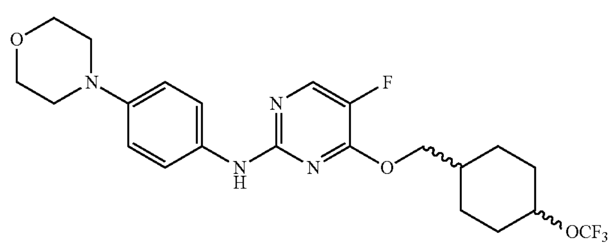 [SMILES: Fc1cnc(Nc2ccc(N3CCOCC3)cc2)nc1OCC1CCC(OC(F)(F)F)CC1] | 5-fluoro-N-(4-morpholinophenyl)-4-((4-(trifluoromethoxy)cyclohexyl)methoxy)pyrimidin-2-amine | LCMS: 471.2 [M + H]. Enantiomer separated by SFC chiral purification (second eluting peak, SFC chiral purity = 97.65% ee) |
| 283 | 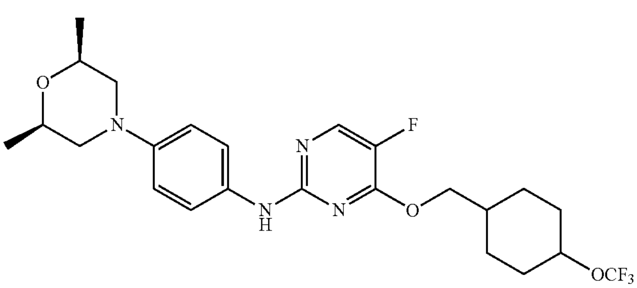 [SMILES: C[C@@H]1CN(c2ccc(Nc3ncc(F)c(OCC4CCC(OC(F)(F)F)CC4)n3)cc2)C[C@H](C)O1] | N-(4-((2S,6R)-2,6-dimethylmorpholino)phenyl)-5-fluoro-4-((4-(trifluoromethoxy)cyclohexyl)methoxy)pyrimidin-2-amine | (CD$_3$OD) δ = 8.12 (d, J = 3.2 Hz, 1H), 7.76 (d, J = 8.8 Hz, 2H), 7.39 (d, J = 8.4 Hz, 2H), 4.24-4.37 (m, 3H), 3.97-4.01 (m, 2H), 3.59-3.62 (m, 2H), 2.99-3.05 (m, 2H), 1.73-2.18 (m, 5H), 1.54-1.60 (m, 2H), 1.30-1.31 (m, 8H). LCMS: 499.5 [M + H] |

-continued

| Example | Structure | Name | †Spectral data |
|---|---|---|---|
| 284 | 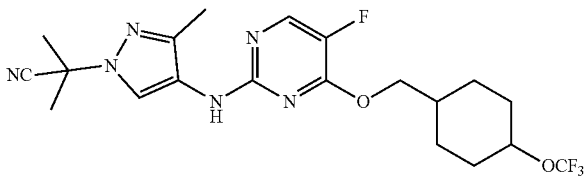 [SMILES: Cc1nn(C(C)(C)C#N)cc1Nc1ncc(F)c(OCC2CCC(OC(F)(F)F)CC2)n1] | 2-(4-((5-fluoro-4-((4-(trifluoromethoxy)cyclohexyl)methoxy)pyrimidin-2-yl)amino)-3-methyl-1H-pyrazol-1-yl)-2-methylpropanenitrile | (DMSO-$d_6$) δ = 8.91 (bs, 1H), 8.23 (d, J = 3.2 Hz, 1H), 8.12 (d, J = 3.6 Hz, 1H), 4.24-4.31 (m, 3H), 2.25 (s, 3H), 2.14-2.18 (m, 2H), 1.72-2.06 (m, 9H), 1.52-1.59 (m, 2H), 1.24-1.31 (m, 2H). LCMS: 457.2 [M + H] (racemic mixture) |
| 285 | 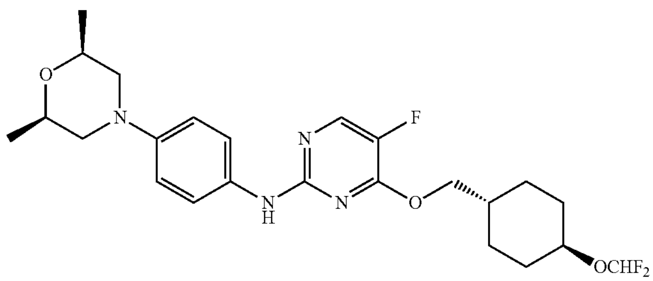 [SMILES: C[C@@H]1CN(c2ccc(Nc3ncc(F)c(OC[C@H]4CC[C@H](OC(F)F)CC4)n3)cc2)C[C@H](C)O1] | 4-(((1R,4R)-4-(difluoromethoxy)cyclohexyl)methoxy)-N-(4-((2S,6R)-2,6-dimethylmorpholino)phenyl)-5-fluoropyrimidin-2-amine | (CD$_3$OD) δ = 8.00 (d, J = 3.2 Hz, 1H), 7.45-7.49 (m, 2H), 6.93-6.97 (m, 2H), 6.40 (t, J = 76.40 Hz, 1H), 4.26 (d, J = 6.4 Hz, 2H), 4.01-4.07 (m, 1H), 3.80-3.85 (m, 2H), 3.44-3.47 (m, 2H), 2.29-2.35 (m, 2H), 1.86-2.11 (m, 5H), 1.42-1.49 (m, 2H), 1.21-1.28 (m, 8H). LCMS: 481.2 [M + H] |
| 286 | 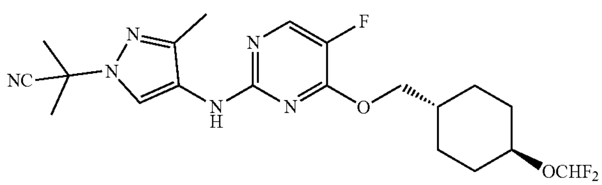 [SMILES: Cc1nn(C(C)(C)C#N)cc1Nc1ncc(F)c(OC[C@H]2CC[C@H](OC(F)F)CC2)n1] | 2-(4-((4-(((1R,4R)-4-(difluoromethoxy)cyclohexyl)methoxy)-5-fluoropyrimidin-2-yl)amino)-3-methyl-1H-pyrazol-1-yl)-2-methylpropanenitrile | (CD$_3$OD) δ = 7.99 (s, 1H), 7.94 (d, J = 3.6 Hz, 1H), 6.29 (t, J = 76.00 Hz, 1H), 4.17-4.19 (m, 2H), 3.92-3.98 (m, 1H), 2.12 (s, 3H), 1.96-1.99 (m, 2H), 1.75-1.88 (m, 9H), 1.35-1.38 (m, 2H), 1.09-1.13 (m, 2H). LCMS: 439.2 [M + H] |
| 287 | 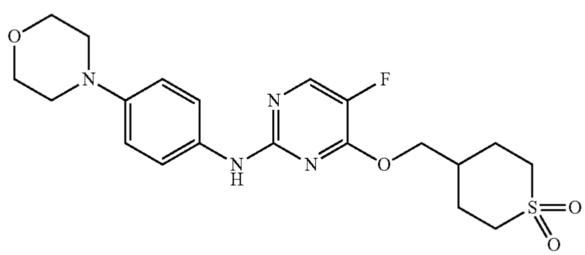 [SMILES: O=S1(=O)CCC(COc2nc(Nc3ccc(N4CCOCC4)cc3)ncc2F)CC1] | 4-(((5-fluoro-2-((4-morpholinophenyl)amino)pyrimidin-4-yl)oxy)methyl)tetrahydro-2H-thiopyran 1,1-dioxide | (DMSO-$d_6$) δ = 9.42 (s, 1H), 8.26 (d, J = 2.0 Hz, 1H), 7.58 (d, J = 8.4 Hz, 2H), 7.00 (d, J = 8.0 Hz, 2H), 4.32 (d, J = 6.4 Hz, 2H), 3.78 (s, 4H), 3.07-3.24 (m, 8H), 2.10-2.18 (m, 3H), 1.73-1.82 (m, 2H). LCMS: 437.2 [M + H] |
| 288 | 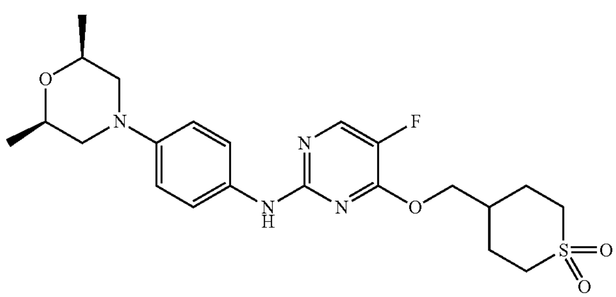 [SMILES: C[C@@H]1CN(c2ccc(Nc3ncc(F)c(OCC4CCS(=O)(=O)CC4)n3)cc2)C[C@H](C)O1] | 4-(((2-((4-((2R,6S)-2,6-dimethylmorpholino)phenyl)amino)-5-fluoropyrimidin-4-yl)oxy)methyl)tetrahydro-2H-thiopyran 1,1-dioxide | (CD$_3$OD) δ = 8.14 (d, J = 2.8 Hz, 1H), 7.76 (d, J = 8.8 Hz, 2H), 7.39 (d, J = 8.0 Hz, 2H), 4.42 (d, J = 6.0 Hz, 2H), 3.97-4.00 (m, 2H), 3.58-3.61 (m, 2H), 3.01-3.28 (m, 6H), 2.24-2.25 (m, 3H), 1.95-1.98 (m, 2H), 1.29 (d, J = 5.60 Hz, 6H). LCMS: 465.2 [M + H] |
| 289 | 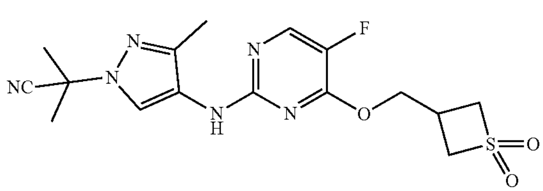 [SMILES: Cc1nn(C(C)(C)C#N)cc1Nc1ncc(F)c(OCC2CS(=O)(=O)C2)n1] | 2-(4-((4-((1,1-dioxidothietan-3-yl)methoxy)-5-fluoropyrimidin-2-yl)amino)-3-methyl-1H-pyrazol-1-yl)-2-methylpropanenitrile | (CD$_3$OD) δ = 8.13 (s, 1H), 8.08 (d, J = 3.2 Hz, 1H), 4.50-4.65 (m, 2H), 4.30-4.36 (m, 2H), 4.03-4.08 (m, 2H), 3.07-3.15 (m, 1H), 2.25 (s, 3H), 2.00 (s, 6H). LCMS: 395.1 [M + H] |

| Example | Structure | Name | †Spectral data |
|---|---|---|---|
| 290 | 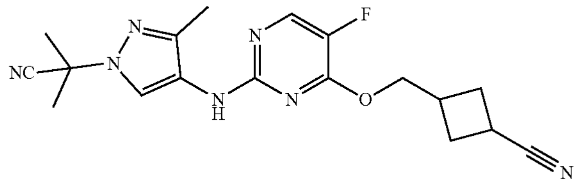 [SMILES: Cc1nn(C(C)(C)C#N)cc1Nc1ncc(F)c(OCC2CC(C#N)C2)n1] | 3-(((2-((1-(2-cyanopropan-2-yl)-3-methyl-1H-pyrazol-4-yl)amino)-5-fluoropyrimidin-4-yl)oxy)methyl)cyclobutane-1-carbonitrile | (CD$_3$OD) δ = 8.12 (s, 1H), 8.08 (d, J = 3.6 Hz, 1H), 4.47-4.51 (m, 2H), 3.23-3.27 (m, 1H), 2.90-2.92 (m, 1H), 2.53-2.61 (m, 2H), 2.27-2.34 (m, 2H), 2.26 (s, 3H), 2.00 (s, 6H). LCMS: 370.1 [M + H] (first eluting peak) |
| 291 | 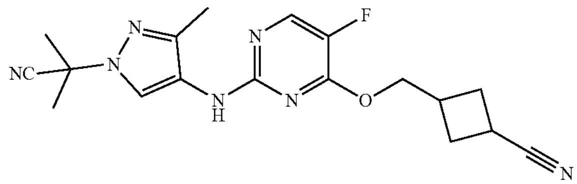 [SMILES: Cc1nn(C(C)(C)C#N)cc1Nc1ncc(F)c(OCC2CC(C#N)C2)n1] | 3-(((2-((1-(2-cyanopropan-2-yl)-3-methyl-1H-pyrazol-4-yl)amino)-5-fluoropyrimidin-4-yl)oxy)methyl)cyclobutane-1-carbonitrile | (CD$_3$OD) δ = 8.12 (s, 1H), 8.08 (d, J = 3.6 Hz, 1H), 4.46-4.48 (m, 2H), 3.23-3.27 (m, 1H), 2.90-2.92 (m, 1H), 2.53-2.58 (m, 2H), 2.29-2.32 (m, 2H), 2.25 (s, 3H), 2.00 (s, 6H). LCMS: 370.2 [M + H] (second eluting peak) |

†All $^1$H NMR recorded at 400 MHz

Enzymatic Assay

LRRK2 ENZYMATIC ASSAY

LRRKtide substrate (peptide sequence RLGRDKYKTLRQIRQ (SEQ ID NO. 1), derived from human ezrin [amino acids 561-573], moesin [amino acids 539-553] and radixin [amino acids 558-570], obtained from SignalChem, catalogue #L10-58, reconstituted in 20 mM Tris-HCl at pH 7.5 to a final concentration of 1 mg/mL, assay concentration 20 µM) and recombinant human LRRK2 (catalytic domain only [amino acids 970-2527], GST-tagged, expressed in insect cells, obtained from ThermoFisher Scientific, catalogue #PV4874, 0.35 mg/mL, assay concentration 30 nM) were mixed in assay buffer (20 mM Hepes pH 7.5, 10 mM MgCl$_2$, 1 mM EGTA, 0.02% Brij35, 0.02 mg/ml BSA, 0.1 mM Na$_3$VO$_4$, 2 mM DTT, 1% DMSO). Compounds of interest (in DMSO, serial 3-fold dilution from 10 µM to 0.5 nM) or control (1% DMSO) were dispensed into the kinase reaction mixture by Acoustic technology (Echo550; nanoliter range). After incubation at room temperature for 20 minutes, the kinase reaction was initiated by addition of [$^{32}$P]-ATP (Specific activity 10 µCi/µl) and the mixture was incubated at room temperature for 2 hours. The reaction was then stopped by spotting the reaction mixture on strips of phosphocellulose P81 paper. Following washing, the radioactivity of the P81 paper was measured and kinase activity data were expressed as the percent remaining kinase activity in test samples compared to vehicle (dimethyl sulfoxide) reactions. IC$_{50}$ values and curve fits were obtained using Prism (GraphPad Software).

TABLE 2

Activity of Representative Compounds

| Cmpd No. | LRRK2 IC$_{50}$ (nM) |
|---|---|
| 1 | ++++ |
| 2 | ++++ |
| 3 | +++ |
| 4 | +++ |
| 5 | +++ |
| 6 | ++++ |
| 7 | + |
| 8 | ++++ |
| 9 | ++++ |
| 10 | ++++ |
| 11 | +++ |
| 12 | ++++ |
| 13 | ++++ |
| 14 | ++++ |
| 15 | +++ |
| 16 | ++++ |
| 17 | ++ |
| 18 | +++ |
| 19 | ++ |
| 20 | ++++ |
| 21 | ++++ |
| 22 | ++++ |
| 23 | ++++ |
| 24 | +++ |
| 25 | ++++ |
| 26 | +++ |
| 27 | + |
| 28 | ++++ |
| 29 | ++++ |
| 30 | ++++ |
| 31 | ++++ |
| 32 | ++++ |
| 33 | + |
| 34 | +++ |
| 35 | ++++ |
| 36 | ++++ |
| 37 | ++++ |
| 38 | ++++ |
| 39 | ++++ |
| 40 | ++++ |
| 41 | ++++ |
| 42 | ++++ |
| 43 | ++++ |
| 44 | ++++ |
| 45 | +++ |
| 46 | ++++ |
| 47 | ++ |
| 48 | +++ |
| 49 | ++++ |
| 50 | ++++ |
| 51 | ++++ |
| 52 | ++++ |
| 53 | ++++ |

TABLE 2-continued

Activity of Representative Compounds

| Cmpd No. | LRRK2 IC$_{50}$ (nM) |
|---|---|
| 54 | ++ |
| 55 | ++++ |
| 56 | ++++ |
| 57 | +++ |
| 58 | ++++ |
| 59 | ++ |
| 60 | + |
| 61 | ++++ |
| 62 | ++ |
| 63 | + |
| 64 | + |
| 65 | +++ |
| 66 | + |
| 67 | + |
| 68 | + |
| 69 | + |
| 70 | ++++ |
| 71 | + |
| 72 | +++ |
| 73 | +++ |
| 74 | +++ |
| 75 | + |
| 76 | +++ |
| 77 | + |
| 78 | ++ |
| 79 | ++ |
| 80 | ++++ |
| 81 | ++++ |
| 82 | ++++ |
| 83 | ++++ |
| 84 | ++++ |
| 85 | ++++ |
| 86 | ++++ |
| 87 | ++++ |
| 88 | +++ |
| 89 | + |
| 90 | + |
| 91 | + |
| 92 | ++ |
| 93 | ++++ |
| 94 | + |
| 95 | ++++ |
| 96 | ++++ |
| 97 | + |
| 98 | +++ |
| 99 | ++++ |
| 100 | ++++ |
| 101 | ++++ |
| 102 | ++++ |
| 103 | ++++ |
| 104 | +++ |
| 105 | +++ |
| 106 | ++++ |
| 107 | ++++ |
| 108 | ++++ |
| 109 | ++++ |
| 110 | ++++ |
| 111 | ++++ |
| 112 | +++ |
| 113 | ++++ |
| 114 | + |
| 115 | + |
| 116 | ++ |
| 117 | ++ |
| 118 | +++ |
| 119 | ++ |
| 120 | ++++ |
| 121 | ++++ |
| 122 | ++++ |
| 123 | +++ |
| 124 | ++++ |
| 125 | ++++ |
| 126 | ++++ |
| 127 | ++++ |
| 128 | ++++ |
| 129 | ++++ |
| 130 | +++ |
| 131 | + |
| 132 | +++ |
| 133 | + |
| 134 | ++++ |
| 135 | ++++ |
| 136 | +++ |
| 137 | ++++ |
| 138 | ++++ |
| 139 | +++ |
| 140 | + |
| 141 | +++ |
| 142 | + |
| 143 | +++ |
| 144 | +++ |
| 145 | ++++ |
| 146 | ++++ |
| 147 | ++++ |
| 148 | ++++ |
| 149 | ++++ |
| 150 | +++ |
| 151 | ++++ |
| 152 | ++++ |
| 153 | +++ |
| 154 | ++++ |
| 155 | +++ |
| 156 | +++ |
| 157 | +++ |
| 158 | +++ |
| 159 | ++++ |
| 160- | +++ |
| 161 | ++++ |
| 162 | ++ |
| 163 | +++ |
| 164 | ++++ |
| 165 | ++++ |
| 166 | ++++ |
| 167 | ++++ |
| 168 | +++ |
| 169 | +++ |
| 170 | +++ |
| 171 | ++ |
| 172 | +++ |
| 173 | ++++ |
| 174 | ++ |
| 175 | ++ |
| 176 | ++ |
| 177 | + |
| 178 | +++ |
| 179 | ++++ |
| 180 | ++++ |
| 181 | ++++ |
| 182 | +++ |
| 183 | +++ |
| 184 | ++++ |
| 185 | ++++ |
| 186 | ++++ |
| 187 | ++ |
| 188 | ++++ |
| 189 | ++++ |
| 190 | ++++ |
| 191 | ++++ |
| 192 | +++ |
| 193 | ++++ |
| 194 | +++ |
| 195 | ++++ |
| 196 | ++++ |
| 197 | +++ |
| 198 | ++++ |
| 199 | ++++ |
| 200 | ++++ |
| 201 | ++++ |
| 202 | ++++ |
| 203 | ++++ |

TABLE 2-continued

Activity of Representative Compounds

| Cmpd No. | LRRK2 IC$_{50}$ (nM) |
|---|---|
| 204 | ++++ |
| 205 | ++++ |
| 206 | ++++ |
| 207 | +++ |
| 208 | ++++ |
| 209 | ++++ |
| 210 | ++++ |
| 211 | ++++ |
| 212 | +++ |
| 213 | ++++ |
| 214 | +++ |
| 215 | ++++ |
| 216 | ++++ |
| 217 | +++ |
| 218 | +++ |
| 219 | + |
| 220 | +++ |
| 221 | +++ |
| 222 | + |
| 223 | +++ |
| 224 | ++++ |
| 225 | ++++ |
| 226 | +++ |
| 227 | ++ |
| 228 | ++ |
| 229 | +++ |
| 230 | +++ |
| 231 | +++ |
| 232 | +++ |
| 233 | ++++ |
| 234 | ++++ |
| 235 | +++ |
| 236 | ++++ |
| 237 | +++ |
| 238 | ++ |
| 239 | ++ |
| 240 | +++ |
| 241 | +++ |
| 242 | ++++ |
| 243 | ++ |
| 244 | + |
| 245 | ++ |
| 246 | + |
| 247 | + |
| 248 | + |
| 249 | ++++ |
| 250 | ++++ |
| 251 | +++ |
| 252 | ++++ |
| 253 | ++++ |
| 254 | +++ |
| 255 | +++ |
| 256 | ++++ |
| 257 | +++ |
| 258 | +++ |
| 259 | ++++ |
| 260 | +++ |
| 261 | +++ |
| 262 | +++ |
| 263 | ++++ |
| 264 | ND |
| 265 | + |
| 266 | + |
| 267 | + |
| 268 | +++ |
| 269 | ++ |
| 270 | +++ |
| 271 | +++ |
| 272 | ++++ |
| 273 | ++++ |
| 274 | ++++ |
| 275 | +++ |
| 276 | +++ |
| 277 | ++++ |
| 278 | +++ |
| 279 | ++ |
| 280 | +++ |
| 281 | + |
| 282 | + |
| 283 | + |
| 284 | ++ |
| 285 | ++ |
| 286 | +++ |
| 287 | + |
| 288 | + |
| 289 | + |
| 290 | ++++ |
| 291 | ++++ |

+ IC$_{50}$ greater than 400 nM+
+ IC$_{50}$ range from 200-400 nM
+++ IC$_{50}$ range from 50-200 nM
++++ IC$_{50}$ less than 50 nM
ND = Not determined The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the following Structure (I):

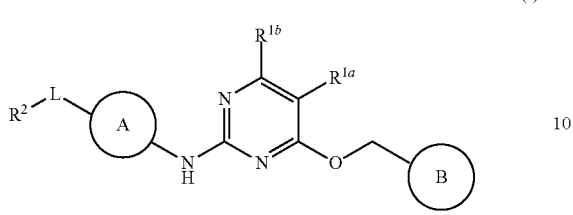

(I)

or a pharmaceutically acceptable salt, or stereoisomer thereof, wherein:

A is phenylene or 5 or 6-membered heteroarylene;

B is $C_3$-$C_8$ monocyclic cycloalkyl optionally substituted with one or more substituents selected from amino, halo, hydroxyl, oxo, cyano, $C_1$-$C_6$ alkyl, $C_1$-$C_6$ haloalkyl, $C_1$-$C_6$ hydroxylalkyl, $C_1$-$C_6$ aminoalkyl, $C_1$-$C_6$ alkylaminylalkyl, $C_1$-$C_6$ alkoxy; $C_1$-$C_6$ haloalkoxy, $C_1$-$C_6$ alkylcarbonyl, $C_1$-$C_6$ haloalkylcarbonyl, $C_1$-$C_6$ alkylaminyl, $C_1$-$C_6$ haloalkylaminyl, $C_1$-$C_6$ alkylcarbonylaminyl, $C_1$-$C_6$ haloalkylcarbonylaminyl, $C_3$-$C_8$ cycloalkyl, $C_3$-$C_8$ cycloalkylcarbonyl, $C_3$-$C_8$ halocycloalkylaminyl, and $C_3$-$C_8$ cycloalkylcarbonylaminyl;

L is a direct bond;

$R^{1a}$ and $R^{1b}$ are each independently H, halo, cyano, $C_1$-$C_6$ alkyl, $C_1$-$C_6$ haloalkyl, $C_1$-$C_6$ alkoxy or $C_3$-$C_8$ cycloalkyl; and $R^2$ is 3-8-membered heterocyclyl optionally substituted with one or more substituents selected from halo, cyano, $C_1$-$C_6$ alkyl, hydroxyl, alkoxy, and $C_1$-$C_6$ haloalkyl.

2. The compound of claim 1, wherein A is phenylene.

3. The compound of claim 1, wherein A is unsubstituted phenylene.

4. The compound of claim 1, wherein A is a 5 or 6-membered heteroarylene.

5. The compound of claim 1, wherein A is pyrazolylene.

6. The compound of claim 1, wherein B is substituted.

7. The compound of claim 1, wherein B has one of the following structures:

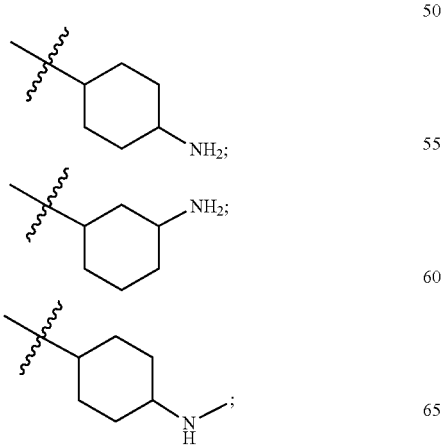

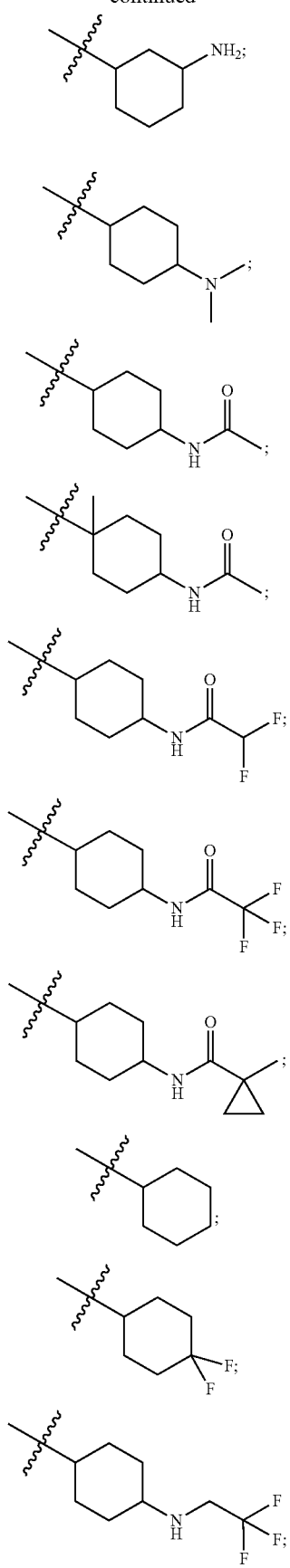

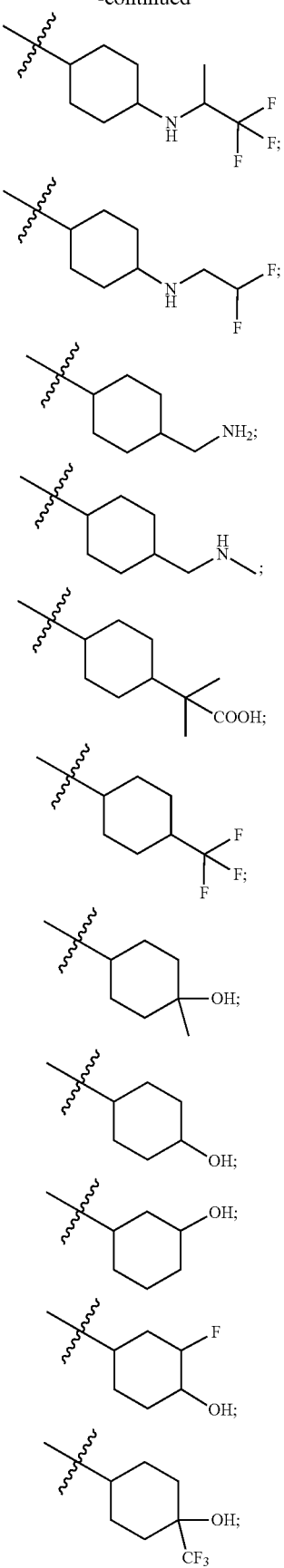
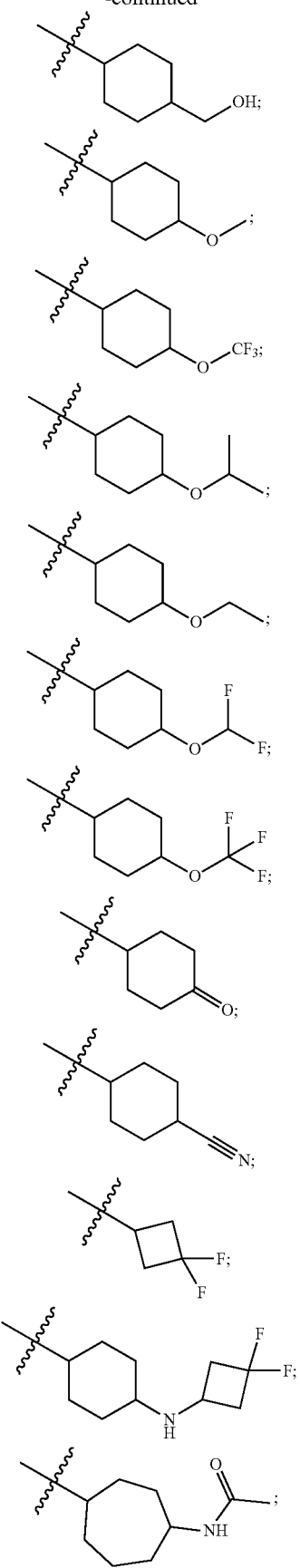

-continued
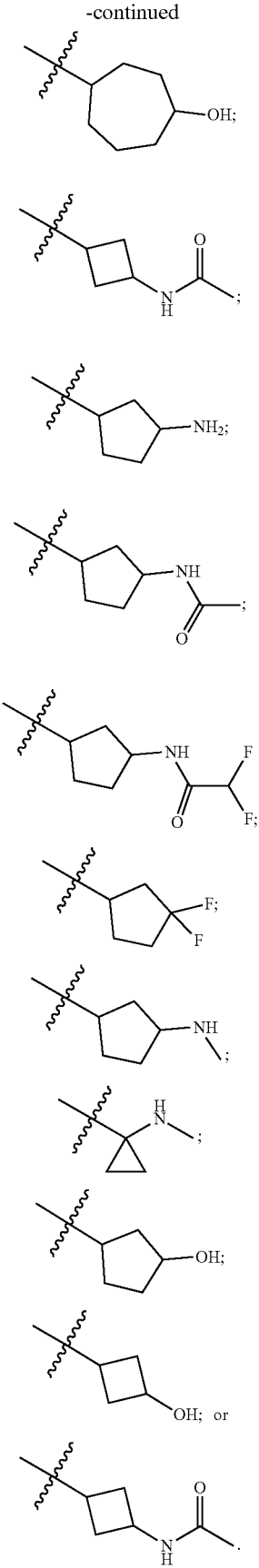
8. The compound of claim 1, wherein B has one of the following structures:
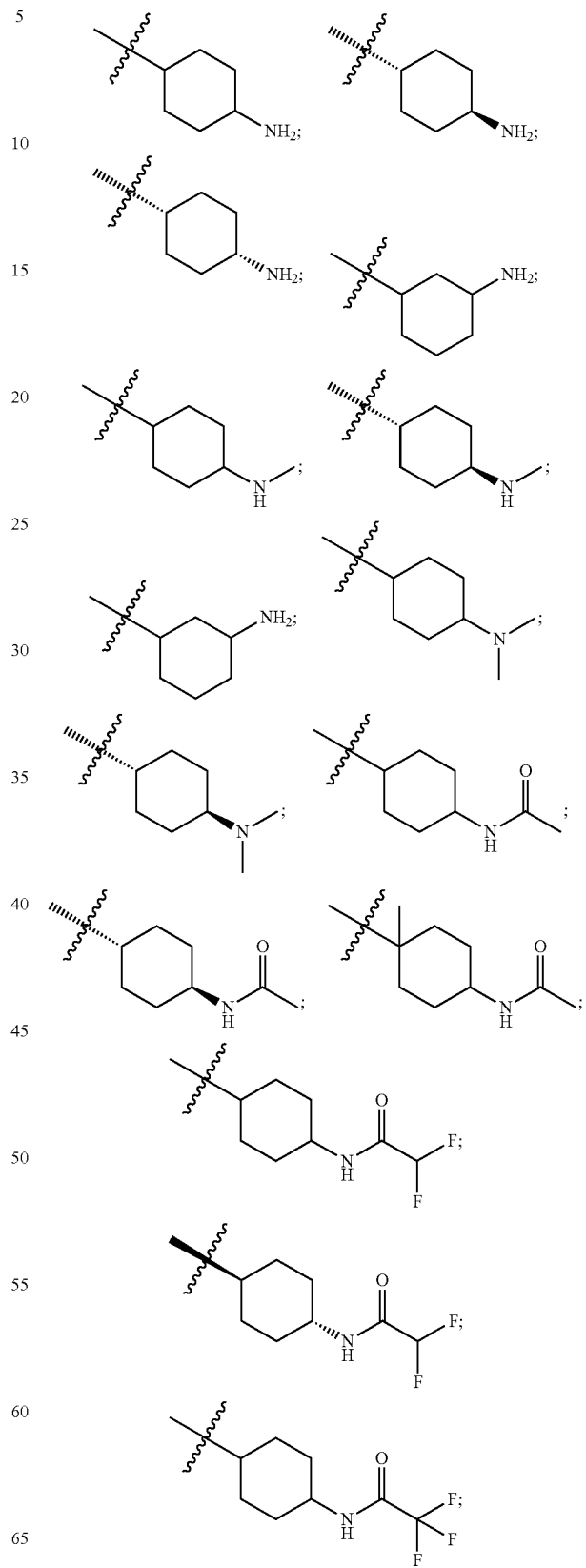

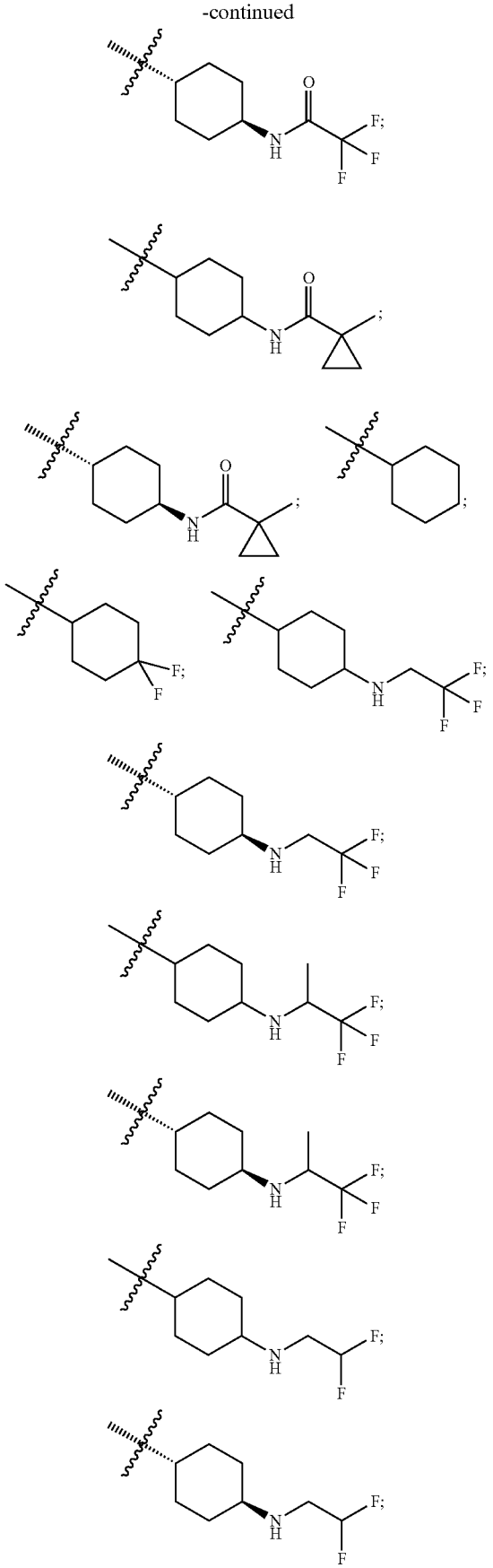
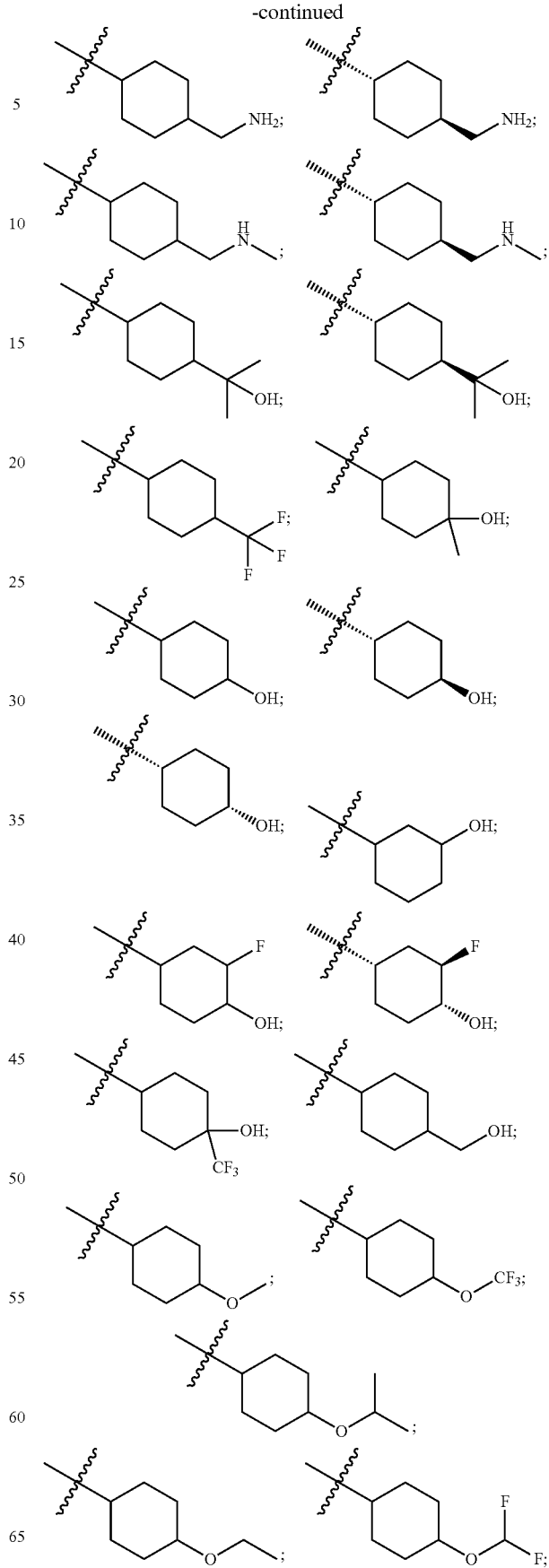

-continued

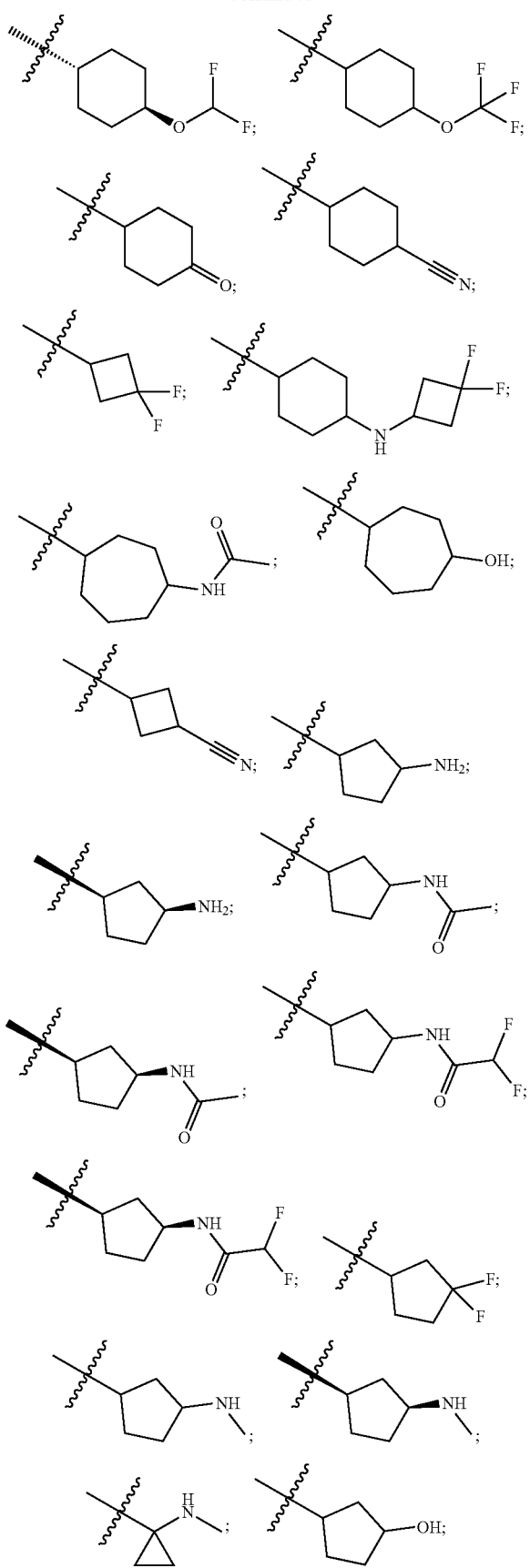

-continued

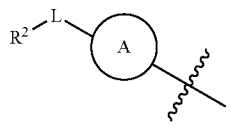

9. The compound of claim 1, wherein $R^{1a}$, $R^{1b}$, or both are selected from the group consisting of H, methyl, fluoro, chloro, cyano, methoxy, trifluoromethyl, and cyclopropyl.

10. The compound of claim 1, wherein $R^{1b}$ is H and $R^{1a}$ is fluoro.

11. The compound of claim 1, wherein $R^2$ is substituted.

12. The compound of claim 1, wherein $R^2$ is substituted with one or more substituents selected from the group consisting of methyl, ethyl, iso-propyl, fluoro, trifluoromethyl, and cyano.

13. The compound of claim 1, wherein $R^2$ is unsubstituted.

14. The compound of claim 1, wherein

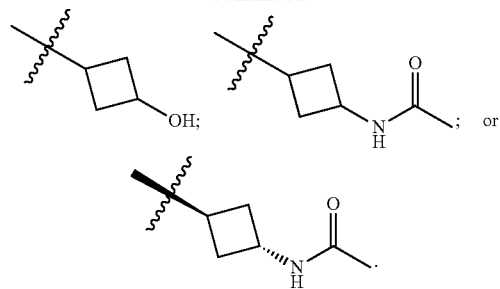

has one of the following structures:

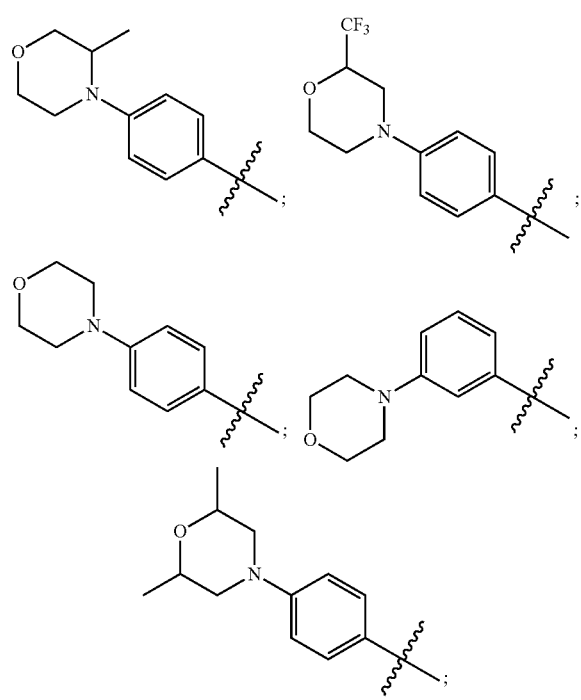

-continued
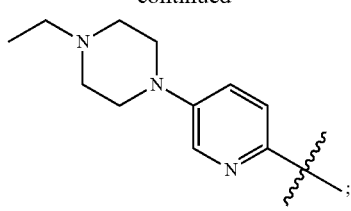
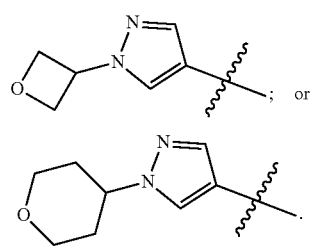; or
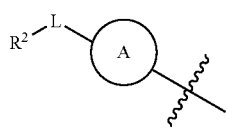.
15. The compound of claim 1, wherein
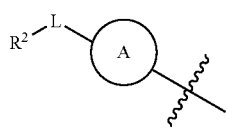
has one of the following structures:
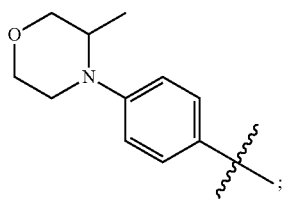;
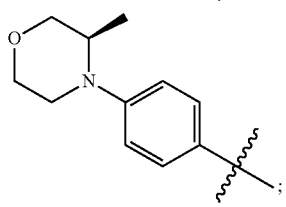;
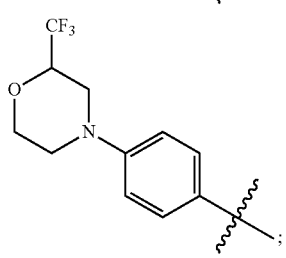;
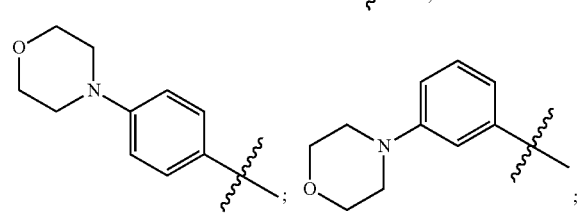;
-continued
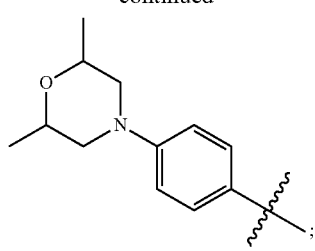;
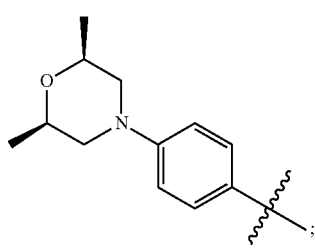;
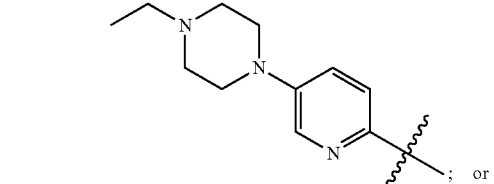; or
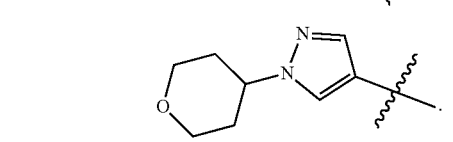.
16. The compound of claim 1, wherein the compound has one of the following structures:
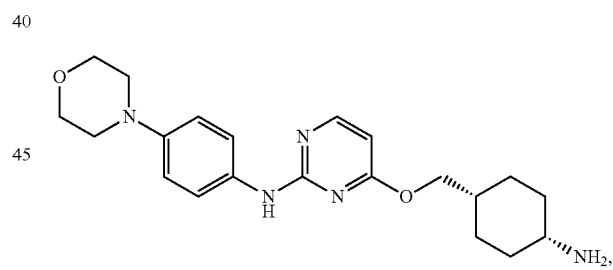,
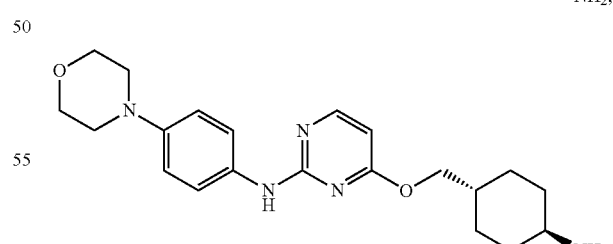,
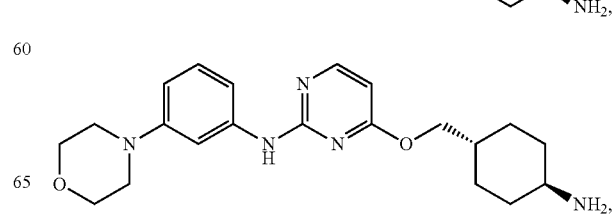,

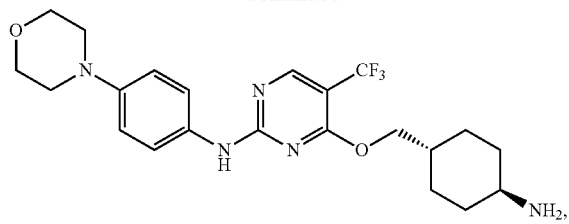
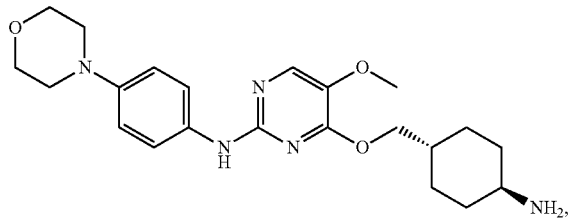
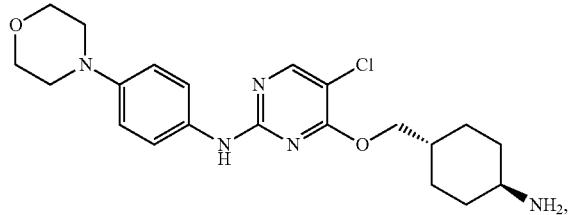
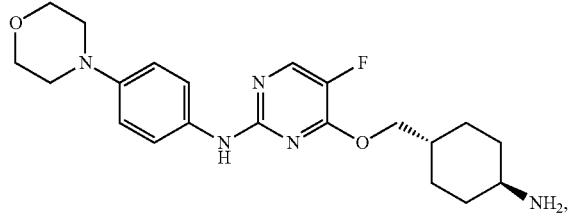
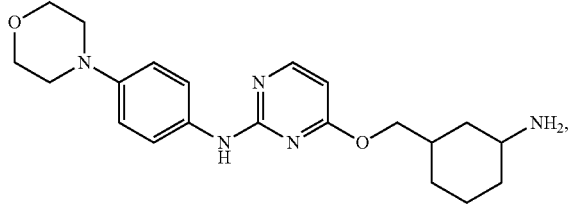
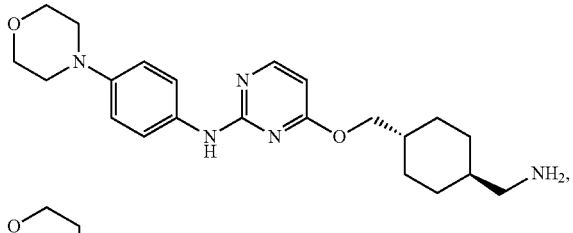
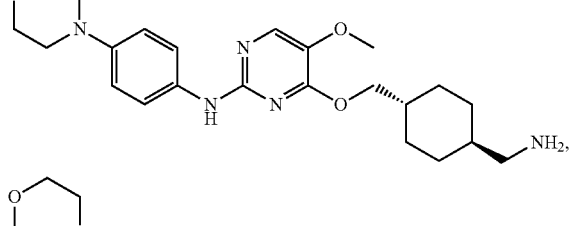
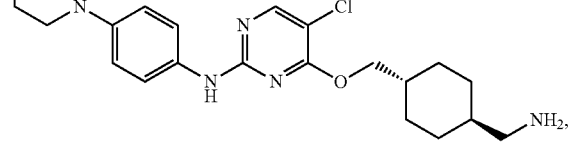
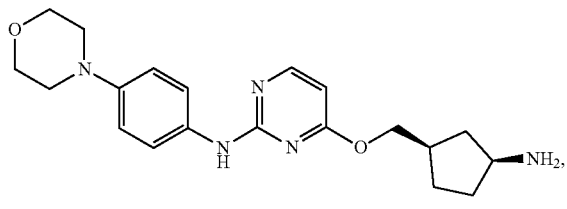
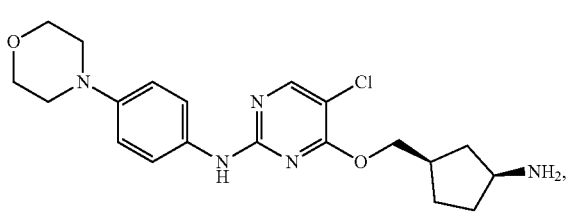
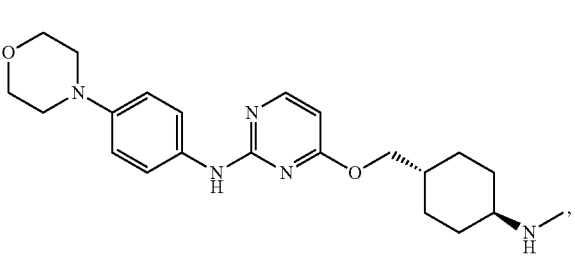
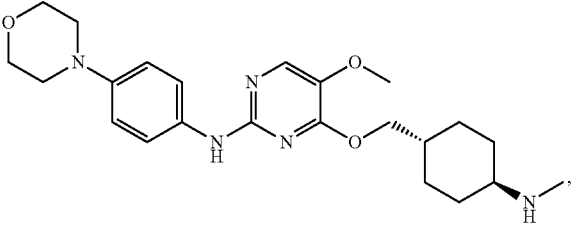
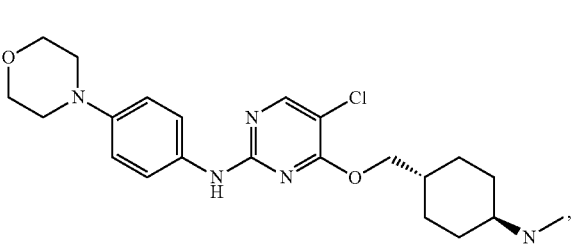
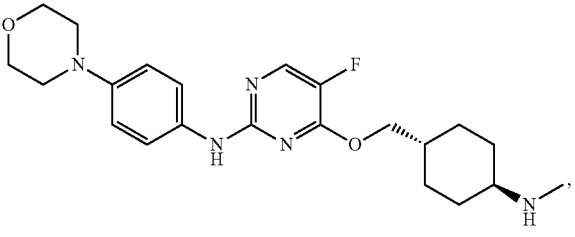
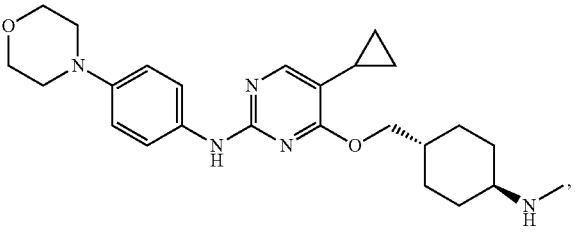

321
-continued
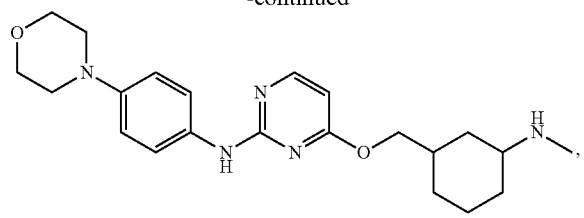
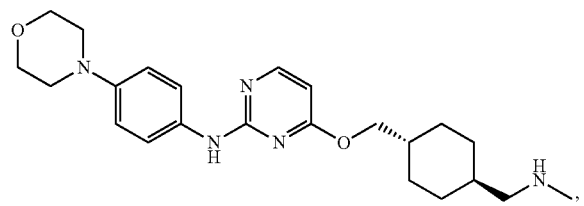
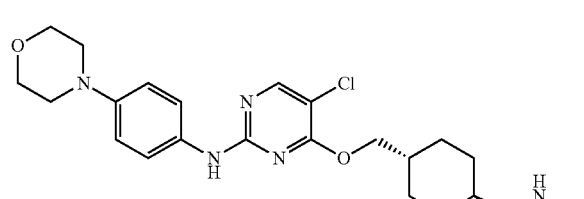
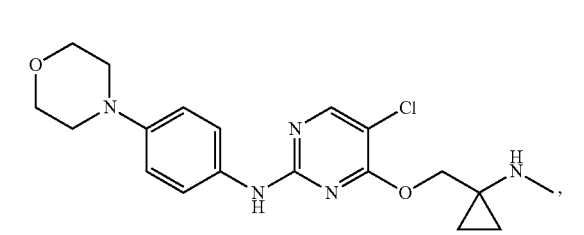
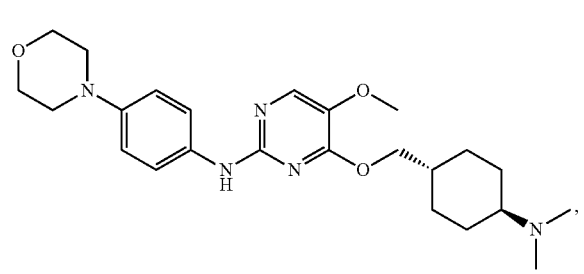
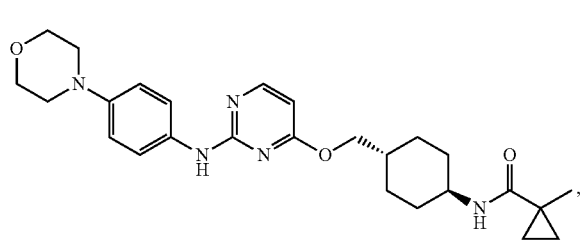
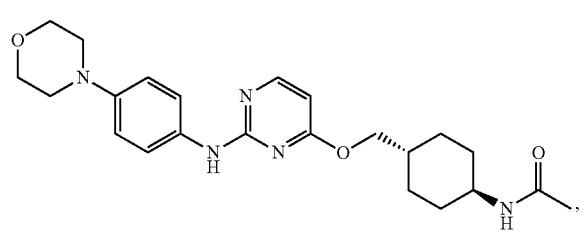
322
-continued
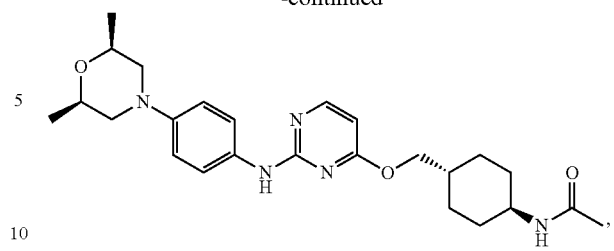
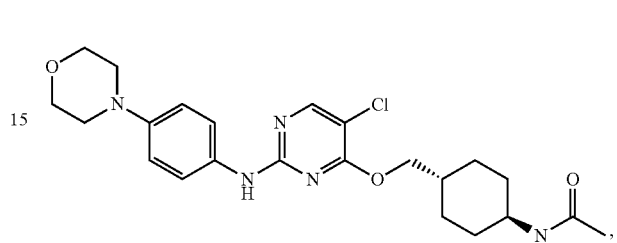
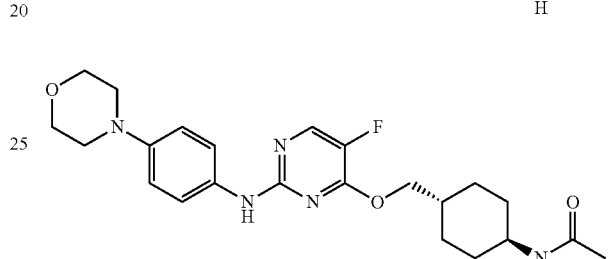
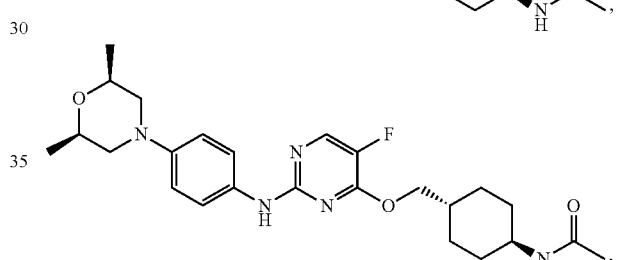
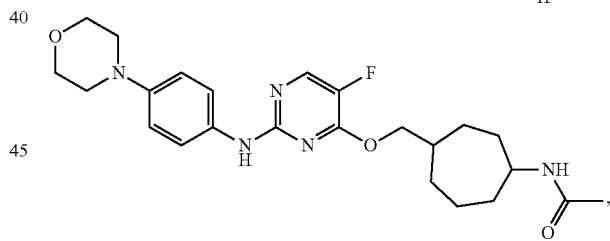
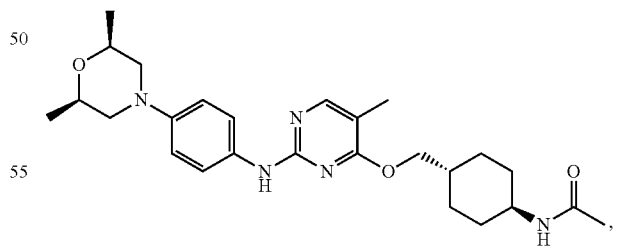
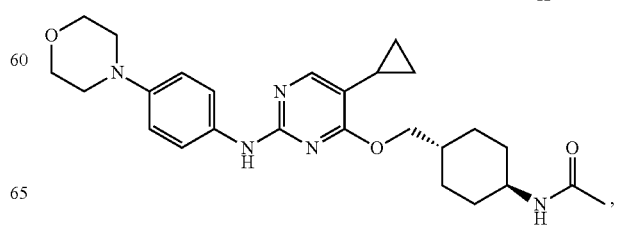

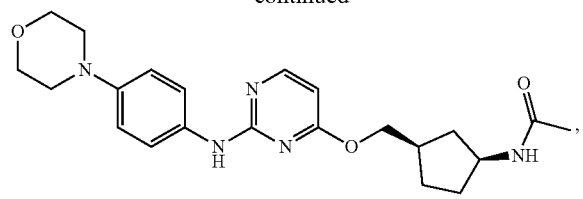
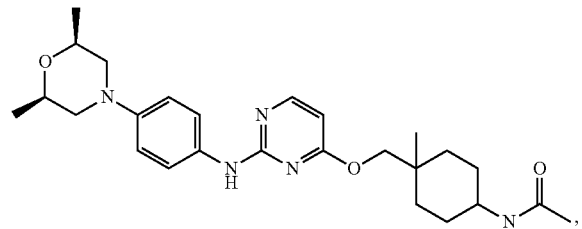
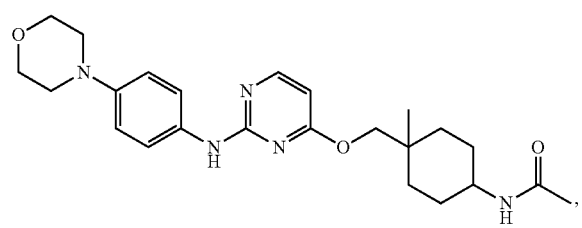
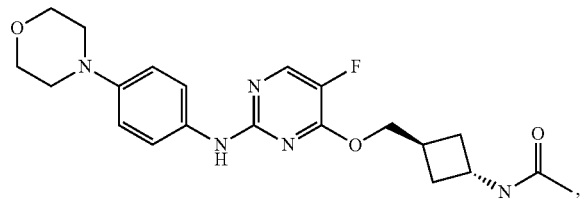
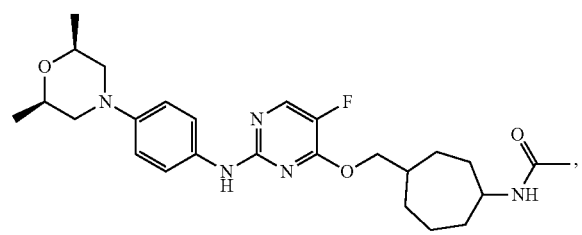
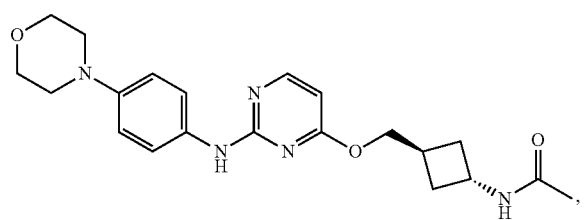
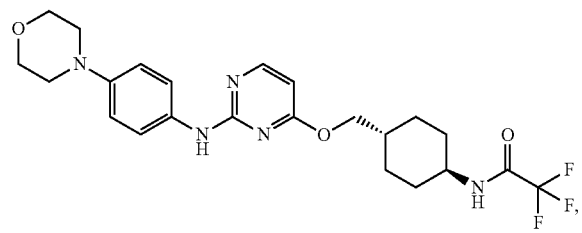
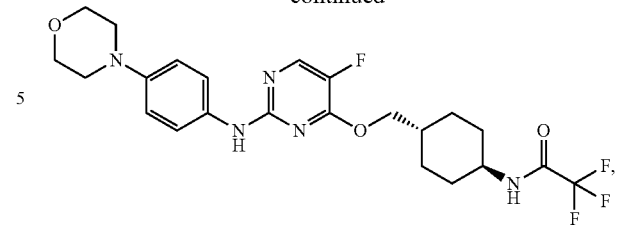
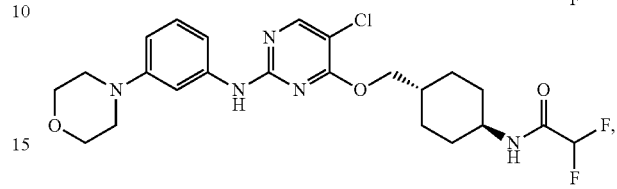
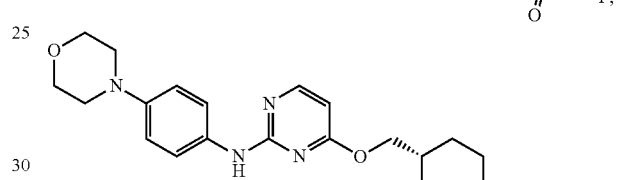
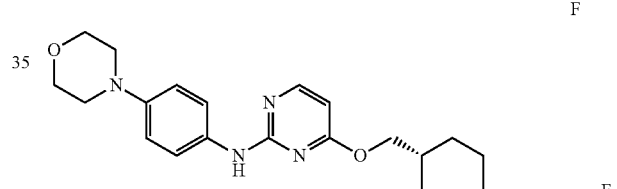
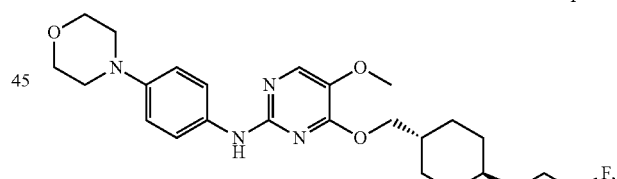
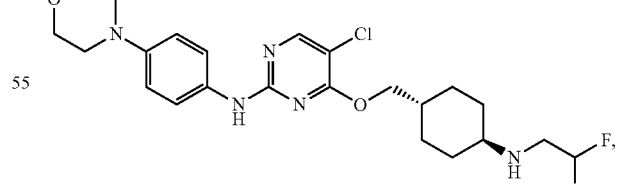
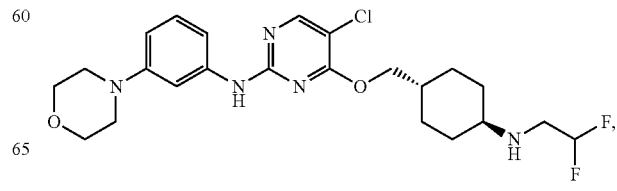

325
-continued
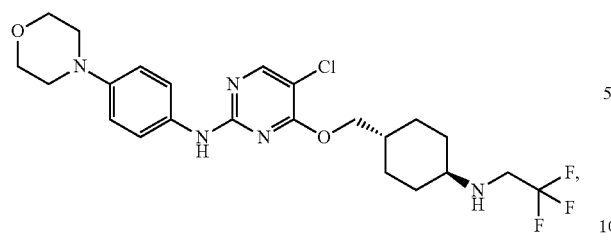
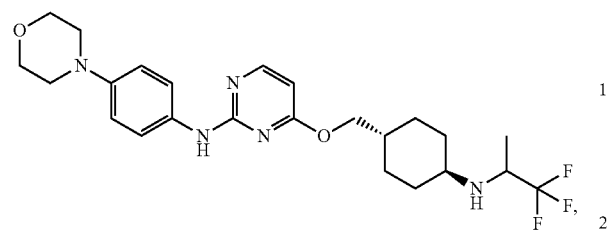
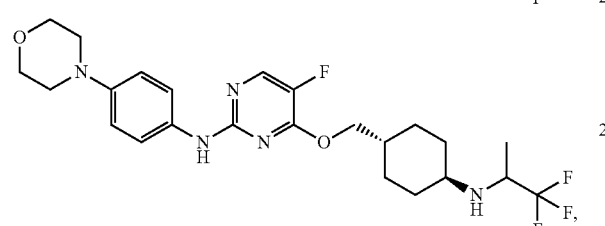
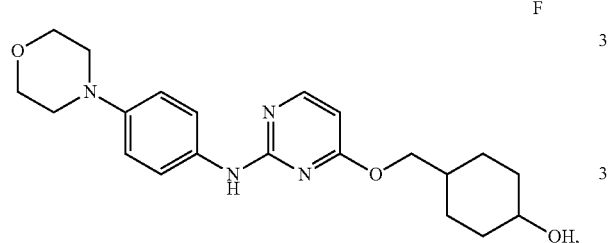
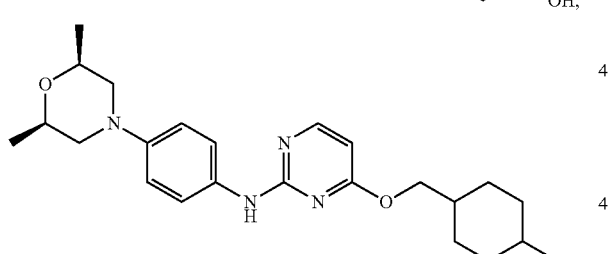
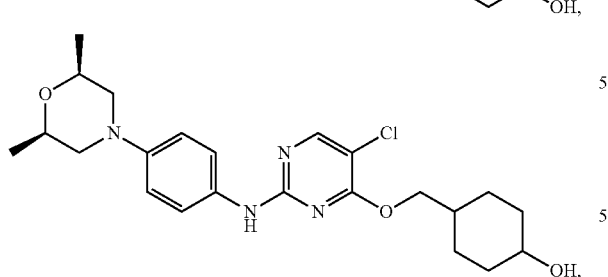
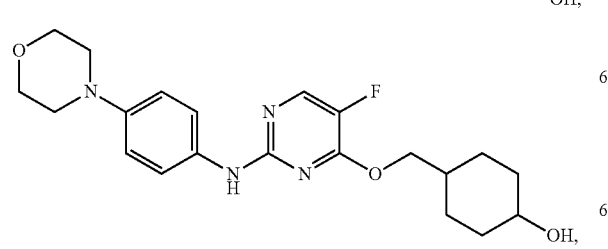
326
-continued
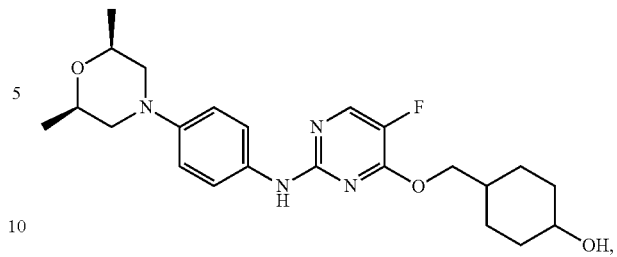
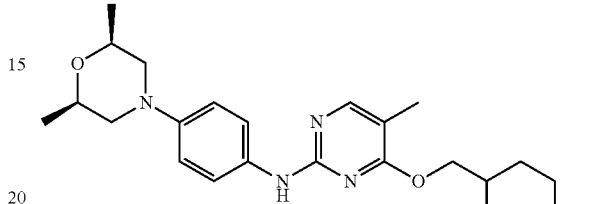
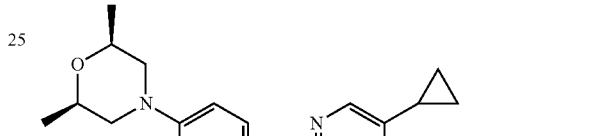
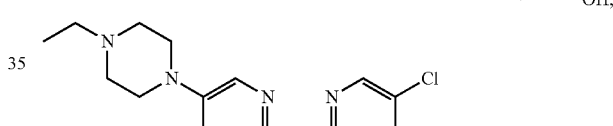
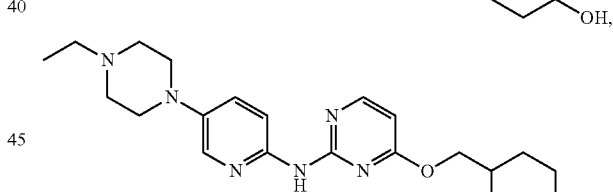
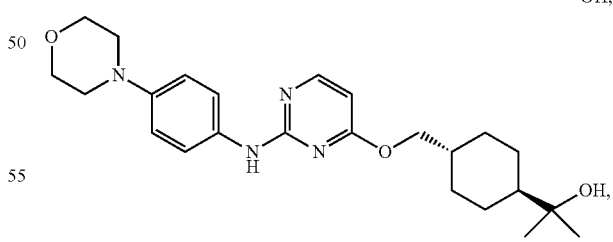
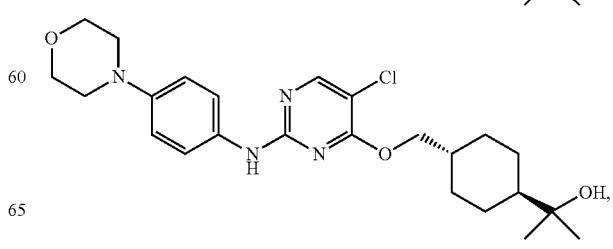

327
-continued
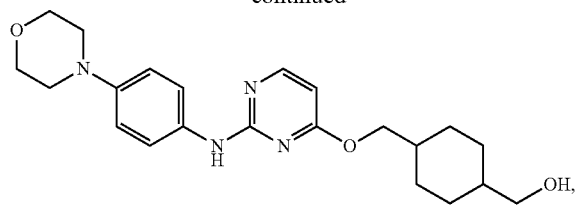
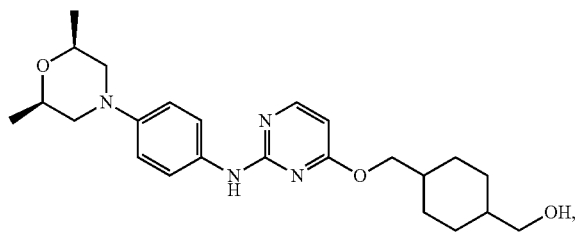
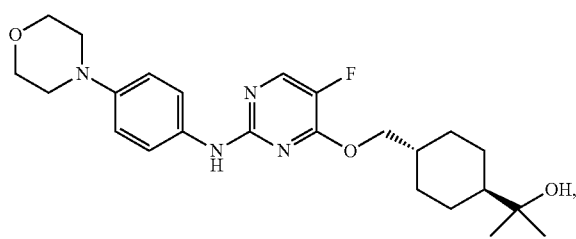
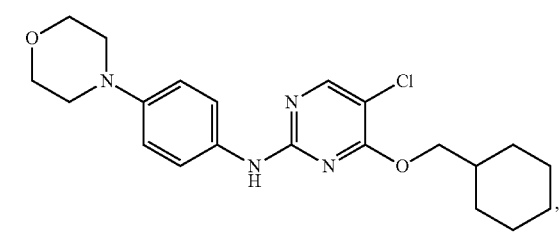
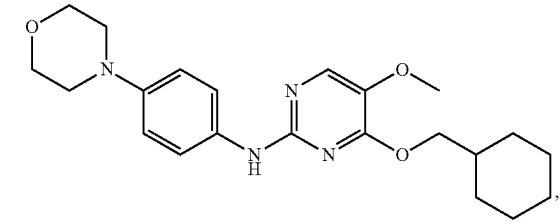
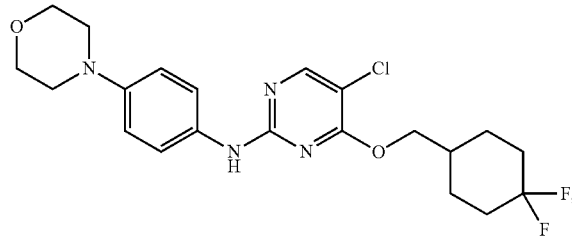
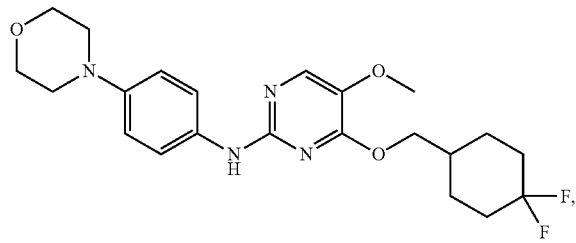
328
-continued
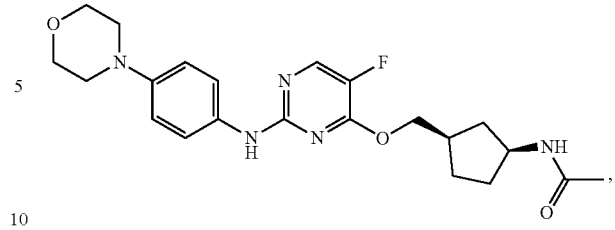
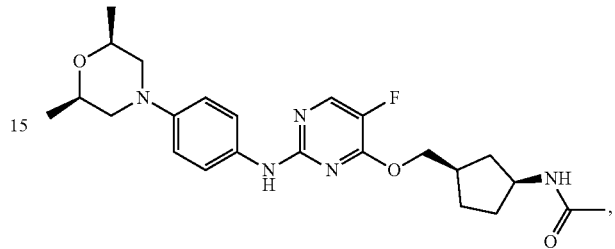
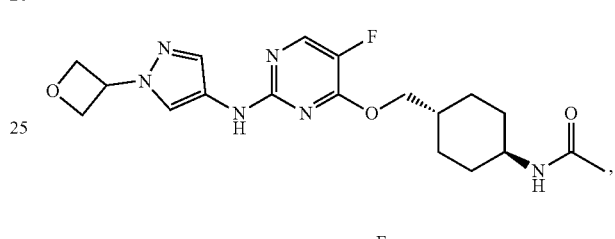
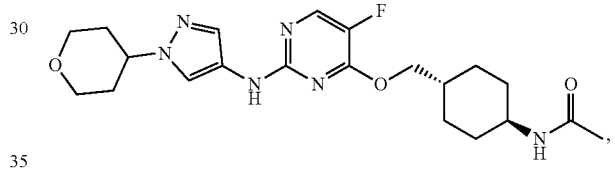
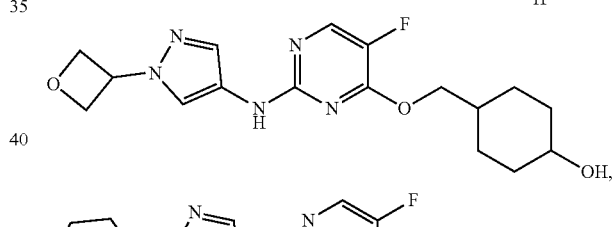
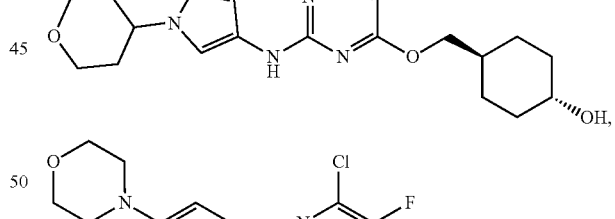
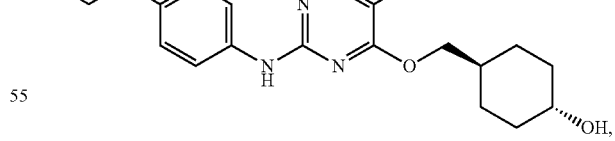
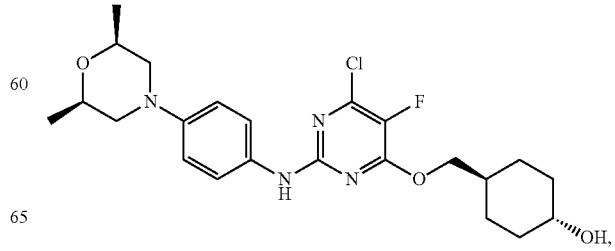

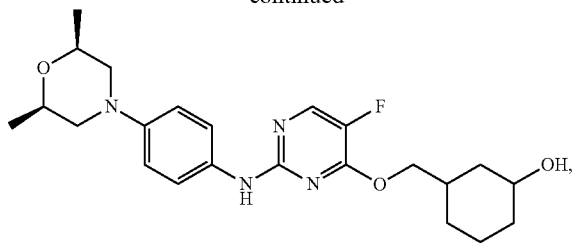
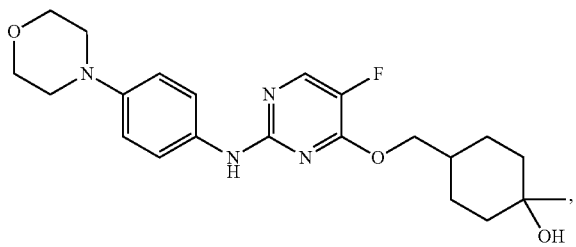
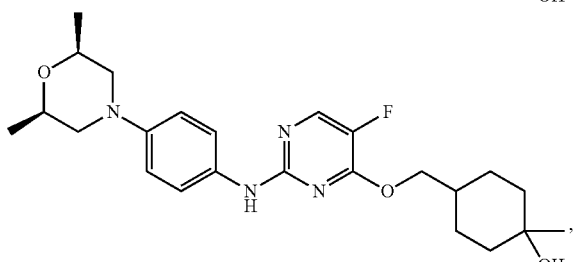
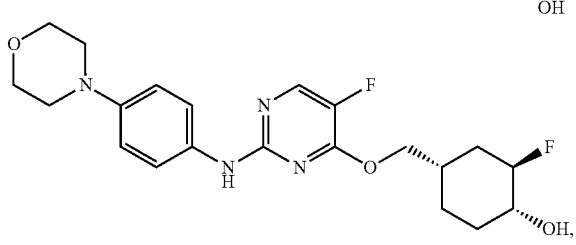
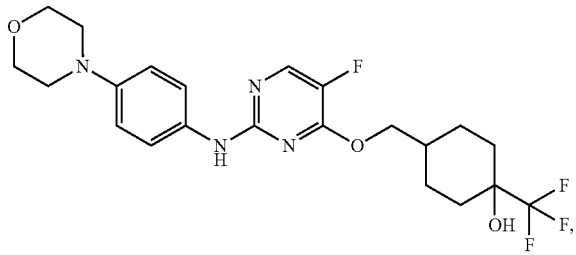
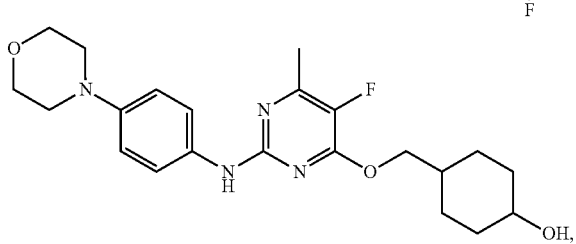
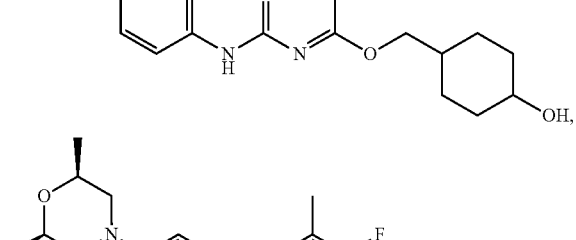
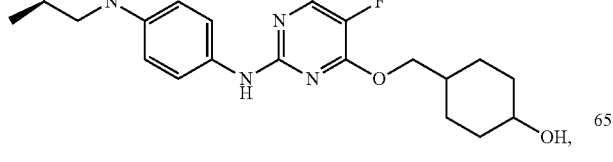
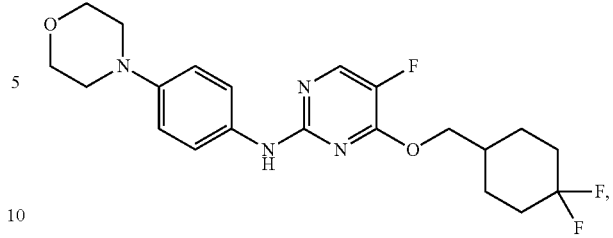

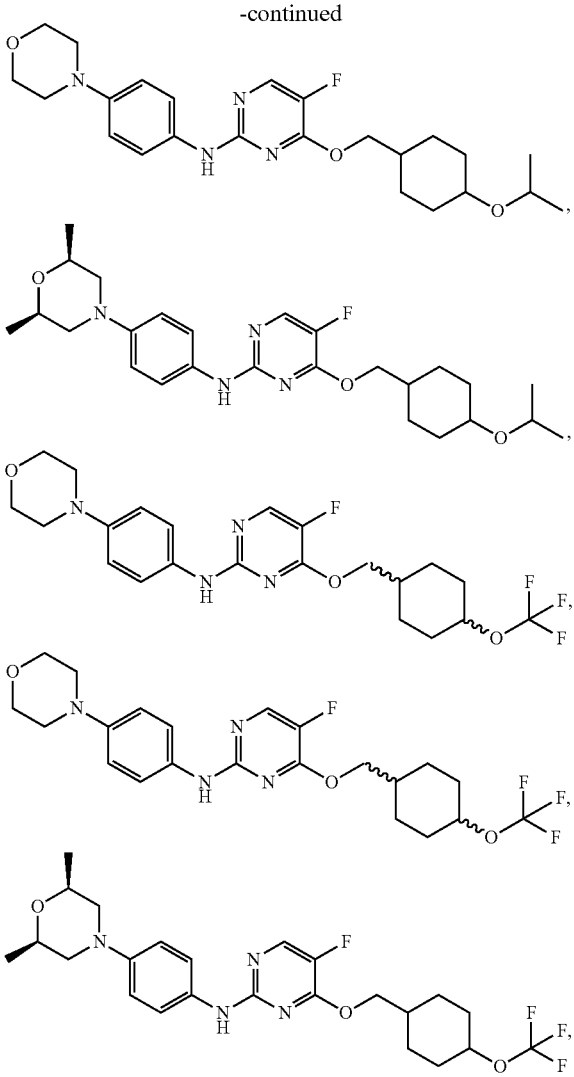

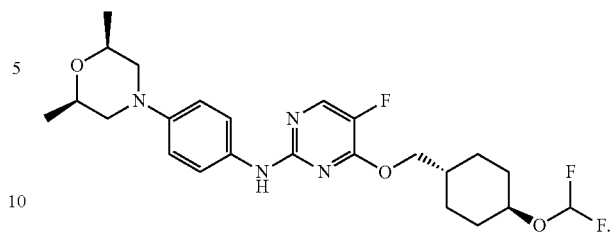

or

17. A pharmaceutical composition comprising the compound of claim 1, and a pharmaceutically acceptable carrier, diluent, or excipient.

18. A method of treating a LRRK2-mediated disease or disorder selected from the group consisting of Parkinson's disease, Lewy body dementia, Alzheimer's disease, L-DOPA induced dyskinesia, kidney cancer, breast cancer, prostate cancer, a blood cancer, papillary cancer, lung cancer, acute myelogenous leukemia, multiple myeloma leprosy, Crohn's disease, amyotrophic lateral sclerosis, rheumatoid arthritis, and ankylosing spondylitis, the method comprising administering a therapeutically effective amount of a compound of claim 1, to a subject in need thereof.

19. The method of claim 18, wherein the LRRK2-mediated disease or disorder is Parkinson's disease, or Lewy body dementia.

20. The method of claim 18, wherein the LRRK2-mediated disease or disorder is Alzheimer's disease or L-DOPA induced dyskinesia.

21. The method of claim 18, wherein the LRRK2-mediated disease or disorder is kidney cancer, breast cancer, prostate cancer, a blood cancer, papillary cancer, lung cancer, acute myelogenous leukemia, or multiple myeloma.

22. The method of claim 18, wherein the LRRK2-mediated disease or disorder is leprosy, Crohn's disease, amyotrophic lateral sclerosis, rheumatoid arthritis, or ankylosing spondylitis.

\* \* \* \* \*

UNITED STATES PATENT AND TRADEMARK OFFICE
CERTIFICATE OF CORRECTION

| | | |
|---|---|---|
| PATENT NO. | : 12,428,404 B2 | Page 1 of 1 |
| APPLICATION NO. | : 18/514959 | |
| DATED | : September 30, 2025 | |
| INVENTOR(S) | : David James Bearss et al. | |

It is certified that error appears in the above-identified patent and that said Letters Patent is hereby corrected as shown below:

In the Claims

Column 309, Claim 7, Lines 25-32:

" 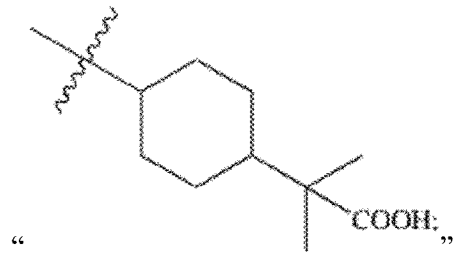 ,"

Should read:

-- 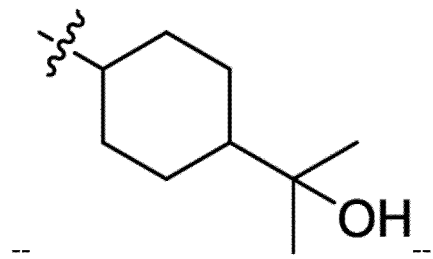 --

Signed and Sealed this
Sixteenth Day of December, 2025

John A. Squires
*Director of the United States Patent and Trademark Office*